US011820793B2

(12) United States Patent
Igawa et al.

(10) Patent No.: US 11,820,793 B2
(45) Date of Patent: Nov. 21, 2023

(54) DRUG CONTAINING CARRIER INTO CELL FOR FORMING IMMUNE COMPLEX

(71) Applicant: Chugai Seiyaku Kabushiki Kaisha, Tokyo (JP)

(72) Inventors: Tomoyuki Igawa, Shizuoka (JP); Naoka Hironiwa, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 554 days.

(21) Appl. No.: 16/108,897

(22) Filed: Aug. 22, 2018

(65) Prior Publication Data

US 2019/0218309 A1 Jul. 18, 2019

Related U.S. Application Data

(63) Continuation of application No. 14/361,013, filed as application No. PCT/JP2012/081185 on Nov. 30, 2012, now abandoned.

(51) Int. Cl.
| | |
|---|---|
| *A61K 39/00* | (2006.01) |
| *C07K 16/42* | (2006.01) |
| *C07K 16/24* | (2006.01) |
| *C07K 16/30* | (2006.01) |
| *G01N 33/68* | (2006.01) |

(52) U.S. Cl.
CPC ........ *C07K 16/4291* (2013.01); *C07K 16/248* (2013.01); *C07K 16/303* (2013.01); *C07K 16/4283* (2013.01); *G01N 33/686* (2013.01); *A61K 2039/505* (2013.01); *C07K 2317/31* (2013.01); *C07K 2317/52* (2013.01); *C07K 2317/92* (2013.01); *C07K 2317/94* (2013.01); *G01N 2500/04* (2013.01)

(58) Field of Classification Search
CPC .............................................. A61K 2039/505
See application file for complete search history.

(56) References Cited

U.S. PATENT DOCUMENTS

| | | | |
|---|---|---|---|
| 4,689,299 A | 8/1987 | Insel et al. | |
| 4,801,687 A | 1/1989 | Ngo | |
| 5,585,089 A | 12/1996 | Queen et al. | |
| 5,935,935 A | 8/1999 | Connelly et al. | |
| 6,074,642 A | 6/2000 | Wang et al. | |
| 6,737,056 B1 | 5/2004 | Presta | |
| 7,662,925 B2 | 2/2010 | Lazar et al. | |
| 7,960,512 B2 | 6/2011 | Stavenhagen et al. | |
| 8,101,720 B2 | 1/2012 | Lazar et al. | |
| 8,188,231 B2 | 5/2012 | Lazar et al. | |
| 8,562,991 B2 | 10/2013 | Igawa et al. | |
| 8,568,726 B2 | 10/2013 | Beaumont et al. | |
| 8,735,545 B2 | 5/2014 | Lazar et al. | |
| 9,029,515 B2 | 5/2015 | Pons et al. | |
| 9,079,949 B1 | 7/2015 | Andrien et al. | |
| 9,107,861 B1 | 8/2015 | Andrien, Jr. et al. | |
| 9,969,800 B2 | 5/2018 | Igawa et al. | |
| 10,253,100 B2 | 4/2019 | Igawa et al. | |
| 10,618,965 B2 | 4/2020 | Igawa et al. | |
| 10,919,953 B2 | 2/2021 | Katada et al. | |
| 11,267,868 B2 | 3/2022 | Mimoto et al. | |
| 2002/0098193 A1 | 7/2002 | Ward | |
| 2004/0001822 A1 | 1/2004 | Levanon et al. | |
| 2004/0001839 A1 | 1/2004 | Levanon et al. | |
| 2004/0002450 A1 | 1/2004 | Lazarovits et al. | |
| 2004/0110226 A1 | 6/2004 | Lazar et al. | |
| 2004/0133357 A1 | 7/2004 | Zhong et al. | |
| 2005/0032114 A1 | 2/2005 | Hinton et al. | |
| 2005/0260213 A1 | 11/2005 | Koenig et al. | |
| 2006/0024298 A1 | 2/2006 | Lazar et al. | |
| 2006/0134709 A1 | 6/2006 | Stavenhagen et al. | |
| 2006/0141456 A1 | 6/2006 | Edwards et al. | |
| 2006/0153860 A1 | 7/2006 | Cho et al. | |
| 2007/0003546 A1 | 1/2007 | Lazar et al. | |
| 2007/0009523 A1 | 1/2007 | Presta | |
| 2007/0037734 A1 | 2/2007 | Rossi et al. | |
| 2007/0148164 A1 | 6/2007 | Farrington et al. | |
| 2007/0160598 A1 | 7/2007 | Dennis et al. | |
| 2007/0224188 A1 | 9/2007 | Allan et al. | |
| 2007/0231329 A1 | 10/2007 | Lazar et al. | |
| 2007/0237767 A1 | 10/2007 | Lazar et al. | |

(Continued)

FOREIGN PATENT DOCUMENTS

| | | |
|---|---|---|
| AU | 2012/222252 | 10/2013 |
| CA | 2 721 052 | 10/2009 |

(Continued)

OTHER PUBLICATIONS

Ramos et al. (Rev. Assoc. Med. Bras. (1992). Jan.-Feb. 2012; 58 (1): 26-32).*
Ito et al. (FEBS Lett. Aug. 31, 1992; 309 (1): 85-8).*
Murtaugh et al. (Protein Sci. Sep. 2011; 20 (9): 1619-31).*
U.S. Appl. No. 14/007,947, Igawa et al., filed Sep. 26, 2013.
U.S. Appl. No. 15/977,757, Igawa et al., filed May 11, 2018.
U.S. Appl. No. 14/347,187, Igawa et al., filed Mar. 25, 2014.
U.S. Appl. No. 14/423,269, Igawa et al., filed Feb. 23, 2015.
U.S. Appl. No. 14/781,069, Igawa et al., filed Sep. 29, 2015.
Kamata et al., "Comparison of pH and Ionic Strength Dependence of Interactions between Monoclonal Antibodies and Bovine β-Lactoglobulin," Biosci Biotechnol Biochem, Jan. 1996, 60(1):25-9.
USPTO Notice of Allowance in U.S. Appl. No. 14/347,187, dated Jan. 7, 2019, 13 pages.

(Continued)

*Primary Examiner* — Stephen L Rawlings
(74) *Attorney, Agent, or Firm* — Fish & Richardson P.C.

(57) ABSTRACT

The present inventors discovered that by forming a large immune complex comprising antigens containing two or more antigenic binding units (epitopes) and two or more antigen-binding molecules (for example, antibodies), elimination from the plasma of the antigens containing two or more antigenic binding units can be accelerated. Moreover, they found that by using this characteristic and by further using antigen-binding molecules having an ion-dependent antigen-binding activity, elimination of the antigens can further be accelerated and the above problem can be solved.

25 Claims, 27 Drawing Sheets

Specification includes a Sequence Listing.

(56) References Cited

U.S. PATENT DOCUMENTS

| | | |
|---|---|---|
| 2007/0248602 A1 | 10/2007 | Lazar et al. |
| 2007/0253951 A1 | 11/2007 | Ng et al. |
| 2007/0269371 A1 | 11/2007 | Krummen et al. |
| 2008/0044417 A1 | 2/2008 | Johnson et al. |
| 2008/0089892 A1 | 4/2008 | Allan et al. |
| 2008/0138349 A1 | 6/2008 | Stavenhagen et al. |
| 2008/0181890 A1 | 7/2008 | Lazar et al. |
| 2008/0199471 A1 | 8/2008 | Bernett et al. |
| 2009/0035836 A1 | 2/2009 | Datta et al. |
| 2009/0041770 A1 | 2/2009 | Chamberlain et al. |
| 2009/0076251 A1 | 3/2009 | Koenig et al. |
| 2009/0136485 A1 | 5/2009 | Chu et al. |
| 2009/0142340 A1* | 6/2009 | Lazar ............... C07K 16/2893 424/133.1 |
| 2009/0163699 A1 | 6/2009 | Chamberlain et al. |
| 2010/0098730 A1 | 4/2010 | Lowman et al. |
| 2010/0184959 A1 | 7/2010 | Guler-Gane et al. |
| 2010/0216187 A1 | 8/2010 | Lasters et al. |
| 2010/0249482 A1 | 9/2010 | Chung et al. |
| 2010/0292443 A1 | 11/2010 | Sabbadini et al. |
| 2011/0044986 A1 | 2/2011 | Biere-Citron et al. |
| 2011/0111406 A1 | 5/2011 | Igawa et al. |
| 2011/0150888 A1 | 6/2011 | Foltz et al. |
| 2011/0223658 A1 | 9/2011 | Beliard et al. |
| 2011/0229489 A1 | 9/2011 | Pons et al. |
| 2011/0287032 A1 | 11/2011 | Lazar et al. |
| 2012/0009188 A1 | 1/2012 | Behrens et al. |
| 2012/0070466 A1 | 3/2012 | Lazar et al. |
| 2012/0093818 A1 | 4/2012 | Jackson et al. |
| 2012/0321620 A1* | 12/2012 | Chu ............... C07K 16/00 424/133.1 |
| 2013/0011866 A1 | 1/2013 | Igawa et al. |
| 2013/0085265 A1 | 4/2013 | Jackson et al. |
| 2013/0131319 A1 | 5/2013 | Igawa et al. |
| 2013/0247234 A1 | 9/2013 | McWhirter et al. |
| 2013/0259876 A1 | 10/2013 | Murphy et al. |
| 2013/0303396 A1 | 11/2013 | Igawa et al. |
| 2013/0336963 A1 | 12/2013 | Igawa et al. |
| 2014/0044730 A1 | 2/2014 | Yancopoulos et al. |
| 2014/0082760 A1 | 3/2014 | McWhirter et al. |
| 2014/0086916 A1* | 3/2014 | Zha ............... A61P 29/00 424/133.1 |
| 2014/0093496 A1 | 4/2014 | Mimoto et al. |
| 2014/0105889 A1 | 4/2014 | Igawa et al. |
| 2014/0112926 A1* | 4/2014 | Liu ............... A61K 39/39558 424/136.1 |
| 2014/0234340 A1 | 8/2014 | Igawa et al. |
| 2014/0255398 A1 | 9/2014 | Igawa et al. |
| 2014/0271617 A1 | 9/2014 | Igawa et al. |
| 2014/0335089 A1* | 11/2014 | Igawa ............... A61P 35/00 424/136.1 |
| 2014/0356371 A1 | 12/2014 | Swergold et al. |
| 2014/0363428 A1* | 12/2014 | Igawa ............... A61P 19/02 424/133.1 |
| 2015/0050269 A1 | 2/2015 | Igawa et al. |
| 2015/0056182 A1 | 2/2015 | Igawa et al. |
| 2015/0166654 A1 | 6/2015 | Igawa et al. |
| 2015/0203577 A1 | 7/2015 | Igawa et al. |
| 2015/0252107 A1 | 9/2015 | Stevis et al. |
| 2015/0299296 A1 | 10/2015 | Katada et al. |
| 2015/0299313 A1 | 10/2015 | Igawa et al. |
| 2015/0353630 A1 | 12/2015 | Igawa et al. |
| 2016/0039912 A1 | 2/2016 | Mimoto et al. |
| 2016/0046693 A1 | 2/2016 | Igawa et al. |
| 2016/0176954 A1 | 6/2016 | Ruike et al. |
| 2016/0200807 A1 | 7/2016 | Ruike et al. |
| 2016/0229908 A1 | 8/2016 | Igawa et al. |
| 2016/0244526 A1 | 8/2016 | Igawa et al. |
| 2017/0002066 A1 | 1/2017 | Igawa et al. |
| 2017/0002080 A1 | 1/2017 | Igawa et al. |
| 2017/0022270 A1 | 1/2017 | Igawa et al. |
| 2018/0282719 A1 | 10/2018 | Igawa et al. |
| 2019/0112393 A1 | 4/2019 | Igawa et al. |
| 2019/0185557 A1 | 6/2019 | Igawa et al. |
| 2019/0233525 A1 | 8/2019 | Igawa et al. |
| 2019/0359704 A1 | 11/2019 | Igawa et al. |
| 2020/0199241 A1 | 6/2020 | Igawa et al. |
| 2021/0079379 A1 | 3/2021 | Igawa et al. |
| 2021/0122812 A1 | 4/2021 | Igawa et al. |
| 2021/0261648 A1 | 8/2021 | Katada et al. |
| 2022/0389118 A1 | 12/2022 | Igawa et al. |
| 2022/0411483 A1 | 12/2022 | Mimoto et al. |
| 2023/0140797 A1 | 5/2023 | Igawa et al. |

FOREIGN PATENT DOCUMENTS

| | | |
|---|---|---|
| CA | 2 794 860 | 10/2011 |
| CA | 2 827 923 | 8/2012 |
| CA | 2 831 770 | 10/2012 |
| CN | 1763097 | 4/2006 |
| CN | 101001873 | 7/2007 |
| CN | 101014619 | 8/2007 |
| CN | 101098890 | 1/2008 |
| CN | 101932593 | 12/2010 |
| CN | 102056946 | 5/2011 |
| CN | 102149729 | 8/2011 |
| CN | 103492565 | 1/2014 |
| CN | 102633880 | 2/2015 |
| EA | 004317 | 2/2004 |
| EP | 0 091 539 A | 10/1983 |
| EP | 2 196 541 | 6/2010 |
| EP | 2 206 775 A | 7/2010 |
| EP | 2 275 443 | 1/2011 |
| EP | 2 314 618 | 4/2011 |
| EP | 2 366 713 | 9/2011 |
| EP | 2 368 911 | 9/2011 |
| EP | 2 409 990 | 1/2012 |
| EP | 2 647 706 | 10/2013 |
| EP | 2 679 681 | 1/2014 |
| EP | 2 698 431 | 2/2014 |
| EP | 2 762 166 | 8/2014 |
| EP | 2 765 192 | 8/2014 |
| EP | 2 818 183 | 12/2014 |
| EP | 2 889 377 | 7/2015 |
| JP | H01-144991 | 6/1989 |
| JP | H02-501112 | 4/1990 |
| JP | H02-163085 | 6/1990 |
| JP | 2003-512019 | 4/2003 |
| JP | 2007-532139 | 11/2007 |
| JP | 2008-505174 | 2/2008 |
| JP | 2008-510466 | 4/2008 |
| JP | 2008-511292 | 4/2008 |
| JP | 2008-519860 | 6/2008 |
| JP | 2010-079667 | 3/2010 |
| JP | 2010-514460 | 5/2010 |
| JP | 2010-250830 | 11/2010 |
| JP | 2011-507963 | 3/2011 |
| JP | 2011-184418 | 9/2011 |
| JP | 2012-505833 | 3/2012 |
| JP | 2013-521772 | 6/2013 |
| JP | 2014-528906 | 10/2014 |
| KR | 2011/0004435 | 1/2011 |
| RU | 2004/128259 | 8/2005 |
| RU | 2005/112742 | 1/2006 |
| RU | 2337107 | 10/2008 |
| RU | 2007/121679 | 12/2008 |
| RU | 2367667 | 9/2009 |
| RU | 2390527 | 5/2010 |
| RU | 2434882 | 11/2011 |
| SG | 183867 | 10/2012 |
| SG | 192945 | 9/2013 |
| TW | 2010/00127 | 1/2010 |
| TW | 2012/02419 | 1/2012 |
| WO | WO 83/03678 | 10/1983 |
| WO | WO 88/04692 | 6/1988 |
| WO | WO 91/12023 | 8/1991 |
| WO | WO 95/02187 | 1/1995 |
| WO | WO 95/14710 | 6/1995 |
| WO | WO 95/29697 | 11/1995 |
| WO | WO 97/34631 | 9/1997 |
| WO | WO 99/58572 | 11/1999 |
| WO | WO 00/42072 | 7/2000 |
| WO | WO 01/70968 | 9/2001 |

(56) References Cited

FOREIGN PATENT DOCUMENTS

| | | |
|---|---|---|
| WO | WO 02/060919 | 8/2002 |
| WO | WO 03/057881 | 7/2003 |
| WO | WO 03/070760 | 8/2003 |
| WO | WO 03/105757 | 12/2003 |
| WO | WO 03/107009 | 12/2003 |
| WO | WO 2004/007553 | 1/2004 |
| WO | WO 2004/029207 | 4/2004 |
| WO | WO 2004/035752 | 4/2004 |
| WO | WO 2004/039826 | 5/2004 |
| WO | WO 2004/092219 | 10/2004 |
| WO | WO 2004/099249 | 11/2004 |
| WO | WO 2005/037867 | 4/2005 |
| WO | WO 2005/047327 | 5/2005 |
| WO | WO 2005/059106 | 6/2005 |
| WO | WO 2005/070963 | 8/2005 |
| WO | WO 2005/077981 | 8/2005 |
| WO | WO 2005/080429 | 9/2005 |
| WO | WO 2005/115452 | 12/2005 |
| WO | WO 2005/123780 | 12/2005 |
| WO | WO 2006/019447 | 2/2006 |
| WO | WO 2006/020114 | 2/2006 |
| WO | WO 2006/023144 | 3/2006 |
| WO | WO 2006/023403 | 3/2006 |
| WO | WO 2006/031370 | 3/2006 |
| WO | WO 2006/050166 | 5/2006 |
| WO | WO 2006/053301 | 5/2006 |
| WO | WO 2006/105338 | 10/2006 |
| WO | WO 2006/116260 | 11/2006 |
| WO | WO 2006/130834 | 12/2006 |
| WO | WO 2007/012614 | 2/2007 |
| WO | WO 2007/021841 | 2/2007 |
| WO | WO 2007/024249 | 3/2007 |
| WO | WO 2007/041635 | 4/2007 |
| WO | WO 2007/084253 | 7/2007 |
| WO | WO-2007114325 A1 * 10/2007 ............. A61P 35/00 |
| WO | WO 2007/114325 | 11/2007 |
| WO | WO 2008/002933 | 1/2008 |
| WO | WO 2008/022152 | 2/2008 |
| WO | WO 2008/060785 | 5/2008 |
| WO | WO 2008/091954 | 7/2008 |
| WO | WO 2008/092117 | 7/2008 |
| WO | WO 2008/143954 | 11/2008 |
| WO | WO 2008/150494 | 12/2008 |
| WO | WO 2009/041062 | 4/2009 |
| WO | WO 2009/041643 | 4/2009 |
| WO | WO 2009/053358 | 4/2009 |
| WO | WO 2009/058492 | 5/2009 |
| WO | WO 2009/062083 | 5/2009 |
| WO | WO 2009/086320 | 7/2009 |
| WO | WO 2009/089846 | 7/2009 |
| WO | WO 2009/095235 | 8/2009 |
| WO | WO 2009/125825 | 10/2009 |
| WO | WO 2009/131702 | 10/2009 |
| WO | WO 2009/139822 | 11/2009 |
| WO | WO 2009/155513 | 12/2009 |
| WO | WO 2010/015608 | 2/2010 |
| WO | WO 2010/035769 | 4/2010 |
| WO | WO 2010/045193 | 4/2010 |
| WO | WO 2010/058860 | 5/2010 |
| WO | WO 2010/077854 | 7/2010 |
| WO | WO 2010/081173 | 7/2010 |
| WO | WO 2010/085682 | 7/2010 |
| WO | WO 2010/106180 | 9/2010 |
| WO | WO 2010/106812 | 9/2010 |
| WO | WO 2010/107109 | 9/2010 |
| WO | WO 2010/151792 | 12/2010 |
| WO | WO 2011/008517 | 1/2011 |
| WO | WO 2011/043643 | 4/2011 |
| WO | WO 2011/044368 | 4/2011 |
| WO | WO 2011/091078 | 7/2011 |
| WO | WO 2011/111007 | 9/2011 |
| WO | WO 2011/122011 | 10/2011 |
| WO | WO 2012/033953 | 3/2012 |
| WO | WO 2012/044831 | 4/2012 |
| WO | WO 2012/073992 | 6/2012 |
| WO | WO 2012/115241 | 8/2012 |
| WO | WO 2012/132067 | 10/2012 |
| WO | WO 2012/133782 | 10/2012 |
| WO | WO 2013/004842 | 1/2013 |
| WO | WO 2013/046704 | 4/2013 |
| WO | WO 2013/047729 | 4/2013 |
| WO | WO 2013/047748 | 4/2013 |
| WO | WO 2013/047752 | 4/2013 |
| WO | WO 2013/125667 | 8/2013 |
| WO | WO 2013/138681 | 9/2013 |
| WO | WO 2013/180200 | 12/2013 |
| WO | WO 2014/028354 | 2/2014 |
| WO | WO 2014/030728 | 2/2014 |
| WO | WO 2014/140366 | 9/2014 |
| WO | WO 2014/144080 | 9/2014 |
| WO | WO 2014/144577 | 9/2014 |
| WO | WO 2014/150983 | 9/2014 |
| WO | WO 2014/163101 | 10/2014 |
| WO | WO 2014/164959 | 10/2014 |
| WO | WO 2015/042250 | 3/2015 |
| WO | WO 2015/077491 | 5/2015 |
| WO | WO 2015/134894 | 9/2015 |
| WO | WO 2016/000813 | 1/2016 |
| WO | WO 2016/098356 | 6/2016 |
| WO | WO 2018/169993 | 9/2018 |

OTHER PUBLICATIONS

Sazinsky et al., "Aglycosylated immunoglobulin $G_1$ variants productively engage activating Fc receptors," Proc Natl Acad Sci USA, Dec. 23, 2008, 105(51):20167-72. doi: 10.1073/pnas.0809257105. Epub Dec. 12, 2008.
Travis et al., "Isolation of Albumin from Whole Human Plasma and Fractionation of Albumin-Depleted Plasma," Biochem J, Aug. 1, 1976, 157(2):301-6.
U.S. Appl. No. 14/423,269, Katada et al., filed Feb. 23, 2015.
U.S. Appl. No. 14/781,069, Mimoto et al., filed Sep. 29, 2015.
U.S. Appl. No. 16/264,735, filed Feb. 1, 2019, Igawa et al.
U.S. Appl. No. 14/977,757, Igawa et al., filed May 11, 2018.
U.S. Appl. No. 17/028,210, Katada et al., filed Sep. 22, 2020.
Ghetie et al., "Multiple Roles for the Major Histocompatibility Complex Class I-Related Receptor FcRn," Annu Rev Immunol, Apr. 2000, 18:739-66.
Medesan et al., "Comparative studies of rat IgG to further delineate the Fc:FcRn interaction site," Eur J Immunol, Jul. 1998, 28(7):2092-100.
Examination report No. 1 for AU 2013306700 (IP Australia) dated Jun. 7, 2018, 3 pages.
Fan et al., "Self-Association of Human PCSK9 Correlates with Its LDLR-Degrading Activity," Biochemistry, Feb. 12, 2008, 47(6):1631-9. doi: 10.1021/bi7016359. Epub Jan. 16, 2008.
Male et al., Immunology, 7th edition, published by Elsevier Ltd., 2006, pp. 77-78.
Murtaugh et al., "A Combinatorial Histidine Scanning Library Approach to Engineer Highly pH-Dependent Protein Switches," Protein Sci, Sep. 2011, 20(9): 1619-31. doi: 10.1002/pro.696. Epub Aug. 3, 2011.
Roitt et al., Immunology, Moscow, "Mir", 2000:111-2 (in Russian, with what is believed to be an English version of these pages).
Weiss et al., "Rapid mapping of protein functional epitopes by combinatorial alanine scanning," Proc Natl Acad Sci USA, Aug. 1, 2000, 97(16):8950-4.
U.S. Appl. No. 15/977,757, Igawa et al., filed May 11, 2014.
Igawa et al., "Engineering the variable region of therapeutic IgG antibodies," mAbs, May-Jun. 2011, 3(3):243-52. Epub May 1, 2011.
Alley et al., "Antibody-drug conjugates: targeted drug delivery for cancer," Curr Opin Chem Biol., Aug. 2010, 14(4):529-37. doi: 10.1016/j.cbpa.2010.06.170. Epub Jul. 17, 2010.
Amigorena et al., "Fc gamma RII expression in resting and activated B lymphocytes," Eur J Immunol., 1989, 19(8):1379-85.
Amigorena et al., "Cytoplasmic domain heterogeneity and functions of IgG Fc receptors in B lymphocytes," Science, 1992, 256(5065):1808-12.

(56) References Cited

OTHER PUBLICATIONS

Araujo et al., "Increased rheumatoid factor interference observed during immunogenicity assessment of an Fc-engineered therapeutic antibody," J Pharm Biomed Anal., Jul. 15, 2011, 55(5):1041-9. doi: 10.1016/j.jpba.2011.03.008. Epub Mar. 11, 2011.
Armour et al., "Differential binding to human FcgammaRIIa and FcgammaRIIb receptors by human IgG wildtype and mutant antibodies," Mol Immunol., 2003, 40(9):585-93.
Baeuerle et al., "BiTE: Teaching antibodies to engage T-cells for cancer therapy," Curr Opin Mol Ther., 2009, 11(1):22-30.
Beringhelli et al., "pH and ionic strength dependence of protein (un)folding and ligand binding to bovine beta-lactoglobulins A and B," Biochemistry, Dec. 27, 2002, 41(51):15415-22.
Blank et al., Decreased transcription of the human FCGR2B gene mediated by the -343 G/C promoter polymorphism and association with systemic lupus erythematosus. Hum Genet., Jul. 2005, 117(2-3):220-7. Epub May 14, 2005.
Boruchov et al., "Activating and inhibitory IgG Fc receptors on human DCs mediate opposing functions," J Clin Invest., Oct. 2005, 115(10):2914-23. Epub Sep. 15, 2005.
Boumpas et al., "A short course of BG9588 (anti-CD40 ligand antibody) improves serologic activity and decreases hematuria in patients with proliferative lupus glomerulonephritis," Arthritis Rheum., 2003, 48(3):719-27.
Bruhns et al., "Specificity and affinity of human Fcgamma receptors and their polymorphic variants for human IgG subclasses," Blood, Apr. 16, 2009, 113(16):3716-25. doi: 10.1182/blood-2008-09-179754. Epub Nov. 18, 2008.
Bruhns, "Properties of mouse and human IgG receptors and their contribution to disease models," Blood, Jun. 14, 2012, 119(24):5640-9. doi: 10.1182/blood-2012-01-380121. Epub Apr. 25, 2012.
Burmeister et al., "Crystal structure of the complex of rat neonatal Fc receptor with Fc," Nature, Nov. 24, 1994, 372(6504):379-83.
Cartron et al., "Therapeutic activity of humanized anti-CD20 monoclonal antibody and polymorphism in IgG Fc receptor FcgammaRIIIa gene," Blood, 2002, 99(3):754-8.
Cemerski et al., "Suppression of mast cell degranulation through a dual-targeting tandem IgE-IgG Fc domain biologic engineered to bind with high affinity to FcγRIIb," Immunol Lett., Mar. 30, 2012, 143(1):34-43. doi: 10.1016/j.imlet.2012.01.008. Epub Jan. 25, 2012.
Chen et al., "Association of a transmembrane polymorphism of Fcgamma receptor IIb (FCGR2B) with systemic lupus erythematosus in Taiwanese patients," Arthritis Rheum., 2006, 54(12):3908-17.
Chu et al., "Inhibition of B cell receptor-mediated activation of primary human B cells by coengagement of CD19 and FcgammaRIIb with Fc-engineered antibodies," Mol Immunol., Sep. 2008, 45(15):3926-33. doi: 10.1016/j.molimm.2008.06.027. Epub Aug. 8, 2008.
Chu et al., "Reduction of total IgE by targeted coengagement of IgE B-cell receptor and FcγRIIb with Fc-engineered antibody," J Allergy Clin Immunol., Apr. 2012, 129(4):1102-15. doi: 10.1016/j.jaci.2011.11.029. Epub Jan. 16, 2012.
Chuntharapai et al., "Isotype-dependent inhibition of tumor growth in vivo by monoclonal antibodies to death receptor 4," J Immunol., 2001, 166(8):4891-8.
Clark, "IgG effector mechanisms," Chem Immunol., 1997, 65:88-110.
Clark, "An alignment of IgG sequences from Human, Mouse and Rat," Part II Immunoglobulin lectures (v4), pp. 5(i)-(ii) [retrieved on Jul. 25, 2014]. Retrieved from the Internet: http://www.path.cam.ac.uk/~mrc7/lecturenotes/handout1a.pdf.
Clynes et al., "Fc receptors are required in passive and active immunity to melanoma," Proc Natl Acad Sci USA, 1998, 95(2):652-6.
Clynes et al., "Inhibitory Fc receptors modulate in vivo cytotoxicity against tumor targets," Nat Med., 2000, 6(4):443-6.
Dall'Acqua et al., "Increasing the affinity of a human IgG1 for the neonatal Fc receptor: biological consequences," J. Immunol., 2002, 169(9):5171-80.

Dall'Acqua et al., "Properties of human IgG1s engineered for enhanced binding to the neonatal Fc receptor (FcRn)," J Biol Chem., Aug. 18, 2006, 281(33):23514-24. Epub Jun. 21, 2006.
Datta-Mannan et al., "Monoclonal antibody clearance. Impact of modulating the interaction of IgG with the neonatal Fc receptor," J Biol Chem., Jan. 19, 2007, 282(3):1709-17. Epub Nov. 29, 2006.
Davda et al., "Properties of a general PK/PD model of antibody-ligand interactions for therapeutic antibodies that bind to soluble endogenous targets," mAbs, Sep.-Oct. 2010, 2(5):576-88. doi: 10.4161/mabs.2.5.12833. Epub Sep. 1, 2010.
De Bono et al., "ING-1, a monoclonal antibody targeting Ep-CAM in patients with advanced adenocarcinomas," Clin Cancer Res., 2004, 2004, 10(22):7555-65.
Deng et al., "Pharmacokinetics of humanized monoclonal anti-tumor necrosis factor-{alpha} antibody and its neonatal Fc receptor variants in mice and cynomolgus monkeys," Drug Metab Dispos., Apr. 2010, 38(4):600-5. doi: 10.1124/dmd.109.031310. Epub Jan. 13, 2010.
Desai et al., "Fc gamma receptor IIB on dendritic cells enforces peripheral tolerance by inhibiting effector T cell responses," J Immunol., 2007, 178(10):6217-26.
Desjarlais et al., "Optimizing engagement of the immune system by anti-tumor antibodies: an engineer's perspective," Drug Discov Today, Nov. 2007, 12(21-22):898-910. Epub Oct. 22, 2007.
Dhodapkar et al., "Selective blockade of inhibitory Fcgamma receptor enables human dendritic cell maturation with IL-12p70 production and immunity to antibody-coated tumor cells," Proc Natl Acad Sci USA, Feb. 22, 2005, 102(8):2910-5. Epub Feb. 9, 2005.
Duffau et al., "Platelet CD154 potentiates interferon-alpha secretion by plasmacytoid dendritic cells in systemic lupus erythematosus," Sci Transl Med., Sep. 1, 2010, 2(47):47ra63. doi: 10.1126/scitranslmed.3001001.
Dufner et al., "Harnessing phage and ribosome display for antibody optimization," Trends Biotechnol., Nov. 2006, 24(11):523-9. Epub Sep. 26, 2006.
Epstein, "Non-randomness of amino-acid changes in the evolution of homologous proteins," Nature, Jul. 22, 1967, 215(5099):355-9.
Fillipovic, Biochemical basis of human life, Vlados, 2005, pp. 49-50 (with English translation).
Floto et al., "Loss of function of a lupus-associated FcgammaRIIb polymorphism through exclusion from lipid rafts," Nat Med., Oct. 2005, 11(10):1056-8. Epub Sep. 18, 2005.
Fournier et al., "Activation of human peripheral IgM+B cells is transiently inhibited by BCR-independent aggregation of Fc gammaRIIB," J Immunol., Oct. 15, 2008, 181(8):5350-9.
Ghetie et al., "Increasing the serum persistence of an IgG fragment by random mutagenesis," Nat. Biotechnol., 1997, 15(7):637-40.
Greenwood et al., "Structural motifs involved in human IgG antibody effector functions," Eur J Immunol., 1993, 23(5):1098-104.
Haakenstad et al., "The disappearance kinetics and glomerular deposition of small-latticed soluble immune complexes," Immunology, 1982, 47(3):407-14.
Hamilton, "Molecular Engineering; Applications to the Clinical Laboratory," Clin Chem. Sep. 1993, 39(9):1988-97.
Hanson et al., "Catalytic antibodies and their applications," Curr Opin Biotechnol., 2005, 16(6):631-6.
Haringman et al., "A randomized controlled trial with an anti-CCL2 (anti-monocyte chemotactic protein 1) monoclonal antibody in patients with rheumatoid arthritis," Arthritis Rheum., 2006, 54(8):2387-92.
Hebert LA, "The clearance of immune complexes from the circulation of man and other primates," Am J Kidney Dis., 1991, 17(3):352-61.
Heyman, "Feedback regulation by IgG antibodies," Immunol Lett., 2003, 88(2):157-61.
Hinton et al., "An engineered human IgG1 antibody with longer serum half-life," J Immunol., 2006, 176(1):346-56.
Hinton et al., "Engineered human IgG antibodies with longer serum half-lives in primates," J Biol. Chem., Feb. 20, 2004, 279(8):6213-6. Epub Dec. 29, 2003.
Hjelm et al., "Antibody-mediated regulation of the immune response," Scand J Immunol., Sep. 2006, 64(3):177-84.

(56) References Cited

OTHER PUBLICATIONS

Horn et al., "Analysis of the binding of pro-urokinase and urokinase-plasminogen activator inhibitor-1 complex to the low density lipoprotein receptor-related protein using a Fab fragment selected from a phage-displayed Fab library," J Biol Chem., May 19, 1995, 270(20):11770-5.

Horton et al., "Potent in vitro and in vivo activity of an Fc-engineered anti-CD19 monoclonal antibody against lymphoma and leukemia," Cancer Res., Oct. 1, 2008, 68(19):8049-57. doi: 10.1158/0008-5472.CAN-08-2268.

Idusogie et al., "Mapping of the C1q binding site on rituxan, a chimeric antibody with a human IgG1 Fc," J Immunol., Apr. 15, 2000, 164(8):4178-84.

Idusogie et al., "Engineered antibodies with increased activity to recruit complement," J Immunol., Feb. 15, 2001, 166(4):2571-5.

Igawa et al., "Antibody optimization technologies for developing next generation antibody therapeutics," Bio Industry, 2011, 28(7):15-21 (with English translation).

Igawa et al., "Reduced elimination of IgG antibodies by engineering the variable region," Protein Eng Des Sel., 2010, 23(5):385-92.

Igawa et al., "Antibody recycling by engineered pH-dependent antigen binding improves the duration of antigen neutralization," Nat Biotechnol., 2010, 28(11):1203-7.

Ishii et al., "FcRn, a critical regulator of antibody pharmacokinetics," Folia Pharmacol. Jpn., 2010, 136(5):280-4 (with English translation).

Ito et al., "The His-probe method: effects of histidine residues introduced into the complementarity-determining regions of antibodies on antigen-antibody interactions at different pH values," FEBS Lett., 309(1):85-8 (1992).

Janeway et al., Immunobiology, The Immune System in Health and Disease, 3rd Edition, 1997 Garland Publishing Inc., pp. 3:1-3:11.

Jefferis et al., "Interaction sites on human IgG-Fc for FcgammaR: current Models," Immunol Lett., 2002, 82(1-2):57-65.

Juszczak et al., "Ipilimumab: a novel immunomodulating therapy causing autoimmune hypophysitis: a case report and review," Eur J Endocrinol., Jul. 2012, 167(1):1-5. doi: 10.1530/EJE-12-0167. Epub Apr. 10, 2012.

Kamei et al., "Quantitative methods for developing Fc mutants with extended half-lives," Biotechnol Bioeng., Dec. 20, 2005, 92(6):748-60.

Kim et al., "Antibody Engineering for the Development of Therapeutic Antibodies," Mol Cells, 2005, 20(1):17-29.

Kohrt et al., "Stimulation of natural killer cells with a CD137-specific antibody enhances trastuzumab efficacy in xenotransplant models of breast cancer," J Clin Invest., Mar. 1, 2012, 122(3):1066-75. doi: 10.1172/JCI61226. Epub Feb. 13, 2012.

Lazar et al., "Engineered antibody Fc variants with enhanced effector function," Proc Natl Acad Sci USA, Mar. 14, 2006, 103(11):4005-10. Epub Mar. 6, 2006.

Lewis et al., "Differential responses of human tumor cell lines to anti-p185$^{HER2}$ monoclonal antibodies," Cancer Immunol Immunother., 1993, 37(4):255-63.

Li et al., "CD72 down-modulates BCR-induced signal transduction and diminishes survival in primary mature B lymphocytes," J Immunol., 2006, 176(9):5321-8.

Li et al., "Apoptotic and antitumor activity of death receptor antibodies require inhibitory Fcγ receptor engagement," Proc Natl Acad Sci USA., Jul. 3, 2012, 109(27):10966-71. doi: 10.1073/pnas.1208698109. Epub Jun. 20, 2012.

Li et al., "Inhibitory Fcγ receptor engagement drives adjuvant and anti-tumor activities of agonistic CD40 antibodies," Science, Aug. 19, 2011, 333(6045):1030-4. doi: 10.1126/science.1206954.

Liang, et al., "Immunity against a therapeutic xenoprotein/Fc construct delivered by gene transfer is reduced through binding to the inhibitory receptor FcγRIIb", J Gene Med., Sep. 2011, 13(9):470-7.

Lutterbuese et al., "T cell-engaging BiTE antibodies specific for EGFR potently eliminate KRAS- and BRAF-mutated colorectal cancer cells," Proc Natl Acad Sci USA, Jul. 13, 2010, 107(28):12605-10. doi: 10.1073/pnas.1000976107. Epub Jun. 28, 2010.

Luttrell et al., "Reaction coupling of chelation and antigen binding in the calcium ion-dependent antibody binding of cyclic Amp," J Biol Chem., Nov. 15, 1991, 266(32):21626-30.

Mackay et al., "Selective dysregulation of the FcγIIB receptor on memory B cells in SLE," J Exp Med., Sep. 4, 2006, 203(9):2157-64. Epub Aug. 21, 2006.

Malbec et al., "Antibodies against growth factor receptors can inhibit the proliferation of transformed cells via a cis-interaction with inhibitory FcR," Immunol Lett., Mar. 30, 2012, 143(1):28-33.

Manger et al., "Fcγ receptor IIa polymorphism in Caucasian patients with systemic lupus erythematosus: association with clinical symptoms," Arthritis Rheum., 1998, 41(7):1181-9.

Martin et al., "Preclinical safety and immune-modulating effects of therapeutic monoclonal antibodies to interleukin-6 and tumor necrosis factor-a in cynomolgus macaques," J Immunotoxicol., Jul. 1, 2004, 1(3):131-9. doi:10.1080/15476910490894904.

Matsumiya et al., "Structural comparison of fucosylated and nonfucosylated Fc fragments of human immunoglobulin G1," J Mol Biol., May 4, 2007, 368(3):767-79. Epub Feb. 22, 2007.

Maurer et al., "Antigenicity of polypeptides (poly alpha amino acids): calcium-dependent and independent antibodies," J Immunol., Sep. 1970;105(3):567-73.

Meyer et al., "Bevacizumab immune complexes activate platelets and induce thrombosis in FCGR2A transgenic mice," J Thromb Haemost., Jan. 2009, 7(1):171-81. doi: 10.1111/j.1538-7836.2008.03212.x. Epub Oct. 30, 2008.

Mi et al., "Targeting the neonatal fc receptor for antigen delivery using engineered fc fragments," J Immunol., 2008, 181(11):7550-61.

Mimoto et al., "Engineered antibody Fc variant with selectively enhanced FcγRIIb binding over both FcγRIIa(R131) and FcγRIIa(H131)," Protein Eng Des Sel., Oct. 2013, 26(10):589-98. doi: 10.1093/protein/gzt022. Epub Jun. 5, 2013.

Montero-Julian et al., "Pharmacokinetic study of anti-interleukin-6 (IL-6) therapy with monoclonal antibodies: enhancement of IL-6 clearance by cocktails of anti-IL-6 antibodies," Blood, 1995, 85(4):917-24.

Moore et al., "Engineered Fc variant antibodies with enhanced ability to recruit complement and mediate effector functions," mAbs., Mar.-Apr. 2010, 2(2):181-9.

Morgan et al., "The N-terminal end of the CH2 domain of chimeric human IgG1 anti-HLA-DR is necessary for C1q, Fc gamma RI and Fc gamma RIII binding," Immunology, 1995, 86(2):319-24.

Muta et al., "A 13-amino-acid motif in the cytoplasmic domain of Fc gamma RIIB modulates B-cell receptor signaling," Nature, 1994, 368(6466):70-3.

Nakamura et al., "Fcgamma receptor IIB-deficient mice develop Goodpasture's syndrome upon immunization with type IV collagen: a novel murine model for autoimmune glomerular basement membrane disease," J Exp Med., 2000, 191(5):899-906.

Nam et al., "Current evidence for the management of rheumatoid arthritis with biological disease-modifying antirheumatic drugs: a systematic literature review informing the EULAR recommendations for the management of RA," Ann Rheum Dis., Jun. 2010, 69(6):976-86. doi: 10.1136/ard.2009.126573. Epub May 6, 2010.

Nicholas et al., "Regulation of the immune response. I. Reduction in ability of specific antibody to inhibit long-lasting IgG immunological priming after removal of the Fc fragment," J Exp Med., 1969, 129(6):1183-201.

Niebecker et al., "Safety of therapeutic monoclonal antibodies," Curr Drug Saf., 2010, 5(4):275-86.

Nimmerjahn et al., "Fcgamma receptors as regulators of immune responses," Nat Rev Immunol., 2008, 8(1):34-47.

Nimmerjahn et al., "Divergent immunoglobulin g subclass activity through selective Fc receptor binding," Science, 2005, 310(5753):1510-2.

Nishimoto et al., "Mechanisms and pathologic significances in increase in serum interleukin-6 (IL-6) and soluble IL-6 receptor after administration of an anti-IL-6 receptor antibody, tocilizumab, in patients with rheumatoid arthritis and Castleman disease," Blood, Nov. 15, 2008, 112(10):3959-64. doi: 10.1182/blood-2008-05-155846. Epub Sep. 10, 2008.

(56) References Cited

OTHER PUBLICATIONS

Olferiev et al., "The role of activating protein 1 in the transcriptional regulation of the human FCGR2B promoter mediated by the -343 G -> C polymorphism associated with systemic lupus erythematosus," J Biol Chem., Jan. 19, 2007, 282(3):1738-46. Epub Nov. 27, 2006.
Pakula et al., "Genetic Analysis of Protein Stability and Function," Annu. Rev. Genet., 1989, 23:289-310.
Patton et al., "An acid dissociation bridging ELISA for detection of antibodies directed against therapeutic proteins in the presence of antigen," J Immunol Methods, Sep. 2005, 304(1-2):189-95.
Pavlou et al., "The therapeutic antibodies market to 2008," Eur J Pharm Biopharm., 2005, 59(3):389-96.
Petkova et al., "Enhanced half-life of genetically engineered human IgG1 antibodies in a humanized FcRn mouse model: potential application in humorally mediated autoimmune disease," Int Immunol., Dec. 2006, 18(12):1759-69. Epub Oct. 31, 2006.
Qiao et al., "Dependence of antibody-mediated presentation of antigen on FcRn," Proc Natl Acad Sci USA, 2008, 105(27):9337-42.
Radaev et al., "The role of Fc glycosylation and the binding of peptide inhibitors," J Biol Chem., May 11, 2001, 276(19):16478-83. Epub Jan. 31, 2001.
Radaev et al., "The structure of a human type III Fcgamma receptor in complex with Fc," J Biol Chem., May 11, 2001, 276(19):16469-77. Epub Jan. 31, 2001.
Rajpal et al., A general method for greatly improving the affinity of antibodies by using combinatorial libraries, Proc Natl Acad Sci USA, 2005, 102(24):8466-71.
Ramos et al., "Evaluation of CA-125 and soluble CD-23 in patients with pelvic endometriosis: a case-control study," Rev. Assoc. Med. Bras., 1992, Jan.-Feb. 2012, 58(1):26-32).
Rathanaswami et al., "Demonstration of an in vivo generated sub-picomolar affinity fully human monoclonal antibody to interleukin-8," Biochem Biophys Res Commun., 2005, 334(4):1004-13.
Ravetch et al., "Immune inhibitory receptors," Science, 2000, 290(5489):84-9.
Reichert et al., "Monoclonal antibody successes in the clinic," Nat Biotechnol., 2005, 23(9):1073-8.
Reverberi et al., "Factors affecting the antigen-antibody reaction," Blood Transfus., Nov. 2007, 5(4):227-40. doi: 10.2450/2007.0047-07.
Richards et al., "Optimization of antibody binding to FcgammaRIIa enhances macrophage phagocytosis of tumor cells," Mol Cancer Ther., Aug. 2008, 7(8):2517-27. doi: 10.1158/1535-7163.MCT-08-0201.
Riechelmann et al., "Phase I trial with the CD44v6-targeting immunoconjugate bivatuzumab mertansine in head and neck squamous cell carcinoma," Oral Oncol., Sep. 2008, 44(9):823-9. doi: 10.1016/j.oraloncology.2007.10.009. Epub Jan. 18, 2008.
Robles-Carrillo et al., "Anti-CD40L immune complexes potently activate platelets in vitro and cause thrombosis in FCGR2A transgenic mice," J Immunol., Aug. 1, 2010, 185(3):1577-83. doi: 10.4049/jimmunol.0903888. Epub Jun. 28, 2010.
Roopenian et al., "FcRn: the neonatal Fc receptor comes of age," Nat Rev Immunol., Sep. 2007, 7(9):715-25. Epub Aug. 17, 2007.
Rudge et al.,, "VEGF Trap complex formation measures production rates of VEGF, providing a biomarker for predicting efficacious angiogenic blockade," Proc Natl Acad Sci USA, 2007, 104(47):18363-70.
Rudikoff et al., "Single amino acid substitution altering antigen-binding specificity," Proc Natl Acad Sci USA, Mar. 1982, 79(6):1979-83.
Salmon et al., "Fc gamma RIIA alleles are heritable risk factors for lupus nephritis in African Americans," J Clin Invest., 1996, 97(5):1348-54.
Satoh et al., "Non-fucosylated therapeutic antibodies as next-generation therapeutic antibodies," Expert Opin Biol Ther., 2006, 6(11):1161-73.

Scappaticci et al., "Arterial thromboembolic events in patients with metastatic carcinoma treated with chemotherapy and bevacizumab," J Natl Cancer Inst., Aug. 15, 2007, 99(16):1232-9. Epub Aug. 8, 2007.
Schuster et al., "Signaling of human ciliary neurotrophic factor (CNTF) revisited. The interleukin-6 receptor can serve as an alpha-receptor for CTNF," J Biol Chem., Mar. 14, 2003, 278(11):9528-35.
Seda et al., "B-cell receptor signalling and its crosstalk with other pathways in normal and malignant cells," Eur J Haematol., Aug. 1, 2014. doi: 10.1111/ejh.12427.
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., Mar. 2, 2001, 276(9):6591-604. Epub Nov. 28, 2000.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," J Biol Chem., Jan. 31, 2003, 278(5):3466-73. Epub Nov. 8, 2002.
Sims et al., "HMGB1 and RAGE in inflammation and cancer," Annu Rev Immunol., 2010, 28:367-88.
Singer et al., "Genes & Genomes," Moscow, "Mir," 1998, 1:63-64.
Smith et al., "FcgammaRIIB in autoimmunity and infection: evolutionary and therapeutic implications," Nat Rev Immunol., May 2010, 10(5):328-43.
Sondermann et al., "The 3.2-A crystal structure of the human IgG1 Fc fragment-Fc gammaRIII complex," Nature, Jul. 20, 2000, 406(6793):267-73.
Strohl WR, Optimization of Fc-mediated effector functions of monoclonal antibodies, Curr Opin Biotechnol., Dec. 2009, 20(6):685-91. doi: 10.1016/j.copbio.2009.10.011. Epub Nov. 4, 2009.
Su et al., Expression profile of FcgammaRIIb on leukocytes and its dysregulation in systemic lupus erythematosus, J Immunol., 2007, 178(5):3272-80.
Suzuki et al., "Importance of neonatal FcR in regulating the serum half-life of therapeutic proteins containing the Fc domain of human IgG1: a comparative study of the affinity of monoclonal antibodies and Fc-fusion proteins to human neonatal FcR," J. Immunol., 2010, 184(4):1968-76.
Takeuchi et al., "The Japanese experience with biologic therapies for rheumatoid arthritis," Nat Rev Rheumatol., Nov. 2010, 6(11):644-52. doi: 10.1038/nrrheum.2010.154. Epub Sep. 28, 2010.
Tanabe et al., "Characterization of the Monoclonal Antibodies Against Human Protein C Specific for Calcium Ion-induced Conformers," Japanese Journal of Thrombosis and Hemostasis, 1992, 3(1):29-35.
Trinh et al., "Ipilimumab in the treatment of melanoma," Expert Opin Biol Ther., Jun. 2012, 12(6):773-82. doi: 10.1517/14712598.2012.675325. Epub Apr. 14, 2012.
Vaccaro et al., "Engineering the Fc region of immunoglobulin G to modulate in vivo antibody levels," Nat Biotechnol., Oct. 2005, 23(10):1283-8. Epub Sep. 25, 2005.
Veri et al., "Monoclonal antibodies capable of discriminating the human inhibitory Fcgamma-receptor IIB (CD32B) from the activating Fcgamma-receptor IIA (CD32A): biochemical, biological and functional characterization," Immunology, Jul. 2007, 121(3):392-404. Epub Mar. 26, 2007.
Veri et al., "Therapeutic control of B cell activation via recruitment of Fcgamma receptor IIb (CD32B) inhibitory function with a novel bispecific antibody scaffold," Arthritis Rheum., Jul. 2010, 62(7):1933-43. doi: 10.1002/art.27477.
Wang et al., "HMG-1 as a late mediator of endotoxin lethality in mice," Science, 1999, 285(5425):248-51.
Wang et al., "Monoclonal Antibodies with Identical Fc Sequences Can Bind to FcRn Differentially with Pharmacokinetic Consequences," Drug Metabolism and Disposition, Sep. 2011, 39(9):1469-77.
Ward et al., "A calcium-binding monoclonal antibody that recognizes a non-calcium-binding epitope in the short consensus repeat units (SCRs) of complement C1r," Mol Immunol., Jan. 1992, 29(1):83-93.

(56) References Cited

OTHER PUBLICATIONS

Warmerdam et al., Molecular basis for a polymorphism of human Fc gamma receptor II (CD32), J Exp Med., 1990, 172(1):19-25.

Weiner et al., "Monoclonal antibodies: versatile platforms for cancer immunotherapy," Nat Rev Immunol., May 2010, 10(5):317-27. doi: 10.1038/nri2744.

Wenink et al., "The inhibitory Fc gamma IIb receptor dampens TLR4-mediated immune responses and is selectively up-regulated on dendritic cells from rheumatoid arthritis patients with quiescent disease," J Immunol., Oct. 1, 2009, 183(7):4509-20. doi: 10.4049/jimmunol.0900153. Epub Sep. 4, 2009.

Wernersson et al., "IgG-mediated enhancement of antibody responses is low in Fc receptor gamma chain-deficient mice and increased in Fc gamma RII-deficient mice," J Immunol., 1999, 163(2):618-22.

Wilson et al., "An Fcγ receptor-dependent mechanism drives antibody-mediated target-receptor signaling in cancer cells," Cancer Cell, Jan. 18, 2011, 19(1):101-13. doi: 10.1016/j.ccr.2010.11.012.

Wu et al., "Development of motavizumab, an ultra-potent antibody for the prevention of respiratory syncytial virus infection in the upper and lower respiratory tract," J Mol Biol., 2007, 368(3):652-65.

Wu et al., "Humanization of a murine monoclonal antibody by simultaneous optimization of framework and CDR residues," J Mol Biol., Nov. 19, 1999, 294(1):151-62.

Xiao et al., "Pharmacokinetics of anti-hepcidin monoclonal antibody Ab 12B9m and hepcidin in cynomolgus monkeys," AAPS J., Dec. 2010, 12(4):646-57. doi: 10.1208/s12248-010-9222-0. Epub Aug. 25, 2010.

Xu et al., "FcγRs modulate cytotoxicity of anti-Fas antibodies: implications for agonistic antibody-based therapeutics," J Immunol., 2003, 171(2):562-8.

Yeung et al., "Engineering human IgG1 affinity to human neonatal Fc receptor: impact of affinity improvement on pharmacokinetics in primates," J. Immunol., Jun. 15, 2009, 182(12):7663-71. doi: 10.4049/jimmunol.0804182.

Yuasa et al., "Deletion of Fcγ receptor IIB renders H-2(b) mice susceptible to collagen-induced arthritis," J Exp Med., 1999, 189(1):187-94.

Zalevsky et al., "Enhanced antibody half-life improves in vivo activity," Nat. Biotechnol., 2010, 28(2):157-9.

Zalevsky et al., "The impact of Fc engineering on an anti-CD19 antibody: increased Fcgamma receptor affinity enhances B-cell clearing in nonhuman primates," Blood, 2009, 113(16):3735-43. Epub Dec. 24, 2008.

Zhang et al., "Effective therapy for a murine model of human anaplastic large-cell lymphoma with the anti-CD30 monoclonal antibody, HeFi-1,does not require activating Fc receptors," Blood, Jul. 15, 2006, 108(2):705-10. Epub Mar. 21, 2006.

Zhang et al., "Immune complex/Ig negatively regulate TLR4-triggered inflammatory response in macrophages through Fc gamma RIIb-dependent PGE2 production," J Immunol., Jan. 1, 2009, 182(1):554-62.

Zheng et al., "Translational pharmacokinetics and pharmacodynamics of an FcRn-variant anti-CD4 monoclonal antibody from preclinical model to phase I study," Clin Pharmacol Ther., Feb. 2011, 89(2):283-90. doi: 10.1038/clpt.2010.311. Epub Dec. 29, 2010.

International Preliminary Report on Patentability for App. Ser. No. PCT/JP2012/081185, dated Jun. 3, 2014, 9 pages.

International Search Report for App. Ser. No. PCT/JP2012/081185, dated Feb. 26, 2013, 9 pages.

International Search Report for App. Ser. No. PCT/JP2012/006218, dated Mar. 26, 2013, 11 pages.

International Search Report for App. Ser. No. PCT/JP2013/054461, dated May 7, 2013, 7 pages.

International Preliminary Report on Patentability for App. Ser. No. PCT/JP2013/054461, dated Aug. 26, 2014, 6 pages.

International Search Report for App. Ser. No. PCT/JP2012/075092, dated Dec. 25, 2012, 4 pages.

International Preliminary Report on Patentability for App. Ser. No. PCT/JP2012/075092, dated Apr. 1, 2014, 10 pages.

International Search Report for App. Ser. No. PCT/JP2013/072507, dated Oct. 29, 2013, 4 pages.

International Preliminary Report on Patentability for App. Ser. No. PCT/JP2013/072507, dated Feb. 24, 2015, 6 pages.

USPTO Restriction Requirement in U.S. Appl. No. 14/347,034, dated Dec. 18, 2014, 9 pages.

Fish & Richardson P.C., Reply to Restriction Requirement dated Dec. 18, 2014 in U.S. App. U.S. Appl. No. 14/347,034, filed Mar. 18, 2015, 2 pages.

USPTO Non-Final Office Action in U.S. App. U.S. Appl. No. 14/347,034, dated Apr. 16, 2015, 9 pages.

USPTO Interview Summary in U.S. App. U.S. Appl. No. 14/347,034, dated Aug. 17, 2015, 3 pages.

Fish & Richardson P.C., Reply to Non-Final Office Action dated Apr. 16, 2015 in U.S. Appl. No. 14/347,034, filed Sep. 16, 2015, 28 pages.

USPTO Final Office Action in U.S. Appl. No. 14/347,034, dated Oct. 16, 2015, 5 pages.

Fish & Richardson P.C., Reply to Final Office Action dated Oct. 16, 2015 in U.S. Appl. No. 14/347,034, filed Jan. 13, 2016, 28 pages.

USPTO Notice of Allowance in U.S. Appl. No. 14/347,034, dated Feb. 17, 2016, 6 pages.

USPTO Notice of Allowance in U.S. Appl. No. 14/347,034, dated Jun. 3, 2016, 5 pages.

International Search Report for App. Ser. No. PCT/JP2014/059706, dated Jul. 15, 2014, 4 pages.

International Preliminary Report on Patentability for App. Ser. No. PCT/JP2014/059706, dated Oct. 6, 2015, 10 pages.

USPTO Restriction Requirement in U.S. Appl. No. 14/347,321, dated Dec. 17, 2015, 10 pages.

Fish & Richardson P.C., Reply to Restriction Requirement dated Dec. 17, 2015 in U.S. App. U.S. Appl. No. 14/347,321, filed Feb. 16, 2016, 3 pages.

USPTO Office Action in U.S. Appl. No. 14/347,321, dated May 2, 2016, 35 pages.

Fish & Richardson P.C., Reply to Office Action dated May 2, 2016 in U.S. Appl. No. 14/347,321, filed Nov. 2, 2016, 35 pages.

USPTO Final Office Action in U.S. Appl. No. 14/347,321 dated Jan. 9, 2017, 60 pages.

USPTO Restriction Requirement in U.S. Appl. No. 14/347,187, dated Jan. 26, 2017, 9 pages.

Fish & Richardson P.C., Reply to Restriction Requirement dated Jan. 26, 2017 in U.S. Appl. No. 14/347,187, filed Mar. 27, 2017, 2 pages.

U.S. Appl. No. 14/361,013, Igawa et al., filed May 26, 2014 (abandoned).

U.S. Appl. No. 15/952,945, Igawa et al., filed Apr. 13, 2018.

U.S. Appl. No. 61/313,102, Pons, filed Mar. 11, 2010.

Akbarzadeh-Sharbaf et al., "In silico design, construction and cloning of Trastuzumab humanized monoclonal antibody: A possible biosimilar for Herceptin," Adv Biomed Res, Feb. 23, 2012, 1:21 . doi: 10. 4103/ 2277-9175. 98122. Epub Jul. 6, 2012.

Alignment of constant region sequences from WO 2009/125825 (document submitted in EP opposition and posted by EPO on Feb. 2, 2018); 1 page.

Alignment of the amino acid sequences of the Fc regions of antibodies exemplified in EP 2275443 (document submitted in EP opposition and posted by EPO on Feb. 2, 2018); 1 page.

Alignment of variable heavy and light chain amino acid sequences from WO 2009/125825 (document submitted in EP opposition and posted by EPO on Feb. 2, 2018); 2 pages.

Antibodies from bioinf.org.uk: Dr. Andrew C.R. Martin's Group, downloaded Jul. 11, 2018, 9 pages.

Atherton et al., "Acid-base balance: maintenance of plasma pH," Anaesthesia & Intensive Care Medicine, 2009, 10(11):557-61 (Abstract).

Brown et al., "Tolerance to Single, but Not Multiple, Amino Acid Replacements in Antibody VHCDR2," J Immunol, May 1, 1996, 156(9):3285-91.

Claims as granted for Publication No. EP 2275443, dated Jan. 19, 2011 (document submitted in EP opposition); 6 pages.

Datta-Mannan et al., "Humanized IgG1 Variants with Differential Binding Properties to the Neonatal Fc Receptor: Relationship to

(56) References Cited

OTHER PUBLICATIONS

Pharmacokinetics in Mice and Primates," Drug Metab Dispos, Jan. 2007, 35(1):86-94. Epub Oct. 18, 2006.

Davydov, "Omalizuman (Xolair) for Treatment of Asthma," Am Fam Physician, Jan. 15, 2005, 71(2):341-2.

Declaration of Nimish Gera, Ph.D., CV and Exhibits, Sep. 1, 2016 (submitted in the matter of EP 2275443, Opposition thereto by Alexion Pharmaceuticals, Inc.); 24 pages.

De Felice et al., "Formation of amyloid aggregates from human lysozyme and its disease-associated variants using hydrostatic pressure," FASEB J, Jul. 2004, 18(10):1099-101. (doi:10.1096/fj.03-1072fje; PMID 15155566).

EMA product information: Annexes to file of the tocilizumab preparation RoActemra (WC500054890).

Experimental data characterizing the binding of rituximab to its antigen CD20 and to human FcRn (document submitted in EP opposition and posted by EPO on Feb. 5, 2018); 6 pages.

Experimental information regarding off-rate of Xolair Fab for binding to human IgE at pH7.4 and pH5.5 (document submitted in EP opposition and posted by EPO on Feb. 2, 2018); 3 pages.

Expert Declaration by Dr. Madhusudan Natarajan, submitted in EP opposition regarding EP 2552955 and posted by EPO on Feb. 5, 2018; 4 pages.

Fillipovic et al., Biochemical basis of human life activity, VLADOS, 2005:38-43 (with English translation).

Goebl et al., "Neonatal Fc Receptor Mediates Internalization of Fc Transfected Human Endothelial Cells," Molecular Biology of the Cell, Dec. 2008, 19(12):5490-5505.

Gurbaxani et al., "Analysis of a family of antibodies with different half-lives in mice fails to find a correlation between affinity for FcRn and serum half-life," Mol Immunol, Mar. 2006, 43(9):1462-73. Epub Sep. 1, 2005.

Irani et al., "Molecular properties of human IgG subclasses and their implications for designing therapeutic monoclonal antibodies against infectious diseases," Mol Immunol, Oct. 2015, 67(2 Pt A): 171-82. doi : 10. 1016/ j. molimm. 2015. 03. 255. Epub Apr. 18, 2015.

Jaeger, Clinical Immunology and Allergology, 2nd edition, M.: Medicina, 1990, 2:484-5 (with English translation).

King, Applications and Engineering of Monoclonal Antibodies, 1998, pp. 68-71.

MacCallum et al., "Antibody-antigen Interactions: Contact Analysis and Binding Site Topography," J Mol Biol, 1996, 262:732-745.

Maxfield et al., "Endocytic Recycling," Nat Rev Mol Cell Biol, Feb. 2004, 5(2):121-32.

Maxwell et al., "Crystal structure of the human leukocyte Fc Receptor, FcγRIIa," Nat Struct Biol, May 1999, 6(5):437-42.

Molina et al., "Trastuzumab (Herceptin), a Humanized Anti-HER2 Receptor Monoclonal Antibody, Inhibits Basal and Activated HER2 Ectodomain Cleavage in Breast Cancer Cells," Cancer Res, Jun. 15, 2001, 61(12):4744-9.

O'Donovan et al., "EGFR and HER-2 Antagonists in Breast Cancer," Anticancer Res, May-Jun. 2007, 27 (3A):1285-94.

Official Action dated Oct. 13, 2016, issued for EP Application No. 11714860.1 and submitted as evidence during EP opposition; 3 pages.

Popov et al., "The Stoichiometry and Affinity of the Interaction of Murine Fc Fragments with the MHC Class I-Related Receptor, FcRn," Mol Immunol, Apr. 1996, 33(6):521-30.

Presta, "Molecular engineering and design of therapeutic antibodies," Curr Opin Immunol, Aug. 2008, 20(4):460-70. doi : 10.1016/j.coi.2008. 06.012.

PRESTA at el., "Humanization of an Anti-Vascular Endothelial Growth Factor Monoclonal Antibody for the Therapy of Solid Tumors and Other Disorders," Cancer Res, Oct. 15, 1997, 57(20):4593-9.

Product labelling information for Rituxan (Rituximab), dated Nov. 1997.

Raghavan et al., "Analysis of the pH Dependence of the Neonatal Fc Receptor/Immunoglobulin G Interaction Using Antibody and Receptor Variants," Biochemistry, Nov. 14, 1995, 34(45):14649-57.

Roitt et al., Immunology, Moscow: Mir, 2000, pp. 373-374 (with English translation).

Sondermann et al., "Molecular Basis for Immune Complex Recognition: A Comparison of Fc-Receptor Structures," J Mol Biol, Jun. 8, 2001, 309(3):737-49.

Sondermann et al., "Crystal structure of the soluble form of the human Fcγ-receptor IIb: a new member of the immunoglobulin superfamily at 1.7 A resolution," EMBO J, Mar. 1, 1999, 18(5):1095-103.

Stepanov, "Chapter 4, Primary Structure of Protein, 4.1 Primary structure as a level of protein organization," Molecular biology, Structure and functions of proteins, M.:NAUKA, 2005, pp. 61-62 (with English abstract).

Supplementary data provided by opponent for EP Application No. 11714860.1 (document submitted in EP opposition and posted by EPO on Feb. 20, 2018); 3 pages.

Tanzi et al., "Twenty years of the Alzheimer's disease amyloid hypothesis: a genetic perspective," Cell, Feb. 2005, 120(4):545-55. (doi:10.1016/j.cell.2005.02.008; PMID 15734686).

Vaccaro et al., "Divergent activities of an engineered antibody in murine and human systems have implications for therapeutic antibodies," Proc Natl Acad Sci USA, Dec. 5, 2006, 103(49):18709-14. Epub Nov. 20, 2006.

Vajdos et al., "Comprehensive Functional Maps of the Antigen binding Site of an Anti-ErbB2 Antibody Obtained with Shotgun Scanning Mutagenesis," J Mol Biol, Jul. 5, 2002, 320(2):415-28.

Vidarsson et al., "IgG subclasses and allotypes: from structure to effector functions," Front Immunol, Oct. 20, 2014, 5:520. doi: 10.3389/fimmu.2014.00520. eCollection 2014.

Waelbroeck et al., "The pH Dependence of Insulin Binding," J Biol Chem, Jul. 25, 1982, 257(14) :8284-91.

Ward et al., "Evidence to support the cellular mechanism involved in serum IgG homeostasis in humans," Int Immunol, Feb. 2003, 15(2):187-95.

Welch et al., "Adalimumab (Humira) for the Treatment of Rheumatoid Arthritis," Am Fam Physician, Dec. 15, 2008, 78 (12):1406-1408.

Xolair (omalizumab) Prescribing Information, https://www.gene.com/download/pdf/xolair_prescribing.pdf, Jul. 2016, 27 pages.

Yang et al., "Dataset of the binding kinetic rate constants of anti-PCSK9 antibodies obtained using the Biacore T100, Protean XPR36, Octet RED384, and IBIS MX96 biosensor platforms," Data Brief, Jul. 27, 2016, 8:1173-83. doi : 10. 1016/ J. dib. 2016.07.044. eCollection Sep. 2016.

Yang et al., "Maximizing in vivo target clearance by design of pH-dependent target binding antibodies with altered affinity to FcRn," mAbs, Oct. 2017, 9(7):1105-1117. doi : 10. 1080/ 19420862. 2017. 1359455. Epub Aug. 8, 2017.

Yarilin, Fundamentals of Immunology, M: Medicina, 1999, pp. 169-172, 354-8 (with English translation).

Yarilin, Fundamentals of Immunology, M: Medicina, 1999, pp. 175, 182 (with English translation).

Yarilin, Fundamentals of Immunology, M: Medicina, 1999, pp. 172-4 (with English translation).

Yeung et al., "A Therapeutic Anti-VEGF Antibody with Increased Potency Independent of Pharmacokinetic Half-life," Cancer Res, Apr. 15, 2010, 70(8):3269-77. doi : 10. 1158/ 0008-5472. CAN-09-4580. Epub Mar. 30, 2010.

USPTO Restriction Requirement in U.S. Appl. No. 14/361,013, dated Mar. 16, 2016, 15 pages.

USPTO Non-Final Office Action in U.S. Appl. No. 14/361,013, dated Oct. 28, 2016, 33 pages.

USPTO Final Office Action in U.S. Appl. No. 14/361,013, dated Jul. 24, 2017, 43 pages.

USPTO Notice of Allowance in U.S. Appl. No. 14/347,034, dated Sep. 22, 2016, 9 pages.

USPTO Non-Final Office Action in U.S. Appl. No. 14/347,034, dated May 25, 2017, 16 pages.

USPTO Non-Final Office Action in U.S. Appl. No. 14/347,034, dated Jan. 8, 2018, 15 pages.

USPTO Non-Final Office Action in U.S. Appl. No. 14/347,321, dated Nov. 13, 2017, 64 pages.

(56) References Cited

OTHER PUBLICATIONS

USPTO Non-Final Office Action in U.S. Appl. No. 14/347,187, dated Jun. 14, 2017, 23 pages.
USPTO Final Office Action in U.S. Appl. No. 14/347,187, dated Jan. 19, 2018, 24 pages.
USPTO Applicant-Initiated Interview Summary in U.S. Appl. No. 14/347,187, dated Jul. 10, 2018, 3 pages.
USPTO Non-Final Office Action in U.S. Appl. No. 14/347,187, dated Sep. 4, 2018, 22 pages.
USPTO Non-Final Office Action in U.S. Appl. No. 15/230,904 dated May 25, 2017, 43 pages.
USPTO Non-Final Office Action for U.S. Appl. No. 15/230,904, dated Jan. 8, 2018, 16 pages.
Diamond et al., "Somatic mutation of the T15 heavy chain gives rise to an antibody with autoantibody specificity," Proc Natl Acad Sci USA, Sep. 1984, 81(18):5841-4.
Hasemann et al., "Mutational Analysis of Arsonate Binding by a $CRI_{A+}$Antibody," J Biol Chem, Apr. 25, 1991, 266(12):7626-32.
Ohno et al., "Antigen-binding specificities of antibodies are primarily determined by seven residues of $V_H$," Proc Natl Acad Sci USA, May 1985, 82(9):2945-9.
Roitt et al., Immunology, M., Mir, 2000, p. 9 (in Russian, with what is believed to be a published English equivalent of that page).
Roitt et al., Immunology, M., Mir, 2000, p. 110 (with English translation).
Ellison et al., "Linkage and sequence homology of two human immunoglobulin gamma heavy chain constant region genes," Proc Natl Acad Sci USA, Mar. 1982, 79(6):1984-1988.
Huck et al., "Sequence of a human immunoglobulin gamma 3 heavy chain constant region gene: comparison with the other human C gamma genes," Nucleic Acids Res, Feb. 25, 1986, 14(4):1779-1789.
NCBI database: GenBank Accession No. AAC82527.1, Jun. 10, 2016, "immunoglobulin gamma-1 heavy chain constant region, partial [*Homo sapiens*]" (https://www.ncbi.nlm.nih.gov/protein/AAC82527.1).
NCBI database: GenBank Accession No. AAB59393.1, Aug. 1, 2016, "immunoglobulin gamma-2 heavy chain, partial [*Homo sapiens*]" (https://www.ncbi.nlm.nih.gov/protein/AAB59393.1).
NCBI database: GenBank Accession No. AAB59394.1, Aug. 1, 2016, "immunoglobulin gamma-4 heavy chain, partial [*Homo sapiens*]" (https://www.ncbi.nlm.nih.gov/protein/AAB59394.1).
NCBI database: GenBank Accession No. CAA27268.1, Jul. 25, 2016, "C gamma 3, partial [*Homo sapiens*]" (https://www.ncbi.nlm.nih.gov/protein/CAA27268.1).
Takahashi et al., "Structure of human immunoglobulin gamma genes: implications for evolution of a gene family," Cell, Jun. 1982, 29(2):671-679.
Decision of the Opposition Division dated Dec. 19, 2019 in EP 2 552 955, 18 pages (document submitted by Patentee (Chugai Seiyaku Kabushiki Kaisha) in the grounds of appeal on Apr. 28, 2020 in EP 2 552 955).
English translation of JP 2010-266121 (priority document for EP 2 647 706), submitted to European Patent Office dated May 25, 2020, by Applicant during the examination procedure for EP 3 517 550.
English translation of JP 2011-217886 (priority document for EP 2 647 706), submitted to European Patent Office dated May 25, 2020, by Applicant during the examination procedure for EP 3 517 550.
Safdari et al., "Antibody humanization methods—a review and update," Biotechnol Genet Eng Rev, 2013, 29:175-186.
Bonvin et al., "De novo isolation of antibodies with pH-dependent binding properties," mAbs, Mar.-Apr. 2015, 7(2): 294-302.
Chaparro-Riggers et al., "Increasing serum half-life and extending cholesterol lowering in vivo by engineering antibody with pH-sensitive binding to PCSK9," J Biol Chem, Mar. 30, 2012, 287(14):11090-11097. doi: 10.1074/jbc.M111.319764. Epub Jan. 31, 2012.
Schroter et al., "A generic approach to engineer antibody pH-switches using combinatorial histidine scanning libraries and yeast display," mAbs, Jan.-Feb. 2015, 7(1):138-151. doi: 10.4161/19420862.2014.985993.

Yarilin, Fundamentals of Immunology, M.: Medicina, 1999, pp. 181-184 (with English translation).
U.S. Appl. No. 14/347,034, Igawa et al., filed Mar. 26, 2014 (abandoned).
Abe et al., "Effect of $\beta^2$-microglobulin adsorption column on dialysis-related amyloidosis," Kidney Int, Oct. 2003, 64(4):1522-1528. doi: 10.1046/j.1523-1755.2003.00235.x.
Annex 1 accompanying Response to Statement of Grounds of Appeal of Opponent 2 (Alexion Pharmaceuticals, Inc.), dated Sep. 16, 2020 in opposition against EP 2 552 955, 29 pages.
Annotated amino acid sequence of the variable heavy (VH) and variable light (VL) domains of the monoclonal antibodies bevacizumab/Avastin, adalimumab/Humira, omalizumab/Xolair, and rituximab/Mabthera (submitted to the EPO on Sep. 6, 2019 by Opponent 1 in opposition against EP 11714860.1).
Bayry et al., "Immuno affinity purification of foot and mouth disease virus type specific antibodies using recombinant protein adsorbed to polystyrene wells," J Virol Methods, Aug. 1999, 81(1-2):21-30.
Biacore—Sensor Surface Handbook, GE Healthcare, 2007, pp. 1-100.
Edwards et al., "The Remarkable Flexibility of the Human Antibody Repertoire; Isolation of Over One Thousand Different Antibodies to a Single Protein, BLyS," J Mol Biol, Nov. 14, 2003, 334(1):103-118.
Ejima et al., "Effective elution of antibodies by arginine and arginine derivatives in affinity column chromatography," Anal Biochem, Oct. 15, 2005, 345(2):250-257.
EUTM register extract—Biacore, 4 pages (document downloaded on Aug. 26, 2020, submitted in opposition against EP 2 552 955, and posted by EPO on Sep. 15, 2020).
Evidence for the publication date of Zalevsky et al., Nat Biotechnol, Feb. 2010, 28(2):157-159 (submitted to the EPO on Sep. 6, 2019 by Opponent 1 in opposition against EP 11714860.1).
Expert Declaration of J. Boucneau, dated Sep. 6, 2019 (submitted to the EPO on Sep. 6, 2019 by Opponent 1 in opposition against EP 11714860.1).
Goel et al., "Plasticity within the Antigen-Combining Site May Manifest as Molecular Mimicry in the Humoral Immune Response," J Immunol, Dec. 15, 2004, 173(12):7358-7367.
Guidance on the use of International Nonproprietary Names (INNs) for Pharmaceutical Substances, World Health Organisation, 2017, 54 pages (document submitted in opposition against EP 2 552 955 and posted by EPO on Sep. 16, 2020).
Hughes et al. "Report of the Use of Drug Sensitivity Tests in General Practice," Med J Aust, Jan. 18, 1964, 1:72-74.
Kabat et al., "Sequences of Proteins of Immunological Interest," 1991, National Institute of Health Publication No. 91-3242, pp. 103, 310.
Kanyavuz et al., "Breaking the law: unconventional strategies for antibody diversification," Nat Rev Immunol, Jun. 2019, 19(6):355-368. doi: 10.1038/s41577-019-0126-7.
King, Applications and Engineering of Monoclonal Antibodies, Taylor & Francis, ISBN 0-203-21169-3, 2005, pp. 1-236.
Kipriyanov et al., "Generation of Recombinant Antibodies," Mol Biotechnol, Sep. 1999, 12(2):173-201.
Kontermann et al., Chapter 4 "Mouse Immune Libraries for the Generation of ScFv Fragments Directed Against Human Cell Surface Antigens," 1:47-62 and Chapter 27 Engineering of the Fc Region for Improved PK (FcRn Interaction), Antibody Engineering, 2010, 1:415-427.
Liberti et al., "Antigenicity of Polypeptides (Poly-α-amino Acids). Physicochemical Studies of a Calcium-Dependent Antigen-Antibody Reaction," Biochemistry, Apr. 27, 1971, 10(9):1632-1639.
Lloyd et al., "Modelling the human immune response: performance of a $10^{11}$ human antibody repertoire against a broad panel of therapeutically relevant antigens," Protein Eng Des Sel, Mar. 2009, 22(3):159-168. doi: 10.1093/protein/gzn058. Epub Oct. 29, 2008.
Mellman, "The Importance of Being Acid: The Role of Acidification in Intracellular Membrane Traffic," J Exp Biol, Nov. 1992, 172:39-45.
Notice of Opposition by Opponent 1 (Ablynx N.V.), dated Feb. 2, 2018, submitted in opposition against EP 2 552 955, 50 pages.

(56) References Cited

OTHER PUBLICATIONS

Statement of Facts and Arguments in Support of Opposition by Opponent 2 (Alexion Pharmaceuticals, Inc.), dated Feb. 2, 2018, submitted in opposition against EP 2 552 955, 39 pages.
Opposition Statement of Opponent 5 (Shire Human Genetic Therapies, Inc.), dated Feb. 5, 2018, submitted in opposition against EP 2 552 955, 70 pages.
Poosarla et al., "Computational de novo Design of Antibodies binding to a Peptide with High Affinity," Biotechn Bioeng, Jun. 2017, 114(6):1331-1342.
Proprietor's (Chugai Seiyaku Kabushiki Kaisha) Submission, dated Sep. 5, 2016, in the opposition of EP11714860.1, 6 pages.
Proprietor's (Chugai Seiyaku Kabushiki Kaisha) Submission, dated Sep. 19, 2016, in the opposition of EP11714860.1, 3 pages.
Proprietor's (Chugai Seiyaku Kabushiki Kaisha) Submission, dated Feb. 20, 2017, in the opposition of EP 2 275 443, 35 pages.
Rich et al., "A global benchmark study using affinity-based biosensors" Anal Biochem, Mar. 15, 2009, 386(2):194-216. doi: 10.1016/j.ab.2008.11.021. Epub Nov. 27, 2008.
Roitt et al., "Antibodies and Their Receptors," Immunology, M., Mir, 2000, p. 110-111 (with what are believed to be the corresponding pages from an English version of Immunology).
Rojas et al., "Formation, Distribution, and Elimination of Infliximab and Anti-Infliximab Immune Complexes in Cynomolgus Monkeys," J Pharmacol Exp Ther, May 2005, 313(2):578-585. Epub Jan. 12, 2005.
Schuster et al., "The human interleukin-6 (IL-6) receptor exists as a preformed dimer in the plasma membrane," FEBS Lett, Mar. 13, 2003, 538(1-3):113-116.
Sebba et al., "Tocilizumab: The first interleukin-6-receptor inhibitor," Am J Health Syst Pharm, Aug. 1, 2008, 65(15):1413-1418. doi: 10.2146/ajhp070449.
Siberil et al., "Molecular aspects of human FcγR interactions with IgG: Functional and therapeutic consequences," Immunol Lett, Aug. 15, 2006, 106(2):111-118. Epub Jun. 12, 2006.
Sigma product information for ACES buffer (submitted to the EPO on Sep. 6, 2019 by Opponent 1 in opposition against EP 11714860.1).
Response by Opponent 1 (Ablynx N.V.), dated Sep. 6, 2019, submitted in opposition against EP 2 552 955, 57 pages.
Final Written Submissions of Opponent 2 (Alexion Pharmaceuticals, Inc.), dated Sep. 6, 2019, submitted in opposition against EP 2 552 955, 26 pages.
Reply from Opponent 5 (Shire Human Genetic Therapies, Inc.), dated Sep. 6, 2019, submitted in opposition against EP 2 552 955, 15 pages.
Table submitted to the EPO on Sep. 6, 2019 by Opponent 1 in opposition against EP 11714860.1.
Takkinen et al., Chapter 38 "Affinity and Specificity Maturation by CDR Walking," Antibody Engineering, Springer Lab Manuals, 2001, pp. 540-545.
Torres et al., "The immunoglobulin constant region contributes to affinity and specificity," Trend Immunol, 2008, 29(2):91-97.
Yang et al., "Comparison of biosensor platforms in the evaluation of high affinity antibody-antigen binding kinetics," Anal Biochem, Sep. 1, 2016, 508:78-96. doi: 10.1016/j.ab.2016.06.024. Epub Jun. 27, 2016.
USPTO Non-Final Office Action in U.S. Appl. No. 13/595,139, dated Nov. 14, 2012, 10 pages.
Fish & Richardson P.C., Amendment in Reply to Office Action dated Nov. 14, 2012, in U.S. Appl. No. 13/595,139, filed May 14, 2013, 19 pages.
USPTO Non-Final Office Action in U.S. Appl. No. 13/595,139, dated Mar. 13, 2015, 12 pages.
Fish & Richardson P.C., Amendment & Reply to Office Action dated Mar. 13, 2015, in U.S. Appl. No. 13/595,139, filed Jun. 11, 2015, 19 pages.
USPTO Non-Final Office Action in U.S. Appl. No. 13/595,139, dated Aug. 3, 2015, 13 pages.
Fish & Richardson P.C., Reply to Office Action dated Aug. 3, 2015, in U.S. Appl. No. 13/595,139, filed Dec. 2, 2015, 28 pages.
USPTO Final Office Action in U.S. Appl. No. 13/595,139, dated Feb. 12, 2016, 12 pages.
Fish & Richardson P.C., Reply to Office Action dated Feb. 12, 2016, in U.S. Appl. No. 13/595,139, filed Jul. 11, 2016, 4 pages.
USPTO Non-Final Office Action in U.S. Appl. No. 13/595,139, dated Nov. 23, 2016, 11 pages.
USPTO Final Office Action in U.S. Appl. No. 13/595,139, dated May 30, 2017, 16 pages.
USPTO Final Office Action in U.S. Appl. No. 13/595,139, dated Aug. 1, 2013, 8 pages.
USPTO Non-Final Office Action in U.S. Appl. No. 13/595,139, dated Sep. 26, 2018, 32 pages.
USPTO Non-Final Office Action in U.S. Appl. No. 15/952,945, dated Sep. 20, 2018, 32 pages.
USPTO Final Office Action in U.S. Appl. No. 15/952,945, dated Jun. 3, 2019, 18 pages.
King, "Preparation, structure and function of monoclonal antibodies," Applications and Engineering of Monoclonal Antibodies, CRC Press, 1998, pp. 2, 13-4.
U.S. Pat. No. 10,618,965, Igawa et al., issued Apr. 14, 2020.
U.S. Appl. No. 16/806,027, Igawa et al., filed Mar. 2, 2020.
U.S. Appl. No. 14/347,034, Igawa et al., filed Mar. 25, 2014 (abandoned).
U.S. Appl. No. 15/230,904, Igawa et al., filed Aug. 8, 2016 (abandoned).
U.S. Appl. No. 16/028,140, Igawa et al., filed Jul. 5, 2018.
U.S. Appl. No. 14/347,321, Igawa et al., filed Mar. 26, 2014 (abandoned).
U.S. Appl. No. 15/977,757, Igawa et al., filed May 11, 2018 (abandoned).
U.S. Appl. No. 14/361,013, Igawa et al., filed May 28, 2014 (abandoned).
U.S. Pat. No. 10,253,100, Igawa et al., issued Apr. 9, 2019.
U.S. Appl. No. 16/264,735, Igawa et al., filed Feb. 1, 2019.
U.S. Appl. No. 14/379,825, Igawa et al., filed Aug. 20, 2014.
U.S. Pat. No. 10,919,953, Katada et al., issued Feb. 16, 2021.
U.S. Appl. No. 17/028,210, Igawa et al., filed Sep. 22, 2020.
U.S. Pat. No. 11,267,868, Mimoto et al., issued Mar. 8, 2022.
U.S. Appl. No. 17/671,185, Igawa et al., filed Feb. 14, 2022.
U.S. Appl. No. 15/210,353, Igawa et al., filed Jul. 14, 2016.
U.S. Appl. No. 15/210,360, Igawa et al., filed Jul. 14, 2016.
U.S. Appl. No. 13/637,415, Igawa et al., filed Feb. 4, 2013.
U.S. Appl. No. 15/050,145, Igawa et al., filed Feb. 22, 2016.
U.S. Appl. No. 15/495,026, Igawa et al., filed Apr. 24, 2017.
U.S. Appl. No. 17/561,207, IGA16108897WA et al., filed Dec. 23, 2021.
U.S. Appl. No. 17/671,185, Mimoto et al., filed Feb. 14, 2022.
Application as filed for EP 2 698 431, 375 pages (document cited during EPO opposition proceedings of EP 2 698 431 on Jun. 23, 2021).
Borrok et al., "pH-dependent Binding Engineering Reveals an FcRn Affinity Threshold That Governs IgG Recycling," J Chem, Feb. 13, 2015, 290(7):4282-4290. doi: 10.1074/jbc.M114.603712. Epub Dec. 23, 2014.
Decision of the Opposition Division in EP 2 275 443, dated Apr. 26, 2018, 29 pages (document submitted on Sep. 3, 2021 with the response to office action in EP 3 702 368).
English translation of PCT/JP2011/072550 (corresponding to WO 2012/132067, which was cited in the IDS filed on Sep. 27, 2018), 283 pages. The translation was submitted in the EPO opposition proceedings for EP 2 698 431 dated Jun. 23, 2021.
English translation of PCT/JP2012/054624 (corresponding to WO 2012/115241, which was cited in the IDS filed on Sep. 27, 2018), 110 pages. The document was submitted in the EPO opposition proceedings of EP 2 698 431 on Jun. 23, 2021.
Fillipovic, Biochemical basis of human life, Vlados, 2005, p. 70 (with English translation).
Han et al., "Monoclonal antibodies: interspecies scaling with minimal preclinical information," Ther Deliv, Mar. 2011, 2(3):359-368.

(56) References Cited

OTHER PUBLICATIONS

Jung et al., "Aglycosylated IgG variants expressed in bacteria that selectively bind FcγRI potentiate tumor cell killing by monocyte-dendritic cells," Proc Natl Acad Sci USA, Jan. 12, 2010, 107(2):604-609.

King, Chapter 2 "Antibody Engineering: Design for Specific Applications," Applications and Engineering of Monoclonal Antibodies, 1998, pp. 27-75.

Lescar et al., "Crystal Structure of a Cross-reaction Complex between Fab F9.13.7 and Guinea Fowl Lysozyme," J Biol Chem, Jul. 28, 1995, 270(30):18067-18076.

Palladino et al., "Anti-TNF-α Therapies: The Next Generation," Nat Rev Drug Discov, Sep. 2003, 2(9):736-746.

PCT/JP2011/001888, 203 pages (document cited in EPO opposition proceedings of EP 2 698 431 on Jun. 23, 2021).

Presta et al., "Engineering therapeutic antibodies for improved function," Biochem Soc Trans, Aug. 2002, 30(4):487-490.

Raso et al., "Antibodies Capable of Releasing Diphtheria Toxin in Response to the Low pH Found in Endosomes," J Biol Chem, Oct. 31, 1997, 272(44):27618-27622.

Salfeld et al., "Isotype selection in antibody engineering," Nat Biotechnol, 2007, 25:1369-1372.

Wines et al., "The IgG Fc Contains Distinct Fc Receptor (FcR) Binding Sites: The Leukocyte Receptors FcγRI and FcRγIIa Bind to a Region in the Fc Distinct from That Recognized by Neonatal FcR and Protein A," J Immunol, May 15, 2000, 164(10):5313-5318.

Fish & Richardson P.C., Preliminary Amendment and Response to Restriction Requirement dated Mar. 16, 2016 in U.S. Appl. No. 14/361,013, filed Aug. 1, 2016, 21 pages.

USPTO Amendment and Reply to Action dated Oct. 26, 2016 in U.S. Appl. No. 14/361,013, dated Apr. 26, 2017, 117 pages.

USPTO Non-Final Office Action in U.S. Appl. No. 13/889,512, dated Mar. 26, 2015, 12 pages.

USPTO Non-Final Office Action in U.S. Appl. No. 13/889,512, dated Aug. 4, 2015, 12 pages.

USPTO Final Office Action in U.S. Appl. No. 13/889,512, dated Dec. 17, 2015, 11 pages.

USPTO Non-Final Office Action in U.S. Appl. No. 13/889,512, dated Nov. 28, 2016, 10 pages.

USPTO Final Office Action in U.S. Appl. No. 13/889,512, dated May 31, 2017, 15 pages.

USPTO Non-Final Office Action in U.S. Appl. No. 17/020,497, dated Jan. 29, 2021, 23 pages.

USPTO Non-Final Office Action in U.S. Appl. No. 17/020,497, dated Sep. 21, 2021, 21 pages.

U.S. Appl. No. 17/854,023, Igawa et al., filed Jun. 30, 2022.
U.S. Appl. No. 18/052,258, Igawa et al., filed Nov. 3, 2022.
U.S. Appl. No. 17/561,207, Igawa et al., filed Dec. 23, 2021
Beranger et al., "IMGT Scientific Chart," Jun. 8, 2016, 7 pages.
Perrakis et al., "AI revolutions in biology," EMBO Rep, Nov. 4, 2021, 22(11):e54046, 6 pages.
U.S. Appl. No. 17/298,743, Igawa et al., filed Apr. 11, 2023.
U.S. Appl. No. 18/298,743, Igawa et al., filed Apr. 11, 2023.
Attwood, "The Babel of Bioinformatics," Science, Oct. 20, 2000, 290(5491):471-473. doi: 10.1126/science.290.5491.471. PMID: 11183771.
Skolnick et al., "From genes to protein structure and function: novel applications of computational approaches in the genomic era," Trends Biotechnol, Jan. 2000, 18(1):34-39. doi: 10.1016/s0167-7799(99)01398-0. PMID: 10631780.

\* cited by examiner

SEQUENCE LISTING

```
<160> NUMBER OF SEQ ID NOS: 78

<210> SEQ ID NO 1
<211> LENGTH: 468
<212> TYPE: PRT
<213> ORGANISM: Homo sapiens

<400> SEQUENCE: 1

Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110
```

```
Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
                180                 185                 190

Cys Val Ala Ser Ser Val Gly Ser Lys Phe Ser Lys Thr Gln Thr Phe
                195                 200                 205

Gln Gly Cys Gly Ile Leu Gln Pro Asp Pro Pro Ala Asn Ile Thr Val
        210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
                260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
        290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
                340                 345                 350

Ser Leu Pro Val Gln Asp Ser Ser Val Pro Leu Pro Thr Phe Leu
        355                 360                 365

Val Ala Gly Gly Ser Leu Ala Phe Gly Thr Leu Leu Cys Ile Ala Ile
        370                 375                 380

Val Leu Arg Phe Lys Lys Thr Trp Lys Leu Arg Ala Leu Lys Glu Gly
385                 390                 395                 400

Lys Thr Ser Met His Pro Pro Tyr Ser Leu Gly Gln Leu Val Pro Glu
                405                 410                 415

Arg Pro Arg Pro Thr Pro Val Leu Val Pro Leu Ile Ser Pro Pro Val
                420                 425                 430

Ser Pro Ser Ser Leu Gly Ser Asp Asn Thr Ser Ser His Asn Arg Pro
        435                 440                 445

Asp Ala Arg Asp Pro Arg Ser Pro Tyr Asp Ile Ser Asn Thr Asp Tyr
450                 455                 460

Phe Phe Pro Arg
465

<210> SEQ ID NO 2
<211> LENGTH: 428
<212> TYPE: PRT
<213> ORGANISM: Homo sapiens

<400> SEQUENCE: 2

Ala Ser Thr Gln Ser Pro Ser Val Phe Pro Leu Thr Arg Cys Cys Lys
```

-continued

```
1               5                   10                  15
Asn Ile Pro Ser Asn Ala Thr Ser Val Thr Leu Gly Cys Leu Ala Thr
                20                  25                  30
Gly Tyr Phe Pro Glu Pro Val Met Val Thr Trp Asp Thr Gly Ser Leu
                35                  40                  45
Asn Gly Thr Thr Met Thr Leu Pro Ala Thr Thr Leu Thr Leu Ser Gly
                50                  55                  60
His Tyr Ala Thr Ile Ser Leu Leu Thr Val Ser Gly Ala Trp Ala Lys
65                  70                  75                  80
Gln Met Phe Thr Cys Arg Val Ala His Thr Pro Ser Ser Thr Asp Trp
                    85                  90                  95
Val Asp Asn Lys Thr Phe Ser Val Cys Ser Arg Asp Phe Thr Pro Pro
                100                 105                 110
Thr Val Lys Ile Leu Gln Ser Ser Cys Asp Gly Gly His Phe Pro
                115                 120                 125
Pro Thr Ile Gln Leu Leu Cys Leu Val Ser Gly Tyr Thr Pro Gly Thr
                130                 135                 140
Ile Asn Ile Thr Trp Leu Glu Asp Gly Gln Val Met Asp Val Asp Leu
145                 150                 155                 160
Ser Thr Ala Ser Thr Thr Gln Glu Gly Glu Leu Ala Ser Thr Gln Ser
                    165                 170                 175
Glu Leu Thr Leu Ser Gln Lys His Trp Leu Ser Asp Arg Thr Tyr Thr
                180                 185                 190
Cys Gln Val Thr Tyr Gln Gly His Thr Phe Glu Asp Ser Thr Lys Lys
                195                 200                 205
Cys Ala Asp Ser Asn Pro Arg Gly Val Ser Ala Tyr Leu Ser Arg Pro
210                 215                 220
Ser Pro Phe Asp Leu Phe Ile Arg Lys Ser Pro Thr Ile Thr Cys Leu
225                 230                 235                 240
Val Val Asp Leu Ala Pro Ser Lys Gly Thr Val Asn Leu Thr Trp Ser
                    245                 250                 255
Arg Ala Ser Gly Lys Pro Val Asn His Ser Thr Arg Lys Glu Glu Lys
                    260                 265                 270
Gln Arg Asn Gly Thr Leu Thr Val Thr Ser Thr Leu Pro Val Gly Thr
                275                 280                 285
Arg Asp Trp Ile Glu Gly Glu Thr Tyr Gln Cys Arg Val Thr His Pro
                290                 295                 300
His Leu Pro Arg Ala Leu Met Arg Ser Thr Thr Lys Thr Ser Gly Pro
305                 310                 315                 320
Arg Ala Ala Pro Glu Val Tyr Ala Phe Ala Thr Pro Glu Trp Pro Gly
                    325                 330                 335
Ser Arg Asp Lys Arg Thr Leu Ala Cys Leu Ile Gln Asn Phe Met Pro
                340                 345                 350
Glu Asp Ile Ser Val Gln Trp Leu His Asn Glu Val Gln Leu Pro Asp
                    355                 360                 365
Ala Arg His Ser Thr Thr Gln Pro Arg Lys Thr Lys Gly Ser Gly Phe
                370                 375                 380
Phe Val Phe Ser Arg Leu Glu Val Thr Arg Ala Glu Trp Glu Gln Lys
385                 390                 395                 400
Asp Glu Phe Ile Cys Arg Ala Val His Glu Ala Ala Ser Pro Ser Gln
                    405                 410                 415
Thr Val Gln Arg Ala Val Ser Val Asn Pro Gly Lys
                420                 425
```

<210> SEQ ID NO 3
<211> LENGTH: 1482
<212> TYPE: DNA
<213> ORGANISM: Homo sapiens

<400> SEQUENCE: 3

```
gcctccacac agagcccatc cgtcttcccc ttgacccgct gctgcaaaaa cattccctcc      60
aatgccacct ccgtgactct gggctgcctg gccacgggct acttcccgga gccggtgatg     120
gtgacctgcg acacaggctc cctcaacggg acaactatga ccttaccagc caccaccctc     180
acgctctctg gtcactatgc caccatcagc ttgctgaccg tctcgggtgc gtgggccaag     240
cagatgttca cctgccgtgt ggcacacact ccatcgtcca cagactgggt cgacaacaaa     300
accttcagcg tctgctccag ggacttcacc ccgcccaccg tgaagatctt acagtcgtcc     360
tgcgacggcg gcgggcactt ccccccgacc atccagctcc tgtgcctcgt ctctgggtac     420
accccaggga ctatcaacat cacctggctg gaggacgggc aggtcatgga cgtggacttg     480
tccaccgcct ctaccacgca ggagggtgag ctggcctcca cacaaagcga gctcaccctc     540
agccagaagc actggctgtc agaccgcacc tacacctgcc aggtcaccta tcaaggtcac     600
acctttgagg acagcaccaa gaagtgtgca gattccaacc cgagaggggt gagcgcctac     660
ctaagccggc ccagcccgtt cgacctgttc atccgcaagt cgcccacgat cacctgtctg     720
gtggtggacc tggcacccag caaggggacc gtgaacctga cctggtcccg ggccagtggg     780
aagcctgtga accactccac cagaaaggag gagaagcagc gcaatggcac gttaaccgtc     840
acgtccaccc tgccggtggg caccccgagac tggatcgagg gggagaccta ccagtgcagg     900
gtgacccacc cccacctgcc cagggccctc atgcggtcca cgaccaagac cagcggcccg     960
cgtgctgccc cggaagtcta tgcgtttgcg acgccggagt ggccggggag ccgggacaag    1020
cgcacccctcg cctgcctgat ccagaacttc atgcctgagg acatctcggt gcagtggctg    1080
cacaacgagg tgcagctccc ggacgcccgg cacagcacga cgcagccccg caagaccaag    1140
ggctccggct tcttcgtctt cagccgcctg gaggtgacca gggccgaatg ggagcagaaa    1200
gatgagttca tctgccgtgc agtccatgag gcagcgagcc cctcacagac cgtccagcga    1260
gcggtgtctg taaatcccga gctggacgtg tgcgtggagg aggccgaggg cgaggcgccg    1320
tggacgtgga ccgcctctg catcttcgcc gcactcttcc tgctcagcgt gagctacagc    1380
gccgccctca cgctcctcat ggtgcagcgg ttcctctcag ccacgcggca ggggaggccc    1440
cagacctccc tcgactacac caacgtcctc cagccccacg cc                       1482
```

<210> SEQ ID NO 4
<211> LENGTH: 15
<212> TYPE: PRT
<213> ORGANISM: Artificial Sequence
<220> FEATURE:
<223> OTHER INFORMATION: an artificially synthesized sequence

<400> SEQUENCE: 4

Gly Leu Asn Asp Ile Phe Glu Ala Gln Lys Ile Glu Trp His Glu
1               5                   10                  15

<210> SEQ ID NO 5
<211> LENGTH: 19
<212> TYPE: PRT
<213> ORGANISM: Artificial Sequence
<220> FEATURE:
<223> OTHER INFORMATION: an artificially synthesized sequence

<400> SEQUENCE: 5

Met Gly Trp Ser Cys Ile Ile Leu Phe Leu Val Ala Thr Ala Thr Gly
1               5                   10                  15

Val His Ser

<210> SEQ ID NO 6
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 6

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
                20                  25                  30

Met Asn Trp Tyr Gln Gln Lys Pro Gly Glu Ala Ala Ile Phe Ile Ile
            35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys
            100                 105

<210> SEQ ID NO 7
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys
            100                 105

<210> SEQ ID NO 8
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 8

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asp Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Met Gln Val
                85                  90                  95

Leu Arg Asn Pro Leu Thr Phe Gly Gly Gly Thr Lys Val Glu Ile Gln
            100                 105                 110
```

<210> SEQ ID NO 9
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 9

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65              70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105
```

<210> SEQ ID NO 10
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 10

```
Asp Ile Val Met Thr Gln Ser Pro Glu Ser Leu Val Leu Ser Leu Gly
1               5                   10                  15

Gly Thr Ala Thr Ile Asn Cys Arg Ser Ser Gln Ser Val Leu Tyr Ser
            20                  25                  30

Ser Asn Asn Lys Asn Tyr Leu Thr Trp Tyr Gln Gln Lys Pro Gly Gln
        35                  40                  45

Pro Pro Thr Leu Leu Phe Ser Trp Ala Ser Ile Arg Asp Ser Gly Val
    50                  55                  60

Pro Asp Arg Phe Ser Ala Ser Gly Ser Gly Thr Glu Phe Thr Leu Thr
65              70                  75                  80

Ile Ser Asp Leu Gln Ala Glu Asp Ala Ala Val Tyr Tyr Cys Gln Gln
```

```
                    85                  90                  95

Tyr Tyr Arg Ala Pro Ser Phe Gly Gln Gly Thr Lys Leu Gln Ile Lys
                100                 105                 110

<210> SEQ ID NO 11
<211> LENGTH: 121
<212> TYPE: PRT
<213> ORGANISM: Artificial Sequence
<220> FEATURE:
<223> OTHER INFORMATION: an artificially synthesized sequence

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Pro Gly Gly Gly Glu Tyr Tyr Phe Asp Tyr Trp Gly
                100                 105                 110

Gln Gly Thr Leu Val Thr Val Ser Ser
            115                 120

<210> SEQ ID NO 12
<211> LENGTH: 126
<212> TYPE: PRT
<213> ORGANISM: Artificial Sequence
<220> FEATURE:
<223> OTHER INFORMATION: an artificially synthesized sequence

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Glu Met Asn Trp Val Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Tyr Tyr Tyr Asp Ser Ser Gly Tyr Thr Asp Ala
                100                 105                 110

Phe Asp Ile Trp Gly Gln Gly Thr Met Val Thr Val Ser Ser
            115                 120                 125

<210> SEQ ID NO 13
<211> LENGTH: 330
<212> TYPE: PRT
<213> ORGANISM: Artificial Sequence
<220> FEATURE:
```

<223> OTHER INFORMATION: an artificially synthesized sequence

<400> SEQUENCE: 13

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 14
<211> LENGTH: 326
<212> TYPE: PRT
<213> ORGANISM: Artificial Sequence
<220> FEATURE:
<223> OTHER INFORMATION: an artificially synthesized sequence

<400> SEQUENCE: 14

```
Ala Ser Thr Lys Gly Pro Ser Val Phe Pro Leu Ala Pro Cys Ser Arg
1               5                   10                  15
```

-continued

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 15
<211> LENGTH: 377
<212> TYPE: PRT
<213> ORGANISM: Homo sapiens

<400> SEQUENCE: 15

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser

```
                50                  55                  60
Leu Ser Ser Val Val Thr Val Pro Ser Ser Leu Gly Thr Gln Thr
 65                  70                  75                  80

Tyr Thr Cys Asn Val Asn His Lys Pro Ser Asn Thr Lys Val Asp Lys
                 85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Cys Pro Arg
                115                 120                 125

Cys Pro Glu Pro Lys Ser Cys Asp Thr Pro Pro Cys Pro Arg Cys
                130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
                180                 185                 190

Val Val Asp Val Ser His Glu Asp Pro Glu Val Gln Phe Lys Trp Tyr
                195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
                275                 280                 285

Thr Lys Asn Gln Val Ser Leu Thr Cys Leu Val Lys Gly Phe Tyr Pro
                290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Phe Thr Gln
                355                 360                 365

Lys Ser Leu Ser Leu Ser Pro Gly Lys
                370                 375

<210> SEQ ID NO 16
<211> LENGTH: 327
<212> TYPE: PRT
<213> ORGANISM: Artificial Sequence
<220> FEATURE:
<223> OTHER INFORMATION: an artificially synthesized sequence

<400> SEQUENCE: 16

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
```

```
            35                  40                  45
Gly Val His Thr Phe Pro Ala Val Leu Gln Ser Ser Gly Leu Tyr Ser
             50                  55                  60
Leu Ser Ser Val Val Thr Val Pro Ser Ser Leu Gly Thr Lys Thr
 65                  70                  75                  80
Tyr Thr Cys Asn Val Asp His Lys Pro Ser Asn Thr Lys Val Asp Lys
                 85                  90                  95
Arg Val Glu Ser Lys Tyr Gly Pro Pro Cys Pro Ser Cys Pro Ala Pro
                100                 105                 110
Glu Phe Leu Gly Gly Pro Ser Val Phe Leu Phe Pro Pro Lys Pro Lys
                115                 120                 125
Asp Thr Leu Met Ile Ser Arg Thr Pro Glu Val Thr Cys Val Val Val
            130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
                180                 185                 190
Trp Leu Asn Gly Lys Glu Tyr Lys Cys Lys Val Ser Asn Lys Gly Leu
            195                 200                 205
Pro Ser Ser Ile Glu Lys Thr Ile Ser Lys Ala Lys Gly Gln Pro Arg
210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
            275                 280                 285
Arg Leu Thr Val Asp Lys Ser Arg Trp Gln Glu Gly Asn Val Phe Ser
290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 17
<211> LENGTH: 365
<212> TYPE: PRT
<213> ORGANISM: Homo sapiens

<400> SEQUENCE: 17

Met Gly Val Pro Arg Pro Gln Pro Trp Ala Leu Gly Leu Leu Leu Phe
1               5                  10                  15
Leu Leu Pro Gly Ser Leu Gly Ala Glu Ser His Leu Ser Leu Leu Tyr
                20                  25                  30
His Leu Thr Ala Val Ser Ser Pro Ala Pro Gly Thr Pro Ala Phe Trp
            35                  40                  45
Val Ser Gly Trp Leu Gly Pro Gln Gln Tyr Leu Ser Tyr Asn Ser Leu
         50                  55                  60
Arg Gly Glu Ala Glu Pro Cys Gly Ala Trp Val Trp Glu Asn Gln Val
 65                  70                  75                  80
```

```
Ser Trp Tyr Trp Glu Lys Glu Thr Thr Asp Leu Arg Ile Lys Glu Lys
                85                  90                  95

Leu Phe Leu Glu Ala Phe Lys Ala Leu Gly Gly Lys Gly Pro Tyr Thr
            100                 105                 110

Leu Gln Gly Leu Leu Gly Cys Glu Leu Gly Pro Asp Asn Thr Ser Val
        115                 120                 125

Pro Thr Ala Lys Phe Ala Leu Asn Gly Glu Glu Phe Met Asn Phe Asp
    130                 135                 140

Leu Lys Gln Gly Thr Trp Gly Gly Asp Trp Pro Glu Ala Leu Ala Ile
145                 150                 155                 160

Ser Gln Arg Trp Gln Gln Asp Lys Ala Ala Asn Lys Glu Leu Thr
                165                 170                 175

Phe Leu Leu Phe Ser Cys Pro His Arg Leu Arg Glu His Leu Glu Arg
            180                 185                 190

Gly Arg Gly Asn Leu Glu Trp Lys Glu Pro Pro Ser Met Arg Leu Lys
        195                 200                 205

Ala Arg Pro Ser Ser Pro Gly Phe Ser Val Leu Thr Cys Ser Ala Phe
    210                 215                 220

Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
                245                 250                 255

Phe His Ala Ser Ser Ser Leu Thr Val Lys Ser Gly Asp Glu His His
            260                 265                 270

Tyr Cys Cys Ile Val Gln His Ala Gly Leu Ala Gln Pro Leu Arg Val
        275                 280                 285

Glu Leu Glu Ser Pro Ala Lys Ser Ser Val Leu Val Val Gly Ile Val
    290                 295                 300

Ile Gly Val Leu Leu Leu Thr Ala Ala Ala Val Gly Gly Ala Leu Leu
305                 310                 315                 320

Trp Arg Arg Met Arg Ser Gly Leu Pro Ala Pro Trp Ile Ser Leu Arg
                325                 330                 335

Gly Asp Asp Thr Gly Val Leu Leu Pro Thr Pro Gly Glu Ala Gln Asp
            340                 345                 350

Ala Asp Leu Lys Asp Val Asn Val Ile Pro Ala Thr Ala
        355                 360                 365

<210> SEQ ID NO 18
<211> LENGTH: 119
<212> TYPE: PRT
<213> ORGANISM: Homo sapiens

<400> SEQUENCE: 18

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95
```

Glu Tyr Ala Cys Arg Val Asn His Val Thr Leu Ser Gln Pro Lys Ile
            100                 105                 110

Val Lys Trp Asp Arg Asp Met
            115

<210> SEQ ID NO 19
<211> LENGTH: 1125
<212> TYPE: DNA
<213> ORGANISM: Homo sapiens
<220> FEATURE:
<221> NAME/KEY: CDS
<222> LOCATION: (1)..(1125)

<400> SEQUENCE: 19

| | | |
|---|---|---|
| atg tgg ttc ttg aca act ctg ctc ctt tgg gtt cca gtt gat ggg caa<br>Met Trp Phe Leu Thr Thr Leu Leu Leu Trp Val Pro Val Asp Gly Gln<br>1               5                   10                  15 | | 48 |
| gtg gac acc aca aag gca gtg atc act ttg cag cct cca tgg gtc agc<br>Val Asp Thr Thr Lys Ala Val Ile Thr Leu Gln Pro Pro Trp Val Ser<br>            20                  25                  30 | | 96 |
| gtg ttc caa gag gaa acc gta acc ttg cac tgt gag gtg ctc cat ctg<br>Val Phe Gln Glu Glu Thr Val Thr Leu His Cys Glu Val Leu His Leu<br>        35                  40                  45 | | 144 |
| cct ggg agc agc tct aca cag tgg ttt ctc aat ggc aca gcc act cag<br>Pro Gly Ser Ser Ser Thr Gln Trp Phe Leu Asn Gly Thr Ala Thr Gln<br>    50                  55                  60 | | 192 |
| acc tcg acc ccc agc tac aga atc acc tct gcc agt gtc aat gac agt<br>Thr Ser Thr Pro Ser Tyr Arg Ile Thr Ser Ala Ser Val Asn Asp Ser<br>65                  70                  75                  80 | | 240 |
| ggt gaa tac agg tgc cag aga ggt ctc tca ggg cga agt gac ccc ata<br>Gly Glu Tyr Arg Cys Gln Arg Gly Leu Ser Gly Arg Ser Asp Pro Ile<br>                85                  90                  95 | | 288 |
| cag ctg gaa atc cac aga ggc tgg cta cta ctg cag gtc tcc agc aga<br>Gln Leu Glu Ile His Arg Gly Trp Leu Leu Leu Gln Val Ser Ser Arg<br>            100                 105                 110 | | 336 |
| gtc ttc acg gaa gga gaa cct ctg gcc ttg agg tgt cat gcg tgg aag<br>Val Phe Thr Glu Gly Glu Pro Leu Ala Leu Arg Cys His Ala Trp Lys<br>        115                 120                 125 | | 384 |
| gat aag ctg gtg tac aat gtg ctt tac tat cga aat ggc aaa gcc ttt<br>Asp Lys Leu Val Tyr Asn Val Leu Tyr Tyr Arg Asn Gly Lys Ala Phe<br>    130                 135                 140 | | 432 |
| aag ttt ttc cac tgg aat tct aac ctc acc att ctg aaa acc aac ata<br>Lys Phe Phe His Trp Asn Ser Asn Leu Thr Ile Leu Lys Thr Asn Ile<br>145                 150                 155                 160 | | 480 |
| agt cac aat ggc acc tac cat tgc tca ggc atg gga aag cat cgc tac<br>Ser His Asn Gly Thr Tyr His Cys Ser Gly Met Gly Lys His Arg Tyr<br>                165                 170                 175 | | 528 |
| aca tca gca gga ata tct gtc act gtg aaa gag cta ttt cca gct cca<br>Thr Ser Ala Gly Ile Ser Val Thr Val Lys Glu Leu Phe Pro Ala Pro<br>            180                 185                 190 | | 576 |
| gtg ctg aat gca tct gtg aca tcc cca ctc ctg gag ggg aat ctg gtc<br>Val Leu Asn Ala Ser Val Thr Ser Pro Leu Leu Glu Gly Asn Leu Val<br>        195                 200                 205 | | 624 |
| acc ctg agc tgt gaa aca aag ttg ctc ttg cag agg cct ggt ttg cag<br>Thr Leu Ser Cys Glu Thr Lys Leu Leu Leu Gln Arg Pro Gly Leu Gln<br>    210                 215                 220 | | 672 |
| ctt tac ttc tcc ttc tac atg ggc agc aag acc ctg cga ggc agg aac<br>Leu Tyr Phe Ser Phe Tyr Met Gly Ser Lys Thr Leu Arg Gly Arg Asn<br>225                 230                 235                 240 | | 720 |
| aca tcc tct gaa tac caa ata cta act gct aga aga gaa gac tct ggg | | 768 |

```
Thr Ser Ser Glu Tyr Gln Ile Leu Thr Ala Arg Arg Glu Asp Ser Gly
            245                 250                 255 tta tac tgg tgc gag gct gcc aca gag gat gga aat gtc ctt aag cgc      816
Leu Tyr Trp Cys Glu Ala Ala Thr Glu Asp Gly Asn Val Leu Lys Arg
        260                 265                 270 agc cct gag ttg gag ctt caa gtg ctt ggc ctc cag tta cca act cct      864
Ser Pro Glu Leu Glu Leu Gln Val Leu Gly Leu Gln Leu Pro Thr Pro
            275                 280                 285 gtc tgg ttt cat gtc ctt ttc tat ctg gca gtg gga ata atg ttt tta      912
Val Trp Phe His Val Leu Phe Tyr Leu Ala Val Gly Ile Met Phe Leu
        290                 295                 300 gtg aac act gtt ctc tgg gtg aca ata cgt aaa gaa ctg aaa aga aag      960
Val Asn Thr Val Leu Trp Val Thr Ile Arg Lys Glu Leu Lys Arg Lys
305                 310                 315                 320 aaa aag tgg gat tta gaa atc tct ttg gat tct ggt cat gag aag aag     1008
Lys Lys Trp Asp Leu Glu Ile Ser Leu Asp Ser Gly His Glu Lys Lys
                325                 330                 335 gta att tcc agc ctt caa gaa gac aga cat tta gaa gaa gag ctg aaa     1056
Val Ile Ser Ser Leu Gln Glu Asp Arg His Leu Glu Glu Glu Leu Lys
            340                 345                 350 tgt cag gaa caa aaa gaa gaa cag ctg cag gaa ggg gtg cac cgg aag     1104
Cys Gln Glu Gln Lys Glu Glu Gln Leu Gln Glu Gly Val His Arg Lys
        355                 360                 365 gag ccc cag ggg gcc acg tag                                         1125
Glu Pro Gln Gly Ala Thr
    370

<210> SEQ ID NO 20
<211> LENGTH: 374
<212> TYPE: PRT
<213> ORGANISM: Homo sapiens

<400> SEQUENCE: 20

Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190
```

```
Val Leu Asn Ala Ser Val Thr Ser Pro Leu Leu Glu Gly Asn Leu Val
        195                 200                 205

Thr Leu Ser Cys Glu Thr Lys Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His Val Leu Phe Tyr Leu Ala Val Gly Ile Met Phe Leu
    290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Leu Lys
            340                 345                 350

Cys Gln Glu Gln Lys Glu Glu Gln Leu Gln Glu Gly Val His Arg Lys
        355                 360                 365

Glu Pro Gln Gly Ala Thr
    370

<210> SEQ ID NO 21
<211> LENGTH: 951
<212> TYPE: DNA
<213> ORGANISM: Homo sapiens
<220> FEATURE:
<221> NAME/KEY: CDS
<222> LOCATION: (1)..(951)

<400> SEQUENCE: 21 atg act atg gag acc caa atg tct cag aat gta tgt ccc aga aac ctg      48
Met Thr Met Glu Thr Gln Met Ser Gln Asn Val Cys Pro Arg Asn Leu
1               5                   10                  15 tgg ctg ctt caa cca ttg aca gtt ttg ctg ctg gct tct gca gac         96
Trp Leu Leu Gln Pro Leu Thr Val Leu Leu Leu Ala Ser Ala Asp
                20                  25                  30 agt caa gct gct ccc cca aag gct gtg ctg aaa ctt gag ccc ccg tgg    144
Ser Gln Ala Ala Pro Pro Lys Ala Val Leu Lys Leu Glu Pro Pro Trp
            35                  40                  45 atc aac gtg ctc cag gag gac tct gtg act ctg aca tgc cag ggg gct    192
Ile Asn Val Leu Gln Glu Asp Ser Val Thr Leu Thr Cys Gln Gly Ala
50                  55                  60 cgc agc cct gag agc gac tcc att cag tgg ttc cac aat ggg aat ctc    240
Arg Ser Pro Glu Ser Asp Ser Ile Gln Trp Phe His Asn Gly Asn Leu
65                  70                  75                  80 att ccc acc cac acg cag ccc agc tac agg ttc aag gcc aac aac aat    288
Ile Pro Thr His Thr Gln Pro Ser Tyr Arg Phe Lys Ala Asn Asn Asn
                85                  90                  95 gac agc ggg gag tac acg tgc cag act ggc cag acc agc ctc agc gac    336
Asp Ser Gly Glu Tyr Thr Cys Gln Thr Gly Gln Thr Ser Leu Ser Asp
            100                 105                 110 cct gtg cat ctg act gtg ctt tcc gaa tgg ctg gtg ctc cag acc cct    384
Pro Val His Leu Thr Val Leu Ser Glu Trp Leu Val Leu Gln Thr Pro
        115                 120                 125
```

```
cac ctg gag ttc cag gag gga gaa acc atc atg ctg agg tgc cac agc        432
His Leu Glu Phe Gln Glu Gly Glu Thr Ile Met Leu Arg Cys His Ser
        130                 135                 140 tgg aag gac aag cct ctg gtc aag gtc aca ttc ttc cag aat gga aaa        480
Trp Lys Asp Lys Pro Leu Val Lys Val Thr Phe Phe Gln Asn Gly Lys
145                 150                 155                 160 tcc cag aaa ttc tcc cat ttg gat ccc acc ttc tcc atc cca caa gca        528
Ser Gln Lys Phe Ser His Leu Asp Pro Thr Phe Ser Ile Pro Gln Ala
                165                 170                 175 aac cac agt cac agt ggt gat tac cac tgc aca gga aac ata ggc tac        576
Asn His Ser His Ser Gly Asp Tyr His Cys Thr Gly Asn Ile Gly Tyr
            180                 185                 190 acg ctg ttc tca tcc aag cct gtg acc atc act gtc caa gtg ccc agc        624
Thr Leu Phe Ser Ser Lys Pro Val Thr Ile Thr Val Gln Val Pro Ser
        195                 200                 205 atg ggc agc tct tca cca atg ggg gtc att gtg gct gtg gtc att gcg        672
Met Gly Ser Ser Ser Pro Met Gly Val Ile Val Ala Val Val Ile Ala
    210                 215                 220 act gct gta gca gcc att gtt gct gct gta gtg gcc ttg atc tac tgc        720
Thr Ala Val Ala Ala Ile Val Ala Ala Val Val Ala Leu Ile Tyr Cys
225                 230                 235                 240 agg aaa aag cgg att tca gcc aat tcc act gat cct gtg aag gct gcc        768
Arg Lys Lys Arg Ile Ser Ala Asn Ser Thr Asp Pro Val Lys Ala Ala
                245                 250                 255 caa ttt gag cca cct gga cgt caa atg att gcc atc aga aag aga caa        816
Gln Phe Glu Pro Pro Gly Arg Gln Met Ile Ala Ile Arg Lys Arg Gln
            260                 265                 270 ctt gaa gaa acc aac aat gac tat gaa aca gct gac ggc ggc tac atg        864
Leu Glu Glu Thr Asn Asn Asp Tyr Glu Thr Ala Asp Gly Gly Tyr Met
        275                 280                 285 act ctg aac ccc agg gca cct act gac gat gat aaa aac atc tac ctg        912
Thr Leu Asn Pro Arg Ala Pro Thr Asp Asp Asp Lys Asn Ile Tyr Leu
    290                 295                 300 act ctt cct ccc aac gac cat gtc aac agt aat aac taa                    951
Thr Leu Pro Pro Asn Asp His Val Asn Ser Asn Asn
305                 310                 315

<210> SEQ ID NO 22
<211> LENGTH: 316
<212> TYPE: PRT
<213> ORGANISM: Homo sapiens

<400> SEQUENCE: 22

Met Thr Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
                20                  25                  30

Ser Gln Ala Ala Pro Pro Lys Ala Val Leu Lys Leu Glu Pro Pro Trp
        35                  40                  45

Ile Asn Val Leu Gln Glu Asp Ser Val Thr Leu Thr Cys Gln Gly Ala
    50                  55                  60

Arg Ser Pro Glu Ser Asp Ser Ile Gln Trp Phe His Asn Gly Asn Leu
65                  70                  75                  80

Ile Pro Thr His Thr Gln Pro Ser Tyr Arg Phe Lys Ala Asn Asn Asn
                85                  90                  95

Asp Ser Gly Glu Tyr Thr Cys Gln Thr Gly Gln Thr Ser Leu Ser Asp
            100                 105                 110

Pro Val His Leu Thr Val Leu Ser Glu Trp Leu Val Leu Gln Thr Pro
        115                 120                 125
```

```
His Leu Glu Phe Gln Glu Gly Glu Thr Ile Met Leu Arg Cys His Ser
    130                 135                 140
Trp Lys Asp Lys Pro Leu Val Lys Val Thr Phe Gln Asn Gly Lys
145                 150                 155                 160
Ser Gln Lys Phe Ser His Leu Asp Pro Thr Phe Ser Ile Pro Gln Ala
                165                 170                 175
Asn His Ser His Ser Gly Asp Tyr His Cys Thr Gly Asn Ile Gly Tyr
                180                 185                 190
Thr Leu Phe Ser Ser Lys Pro Val Thr Ile Thr Val Gln Val Pro Ser
                195                 200                 205
Met Gly Ser Ser Ser Pro Met Gly Val Ile Val Ala Val Val Ile Ala
    210                 215                 220
Thr Ala Val Ala Ala Ile Val Ala Ala Val Val Ala Leu Ile Tyr Cys
225                 230                 235                 240
Arg Lys Lys Arg Ile Ser Ala Asn Ser Thr Asp Pro Val Lys Ala Ala
                245                 250                 255
Gln Phe Glu Pro Pro Gly Arg Gln Met Ile Ala Ile Arg Lys Arg Gln
                260                 265                 270
Leu Glu Glu Thr Asn Asn Asp Tyr Glu Thr Ala Asp Gly Gly Tyr Met
            275                 280                 285
Thr Leu Asn Pro Arg Ala Pro Thr Asp Asp Asp Lys Asn Ile Tyr Leu
        290                 295                 300
Thr Leu Pro Pro Asn Asp His Val Asn Ser Asn Asn
305                 310                 315

<210> SEQ ID NO 23
<211> LENGTH: 876
<212> TYPE: DNA
<213> ORGANISM: Homo sapiens
<220> FEATURE:
<221> NAME/KEY: CDS
<222> LOCATION: (1)..(876)

<400> SEQUENCE: 23 atg gga atc ctg tca ttc tta cct gtc ctt gcc act gag agt gac tgg      48
Met Gly Ile Leu Ser Phe Leu Pro Val Leu Ala Thr Glu Ser Asp Trp
1               5                   10                  15 gct gac tgc aag tcc ccc cag cct tgg ggt cat atg ctt ctg tgg aca      96
Ala Asp Cys Lys Ser Pro Gln Pro Trp Gly His Met Leu Leu Trp Thr
                20                  25                  30 gct gtg cta ttc ctg gct cct gtt gct ggg aca cct gca gct ccc cca     144
Ala Val Leu Phe Leu Ala Pro Val Ala Gly Thr Pro Ala Ala Pro Pro
            35                  40                  45 aag gct gtg ctg aaa ctc gag ccc cag tgg atc aac gtg ctc cag gag     192
Lys Ala Val Leu Lys Leu Glu Pro Gln Trp Ile Asn Val Leu Gln Glu
        50                  55                  60 gac tct gtg act ctg aca tgc cgg ggg act cac agc cct gag agc gac     240
Asp Ser Val Thr Leu Thr Cys Arg Gly Thr His Ser Pro Glu Ser Asp
65                  70                  75                  80 tcc att cag tgg ttc cac aat ggg aat ctc att ccc acc cac acg cag     288
Ser Ile Gln Trp Phe His Asn Gly Asn Leu Ile Pro Thr His Thr Gln
                85                  90                  95 ccc agc tac agg ttc aag gcc aac aac aat gac agc ggg gag tac acg     336
Pro Ser Tyr Arg Phe Lys Ala Asn Asn Asn Asp Ser Gly Glu Tyr Thr
                100                 105                 110 tgc cag act ggc cag acc agc ctc agc gac cct gtg cat ctg act gtg     384
Cys Gln Thr Gly Gln Thr Ser Leu Ser Asp Pro Val His Leu Thr Val
            115                 120                 125
```

```
ctt tct gag tgg ctg gtg ctc cag acc cct cac ctg gag ttc cag gag      432
Leu Ser Glu Trp Leu Val Leu Gln Thr Pro His Leu Glu Phe Gln Glu
    130                 135                 140 gga gaa acc atc gtg ctg agg tgc cac agc tgg aag gac aag cct ctg      480
Gly Glu Thr Ile Val Leu Arg Cys His Ser Trp Lys Asp Lys Pro Leu
145                 150                 155                 160 gtc aag gtc aca ttc ttc cag aat gga aaa tcc aag aaa ttt tcc cgt      528
Val Lys Val Thr Phe Phe Gln Asn Gly Lys Ser Lys Lys Phe Ser Arg
                165                 170                 175 tcg gat ccc aac ttc tcc atc cca caa gca aac cac agt cac agt ggt      576
Ser Asp Pro Asn Phe Ser Ile Pro Gln Ala Asn His Ser His Ser Gly
            180                 185                 190 gat tac cac tgc aca gga aac ata ggc tac acg ctg tac tca tcc aag      624
Asp Tyr His Cys Thr Gly Asn Ile Gly Tyr Thr Leu Tyr Ser Ser Lys
        195                 200                 205 cct gtg acc atc act gtc caa gct ccc agc tct tca ccg atg ggg atc      672
Pro Val Thr Ile Thr Val Gln Ala Pro Ser Ser Ser Pro Met Gly Ile
    210                 215                 220 att gtg gct gtg gtc act ggg att gct gta gcg gcc att gtt gct gct      720
Ile Val Ala Val Val Thr Gly Ile Ala Val Ala Ala Ile Val Ala Ala
225                 230                 235                 240 gta gtg gcc ttg atc tac tgc agg aaa aag cgg att tca gcc aat ccc      768
Val Val Ala Leu Ile Tyr Cys Arg Lys Lys Arg Ile Ser Ala Asn Pro
                245                 250                 255 act aat cct gat gag gct gac aaa gtt ggg gct gag aac aca atc acc      816
Thr Asn Pro Asp Glu Ala Asp Lys Val Gly Ala Glu Asn Thr Ile Thr
            260                 265                 270 tat tca ctt ctc atg cac ccg gat gct ctg gaa gag cct gat gac cag      864
Tyr Ser Leu Leu Met His Pro Asp Ala Leu Glu Glu Pro Asp Asp Gln
        275                 280                 285 aac cgt att tag                                                       876
Asn Arg Ile
    290
```

<210> SEQ ID NO 24
<211> LENGTH: 291
<212> TYPE: PRT
<213> ORGANISM: Homo sapiens

<400> SEQUENCE: 24

```
Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
        35                  40                  45

Lys Ala Val Leu Lys Leu Glu Pro Gln Trp Ile Asn Val Leu Gln Glu
    50                  55                  60

Asp Ser Val Thr Leu Thr Cys Arg Gly Thr His Ser Pro Glu Ser Asp
65                  70                  75                  80

Ser Ile Gln Trp Phe His Asn Gly Asn Leu Ile Pro Thr His Thr Gln
                85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
        115                 120                 125

Leu Ser Glu Trp Leu Val Leu Gln Thr Pro His Leu Glu Phe Gln Glu
    130                 135                 140
```

```
Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Phe Ser Arg
            165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
            195                 200                 205

Pro Val Thr Ile Thr Val Gln Ala Pro Ser Ser Ser Pro Met Gly Ile
            210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Asn Pro
                245                 250                 255

Thr Asn Pro Asp Glu Ala Asp Lys Val Gly Ala Glu Asn Thr Ile Thr
            260                 265                 270

Tyr Ser Leu Leu Met His Pro Asp Ala Leu Glu Glu Pro Asp Asp Gln
            275                 280                 285

Asn Arg Ile
    290
```

<210> SEQ ID NO 25
<211> LENGTH: 765
<212> TYPE: DNA
<213> ORGANISM: Homo sapiens
<220> FEATURE:
<221> NAME/KEY: CDS
<222> LOCATION: (1)..(765)

<400> SEQUENCE: 25

```
atg tgg cag ctg ctc ctc cca act gct ctg cta ctt cta gtt tca gct      48
Met Trp Gln Leu Leu Leu Pro Thr Ala Leu Leu Leu Leu Val Ser Ala
1               5                   10                  15 ggc atg cgg act gaa gat ctc cca aag gct gtg gtg ttc ctg gag cct      96
Gly Met Arg Thr Glu Asp Leu Pro Lys Ala Val Val Phe Leu Glu Pro
                20                  25                  30 caa tgg tac agg gtg ctc gag aag gac agt gtg act ctg aag tgc cag     144
Gln Trp Tyr Arg Val Leu Glu Lys Asp Ser Val Thr Leu Lys Cys Gln
            35                  40                  45 gga gcc tac tcc cct gag gac aat tcc aca cag tgg ttt cac aat gag     192
Gly Ala Tyr Ser Pro Glu Asp Asn Ser Thr Gln Trp Phe His Asn Glu
        50                  55                  60 agc ctc atc tca agc cag gcc tcg agc tac ttc att gac gct gcc aca     240
Ser Leu Ile Ser Ser Gln Ala Ser Ser Tyr Phe Ile Asp Ala Ala Thr
65                  70                  75                  80 gtt gac gac agt gga gag tac agg tgc cag aca aac ctc tcc acc ctc     288
Val Asp Asp Ser Gly Glu Tyr Arg Cys Gln Thr Asn Leu Ser Thr Leu
                85                  90                  95 agt gac ccg gtg cag cta gaa gtc cat atc ggc tgg ctg ttg ctc cag     336
Ser Asp Pro Val Gln Leu Glu Val His Ile Gly Trp Leu Leu Leu Gln
            100                 105                 110 gcc cct cgg tgg gtg ttc aag gag gaa gac cct att cac ctg agg tgt     384
Ala Pro Arg Trp Val Phe Lys Glu Glu Asp Pro Ile His Leu Arg Cys
        115                 120                 125 cac agc tgg aag aac act gct ctg cat aag gtc aca tat tta cag aat     432
His Ser Trp Lys Asn Thr Ala Leu His Lys Val Thr Tyr Leu Gln Asn
130                 135                 140 ggc aaa ggc agg aag tat ttt cat cat aat tct gac ttc tac att cca     480
```

```
Gly Lys Gly Arg Lys Tyr Phe His His Asn Ser Asp Phe Tyr Ile Pro
145                 150                 155                 160 aaa gcc aca ctc aaa gac agc ggc tcc tac ttc tgc agg ggg ctt gtt        528
Lys Ala Thr Leu Lys Asp Ser Gly Ser Tyr Phe Cys Arg Gly Leu Val
                165                 170                 175 ggg agt aaa aat gtg tct tca gag act gtg aac atc acc atc act caa        576
Gly Ser Lys Asn Val Ser Ser Glu Thr Val Asn Ile Thr Ile Thr Gln
            180                 185                 190 ggt ttg tca gtg tca acc atc tca tca ttc ttt cca cct ggg tac caa        624
Gly Leu Ser Val Ser Thr Ile Ser Ser Phe Phe Pro Pro Gly Tyr Gln
        195                 200                 205 gtc tct ttc tgc ttg gtg atg gta ctc ctt ttt gca gtg gac aca gga        672
Val Ser Phe Cys Leu Val Met Val Leu Leu Phe Ala Val Asp Thr Gly
    210                 215                 220 cta tat ttc tct gtg aag aca aac att cga agc tca aca aga gac tgg        720
Leu Tyr Phe Ser Val Lys Thr Asn Ile Arg Ser Ser Thr Arg Asp Trp
225                 230                 235                 240 aag gac cat aaa ttt aaa tgg aga aag gac cct caa gac aaa tga            765
Lys Asp His Lys Phe Lys Trp Arg Lys Asp Pro Gln Asp Lys
                245                 250

<210> SEQ ID NO 26
<211> LENGTH: 254
<212> TYPE: PRT
<213> ORGANISM: Homo sapiens

<400> SEQUENCE: 26

Met Trp Gln Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ser Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240
```

```
Lys Asp His Lys Phe Lys Trp Arg Lys Asp Pro Gln Asp Lys
                245                 250
```

```
<210> SEQ ID NO 27
<211> LENGTH: 702
<212> TYPE: DNA
<213> ORGANISM: Homo sapiens
<220> FEATURE:
<221> NAME/KEY: CDS
<222> LOCATION: (1)..(702)

<400> SEQUENCE: 27
```

| | | | | | | | | | | | | | | | | |
|---|---|---|---|---|---|---|---|---|---|---|---|---|---|---|---|---|
| atg | tgg | cag | ctg | ctc | ctc | cca | act | gct | ctg | cta | ctt | cta | gtt | tca | gct | 48 |
| Met | Trp | Gln | Leu | Leu | Leu | Pro | Thr | Ala | Leu | Leu | Leu | Leu | Val | Ser | Ala | |
| 1 | | | | 5 | | | | | 10 | | | | | 15 | | |
| ggc | atg | cgg | act | gaa | gat | ctc | cca | aag | gct | gtg | gtg | ttc | ctg | gag | cct | 96 |
| Gly | Met | Arg | Thr | Glu | Asp | Leu | Pro | Lys | Ala | Val | Val | Phe | Leu | Glu | Pro | |
| | | | 20 | | | | | 25 | | | | | 30 | | | |
| caa | tgg | tac | agc | gtg | ctt | gag | aag | gac | agt | gtg | act | ctg | aag | tgc | cag | 144 |
| Gln | Trp | Tyr | Ser | Val | Leu | Glu | Lys | Asp | Ser | Val | Thr | Leu | Lys | Cys | Gln | |
| | | 35 | | | | | 40 | | | | | 45 | | | | |
| gga | gcc | tac | tcc | cct | gag | gac | aat | tcc | aca | cag | tgg | ttt | cac | aat | gag | 192 |
| Gly | Ala | Tyr | Ser | Pro | Glu | Asp | Asn | Ser | Thr | Gln | Trp | Phe | His | Asn | Glu | |
| 50 | | | | | 55 | | | | | 60 | | | | | | |
| agc | ctc | atc | tca | agc | cag | gcc | tcg | agc | tac | ttc | att | gac | gct | gcc | aca | 240 |
| Ser | Leu | Ile | Ser | Ser | Gln | Ala | Ser | Ser | Tyr | Phe | Ile | Asp | Ala | Ala | Thr | |
| 65 | | | | | 70 | | | | | 75 | | | | | 80 | |
| gtc | aac | gac | agt | gga | gag | tac | agg | tgc | cag | aca | aac | ctc | tcc | acc | ctc | 288 |
| Val | Asn | Asp | Ser | Gly | Glu | Tyr | Arg | Cys | Gln | Thr | Asn | Leu | Ser | Thr | Leu | |
| | | | | 85 | | | | | 90 | | | | | 95 | | |
| agt | gac | ccg | gtg | cag | cta | gaa | gtc | cat | atc | ggc | tgg | ctg | ttg | ctc | cag | 336 |
| Ser | Asp | Pro | Val | Gln | Leu | Glu | Val | His | Ile | Gly | Trp | Leu | Leu | Leu | Gln | |
| | | | 100 | | | | | 105 | | | | | 110 | | | |
| gcc | cct | cgg | tgg | gtg | ttc | aag | gag | gaa | gac | cct | att | cac | ctg | agg | tgt | 384 |
| Ala | Pro | Arg | Trp | Val | Phe | Lys | Glu | Glu | Asp | Pro | Ile | His | Leu | Arg | Cys | |
| | | 115 | | | | | 120 | | | | | 125 | | | | |
| cac | agc | tgg | aag | aac | act | gct | ctg | cat | aag | gtc | aca | tat | tta | cag | aat | 432 |
| His | Ser | Trp | Lys | Asn | Thr | Ala | Leu | His | Lys | Val | Thr | Tyr | Leu | Gln | Asn | |
| 130 | | | | | 135 | | | | | 140 | | | | | | |
| ggc | aaa | gac | agg | aag | tat | ttt | cat | cat | aat | tct | gac | ttc | cac | att | cca | 480 |
| Gly | Lys | Asp | Arg | Lys | Tyr | Phe | His | His | Asn | Ser | Asp | Phe | His | Ile | Pro | |
| 145 | | | | 150 | | | | | 155 | | | | | 160 | | |
| aaa | gcc | aca | ctc | aaa | gat | agc | ggc | tcc | tac | ttc | tgc | agg | ggg | ctt | gtt | 528 |
| Lys | Ala | Thr | Leu | Lys | Asp | Ser | Gly | Ser | Tyr | Phe | Cys | Arg | Gly | Leu | Val | |
| | | | 165 | | | | | 170 | | | | | 175 | | | |
| ggg | agt | aaa | aat | gtg | tct | tca | gag | act | gtg | aac | atc | acc | atc | act | caa | 576 |
| Gly | Ser | Lys | Asn | Val | Ser | Ser | Glu | Thr | Val | Asn | Ile | Thr | Ile | Thr | Gln | |
| | | 180 | | | | | 185 | | | | | 190 | | | | |
| ggt | ttg | gca | gtg | tca | acc | atc | tca | tca | ttc | tct | cca | cct | ggg | tac | caa | 624 |
| Gly | Leu | Ala | Val | Ser | Thr | Ile | Ser | Ser | Phe | Ser | Pro | Pro | Gly | Tyr | Gln | |
| | | 195 | | | | | 200 | | | | | 205 | | | | |
| gtc | tct | ttc | tgc | ttg | gtg | atg | gta | ctc | ctt | ttt | gca | gtg | gac | aca | gga | 672 |
| Val | Ser | Phe | Cys | Leu | Val | Met | Val | Leu | Leu | Phe | Ala | Val | Asp | Thr | Gly | |
| 210 | | | | | 215 | | | | | 220 | | | | | | |
| cta | tat | ttc | tct | gtg | aag | aca | aac | att | tga | | | | | | | 702 |
| Leu | Tyr | Phe | Ser | Val | Lys | Thr | Asn | Ile | | | | | | | | |
| 225 | | | | | 230 | | | | | | | | | | | |

```
<210> SEQ ID NO 28
<211> LENGTH: 233
<212> TYPE: PRT
```

<213> ORGANISM: Homo sapiens

<400> SEQUENCE: 28

```
Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
            130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
            195                 200                 205

Val Ser Phe Cys Leu Val Met Val Leu Leu Phe Ala Val Asp Thr Gly
            210                 215                 220

Leu Tyr Phe Ser Val Lys Thr Asn Ile
225                 230
```

<210> SEQ ID NO 29
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 29

Gly Gly Gly Ser
1

<210> SEQ ID NO 30
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 30

Ser Gly Gly Gly
1

<210> SEQ ID NO 31
<211> LENGTH: 5
<212> TYPE: PRT

```
<213> ORGANISM: Artificial Sequence
<220> FEATURE:
<223> OTHER INFORMATION: an artificially synthesized sequence

<400> SEQUENCE: 31

Gly Gly Gly Gly Ser
1               5

<210> SEQ ID NO 32
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 32

Ser Gly Gly Gly Gly
1               5

<210> SEQ ID NO 33
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 33

Gly Gly Gly Gly Gly Ser
1               5

<210> SEQ ID NO 34
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 34

Ser Gly Gly Gly Gly Gly
1               5

<210> SEQ ID NO 35
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 35

Gly Gly Gly Gly Gly Gly Ser
1               5

<210> SEQ ID NO 36
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 36

Ser Gly Gly Gly Gly Gly Gly
1               5

<210> SEQ ID NO 37
<211> LENGTH: 450
<212> TYPE: PRT
<213> ORGANISM: Artificial Sequence
```

<220> FEATURE:
<223> OTHER INFORMATION: an artificially synthesized sequence

<400> SEQUENCE: 37

```
Glu Val Gln Leu Val Gln Ser Gly Ala Glu Val Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Ala Pro Gly Asn Trp Gly Ser Pro Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400
```

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro
    450

<210> SEQ ID NO 38
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Asp Ser Ser Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 39
<211> LENGTH: 451
<212> TYPE: PRT
<213> ORGANISM: Artificial Sequence
<220> FEATURE:
<223> OTHER INFORMATION: an artificially synthesized sequence

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr

-continued

```
                20                  25                  30
Ala Ile Ser Trp Val Arg Gln Ala Pro Gly Gln Gly Leu Glu Trp Met
            35                  40                  45
Gly Gly Ile Ile Pro Ile Phe Gly Thr Ala Asn Tyr Ala Gln Lys Phe
        50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Pro Arg Trp Glu Thr Ala Ile Ser Ser Asp Ala Phe Asp Ile
            100                 105                 110
Trp Gly Gln Gly Thr Met Val Thr Val Ser Ser Ala Ser Thr Lys Gly
        115                 120                 125
Pro Ser Val Phe Pro Leu Ala Pro Ser Ser Lys Ser Thr Ser Gly Gly
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Asp Glu Leu Thr Lys Asn Gln
        355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
```

```
Leu Ser Pro
    450

<210> SEQ ID NO 40
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Asp
            20                  25                  30

Leu Asn Trp Tyr Gln Gln Lys Pro Gly Lys Ala Pro Lys Leu Leu Ile
        35                  40                  45

Tyr Glu Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Ser Ser Ser Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 41
<211> LENGTH: 451
<212> TYPE: PRT
<213> ORGANISM: Artificial Sequence
<220> FEATURE:
<223> OTHER INFORMATION: an artificially synthesized sequence

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
```

```
                65                  70                  75                  80
Met Glu Leu Ser Ser Leu Arg Ser Glu Asp Thr Ala Val Tyr Tyr Cys
                    85                  90                  95

Ala Arg Pro Arg Trp Glu Thr Ala Ile Ser Ser Asp Ala Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Trp His Tyr Thr Gln Lys Ser Leu Ser
        435                 440                 445

Leu Ser Pro
    450

<210> SEQ ID NO 42
<211> LENGTH: 451
<212> TYPE: PRT
<213> ORGANISM: Artificial Sequence
```

<220> FEATURE:
<223> OTHER INFORMATION: an artificially synthesized sequence

<400> SEQUENCE: 42

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Arg Trp Glu Thr Ala Ile Ser Ser Asp Ala Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Arg Gly Gly Pro Lys Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400
```

```
Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro
    450

<210> SEQ ID NO 43
<211> LENGTH: 543
<212> TYPE: PRT
<213> ORGANISM: Artificial Sequence
<220> FEATURE:
<223> OTHER INFORMATION: an artificially synthesized sequence

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Gln Ser Pro Ser Val Phe Pro Leu Thr Arg
        115                 120                 125

Cys Cys Lys Asn Ile Pro Ser Asn Ala Thr Ser Val Thr Leu Gly Cys
    130                 135                 140

Leu Ala Thr Gly Tyr Phe Pro Glu Pro Val Met Val Thr Trp Asp Thr
145                 150                 155                 160

Gly Ser Leu Asn Gly Thr Thr Met Thr Leu Pro Ala Thr Thr Leu Thr
                165                 170                 175

Leu Ser Gly His Tyr Ala Thr Ile Ser Leu Leu Thr Val Ser Gly Ala
            180                 185                 190

Trp Ala Lys Gln Met Phe Thr Cys Arg Val Ala His Thr Pro Ser Ser
        195                 200                 205

Thr Asp Trp Val Asp Asn Lys Thr Phe Ser Val Cys Ser Arg Asp Phe
    210                 215                 220

Thr Pro Pro Thr Val Lys Ile Leu Gln Ser Ser Cys Asp Gly Gly Gly
225                 230                 235                 240

His Phe Pro Pro Thr Ile Gln Leu Leu Cys Leu Val Ser Gly Tyr Thr
                245                 250                 255

Pro Gly Thr Ile Asn Ile Thr Trp Leu Glu Asp Gly Gln Val Met Asp
            260                 265                 270

Val Asp Leu Ser Thr Ala Ser Thr Thr Gln Glu Gly Glu Leu Ala Ser
        275                 280                 285

Thr Gln Ser Glu Leu Thr Leu Ser Gln Lys His Trp Leu Ser Asp Arg
    290                 295                 300
```

```
Thr Tyr Thr Cys Gln Val Thr Tyr Gln Gly His Thr Phe Glu Asp Ser
305                 310                 315                 320

Thr Lys Lys Cys Ala Asp Ser Asn Pro Arg Gly Val Ser Ala Tyr Leu
                325                 330                 335

Ser Arg Pro Ser Pro Phe Asp Leu Phe Ile Arg Lys Ser Pro Thr Ile
            340                 345                 350

Thr Cys Leu Val Val Asp Leu Ala Pro Ser Lys Gly Thr Val Asn Leu
        355                 360                 365

Thr Trp Ser Arg Ala Ser Gly Lys Pro Val Asn His Ser Thr Arg Lys
370                 375                 380

Glu Glu Lys Gln Arg Asn Gly Thr Leu Thr Val Thr Ser Thr Leu Pro
385                 390                 395                 400

Val Gly Thr Arg Asp Trp Ile Glu Gly Glu Thr Tyr Gln Cys Arg Val
                405                 410                 415

Thr His Pro His Leu Pro Arg Ala Leu Met Arg Ser Thr Thr Lys Thr
                420                 425                 430

Ser Gly Pro Arg Ala Ala Pro Glu Val Tyr Ala Phe Ala Thr Pro Glu
            435                 440                 445

Trp Pro Gly Ser Arg Asp Lys Arg Thr Leu Ala Cys Leu Ile Gln Asn
450                 455                 460

Phe Met Pro Glu Asp Ile Ser Val Gln Trp Leu His Asn Glu Val Gln
465                 470                 475                 480

Leu Pro Asp Ala Arg His Ser Thr Thr Gln Pro Arg Lys Thr Lys Gly
                485                 490                 495

Ser Gly Phe Phe Val Phe Ser Arg Leu Glu Val Thr Arg Ala Glu Trp
            500                 505                 510

Glu Gln Lys Asp Glu Phe Ile Cys Arg Ala Val His Glu Ala Ala Ser
        515                 520                 525

Pro Ser Gln Thr Val Gln Arg Ala Val Ser Val Asn Pro Gly Lys
    530                 535                 540

<210> SEQ ID NO 44
<211> LENGTH: 219
<212> TYPE: PRT
<213> ORGANISM: Artificial Sequence
<220> FEATURE:
<223> OTHER INFORMATION: an artificially synthesized sequence

<400> SEQUENCE: 44

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125
```

```
Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 45
<211> LENGTH: 443
<212> TYPE: PRT
<213> ORGANISM: Artificial Sequence
<220> FEATURE:
<223> OTHER INFORMATION: an artificially synthesized sequence

<400> SEQUENCE: 45

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr His
            20                  25                  30

Met Ser Trp Val Arg Gln Ala Pro Gly Lys Gly Leu Glu Trp Ile Gly
        35                  40                  45

Val Ile Asn Ser Ala Gly Asn Thr Tyr Tyr Ala Ser Trp Ala Lys Gly
    50                  55                  60

Arg Phe Thr Val Ser Lys Thr Ser Thr Thr Val Asp Leu Asn Leu Thr
65                  70                  75                  80

Ser Leu Thr Thr Glu Asp Thr Ala Thr Tyr Phe Cys Ala Arg Tyr Val
                85                  90                  95

Phe Ser Ser Gly Ser His Asp Ile Trp Gly Pro Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270
```

```
Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
            435                 440

<210> SEQ ID NO 46
<211> LENGTH: 217
<212> TYPE: PRT
<213> ORGANISM: Artificial Sequence
<220> FEATURE:
<223> OTHER INFORMATION: an artificially synthesized sequence

<400> SEQUENCE: 46

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Gly Ser Trp
            20                  25                  30

Leu Ala Trp Tyr Gln Gln Lys Pro Gly Gln Pro Pro Lys Glu Leu Ile
        35                  40                  45

Tyr Gly Thr Ser Thr Leu Glu Ser Gly Val Pro Ser Arg Phe Ile Gly
    50                  55                  60

Ser Gly Ser Gly Thr Glu Phe Thr Leu Thr Ile Ser Gly Val Glu Cys
65                  70                  75                  80

Ala Asp Ala Ala Thr Tyr Tyr Cys Gln Gln Gly Tyr Ser Glu Asp Asn
                85                  90                  95

Ile Asp Asn Ala Phe Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190
```

```
Lys Val Tyr Ala Cys Glu Val Thr His Gln Gly Leu Ser Ser Pro Val
            195                 200                 205

Thr Lys Ser Phe Asn Arg Gly Glu Cys
    210                 215
```

<210> SEQ ID NO 47
<211> LENGTH: 32
<212> TYPE: PRT
<213> ORGANISM: Artificial Sequence
<220> FEATURE:
<223> OTHER INFORMATION: an artificially synthesized sequence

<400> SEQUENCE: 47

```
Val Asp Asp Ala Pro Gly Asn Ser Gln Gln Ala Thr Pro Lys Asp Asn
1               5                   10                  15

Glu Ile Ser Thr Phe His Asn Leu Gly Asn Val His Ser Pro Leu Lys
            20                  25                  30
```

<210> SEQ ID NO 48
<211> LENGTH: 543
<212> TYPE: PRT
<213> ORGANISM: Artificial Sequence
<220> FEATURE:
<223> OTHER INFORMATION: an artificially synthesized sequence

<400> SEQUENCE: 48

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Gln Ser Pro Ser Val Phe Pro Leu Thr Arg
        115                 120                 125

Cys Cys Lys Asn Ile Pro Ser Asp Ala Thr Ser Val Thr Leu Gly Cys
    130                 135                 140

Leu Ala Thr Gly Tyr Phe Pro Glu Pro Val Met Val Thr Trp Asp Thr
145                 150                 155                 160

Gly Ser Leu Asp Gly Thr Thr Met Thr Leu Pro Ala Thr Thr Leu Thr
                165                 170                 175

Leu Ser Gly His Tyr Ala Thr Ile Ser Leu Leu Thr Val Ser Gly Ala
            180                 185                 190

Trp Ala Lys Gln Met Phe Thr Cys Arg Val Ala His Thr Pro Ser Ser
        195                 200                 205

Thr Asp Trp Val Asp Lys Thr Phe Ser Val Cys Ser Arg Asp Phe
    210                 215                 220

Thr Pro Pro Thr Val Lys Ile Leu Gln Ser Ser Cys Asp Gly Gly
225                 230                 235                 240

His Phe Pro Pro Thr Ile Gln Leu Leu Cys Leu Val Ser Gly Tyr Thr
```

```
                        245                 250                 255
Pro Gly Thr Ile Asp Ile Thr Trp Leu Glu Asp Gly Gln Val Met Asp
            260                 265                 270

Val Asp Leu Ser Thr Ala Ser Thr Gln Glu Gly Glu Leu Ala Ser
        275                 280                 285

Thr Gln Ser Glu Leu Thr Leu Ser Gln Lys His Trp Leu Ser Asp Arg
    290                 295                 300

Thr Tyr Thr Cys Gln Val Thr Tyr Gln Gly His Thr Phe Glu Asp Ser
305                 310                 315                 320

Thr Lys Lys Cys Ala Asp Ser Asn Pro Arg Gly Val Ser Ala Tyr Leu
                325                 330                 335

Ser Arg Pro Ser Pro Phe Asp Leu Phe Ile Arg Lys Ser Pro Thr Ile
            340                 345                 350

Thr Cys Leu Val Val Asp Leu Ala Pro Ser Lys Gly Thr Val Asp Leu
        355                 360                 365

Thr Trp Ser Arg Ala Ser Gly Lys Pro Val Asp His Ser Thr Arg Lys
    370                 375                 380

Glu Glu Lys Gln Arg Asn Gly Thr Leu Thr Val Thr Ser Thr Leu Pro
385                 390                 395                 400

Val Gly Thr Arg Asp Trp Ile Glu Gly Glu Thr Tyr Gln Cys Arg Val
                405                 410                 415

Thr His Pro His Leu Pro Arg Ala Leu Met Arg Ser Thr Thr Lys Thr
            420                 425                 430

Ser Gly Pro Arg Ala Ala Pro Glu Val Tyr Ala Phe Ala Thr Pro Glu
        435                 440                 445

Trp Pro Gly Ser Arg Asp Lys Arg Thr Leu Ala Cys Leu Ile Gln Asn
    450                 455                 460

Phe Met Pro Glu Asp Ile Ser Val Gln Trp Leu His Asn Glu Val Gln
465                 470                 475                 480

Leu Pro Asp Ala Arg His Ser Thr Thr Gln Pro Arg Lys Thr Lys Gly
                485                 490                 495

Ser Gly Phe Phe Val Phe Ser Arg Leu Glu Val Thr Arg Ala Glu Trp
            500                 505                 510

Glu Gln Lys Asp Glu Phe Ile Cys Arg Ala Val His Glu Ala Ala Ser
        515                 520                 525

Pro Ser Gln Thr Val Gln Arg Ala Val Ser Val Asn Pro Gly Lys
    530                 535                 540

<210> SEQ ID NO 49
<211> LENGTH: 464
<212> TYPE: PRT
<213> ORGANISM: Artificial Sequence
<220> FEATURE:
<223> OTHER INFORMATION: an artificially synthesized sequence

<400> SEQUENCE: 49

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
```

```
            65                  70                  75                  80
Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Pro Thr Ser Pro Lys Val Phe
            115                 120                 125

Pro Leu Ser Leu Cys Ser Thr Gln Pro Asp Gly Asn Val Val Ile Ala
        130                 135                 140

Cys Leu Val Gln Gly Phe Phe Pro Gln Glu Pro Leu Ser Val Thr Trp
145                 150                 155                 160

Ser Glu Ser Gly Gln Gly Val Thr Ala Arg Asn Phe Pro Pro Ser Gln
                165                 170                 175

Asp Ala Ser Gly Asp Leu Tyr Thr Thr Ser Ser Gln Leu Thr Leu Pro
            180                 185                 190

Ala Thr Gln Cys Leu Ala Gly Lys Ser Val Thr Cys His Val Lys His
            195                 200                 205

Tyr Thr Asn Pro Ser Gln Asp Val Thr Val Pro Cys Pro Val Pro Ser
        210                 215                 220

Thr Pro Pro Thr Pro Ser Pro Ser Thr Pro Pro Thr Pro Ser Pro Ser
225                 230                 235                 240

Cys Cys His Pro Arg Leu Ser Leu His Arg Pro Ala Leu Glu Asp Leu
                245                 250                 255

Leu Leu Gly Ser Glu Ala Asn Leu Thr Cys Thr Leu Thr Gly Leu Arg
            260                 265                 270

Asp Ala Ser Gly Val Thr Phe Thr Trp Thr Pro Ser Ser Gly Lys Ser
            275                 280                 285

Ala Val Gln Gly Pro Pro Glu Arg Asp Leu Cys Gly Cys Tyr Ser Val
        290                 295                 300

Ser Ser Val Leu Pro Gly Cys Ala Glu Pro Trp Asn His Gly Lys Thr
305                 310                 315                 320

Phe Thr Cys Thr Ala Ala Tyr Pro Glu Ser Lys Thr Pro Leu Thr Ala
                325                 330                 335

Thr Leu Ser Lys Ser Gly Asn Thr Phe Arg Pro Glu Val His Leu Leu
            340                 345                 350

Pro Pro Pro Ser Glu Glu Leu Ala Leu Asn Glu Leu Val Thr Leu Thr
        355                 360                 365

Cys Leu Ala Arg Gly Phe Ser Pro Lys Asp Val Leu Val Arg Trp Leu
370                 375                 380

Gln Gly Ser Gln Glu Leu Pro Arg Glu Lys Tyr Leu Thr Trp Ala Ser
385                 390                 395                 400

Arg Gln Glu Pro Ser Gln Gly Thr Thr Thr Phe Ala Val Thr Ser Ile
                405                 410                 415

Leu Arg Val Ala Ala Glu Asp Trp Lys Lys Gly Asp Thr Phe Ser Cys
            420                 425                 430

Met Val Gly His Glu Ala Leu Pro Leu Ala Phe Thr Gln Lys Thr Ile
        435                 440                 445

Asp Arg Leu Ala Gly Lys Glu Gln Lys Leu Ile Ser Glu Glu Asp Leu
            450                 455                 460

<210> SEQ ID NO 50
<211> LENGTH: 214
<212> TYPE: PRT
<213> ORGANISM: Artificial Sequence
```

```
<220> FEATURE:
<223> OTHER INFORMATION: an artificially synthesized sequence

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 51
<211> LENGTH: 545
<212> TYPE: PRT
<213> ORGANISM: Homo sapiens

<400> SEQUENCE: 51

Gln Pro Pro Pro Pro Pro Asp Ala Thr Cys His Gln Val Arg Ser
1               5                   10                  15

Phe Phe Gln Arg Leu Gln Pro Gly Leu Lys Trp Val Pro Glu Thr Pro
            20                  25                  30

Val Pro Gly Ser Asp Leu Gln Val Cys Leu Pro Lys Gly Pro Thr Cys
        35                  40                  45

Cys Ser Arg Lys Met Glu Glu Lys Tyr Gln Leu Thr Ala Arg Leu Asn
50                  55                  60

Met Glu Gln Leu Leu Gln Ser Ala Ser Met Glu Leu Lys Phe Leu Ile
65                  70                  75                  80

Ile Gln Asn Ala Ala Val Phe Gln Glu Ala Phe Glu Ile Val Val Arg
                85                  90                  95

His Ala Lys Asn Tyr Thr Asn Ala Met Phe Lys Asn Asn Tyr Pro Ser
            100                 105                 110

Leu Thr Pro Gln Ala Phe Glu Phe Val Gly Glu Phe Phe Thr Asp Val
        115                 120                 125
```

```
Ser Leu Tyr Ile Leu Gly Ser Asp Ile Asn Val Asp Asp Met Val Asn
    130                 135                 140

Glu Leu Phe Asp Ser Leu Phe Pro Val Ile Tyr Thr Gln Leu Met Asn
145                 150                 155                 160

Pro Gly Leu Pro Asp Ser Ala Leu Asp Ile Asn Glu Cys Leu Arg Gly
                165                 170                 175

Ala Arg Arg Asp Leu Lys Val Phe Gly Asn Phe Pro Lys Leu Ile Met
            180                 185                 190

Thr Gln Val Ser Lys Ser Leu Gln Val Thr Arg Ile Phe Leu Gln Ala
        195                 200                 205

Leu Asn Leu Gly Ile Glu Val Ile Asn Thr Thr Asp His Leu Lys Phe
210                 215                 220

Ser Lys Asp Cys Gly Arg Met Leu Thr Arg Met Trp Tyr Cys Ser Tyr
225                 230                 235                 240

Cys Gln Gly Leu Met Met Val Lys Pro Cys Gly Gly Tyr Cys Asn Val
                245                 250                 255

Val Met Gln Gly Cys Met Ala Gly Val Val Glu Ile Asp Lys Tyr Trp
            260                 265                 270

Arg Glu Tyr Ile Leu Ser Leu Glu Glu Leu Val Asn Gly Met Tyr Arg
        275                 280                 285

Ile Tyr Asp Met Glu Asn Val Leu Leu Gly Leu Phe Ser Thr Ile His
290                 295                 300

Asp Ser Ile Gln Tyr Val Gln Lys Asn Ala Gly Lys Leu Thr Thr Thr
305                 310                 315                 320

Ile Gly Lys Leu Cys Ala His Ser Gln Gln Arg Gln Tyr Arg Ser Ala
                325                 330                 335

Tyr Tyr Pro Glu Asp Leu Phe Ile Asp Lys Lys Val Leu Lys Val Ala
            340                 345                 350

His Val Glu His Glu Thr Leu Ser Ser Arg Arg Arg Glu Leu Ile
        355                 360                 365

Gln Lys Leu Lys Ser Phe Ile Ser Phe Tyr Ser Ala Leu Pro Gly Tyr
370                 375                 380

Ile Cys Ser His Ser Pro Val Ala Glu Asn Asp Thr Leu Cys Trp Asn
385                 390                 395                 400

Gly Gln Glu Leu Val Glu Arg Tyr Ser Gln Lys Ala Ala Arg Asn Gly
                405                 410                 415

Met Lys Asn Gln Phe Asn Leu His Glu Leu Lys Met Lys Gly Pro Glu
            420                 425                 430

Pro Val Val Ser Gln Ile Ile Asp Lys Leu Lys His Ile Asn Gln Leu
        435                 440                 445

Leu Arg Thr Met Ser Met Pro Lys Gly Arg Val Leu Asp Lys Asn Leu
450                 455                 460

Asp Glu Glu Gly Phe Glu Ala Gly Asp Cys Gly Asp Asp Glu Asp
465                 470                 475                 480

Cys Ile Gly Gly Ala Gly Asp Gly Met Ile Lys Val Lys Asn Gln Leu
                485                 490                 495

Arg Phe Leu Ala Glu Leu Ala Tyr Asp Leu Asp Val Asp Asp Ala Pro
            500                 505                 510

Gly Asn Ser Gln Gln Ala Thr Pro Lys Asp Asn Glu Ile Ser Thr Phe
        515                 520                 525

His Asn Leu Gly Asn Val His Ser Pro Leu Lys His His His His
530                 535                 540

His
```

545

<210> SEQ ID NO 52
<211> LENGTH: 451
<212> TYPE: PRT
<213> ORGANISM: Artificial Sequence
<220> FEATURE:
<223> OTHER INFORMATION: an artificially synthesized sequence

<400> SEQUENCE: 52

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Thr Ala Val Tyr Tyr Cys
                85                  90                  95

Ala Arg Pro Arg Trp Glu Thr Ala Ile Ser Ser Asp Ala Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Tyr Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
```

355                 360                 365
Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
        435                 440                 445

Leu Ser Pro
        450

<210> SEQ ID NO 53
<211> LENGTH: 443
<212> TYPE: PRT
<213> ORGANISM: Artificial Sequence
<220> FEATURE:
<223> OTHER INFORMATION: an artificially synthesized sequence

<400> SEQUENCE: 53

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr His
                20                  25                  30

Met Ser Trp Val Arg Gln Ala Pro Gly Lys Gly Leu Glu Trp Ile Gly
            35                  40                  45

Val Ile Asn Ser Ala Gly Asn Thr Tyr Tyr Ala Ser Trp Ala Lys Gly
        50                  55                  60

Arg Phe Thr Val Ser Lys Thr Ser Thr Val Asp Leu Asn Leu Thr
65                  70                  75                  80

Ser Leu Thr Thr Glu Asp Thr Ala Thr Tyr Phe Cys Ala Arg Tyr Val
                85                  90                  95

Phe Ser Ser Gly Ser His Asp Ile Trp Gly Pro Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
        210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys

```
                    260                 265                 270
Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Tyr Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
        435                 440

<210> SEQ ID NO 54
<211> LENGTH: 443
<212> TYPE: PRT
<213> ORGANISM: Artificial Sequence
<220> FEATURE:
<223> OTHER INFORMATION: an artificially synthesized sequence

<400> SEQUENCE: 54

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr His
            20                  25                  30

Met Ser Trp Val Arg Gln Ala Pro Gly Lys Gly Leu Glu Trp Ile Gly
        35                  40                  45

Val Ile Asn Ser Ala Gly Asn Thr Tyr Tyr Ala Ser Trp Ala Lys Gly
    50                  55                  60

Arg Phe Thr Val Ser Lys Thr Ser Thr Val Asp Leu Asn Leu Thr
65                  70                  75                  80

Ser Leu Thr Thr Glu Asp Thr Ala Thr Tyr Phe Cys Ala Arg Tyr Val
                85                  90                  95

Phe Ser Ser Gly Ser His Asp Ile Trp Gly Pro Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
```

```
            180                 185                 190
Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
        210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Asp Ala Tyr Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
        435                 440

<210> SEQ ID NO 55
<211> LENGTH: 443
<212> TYPE: PRT
<213> ORGANISM: Artificial Sequence
<220> FEATURE:
<223> OTHER INFORMATION: an artificially synthesized sequence

<400> SEQUENCE: 55

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr His
            20                  25                  30

Met Ser Trp Val Arg Gln Ala Pro Gly Lys Gly Leu Glu Trp Ile Gly
        35                  40                  45

Val Ile Asn Ser Ala Gly Asn Thr Tyr Tyr Ala Ser Trp Ala Lys Gly
    50                  55                  60

Arg Phe Thr Val Ser Lys Thr Ser Thr Thr Val Asp Leu Asn Leu Thr
65                  70                  75                  80

Ser Leu Thr Thr Glu Asp Thr Ala Thr Tyr Phe Cys Ala Arg Tyr Val
                85                  90                  95

Phe Ser Ser Gly Ser His Asp Ile Trp Gly Pro Gly Thr Leu Val Thr
```

```
                100             105             110
Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135             140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
                195                 200                 205

Val Asp Lys Lys Val Glu Pro Lys Ser Cys Asp Lys Thr His Thr Cys
            210                 215                 220

Pro Pro Cys Pro Ala Pro Glu Leu Arg Gly Gly Pro Lys Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
                275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
                435                 440

<210> SEQ ID NO 56
<211> LENGTH: 451
<212> TYPE: PRT
<213> ORGANISM: Artificial Sequence
<220> FEATURE:
<223> OTHER INFORMATION: an artificially synthesized sequence

<400> SEQUENCE: 56

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
```

```
                    20                  25                  30
Ala Ile Ser Trp Val Arg Gln Ala Pro Gly Gln Gly Leu Glu Trp Met
                35                  40                  45
Gly Gly Ile Ile Pro Ile Phe Gly Thr Ala Asn Tyr Ala Gln Lys Phe
            50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Pro Arg Trp Glu Thr Ala Ile Ser Ser Asp Ala Phe Asp Ile
            100                 105                 110
Trp Gly Gln Gly Thr Met Val Thr Val Ser Ser Ala Ser Thr Lys Gly
            115                 120                 125
Pro Ser Val Phe Pro Leu Ala Pro Ser Ser Lys Ser Thr Ser Gly Gly
        130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
            195                 200                 205
Asn His Lys Pro Ser Asn Thr Lys Val Asp Lys Lys Val Glu Pro Lys
        210                 215                 220
Ser Cys Asp Lys Thr His Thr Cys Pro Pro Cys Pro Ala Pro Glu Leu
225                 230                 235                 240
Arg Arg Gly Pro Lys Val Phe Leu Phe Pro Pro Lys Pro Lys Asp Thr
                245                 250                 255
Leu Tyr Ile Thr Arg Glu Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Asp Glu Leu Thr Lys Asn Gln
        355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Tyr His Val Thr Arg Lys Glu Leu Ser
        435                 440                 445
```

Leu Ser Pro
    450

<210> SEQ ID NO 57
<211> LENGTH: 451
<212> TYPE: PRT
<213> ORGANISM: Artificial Sequence
<220> FEATURE:
<223> OTHER INFORMATION: an artificially synthesized sequence

<400> SEQUENCE: 57

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Arg Trp Glu Thr Ala Ile Ser Ser Asp Ala Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Arg Gly Gly Pro Lys Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

-continued

```
Gln Val Tyr Thr Leu Pro Pro Ser Arg Asp Glu Leu Thr Lys Asn Gln
                355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
                435                 440                 445

Leu Ser Pro
    450

<210> SEQ ID NO 58
<211> LENGTH: 443
<212> TYPE: PRT
<213> ORGANISM: Artificial Sequence
<220> FEATURE:
<223> OTHER INFORMATION: an artificially synthesized sequence

<400> SEQUENCE: 58

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr His
                20                  25                  30

Met Ser Trp Val Arg Gln Ala Pro Gly Lys Gly Leu Glu Trp Ile Gly
            35                  40                  45

Val Ile Asn Ser Ala Gly Asn Thr Tyr Tyr Ala Ser Trp Ala Lys Gly
    50                  55                  60

Arg Phe Thr Val Ser Lys Thr Ser Thr Val Asp Leu Asn Leu Thr
65                  70                  75                  80

Ser Leu Thr Thr Glu Asp Thr Ala Thr Tyr Phe Cys Ala Arg Tyr Val
                85                  90                  95

Phe Ser Ser Gly Ser His Asp Ile Trp Gly Pro Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Arg Arg Gly Pro Lys Val Phe Leu
225                 230                 235                 240

Phe Pro Pro Lys Pro Lys Asp Thr Leu Tyr Ile Thr Arg Glu Pro Glu
                245                 250                 255
```

Val Thr Cys Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Tyr
            420                 425                 430

His Val Thr Arg Lys Glu Leu Ser Leu Ser Pro
        435                 440

<210> SEQ ID NO 59
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 59

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 60
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 60

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

```
Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
            210

<210> SEQ ID NO 61
<211> LENGTH: 452
<212> TYPE: PRT
<213> ORGANISM: Artificial Sequence
<220> FEATURE:
<223> OTHER INFORMATION: an artificially synthesized sequence

<400> SEQUENCE: 61

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Pro Val Pro Gly Val Tyr Tyr Tyr Tyr Gly Met Asp
            100                 105                 110

Val Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240
```

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro
    450

<210> SEQ ID NO 62
<211> LENGTH: 215
<212> TYPE: PRT
<213> ORGANISM: Artificial Sequence
<220> FEATURE:
<223> OTHER INFORMATION: an artificially synthesized sequence

<400> SEQUENCE: 62

Glu Ile Val Leu Thr Gln Ser Pro Ala Thr Leu Ser Val Ser Pro Gly
1               5                   10                  15

Glu Arg Val Thr Leu Ser Cys Arg Ala Ser Gln Ser Val Ala Asn His
            20                  25                  30

Leu Ala Trp Tyr Gln Gln Lys Pro Gly Gln Pro Pro Ser Leu Leu Ile
        35                  40                  45

Tyr Asp Ala Ser Thr Arg Ala Thr Asp Val Pro Ala Arg Phe Ser Gly
    50                  55                  60

Ser Gly Ser Gly Thr Glu Phe Thr Leu Ser Ile Ser Gly Leu Gln Ser
65                  70                  75                  80

Glu Asp Phe Ala Val Tyr Tyr Cys Gln Gln Tyr Lys Asp Trp Pro Pro
                85                  90                  95

Leu Thr Phe Gly Gly Gly Thr Lys Val Glu Phe Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
        180                 185                 190

Tyr Ala Cys Glu Val Thr His Gln Gly Leu Ser Ser Pro Val Thr Lys
    195                 200                 205

Ser Phe Asn Arg Gly Glu Cys
    210                 215

<210> SEQ ID NO 63
<211> LENGTH: 452
<212> TYPE: PRT
<213> ORGANISM: Artificial Sequence
<220> FEATURE:
<223> OTHER INFORMATION: an artificially synthesized sequence

<400> SEQUENCE: 63

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Pro Val Pro Gly Val Tyr Tyr Tyr Tyr Gly Met Asp
            100                 105                 110

Val Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

```
Val Glu Val His Asn Ala Lys Thr Lys Pro Arg Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Val Glu Lys Thr Ile Ser Lys Ala Lys Gly Gln Pro Arg Glu
                340                 345                 350

Pro Gln Val Tyr Thr Leu Pro Pro Ser Arg Asp Glu Leu Thr Lys Asn
                355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Tyr His Tyr Thr Gln Lys Ser Leu
                435                 440                 445

Ser Leu Ser Pro
    450

<210> SEQ ID NO 64
<211> LENGTH: 449
<212> TYPE: PRT
<213> ORGANISM: Artificial Sequence
<220> FEATURE:
<223> OTHER INFORMATION: an artificially synthesized sequence

<400> SEQUENCE: 64

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
                100                 105                 110

Ser Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190
```

Ser Ser Leu Gly Thr Gln Thr Tyr Ile Cys Asn Val Asn His Lys Pro
        195                 200                 205

Ser Asn Thr Lys Val Asp Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 65
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

```
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 66
<211> LENGTH: 460
<212> TYPE: PRT
<213> ORGANISM: Artificial Sequence
<220> FEATURE:
<223> OTHER INFORMATION: an artificially synthesized sequence

<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Pro Thr Ser Pro Lys Val Phe Pro Leu Ser Leu
        115                 120                 125

Cys Ser Thr Gln Pro Asp Gly Asn Val Val Ile Ala Cys Leu Val Gln
130                 135                 140

Gly Phe Phe Pro Gln Glu Pro Leu Ser Val Thr Trp Ser Glu Ser Gly
145                 150                 155                 160

Gln Gly Val Thr Ala Arg Asn Phe Pro Pro Ser Gln Asp Ala Ser Gly
                165                 170                 175

Asp Leu Tyr Thr Thr Ser Ser Gln Leu Thr Leu Pro Ala Thr Gln Cys
            180                 185                 190

Leu Ala Gly Lys Ser Val Thr Cys His Val Lys His Tyr Thr Asn Pro
        195                 200                 205

Ser Gln Asp Val Thr Val Pro Cys Pro Val Pro Ser Thr Pro Pro Thr
210                 215                 220

Pro Ser Pro Ser Thr Pro Pro Thr Pro Ser Pro Ser Cys Cys His Pro
225                 230                 235                 240
```

```
Arg Leu Ser Leu His Arg Pro Ala Leu Glu Asp Leu Leu Leu Gly Ser
                245                 250                 255

Glu Ala Asn Leu Thr Cys Thr Leu Thr Gly Leu Arg Asp Ala Ser Gly
        260                 265                 270

Val Thr Phe Thr Trp Thr Pro Ser Ser Gly Lys Ser Ala Val Gln Gly
            275                 280                 285

Pro Pro Glu Arg Asp Leu Cys Gly Cys Tyr Ser Val Ser Ser Val Leu
    290                 295                 300

Pro Gly Cys Ala Glu Pro Trp Asn His Gly Lys Thr Phe Thr Cys Thr
305                 310                 315                 320

Ala Ala Tyr Pro Glu Ser Lys Thr Pro Leu Thr Ala Thr Leu Ser Lys
                325                 330                 335

Ser Gly Asn Thr Phe Arg Pro Glu Val His Leu Leu Pro Pro Pro Ser
        340                 345                 350

Glu Glu Leu Ala Leu Asn Glu Leu Val Thr Leu Thr Cys Leu Ala Arg
    355                 360                 365

Gly Phe Ser Pro Lys Asp Val Leu Val Arg Trp Leu Gln Gly Ser Gln
    370                 375                 380

Glu Leu Pro Arg Glu Lys Tyr Leu Thr Trp Ala Ser Arg Gln Glu Pro
385                 390                 395                 400

Ser Gln Gly Thr Thr Thr Phe Ala Val Thr Ser Ile Leu Arg Val Ala
                405                 410                 415

Ala Glu Asp Trp Lys Lys Gly Asp Thr Phe Ser Cys Met Val Gly His
                420                 425                 430

Glu Ala Leu Pro Leu Ala Phe Thr Gln Lys Thr Ile Asp Arg Leu Ala
                435                 440                 445

Gly Lys Glu Gln Lys Leu Ile Ser Glu Glu Asp Leu
    450                 455                 460

<210> SEQ ID NO 67
<211> LENGTH: 219
<212> TYPE: PRT
<213> ORGANISM: Artificial Sequence
<220> FEATURE:
<223> OTHER INFORMATION: an artificially synthesized sequence

<400> SEQUENCE: 67

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140
```

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 68
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 68

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

```
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
                355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Leu His Glu
                420                 425                 430
Ala Leu His Ser His Tyr Thr Gln Lys Ser Leu Ser Leu Ser Pro
            435                 440                 445

<210> SEQ ID NO 69
<211> LENGTH: 449
<212> TYPE: PRT
<213> ORGANISM: Artificial Sequence
<220> FEATURE:
<223> OTHER INFORMATION: an artificially synthesized sequence

<400> SEQUENCE: 69

Glu Val Gln Leu Val Glu Ser Gly Gly Gly Leu Val Gln Pro Gly Gly
1               5                   10                  15
Ser Leu Arg Leu Ser Cys Ala Val Ser Gly Tyr Ser Ile Thr Ser Gly
            20                  25                  30
Tyr Ser Trp Asn Trp Ile Arg Gln Ala Pro Gly Lys Gly Leu Glu Trp
        35                  40                  45
Val Ala Ser Ile Thr Tyr Asp Gly Ser Thr Asn Tyr Asn Pro Ser Val
    50                  55                  60
Lys Gly Arg Ile Thr Ile Ser Arg Asp Asp Ser Lys Asn Thr Phe Tyr
65                  70                  75                  80
Leu Gln Met Asn Ser Leu Arg Ala Glu Asp Thr Ala Val Tyr Tyr Cys
                85                  90                  95
Ala Arg Gly Ser His Tyr Phe Gly His Trp His Phe Ala Val Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
```

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Leu
            420                 425                 430

His Glu Ala Leu His Ser His Tyr Thr Gln Lys Ser Leu Ser Leu Ser
        435                 440                 445

Pro

<210> SEQ ID NO 70
<211> LENGTH: 218
<212> TYPE: PRT
<213> ORGANISM: Artificial Sequence
<220> FEATURE:
<223> OTHER INFORMATION: an artificially synthesized sequence

<400> SEQUENCE: 70

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln

```
                115                 120                 125
Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
210                 215

<210> SEQ ID NO 71
<211> LENGTH: 365
<212> TYPE: PRT
<213> ORGANISM: Homo sapiens

<400> SEQUENCE: 71

Met Gly Val Pro Arg Pro Gln Pro Trp Ala Leu Gly Leu Leu Leu Phe
1               5                   10                  15

Leu Leu Pro Gly Ser Leu Gly Ala Glu Ser His Leu Ser Leu Leu Tyr
                20                  25                  30

His Leu Thr Ala Val Ser Ser Pro Ala Pro Gly Thr Pro Ala Phe Trp
            35                  40                  45

Val Ser Gly Trp Leu Gly Pro Gln Gln Tyr Leu Ser Tyr Asn Ser Leu
    50                  55                  60

Arg Gly Glu Ala Glu Pro Cys Gly Ala Trp Val Trp Glu Asn Gln Val
65                  70                  75                  80

Ser Trp Tyr Trp Glu Lys Glu Thr Thr Asp Leu Arg Ile Lys Glu Lys
                85                  90                  95

Leu Phe Leu Glu Ala Phe Lys Ala Leu Gly Gly Lys Gly Pro Tyr Thr
            100                 105                 110

Leu Gln Gly Leu Leu Gly Cys Glu Leu Gly Pro Asp Asn Thr Ser Val
        115                 120                 125

Pro Thr Ala Lys Phe Ala Leu Asn Gly Glu Glu Phe Met Asn Phe Asp
    130                 135                 140

Leu Lys Gln Gly Thr Trp Gly Gly Asp Trp Pro Glu Ala Leu Ala Ile
145                 150                 155                 160

Ser Gln Arg Trp Gln Gln Asp Lys Ala Ala Asn Lys Glu Leu Thr
                165                 170                 175

Phe Leu Leu Phe Ser Cys Pro His Arg Leu Arg Glu His Leu Glu Arg
            180                 185                 190

Gly Arg Gly Asn Leu Glu Trp Lys Glu Pro Pro Ser Met Arg Leu Lys
        195                 200                 205

Ala Arg Pro Ser Ser Pro Gly Phe Ser Val Leu Thr Cys Ser Ala Phe
    210                 215                 220

Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
                245                 250                 255

Phe His Ala Ser Ser Ser Leu Thr Val Lys Ser Gly Asp Glu His His
            260                 265                 270
```

```
Tyr Cys Cys Ile Val Gln His Ala Gly Leu Ala Gln Pro Leu Arg Val
            275                 280                 285

Glu Leu Glu Ser Pro Ala Lys Ser Ser Val Leu Val Gly Ile Val
290                 295                 300

Ile Gly Val Leu Leu Leu Thr Ala Ala Val Gly Gly Ala Leu Leu
305                 310                 315                 320

Trp Arg Arg Met Arg Ser Gly Leu Pro Ala Pro Trp Ile Ser Leu Arg
                325                 330                 335

Gly Asp Asp Thr Gly Val Leu Leu Pro Thr Pro Gly Glu Ala Gln Asp
                340                 345                 350

Ala Asp Leu Lys Asp Val Asn Val Ile Pro Ala Thr Ala
            355                 360                 365
```

<210> SEQ ID NO 72
<211> LENGTH: 119
<212> TYPE: PRT
<213> ORGANISM: Homo sapiens

<400> SEQUENCE: 72

```
Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
                20                  25                  30

His Pro Ala Glu Asn Gly Lys Ser Asn Phe Leu Asn Cys Tyr Val Ser
            35                  40                  45

Gly Phe His Pro Ser Asp Ile Glu Val Asp Leu Leu Lys Asn Gly Glu
        50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115
```

<210> SEQ ID NO 73
<211> LENGTH: 290
<212> TYPE: PRT
<213> ORGANISM: Mus musculus

<400> SEQUENCE: 73

```
Met Gly Met Pro Leu Pro Trp Ala Leu Ser Leu Leu Val Leu Leu
1               5                   10                  15

Pro Gln Thr Trp Gly Ser Glu Thr Arg Pro Pro Leu Met Tyr His Leu
                20                  25                  30

Thr Ala Val Ser Asn Pro Ser Thr Gly Leu Pro Ser Phe Trp Ala Thr
            35                  40                  45

Gly Trp Leu Gly Pro Gln Gln Tyr Leu Thr Tyr Asn Ser Leu Arg Gln
        50                  55                  60

Glu Ala Asp Pro Cys Gly Ala Trp Met Trp Glu Asn Gln Val Ser Trp
65                  70                  75                  80

Tyr Trp Glu Lys Glu Thr Thr Asp Leu Lys Ser Lys Glu Gln Leu Phe
                85                  90                  95

Leu Glu Ala Leu Lys Thr Leu Glu Lys Ile Leu Asn Gly Thr Tyr Thr
            100                 105                 110
```

-continued

Leu Gln Gly Leu Leu Gly Cys Glu Leu Ala Ser Asp Asn Ser Ser Val
         115                 120                 125

Pro Thr Ala Val Phe Ala Leu Asn Gly Glu Glu Phe Met Lys Phe Asn
130                 135                 140

Pro Arg Ile Gly Asn Trp Thr Gly Glu Trp Pro Glu Thr Glu Ile Val
145                 150                 155                 160

Ala Asn Leu Trp Met Lys Gln Pro Asp Ala Ala Arg Lys Glu Ser Glu
                165                 170                 175

Phe Leu Leu Asn Ser Cys Pro Glu Arg Leu Leu Gly His Leu Glu Arg
                180                 185                 190

Gly Arg Arg Asn Leu Glu Trp Lys Glu Pro Pro Ser Met Arg Leu Lys
            195                 200                 205

Ala Arg Pro Gly Asn Ser Gly Ser Ser Val Leu Thr Cys Ala Ala Phe
        210                 215                 220

Ser Phe Tyr Pro Pro Glu Leu Lys Phe Arg Phe Leu Arg Asn Gly Leu
225                 230                 235                 240

Ala Ser Gly Ser Gly Asn Cys Ser Thr Gly Pro Asn Gly Asp Gly Ser
                245                 250                 255

Phe His Ala Trp Ser Leu Leu Glu Val Lys Arg Gly Asp Glu His His
                260                 265                 270

Tyr Gln Cys Gln Val Glu His Glu Gly Leu Ala Gln Pro Leu Thr Val
            275                 280                 285

Asp Leu
    290

<210> SEQ ID NO 74
<211> LENGTH: 119
<212> TYPE: PRT
<213> ORGANISM: Mus musculus

<400> SEQUENCE: 74

Met Ala Arg Ser Val Thr Leu Val Phe Leu Val Leu Val Ser Leu Thr
1               5                   10                  15

Gly Leu Tyr Ala Ile Gln Lys Thr Pro Gln Ile Gln Val Tyr Ser Arg
            20                  25                  30

His Pro Pro Glu Asn Gly Lys Pro Asn Ile Leu Asn Cys Tyr Val Thr
        35                  40                  45

Gln Phe His Pro Pro His Ile Glu Ile Gln Met Leu Lys Asn Gly Lys
    50                  55                  60

Lys Ile Pro Lys Val Glu Met Ser Asp Met Ser Phe Ser Lys Asp Trp
65                  70                  75                  80

Ser Phe Tyr Ile Leu Ala His Thr Glu Phe Thr Pro Thr Glu Thr Asp
                85                  90                  95

Thr Tyr Ala Cys Arg Val Lys His Ala Ser Met Ala Glu Pro Lys Thr
            100                 105                 110

Val Tyr Trp Asp Arg Asp Met
        115

<210> SEQ ID NO 75
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 75

Gln Val Gln Leu Gln Glu Ser Gly Pro Gly Leu Val Lys Pro Ser Glu

-continued

```
1               5               10              15
Thr Leu Ser Leu Thr Cys Ala Val Ser Gly His Ser Ile Ser His Asp
                20                  25                  30
His Ala Trp Ser Trp Val Arg Gln Pro Pro Gly Glu Gly Leu Glu Trp
                35                  40                  45
Ile Gly Phe Ile Ser Tyr Ser Gly Ile Thr Asn Tyr Asn Pro Ser Leu
                50                  55                  60
Gln Gly Arg Val Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ser Leu Ala Arg Thr Thr Ala Met Asp Tyr Trp Gly Glu Gly
                100                 105                 110
Thr Leu Val Thr Val Ser Ser Ala Ser Thr Lys Gly Pro Ser Val Phe
                115                 120                 125
Pro Leu Ala Pro Ser Ser Lys Ser Thr Ser Gly Gly Thr Ala Ala Leu
                130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
                195                 200                 205
Ser Asn Thr Lys Val Asp Lys Lys Val Glu Pro Lys Ser Cys Asp Lys
                210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
                275                 280                 285
Ala Lys Thr Lys Pro Arg Glu Glu Gln Tyr Asn Ser Thr Tyr Arg Val
                290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Tyr Pro Ala Pro Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Arg Asp Glu Leu Thr Lys Asn Gln Val Ser Leu Thr
                355                 360                 365
Cys Leu Val Lys Gly Phe Tyr Pro Ser Asp Ile Ala Val Glu Trp Glu
                370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
```

```
Ala Leu His Asn His Tyr Thr Gln Lys Ser Leu Ser Leu Ser Pro
        435                 440                 445

<210> SEQ ID NO 76
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 76

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Asp Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Glu Glu Lys
                325                 330                 335

Thr Ile Ser Lys Ala Lys Gly Gln Pro Arg Glu Pro Gln Val Tyr Thr
            340                 345                 350
```

-continued

Leu Pro Pro Ser Arg Asp Glu Leu Thr Lys Asn Gln Val Ser Leu Thr
         355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
            435                 440                 445

<210> SEQ ID NO 77
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 77

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 78
<211> LENGTH: 214
<212> TYPE: PRT
<213> ORGANISM: Artificial Sequence
<220> FEATURE:
<223> OTHER INFORMATION: an artificially synthesized sequence

```
<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210
```

DRUG CONTAINING CARRIER INTO CELL FOR FORMING IMMUNE COMPLEX

CROSS-REFERENCE TO RELATED APPLICATIONS

This application is a continuation of U.S. application Ser. No. 14/361,013, filed on May 28, 2014, which is the National Stage of International Application Serial No. PCT/JP2012/081185, filed on Nov. 30, 2012, which claims the benefit of Japanese Application Serial No. 2012-123773, filed on May 30, 2012, and PCT Application Serial No. PCT/JP2011/077619, filed on Nov. 30, 2011.

TECHNICAL FIELD

The present invention provides uses of antigen-binding molecules for eliminating antigens from plasma; methods for eliminating antigens from plasma, which comprise administering antigen-binding molecules; pharmaceutical compositions comprising antigen-binding molecules that are capable of eliminating antigens from plasma; methods of screening for antigen-binding molecules for eliminating antigens from plasma; and methods for producing antigen-binding molecules for eliminating antigens from plasma.

BACKGROUND ART

Antibodies are drawing attention as pharmaceuticals as they have a high stability in plasma and have few side effects. At present, a number of IgG-type antibody pharmaceuticals are available on the market and many antibody pharmaceuticals are currently under development (Non-patent Documents 1 and 2). Meanwhile, various technologies applicable to second-generation antibody pharmaceuticals have been reported, including those that enhance effector function, antigen-binding ability, pharmacokinetics, and stability, and those that reduce the risk of immunogenicity (Non-patent Document 3). In general, the requisite dose of an antibody pharmaceutical is very high. This in turn has led to problems such as high production cost, as well as the difficulty in producing subcutaneous formulations. In theory, the dose of an antibody pharmaceutical may be reduced by improving antibody pharmacokinetics or improving the affinity between antibodies and antigens.

The literature has reported methods for improving antibody pharmacokinetics using artificial substitution of amino acids in constant regions (Non-patent Documents 4 and 5). Similarly, affinity maturation has been reported as a technology for enhancing antigen-binding ability or antigen-neutralizing activity (Non-patent Document 6). This technology enables enhancement of antigen-binding activity by introducing amino acid mutations into the CDR region of a variable region or such. The enhancement of antigen-binding ability enables improvement of in vitro biological activity or reduction of dosage, and further enables improvement of in vivo (in the body) efficacy (Non-patent Document 7).

Meanwhile, the antigen-neutralizing capacity of a single antibody molecule depends on its affinity. By increasing the affinity, an antigen can be neutralized by a smaller amount of an antibody. Various methods can be used to enhance antibody affinity (Non-patent Document 6). Furthermore, if the affinity could be made infinite by covalently binding the antibody to the antigen, a single antibody molecule could neutralize one antigen molecule (a divalent antibody can neutralize two antigen molecules). However, conventional methods have a limitation in which a single antibody molecule binds to one single antigen molecule (two antigens when it is bivalent). However, it has been recently reported that a single antigen-binding molecule can bind to a plurality of antigen molecules by using an antigen-binding molecule that binds to antigen in a pH-dependent manner (Patent Document 1 and Non-Patent Document 8). A pH-dependent antigen-binding molecule binds strongly to an antigen under the neutral condition in plasma, and releases the antigen under the acidic condition in the endosome. Furthermore, after release of the antigen, the antigen-binding molecule is released into the plasma via FcRn and binds to an antigen again; therefore, a single pH-dependent antigen-binding molecule can repeatedly bind to a number of antigens.

Furthermore, since pH-dependent antigen-binding molecules which have been modified to enhance FcRn binding under a neutral condition (pH7.4) have the advantage of being able to bind repeatedly to antigens and the effect of eliminating antigens from plasma, administration of such antigen-binding molecules has been reported to enable antigen elimination from plasma (Patent Document 2). Conventional pH-dependent antigen-binding molecules comprising an IgG antibody Fc region hardly show FcRn binding under neutral conditions. Therefore, uptake of complexes formed between an antigen-binding molecule and an antigen into cells may be mainly through non-specific uptake. According to this report, pH-dependent antigen-binding molecules that have been modified to enhance FcRn binding under a neutral condition (pH7.4) can accelerate antigen elimination more than conventional pH-dependent antigen-binding molecules comprising an IgG antibody Fc region (Patent Document 2).

Since antigens have very short retentivity in plasma compared to antibodies having an FcRn-mediated recycling mechanism, binding of an antigen in plasma to an antibody having a recycling mechanism (wherein the binding is not pH-dependent) lengthens the normal retentivity in plasma and increases the plasma antigen concentration. For example, when a plasma antigen has multiple types of physiological functions, even if one type of physiological activity is blocked by antibody binding, the plasma concentration of the antigen may exacerbate symptoms caused by other physiological functions due to antibody binding. From such viewpoint, eliminating plasma antigens is sometimes favorable, and methods similar to those described above for making modifications to the Fc region to enhance FcRn binding with the objective of accelerating antigen elimination have been reported, but other methods for accelerating antigen elimination have not been reported so far.

Prior art documents of the present invention are shown below.

PRIOR ART DOCUMENTS

Patent Documents

[Patent Document 1] International Publication WO2009/125825
[Patent Document 2] International Publication WO2011/122011

Non-Patent Documents

[Non-patent Document 1] Monoclonal antibody successes in the clinic, Janice M Reichert, Clark J Rosensweig, Laura B Faden & Matthew C Dewitz, Nat. Biotechnol. (2005) 23, 1073-1078

[Non-patent Document 2] Pavlou A K, Belsey M J., The therapeutic antibodies market to 2008., Eur. J. Pharm. Biopharm. (2005) 59 (3), 389-396

[Non-patent Document 3] Kim S J, Park Y, Hong H J., Antibody engineering for the development of therapeutic antibodies, Mol. Cells. (2005) 20 (1), 17-29

[Non-patent Document 4] Hinton P R, Xiong J M, Johlfs M G, Tang M T, Keller S, Tsurushita N, J. Immunol. (2006) 176 (1), 346-356

[Non-patent Document 5] Ghetie V, Popov S, Borvak J, Radu C, Matesoi D, Medesan C, Ober R J, Ward E S., Nat. Biotechnol. (1997) 15 (7), 637-640

[Non-patent Document 6] Rajpal A, Beyaz N, Haber L, Cappuccilli G, Yee H, Bhatt R R, Takeuchi T, Lerner R A, Crea R., Proc. Natl. Acad. Sci. USA. (2005) 102 (24), 8466-8471

[Non-patent Document 7] Wu H, Pfarr D S, Johnson S, Brewah Y A, Woods R M, Patel N K, White W I, Young J F, Kiener P A., J. Mol. Biol. (2007) 368, 652-665

[Non-patent Document 8] Igawa T, et al., Nat. Biotechnol. (2010) 28, 1203-1207

SUMMARY OF THE INVENTION

Problems to be Solved by the Invention

The present invention was achieved in view of the above circumstances. An objective of the present invention is to provide uses of antigen-binding molecules for eliminating antigens from plasma; methods for eliminating antigens from plasma, which comprise administering antigen-binding molecules; pharmaceutical compositions comprising antigen-binding molecules that are capable of eliminating antigens from plasma; methods of screening for antigen-binding molecules for eliminating antigens from plasma; and methods for producing antigen-binding molecules for eliminating antigens from plasma.

Means for Solving the Problems

The present inventors conducted dedicated studies to achieve the above-described objectives. As a result, the present inventors produced antigen-binding molecules comprising (i) an Fc region and (ii) two or more antigen-binding domains where at least one of the domains is an antigen-binding domain whose antigen binding activity varies depending on the ion concentration condition, which are antigen-binding molecules that can form an immune complex comprising (a) two or more of the antigen-binding molecules and (b) two or more antigen molecules comprising two or more antigenic binding units. Furthermore, the present inventors discovered that the antigen-binding molecules can be used to eliminate antigens from plasma. Furthermore, the present inventors discovered that the antigen-binding molecules are useful as pharmaceutical compositions, and they produced methods for eliminating antigens from plasma, which comprise administering the antigen-binding molecules. Furthermore, the present inventors discovered methods of screening for antigen-binding molecules having the aforementioned properties, and created methods for producing the molecules, thereby completing the present invention.

More specifically, the present invention provides the following:

[1] use of an antigen-binding molecule comprising
(i) an Fc region and
(ii) two or more antigen-binding domains,
wherein at least one of the domains is an antigen-binding domain of which antigen-binding activity varies depending on an ion concentration condition, and
wherein the antigen-binding molecule can form an immune complex which comprises
(a) two or more of the antigen-binding molecules and
(b) two or more antigens, wherein the antigens comprise two or more antigenic binding units, for eliminating the antigens from plasma;

[2] the use of [1], wherein the ion concentration condition is a calcium ion concentration condition;

[3] the use of [2], wherein the antigen-binding domain has an antigen-binding activity under a low calcium-ion concentration condition that is lower than the antigen-binding activity under a high calcium-ion concentration condition;

[4] the use of any one of [1] to [3], wherein the ion concentration condition is a pH condition;

[5] the use of [4], wherein the antigen-binding domain has an antigen binding activity in an acidic pH range that is lower than the antigen-binding activity in a neutral pH range condition;

[6] the use of any one of [1] to [5], wherein the antigens comprising two or more antigenic binding units are multimers;

[7] the use of [6], wherein the antigen is any one of GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (myostatin), GDF-9, GDF-15 (MIC-1), TNF, TNF-alphabeta, TNF-beta2, TNFSF10 (TRAIL, Apo-2 ligand, TL2), TNFSF11 (TRANCE/RANK ligand, ODF, OPG ligand), TNFSF12 (TWEAK, Apo-3 ligand, DR3 ligand), TNFSF13 (APRIL, TALL2), TNFSF13B (BAFF, BLYS, TALL1, THANK, TNFSF20), TNFSF14 (LIGHT, HVEM ligand, LTg), TNFSF15 (TL1A/VEGI), TNFSF18 (GITR ligand, AITR ligand, TL6), TNFSF1A (TNF-a, Cachectin, DIF, TNFSF2), TNFSF1B (TNF-bLTa, TNFSF1), TNFSF3 (LTb, TNFC, p33), TNFSF4 (OX40 ligandgp34, TXGP1), TNFSF5 (CD40 ligand, CD154, gp39, HIGM1, IMD3, TRAP), TNFSF6 (Fas ligand, Apo-1 ligand, APT1 ligand), TNFSF7 (CD27 CD70), TNFSF8 (CD30 ligand, CD153), TNFSF9 (4-1BB ligand, CD137 ligand), VEGF, IgE, IgA, IgG, IgM, RANKL, TGF-alpha, TGF-beta, TGF-beta Pan Specific, and IL-8;

[8] the use of any one of [1] to [5], wherein the antigens comprising two or more antigenic binding units are monomers;

[9] the use of any one of [1] to [8], wherein the antigen-binding molecules are a multispecific or multiparatopic antigen-binding molecule, or a cocktail of antigen-binding molecules;

[10] the use of any one of [1] to [9], wherein the Fc region is represented by any one of SEQ ID NOs: 13, 14, 15, and 16;

[11] the use of any one of [1] to [9], wherein the Fc region is an Fc region with an enhanced FcRn-binding activity under an acidic pH range condition compared to that of the Fc region represented by any one of SEQ ID NOs: 13, 14, 15, and 16;

[12] the use of [11], wherein the Fc region is an Fc region with a substitution of at least one or more amino acids selected from the group consisting of amino acids at positions 238, 244, 245, 249, 250, 251, 252, 253, 254, 255, 256, 257, 258, 260, 262, 265, 270, 272, 279, 283, 285, 286, 288, 293, 303, 305, 307, 308, 309, 311, 312, 314, 316, 317, 318, 332, 339, 340, 341, 343, 356, 360, 362, 375, 376, 377, 378, 380, 382, 385, 386, 387, 388, 389, 400, 413, 415, 423, 424, 427, 428, 430, 431, 433, 434, 435, 436, 438, 439, 440, 442, and 447 (EU numbering) in the amino acid sequence of the Fc region represented by any one of SEQ ID NOs: 13, 14, 15, and 16;

[13] the use of [12], wherein the Fc region comprises at least one or more amino acids selected from the group consisting of:
Leu for the amino acid of position 238;
Leu for the amino acid of position 244;
Arg for the amino acid of position 245;
Pro for the amino acid of position 249;
Gln or Glu for the amino acid of position 250;
Arg, Asp, Glu, or Leu for the amino acid of position 251;
Phe, Ser, Thr, or Tyr for the amino acid of position 252;
Ser or Thr for the amino acid of position 254;
Arg, Gly, Ile, or Leu for the amino acid of position 255;
Ala, Arg, Asn, Asp, Gln, Glu, Pro, or Thr for the amino acid of position 256;
Ala, Ile, Met, Asn, Ser, or Val for the amino acid of position 257;
Asp for the amino acid of position 258;
Ser for the amino acid of position 260;
Leu for the amino acid of position 262;
Lys for the amino acid of position 270;
Leu or Arg for the amino acid of position 272;
Ala, Asp, Gly, His, Met, Asn, Gln, Arg, Ser, Thr, Trp, or Tyr for the amino acid of position 279;
Ala, Asp, Phe, Gly, His, Ile, Lys, Leu, Asn, Pro, Gln, Arg, Ser, Thr, Trp, or Tyr for the amino
acid of position 283;
Asn for the amino acid of position 285;
Phe for the amino acid of position 286;
Asn or Pro for the amino acid of position 288;
Val for the amino acid of position 293;
Ala, Glu, Gln, or Met for the amino acid of position 307;
Ala, Glu, Ile, Lys, Leu, Met, Ser, Val, or Trp for the amino acid of position 311;
Pro for the amino acid of position 309;
Ala, Asp, or Pro for the amino acid of position 312;
Ala or Leu for the amino acid of position 314;
Lys for the amino acid of position 316;
Pro for the amino acid of position 317;
Asn or Thr for the amino acid of position 318;
Phe, His, Lys, Leu, Met, Arg, Ser, or Trp for the amino acid of position 332;
Asn, Thr, or Trp for the amino acid of position 339;
Pro for the amino acid of position 341;
Glu, His, Lys, Gln, Arg, Thr, or Tyr for the amino acid of position 343;
Arg for the amino acid of position 375;
Gly, Ile, Met, Pro, Thr, or Val for the amino acid of position 376;
Lys for the amino acid of position 377;
Asp, Asn, or Val for the amino acid of position 378;
Ala, Asn, Ser, or Thr for the amino acid of position 380;
Phe, His, Ile, Lys, Leu, Met, Asn, Gln, Arg, Ser, Thr, Val, Trp, or Tyr for the amino acid of position 382;
Ala, Arg, Asp, Gly, His, Lys, Ser, or Thr for the amino acid of position 385;
Arg, Asp, Ile, Lys, Met, Pro, Ser, or Thr for the amino acid of position 386;
Ala, Arg, His, Pro, Ser, or Thr for the amino acid of position 387;
Asn, Pro, or Ser for the amino acid of position 389;
Asn for the amino acid of position 423;
Asn for the amino acid of position 427;
Leu, Met, Phe, Ser, or Thr for the amino acid of position 428;
Ala, Phe, Gly, His, Ile, Lys, Leu, Met, Asn, Gln, Arg, Ser, Thr, Val, or Tyr for the amino acid of position 430;
His or Asn for the amino acid of position 431;
Arg, Gln, His, Ile, Lys, Pro, or Ser for the amino acid of position 433;
Ala, Gly, His, Phe, Ser, Trp, or Tyr for the amino acid of position 434;
Arg, Asn, His, Ile, Leu, Lys, Met, or Thr for the amino acid of position 436;
Lys, Leu, Thr, or Trp for the amino acid of position 438;
Lys for the amino acid of position 440; and
Lys for the amino acid of position 442; Ile, Pro, or Thr for the amino acid of position 308; as indicated by EU numbering in the amino acid sequence of the Fc region represented by any one of SEQ ID NOs: 13, 14, 15, and 16;

[14] the use of any one of [1] to [9], wherein the Fc region is an Fc region with an enhanced FcRn-binding activity under a neutral pH range condition compared to that of the Fc region represented by any one of SEQ ID NOs: 13, 14, 15, and 16;

[15] the use of [14], wherein the Fc region is an Fc region with a substitution of at least one or more amino acids selected from the group consisting of positions 237, 248, 250, 252, 254, 255, 256, 257, 258, 265, 286, 289, 297, 298, 303, 305, 307, 308, 309, 311, 312, 314, 315, 317, 332, 334, 360, 376, 380, 382, 384, 385, 386, 387, 389, 424, 428, 433, 434, and 436 (EU numbering) in the amino acid sequence of the Fc region represented by any one of SEQ ID NOs: 13, 14, 15, and 16;

[16] the use of [15], wherein the Fc region comprises at least one or more amino acids selected from the group consisting of:
Met for the amino acid of position 237;
Ile for the amino acid of position 248;
Ala, Phe, Ile, Met, Gln, Ser, Val, Trp, or Tyr for the amino acid of position 250;
Phe, Trp, or Tyr for the amino acid of position 252;
Thr for the amino acid of position 254;
Glu for the amino acid of position 255;
Asp, Asn, Glu, or Gln for the amino acid of position 256;
Ala, Gly, Ile, Leu, Met, Asn, Ser, Thr, or Val for the amino acid of position 257;
His for the amino acid of position 258;
Ala for the amino acid of position 265;
Ala or Glu for the amino acid of position 286;
His for the amino acid of position 289;
Ala for the amino acid of position 297;
Ala for the amino acid of position 303;
Ala for the amino acid of position 305;
Ala, Asp, Phe, Gly, His, Ile, Lys, Leu, Met, Asn, Pro, Gln, Arg, Ser, Val, Trp, or Tyr for the amino acid of position 307;
Ala, Phe, Ile, Leu, Met, Pro, Gln, or Thr for the amino acid of position 308;
Ala, Asp, Glu, Pro, or Arg for the amino acid of position 309;
Ala, His, or Ile for the amino acid of position 311;
Ala or His for the amino acid of position 312;
Lys or Arg for the amino acid of position 314;
Ala, Asp, or His for the amino acid of position 315;
Ala for the amino acid of position 317;
Val for the amino acid of position 332;
Leu for the amino acid of position 334;
His for the amino acid of position 360;
Ala for the amino acid of position 376;

Ala for the amino acid of position 380;
Ala for the amino acid of position 382;
Ala for the amino acid of position 384;
Asp or His for the amino acid of position 385;
Pro for the amino acid of position 386;
Glu for the amino acid of position 387;
Ala or Ser for the amino acid of position 389;
Ala for the amino acid of position 424;
Ala, Asp, Phe, Gly, His, Ile, Lys, Leu, Asn, Pro, Gln, Ser, Thr, Val, Trp, or Tyr for the amino acid of position 428;
Lys for the amino acid of position 433;
Ala, Phe, His, Ser, Trp, or Tyr for the amino acid of position 434; and
His Ile, Leu, Phe, Thr, or Val for the amino acid of position 436; as indicated by EU numbering in the amino acid sequence of the Fc region represented by any one of SEQ ID NOs: 13, 14, 15, and 16;

[17] the use of any one of [1] to [13], wherein the Fc region includes an Fc region that has a higher Fcγ receptor-binding activity than that of the Fc region of a native human IgG;

[18] the use of [17], wherein the Fc region comprises in its amino acid sequence at least one or more amino acids that are different from amino acids of the native human IgG Fc region selected from the group consisting of positions 221, 222, 223, 224, 225, 227, 228, 230, 231, 232, 233, 234, 235, 236, 237, 238, 239, 240, 241, 243, 244, 245, 246, 247, 249, 250, 251, 254, 255, 256, 258, 260, 262, 263, 264, 265, 266, 267, 268, 269, 270, 271, 272, 273, 274, 275, 276, 278, 279, 280, 281, 282, 283, 284, 285, 286, 288, 290, 291, 292, 293, 294, 295, 296, 297, 298, 299, 300, 301, 302, 303, 304, 305, 311, 313, 315, 317, 318, 320, 322, 323, 324, 325, 326, 327, 328, 329, 330, 331, 332, 333, 334, 335, 336, 337, 339, 376, 377, 378, 379, 380, 382, 385, 392, 396, 421, 427, 428, 429, 434, 436, and 440 (EU numbering);

[19] the use of [18], wherein the Fc region comprises in its amino acid sequence at least one or more amino acids selected from the group consisting of:
Lys or Tyr for the amino acid of position 221;
Phe, Trp, Glu, or Tyr for the amino acid of position 222;
Phe, Trp, Glu, or Lys for the amino acid of position 223;
Phe, Trp, Glu, or Tyr for the amino acid of position 224;
Glu, Lys, or Trp for the amino acid of position 225;
Glu, Gly, Lys, or Tyr for the amino acid of position 227;
Glu, Gly, Lys, or Tyr for the amino acid of position 228;
Ala, Glu, Gly, or Tyr for the amino acid of position 230;
Glu, Gly, Lys, Pro, or Tyr for the amino acid of position 231;
Glu, Gly, Lys, or Tyr for the amino acid of position 232;
Ala, Asp, Phe, Gly, His, Ile, Lys, Leu, Met, Asn, Gln, Arg, Ser, Thr, Val, Trp, or Tyr for the amino acid of position 233;
Ala, Asp, Glu, Phe, Gly, His, Ile, Lys, Met, Asn, Pro, Gln, Arg, Ser, Thr, Val, Trp, or Tyr for the amino acid of position 234;
Ala, Asp, Glu, Phe, Gly, His, Ile, Lys, Met, Asn, Pro, Gln, Arg, Ser, Thr, Val, Trp, or Tyr for the amino acid of position 235;
Ala, Asp, Glu, Phe, His, Ile, Lys, Leu, Met, Asn, Pro, Gln, Arg, Ser, Thr, Val, Trp, or Tyr for the amino acid of position 236;
Asp, Glu, Phe, His, Ile, Lys, Leu, Met, Asn, Pro, Gln, Arg, Ser, Thr, Val, Trp, or Tyr for the amino acid of position 237;
Asp, Glu, Phe, Gly, His, Ile, Lys, Leu, Met, Asn, Gln, Arg, Ser, Thr, Val, Trp, or Tyr for the amino acid of position 238;
Asp, Glu, Phe, Gly, His, Ile, Lys, Leu, Met, Asn, Pro, Gln, Arg, Thr, Val, Trp, or Tyr for the amino acid of position 239;
Ala, Ile, Met, or Thr for the amino acid of position 240;
Asp, Glu, Leu, Arg, Trp, or Tyr for the amino acid of position 241;
Leu, Glu, Leu, Gln, Arg, Trp, or Tyr for the amino acid of position 243;
His for the amino acid of position 244;
Ala for the amino acid of position 245;
Asp, Glu, His, or Tyr for the amino acid of position 246;
Ala, Phe, Gly, His, Ile, Leu, Met, Thr, Val, or Tyr for the amino acid of position 247;
Glu, His, Gln, or Tyr for the amino acid of position 249;
Glu or Gln for the amino acid of position 250;
Phe for the amino acid of position 251;
Phe, Met, or Tyr for the amino acid of position 254;
Glu, Leu, or Tyr for the amino acid of position 255;
Ala, Met, or Pro for the amino acid of position 256;
Asp, Glu, His, Ser, or Tyr for the amino acid of position 258;
Asp, Glu, His, or Tyr for the amino acid of position 260;
Ala, Glu, Phe, Ile, or Thr for the amino acid of position 262;
Ala, Ile, Met, or Thr for the amino acid of position 263;
Asp, Glu, Phe, Gly, His, Ile, Lys, Leu, Met, Asn, Pro, Gln, Arg, Ser, Thr, Trp, or Tyr for the amino acid of position 264;
Ala, Leu, Phe, Gly, His, Ile, Lys, Leu, Met, Asn, Pro, Gln, Arg, Ser, Thr, Val, Trp, or Tyr for the amino acid of position 265;
Ala, Ile, Met, or Thr for the amino acid of position 266;
Asp, Glu, Phe, His, Ile, Lys, Leu, Met, Asn, Pro, Gln, Arg, Thr, Val, Trp, or Tyr for the amino acid of position 267;
Asp, Glu, Phe, Gly, Ile, Lys, Leu, Met, Pro, Gln, Arg, Thr, Val, or Trp for the amino acid of position 268;
Phe, Gly, His, Ile, Lys, Leu, Met, Asn, Pro, Arg, Ser, Thr, Val, Trp, or Tyr for the amino acid of position 269;
Glu, Phe, Gly, His, Ile, Leu, Met, Pro, Gln, Arg, Ser, Thr, Trp, or Tyr for the amino acid of position 270;
Ala, Asp, Glu, Phe, Gly, His, Ile, Lys, Leu, Met, Asn, Gln, Arg, Ser, Thr, Val, Trp, or Tyr for the amino acid of position 271;
Asp, Phe, Gly, His, Ile, Lys, Leu, Met, Pro, Arg, Ser, Thr, Val, Trp, or Tyr for the amino acid of position 272;
Phe or Ile for the amino acid of position 273;
Asp, Glu, Phe, Gly, His, Ile, Leu, Met, Asn, Pro, Arg, Ser, Thr, Val, Trp, or Tyr for the amino acid of position 274;
Leu or Trp for the amino acid of position 275;
Asp, Glu, Phe, Gly, His, Ile, Leu, Met, Pro, Arg, Ser, Thr, Val, Trp, or Tyr for the amino acid of position 276;
Asp, Glu, Gly, His, Ile, Lys, Leu, Met, Asn, Pro, Gln, Arg, Ser, Thr, Val, or Trp for the amino acid of position 278;
Ala for the amino acid of position 279;
Ala, Gly, His, Lys, Leu, Pro, Gln, Trp, or Tyr for the amino acid of position 280;
Asp, Lys, Pro, or Tyr for the amino acid of position 281;
Glu, Gly, Lys, Pro, or Tyr for the amino acid of position 282;
Ala, Gly, His, Ile, Lys, Leu, Met, Pro, Arg, or Tyr for the amino acid of position 283;
Asp, Glu, Leu, Asn, Thr, or Tyr for the amino acid of position 284;
Asp, Glu, Lys, Gln, Trp, or Tyr for the amino acid of position 285;
Glu, Gly, Pro, or Tyr for the amino acid of position 286;
Asn, Asp, Glu, or Tyr for the amino acid of position 288;
Asp, Gly, His, Leu, Asn, Ser, Thr, Trp, or Tyr for the amino acid of position 290;
Asp, Glu, Gly, His, Ile, Gln, or Thr for the amino acid of position 291;
Ala, Asp, Glu, Pro, Thr, or Tyr for the amino acid of position 292;
Phe, Gly, His, Ile, Leu, Met, Asn, Pro, Arg, Ser, Thr, Val, Trp, or Tyr for the amino acid of position 293;
Phe, Gly, His, Ile, Lys, Leu, Met, Asn, Pro, Arg, Ser, Thr, Val, Trp, or Tyr for the amino acid of position 294;

Asp, Glu, Phe, Gly, His, Ile, Lys, Met, Asn, Pro, Arg, Ser, Thr, Val, Trp, or Tyr for the amino acid of position 295;
Ala, Asp, Glu, Gly, His, Ile, Lys, Leu, Met, Asn, Gln, Arg, Ser, Thr, or Val for the amino acid of position 296;
Asp, Glu, Phe, Gly, His, Ile, Lys, Leu, Met, Pro, Gln, Arg, Ser, Thr, Val, Trp, or Tyr for the amino acid of position 297;
Ala, Asp, Glu, Phe, His, Ile, Lys, Met, Asn, Gln, Arg, Thr, Val, Trp, or Tyr for the amino acid of position 298;
Ala, Asp, Glu, Phe, Gly, His, Ile, Lys, Leu, Met, Asn, Pro, Gln, Arg, Ser, Val, Trp, or Tyr for the amino acid of position 299;
Ala, Asp, Glu, Gly, His, Ile, Lys, Leu, Met, Asn, Pro, Gln, Arg, Ser, Thr, Val, or Trp for the amino acid of position 300;
Asp, Glu, His, or Tyr for the amino acid of position 301;
Ile for the amino acid of position 302;
Asp, Gly, or Tyr for the amino acid of position 303;
Asp, His, Leu, Asn, or Thr for the amino acid of position 304;
Glu, Ile, Thr, or Tyr for the amino acid of position 305;
Ala, Asp, Asn, Thr, Val, or Tyr for the amino acid of position 311;
Phe for the amino acid of position 313;
Leu for the amino acid of position 315;
Glu or Gln for the amino acid of position 317;
His, Leu, Asn, Pro, Gln, Arg, Thr, Val, or Tyr for the amino acid of position 318;
Asp, Phe, Gly, His, Ile, Leu, Asn, Pro, Ser, Thr, Val, Trp, or Tyr for the amino acid of position 320;
Ala, Asp, Phe, Gly, His, Ile, Pro, Ser, Thr, Val, Trp, or Tyr for the amino acid of position 322;
Ile for the amino acid of position 323;
Asp, Phe, Gly, His, Ile, Leu, Met, Pro, Arg, Thr, Val, Trp, or Tyr for the amino acid of position 324;
Ala, Asp, Glu, Phe, Gly, His, Ile, Lys, Leu, Met, Pro, Gln, Arg, Ser, Thr, Val, Trp, or Tyr for the amino acid of position 325;
Ala, Asp, Glu, Gly, Ile, Leu, Met, Asn, Pro, Gln, Ser, Thr, Val, Trp, or Tyr for the amino acid of position 326;
Ala, Asp, Glu, Phe, Gly, His, Ile, Lys, Leu, Met, Asn, Pro, Arg, Thr, Val, Trp, or Tyr for the amino acid of position 327;
Ala, Asp, Glu, Phe, Gly, His, Ile, Lys, Met, Asn, Pro, Gln, Arg, Ser, Thr, Val, Trp, or Tyr for the amino acid of position 328;
Asp, Glu, Phe, Gly, His, Ile, Lys, Leu, Met, Asn, Gln, Arg, Ser, Thr, Val, Trp, or Tyr for the amino acid of position 329;
Cys, Glu, Phe, Gly, His, Ile, Lys, Leu, Met, Asn, Pro, Arg, Ser, Thr, Val, Trp, or Tyr for the amino acid of position 330;
Asp, Phe, His, Ile, Leu, Met, Gln, Arg, Thr, Val, Trp, or Tyr for the amino acid of position 331;
Ala, Asp, Glu, Phe, Gly, His, Lys, Leu, Met, Asn, Pro, Gln, Arg, Ser, Thr, Val, Trp, or Tyr for the amino acid of position 332;
Ala, Asp, Glu, Phe, Gly, His, Ile, Leu, Met, Pro, Ser, Thr, Val, or Tyr for the amino acid of position 333;
Ala, Glu, Phe, Ile, Leu, Pro, or Thr for the amino acid of position 334;
Asp, Phe, Gly, His, Ile, Leu, Met, Asn, Pro, Arg, Ser, Val, Trp, or Tyr for the amino acid of position 335;
Glu, Lys, or Tyr for the amino acid of position 336;
Glu, His, or Asn for the amino acid of position 337;
Asp, Phe, Gly, Ile, Lys, Met, Asn, Gln, Arg, Ser, or Thr for the amino acid of position 339;
Ala or Val for the amino acid of position 376;
Gly or Lys for the amino acid of position 377;
Asp for the amino acid of position 378;
Asn for the amino acid of position 379;
Ala, Asn, or Ser for the amino acid of position 380;
Ala or Ile for the amino acid of position 382;
Glu for the amino acid of position 385;
Thr for the amino acid of position 392;
Leu for the amino acid of position 396;
Lys for the amino acid of position 421;
Asn for the amino acid of position 427;
Phe or Leu for the amino acid of position 428;
Met for the amino acid of position 429;
Trp for the amino acid of position 434;
Ile for the amino acid of position 436; and
Gly, His, Ile, Leu, or Tyr for the amino acid of position 440; as indicated by EU numbering;

[20] the use of any one of [1] to [16], wherein the Fc region has a higher binding activity toward an inhibitory Fcγ receptor than toward an activating Fcγ receptor;

[21] the use of [20], wherein the inhibitory Fcγ receptor is human FcγRIIb;

[22] the use of [20] or [21], wherein the activating Fcγ receptor is human FcγRIa, human FcγRIIa (R), human FcγRIIa (H), human FcγRIIIa (V), or human FcγRIIIa (F);

[23] the use of any one of [20] to [22], wherein the amino acid at position 238 or 328 (EU numbering) in the Fc region is different from the amino acid in the native human IgG Fc region;

[24] the use of [23], wherein the amino acid at position 238 of the Fc region is Asp or the amino acid of position 328 of the Fc region is Glu as indicated by EU numbering;

[25] the use of [23] or [24], wherein the amino acid sequence of the Fc region comprises at least one or more amino acids selected from the group consisting of:
Asp for the amino acid of position 233;
Trp or Tyr for the amino acid of position 234;
Ala, Asp, Glu, Leu, Met, Phe, Trp, or Tyr for the amino acid of position 237;
Asp for the amino acid of position 239;
Ala, Gln, or Val for the amino acid of position 267;
Asn, Asp, or Glu for the amino acid of position 268;
Gly for the amino acid of position 271;
Ala, Asn, Asp, Gln, Glu, Leu, Met, Ser, or Thr for the amino acid of position 326;
Arg, Lys, or Met for the amino acid of position 330;
Ile, Leu, or Met for the amino acid of position 323; and
Asp for the amino acid of position 296; as indicated by EU numbering;

[26] a method of screening for an antigen-binding molecule having a function of eliminating an antigen from the plasma, wherein the method comprises:
(a) obtaining an antigen-binding domain of which antigen-binding activity varies depending on an ion concentration condition;
(b) obtaining a gene encoding the antigen-binding domain selected in (a) above;
(c) operably linking the gene obtained in (b) above with a gene encoding an Fc region;
(d) culturing a host cell comprising the genes operably linked in (c) above;
(e) isolating an antigen-binding molecule from a culture solution obtained in (d) above;
(f) contacting the antigen-binding molecule obtained in (e) above with an antigen; and
(g) evaluating the formation of an immune complex comprising the antigen-binding molecule and the antigen;

[27] a method for producing an antigen-binding molecule having a function of eliminating an antigen from the plasma, wherein the method comprises:
(a) contacting an antigen with an antigen-binding molecule comprising an Fc region and two or more antigen-binding domains, wherein at least one of the antigen-binding domains has an antigen-binding activity that varies depending on an ion concentration condition;
(b) evaluating formation of an immune complex comprising the antigen-binding molecule and the antigen;
(c) culturing a host cell comprising a vector that carries a gene encoding an antigen-binding molecule which is confirmed to form an immune complex in (b) above; and
(d) isolating the antigen-binding molecule from a culture solution obtained in (c) above;

[28] a method for producing an antigen-binding molecule having a function of eliminating an antigen from the plasma, wherein the method comprises:
(a) obtaining an antigen-binding domain of which antigen-binding activity varies depending on an ion concentration condition;
(b) obtaining a gene encoding the antigen-binding domain selected in (a) above;
(c) operably linking the gene obtained in (b) above with a gene encoding an Fc region;
(d) culturing a host cell comprising the genes operably linked in (c) above;
(e) isolating an antigen-binding molecule from a culture solution obtained in (d) above;
(f) contacting the antigen-binding molecule obtained in (e) above with an antigen;
(g) evaluating formation of an immune complex comprising the antigen-binding molecule and the antigen;
(h) culturing a host cell comprising a vector that carries a gene encoding an antigen-binding molecule which is confirmed to form an immune complex in (g) above; and
(i) isolating the antigen-binding molecule from a culture solution obtained in (h) above; and

[29] a method for producing an antigen-binding molecule having a function of eliminating an antigen from the plasma, wherein the method comprises:
(a) obtaining an antigen-binding domain of which antigen-binding activity varies depending on an ion concentration condition;
(b) obtaining a gene encoding the antigen-binding domain selected in (a) above;
(c) operably linking the gene obtained in (b) above with a gene encoding an Fc region;
(d) culturing a host cell comprising the genes operably linked in (c) above; and
(e) isolating an antigen-binding molecule from a culture solution obtained in (d) above; and
wherein the method further comprises contacting the antigen-binding molecule obtained by the production method with an antigen, and evaluating the formation of an immune complex comprising the antigen-binding molecule and the antigen.

The above-mentioned [1] to [25] may be restated as follows:

[1'] a pharmaceutical composition for eliminating an antigen from plasma, wherein the pharmaceutical composition comprises an antigen-binding molecule comprising
(i) an Fc region and
(ii) two or more antigen-binding domains,
wherein at least one of the domains is an antigen-binding domain of which antigen-binding activity varies depending on an ion concentration condition, and wherein the antigen-binding molecule can form an immune complex which comprises
(a) two or more of the antigen-binding molecules and
(b) two or more antigens, wherein the antigens comprise two or more antigenic binding units;

[2'] the pharmaceutical composition of [1'], wherein the ion concentration condition is a calcium ion concentration condition;

[3'] the pharmaceutical composition of [2'], wherein the antigen-binding domain has an antigen-binding activity under a low calcium-ion concentration condition that is lower than the antigen-binding activity under a high calcium-ion concentration condition;

[4'] the pharmaceutical composition of any one of [1'] to [3'], wherein the ion concentration condition is a pH condition;

[5'] the pharmaceutical composition of [4'], wherein the antigen-binding domain has an antigen binding activity in an acidic pH range that is lower than the antigen-binding activity in a neutral pH range condition;

[6'] the pharmaceutical composition of any one of [1'] to [5'], wherein the antigens comprising two or more antigenic binding units are multimers;

[7'] the pharmaceutical composition of [6'], wherein the antigen is any one of GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (myostatin), GDF-9, GDF-15 (MIC-1), TNF, TNF-alphabeta, TNF-beta2, TNFSF10 (TRAIL, Apo-2 ligand, TL2), TNFSF11 (TRANCE/RANK ligand, ODF, OPG ligand), TNFSF12 (TWEAK, Apo-3 ligand, DR3 ligand), TNFSF13 (APRIL, TALL2), TNFSF13B (BAFF, BLYS, TALL1, THANK, TNFSF20), TNFSF14 (LIGHT, HVEM ligand, LTg), TNFSF15 (TL1A/VEGI), TNFSF18 (GITR ligand AITR ligand, TL6), TNFSF1A (TNF-a, Cachectin, DIF, TNFSF2), TNFSF1B (TNF-b, LTa, TNFSF1), TNFSF3 (LTb, TNFC, p33), TNFSF4 (OX40 ligand, gp34, TXGP1), TNFSF5 (CD40 ligand, CD154, gp39, HIGM1, IMD3, TRAP), TNFSF6 (Fas ligand, Apo-1 ligand, APT1 ligand), TNFSF7 (CD27 ligand, CD70), TNFSF8 (CD30 ligand, CD153), TNFSF9 (4-1BB ligand, CD137 ligand), VEGF, IgE, IgA, IgG, IgM, RANKL, TGF-alpha, TGF-beta, TGF-beta Pan Specific, and IL-8;

[8'] the pharmaceutical composition of any one of [1'] to [5'], wherein the antigens comprising two or more antigenic binding units are monomers;

[9'] the pharmaceutical composition of any one of [1'] to [8'], wherein the antigen-binding molecules are a multispecific or multiparatopic antigen-binding molecule, or a cocktail of antigen-binding molecules;

[10'] the pharmaceutical composition of any one of [1'] to [9'], wherein the Fc region is represented by any one of SEQ ID NOs: 13, 14, 15, and 16;

[11'] the pharmaceutical composition of any one of [1'] to [9'], wherein the Fc region is an Fc region with an enhanced FcRn-binding activity under an acidic pH range condition compared to that of the Fc region represented by any one of SEQ ID NOs: 13, 14, 15, and 16;

[12'] the pharmaceutical composition of [11'], wherein the Fc region is an Fc region with an amino acid substitution of at least one or more amino acids selected from the group consisting of positions 238, 244, 245, 249, 250, 251, 252, 253, 254, 255, 256, 257, 258, 260, 262, 265, 270, 272, 279, 283, 285, 286, 288, 293, 303, 305, 307, 308, 309, 311, 312, 314, 316, 317, 318, 332, 339, 340, 341, 343, 356, 360, 362, 375, 376, 377, 378, 380, 382, 385, 386, 387, 388, 389, 400, 413, 415, 423, 424, 427, 428, 430, 431, 433, 434, 435, 436, 438, 439, 440, 442, and 447 (EU numbering) in the amino acid sequence of the Fc region represented by any one of SEQ ID NOs: 13, 14, 15, and 16;

[13'] the pharmaceutical composition of [12'], wherein the Fc region comprises at least one or
more amino acids selected from the group consisting of:
Leu for the amino acid of position 238;
Leu for the amino acid of position 244;
Arg for the amino acid of position 245;
Pro for the amino acid of position 249;
Gln or Glu for the amino acid of position 250;
Arg, Asp, Glu, or Leu for the amino acid of position 251;
Phe, Ser, Thr, or Tyr for the amino acid of position 252;
Ser or Thr for the amino acid of position 254;
Arg, Gly, Ile, or Leu for the amino acid of position 255;
Ala, Arg, Asn, Asp, Gln, Glu, Pro, or Thr for the amino acid of position 256;
Ala, Ile, Met, Asn, Ser, or Val for the amino acid of position 257;
Asp for the amino acid of position 258;
Ser for the amino acid of position 260;
Leu for the amino acid of position 262;
Lys for the amino acid of position 270;
Leu or Arg for the amino acid of position 272;
Ala, Asp, Gly, His, Met, Asn, Gln, Arg, Ser, Thr, Trp, or Tyr for the amino acid of position 279;
Ala, Asp, Phe, Gly, His, Ile, Lys, Leu, Asn, Pro, Gln, Arg, Ser, Thr, Trp, or Tyr for the amino
acid of position 283;
Asn for the amino acid of position 285;
Phe for the amino acid of position 286;
Asn or Pro for the amino acid of position 288;
Val for the amino acid of position 293;
Ala, Glu, Gln, or Met for the amino acid of position 307;
Ala, Glu, Ile, Lys, Leu, Met, Ser, Val, or Trp for the amino acid of position 311;
Pro for the amino acid of position 309;
Ala, Asp, or Pro for the amino acid of position 312;
Ala or Leu for the amino acid of position 314;
Lys for the amino acid of position 316;
Pro for the amino acid of position 317;
Asn or Thr for the amino acid of position 318;
Phe, His, Lys, Leu, Met, Arg, Ser, or Trp for the amino acid of position 332;
Asn, Thr, or Trp for the amino acid of position 339;
Pro for the amino acid of position 341;
Glu, His, Lys, Gln, Arg, Thr, or Tyr for the amino acid of position 343;
Arg for the amino acid of position 375;
Gly, Ile, Met, Pro, Thr, or Val for the amino acid of position 376;
Lys for the amino acid of position 377;
Asp, Asn, or Val for the amino acid of position 378;
Ala, Asn, Ser, or Thr for the amino acid of position 380;
Phe, His, Ile, Lys, Leu, Met, Asn, Gln, Arg, Ser, Thr, Val, Trp, or Tyr for the amino acid of position 382;
Ala, Arg, Asp, Gly, His, Lys, Ser, or Thr for the amino acid of position 385;
Arg, Asp, Ile, Lys, Met, Pro, Ser, or Thr for the amino acid of position 386;
Ala, Arg, His, Pro, Ser, or Thr for the amino acid of position 387;
Asn, Pro, or Ser for the amino acid of position 389;
Asn for the amino acid of position 423;
Asn for the amino acid of position 427;
Leu, Met, Phe, Ser, or Thr for the amino acid of position 428;
Ala, Phe, Gly, His, Ile, Lys, Leu, Met, Asn, Gln, Arg, Ser, Thr, Val, or Tyr for the amino acid of position 430;
His or Asn for the amino acid of position 431;

Arg, Gln, His, Ile, Lys, Pro, or Ser for the amino acid of position 433;
Ala, Gly, His, Phe, Ser, Trp, or Tyr for the amino acid of position 434;
Arg, Asn, His, Ile, Leu, Lys, Met, or Thr for the amino acid of position 436;
Lys, Leu, Thr, or Trp for the amino acid of position 438;
Lys for the amino acid of position 440; and
Lys for the amino acid of position 442; Ile, Pro, or Thr for the amino acid of position 308; as indicated by EU numbering in the amino acid sequence of the Fc region represented by any one of SEQ ID NOs: 13, 14, 15, and 16;
[14'] the pharmaceutical composition of any one of [1'] to [9'], wherein the Fc region is an Fc region with an enhanced FcRn-binding activity under a neutral pH range condition compared to that of the Fc region represented by any one of SEQ ID NOs: 13, 14, 15, and 16;
[15'] the pharmaceutical composition of [14'], wherein the Fc region is an Fc region with a substitution of at least one or more amino acids selected from the group consisting of positions 237, 248, 250, 252, 254, 255, 256, 257, 258, 265, 286, 289, 297, 298, 303, 305, 307, 308, 309, 311, 312, 314, 315, 317, 332, 334, 360, 376, 380, 382, 384, 385, 386, 387, 389, 424, 428, 433, 434, and 436 (EU numbering) in the amino acid sequence of the Fc region represented by any one of SEQ ID NOs: 13, 14, 15, and 16;
[16'] the pharmaceutical composition of [15'], wherein the Fc region comprises at least one or more amino acids selected from the group consisting of:
Met for the amino acid of position 237;
Ile for the amino acid of position 248;
Ala, Phe, Ile, Met, Gln, Ser, Val, Trp, or Tyr for the amino acid of position 250;
Phe, Trp, or Tyr for the amino acid of position 252;
Thr for the amino acid of position 254;
Glu for the amino acid of position 255;
Asp, Asn, Glu, or Gln for the amino acid of position 256;
Ala, Gly, Ile, Leu, Met, Asn, Ser, Thr, or Val for the amino acid of position 257;
His for the amino acid of position 258;
Ala for the amino acid of position 265;
Ala or Glu for the amino acid of position 286;
His for the amino acid of position 289;
Ala for the amino acid of position 297;
Ala for the amino acid of position 303;
Ala for the amino acid of position 305;
Ala, Asp, Phe, Gly, His, Ile, Lys, Leu, Met, Asn, Pro, Gln, Arg, Ser, Val, Trp, or Tyr for the amino acid of position 307;
Ala, Phe, Ile, Leu, Met, Pro, Gln, or Thr for the amino acid of position 308;
Ala, Asp, Glu, Pro, or Arg for the amino acid of position 309;
Ala, His, or Ile for the amino acid of position 311;
Ala or His for the amino acid of position 312;
Lys or Arg for the amino acid of position 314;
Ala, Asp, or His for the amino acid of position 315;
Ala for the amino acid of position 317;
Val for the amino acid of position 332;
Leu for the amino acid of position 334;
His for the amino acid of position 360;
Ala for the amino acid of position 376;
Ala for the amino acid of position 380;
Ala for the amino acid of position 382;
Ala for the amino acid of position 384;
Asp or His for the amino acid of position 385;
Pro for the amino acid of position 386;
Glu for the amino acid of position 387;
Ala or Ser for the amino acid of position 389;

Ala for the amino acid of position 424;
Ala, Asp, Phe, Gly, His, Ile, Lys, Leu, Asn, Pro, Gln, Ser, Thr, Val, Trp, or Tyr for the amino
acid of position 428;
Lys for the amino acid of position 433;
Ala, Phe, His, Ser, Trp, or Tyr for the amino acid of position 434; and
His Ile, Leu, Phe, Thr, or Val for the amino acid of position 436; as indicated by EU numbering in the amino acid sequence of the Fc region represented by any one of SEQ ID NOs: 13, 14, 15, and 16;
[17'] the pharmaceutical composition of any one of [1'] to [13'], wherein the Fc region includes an Fc region that has a higher Fcγ receptor-binding activity than that of the Fc region of a native human IgG;
[18'] the pharmaceutical composition of [17'], wherein the Fc region comprises in its amino acid sequence at least one or more amino acids that are different from amino acids of the native human IgG Fc region selected from the group consisting of positions 221, 222, 223, 224, 225, 227, 228, 230, 231, 232, 233, 234, 235, 236, 237, 238, 239, 240, 241, 243, 244, 245, 246, 247, 249, 250, 251, 254, 255, 256, 258, 260, 262, 263, 264, 265, 266, 267, 268, 269, 270, 271, 272, 273, 274, 275, 276, 278, 279, 280, 281, 282, 283, 284, 285, 286, 288, 290, 291, 292, 293, 294, 295, 296, 297, 298, 299, 300, 301, 302, 303, 304, 305, 311, 313, 315, 317, 318, 320, 322, 323, 324, 325, 326, 327, 328, 329, 330, 331, 332, 333, 334, 335, 336, 337, 339, 376, 377, 378, 379, 380, 382, 385, 392, 396, 421, 427, 428, 429, 434, 436, and 440 (EU numbering);
[19'] the pharmaceutical composition of [18'], wherein the Fc region comprises in its amino acid sequence at least one or more amino acids selected from the group consisting of:
Lys or Tyr for the amino acid of position 221;
Phe, Trp, Glu, or Tyr for the amino acid of position 222;
Phe, Trp, Glu, or Lys for the amino acid of position 223;
Phe, Trp, Glu, or Tyr for the amino acid of position 224;
Glu, Lys, or Trp for the amino acid of position 225;
Glu, Gly, Lys, or Tyr for the amino acid of position 227;
Glu, Gly, Lys, or Tyr for the amino acid of position 228;
Ala, Glu, Gly, or Tyr for the amino acid of position 230;
Glu, Gly, Lys, Pro, or Tyr for the amino acid of position 231;
Glu, Gly, Lys, or Tyr for the amino acid of position 232;
Ala, Asp, Phe, Gly, His, Ile, Lys, Leu, Met, Asn, Gln, Arg, Ser, Thr, Val, Trp, or Tyr for the amino acid of position 233;
Ala, Asp, Glu, Phe, Gly, His, Ile, Lys, Met, Asn, Pro, Gln, Arg, Ser, Thr, Val, Trp, or Tyr for the amino acid of position 234;
Ala, Asp, Glu, Phe, Gly, His, Ile, Lys, Met, Asn, Pro, Gln, Arg, Ser, Thr, Val, Trp, or Tyr for the amino acid of position 235;
Ala, Asp, Glu, Phe, His, Ile, Lys, Leu, Met, Asn, Pro, Gln, Arg, Ser, Thr, Val, Trp, or Tyr for the amino acid of position 236;
Asp, Glu, Phe, His, Ile, Lys, Leu, Met, Asn, Pro, Gln, Arg, Ser, Thr, Val, Trp, or Tyr for the amino acid of position 237;
Asp, Glu, Phe, Gly, His, Ile, Lys, Leu, Met, Asn, Gln, Arg, Ser, Thr, Val, Trp, or Tyr for the amino acid of position 238;
Asp, Glu, Phe, Gly, His, Ile, Lys, Leu, Met, Asn, Pro, Gln, Arg, Thr, Val, Trp, or Tyr for the amino acid of position 239;
Ala, Ile, Met, or Thr for the amino acid of position 240;
Asp, Glu, Leu, Arg, Trp, or Tyr for the amino acid of position 241;
Leu, Glu, Leu, Gln, Arg, Trp, or Tyr for the amino acid of position 243;
His for the amino acid of position 244;
Ala for the amino acid of position 245;

Asp, Glu, His, or Tyr for the amino acid of position 246;
Ala, Phe, Gly, His, Ile, Leu, Met, Thr, Val, or Tyr for the amino acid of position 247;
Glu, His, Gln, or Tyr for the amino acid of position 249;
Glu or Gln for the amino acid of position 250;
Phe for the amino acid of position 251;
Phe, Met, or Tyr for the amino acid of position 254;
Glu, Leu, or Tyr for the amino acid of position 255;
Ala, Met, or Pro for the amino acid of position 256;
Asp, Glu, His, Ser, or Tyr for the amino acid of position 258;
Asp, Glu, His, or Tyr for the amino acid of position 260;
Ala, Glu, Phe, Ile, or Thr for the amino acid of position 262;
Ala, Ile, Met, or Thr for the amino acid of position 263;
Asp, Glu, Phe, Gly, His, Ile, Lys, Leu, Met, Asn, Pro, Gln, Arg, Ser, Thr, Trp, or Tyr for the amino acid of position 264;
Ala, Leu, Phe, Gly, His, Ile, Lys, Leu, Met, Asn, Pro, Gln, Arg, Ser, Thr, Val, Trp, or Tyr for the amino acid of position 265;
Ala, Ile, Met, or Thr for the amino acid of position 266;
Asp, Glu, Phe, His, Ile, Lys, Leu, Met, Asn, Pro, Gln, Arg, Thr, Val, Trp, or Tyr for the amino acid of position 267;
Asp, Glu, Phe, Gly, Ile, Lys, Leu, Met, Pro, Gln, Arg, Thr, Val, or Trp for the amino acid of position 268;
Phe, Gly, His, Ile, Lys, Leu, Met, Asn, Pro, Arg, Ser, Thr, Val, Trp, or Tyr for the amino acid of position 269;
Glu, Phe, Gly, His, Ile, Leu, Met, Pro, Gln, Arg, Ser, Thr, Trp, or Tyr for the amino acid of position 270;
Ala, Asp, Glu, Phe, Gly, His, Ile, Lys, Leu, Met, Asn, Gln, Arg, Ser, Thr, Val, Trp, or Tyr for the amino acid of position 271;
Asp, Phe, Gly, His, Ile, Lys, Leu, Met, Pro, Arg, Ser, Thr, Val, Trp, or Tyr for the amino acid of position 272;
Phe or Ile for the amino acid of position 273;
Asp, Glu, Phe, Gly, His, Ile, Leu, Met, Asn, Pro, Arg, Ser, Thr, Val, Trp, or Tyr for the amino acid of position 274;
Leu or Trp for the amino acid of position 275;
Asp, Glu, Phe, Gly, His, Ile, Leu, Met, Pro, Arg, Ser, Thr, Val, Trp, or Tyr for the amino acid of position 276;
Asp, Glu, Gly, His, Ile, Lys, Leu, Met, Asn, Pro, Gln, Arg, Ser, Thr, Val, or Trp for the amino acid of position 278;
Ala for the amino acid of position 279;
Ala, Gly, His, Lys, Leu, Pro, Gln, Trp, or Tyr for the amino acid of position 280;
Asp, Lys, Pro, or Tyr for the amino acid of position 281;
Glu, Gly, Lys, Pro, or Tyr for the amino acid of position 282;
Ala, Gly, His, Ile, Lys, Leu, Met, Pro, Arg, or Tyr for the amino acid of position 283;
Asp, Glu, Leu, Asn, Thr, or Tyr for the amino acid of position 284;
Asp, Glu, Lys, Gln, Trp, or Tyr for the amino acid of position 285;
Glu, Gly, Pro, or Tyr for the amino acid of position 286;
Asn, Asp, Glu, or Tyr for the amino acid of position 288;
Asp, Gly, His, Leu, Asn, Ser, Thr, Trp, or Tyr for the amino acid of position 290;
Asp, Glu, Gly, His, Ile, Gln, or Thr for the amino acid of position 291;
Ala, Asp, Glu, Pro, Thr, or Tyr for the amino acid of position 292;
Phe, Gly, His, Ile, Leu, Met, Asn, Pro, Arg, Ser, Thr, Val, Trp, or Tyr for the amino acid of position 293;
Phe, Gly, His, Ile, Lys, Leu, Met, Asn, Pro, Arg, Ser, Thr, Val, Trp, or Tyr for the amino acid of position 294;
Asp, Glu, Phe, Gly, His, Ile, Lys, Met, Asn, Pro, Arg, Ser, Thr, Val, Trp, or Tyr for the amino acid of position 295;
Ala, Asp, Glu, Gly, His, Ile, Lys, Leu, Met, Asn, Gln, Arg, Ser, Thr, or Val for the amino acid of position 296;

Asp, Glu, Phe, Gly, His, Ile, Lys, Leu, Met, Pro, Gln, Arg, Ser, Thr, Val, Trp, or Tyr for the amino acid of position 297;
Ala, Asp, Glu, Phe, His, Ile, Lys, Met, Asn, Gln, Arg, Thr, Val, Trp, or Tyr for the amino acid of position 298;
Ala, Asp, Glu, Phe, Gly, His, Ile, Lys, Leu, Met, Asn, Pro, Gln, Arg, Ser, Val, Trp, or Tyr for the amino acid of position 299;
Ala, Asp, Glu, Gly, His, Ile, Lys, Leu, Met, Asn, Pro, Gln, Arg, Ser, Thr, Val, or Trp for the amino acid of position 300;
Asp, Glu, His, or Tyr for the amino acid of position 301;
Ile for the amino acid of position 302;
Asp, Gly, or Tyr for the amino acid of position 303;
Asp, His, Leu, Asn, or Thr for the amino acid of position 304;
Glu, Ile, Thr, or Tyr for the amino acid of position 305;
Ala, Asp, Asn, Thr, Val, or Tyr for the amino acid of position 311;
Phe for the amino acid of position 313;
Leu for the amino acid of position 315;
Glu or Gln for the amino acid of position 317;
His, Leu, Asn, Pro, Gln, Arg, Thr, Val, or Tyr for the amino acid of position 318;
Asp, Phe, Gly, His, Ile, Leu, Asn, Pro, Ser, Thr, Val, Trp, or Tyr for the amino acid of position 320;
Ala, Asp, Phe, Gly, His, Ile, Pro, Ser, Thr, Val, Trp, or Tyr for the amino acid of position 322;
Ile for the amino acid of position 323;
Asp, Phe, Gly, His, Ile, Leu, Met, Pro, Arg, Thr, Val, Trp, or Tyr for the amino acid of position 324;
Ala, Asp, Glu, Phe, Gly, His, Ile, Lys, Leu, Met, Pro, Gln, Arg, Ser, Thr, Val, Trp, or Tyr for the amino acid of position 325;
Ala, Asp, Glu, Gly, Ile, Leu, Met, Asn, Pro, Gln, Ser, Thr, Val, Trp, or Tyr for the amino acid of position 326;
Ala, Asp, Glu, Phe, Gly, His, Ile, Lys, Leu, Met, Asn, Pro, Arg, Thr, Val, Trp, or Tyr for the amino acid of position 327;
Ala, Asp, Glu, Phe, Gly, His, Ile, Lys, Met, Asn, Pro, Gln, Arg, Ser, Thr, Val, Trp, or Tyr for the amino acid of position 328;
Asp, Glu, Phe, Gly, His, Ile, Lys, Leu, Met, Asn, Gln, Arg, Ser, Thr, Val, Trp, or Tyr for the amino acid of position 329;
Cys, Glu, Phe, Gly, His, Ile, Lys, Leu, Met, Asn, Pro, Arg, Ser, Thr, Val, Trp, or Tyr for the amino acid of position 330;
Asp, Phe, His, Ile, Leu, Met, Gln, Arg, Thr, Val, Trp, or Tyr for the amino acid of position 331;
Ala, Asp, Glu, Phe, Gly, His, Lys, Leu, Met, Asn, Pro, Gln, Arg, Ser, Thr, Val, Trp, or Tyr for the amino acid of position 332;
Ala, Asp, Glu, Phe, Gly, His, Ile, Leu, Met, Pro, Ser, Thr, Val, or Tyr for the amino acid of position 333;
Ala, Glu, Phe, Ile, Leu, Pro, or Thr for the amino acid of position 334;
Asp, Phe, Gly, His, Ile, Leu, Met, Asn, Pro, Arg, Ser, Val, Trp, or Tyr for the amino acid of position 335;
Glu, Lys, or Tyr for the amino acid of position 336;
Glu, His, or Asn for the amino acid of position 337;
Asp, Phe, Gly, Ile, Lys, Met, Asn, Gln, Arg, Ser, or Thr for the amino acid of position 339;
Ala or Val for the amino acid of position 376;
Gly or Lys for the amino acid of position 377;
Asp for the amino acid of position 378;
Asn for the amino acid of position 379;
Ala, Asn, or Ser for the amino acid of position 380;
Ala or Ile for the amino acid of position 382;
Glu for the amino acid of position 385;
Thr for the amino acid of position 392;
Leu for the amino acid of position 396;
Lys for the amino acid of position 421;
Asn for the amino acid of position 427;
Phe or Leu for the amino acid of position 428;
Met for the amino acid of position 429;
Trp for the amino acid of position 434;
Ile for the amino acid of position 436; and
Gly, His, Ile, Leu, or Tyr for the amino acid of position 440;
as indicated by EU numbering;

[20'] the pharmaceutical composition of any one of [1'] to [16'], wherein the Fc region has a higher binding activity toward an inhibitory Fcγ receptor than toward an activating Fcγ receptor;

[21'] the pharmaceutical composition of [20'], wherein the inhibitory Fcγ receptor is human FcγRIIb;

[22'] the pharmaceutical composition of [20'] or [21'], wherein the activating Fcγ receptor is human FcγRIa, human FcγRIIa (R), human FcγRIIa (H), human FcγRIIIa (V), or human FcγRIIIa (F);

[23'] the pharmaceutical composition of any one of [20] to [22'], wherein the amino acid at position 238 or 328 (EU numbering) in the Fc region is different from the amino acid in the native human IgG Fc region;

[24'] the pharmaceutical composition of [23'], wherein the amino acid at position 238 of the Fc region is Asp or the amino acid of position 328 of the Fc region is Glu as indicated by EU numbering; and

[25'] the pharmaceutical composition of [23'] or [24'], wherein the amino acid sequence of the
Fc region comprises at least one or more amino acids selected from the group consisting of:
Asp for the amino acid of position 233;
Trp or Tyr for the amino acid of position 234;
Ala, Asp, Glu, Leu, Met, Phe, Trp, or Tyr for the amino acid of position 237;
Asp for the amino acid of position 239;
Ala, Gln, or Val for the amino acid of position 267;
Asn, Asp, or Glu for the amino acid of position 268;
Gly for the amino acid of position 271;
Ala, Asn, Asp, Gln, Glu, Leu, Met, Ser, or Thr for the amino acid of position 326;
Arg, Lys, or Met for the amino acid of position 330;
Ile, Leu, or Met for the amino acid of position 323; and
Asp for the amino acid of position 296;
as indicated by EU numbering;

Furthermore, the above-mentioned [1] to [25] may also be restated as follows:

[1"] a method for eliminating an antigen from plasma of a subject, wherein the method comprises administering to the subject an antigen-binding molecule comprising
(i) an Fc region and
(ii) two or more antigen-binding domains,
wherein at least one of the domains is an antigen-binding domain of which antigen-binding activity varies depending on an ion concentration condition, and wherein the antigen-binding molecule can form an immune complex which comprises
(a) two or more of the antigen-binding molecules and
(b) two or more antigens, wherein the antigens comprise two or more antigenic binding units;

[2"] the method of [1"], wherein the ion concentration condition is a calcium ion concentration condition;

[3"] the method of [2"], wherein the antigen-binding domain has an antigen-binding activity under a low calcium-ion concentration condition that is lower than the antigen-binding activity under a high calcium-ion concentration condition;

[4"] the method of any one of [1"] to [3"], wherein the ion concentration condition is a pH condition;
[5"] the method of [4"], wherein the antigen-binding domain has an antigen binding activity in an acidic pH range that is lower than the antigen-binding activity in a neutral pH range condition;
[6"] the method of any one of [1"] to [5"], wherein the antigens comprising two or more antigenic binding units are multimers;
[7"] the method of [6"], wherein the antigen is any one of GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (myostatin), GDF-9, GDF-15 (MIC-1), TNF, TNF-alphabeta, TNF-beta2, TNFSF10 (TRAIL, Apo-2 ligand, TL2), TNFSF11 (TRANCE/RANK ligand, ODF, OPG ligand), TNFSF12 (TWEAK, Apo-3 ligand, DR3 ligand), TNFSF13 (APRIL, TALL2), TNFSF13B (BAFF, BLYS, TALL1, THANK, TNFSF20), TNFSF14 (LIGHT, HVEM ligand, LTg), TNFSF15 (TL1A/VEGI), TNFSF18 (GITR ligand, AITR ligand, TL6), TNFSF1A (TNF-a Cachectin, DIF, TNFSF2), TNFSF1B (TNF-b, LTa, TNFSF1), TNFSF3 (LTb, TNFC, p33), TNFSF4 (OX40 ligand, gp34, TXGP1), TNFSF5 (CD40 ligand, CD154, gp39, HIGM1, IMD3, TRAP), TNFSF6 (Fas ligand, Apo-1 ligand, APT1 ligand), TNFSF7 (CD27 ligand, CD70), TNFSF8 (CD30 ligand, CD153), TNFSF9 (4-1BB ligand, CD137 ligand), VEGF, IgE, IgA, IgG, IgM, RANKL, TGF-alpha, TGF-beta, TGF-beta Pan Specific, and IL-8;
[8"] the method of any one of [11] to [5"], wherein the antigens comprising two or more antigenic binding units are monomers;
[9"] the method of any one of [11] to [9"], wherein the antigen-binding molecules are a multispecific or multi-paratopic antigen-binding molecule, or a cocktail of antigen-binding molecules;
[10"] the method of any one of [1"] to [9"], wherein the Fc region is represented by any one of SEQ ID NOs: 13, 14, 15, and 16;
[11"] the method of any one of [1"] to [9"], wherein the Fc region is an Fc region with an enhanced FcRn-binding activity under an acidic pH range condition compared to that of the Fc region represented by any one of SEQ ID NOs: 13, 14, 15, and 16;
[12"] the method of [11] wherein the Fc region is an Fc region with a substitution of at least one or more amino acids selected from the group consisting of positions 238, 244, 245, 249, 250, 251, 252, 253, 254, 255, 256, 257, 258, 260, 262, 265, 270, 272, 279, 283, 285, 286, 288, 293, 303, 305, 307, 308, 309, 311, 312, 314, 316, 317, 318, 332, 339, 340, 341, 343, 356, 360, 362, 375, 376, 377, 378, 380, 382, 385, 386, 387, 388, 389, 400, 413, 415, 423, 424, 427, 428, 430, 431, 433, 434, 435, 436, 438, 439, 440, 442, and 447 (EU numbering) in the amino acid sequence of the Fc region represented by any one of SEQ ID NOs: 13, 14, 15, and 16;
[13"] the method of [12"], wherein the Fc region comprises at least one or more amino acids selected from the group consisting of:
Leu for the amino acid of position 238;
Leu for the amino acid of position 244;
Arg for the amino acid of position 245;
Pro for the amino acid of position 249;
Gln or Glu for the amino acid of position 250;
Arg, Asp, Glu, or Leu for the amino acid of position 251;
Phe, Ser, Thr, or Tyr for the amino acid of position 252;
Ser or Thr for the amino acid of position 254;
Arg, Gly, Ile, or Leu for the amino acid of position 255;
Ala, Arg, Asn, Asp, Gln, Glu, Pro, or Thr for the amino acid of position 256;
Ala, Ile, Met, Asn, Ser, or Val for the amino acid of position 257;
Asp for the amino acid of position 258;
Ser for the amino acid of position 260;
Leu for the amino acid of position 262;
Lys for the amino acid of position 270;
Leu or Arg for the amino acid of position 272;
Ala, Asp, Gly, His, Met, Asn, Gln, Arg, Ser, Thr, Trp, or Tyr for the amino acid of position 279;
Ala, Asp, Phe, Gly, His, Ile, Lys, Leu, Asn, Pro, Gln, Arg, Ser, Thr, Trp, or Tyr for the amino acid of position 283;
Asn for the amino acid of position 285;
Phe for the amino acid of position 286;
Asn or Pro for the amino acid of position 288;
Val for the amino acid of position 293;
Ala, Glu, Gln, or Met for the amino acid of position 307;
Ala, Glu, Ile, Lys, Leu, Met, Ser, Val, or Trp for the amino acid of position 311;
Pro for the amino acid of position 309;
Ala, Asp, or Pro for the amino acid of position 312;
Ala or Leu for the amino acid of position 314;
Lys for the amino acid of position 316;
Pro for the amino acid of position 317;
Asn or Thr for the amino acid of position 318;
Phe, His, Lys, Leu, Met, Arg, Ser, or Trp for the amino acid of position 332;
Asn, Thr, or Trp for the amino acid of position 339;
Pro for the amino acid of position 341;
Glu, His, Lys, Gln, Arg, Thr, or Tyr for the amino acid of position 343;
Arg for the amino acid of position 375;
Gly, Ile, Met, Pro, Thr, or Val for the amino acid of position 376;
Lys for the amino acid of position 377;
Asp, Asn, or Val for the amino acid of position 378;
Ala, Asn, Ser, or Thr for the amino acid of position 380;
Phe, His, Ile, Lys, Leu, Met, Asn, Gln, Arg, Ser, Thr, Val, Trp, or Tyr for the amino acid of position 382;
Ala, Arg, Asp, Gly, His, Lys, Ser, or Thr for the amino acid of position 385;
Arg, Asp, Ile, Lys, Met, Pro, Ser, or Thr for the amino acid of position 386;
Ala, Arg, His, Pro, Ser, or Thr for the amino acid of position 387;
Asn, Pro, or Ser for the amino acid of position 389;
Asn for the amino acid of position 423;
Asn for the amino acid of position 427;
Leu, Met, Phe, Ser, or Thr for the amino acid of position 428;
Ala, Phe, Gly, His, Ile, Lys, Leu, Met, Asn, Gln, Arg, Ser, Thr, Val, or Tyr for the amino acid of position 430;
His or Asn for the amino acid of position 431;
Arg, Gln, His, Ile, Lys, Pro, or Ser for the amino acid of position 433;
Ala, Gly, His, Phe, Ser, Trp, or Tyr for the amino acid of position 434;
Arg, Asn, His, Ile, Leu, Lys, Met, or Thr for the amino acid of position 436;
Lys, Leu, Thr, or Trp for the amino acid of position 438;
Lys for the amino acid of position 440; and
Lys for the amino acid of position 442; Ile, Pro, or Thr for the amino acid of position 308; as indicated by EU numbering in the amino acid sequence of the Fc region represented by any one of SEQ ID NOs: 13, 14, 15, and 16;
[14"] the method of any one of [1"] to [9"], wherein the Fc region is an Fc region with an enhanced FcRn-binding activity under a neutral pH range condition compared to that of the Fc region represented by any one of SEQ ID NOs: 13, 14, 15, and 16;

[15"] the method of [14] wherein the Fc region is an Fc region with a substitution of at least one or more amino acids selected from the group consisting of positions 237, 248, 250, 252, 254, 255, 256, 257, 258, 265, 286, 289, 297, 298, 303, 305, 307, 308, 309, 311, 312, 314, 315, 317, 332, 334, 360, 376, 380, 382, 384, 385, 386, 387, 389, 424, 428, 433, 434, and 436 (EU numbering) in the amino acid sequence of the Fc region represented by any one of SEQ ID NOs: 13, 14, 15, and 16;

[16"] the method of [15"], wherein the Fc region comprises at least one or more amino acids
selected from the group consisting of:
Met for the amino acid of position 237;
Ile for the amino acid of position 248;
Ala, Phe, Ile, Met, Gln, Ser, Val, Trp, or Tyr for the amino acid of position 250;
Phe, Trp, or Tyr for the amino acid of position 252;
Thr for the amino acid of position 254;
Glu for the amino acid of position 255;
Asp, Asn, Glu, or Gln for the amino acid of position 256;
Ala, Gly, Ile, Leu, Met, Asn, Ser, Thr, or Val for the amino acid of position 257;
His for the amino acid of position 258;
Ala for the amino acid of position 265;
Ala or Glu for the amino acid of position 286;
His for the amino acid of position 289;
Ala for the amino acid of position 297;
Ala for the amino acid of position 303;
Ala for the amino acid of position 305;
Ala, Asp, Phe, Gly, His, Ile, Lys, Leu, Met, Asn, Pro, Gln, Arg, Ser, Val, Trp, or Tyr for the amino acid of position 307;
Ala, Phe, Ile, Leu, Met, Pro, Gln, or Thr for the amino acid of position 308;
Ala, Asp, Glu, Pro, or Arg for the amino acid of position 309;
Ala, His, or Ile for the amino acid of position 311;
Ala or His for the amino acid of position 312;
Lys or Arg for the amino acid of position 314;
Ala, Asp, or His for the amino acid of position 315;
Ala for the amino acid of position 317;
Val for the amino acid of position 332;
Leu for the amino acid of position 334;
His for the amino acid of position 360;
Ala for the amino acid of position 376;
Ala for the amino acid of position 380;
Ala for the amino acid of position 382;
Ala for the amino acid of position 384;
Asp or His for the amino acid of position 385;
Pro for the amino acid of position 386;
Glu for the amino acid of position 387;
Ala or Ser for the amino acid of position 389;
Ala for the amino acid of position 424;
Ala, Asp, Phe, Gly, His, Ile, Lys, Leu, Asn, Pro, Gln, Ser, Thr, Val, Trp, or Tyr for the amino acid of position 428;
Lys for the amino acid of position 433;
Ala, Phe, His, Ser, Trp, or Tyr for the amino acid of position 434; and
His Ile, Leu, Phe, Thr, or Val for the amino acid of position 436;
as indicated by EU numbering in the amino acid sequence of the Fc region represented by any one of SEQ ID NOs: 13, 14, 15, and 16;

[17"] the method of any one of [1"] to [13"], wherein the Fc region includes an Fc region that has a higher Fcγ receptor-binding activity than that of the Fc region of a native human IgG;

[18"] the method of [17"], wherein the Fc region comprises in its amino acid sequence at least one or more amino acids that are different from amino acids of the native human IgG Fc region selected from the group consisting of positions 221, 222, 223, 224, 225, 227, 228, 230, 231, 232, 233, 234, 235, 236, 237, 238, 239, 240, 241, 243, 244, 245, 246, 247, 249, 250, 251, 254, 255, 256, 258, 260, 262, 263, 264, 265, 266, 267, 268, 269, 270, 271, 272, 273, 274, 275, 276, 278, 279, 280, 281, 282, 283, 284, 285, 286, 288, 290, 291, 292, 293, 294, 295, 296, 297, 298, 299, 300, 301, 302, 303, 304, 305, 311, 313, 315, 317, 318, 320, 322, 323, 324, 325, 326, 327, 328, 329, 330, 331, 332, 333, 334, 335, 336, 337, 339, 376, 377, 378, 379, 380, 382, 385, 392, 396, 421, 427, 428, 429, 434, 436, and 440 (EU numbering);

[19"] the method of [18"], wherein the Fc region comprises in its amino acid sequence at least one or more amino acids selected from the group consisting of:
Lys or Tyr for the amino acid of position 221;
Phe, Trp, Glu, or Tyr for the amino acid of position 222;
Phe, Trp, Glu, or Lys for the amino acid of position 223;
Phe, Trp, Glu, or Tyr for the amino acid of position 224;
Glu, Lys, or Trp for the amino acid of position 225;
Glu, Gly, Lys, or Tyr for the amino acid of position 227;
Glu, Gly, Lys, or Tyr for the amino acid of position 228;
Ala, Glu, Gly, or Tyr for the amino acid of position 230;
Glu, Gly, Lys, Pro, or Tyr for the amino acid of position 231;
Glu, Gly, Lys, or Tyr for the amino acid of position 232;
Ala, Asp, Phe, Gly, His, Ile, Lys, Leu, Met, Asn, Gln, Arg, Ser, Thr, Val, Trp, or Tyr for the amino acid of position 233;
Ala, Asp, Glu, Phe, Gly, His, Ile, Lys, Met, Asn, Pro, Gln, Arg, Ser, Thr, Val, Trp, or Tyr for the amino acid of position 234;
Ala, Asp, Glu, Phe, Gly, His, Ile, Lys, Met, Asn, Pro, Gln, Arg, Ser, Thr, Val, Trp, or Tyr for the amino acid of position 235;
Ala, Asp, Glu, Phe, His, Ile, Lys, Leu, Met, Asn, Pro, Gln, Arg, Ser, Thr, Val, Trp, or Tyr for the amino acid of position 236;
Asp, Glu, Phe, His, Ile, Lys, Leu, Met, Asn, Pro, Gln, Arg, Ser, Thr, Val, Trp, or Tyr for the amino acid of position 237;
Asp, Glu, Phe, Gly, His, Ile, Lys, Leu, Met, Asn, Gln, Arg, Ser, Thr, Val, Trp, or Tyr for the amino acid of position 238;
Asp, Glu, Phe, Gly, His, Ile, Lys, Leu, Met, Asn, Pro, Gln, Arg, Thr, Val, Trp, or Tyr for the amino acid of position 239;
Ala, Ile, Met, or Thr for the amino acid of position 240;
Asp, Glu, Leu, Arg, Trp, or Tyr for the amino acid of position 241;
Leu, Glu, Leu, Gln, Arg, Trp, or Tyr for the amino acid of position 243;
His for the amino acid of position 244;
Ala for the amino acid of position 245;
Asp, Glu, His, or Tyr for the amino acid of position 246;
Ala, Phe, Gly, His, Ile, Leu, Met, Thr, Val, or Tyr for the amino acid of position 247;
Glu, His, Gln, or Tyr for the amino acid of position 249;
Glu or Gln for the amino acid of position 250;
Phe for the amino acid of position 251;
Phe, Met, or Tyr for the amino acid of position 254;
Glu, Leu, or Tyr for the amino acid of position 255;
Ala, Met, or Pro for the amino acid of position 256;
Asp, Glu, His, Ser, or Tyr for the amino acid of position 258;
Asp, Glu, His, or Tyr for the amino acid of position 260;
Ala, Glu, Phe, Ile, or Thr for the amino acid of position 262;

Ala, Ile, Met, or Thr for the amino acid of position 263;
Asp, Glu, Phe, Gly, His, Ile, Lys, Leu, Met, Asn, Pro, Gln, Arg, Ser, Thr, Trp, or Tyr for the amino acid of position 264;
Ala, Leu, Phe, Gly, His, Ile, Lys, Leu, Met, Asn, Pro, Gln, Arg, Ser, Thr, Val, Trp, or Tyr for the amino acid of position 265;
Ala, Ile, Met, or Thr for the amino acid of position 266;
Asp, Glu, Phe, His, Ile, Lys, Leu, Met, Asn, Pro, Gln, Arg, Thr, Val, Trp, or Tyr for the amino acid of position 267;
Asp, Glu, Phe, Gly, Ile, Lys, Leu, Met, Pro, Gln, Arg, Thr, Val, or Trp for the amino acid of position 268;
Phe, Gly, His, Ile, Lys, Leu, Met, Asn, Pro, Arg, Ser, Thr, Val, Trp, or Tyr for the amino acid of position 269;
Glu, Phe, Gly, His, Ile, Leu, Met, Pro, Gln, Arg, Ser, Thr, Trp, or Tyr for the amino acid of position 270;
Ala, Asp, Glu, Phe, Gly, His, Ile, Lys, Leu, Met, Asn, Gln, Arg, Ser, Thr, Val, Trp, or Tyr for the amino acid of position 271;
Asp, Phe, Gly, His, Ile, Lys, Leu, Met, Pro, Arg, Ser, Thr, Val, Trp, or Tyr for the amino acid of position 272;
Phe or Ile for the amino acid of position 273;
Asp, Glu, Phe, Gly, His, Ile, Leu, Met, Asn, Pro, Arg, Ser, Thr, Val, Trp, or Tyr for the amino acid of position 274;
Leu or Trp for the amino acid of position 275;
Asp, Glu, Phe, Gly, His, Ile, Leu, Met, Pro, Arg, Ser, Thr, Val, Trp, or Tyr for the amino acid of position 276;
Asp, Glu, Gly, His, Ile, Lys, Leu, Met, Asn, Pro, Gln, Arg, Ser, Thr, Val, or Trp for the amino acid of position 278;
Ala for the amino acid of position 279;
Ala, Gly, His, Lys, Leu, Pro, Gln, Trp, or Tyr for the amino acid of position 280;
Asp, Lys, Pro, or Tyr for the amino acid of position 281;
Glu, Gly, Lys, Pro, or Tyr for the amino acid of position 282;
Ala, Gly, His, Ile, Lys, Leu, Met, Pro, Arg, or Tyr for the amino acid of position 283;
Asp, Glu, Leu, Asn, Thr, or Tyr for the amino acid of position 284;
Asp, Glu, Lys, Gln, Trp, or Tyr for the amino acid of position 285;
Glu, Gly, Pro, or Tyr for the amino acid of position 286;
Asn, Asp, Glu, or Tyr for the amino acid of position 288;
Asp, Gly, His, Leu, Asn, Ser, Thr, Trp, or Tyr for the amino acid of position 290;
Asp, Glu, Gly, His, Ile, Gln, or Thr for the amino acid of position 291;
Ala, Asp, Glu, Pro, Thr, or Tyr for the amino acid of position 292;
Phe, Gly, His, Ile, Leu, Met, Asn, Pro, Arg, Ser, Thr, Val, Trp, or Tyr for the amino acid of position 293;
Phe, Gly, His, Ile, Lys, Leu, Met, Asn, Pro, Arg, Ser, Thr, Val, Trp, or Tyr for the amino acid of position 294;
Asp, Glu, Phe, Gly, His, Ile, Lys, Met, Asn, Pro, Arg, Ser, Thr, Val, Trp, or Tyr for the amino acid of position 295;
Ala, Asp, Glu, Gly, His, Ile, Lys, Leu, Met, Asn, Gln, Arg, Ser, Thr, or Val for the amino acid of position 296;
Asp, Glu, Phe, Gly, His, Ile, Lys, Leu, Met, Pro, Gln, Arg, Ser, Thr, Val, Trp, or Tyr for the amino acid of position 297;
Ala, Asp, Glu, Phe, His, Ile, Lys, Met, Asn, Gln, Arg, Thr, Val, Trp, or Tyr for the amino acid of position 298;
Ala, Asp, Glu, Phe, Gly, His, Ile, Lys, Leu, Met, Asn, Pro, Gln, Arg, Ser, Val, Trp, or Tyr for the amino acid of position 299;
Ala, Asp, Glu, Gly, His, Ile, Lys, Leu, Met, Asn, Pro, Gln, Arg, Ser, Thr, Val, or Trp for the amino acid of position 300;
Asp, Glu, His, or Tyr for the amino acid of position 301;
Ile for the amino acid of position 302;
Asp, Gly, or Tyr for the amino acid of position 303;
Asp, His, Leu, Asn, or Thr for the amino acid of position 304;
Glu, Ile, Thr, or Tyr for the amino acid of position 305;
Ala, Asp, Asn, Thr, Val, or Tyr for the amino acid of position 311;
Phe for the amino acid of position 313;
Leu for the amino acid of position 315;
Glu or Gln for the amino acid of position 317;
His, Leu, Asn, Pro, Gln, Arg, Thr, Val, or Tyr for the amino acid of position 318;
Asp, Phe, Gly, His, Ile, Leu, Asn, Pro, Ser, Thr, Val, Trp, or Tyr for the amino acid of position 320;
Ala, Asp, Phe, Gly, His, Ile, Pro, Ser, Thr, Val, Trp, or Tyr for the amino acid of position 322;
Ile for the amino acid of position 323;
Asp, Phe, Gly, His, Ile, Leu, Met, Pro, Arg, Thr, Val, Trp, or Tyr for the amino acid of position 324;
Ala, Asp, Glu, Phe, Gly, His, Ile, Lys, Leu, Met, Pro, Gln, Arg, Ser, Thr, Val, Trp, or Tyr for the amino acid of position 325;
Ala, Asp, Glu, Gly, Ile, Leu, Met, Asn, Pro, Gln, Ser, Thr, Val, Trp, or Tyr for the amino acid of position 326;
Ala, Asp, Glu, Phe, Gly, His, Ile, Lys, Leu, Met, Asn, Pro, Arg, Thr, Val, Trp, or Tyr for the amino acid of position 327;
Ala, Asp, Glu, Phe, Gly, His, Ile, Lys, Met, Asn, Pro, Gln, Arg, Ser, Thr, Val, Trp, or Tyr for the amino acid of position 328;
Asp, Glu, Phe, Gly, His, Ile, Lys, Leu, Met, Asn, Gln, Arg, Ser, Thr, Val, Trp, or Tyr for the amino acid of position 329;
Cys, Glu, Phe, Gly, His, Ile, Lys, Leu, Met, Asn, Pro, Arg, Ser, Thr, Val, Trp, or Tyr for the amino acid of position 330;
Asp, Phe, His, Ile, Leu, Met, Gln, Arg, Thr, Val, Trp, or Tyr for the amino acid of position 331;
Ala, Asp, Glu, Phe, Gly, His, Lys, Leu, Met, Asn, Pro, Gln, Arg, Ser, Thr, Val, Trp, or Tyr for the amino acid of position 332;
Ala, Asp, Glu, Phe, Gly, His, Ile, Leu, Met, Pro, Ser, Thr, Val, or Tyr for the amino acid of position 333;
Ala, Glu, Phe, Ile, Leu, Pro, or Thr for the amino acid of position 334;
Asp, Phe, Gly, His, Ile, Leu, Met, Asn, Pro, Arg, Ser, Val, Trp, or Tyr for the amino acid of position 335;
Glu, Lys, or Tyr for the amino acid of position 336;
Glu, His, or Asn for the amino acid of position 337;
Asp, Phe, Gly, Ile, Lys, Met, Asn, Gln, Arg, Ser, or Thr for the amino acid of position 339;
Ala or Val for the amino acid of position 376;
Gly or Lys for the amino acid of position 377;
Asp for the amino acid of position 378;
Asn for the amino acid of position 379;
Ala, Asn, or Ser for the amino acid of position 380;
Ala or Ile for the amino acid of position 382;
Glu for the amino acid of position 385;
Thr for the amino acid of position 392;
Leu for the amino acid of position 396;
Lys for the amino acid of position 421;
Asn for the amino acid of position 427;
Phe or Leu for the amino acid of position 428;
Met for the amino acid of position 429;
Trp for the amino acid of position 434;
Ile for the amino acid of position 436; and
Gly, His, Ile, Leu, or Tyr for the amino acid of position 440;
as indicated by EU numbering;

[20"] the method of any one of [1"] to [16"], wherein the Fc region has a higher binding activity toward an inhibitory Fcγ receptor than toward an activating Fcγ receptor;
[21"] the method of [20"], wherein the inhibitory Fcγ receptor is human FcγRIIb;
[22"] the method of [20"] or [21"], wherein the activating Fcγ receptor is human FcγRIa, human FcγRIIa (R), human FcγRIIa (H), human FcγRIIIa (V), or human FcγRIIIa (F);
[23"] the method of any one of [20] to [22"], wherein the amino acid at position 238 or 328 (EU numbering) in the Fc region is different from the amino acid in the native human IgG Fc region;
[24"] the method of [23"], wherein the amino acid at position 238 of the Fc region is Asp or the amino acid of position 328 of the Fc region is Glu as indicated by EU numbering; and
[25"] the method of [23"] or [24"], wherein the amino acid sequence of the Fc region comprises
at least one or more amino acids selected from the group consisting of:
Asp for the amino acid of position 233;
Trp or Tyr for the amino acid of position 234;
Ala, Asp, Glu, Leu, Met, Phe, Trp, or Tyr for the amino acid of position 237;
Asp for the amino acid of position 239;
Ala, Gln, or Val for the amino acid of position 267;
Asn, Asp, or Glu for the amino acid of position 268;
Gly for the amino acid of position 271;
Ala, Asn, Asp, Gln, Glu, Leu, Met, Ser, or Thr for the amino acid of position 326;
Arg, Lys, or Met for the amino acid of position 330;
Ile, Leu, or Met for the amino acid of position 323; and
Asp for the amino acid of position 296;
as indicated by EU numbering;

MODE FOR CARRYING OUT THE INVENTION

Figure 1:
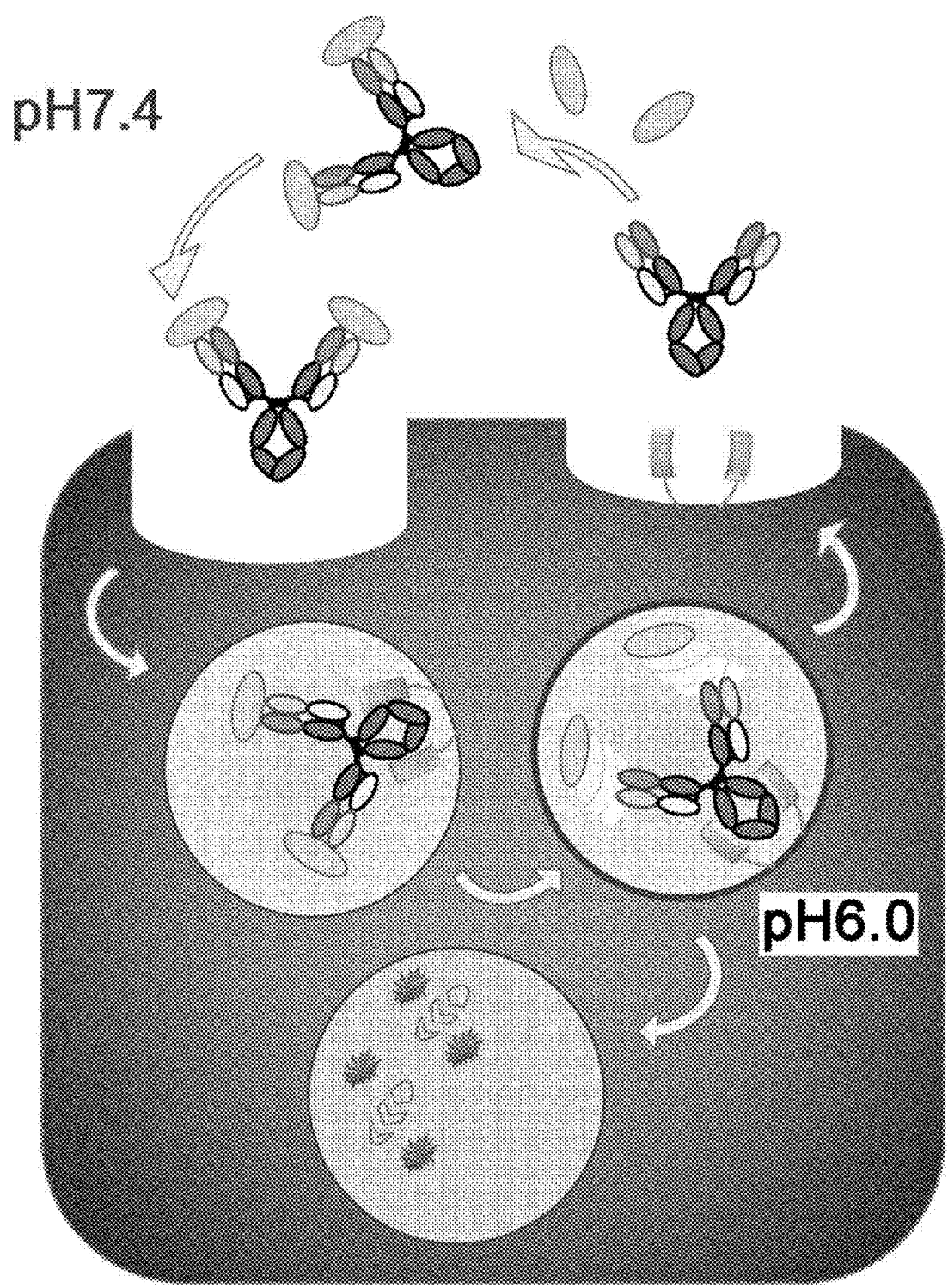
FIG. 1 is a diagram showing that an antibody with pH-dependent binding repeatedly binds to soluble antigens. The following steps are illustrated: an antibody binds to soluble antigens; the antibody is non-specifically internalized into a cell by pinocytosis; the antibody binds to FcRn within the endosome, and the soluble antigens dissociate from the antibody; the soluble antigens are transferred to the lysosome and degraded; after dissociation from the soluble antigens, the antibody is recycled to the plasma via FcRn; and the recycled antibody can bind to soluble antigens again.

The definitions and detailed description below are provided to help the understanding of the present invention illustrated herein.

Amino Acids

Herein, amino acids are described in one- or three-letter codes or both, for example, Ala/A, Leu/L, Arg/R, Lys/K, Asn/N, Met/M, Asp/D, Phe/F, Cys/C, Pro/P, Gln/Q, Ser/S, Glu/E, Thr/T, Gly/G, Trp/W, His/H, Tyr/Y, Ile/I, or Val/V.

Modification of Amino Acids

For amino acid modification in the amino acid sequence of an antigen-binding molecule, known methods such as site-directed mutagenesis methods (Kunkel et al. (Proc. Natl. Acad. Sci. USA (1985) 82, 488-492)) and overlap extension PCR may be appropriately adopted. Furthermore, several known methods may also be adopted as amino acid alteration methods for substitution to non-natural amino acids (Annu. Rev. Biophys. Biomol. Struct. (2006) 35, 225-249; and Proc. Natl. Acad. Sci. U.S.A. (2003) 100 (11), 6353-6357). For example, it is suitable to use a cell-free translation system (Clover Direct (Protein Express)) containing a tRNA that has a non-natural amino acid bound to a complementary amber suppressor tRNA of the UAG codon (amber codon) which is one of the stop codons.

In the present specification, the meaning of the term "and/or" when describing the site of amino acid alteration includes every combination where "and" and "or" are suitably combined. Specifically, for example, "the amino acids at positions 33, 55, and/or 96 are substituted" includes the following variation of amino acid modifications: amino acid(s) at (a) position 33, (b) position 55, (c) position 96, (d) positions 33 and 55, (e) positions 33 and 96, (f) positions 55 and 96, and (g) positions 33, 55, and 96.

Antigenic Binding Units

Herein, "antigenic binding units" refers to "the number of epitopes present in a single antigen molecule in a form normally present in plasma in the absence of an antigen-binding molecule, wherein the antigen molecule comprises an epitope that binds to a monovalent binding unit of an antigen-binding domain contained in an antigen-binding molecule of the present invention". Examples of an antigen that has two antigenic binding units are antigens including multimers generally present in plasma in the form of homodimers such as GDF, PDGF, or VEGF. For example, in homodimerized GDF molecules, there are two units of epitopes each bound by a monovalent binding unit of a variable region contained in an anti-GDF antibody molecule that comprises two variable regions having the same sequence (i.e., not the bispecific antibody to be described later). Immunoglobulin molecules such as IgE are also included as examples of antigens with two antigenic binding units. IgE normally exists in plasma as a tetramer comprising a heavy-chain dimer and a light-chain dimer; and in the tetramer, there are two units of epitopes each bound by a single valence of a variable region contained in an anti-IgE antibody molecule that comprises two variable regions having the same sequence (i.e., not the later-described bispecific antibody). IgA normally exists in the plasma in two forms: a tetramer comprising a heavy-chain dimer and a light-chain dimer, and an octamer produced when the tetramers further form a complex via a J chain; and the tetramer and octamer respectively have two units and four units of epitopes each bound by a single valence of a variable region contained in an anti-IgA antibody molecule that comprises two variable regions having the same sequence (i.e., not the later-described bispecific antibody). Examples of antigens with three antigenic binding units are antigens including multimers generally present in plasma in the form of homotrimers such as TNFα, RANKL, or CD154 of the TNF superfamily.

Examples of antigen molecules with one antigenic binding unit are molecules generally present in plasma in the form of monomers such as soluble IL-6 receptor (hereinafter also referred to as sIL-6R), IL-6, HMGB-1, and CTGF. Heterodimers such as IL-12 comprising IL-12p40 and IL-12p35, IL-23 comprising IL-12p40 and IL-23p19 (also referred to as IL-30B), IL 27 comprising EBI3 and IL27p28, and IL-35 comprising IL-12p35 and EBI3 contain two structurally different subunits molecules. In an anti-subunit antibody molecule comprising two variable regions that bind to one of these subunits (i.e., not the later-described bispecific antibody), the epitope bound by a single valence of the variable regions is one unit; therefore, the antigenic binding unit of these heterodimers is one. The antigenic binding unit of heterotrimers such as the multisubunit complex TNFα-TNFβ-hCG is similarly one unit.

Since "antigenic binding unit" means the number of epitopes bound by a monovalent binding unit of an antigen-binding domain, when there is one type of paratope or multiple types of paratopes present in an antigen-binding molecule, the antigenic binding unit of the antigen will be different even if the antigen bound by these antigen-binding molecules is the same antigen. For example, in the case of the above-mentioned heterodimers, when the monovalent binding unit in the antigen-binding domain contained in the antigen-binding molecule binds to one type of subunit in the heterodimer, the antigenic binding unit of this antigen is one, whereas when the antigen-binding molecule is a biparatopic or a bispecific antigen-binding molecule comprising two monovalent binding units that bind to each of the subunits forming the heterodimer, the antigenic binding unit of this antigen is two.

Multimers

Herein, when the phrase "two or more multimers" is simply recited, the meaning of the term "multimer" includes both homomultimer and heteromultimer. The modes of binding between subunits contained in a multimer are covalent bonds such as peptide bonds or disulfide bonds, and stable non-covalent bonds such as ionic bonds, van der Waals bonds, and hydrogen bonds, but are not limited thereto. Homomultimers include a plurality of identical subunits, whereas heteromultimers contain a plurality of different subunits. For example, the meaning of the term "dimer" includes both homodimer and heterodimer; and while a homodimer contains two identical subunits, a heterodimer contains two different subunits. Furthermore, in the case of a polypeptide, the term "monomer" which expresses each of the units forming a multimer refers to each of the continuous structural units linked by peptide bonds.

Antigens

Herein, "antigens" are not particularly limited in their structure, as long as they comprise epitopes to which antigen-binding domains bind. In other words, antigens can be inorganic or organic substances. Other antigens include, for example, the molecules below: 17-IA, 4-1BB, 4Dc, 6-keto-PGF1a, 8-iso-PGF2a, 8-oxo-dG, A1 adenosine receptor, A33, ACE, ACE-2, activin, activin A, activin AB, activin B, activin C, activin RIA, activin MA ALK-2, activin RIB ALK-4, activin RITA, activin RIM, ADAM, ADAM10, ADAM12, ADAM15, ADAM17/TACE, ADAMS, ADAMS, ADAMTS, ADAMTS4, ADAMTS5, addressin, aFGF, ALCAM, ALK, ALK-1, ALK-7,alpha-1-antitrypsin, alpha-V/beta-1 antagonist, ANG, Ang, APAF-1, APE, APJ, APP, APRIL, AR, ARC, ART, artemin, anti-Id, ASPARTIC, atrial natriuretic peptide, av/b3 integrin, Ax1, b2M, B7-1, B7-2, B7-H, B-lymphocyte stimulating factor (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMP, b-NGF, BOK, bombesin, bone-derived neurotrophic factor, BPDE, BPDE-DNA, BTC, complement factor 3 (C3), C3a, C4, C5, C5a, C10, CA125, CAD-8, calcitonin, cAMP, carcinoembryonic antigen (CEA), cancer associated antigen, cathepsin A, cathepsin B, cathepsin C/DPPI, cathepsin D, cathepsin E, cathepsin H, cathepsin L, cathepsin 0, cathepsin S, cathepsin V, cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 protein), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, Botulinum toxin, Clostridium perfringens toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6,cytokeratin tumor associated antigen, DAN, DCC, DcR3, DC-SIGN, complement regulatory factor (Decay accelerating factor), des (1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, enkephalinase, eNOS, Eot, eotaxin 1, EpCAM, ephrin B2/EphB4, EPO, ERCC, E-selectin, ET-1, factor IIa, factor VII, factor VIIIc, factor IX, fibroblast activation protein (FAP), Fas, FcR1, FEN-1, ferritin, FGF, FGF-19, FGF-2, FGF3, FGF-8, FGFR, FGFR-3, fibrin, FL, FLIP, Flt-3, Flt-4, follicle stimulating hormone, fractalkine, FZD1, FZD2, FZD3, FZD4, FZD5, FZD6, FZD7, FZD8, FZD9, FZD10, G250, Gash, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (myostatin), GDF-9, GDF-15 (MIC-1), GDNF, GDNF, GFAP, GFRa-1, GFR-alpha1, GFR-alpha2, GFR-alpha3, GITR, glucagon, Glut4, glycoprotein IIb/IIIa (GPIIb/IIIa), GM-CSF, gp130, gp72, GRO, growth hormone releasing hormone, hapten (NP-cap or NIP-cap), HB-EGF, HCC, HCMV gB envelope glycoprotein, HCMV gH envelope glycoprotein, HCMV UL, hematopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, high molecular weight melanoma-associated antigen (HMW-MAA), HIV gp120, HIV IIIB gp 120 V3 loop, HLA, HLA-DR, HM1.24, HMFG PEM, HRG, Hrk, human cardiac myosin, human cytomegalovirus (HCMV), human growth hormone (HGH), HVEM, 1-309, IAP, ICAM, ICAM-1, ICAM-3, ICE, ICOS, IFNg, Ig, IgA receptor, IgE, IGF, IGF binding protein, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, inhibin, iNOS, insulin A chain, insulin B chain, insulin-like growth factor1, integrin alpha2, integrin alpha3, integrin alpha4, integrin alpha4/beta1, integrin alpha4/beta7, integrin alpha5 (alpha V), integrin alpha5/beta1, integrin alpha5/beta3, integrin alpha6, integrin beta1, integrin beta2, interferon gamma, IP-10, I-TAC, JE, kallikrein 2, kallikrein 5, kallikrein 6, kallikrein 11, kallikrein 12, kallikrein 14, kallikrein 15, kallikrein L1, kallikrein L2, kallikrein L3, kallikrein L4, KC, KDR, keratinocyte growth factor (KGF), laminin 5, LAMP, LAP, LAP (TGF-1), latent TGF-1, latent TGF-1 bp1, LBP, LDGF, LECT2, lefty, Lewis-Y antigen, Lewis-Y associated antigen, LFA-1, LFA-3, Lfo, LIF, LIGHT, lipoprotein, LIX, LKN, Lptn, L-selectin, LT-a, LT-b, LTB4, LTBP-1, lung surface, luteinizing hormone, lymphotoxin beta receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, Mullerian-inhibiting substance, Mug, MuSK, NAIP, NAP, NCAD, N-C adherin, NCA 90, NCAM, NCAM, neprilysin, neurotrophin-3, -4, or -6, neurturin, nerve growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, parathyroid hormone, PARC, PARP, PBR, PBSF, PCAD, P-cadherin, PCNA, PDGF, PDGF, PDK-1, PECAM, PEM, PF4, PGE, PGF, PGI2, PGJ2, PIN, PLA2, placental alkaline phosphatase (PLAP), P1GF, PLP, PP14, proinsulin, prorelaxin, protein C, PS, PSA, PSCA, prostate-specific membrane antigen (PSMA), PTEN, PTHrp, Ptk, PTN, R51, RANK, RANKL, RANTES, RANTES, relaxin A chain, relaxin B chain, renin, respiratory syncytial virus (RSV) F, RSV Fgp, Ret, Rheumatoid factor, RLIP76, RPA2, RSK, 5100, SCF/KL, SDF-1, SERINE, serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptor (for example, T-cell receptor alpha/beta), TdT, TECK, TEM1, TEMS, TEM7, TEM8, TERT, testis PLAP-like alkaline phosphatase, TfR, TGF, TGF-alpha, TGF-beta, TGF-beta Pan Specific, TGF-betaRI (ALK-5), TGF-betaRII, TGF-betaRIIb, TGF-betaRIII, TGF-beta1, TGF-beta2, TGF-beta3, TGF-beta4, TGF-beta5, thrombin, thymus Ck-1, thyroid-stimulating hormone, Tie, TIMP, TIQ, tissue factor, TMEFF2, Tmpo, TMPRSS2, TNF, TNF-alphabeta, TNF-beta2, TNFc, TNF-RI, TNF-RII, TNFRSF10A (TRAIL R1 Apo-2, DR4), TNFRSF10B (TRAIL R2 DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACT), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p'75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (DcTRAIL R1 TNFRH1), TNFRSF25 (DR3 Apo-3, LARD, TR-3, TRAMP, WSL-1), TNFSF10 (TRAIL, Apo-2 ligand, TL2), TNFSF11 (TRANCE/RANK ligand, ODF, OPG ligand), TNFSF12 (TWEAK, Apo-3 ligand, DR3 ligand), TNFSF13 (APRIL, TALL2), TNFSF13B (BAFF, BLYS, TALL1, THANK, TNFSF20), TNFSF14 (LIGHT, HVEM ligand, LTg), TNFSF15 (TL1/VEGI), TNFSF18 (GITR ligand, AITR ligand, TL6), TNFSF1A (TNF Conectin Cachectin, DIF, TNFSF2), TNFSF1B (TNF-b, LTa, TNFSF1), TNFSF3 (LTb, TNFC, p33), TNFSF4 (OX40 ligand, gp34, TXGP1), TNFSF5 (CD40 ligand, CD154, gp39, HIGM1, IMD3, TRAP), TNFSF6 (Fas ligand, Apo-1 ligand, APT1 ligand), TNFSF7 (CD27 ligand, CD70), TNFSF8 (CD30 ligand, CD153), TNFSF9 (4-1BB ligand, CD137 ligand), TP-1, t-PA, Tpo, TRAIL, TRAIL R, TRAIL-R1, TRAIL-R2, TRANCE, transferrin receptor, TRF, Trk, TROP-2, TSG, TSLP, tumor associated antigen CA125, tumor associated antigen expressing Lewis-Y associated carbohydrates, TWEAK, TXB2, Ung, uPAR, uPAR-1, urokinase, VCAM, VCAM-1, VECAD, VE-Cadherin, VE-cadherin-2, VEFGR-1 (flt-1), VEGF, VEGFR, VEGFR-3 (flt-4), VEGI, VIM, virus antigen, VLA, VLA-1, VLA-4, VNR integrin, von Willebrand factor, WIF-1, WNT1, WNT2, WNT2B/13, WNT3, WNT3A, WNT4, WNTSA, WNTSB, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, HMGB1, IgA, A13, CD81, CD97, CD98, DDR1, DKK1, EREG, Hsp90, IL-17/IL-17R, IL-20/IL-20R, oxidized LDL, PCSK9, prekallikrein, RON, TMEM16F, SOD1, Chromogranin A, Chromogranin B, tau, VAP1, high molecular weight kininogen, IL-31, IL-31R, Nav1.1, Nav1.2, Nav1.3, Nav1.4, Nav1.5, Nav1.6, Nav1.7, Nav1.8, Nav1.9, EPCR, C1, C1q, C1r, C1s, C2, C2a, C2b, C3, C3a, C3b, C4, C4a, C4b, C5, C5a, C5b, C6, C7, C8, C9, factor B, factor D, factor H, properdin, sclerostin, fibrinogen, fibrin, prothrombin, thrombin, tissue factor, factor V, factor Va, factor VII, factor VIIa, factor VIII, factor VIIIa, factor IX, factor IXa, factor X, factor Xa, factor XI, factor XIa, factor XII, factor XIIa, factor XIII, factor XIIIa, TFPI, antithrombin III, EPCR, thrombomodulin, TAPI, tPA, plasminogen, plasmin, PAI-1, PAI-2, GPC3, Syndecan-1, Syndecan-2, Syndecan-3, Syndecan-4, LPA, and S1P; and receptors for hormone and growth factors.

As described later, when an antigen-binding molecule binds to a plurality of epitopes in an antigen molecule as with a bispecific antibody and such, the antigen that can form a complex with the antigen-binding molecule may be any of the antigens exemplified above, or combinations thereof, i.e., monomers or heteromultimers. Non-limiting examples of heteromultimers include heterodimers such as IL-12 comprising IL-12p40 and IL-12p35, IL-23 comprising IL-12p40 and IL-23p19 (also referred to as IL-30B), IL-27 comprising EBI-3 and IL27p28, and IL-35 comprising IL-12p35 and EBI-3.

While receptors are recited as examples of the above-mentioned antigens, when these receptors exist in soluble forms in biological fluids such as plasma, they can form complexes with the antigen-binding molecules of the present invention. Therefore, as long as the above-mentioned receptors exist in their soluble forms in biological fluids such as plasma, they may be used as antigens that may form complexes of the present invention by binding to an antigen-binding molecule of the present invention. An example of a non-limiting embodiment of such a soluble receptor is soluble IL-6R, which is a protein consisting of the amino acids at positions 1 to 357 in the IL-6R polypeptide sequence of SEQ ID NO: 1 as described in Mullberg et al. (J. Immunol. (1994) 152 (10), 4958-4968).

Soluble antigens are recited as examples of the above-mentioned antigens, and the solutions in which the antigens exist are not limited. Soluble antigens may exist in biological fluids, or more specifically in all fluids filling the space between tissues and cells or vessels in organisms. In a non-limiting embodiment, the antigens to which antigen-binding molecules of the present invention bind may be present in extracellular fluids. In vertebrates, extracellular fluid is a general term for plasma, interstitial fluid, lymph, compact connective tissue, cerebrospinal fluid, spinal fluid, puncture fluid, synovial fluid, or such components in the bone and cartilage, alveolar fluid (bronchoalveolar lavage fluid), peritoneal fluid, pleural fluid, pericardial fluid, cyst fluid, aqueous humor (hydatoid), or such transcellular fluids (various fluids in the glandular cavities and fluids in the digestive tract cavity and other body cavity fluids produced as a result of active transport/secretory activities of cells).

When the epitope to which the antigen-binding domain contained in an antigen-binding molecule binds is a single epitope, a non-limiting embodiment of an antigen that may form a complex of the present invention upon binding with the antigen-binding molecule includes the molecules exemplified below, which include a homodimer, homotrimer, or such, as an antigenic binding unit: GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (myostatin), GDF-9, GDF-15 (MIC-1), TNF, TNF-alphabeta, TNF-beta2, TNFSF10 (TRAIL Apo-2 ligand, TL2), TNFSF11 (TRANCE/RANK ligand, ODF, OPG ligand), TNFSF12 (TWEAK, Apo-3 ligand, DR3 ligand), TNFSF13 (APRIL, TALL2), TNFSF13B (BAFF, BLYS, TALL1, THANK, TNFSF20), TNFSF14 (LIGHT, HVEM ligand, LTg), TNFSF15 (TL1A/VEGI), TNFSF18 (GITR ligand, AITR ligand, TL6), TNFSF1A (TNF-a, Cachectin, DIF, TNFSF2), TNFSF1B (TNF-b, LTa, TNFSF1), TNFSF3 (LTb, TNFC, p33), TNFSF4 (OX40 ligand gp34, TXGP1), TNFSF5 (CD40 ligand, CD154, gp39, HIGM1, IMD3, TRAP), TNFSF6 (Fas ligand, Apo-1 ligand, APT1 ligand), TNFSF7 (CD27 ligand CD70), TNFSF8 (CD30 ligand CD153), TNFSF9 (4-1BB ligand CD137 ligand), VEGF, IgE, IgA, IgG, IgM, RANKL, TGF-alpha, TGF-beta, TGF-beta Pan Specific, and IL-8.

Epitopes

"Epitope" means an antigenic determinant in an antigen, and refers to an antigen site to which the antigen-binding domain of an antigen-binding molecule disclosed herein binds. Thus, for example, the epitope can be defined according to its structure. Alternatively, the epitope may be defined according to the antigen-binding activity of an antigen-binding molecule that recognizes the epitope. When the antigen is a peptide or polypeptide, the epitope can be specified by the amino acid residues forming the epitope. Alternatively, when the epitope is a sugar chain, the epitope can be specified by its specific sugar chain structure.

A linear epitope is an epitope that contains an epitope whose primary amino acid sequence has been recognized. Such a linear epitope typically contains at least three and most commonly at least five, for example, about 8 to 10 or 6 to 20 amino acids in a specific sequence.

In contrast to the linear epitope, a "conformational epitope" is an epitope in which the primary amino acid sequence containing the epitope is not the only determinant of the recognized epitope (for example, the primary amino acid sequence of a conformational epitope is not necessarily recognized by an epitope-defining antibody). Conformational epitopes may contain a greater number of amino acids compared to linear epitopes. A conformational epitope-recognizing antibody recognizes the three-dimensional structure of a peptide or protein. For example, when a protein molecule folds and forms a three-dimensional structure, amino acids and/or polypeptide main chains that form a conformational epitope become aligned, and the epitope is made recognizable by the antibody. Methods for determining epitope conformations include, for example, X ray crystallography, two-dimensional nuclear magnetic resonance, site-specific spin labeling, and electron paramagnetic resonance, but are not limited thereto. See, for example, Epitope Mapping Protocols in Methods in Molecular Biology (1996), Vol. 66, Morris (ed.).

The structure of the antigen-binding domain which binds to an epitope is called a paratope. An epitope and a paratope bind with stability through the action of hydrogen bonds, electrostatic force, van der Waals force, hydrophobic bonds, and such between the epitope and the paratope. This strength of binding between the epitope and paratope is called affinity. The total sum of binding strength when a plurality of epitopes and a plurality of paratopes bind is referred to as avidity. When an antibody comprising a plurality of paratopes (i.e., multivalent antibody) or such binds to a plurality of epitopes, the affinity acts additively or synergistically, and therefore avidity becomes higher than affinity.

Binding Activity

Examples of a method for assessing epitope binding by a test antigen-binding molecule containing an antigen-binding domain directed to IgA are described below. According to the examples below, methods for assessing epitope binding by a test antigen-binding molecule containing an antigen-binding domain for an antigen other than IgA can also be appropriately conducted.

For example, whether a test antigen-binding molecule containing an antigen-binding domain against IgA recognizes a linear epitope in the IgA molecule can be confirmed for example as mentioned below. For example, a linear peptide comprising an amino acid sequence forming an IgA constant region is synthesized for the above purpose. The peptide can be synthesized chemically, or obtained by genetic engineering techniques using a region encoding the amino acid sequence corresponding to the constant region in an IgA cDNA. Then, a test antigen-binding molecule containing an antigen-binding domain toward IgA is assessed for its binding activity towards a linear peptide comprising the amino acid sequence forming the constant region. For example, an ELISA using an immobilized linear peptide as an antigen can be performed to evaluate the binding activity of the antigen-binding molecule towards the peptide. Alternatively, the binding activity towards a linear peptide can be assessed based on the level of inhibition by the linear peptide of the binding of the antigen-binding molecule toward IgA cells. These tests can demonstrate the binding activity of the antigen-binding molecule towards the linear peptide.

Recognition of a conformational epitope by a test antigen-binding molecule comprising an antigen-binding domain targeting the IgA protein may be confirmed as stated below. For the above-mentioned objective, as described herein, a general genetic recombination technique is used to transfer an IgA-encoding recombinant gene into host cells (for example, animal cells, insect cells, or yeast cells) that enable formation of the native conformational epitope in the IgA protein. IgA containing the conformational epitope is prepared from the culture of recombinant cells produced in this manner. Recognition of a conformational epitope by a test antigen-binding molecule comprising an antigen-binding domain targeting IgA is, for example, when the test antigen-binding molecule binds strongly to the IgA molecule when it is contacted with immobilized IgA containing the conformational epitope, while the antigen-binding molecule does not substantively bind to a linear peptide comprising an amino acid sequence constituting the amino acid sequence of the immobilized IgA. Alternatively, it is also possible to use, instead of the above-mentioned linear peptide, the test IgA-targeting antigen-binding molecule that has been denatured by a reducing agent that cleaves disulfide bonds, such as dithiothreitol, dithioerythritol, 3-mercaptoethanol, phosphines, and sodium borohydride, and/or chaotropic agents such as surfactants including guanidine hydrochloride, urea, and sodium lauryl sulfate. Here, the phrase "does not substantively bind" refers to a binding activity not greater than 80%, normally not greater than 50%, preferably not greater than 30%, or particularly preferably not greater than 15% of the human-IgA-binding activity.

Methods for assaying the binding activity toward IgA of a test antigen-binding molecule containing an antigen-binding domain against IgA include, for example, the methods described in Antibodies: A Laboratory Manual (Ed Harlow, David Lane, Cold Spring Harbor Laboratory (1988) 359-420). Specifically, the assessment can be performed based on the principle of ELISA or EIA using IgA as antigen.

In the ELISA format, the binding activity of a test antigen-binding molecule containing an IgA antigen-binding domain towards IgA can be assessed quantitatively by comparing the levels of signal generated by enzymatic reaction. Specifically, a test antigen-binding molecule is added to an ELISA plate onto which IgA has been immobilized. Then, the test antigen-binding molecule that bound to IgA immobilized on the plate is detected using an enzyme-labeled antibody that recognizes the test antigen-binding molecule. In the ELISA, a serial dilution of the test antigen-binding molecule can be prepared and the antibody binding titer toward IgA be determined to compare the binding activity of the test antigen-binding molecule towards IgA.

The binding of a test antigen-binding molecule towards an antigen expressed on the surface of cells suspended in buffer or the like can be detected using a flow cytometer. Known flow cytometers include, for example, the following devices:
FACSCanto™ II
FACSAria™
FACSArray™
FACSVantage™ SE
FACSCalibur™ (all are trade names of BD Biosciences)
EPICS ALTRA HyPerSort
Cytomics FC 500
EPICS XL-MCL ADC EPICS XL ADC
Cell Lab Quanta/Cell Lab Quanta SC (all are trade names of Beckman Coulter).

Preferable methods for assaying the binding activity towards an antigen of a test antigen-binding molecule containing an antigen-binding domain against IgE include, for example, the following method. First, IgE-expressing cells are reacted with a test antigen-binding molecule, and then this is stained with an FITC-labeled secondary antibody that recognizes the antigen-binding molecule. The test antigen-binding molecule is appropriately diluted with a suitable buffer to prepare the molecule at a desired concentration. For example, the molecule can be used at a concentration within the range of 10 µg/ml to 10 ng/ml. Then, the fluorescence intensity and cell count are determined using FACSCalibur (BD). The fluorescence intensity obtained by analysis using the CELL QUEST Software (BD), i.e., the Geometric Mean value, reflects the quantity of antibody bound to cells. That is, the binding activity of a test antigen-binding molecule, which is represented by the quantity of the test antigen-binding molecule bound, can be determined by measuring the Geometric Mean value.

Whether a test antigen-binding molecule containing an IgA antigen-binding domain shares a common epitope with another antigen-binding molecule can be assessed based on the competition between the two molecules for the same epitope. The competition between antigen-binding molecules can be detected by cross-blocking assay or the like. For example, the competitive ELISA assay is a preferred cross-blocking assay.

Specifically, in cross-blocking assay, the IgA protein immobilized to the wells of a microtiter plate is pre-incubated in the presence or absence of a candidate competitor antigen-binding molecule, and then a test antigen-binding molecule is added thereto. The quantity of test antigen-binding molecule bound to the IgA protein in the wells is indirectly correlated with the binding ability of a candidate competitor antigen-binding molecule that competes for the binding to the same epitope. That is, the greater the affinity of the competitor antigen-binding molecule for the same epitope, the lower the binding activity of the test antigen-binding molecule towards the IgA protein-coated wells.

The quantity of the test antigen-binding molecule bound to the wells via the IgA protein can be readily determined by labeling the antigen-binding molecule in advance. For example, a biotin-labeled antigen-binding molecule is measured using an avidin/peroxidase conjugate and appropriate substrate. In particular, cross-blocking assay that uses enzyme labels such as peroxidase is called "competitive ELISA assay". The antigen-binding molecule can also be labeled with other labeling substances that enable detection or measurement. Specifically, radiolabels, fluorescent labels, and such are known.

When the candidate competitor antigen-binding molecule can block the binding by a test antigen-binding molecule containing an IgA antigen-binding domain by at least 20%, preferably at least 20 to 50%, and more preferably at least 50% compared to the binding activity in a control experiment conducted in the absence of the competitor antigen-binding molecule, the test antigen-binding molecule is determined to substantially bind to the same epitope bound by the competitor antigen-binding molecule, or compete for the binding to the same epitope.

When the structure of an epitope bound by a test antigen-binding molecule containing an IgA antigen-binding domain has already been identified, whether the test and control antigen-binding molecules share a common epitope can be assessed by comparing the binding activities of the two antigen-binding molecules towards a peptide prepared by introducing amino acid mutations into the peptide forming the epitope.

To measure the above binding activities, for example, the binding activities of test and control antigen-binding molecules towards a linear peptide into which a mutation is introduced are compared in the above ELISA format. Besides the ELISA methods, the binding activity towards the mutant peptide bound to a column can be determined by flowing test and control antigen-binding molecules in the column, and then quantifying the antigen-binding molecule eluted in the elution solution. Methods for adsorbing a mutant peptide to a column, for example, in the form of a GST fusion peptide, are known.

Alternatively, when the identified epitope in an antigen expressed on a cell is a conformational epitope, whether test and control antigen-binding molecules share a common epitope can be assessed, for example, by the following method. Explanation is provided below, using the case of IgE as the antigen as an example. First, IgE-expressing cells and cells expressing IgE with a mutation introduced into the epitope are prepared. The test and control antigen-binding molecules are added to a cell suspension prepared by suspending these cells in an appropriate buffer such as PBS. Then, the cell suspensions are appropriately washed with a buffer, and an FITC-labeled antibody that recognizes the test and control antigen-binding molecules is added thereto. The fluorescence intensity and number of cells stained with the labeled antibody are determined using FACSCalibur (BD). The test and control antigen-binding molecules are appropriately diluted using a suitable buffer, and used at desired concentrations. For example, they may be used at a concentration within the range of 10 µg/ml to 10 ng/ml. The fluorescence intensity determined by analysis using the CELL QUEST Software (BD), i.e., the Geometric Mean value, reflects the quantity of labeled antibody bound to cells. That is, the binding activities of the test and control antigen-binding molecules, which are represented by the quantity of labeled antibody bound, can be determined by measuring the Geometric Mean value.

In the above method, whether an antigen-binding molecule does "not substantially bind to cells expressing mutant IgE" can be assessed, for example, by the following method. First, the test and control antigen-binding molecules bound to cells expressing mutant IgE are stained with a labeled antibody. Then, the fluorescence intensity of the cells is determined. When FACSCalibur is used for fluorescence detection by flow cytometry, the determined fluorescence intensity can be analyzed using the CELL QUEST Software. From the Geometric Mean values in the presence and absence of the polypeptide complex, the comparison value (ΔGeo–Mean) can be calculated according to the following formula to determine the ratio of increase in fluorescence intensity as a result of the binding by the antigen-binding molecule. ΔGeo–Mean=Geo–Mean (in the presence of the polypeptide complex)/Geo–Mean (in the absence of the polypeptide complex)

The Geometric Mean comparison value (ΔGeo–Mean value for the mutant IgE molecule) determined by the above analysis, which reflects the quantity of a test antigen-binding molecule bound to cells expressing mutant IgE, is compared to the ΔGeo–Mean comparison value that reflects the quantity of the test antigen-binding molecule bound to IgE-expressing cells. In this case, the concentrations of the test antigen-binding molecule used to determine the ΔGeo-Mean comparison values for IgE-expressing cells and cells expressing mutant IgE are particularly preferably adjusted to be equal or substantially equal. An antigen-binding molecule that has been confirmed to recognize an epitope in IgE is used as a control antigen-binding molecule.

If the ΔGeo-Mean comparison value of a test antigen-binding molecule for cells expressing mutant IgE is smaller than the ΔGeo-Mean comparison value of the test antigen-binding molecule for IgE-expressing cells by at least 80%, preferably 50%, more preferably 30%, and particularly preferably 15%, then the test antigen-binding molecule "does not substantially bind to cells expressing mutant IgE". The formula for determining the Geo-Mean (Geometric Mean) value is described in the CELL QUEST Software User's Guide (BD biosciences). When the comparison shows that the comparison values are substantially equivalent, the epitope for the test and control antigen-binding molecules can be determined to be the same.

Antigen-Binding Domain

Herein, an "antigen-binding domain" may be of any structure as long as it binds to an antigen of interest. Such domains preferably include, for example:
antibody heavy-chain and light-chain variable regions;
a module of about 35 amino acids called A domain which is contained in the in vivo cell membrane protein Avimer (International Publication No. WO 2004/044011, International Publication No. WO 2005/040229);
Adnectin containing the 10Fn3 domain which binds to the protein moiety of fibronectin, a glycoprotein expressed on cell membrane (International Publication No. WO 2002/032925);
Affibody which is composed of a 58-amino acid three-helix bundle based on the scaffold of the IgG-binding domain of Protein A (International Publication No. WO 1995/001937);
Designed Ankyrin Repeat proteins (DARPins) which are a region exposed on the molecular surface of ankyrin repeats (AR) having a structure in which a subunit consisting of a turn comprising 33 amino acid residues, two antiparallel helices, and a loop is repeatedly stacked (International Publication No. WO 2002/020565);
Anticalins and such, which are domains consisting of four loops that support one side of a barrel structure composed of eight circularly arranged antiparallel strands that are highly conserved among lipocalin molecules such as neutrophil gelatinase-associated lipocalin (NGAL) (International Publication No. WO 2003/029462); and
the concave region formed by the parallel-sheet structure inside the horseshoe-shaped structure constituted by stacked repeats of the leucine-rich-repeat (LRR) module of the variable lymphocyte receptor (VLR) which does not have the immunoglobulin structure and is used in the system of acquired immunity in jawless vertebrate such as lampery and hagfish (International Publication No. WO 2008/016854). Preferred antigen-binding domains of the present invention include, for example, those having antibody heavy-chain and light-chain variable regions. Preferred examples of antigen-binding domains include "single chain Fv (scFv)", "single chain antibody", "Fv", "single chain Fv 2 (scFv2)", "Fab", and "F(ab')2".

The antigen-binding domains of antigen-binding molecules of the present invention can bind to an identical epitope. Such identical epitope can be present, for example, in a protein comprising the amino acid sequence of SEQ ID NO: 2. Alternatively, each of the antigen-binding domains of antigen-binding molecules of the present invention can bind to a different epitope. Herein, the different epitope can be present in, for example, a protein comprising the amino acid sequence of SEQ ID NO: 2.

Immune Complex

Immune complex refers to a relatively stable structure produced when at least one antigen and at least one antigen-binding molecule bind with each other to form a larger molecular-weight complex. A non-limiting embodiment of the immune complex is, for example, an antigen-antibody aggregate. A method for evaluating the formation of immune complexes comprising two or more antigen-binding molecules and two or more antigenic binding units will be described later in this specification.

Specificity

"Specific" means that one of the molecules that specifically bind does not show any significant binding to molecules other than the single or plurality of partner molecules it binds to. Furthermore, "specific" is also used when an antigen-binding domain is specific to a particular epitope among multiple epitopes in an antigen. When an epitope bound by an antigen-binding domain is contained in multiple different antigens, antigen-binding molecules containing the antigen-binding domain can bind to various antigens that have the epitope. Here, "does not show any significant binding" means showing no more than 50%, generally no more than 30%, preferably no more than 15%, particularly preferably no more than 10%, and even more preferably no more than 5% of the binding activity to a partner molecule towards molecules other than the partner molecule.

Antibody

Herein, "antibody" refers to a natural immunoglobulin or an immunoglobulin produced by partial or complete synthesis. Antibodies can be isolated from natural sources such as naturally-occurring plasma and serum, or culture supernatants of antibody-producing hybridomas. Alternatively, antibodies can be partially or completely synthesized using techniques such as genetic recombination. Preferred antibodies include, for example, antibodies of an immunoglobulin isotype or subclass belonging thereto. Known human immunoglobulins include antibodies of the following nine classes (isotypes): IgG1, IgG2, IgG3, IgG4, IgA1, IgA2, IgD, IgE, and IgM. Of these isotypes, antibodies of the present invention include IgG1, IgG2, IgG3, and IgG4. A number of allotype sequences of human IgG1, human IgG2, human IgG3, and human IgG4 constant regions due to gene polymorphisms are described in "Sequences of proteins of immunological interest", NIH Publication No. 91-3242. Any of such sequences may be used in the present invention. In particular, for the human IgG1 sequence, the amino acid sequence at positions 356 to 358 as indicated by EU numbering may be DEL or EEM. Several allotype sequences due to genetic polymorphisms have been described in "Sequences of proteins of immunological interest", NIH Publication No. 91-3242 for the human Igκ (Kappa) constant region and human Igλ (Lambda) constant region, and any of the sequences may be used in the present invention.

Methods for producing an antibody with desired binding activity are known to those skilled in the art. Below is an example that describes a method for producing an antibody that binds to IgA (anti-IgA antibody). Antibodies that bind to an antigen other than IgA can also be produced according to the example described below.

Anti-IgA antibodies can be obtained as polyclonal or monoclonal antibodies using known methods. The anti-IgA antibodies preferably produced are monoclonal antibodies derived from mammals. Such mammal-derived monoclonal antibodies include antibodies produced by hybridomas or host cells transformed with an expression vector carrying an antibody gene by genetic engineering techniques. Meanwhile, "humanized antibodies" or "chimeric antibodies" are included in the monoclonal antibodies of the present invention.

Monoclonal antibody-producing hybridomas can be produced using known techniques, for example, as described below. Specifically, mammals are immunized by conventional immunization methods using an IgA protein as a sensitizing antigen. Resulting immune cells are fused with known parental cells by conventional cell fusion methods. Then, hybridomas producing an anti-IgA antibody can be selected by screening for monoclonal antibody-producing cells using conventional screening methods.

Specifically, monoclonal antibody production is performed, for example, as shown below. For example, a purified native IgA protein may be used as a sensitizing antigen. Furthermore, a recombinant protein comprising an IgA polypeptide sequence of SEQ ID NO: 2, which is registered as L00022|IGHE*02 in IMGT/GENE-DB, is purified to obtain soluble IgA from the culture supernatant. To express the recombinant protein, first, an IgA heavy chain constant region gene of which nucleotide sequence is disclosed in SEQ ID NO: 3 may be expressed to obtain the IgA protein shown in SEQ ID NO: 2, which is used as a sensitizing antigen for obtaining antibodies. That is, suitable host cells are transformed by inserting an IgA-encoding gene sequence into a known expression vector. The desired IgA protein is purified by known methods from the host cells or from their culture supernatant. For expression of the IgA heavy chain constant region gene, the polynucleotide sequence of SEQ ID NO: 3 may be operably linked to the 3' end of the signal sequence. In another non-limiting embodiment, the polynucleotide sequence of SEQ ID NO: 3 may be operably linked to the 3' end of a polynucleotide sequence encoding a heavy chain variable region comprising a signal sequence at the 5' end. Furthermore, to purify the recombinant protein, a tag peptide for purification may be added appropriately to the amino terminus or carboxy terminus of SEQ ID NO: 2. GLNDIFEAQKIEWHE (SEQ ID NO: 4) which is an Avi tag linked via the GGGGS (SEQ ID NO: 31) linker is an example of a non-limiting embodiment of such. A non-limiting example of the production of a recombinant protein similar to that mentioned above is a method such as that described in Example 1, where a recombinant IgA protein which has been expressed in combination with a light chain is collected from the recombinant host cell culture, and then purified.

The purified IgA protein may be used as a sensitizing antigen for immunization of mammals. A partial IgA peptide may also be used as a sensitizing antigen. In this case, a partial peptide can be prepared by chemical synthesis based on the amino acid sequence of human IgA, or by inserting a partial IgA gene into an expression vector for expression. Alternatively, a partial peptide can be produced by degrading an IgA protein with a protease. The length and region of the partial IgA peptide are not limited to particular embodiments. A preferred region can be arbitrarily selected from the amino acid sequence of SEQ ID NO: 2. The number of amino acids forming a peptide to be used as a sensitizing antigen is preferably at least five or more, six or more, or seven or more. More specifically, a peptide of 8 to 50 residues, more preferably 10 to 30 residues can be used as a sensitizing antigen.

For sensitizing antigen, alternatively it is possible to use a fusion protein prepared by fusing a desired partial polypeptide or peptide of the IgA protein with a different polypeptide. For example, antibody Fc fragments and peptide tags are preferably used to produce fusion proteins to be used as sensitizing antigens. Vectors for expression of such fusion proteins can be constructed by fusing in frame genes encoding two or more desired polypeptide fragments and inserting the fusion gene into an expression vector as described above. Methods for producing fusion proteins are described in Molecular Cloning 2nd ed. (Sambrook, J et al., Molecular Cloning 2nd ed., 9.47-9.58 (1989) Cold Spring Harbor Lab. Press). Methods for preparing IgA to be used as a sensitizing antigen, and immunization methods using IgA are specifically described in PCT/JP2011/077619 and such.

There is no particular limitation on the mammals to be immunized with the sensitizing antigen. However, it is preferable to select the mammals by considering their compatibility with the parent cells to be used for cell fusion. In general, rodents such as mice, rats, and hamsters, rabbits, and monkeys are preferably used.

The above animals are immunized with a sensitizing antigen by known methods. Generally performed immunization methods include, for example, intraperitoneal or subcutaneous injection of a sensitizing antigen into mammals. Specifically, a sensitizing antigen is appropriately diluted with PBS (Phosphate-Buffered Saline), physiological saline, or the like. If desired, a conventional adjuvant such as Freund's complete adjuvant is mixed with the antigen, and the mixture is emulsified. Then, the sensitizing antigen is administered to a mammal several times at 4- to 21-day intervals. Appropriate carriers may be used in immunization with the sensitizing antigen. In particular, when a low-molecular-weight partial peptide is used as the sensitizing antigen, it is sometimes desirable to couple the sensitizing antigen peptide to a carrier protein such as albumin or keyhole limpet hemocyanin for immunization.

Alternatively, hybridomas producing a desired antibody can be prepared using DNA immunization as mentioned below. DNA immunization is an immunization method that confers immunostimulation by expressing a sensitizing antigen in an animal immunized as a result of administering a vector DNA constructed to allow expression of an antigen protein-encoding gene in the animal. As compared to conventional immunization methods in which a protein antigen is administered to animals to be immunized, DNA immunization is expected to be superior in that:

in the case the antigen is a membrane protein, immunostimulation can be provided while retaining the structure of the membrane protein; and there is no need to purify the antigen for immunization.

In order to prepare a monoclonal antibody of the present invention using DNA immunization, first, a DNA expressing an IgA protein is administered to an animal to be immunized. The IgA-encoding DNA can be synthesized by known methods such as PCR. The obtained DNA is inserted into an appropriate expression vector, and then this is administered to an animal to be immunized. Preferably used expression vectors include, for example, commercially-available expression vectors such as pcDNA3.1. Vectors can be administered to an organism using conventional methods. For example, DNA immunization is performed by using a gene gun to introduce expression vector-coated gold particles into cells in the body of an animal to be immunized. Antibodies that recognize IgA can also be produced by the methods described in PCT/JP2011/077619.

After immunizing a mammal as described above, an increase in the titer of an IgA-binding antibody is confirmed in the serum. Then, immune cells are collected from the mammal, and then subjected to cell fusion. In particular, splenocytes are preferably used as immune cells.

A mammalian myeloma cell is used as a cell to be fused with the above-mentioned immune cells. The myeloma cells preferably comprise a suitable selection marker for screening. A selection marker confers characteristics to cells for their survival (or death) under a specific culture condition. Hypoxanthine-guanine phosphoribosyltransferase deficiency (hereinafter abbreviated as HGPRT deficiency) and thymidine kinase deficiency (hereinafter abbreviated as TK deficiency) are known as selection markers. Cells with HGPRT or TK deficiency have hypoxanthine-aminopterin-thymidine sensitivity (hereinafter abbreviated as HAT sensitivity). HAT-sensitive cells cannot synthesize DNA in a HAT selection medium, and are thus killed. However, when the cells are fused with normal cells, they can continue DNA synthesis using the salvage pathway of the normal cells, and therefore they can grow even in the HAT selection medium.

HGPRT-deficient and TK-deficient cells can be selected in a medium containing 6-thioguanine, 8-azaguanine (hereinafter abbreviated as 8AG), or 5'-bromodeoxyuridine, respectively. Normal cells are killed because they incorporate these pyrimidine analogs into their DNA. Meanwhile, cells that are deficient in these enzymes can survive in the selection medium, since they cannot incorporate these pyrimidine analogs. In addition, a selection marker referred to as G418 resistance provided by the neomycin-resistant gene confers resistance to 2-deoxystreptamine antibiotics (gentamycin analogs). Various types of myeloma cells that are suitable for cell fusion are known.

For example, myeloma cells including the following cells can be preferably used:

P3(P3x63Ag8.653) (J. Immunol. (1979) 123 (4), 1548-1550);
P3x63Ag8U.1 (Current Topics in Microbiology and Immunology (1978)81, 1-7);
NS-1 (C. Eur. J. Immunol. (1976)6 (7), 511-519);
MPC-11 (Cell (1976) 8 (3), 405-415);
SP2/0 (Nature (1978) 276 (5685), 269-270);
FO (J. Immunol. Methods (1980) 35 (1-2), 1-21);
S194/5.XX0.BU.1 (J. Exp. Med. (1978) 148 (1), 313-323);
R210 (Nature (1979) 277 (5692), 131-133), etc.

Cell fusions between the immunocytes and myeloma cells are essentially carried out using known methods, for example, a method by Kohler and Milstein et al. (Methods Enzymol. (1981) 73: 3-46).

More specifically, cell fusion can be carried out, for example, in a conventional culture medium in the presence of a cell fusion-promoting agent. The fusion-promoting agents include, for example, polyethylene glycol (PEG) and Sendai virus (HVJ). If required, an auxiliary substance such as dimethyl sulfoxide is also added to improve fusion efficiency.

The ratio of immune cells to myeloma cells may be determined at one's own discretion, preferably, for example, one myeloma cell for every one to ten immunocytes. Culture media to be used for cell fusions include, for example, media that are suitable for the growth of myeloma cell lines, such as RPMI1640 medium and MEM medium, and other conventional culture medium used for this type of cell culture. In addition, serum supplements such as fetal calf serum (FCS) may be preferably added to the culture medium.

For cell fusion, predetermined amounts of the above immune cells and myeloma cells are mixed well in the above culture medium. Then, a PEG solution (for example, the average molecular weight is about 1,000 to 6,000) pre-warmed to about 37° C. is added thereto at a concentration of generally 30% to 60% (w/v). This is gently mixed to produce desired fusion cells (hybridomas). Then, an appropriate culture medium mentioned above is gradually added to the cells, and this is repeatedly centrifuged to remove the supernatant. Thus, cell fusion agents and such which are unfavorable to hybridoma growth can be removed.

The hybridomas thus obtained can be selected by culture using a conventional selective medium, for example, HAT medium (a culture medium containing hypoxanthine, aminopterin, and thymidine). Cells other than the desired hybridomas (non-fused cells) can be killed by continuing culture in the above HAT medium for a sufficient period of time. Typically, the period is several days to several weeks. Then, hybridomas producing the desired antibody are screened and singly cloned by conventional limiting dilution methods.

The hybridomas thus obtained can be selected using a selection medium based on the selection marker possessed by the myeloma used for cell fusion. For example, HGPRT- or TK-deficient cells can be selected by culture using the HAT medium (a culture medium containing hypoxanthine, aminopterin, and thymidine). Specifically, when HAT-sensitive myeloma cells are used for cell fusion, cells successfully fused with normal cells can selectively proliferate in the HAT medium. Cells other than the desired hybridomas (non-fused cells) can be killed by continuing culture in the above HAT medium for a sufficient period of time. Specifically, desired hybridomas can be selected by culture for generally several days to several weeks. Then, hybridomas producing the desired antibody are screened and singly cloned by conventional limiting dilution methods.

Desired antibodies can be preferably selected and singly cloned by screening methods based on known antigen/antibody reaction. For example, the activity of an antibody to bind to immobilized IgA can be assessed based on the principle of ELISA. For example, IgA is immobilized to the wells of an ELISA plate. Culture supernatants of hybridomas are contacted with the IgA in the wells, and antibodies that bind to the IgA are detected. When the monoclonal antibodies are derived from mouse, antibodies bound to the cells can be detected using an anti-mouse immunoglobulin antibody. Hybridomas producing a desired antibody having the antigen-binding ability are selected by the above screening, and they can be cloned by a limiting dilution method or the like.

Monoclonal antibody-producing hybridomas thus prepared can be passaged in a conventional culture medium, and stored in liquid nitrogen for a long period.

The above hybridomas are cultured by a conventional method, and desired monoclonal antibodies can be prepared from the culture supernatants. Alternatively, the hybridomas are administered to and grown in compatible mammals, and monoclonal antibodies are prepared from the ascites. The former method is suitable for preparing antibodies with high purity.

Antibodies encoded by antibody genes that are cloned from antibody-producing cells such as the above hybridomas can also be preferably used. A cloned antibody gene is inserted into an appropriate vector, and this is introduced into a host to express the antibody encoded by the gene. Methods for isolating antibody genes, inserting the genes into vectors, and transforming host cells have already been established, for example, by Vandamme et al. (Eur. J. Biochem. (1990) 192(3), 767-775). Methods for producing recombinant antibodies are also known as described below.

For example, a cDNA encoding the variable region (V region) of an anti-IgA antibody is prepared from hybridoma cells producing the anti-IgA antibody. For this purpose, total RNA is first extracted from hybridomas. Methods used for extracting mRNAs from cells include, for example:
  the guanidine ultracentrifugation method (Biochemistry (1979) 18(24), 5294-5299), and
  the AGPC method (Anal. Biochem. (1987) 162(1), 156-159)

Extracted mRNAs can be purified using the mRNA Purification Kit (GE Healthcare Bioscience) or such. Alternatively, kits for extracting total mRNA directly from cells, such as the QuickPrep mRNA Purification Kit (GE Healthcare Bioscience), are also commercially available. mRNAs can be prepared from hybridomas using such kits. cDNAs encoding the antibody V region can be synthesized from the prepared mRNAs using a reverse transcriptase. cDNAs can be synthesized using the AMV Reverse Transcriptase First-strand cDNA Synthesis Kit (Seikagaku Co.) or such. Furthermore, the SMART RACE cDNA amplification kit (Clontech) and the PCR-based 5'-RACE method (Proc. Natl. Acad. Sci. USA (1988) 85(23), 8998-9002; Nucleic Acids Res. (1989) 17(8), 2919-2932) can be appropriately used to synthesize and amplify cDNAs. In such a cDNA synthesis process, appropriate restriction enzyme sites described below may be introduced into both ends of a cDNA.

The cDNA fragment of interest is purified from the resulting PCR product, and then this is ligated to a vector DNA. A recombinant vector is thus constructed, and introduced into E. coli or such. After colony selection, the desired recombinant vector can be prepared from the colony-forming E. coli. Then, whether the recombinant vector has the cDNA nucleotide sequence of interest is tested by a known method such as the dideoxy nucleotide chain termination method.

The 5'-RACE method which uses primers to amplify the variable region gene is conveniently used for isolating the gene encoding the variable region. First, a 5'-RACE cDNA library is constructed by cDNA synthesis using RNAs extracted from hybridoma cells as a template. A commercially available kit such as the SMART RACE cDNA amplification kit is appropriately used to synthesize the 5'-RACE cDNA library.

The antibody gene is amplified by PCR using the prepared 5'-RACE cDNA library as a template. Primers for amplifying the mouse antibody gene can be designed based on known antibody gene sequences. The nucleotide sequences of the primers vary depending on the immunoglobulin subclass. Therefore, it is preferable that the subclass is determined in advance using a commercially available kit such as the Iso Strip mouse monoclonal antibody isotyping kit (Roche Diagnostics).

Specifically, for example, primers that allow amplification of genes encoding γ1, γ2a, γ2b, and γ3 heavy chains and κ and λ light chains are used to isolate mouse IgG-encoding genes. In general, a primer that anneals to a constant region site close to the variable region is used as a 3'-side primer to amplify an IgG variable region gene. Meanwhile, a primer attached to a 5' RACE cDNA library construction kit is used as a 5'-side primer.

PCR products thus amplified are used to reshape immunoglobulins composed of a combination of heavy and light chains. A desired antibody can be selected using the IgA-binding activity of a reshaped immunoglobulin as an indicator. For example, when the objective is to isolate an antibody against IgA, it is more preferred that the binding of the antibody to IgA is specific. An IgA-binding antibody can be screened, for example, by the following steps:
  (1) contacting an IgA with an antibody comprising the V region encoded by a cDNA isolated from a hybridoma;
  (2) detecting the binding of the antibody to the IgA; and
  (3) selecting an antibody that binds to the IgA.

Methods for detecting the binding of an antibody to IgA are known. Specifically, the binding of an antibody to IgA can be detected by the above-described techniques such as ELISA.

Preferred antibody screening methods that use the binding activity as an indicator also include panning methods using phage vectors. Screening methods using phage vectors are advantageous when the antibody genes are isolated from heavy-chain and light-chain subclass libraries from a polyclonal antibody-expressing cell population. Genes encoding the heavy-chain and light-chain variable regions can be linked by an appropriate linker sequence to form a single-chain Fv (scFv). Phages presenting scFv on their surface can be produced by inserting a gene encoding scFv into a phage vector. The phages are contacted with an antigen of interest. Then, a DNA encoding scFv having the binding activity of interest can be isolated by collecting phages bound to the antigen. This process can be repeated as necessary to enrich scFv having the binding activity of interest.

After isolation of the cDNA encoding the V region of the anti-IgA antibody of interest, the cDNA is digested with restriction enzymes that recognize the restriction sites introduced into both ends of the cDNA. Preferred restriction enzymes recognize and cleave a nucleotide sequence that occurs in the nucleotide sequence of the antibody gene at a low frequency. Furthermore, a restriction site for an enzyme that produces a sticky end is preferably introduced into a vector to insert a single-copy digested fragment in the correct orientation. The cDNA encoding the V region of the anti-IgA antibody is digested as described above, and this is inserted into an appropriate expression vector to construct an antibody expression vector. In this case, if a gene encoding the antibody constant region (C region) and a gene encoding the above V region are fused in-frame, a chimeric antibody is obtained. Herein, "chimeric antibody" means that the origin of the constant region is different from that of the variable region. Thus, in addition to mouse/human heterochimeric antibodies, human/human allochimeric antibodies are included in the chimeric antibodies of the present invention. A chimeric antibody expression vector can be constructed by inserting the above V region gene into an expression vector that already has the constant region. Specifically, for example, a recognition sequence for a restriction enzyme that excises the above V region gene can be appropriately placed on the 5' side of an expression vector carrying a DNA encoding a desired antibody constant region (C region). A chimeric antibody expression vector is constructed by fusing in frame the two genes digested with the same combination of restriction enzymes.

To produce an anti-IgA monoclonal antibody, antibody genes are inserted into an expression vector so that the genes are expressed under the control of an expression regulatory region. The expression regulatory region for antibody expression includes, for example, enhancers and promoters. Furthermore, an appropriate signal sequence may be attached to the amino terminus so that the expressed antibody is secreted to the outside of cells. In the Examples described later, a peptide having the amino acid sequence MGWSCIILFLVATATGVHS (SEQ ID NO: 5) are used as a signal sequence. Meanwhile, other appropriate signal sequences may be attached. The expressed polypeptide is cleaved at the carboxyl terminus of the above sequence, and the resulting polypeptide is secreted to the outside of cells as a mature polypeptide. Then, appropriate host cells are transformed with the expression vector, and recombinant cells expressing the anti-IgA antibody-encoding DNA are obtained.

DNAs encoding the antibody heavy chain (H chain) and light chain (L chain) are separately inserted into different expression vectors to express the antibody gene. An antibody molecule having the H and L chains can be expressed by co-transfecting the same host cell with vectors into which the H-chain and L-chain genes are respectively inserted. Alternatively, host cells can be transformed with a single expression vector into which DNAs encoding the H and L chains are inserted (see International Publication No. WO 1994/011523).

There are various known host cell/expression vector combinations for antibody preparation by introducing isolated antibody genes into appropriate hosts. All of these expression systems are applicable to isolation of the antigen-binding molecules of the present invention. Appropriate eukaryotic cells used as host cells include animal cells, plant cells, and fungal cells. Specifically, the animal cells include, for example, the following cells.
(1) mammalian cells: CHO (Chinese hamster ovary cell line), COS (Monkey kidney cell line), myeloma (Sp2/O, NSO, etc), BHK (baby hamster kidney cell line), HEK293 (human embryonic kidney cell line with sheared adenovirus (Ad)5 DNA), PER.C6 cell (human embryonic retinal cell line transformed with the Adenovirus Type 5 (Ad5) E1A and E1B genes), HeLa, Vero, HEK293 (human embryonic kidney cell line with sheared adenovirus (Ad)5 DNA), or such (Current Protocols in Protein Science (May, 2001, Unit 5.9, Table 5.9.1));
(2) amphibian cells: *Xenopus* oocytes, or such; and
(3) insect cells: sf9, sf21, Tn5, or such.

In addition, as a plant cell, an antibody gene expression system using cells derived from the *Nicotiana* genus such as *Nicotiana tabacum* is known. Callus cultured cells can be appropriately used to transform plant cells.

Furthermore, the following cells can be used as fungal cells:
  yeasts: the *Saccharomyces* genus such as *Saccharomyces serevisiae*, and the *Pichia* genus such as *Pichia pastoris*; and
  filamentous fungi: the *Aspergillus* genus such as *Aspergillus niger*.

Furthermore, antibody gene expression systems that utilize prokaryotic cells are also known. For example, when using bacterial cells, *E. coli* cells, *Bacillus subtilis* cells, and such can suitably be utilized in the present invention. Expression vectors carrying the antibody genes of interest are introduced into these cells by transfection. The transfected cells are cultured in vitro, and the desired antibody can be prepared from the culture of transformed cells.

In addition to the above-described host cells, transgenic animals can also be used to produce a recombinant antibody. That is, the antibody can be obtained from an animal into which the gene encoding the antibody of interest is introduced. For example, the antibody gene can be constructed as a fusion gene by inserting in frame into a gene that encodes a protein produced specifically in milk. Goat 3-casein or such can be used, for example, as the protein secreted in milk. DNA fragments containing the fused gene inserted with the antibody gene is injected into a goat embryo, and then this embryo is introduced into a female goat. Desired antibodies can be obtained as a protein fused with the milk protein from milk produced by the transgenic goat born from the embryo-recipient goat (or progeny thereof). In addition, to increase the volume of milk containing the desired antibody produced by the transgenic goat, hormones can be administered to the transgenic goat as necessary (Ebert, K. M. et al., Bio/Technology (1994) 12 (7), 699-702).

When an antigen-binding molecule described herein is administered to human, an antigen-binding domain derived from a genetically recombinant antibody that has been artificially modified to reduce the heterologous antigenicity against human and such, can be appropriately used as the antigen-binding domain of the antigen-binding molecule. Such genetically recombinant antibodies include, for example, humanized antibodies. These modified antibodies are appropriately produced by known methods.

An antibody variable region used to produce the antigen-binding domain of an antigen-binding molecule described herein is generally formed by three complementarity-determining regions (CDRs) that are separated by four framework regions (FRs). CDR is a region that substantially determines the binding specificity of an antibody. The amino acid sequences of CDRs are highly diverse. On the other hand, the FR-forming amino acid sequences often have high identity even among antibodies with different binding specificities. Therefore, generally, the binding specificity of a certain antibody can be introduced to another antibody by CDR grafting.

A humanized antibody is also called a reshaped human antibody. Specifically, humanized antibodies prepared by applying the CDR grafting technology, which grafts the CDRs of a non-human animal antibody such as a mouse antibody to a human antibody, and such are known. Common genetic engineering techniques for obtaining humanized antibodies are also known. Specifically, for example, overlap extension PCR is known as a method for grafting a mouse antibody CDR to a human FR. In overlap extension PCR, a nucleotide sequence encoding a mouse antibody CDR to be grafted is added to primers for synthesizing a human antibody FR. Primers are prepared for each of the four FRs. It is generally considered that when grafting a mouse CDR to a human FR, selecting a human FR that has high identity to a mouse FR is advantageous for maintaining the CDR function. That is, it is generally preferable to use a human FR comprising an amino acid sequence which has high identity to the amino acid sequence of the FR adjacent to the mouse CDR to be grafted.

Nucleotide sequences to be ligated are designed so that they will be connected to each other in frame. Human FRs are individually synthesized using the respective primers. As a result, products in which the mouse CDR-encoding DNA is attached to the individual FR-encoding DNAs are obtained. Nucleotide sequences encoding the mouse CDR of each product are designed so that they overlap with each other. Then, complementary strand synthesis reaction is conducted to anneal the overlapping CDR regions of the products synthesized using a human antibody gene as template. Human FRs are ligated via the mouse CDR sequences by this reaction.

The full length V region gene, in which three CDRs and four FRs are ultimately ligated, is amplified using primers that anneal to its 5'- or 3'-end, which are added with suitable restriction enzyme recognition sequences. An expression vector for humanized antibody can be produced by inserting the DNA obtained as described above and a DNA that encodes a human antibody C region into an expression vector so that they will ligate in frame. After the recombinant vector is transfected into a host to establish recombinant cells, the recombinant cells are cultured, and the DNA encoding the humanized antibody is expressed to produce the humanized antibody in the cell culture (see, European Patent Publication No. EP 239400 and International Patent Publication No. WO 1996/002576).

By qualitatively or quantitatively measuring and evaluating the antigen-binding activity of the humanized antibody produced as described above, one can suitably select human antibody FRs that allow CDRs to form a favorable antigen-binding site when ligated through the CDRs. Amino acid residues in FRs may be substituted as necessary, so that the CDRs of a reshaped human antibody form an appropriate antigen-binding site. For example, amino acid sequence mutations can be introduced into FRs by applying the PCR method used for grafting a mouse CDR into a human FR. More specifically, partial nucleotide sequence mutations can be introduced into primers that anneal to the FR. Nucleotide sequence mutations are introduced into the FRs synthesized by using such primers. Mutant FR sequences having the desired characteristics can be selected by measuring and evaluating the activity of the amino acid-substituted mutant antibody to bind to the antigen by the above-mentioned method (Cancer Res. (1993) 53: 851-856).

Alternatively, desired human antibodies can be obtained by immunizing transgenic animals having the entire repertoire of human antibody genes (see International Publication Nos. WO 1993/012227; WO 1992/003918; WO 1994/002602; WO 1994/025585; WO 1996/034096; WO 1996/033735) by DNA immunization.

Furthermore, techniques for preparing human antibodies by panning using human antibody libraries are also known. For example, the V region of a human antibody is expressed as a single-chain antibody (scFv) on phage surface by the phage display method. Phages expressing an scFv that binds to the antigen can be selected. The DNA sequence encoding the human antibody V region that binds to the antigen can be determined by analyzing the genes of selected phages. The DNA sequence of the scFv that binds to the antigen is determined. An expression vector is prepared by fusing the V region sequence in frame with the C region sequence of a desired human antibody, and inserting this into an appropriate expression vector. The expression vector is introduced into cells appropriate for expression such as those described above. The human antibody can be produced by expressing the human antibody-encoding gene in the cells. These methods are already known (see International Publication Nos. WO 1992/001047; WO 1992/020791; WO 1993/006213; WO 1993/011236; WO 1993/019172; WO 1995/001438; WO 1995/015388).

In addition to the techniques described above, techniques of B cell cloning (identification of each antibody-encoding sequence, cloning and its isolation; use in constructing expression vector in order to prepare each antibody (IgG1, IgG2, IgG3, or IgG4 in particular); and such) such as described in Bemasconi et al. (Science (2002) 298: 2199-2202) or in International Publication No. WO 2008/081008 can be appropriately used to isolate antibody genes.

EU Numbering and Kabat Numbering

According to the methods used in the present invention, amino acid positions assigned to antibody CDR and FR are specified according to Kabat's numbering (Sequences of Proteins of Immunological Interest (National Institute of Health, Bethesda, Md., 1987 and 1991)). Herein, when an antigen-binding molecule is an antibody or antigen-binding fragment, variable region amino acids are indicated according to Kabat's numbering system (Kabat numbering), while constant region amino acids are indicated according to EU numbering system based on Kabat's amino acid positions.

Conditions of Ion Concentration

Conditions of Metal Ion Concentration

In one embodiment of the present invention, the ion concentration refers to a metal ion concentration. "Metal ions" refer to ions of group I elements except hydrogen such as alkaline metals and copper group elements, group II elements such as alkaline earth metals and zinc group elements, group III elements except boron, group IV elements except carbon and silicon, group VIII elements such as iron group and platinum group elements, elements belonging to subgroup A of groups V, VI, and VII, and metal elements such as antimony, bismuth, and polonium. Metal atoms have the property of releasing valence electrons to become cations. This is referred to as ionization tendency. Metals with strong ionization tendency are deemed to be chemically active.

In the present invention, preferred metal ions include, for example, calcium ion. Calcium ion is involved in modulation of many biological phenomena, including contraction of muscles such as skeletal, smooth, and cardiac muscles; activation of movement, phagocytosis, and the like of leukocytes; activation of shape change, secretion, and the like of platelets; activation of lymphocytes; activation of mast cells including secretion of histamine; cell responses mediated by catecholamine at receptor or acetylcholine receptor; exocytosis; release of transmitter substances from neuron terminals; and axoplasmic flow in neurons. Known intracellular calcium ion receptors include troponin C, calmodulin, parvalbumin, and myosin light chain, which have several calcium ion-binding sites and are believed to be derived from a common origin in terms of molecular evolution. There are also many known calcium-binding motifs. Such well-known motifs include, for example, cadherin domains, EF-hand of calmodulin, C2 domain of Protein kinase C, Gla domain of blood coagulation protein Factor IX, C-type lectins of acyaroglycoprotein receptor and mannose-binding receptor, A domains of LDL receptors, annexin, thrombospondin type 3 domain, and EGF-like domains.

In the present invention, when the metal ion is calcium ion, the conditions of calcium ion concentration include low calcium ion concentrations and high calcium ion concentrations. "The binding activity varies depending on calcium ion concentrations" means that the antigen-binding activity of an antigen-binding molecule varies due to the difference in the conditions between low and high calcium ion concentrations. For example, the antigen-binding activity of an antigen-binding molecule may be higher at a high calcium ion concentration than at a low calcium ion concentration. Alternatively, the antigen-binding activity of an antigen-binding molecule may be higher at a low calcium ion concentration than at a high calcium ion concentration.

Herein, the high calcium ion concentration is not particularly limited to a specific value; however, the concentration may preferably be selected between 100 μM and 10 mM. In another embodiment, the concentration may be selected between 200 μM and 5 mM. In an alternative embodiment, the concentration may be selected between 400 μM and 3 mM. In still another embodiment, the concentration may be selected between 200 μM and 2 mM. Furthermore, the concentration may be selected between 400 μM and 1 mM. In particular, a concentration selected between 500 μM and 2.5 mM, which is close to the plasma (blood) concentration of calcium ion in vivo, is preferred.

Herein, the low calcium ion concentration is not particularly limited to a specific value; however, the concentration may preferably be selected between 0.1 μM and 30 μM. In another embodiment, the concentration may be selected between 0.2 μM and 20 μM. In still another embodiment, the concentration may be selected between 0.5 μM and 10 μM. In an alternative embodiment, the concentration may be selected between 1 μM and 5 μM. Furthermore, the concentration may be selected between 2 μM and 4 μM. In particular, a concentration selected between 1 μM and 5 μM, which is close to the concentration of ionized calcium in early endosomes in vivo, is preferred.

Herein, "the antigen-binding activity is lower at a low calcium ion concentration than at a high calcium ion concentration" means that the antigen-binding activity of an antigen-binding molecule is weaker at a calcium ion concentration selected between 0.1 μM and 30 μM than at a calcium ion concentration selected between 100 μM and 10 mM. Preferably, it means that the antigen-binding activity of an antigen-binding molecule is weaker at a calcium ion concentration selected between 0.5 μM and 10 μM than at a calcium ion concentration selected between 200 μM and 5 mM. It particularly preferably means that the antigen-binding activity at the calcium ion concentration in the early endosome in vivo is weaker than that at the in vivo plasma calcium ion concentration; and specifically, it means that the antigen-binding activity of an antigen-binding molecule is weaker at a calcium ion concentration selected between 1 μM and 5 μM than at a calcium ion concentration selected between 500 μM and 2.5 mM.

Whether the antigen-binding activity of an antigen-binding molecule is changed depending on metal ion concentrations can be determined, for example, by the use of known measurement methods such as those described in the section "Binding Activity" above. For example, in order to confirm that the antigen-binding activity of an antigen-binding molecule becomes higher at a high calcium ion concentration than at a low calcium ion concentration, the antigen-binding activity of the antigen-binding molecule at low and high calcium ion concentrations is compared.

In the present invention, the expression "the antigen-binding activity is lower at a low calcium ion concentration than at a high calcium ion concentration" can also be expressed as "the antigen-binding activity of an antigen-binding molecule is higher at a high calcium ion concentration than at a low calcium ion concentration". In the present invention, "the antigen-binding activity is lower at a low calcium ion concentration than at a high calcium ion concentration" is sometimes written as "the antigen-binding ability is weaker at a low calcium ion concentration than at a high calcium ion concentration". Also, "the antigen-binding activity at a low calcium ion concentration is reduced to be lower than that at a high calcium ion concentration" may be written as "the antigen-binding ability at a low calcium ion concentration is made weaker than that at a high calcium ion concentration".

When determining the antigen-binding activity, the conditions other than calcium ion concentration can be appropriately selected by those skilled in the art, and are not particularly limited. For example, the activity can be determined at 37° C. in HEPES buffer. For example, a Biacore™ device (GE Healthcare) or such can be used for the determination. When the antigen is a soluble antigen, the antigen-binding activity of an antigen-binding molecule can be assessed by flowing the antigen as an analyte over a chip onto which the antigen-binding molecule is immobilized. When the antigen is a membrane antigen, the binding activity of an antigen-binding molecule to the membrane antigen can be assessed by flowing the antigen-binding molecule as an analyte over a chip onto which the antigen is immobilized.

As long as the antigen-binding activity of an antigen-binding molecule of the present invention is weaker at a low calcium ion concentration than at a high calcium ion concentration, the ratio of the antigen-binding activity between low and high calcium ion concentrations is not particularly limited. However, the ratio of the KD (dissociation constant) of the antigen-binding molecule for an antigen at a low calcium ion concentration with respect to the KD at a high calcium ion concentration, i.e. the value of KD (3 μM Ca)/KD (2 mM Ca), is preferably 2 or more, more preferably 10 or more, and still more preferably 40 or more. The upper limit of the KD (3 μM Ca)/KD (2 mM Ca) value is not particularly limited, and may be any value such as 400, 1000, or 10000 as long as the molecule can be produced by techniques known to those skilled in the art.

When the antigen is a soluble antigen, KD (dissociation constant) can be used to represent the antigen-binding activity. Meanwhile, when the antigen is a membrane antigen, apparent KD (apparent dissociation constant) can be used to represent the activity. KD (dissociation constant) and apparent KD (apparent dissociation constant) can be determined by methods known to those skilled in the art, for example, using a Biacore™ device (GE Healthcare), Scatchard plot, or flow cytometer.

Alternatively, for example, the dissociation rate constant (kd) can also be preferably used as an index to represent the ratio of the antigen-binding activity of an antigen-binding molecule of the present invention between low and high calcium concentrations. When the dissociation rate constant (kd) is used instead of the dissociation constant (KD) as an index to represent the binding activity ratio, the ratio of the dissociation rate constant (kd) between low and high calcium concentrations, i.e. the value of kd (low calcium concentration)/kd (high calcium concentration), is preferably 2 or more, more preferably 5 or more, still more preferably 10 or more, and yet more preferably 30 or more. The upper limit of the Kd (low calcium concentration)/kd (high calcium concentration) value is not particularly limited, and can be any value such as 50, 100, or 200 as long as the molecule can be produced by techniques known to those skilled in the art.

When the antigen is a soluble antigen, kd (dissociation rate constant) can be used to represent the antigen-binding activity. Meanwhile, when the antigen is a membrane antigen, apparent kd (apparent dissociation rate constant) can be used to represent the antigen-binding activity. The kd (dissociation rate constant) and apparent kd (apparent dissociation rate constant) can be determined by methods known to those skilled in the art, for example, using a Biacore™ device (GE healthcare) or flow cytometer. In the present invention, when the antigen-binding activity of an antigen-binding molecule is determined at different calcium ion concentrations, it is preferable to use the same conditions except for the calcium concentrations.

For example, an antigen-binding domain or antigen-binding molecule whose antigen-binding activity is lower at a low calcium ion concentration than at a high calcium ion concentration, which is one embodiment of the present invention, can be obtained via screening of antigen-binding domains or antibodies including the steps of:
(a) determining the antigen-binding activity of an antigen-binding domain or antigen-binding molecule at a low calcium concentration;
(b) determining the antigen-binding activity of an antigen-binding domain or antigen-binding molecule at a high calcium concentration; and
(c) selecting an antigen-binding domain or antigen-binding molecule whose antigen-binding activity is lower at a low calcium concentration than at a high calcium concentration.

Moreover, an antigen-binding domain or antigen-binding molecule whose antigen-binding activity is lower at a low calcium ion concentration than at a high calcium ion concentration, which is one embodiment of the present invention, can be obtained via screening of antigen-binding domains or antigen-binding molecules, or a library thereof, including the steps of:
(a) contacting an antigen with an antigen-binding domain or antigen-binding molecule, or a library thereof at a high calcium concentration;
(b) incubating at a low calcium concentration an antigen-binding domain or antigen-binding molecule that has bound to the antigen in step (a); and
(c) isolating an antigen-binding domain or antigen-binding molecule dissociated in step (b).

Furthermore, an antigen-binding domain or antigen-binding molecule whose antigen-binding activity is lower at a low calcium ion concentration than at a high calcium ion concentration, which is one embodiment of the present invention, can be obtained via screening of antigen-binding domains or antigen-binding molecules, or a library thereof, including the steps of:
(a) contacting an antigen with a library of antigen-binding domains or antigen-binding molecules at a low calcium concentration;
(b) selecting an antigen-binding domain or antigen-binding molecule which does not bind to the antigen in step (a);
(c) allowing the antigen-binding domain or antigen-binding molecule selected in step (c) to bind to the antigen at a high calcium concentration; and
(d) isolating an antigen-binding domain or antigen-binding molecule that has bound to the antigen in step (c).

In addition, an antigen-binding domain or antigen-binding molecule whose antigen-binding activity is lower at a low calcium ion concentration than at a high calcium ion concentration, which is one embodiment of the present invention, can be obtained by a screening method comprising the steps of:
(a) contacting at a high calcium concentration a library of antigen-binding domains or antigen-binding molecules with a column onto which an antigen is immobilized;
(b) eluting an antigen-binding domain or antigen-binding molecule that has bound to the column in step (a) from the column at a low calcium concentration; and
(c) isolating the antigen-binding domain or antigen-binding molecule eluted in step (b).

Furthermore, an antigen-binding domain or antigen-binding molecule whose antigen-binding activity is lower at a low calcium ion concentration than at a high calcium ion concentration, which is one embodiment of the present invention, can be obtained by a screening method comprising the steps of:
(a) allowing at a low calcium concentration a library of antigen-binding domains or antigen-binding molecules to pass through a column onto which an antigen is immobilized;
(b) collecting an antigen-binding domain or antigen-binding molecule that has been eluted without binding to the column in step (a);
(c) allowing the antigen-binding domain or antigen-binding molecule collected in step (b) to bind to the antigen at a high calcium concentration; and
(d) isolating an antigen-binding domain or antigen-binding molecule that has bound to the antigen in step (c).

Moreover, an antigen-binding domain or antigen-binding molecule whose antigen-binding activity is lower at a low calcium ion concentration than at a high calcium ion concentration, which is one embodiment of the present invention, can be obtained by a screening method comprising the steps of:
(a) contacting an antigen with a library of antigen-binding domains or antigen-binding molecules at a high calcium concentration;
(b) obtaining an antigen-binding domain or antigen-binding molecule that has bound to the antigen in step (a);
(c) incubating at a low calcium concentration the antigen-binding domain or antigen-binding molecule obtained in step (b); and
(d) isolating an antigen-binding domain or antigen-binding molecule whose antigen-binding activity in step (c) is weaker than the criterion for the selection of step (b).

The above-described steps may be repeated twice or more times. Thus, the present invention provides antigen-binding domains or antigen-binding molecules whose antigen-binding activity is lower at a low calcium ion concentration than at a high calcium ion concentration, which are obtained by screening methods that further comprises the step of repeating twice or more times steps (a) to (c) or (a) to (d) in the above-described screening methods. The number of cycles of steps (a) to (c) or (a) to (d) is not particularly limited, but generally is 10 or less.

In the screening methods of the present invention, the antigen-binding activity of an antigen-binding domain or antigen-binding molecule at a low calcium concentration is not particularly limited as long as it is antigen-binding activity at an ionized calcium concentration of between 0.1 µM and 30 µM, but preferably is antigen-binding activity at an ionized calcium concentration of between 0.5 µM and 10 µM. More preferably, it is antigen-binding activity at the ionized calcium concentration in the early endosome in vivo, specifically, between 1 µM and 5 µM. Meanwhile, the antigen-binding activity of an antigen-binding domain or antigen-binding molecule at a high calcium concentration is not particularly limited, as long as it is antigen-binding activity at an ionized calcium concentration of between 100 µM and 10 mM, but preferably is antigen-binding activity at an ionized calcium concentration of between 200 µM and 5 mM. More preferably, it is antigen-binding activity at the ionized calcium concentration in plasma in vivo, specifically, between 0.5 mM and 2.5 mM.

The antigen-binding activity of an antigen-binding domain or antigen-binding molecule can be measured by methods known to those skilled in the art. Conditions other than the ionized calcium concentration can be determined by those skilled in the art. The antigen-binding activity of an antigen-binding domain or antigen-binding molecule can be evaluated as a dissociation constant (KD), apparent dissociation constant (apparent KD), dissociation rate constant (kd), apparent dissociation constant (apparent kd), and such. These can be determined by methods known to those skilled in the art, for example, using a Biacore™ device (GE Healthcare), Scatchard plot, or FACS.

In the present invention, the step of selecting an antigen-binding domain or antigen-binding molecule whose antigen-binding activity is higher at a high calcium concentration than at a low calcium concentration is synonymous with the step of selecting an antigen-binding domain or antigen-binding molecule whose antigen-binding activity is lower at a low calcium concentration than at a high calcium concentration.

As long as the antigen-binding activity is higher at a high calcium concentration than at a low calcium concentration, the difference in the antigen-binding activity between high and low calcium concentrations is not particularly limited; however, the antigen-binding activity at a high calcium concentration is preferably twice or more, more preferably 10 times or more, and still more preferably 40 times or more than that at a low calcium concentration.

Antigen-binding domains or antigen-binding molecules of the present invention to be screened by the screening methods described above may be any antigen-binding domains and antigen-binding molecules. For example, it is possible to screen the above-described antigen-binding domains or antigen-binding molecules. For example, antigen-binding domains or antigen-binding molecules having natural sequences or substituted amino acid sequences may be screened.

Libraries

In an embodiment, an antigen-binding domain or antigen-binding molecule of the present invention can be obtained from a library that is mainly composed of a plurality of antigen-binding molecules whose sequences are different from one another and whose antigen-binding domains have at least one amino acid residue that alters the antigen-binding activity of the antigen-binding molecules depending on ion concentrations. The ion concentrations preferably include, for example, metal ion concentration and proton concentration.

Herein, a "library" refers to a plurality of antigen-binding molecules or a plurality of fusion polypeptides containing antigen-binding molecules, or nucleic acids or polynucleotides encoding their sequences. The sequences of a plurality of antigen-binding molecules or a plurality of fusion polypeptides containing antigen-binding molecules in a library are not identical, but are different from one another.

Herein, the phrase "sequences are different from one another" in the expression "a plurality of antigen-binding molecules whose sequences are different from one another" means that the sequences of antigen-binding molecules in a library are different from one another. Specifically, in a library, the number of sequences different from one another reflects the number of independent clones with different sequences, and may also be referred to as "library size". The library size of a conventional phage display library ranges from $10^6$ to $10^{12}$. The library size can be increased up to $10^{14}$ by the use of known techniques such as ribosome display. However, the actual number of phage particles used in panning selection of a phage library is in general 10-10000 times greater than the library size. This excess multiplicity is also referred to as "the number of library equivalents", and means that there are 10 to 10,000 individual clones that have the same amino acid sequence. Thus, in the present invention, the phrase "sequences are different from one another" means that the sequences of independent antigen-binding molecules in a library, excluding library equivalents, are different from one another. More specifically, the above means that there are $10^6$ to $10^{14}$ antigen-binding molecules whose sequences are different from one another, preferably $10^7$ to $10^{12}$ molecules, more preferably $10^8$ to $10^{11}$ molecules, and particularly preferably $10^8$ to $10^{10}$ molecules whose sequences are different from one another.

Herein, the phrase "a plurality of" in the expression "a library mainly composed of a plurality of antigen-binding molecules" generally refers to, in the case of, for example, antigen-binding molecules, fusion polypeptides, polynucleotide molecules, vectors, or viruses of the present invention, a group of two or more types of the substance. For example, when two or more substances are different from one another in a particular characteristic, this means that there are two or more types of the substance. Such examples may include, for example, mutant amino acids observed at specific amino acid positions in an amino acid sequence. For example, when there are two or more antigen-binding molecules of the present invention whose sequences are substantially the same or preferably the same except for flexible residues or except for particular mutant amino acids at hypervariable positions exposed on the surface, there are a plurality of antigen-binding molecules of the present invention. In another example, when there are two or more polynucleotide molecules whose sequences are substantially the same or preferably the same except for nucleotides encoding flexible residues or nucleotides encoding mutant amino acids of hypervariable positions exposed on the surface, there are a plurality of polynucleotide molecules of the present invention.

In addition, herein, the phrase "mainly composed of" in the expression "a library mainly composed of a plurality of antigen-binding molecules" reflects the number of antigen-binding molecules whose antigen-binding activity varies depending on ion concentrations, among independent clones with different sequences in a library. Specifically, it is preferable that there are at least $10^4$ antigen-binding molecules having such binding activity in a library. More preferably, antigen-binding domains of the present invention can be obtained from a library containing at least $10^5$ antigen-binding molecules having such binding activity. Still more preferably, antigen-binding domains of the present invention can be obtained from a library containing at least $10^6$ antigen-binding molecules having such binding activity. Particularly preferably, antigen-binding domains of the present invention can be obtained from a library containing at least $10^7$ antigen-binding molecules having such binding activity. Yet more preferably, antigen-binding domains of the present invention can be obtained from a library containing at least $10^8$ antigen-binding molecules having such binding activity. Alternatively, this may also be preferably expressed as the ratio of the number of antigen-binding molecules whose antigen-binding activity varies depending on ion concentrations with respect to the number of independent clones having different sequences in a library. Specifically, antigen-binding domains of the present invention can be obtained from a library in which antigen-binding molecules having such binding activity account for 0.1% to 80%, preferably 0.5% to 60%, more preferably 1% to 40%, still more preferably 2% to 20%, and particularly preferably 4% to 10% of independent clones with different sequences in the library. In the case of fusion polypeptides, polynucleotide molecules, or vectors, similar expressions may be possible using the number of molecules or the ratio to the total number of molecules. In the case of viruses, similar expressions may also be possible using the number of virions or the ratio to total number of virions.

Amino Acids that Alter the Antigen-Binding Activity of Antigen-Binding Domains Depending on Calcium Ion Concentrations Antigen-binding domains or antigen-binding molecules of the present invention to be screened by the above-described screening methods may be prepared in any manner. For example, when the metal ion is calcium ion, it is possible to use preexisting antigen-binding molecules, preexisting libraries (phage library, etc.), antibodies or libraries prepared from hybridomas obtained by immunizing animals or from B cells of immunized animals, antibodies or libraries obtained by introducing amino acids capable of chelating calcium (for example, aspartic acid and glutamic acid) or unnatural amino acid mutations into the above-described antibodies or libraries (calcium-cheletable amino acids (such as aspartic acid and glutamic acid), libraries with increased content of unnatural amino acids, libraries prepared by introducing calcium-chelatable amino acids (such as aspartic acid and glutamic acid) or unnatural amino acid mutations at particular positions, or the like.

Examples of the amino acids that alter the antigen-binding activity of antigen-binding molecules depending on ion concentrations as described above may be any types of amino acids as long as the amino acids form a calcium-binding motif. Calcium-binding motifs are well known to those skilled in the art and have been described in details (for example, Springer et al. (Cell (2000) 102, 275-277); Kawasaki and Kretsinger (Protein Prof. (1995) 2, 305-490); Moncrief et al. (J. Mol. Evol. (1990) 30, 522-562); Chauvaux et al. (Biochem. J. (1990) 265, 261-265); Bairoch and Cox (FEBS Lett. (1990) 269, 454-456); Davis (New Biol. (1990) 2, 410-419); Schaefer et al. (Genomics (1995) 25, 638-643); Economou et al. (EMBO J. (1990) 9, 349-354); Wurzburg et al. (Structure. (2006) 14, 6, 1049-1058)). Specifically, any known calcium-binding motifs, including type C lectins such as ASGPR, CD23, MBR, and DC-SIGN, can be included in antigen-binding molecules of the present invention. Preferred examples of such preferred calcium-binding motifs also include, in addition to those described above, for example, the calcium-binding motif in the antigen-binding domain of SEQ ID NO: 6.

Furthermore, as amino acids that alter the antigen-binding activity of antigen-binding molecules depending on calcium ion concentrations, for example, amino acids having metal-chelating activity may also be preferably used. Examples of such metal-chelating amino acids include, for example, serine (Ser(S)), threonine (Thr(T)), asparagine (Asn(N)), glutamine (Gln(Q)), aspartic acid (Asp(D)), and glutamic acid (Glu(E)).

Positions in the antigen-binding domains at which the above-described amino acids are contained are not particularly limited to particular positions, and may be any positions within the heavy chain variable region or light chain variable region that forms an antigen-binding domain, as long as they alter the antigen-binding activity of antigen-binding molecules depending on calcium ion concentrations. Specifically, antigen-binding domains of the present invention can be obtained from a library mainly composed of antigen-binding molecules whose sequences are different from one another and whose heavy chain antigen-binding domains contain amino acids that alter the antigen-binding activity of the antigen-binding molecules depending on calcium ion concentrations. In another embodiment, antigen-binding domains of the present invention can be obtained from a library mainly composed of antigen-binding molecules whose sequences are different from one another and whose heavy chain CDR3 domains contain the above-mentioned amino acids. In still another embodiment, antigen-binding domains of the present invention can be obtained from a library mainly composed of antigen-binding molecules whose sequences are different from one another and whose heavy chain CDR3 domains contain the above-mentioned amino acids at positions 95, 96, 100a, and/or 101 as indicated according to the Kabat numbering system.

Meanwhile, in an embodiment of the present invention, antigen-binding domains of the present invention can be obtained from a library mainly composed of antigen-binding molecules whose sequences are different from one another and whose light chain antigen-binding domains contain amino acids that alter the antigen-binding activity of antigen-binding molecules depending on calcium ion concentrations. In another embodiment, antigen-binding domains of the present invention can be obtained from a library mainly composed of antigen-binding molecules whose sequences are different from one another and whose light chain CDR1 domains contain the above-mentioned amino acids. In still another embodiment, antigen-binding domains of the present invention can be obtained from a library mainly composed of antigen-binding molecules whose sequences are different from one another and whose light chain CDR1 domains contain the above-mentioned amino acids at positions 30, 31, and/or 32 as indicated according to the Kabat numbering system.

In another embodiment, antigen-binding domains of the present invention can be obtained from a library mainly composed of antigen-binding molecules whose sequences are different from one another and whose light chain CDR2 domains contain the above-mentioned amino acid residues. In yet another embodiment, the present invention provides libraries mainly composed of antigen-binding molecules whose sequences are different from one another and whose light chain CDR2 domains contain the above-mentioned amino acid residues at position 50 as indicated according to the Kabat numbering system.

In still another embodiment of the present invention, antigen-binding domains of the present invention can be obtained from a library mainly composed of antigen-binding molecules whose sequences are different from one another and whose light chain CDR3 domains contain the above-mentioned amino acid residues. In an alternative embodiment, antigen-binding domains of the present invention can be obtained from a library mainly composed of antigen-binding molecules whose sequences are different from one another and whose light chain CDR3 domains contain the above-mentioned amino acid residues at position 92 as indicated according to the Kabat numbering system.

Furthermore, in a different embodiment of the present invention, antigen-binding domains of the present invention can be obtained from a library mainly composed of antigen-binding molecules whose sequences are different from one another and in which two or three CDRs selected from the above-described light chain CDR1, CDR2, and CDR3 contain the aforementioned amino acid residues. Moreover, antigen-binding domains of the present invention can be obtained from a library mainly composed of antigen-binding molecules whose sequences are different from one another and whose light chains contain the aforementioned amino acid residues at any one or more of positions 30, 31, 32, 50, and/or 92 as indicated according to the Kabat numbering system.

In a particularly preferred embodiment, the framework sequences of the light chain and/or heavy chain variable region of an antigen-binding molecule preferably contain human germ line framework sequences. Thus, in an embodiment of the present invention, when the framework sequences are completely human sequences, it is expected that when such an antigen-binding molecule of the present invention is administered to humans (for example, to treat diseases), it induces little or no immunogenic response. In the above sense, the phrase "containing a germ line sequence" in the present invention means that a part of the framework sequences of the present invention is identical to a part of any human germ line framework sequences. For example, when the heavy chain FR2 sequence of an antigen-binding molecule of the present invention is a combination of heavy chain FR2 sequences of different human germ line framework sequences, such a molecule is also an antigen-binding molecule of the present invention "containing a germ line sequence".

Preferred examples of the frameworks include, for example, fully human framework region sequences currently known, which are included in the website of V-Base (http://vbase.mrc-cpe.cam.ac.uk/) or others. Those framework region sequences can be appropriately used as a germ line sequence contained in an antigen-binding molecule of the present invention. The germ line sequences may be categorized according to their similarity (Tomlinson et al. (J. Mol. Biol. (1992) 227, 776-798); Williams and Winter (Eur. J. Immunol. (1993) 23, 1456-1461); Cox et al. (Nat. Genetics (1994) 7, 162-168)). Appropriate germ line sequences can be selected from VK, which is grouped into seven subgroups; Vλ, which is grouped into ten subgroups; and VH, which is grouped into seven subgroups.

Fully human VH sequences preferably include, but are not limited to, for example, VH sequences of:
subgroup VH1 (for example, VH1-2, VH1-3, VH1-8, VH1-18, VH1-24, VH1-45, VH1-46, VH1-58, and VH1-69);
subgroup VH2 (for example, VH2-5, VH2-26, and VH2-70);
subgroup VH3 (VH3-7, VH3-9, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-72, VH3-73, and VH3-74);
subgroup VH4 (VH4-4, VH4-28, VH4-31, VH4-34, VH4-39, VH4-59, and VH4-61);
subgroup VH5 (VH5-51);
subgroup VH6 (VH6-1); and
subgroup VH7 (VH7-4 and VH7-81).

These are also described in known documents (Matsuda et al. (J. Exp. Med. (1998) 188, 1973-1975)) and such, and thus persons skilled in the art can appropriately design antigen-binding molecules of the present invention based on the information of these sequences. It is also preferable to use other fully human frameworks or framework sub-regions.

Fully human VK sequences preferably include, but are not limited to, for example:
A20, A30, L1, L4, L5, L8, L9, L11, L12, L14, L15, L18, L19, L22, L23, L24, O2, O4, O8, O12, O14, and O18 grouped into subgroup Vk1;
A1, A2, A3, AS, A7, A17, A18, A19, A23, O1, and O11, grouped into subgroup Vk2;
A11, A27, L2, L6, L10, L16, L20, and L25, grouped into subgroup Vk3;
B3, grouped into subgroup Vk4;
B2 (herein also referred to as Vk5-2), grouped into subgroup Vk5; and
A10, A14, and A26, grouped into subgroup Vk6
(Kawasaki et al. (Eur. J. Immunol. (2001) 31, 1017-1028); Schable and Zachau (Biol. Chem. Hoppe Seyler (1993) 374, 1001-1022); Brensing-Kuppers et al. (Gene (1997) 191, 173-181)).

Fully human Vλ sequences preferably include, but are not limited to, for example:
V1-2, V1-3, V1-4, V1-5, V1-7, V1-9, V1-11, V1-13, V1-16, V1-17, V1-18, V1-19, V1-20, and V1-22, grouped into subgroup VL1;
V2-1, V2-6, V2-7, V2-8, V2-11, V2-13, V2-14, V2-15, V2-17, and V2-19, grouped into subgroup VL1;
V3-2, V3-3, and V3-4, grouped into subgroup VL3;
V4-1, V4-2, V4-3, V4-4, and V4-6, grouped into subgroup VL4; and
V5-1, V5-2, V5-4, and V5-6, grouped into subgroup VL5
(Kawasaki et al. (Genome Res. (1997) 7, 250-261)).

Normally, these framework sequences are different from one another at one or more amino acid residues. These framework sequences can be used in combination with "at least one amino acid residue that alters the antigen-binding activity of an antigen-binding molecule depending on ion concentrations" of the present invention. Other examples of the fully human frameworks used in combination with "at least one amino acid residue that alters the antigen-binding activity of an antigen-binding molecule depending on ion concentrations" of the present invention include, but are not limited to, for example, KOL, NEWM, REI, EU, TUR, TEI, LAY, and POM (for example, Kabat et al. (1991) supra; Wu et al. (J. Exp. Med. (1970) 132, 211-250)).

Without being bound by a particular theory, one reason for the expectation that the use of germ line sequences precludes adverse immune responses in most individuals is believed to be as follows. As a result of the process of affinity maturation during normal immune responses, somatic mutation occurs frequently in the variable regions of immunoglobulin. Such mutations mostly occur around CDRs whose sequences are hypervariable, but also affect residues of framework regions. Such framework mutations do not exist on the germ line genes, and also they are less likely to be immunogenic in patients. On the other hand, the normal human population is exposed to most of the framework sequences expressed from the germ line genes. As a result of immunotolerance, these germ line frameworks are expected to have low or no immunogenicity in patients. To maximize the possibility of immunotolerance, variable region-encoding genes may be selected from a group of commonly occurring functional germ line genes.

Known methods such as site-directed mutagenesis (Kunkel et al. (Proc. Natl. Acad. Sci. USA (1985) 82, 488-492)) and overlap extension PCR can be appropriately employed to produce the antigen-binding molecules of the present invention in which the above-described variable region sequences, heavy or light chain variable region sequences, CDR sequences, or framework sequences contain amino acids that alter the antigen-binding activity of the antigen-binding molecules depending on calcium ion concentrations.

For example, a library which contains a plurality of antigen-binding molecules of the present invention whose sequences are different from one another can be constructed by combining heavy chain variable regions prepared as a randomized variable region sequence library with a light chain variable region selected as a framework sequence originally containing at least one amino acid residue that alters the antigen-binding activity of the antigen-binding molecule depending on calcium ion concentrations. As a non-limiting example, when the ion concentration is calcium ion concentration, such preferred libraries include, for example, those constructed by combining the light chain variable region sequence of SEQ ID NO: 6 (Vk5-2) and the heavy chain variable region produced as a randomized variable region sequence library.

Alternatively, a light chain variable region sequence selected as a framework region originally containing at least one amino acid residue that alters the antigen-binding activity of an antigen-binding molecule as mentioned above can be design to contain various amino acid residues other than the above amino acid residues. Herein, such residues are referred to as flexible residues. The number and position of flexible residues are not particularly limited as long as the antigen-binding activity of the antigen-binding molecule of the present invention varies depending on ion concentrations. Specifically, the CDR sequences and/or FR sequences of the heavy chain and/or light chain may contain one or more flexible residues. For example, when the ion concentration is calcium ion concentration, non-limiting examples of flexible residues to be introduced into the light chain variable region sequence of SEQ ID NO: 6 (Vk5-2) include the amino acid residues listed in Tables 1 or 2.

TABLE 1

| CDR | Position | 70% of the total | | | |
|---|---|---|---|---|---|
| CDR1 | 28 | S; 100% | | | |
| | 29 | I; 100% | | | |
| | 30 | E; 72% | H; 14% | S; 14% | |
| | 31 | D; 100% | | | |
| | 32 | D; 100% | | | |
| | 33 | L; 100% | | | |
| | 34 | A; 70% | N; 30% | | |
| CDR2 | 50 | E; 100% | | | |
| | 51 | A; 100% | | | |
| | 52 | S; 100% | | | |
| | 53 | H; 5% | N; 25% | S; 45% | T; 25% |
| | 54 | L; 100% | | | |
| | 55 | Q; 100% | | | |
| | 56 | S; 100% | | | |
| CDR3 | 90 | Q; 100% | | | |
| | 91 | H; 25% | S; 15% | R; 15% | Y; 45% |
| | 92 | D; 80% | N; 10% | S; 10% | |
| | 93 | D; 5% | G; 10% | N; 25% | S; 50% | R; 10% |
| | 94 | S; 50% | Y; 50% | | |
| | 95 | P; 100% | | | |
| | 96 | L; 50% | Y; 50% | | |

(Position indicates Kabat numbering)

TABLE 2

| CDR | Kabat numbering | 30% amino acids of the total | | | |
|---|---|---|---|---|---|
| CDR1 | 28 | S: 100% | | | |
| | 29 | I: 100% | | | |
| | 30 | E: 83% | S: 17% | | |
| | 31 | D: 100% | | | |
| | 32 | D: 100% | | | |
| | 33 | L: 100% | | | |
| | 34 | A: 70% | N: 30% | | |
| CDR2 | 50 | H: 100% | | | |
| | 51 | A: 100% | | | |
| | 52 | S: 100% | | | |
| | 53 | H: 5% | N: 25% | S: 45% | T: 25% |
| | 54 | L: 100% | | | |
| | 55 | Q: 100% | | | |
| | 56 | S: 100% | | | |
| CDR3 | 90 | Q: 100% | | | |
| | 91 | H: 25% | S: 15% | R: 15% | Y: 45% |
| | 92 | D: 80% | N: 10% | S: 10% | |
| | 93 | D: 5% | G: 10% | N: 25% | S: 50% | R: 10% |
| | 94 | S: 50% | Y: 50% | | |
| | 95 | P: 100% | | | |
| | 96 | L: 50% | Y: 50% | | |

(Position indicates Kabat numbering)

Herein, flexible residues refer to amino acid residue variations present at hypervariable positions at which several different amino acids are present on the light chain and heavy chain variable regions when the amino acid sequences of known and/or native antibodies or antigen-binding domains are compared. Hypervariable positions are generally located in the CDR regions. In an embodiment, the data provided by Kabat, Sequences of Proteins of Immunological Interest (National Institute of Health Bethesda Md.) (1987 and 1991) is useful to determine hypervariable positions in known and/or native antibodies. Furthermore, databases on the Internet (http://vbase.mrc-cpe.cam.ac. uk/, http://www.bioinf org.uk/abs/index.html) provide the collected sequences of many human light chains and heavy chains and their locations. The information on the sequences and locations is useful to determine hypervariable positions in the present invention. According to the present invention, when a certain amino acid position has preferably about 2 to about 20 possible amino acid residue variations, preferably about 3 to about 19, preferably about 4 to about 18, preferably 5 to 17, preferably 6 to 16, preferably 7 to 15, preferably 8 to 14, preferably 9 to 13, and preferably 10 to 12 possible amino acid residue variations, the position is hypervariable. In some embodiments, a certain amino acid position may have preferably at least about 2, preferably at least about 4, preferably at least about 6, preferably at least about 8, preferably about 10, and preferably about 12 amino acid residue variations.

Alternatively, a library containing a plurality of antigen-binding molecules of the present invention whose sequences are different from one another can be constructed by combining heavy chain variable regions produced as a randomized variable region sequence library with light chain variable regions into which at least one amino acid residue that alters the antigen-binding activity of antigen-binding molecules depending on ion concentrations as mentioned above is introduced. When the ion concentration is calcium ion concentration, non-limiting examples of such libraries preferably include, for example, libraries in which heavy chain variable regions produced as a randomized variable region sequence library are combined with light chain variable region sequences in which a particular residue(s) in a germ line sequence such as SEQ ID NO: 7 (Vk1), SEQ ID NO: 8

(Vk2), SEQ ID NO: 9 (Vk3), or SEQ ID NO: 10 (Vk4) has been substituted with at least one amino acid residue that alters the antigen-binding activity of an antigen-binding molecule depending on calcium ion concentrations. Non-limiting examples of such amino acid residues include amino acid residues in light chain CDR1. Furthermore, non-limiting examples of such amino acid residues include amino acid residues in light chain CDR2. In addition, non-limiting examples of such amino acid residues also include amino acid residues in light chain CDR3.

Non-limiting examples of such amino acid residues contained in light chain CDR1 include those at positions 30, 31, and/or 32 in the CDR1 of light chain variable region as indicated by EU numbering. Furthermore, non-limiting examples of such amino acid residues contained in light chain CDR2 include an amino acid residue at position 50 in the CDR2 of light chain variable region as indicated by Kabat numbering. Moreover, non-limiting examples of such amino acid residues contained in light chain CDR3 include an amino acid residue at position 92 in the CDR3 of light chain variable region as indicated by Kabat numbering. These amino acid residues can be contained alone or in combination as long as they form a calcium-binding motif and/or as long as the antigen-binding activity of an antigen-binding molecule varies depending on calcium ion concentrations. Meanwhile, as troponin C, calmodulin, parvalbumin, and myosin light chain, which have several calcium ion-binding sites and are believed to be derived from a common origin in terms of molecular evolution, are known, the light chain CDR1, CDR2, and/or CDR3 can be designed to have their binding motifs. For example, it is possible to use cadherin domains, EF hand of calmodulin, C2 domain of Protein kinase C, Gla domain of blood coagulation protein FactorIX, C type lectins of acyaroglycoprotein receptor and mannose-binding receptor, A domains of LDL receptors, annexin, thrombospondin type 3 domain, and EGF-like domains in an appropriate manner for the above purposes.

When heavy chain variable regions produced as a randomized variable region sequence library and light chain variable regions into which at least one amino acid residue that alters the antigen-binding activity of an antigen-binding molecule depending on ion concentrations has been introduced are combined as described above, the sequences of the light chain variable regions can be designed to contain flexible residues in the same manner as described above. The number and position of such flexible residues are not particularly limited to particular embodiments as long as the antigen-binding activity of antigen-binding molecules of the present invention varies depending on ion concentrations. Specifically, the CDR sequences and/or FR sequences of heavy chain and/or light chain can contain one or more flexible residues. When the ion concentration is calcium ion concentration, non-limiting examples of flexible residues to be introduced into the sequence of light chain variable region include the amino acid residues listed in Tables 1 and 2.

The preferred heavy chain variable regions to be combined include, for example, randomized variable region libraries. Known methods are combined as appropriate to produce a randomized variable region library. In a non-limiting embodiment of the present invention, an immune library constructed based on antibody genes derived from lymphocytes of animals immunized with a specific antigen, patients with infections, persons with an elevated antibody titer in blood as a result of vaccination, cancer patients, or auto immune disease patients, may be preferably used as a randomized variable region library.

In another non-limiting embodiment of the present invention, a synthetic library produced by replacing the CDR sequences of V genes in genomic DNA or functional reshaped V genes with a set of synthetic oligonucleotides containing sequences encoding codon sets of an appropriate length can also be preferably used as a randomized variable region library. In this case, since sequence diversity is observed in the heavy chain CDR3 sequence, it is also possible to replace the CDR3 sequence only. A criterion of giving rise to diversity in amino acids in the variable region of an antigen-binding molecule is that diversity is given to amino acid residues at surface-exposed positions in the antigen-binding molecule. The surface-exposed position refers to a position that is considered to be able to be exposed on the surface and/or contacted with an antigen, based on structure, ensemble of structures, and/or modeled structure of an antigen-binding molecule. In general, such positions are CDRs. Preferably, surface-exposed positions are determined using coordinates from a three-dimensional model of an antigen-binding molecule using a computer program such as the InsightII program (Accelrys). Surface-exposed positions can be determined using algorithms known in the art (for example, Lee and Richards (J. Mol. Biol. (1971) 55, 379-400); Connolly (J. Appl. Cryst. (1983) 16, 548-558)). Determination of surface-exposed positions can be performed using software suitable for protein modeling and three-dimensional structural information obtained from an antibody. Software that can be used for these purposes preferably includes SYBYL Biopolymer Module software (Tripos Associates). Generally or preferably, when an algorithm requires a user input size parameter, the "size" of a probe which is used in the calculation is set at about 1.4 Angstrom or smaller in radius. Furthermore, methods for determining surface-exposed regions and areas using software for personal computers are described by Pacios (Comput. Chem. (1994) 18 (4), 377-386; J. Mol. Model. (1995) 1, 46-53).

In another non-limiting embodiment of the present invention, a naive library, which is constructed from antibody genes derived from lymphocytes of healthy persons and whose repertoire consists of naive sequences, which are antibody sequences with no bias, can also be particularly preferably used as a randomized variable region library (Gejima et al. (Human Antibodies (2002) 11, 121-129); Cardoso et al. (Scand. J. Immunol. (2000) 51, 337-344)). Herein, an amino acid sequence comprising a naive sequence refers to an amino acid sequence obtained from such a naive library.

In one embodiment of the present invention, an antigen-binding domain of the present invention can be obtained from a library containing a plurality of antigen-binding molecules of the present invention whose sequences are different from one another, prepared by combining light chain variable regions constructed as a randomized variable region sequence library with a heavy chain variable region selected as a framework sequence that originally contains "at least one amino acid residue that alters the antigen-binding activity of an antigen-binding molecule depending on ion concentrations". When the ion concentration is calcium ion concentration, non-limiting examples of such libraries preferably include those constructed by combining light chain variable regions constructed as a randomized variable region sequence library with the sequence of heavy chain variable region of SEQ ID NO: 11 (6RL #9-IgG1) or SEQ ID NO: 12 (6KC4-1 #85-IgG1). Alternatively, such a library can be constructed by selecting appropriate light chain variable regions from those having germ line sequences, instead of light chain variable regions constructed as a randomized variable region sequence library. Such preferred libraries include, for example, those in which the sequence of heavy chain variable region of SEQ ID NO: 11 (6RL #9-IgG1) or SEQ ID NO: 12 (6KC4-1 #85-IgG1) is combined with light chain variable regions having germ line sequences.

Alternatively, the sequence of a heavy chain variable region selected as a framework sequence that originally contains "at least one amino acid residue that alters the antigen-binding activity of an antigen-binding molecule" as mentioned above can be designed to contain flexible residues. The number and position of the flexible residues are not particularly limited as long as the antigen-binding activity of an antigen-binding molecule of the present invention varies depending on ion concentrations. Specifically, the CDR and/or FR sequences of heavy chain and/or light chain can contain one or more flexible residues. When the ion concentration is calcium ion concentration, non-limiting examples of flexible residues to be introduced into the sequence of heavy chain variable region of SEQ ID NO: 11 (6RL #9-IgG1) include all amino acid residues of heavy chain CDR1 and CDR2 and the amino acid residues of the heavy chain CDR3 except those at positions 95, 96, and/or 100a. Alternatively, non-limiting examples of flexible residues to be introduced into the sequence of heavy chain variable region of SEQ ID NO: 12 (6KC4-1 #85-IgG1) include all amino acid residues of heavy chain CDR1 and CDR2 and the amino acid residues of the heavy chain CDR3 except those at amino acid positions 95 and/or 101.

Alternatively, a library containing a plurality of antigen-binding molecules whose sequences are different from one another can be constructed by combining light chain variable regions constructed as a randomized variable region sequence library or light chain variable regions having germ line sequences with heavy chain variable regions into which "at least one amino acid residue responsible for the ion concentration-dependent change in the antigen-binding activity of an antigen-binding molecule" has been introduced as mentioned above. When the ion concentration is calcium ion concentration, non-limiting examples of such libraries preferably include those in which light chain variable regions constructed as a randomized variable region sequence library or light chain variable regions having germ line sequences are combined with the sequence of a heavy chain variable region in which a particular residue(s) has been substituted with at least one amino acid residue that alters the antigen-binding activity of an antigen-binding molecule depending on calcium ion concentrations. Non-limiting examples of such amino acid residues include amino acid residues of the heavy chain CDR1. Further non-limiting examples of such amino acid residues include amino acid residues of the heavy chain CDR2. In addition, non-limiting examples of such amino acid residues also include amino acid residues of the heavy chain CDR3. Non-limiting examples of such amino acid residues of heavy chain CDR3 include the amino acids of positions 95, 96, 100a, and/or 101 in the CDR3 of heavy chain variable region as indicated by the Kabat numbering. Furthermore, these amino acid residues can be contained alone or in combination as long as they form a calcium-binding motif and/or the antigen-binding activity of an antigen-binding molecule varies depending on calcium ion concentrations.

When light chain variable regions constructed as a randomized variable region sequence library or light chain variable regions having germ line sequence are combined with a heavy chain variable region into which at least one amino acid residue that alter the antigen-binding activity of an antigen-binding molecule depending on ion concentrations as mentioned above has been introduced, the sequence of the heavy chain variable region can also be designed to contain flexible residues in the same manner as described above. The number and position of flexible residues are not particularly limited as long as the antigen-binding activity of an antigen-binding molecule of the present invention varies depending on ion concentrations. Specifically, the heavy chain CDR and/or FR sequences may contain one or more flexible residues. Furthermore, randomized variable region libraries can be preferably used as amino acid sequences of CDR1, CDR2, and/or CDR3 of the heavy chain variable region other than the amino acid residues that alter the antigen-binding activity of an antigen-binding molecule. When germ line sequences are used as light chain variable regions, non-limiting examples of such sequences include those of SEQ ID NO: 7 (Vk1), SEQ ID NO: 8 (Vk2), SEQ ID NO: 9 (Vk3), and SEQ ID NO: 10 (Vk4).

Any of the above-described amino acids that alter the antigen-binding activity of an antigen-binding molecule depending on calcium ion concentrations can be preferably used, as long as they form a calcium-binding motif. Specifically, such amino acids include electron-donating amino acids. Preferred examples of such electron-donating amino acids include serine, threonine, asparagine, glutamic acid, aspartic acid, and glutamic acid.

Condition of Proton Concentrations

In an embodiment of the present invention, the condition of ion concentrations refers to the condition of proton concentrations or pH condition. In the present invention, the concentration of proton, i.e., the nucleus of hydrogen atom, is treated as synonymous with hydrogen index (pH). When the activity of proton in an aqueous solution is represented as aH+, pH is defined as $-\log 10$ aH+. When the ionic strength of the aqueous solution is low (for example, lower than $10^{-3}$), aH+ is nearly equal to the proton strength. For example, the ionic product of water at 25° C. and 1 atmosphere is Kw=aH+aOH=$10^{-14}$, and therefore in pure water, aH+=aOH=$10^{-7}$. In this case, pH=7 is neutral; an aqueous solution whose pH is lower than 7 is acidic or whose pH is greater than 7 is alkaline.

In the present invention, when pH condition is used as the ion concentration condition, pH conditions include high proton concentrations or low pHs, i.e., an acidic pH range, and low proton concentrations or high pHs, i.e., a neutral pH range. "The binding activity varies depending on pH condition" means that the antigen-binding activity of an antigen-binding molecule varies due to the difference in conditions of a high proton concentration or low pH (an acidic pH range) and a low proton concentration or high pH (a neutral pH range). This includes, for example, the case where the antigen-binding activity of an antigen-binding molecule is higher in a neutral pH range than in an acidic pH range and the case where the antigen-binding activity of an antigen-binding molecule is higher in an acidic pH range than in a neutral pH range.

In the present specification, neutral pH range is not limited to a specific value and is preferably selected from between pH6.7 and pH10.0. In another embodiment, the pH can be selected from between pH6.7 and pH 9.5. In still another embodiment, the pH can be selected from between pH7.0 and pH9.0. In yet another embodiment, the pH can be selected from between pH7.0 and pH8.0. In particular, the preferred pH includes pH 7.4, which is close to the pH of plasma (blood) in vivo.

In the present specification, an acidic pH range is not limited to a specific value and is preferably selected from between pH4.0 and pH6.5. In another embodiment, the pH can be selected from between pH4.5 and pH6.5. In still another embodiment, the pH can be selected from between pH5.0 and pH6.5. In yet another embodiment, the pH can be selected from between pH5.5 and pH6.5. In particular, the preferred pH includes pH 5.8, which is close to the proton concentration in the early endosome in vivo.

In the present invention, "the antigen-binding activity of an antigen-binding molecule at a high proton concentration or low pH (an acidic pH range) is lower than that at a low proton concentration or high pH (a neutral pH range)" means that the antigen-binding activity of an antigen-binding molecule at a pH selected from between pH4.0 and pH6.5 is weaker than that at a pH selected from between pH6.7 and pH10.0; preferably means that the antigen-binding activity of an antigen-binding molecule at a pH selected from between pH4.5 and pH6.5 is weaker than that at a pH selected from between pH6.7 and pH9.5; more preferably, means that the antigen-binding activity of an antigen-binding molecule at a pH selected from between pH5.0 and pH6.5 is weaker than that at a pH selected from between pH7.0 and pH9.0; still more preferably means that the antigen-binding activity of an antigen-binding molecule at a pH selected from between pH5.5 and pH6.5 is weaker than that at a pH selected from between pH7.0 and pH8.0; particularly preferably means that the antigen-binding activity at the pH in the early endosome in vivo is weaker than the antigen-binding activity at the pH of plasma in vivo; and specifically means that the antigen-binding activity of an antigen-binding molecule at pH5.8 is weaker than the antigen-binding activity at pH 7.4.

Whether the antigen-binding activity of an antigen-binding molecule has changed by the pH condition can be determined, for example, by the use of known measurement methods such as those described in the section "Binding Activity" above. Specifically, the binding activity is measured under different pH conditions using the measurement methods described above. For example, the antigen-binding activity of an antigen-binding molecule is compared under the conditions of acidic pH range and neutral pH range to confirm that the antigen-binding activity of the antigen-binding molecule changes to be higher under the condition of neutral pH range than that under the condition of acidic pH range.

Furthermore, in the present invention, the expression "the antigen-binding activity at a high proton concentration or low pH, i.e., in an acidic pH range, is lower than that at a low proton concentration or high pH, i.e., in a neutral pH range" can also be expressed as "the antigen-binding activity of an antigen-binding molecule at a low proton concentration or high pH, i.e., in a neutral pH range, is higher than that at a high proton concentration or low pH, i.e., in an acidic pH range". In the present invention, "the antigen-binding activity at a high proton concentration or low pH, i.e., in an acidic pH range, is lower than that at a low proton concentration or high pH, i.e., in a neutral pH range" may be described as "the antigen-binding activity at a high proton concentration or low pH, i.e., in an acidic pH range, is weaker than the antigen-binding ability at a low proton concentration or high pH, i.e., in a neutral pH range". Alternatively, "the antigen-binding activity at a high proton concentration or low pH, i.e., in an acidic pH range, is reduced to be lower than that at a low proton concentration or high pH, i.e., in a neutral pH range" may be described as "the antigen-binding activity at a high proton concentration or low pH, i.e., in an acidic pH range, is reduced to be weaker than the antigen-binding ability at a low proton concentration or high pH, i.e., in a neutral pH range".

The conditions other than proton concentration or pH for measuring the antigen-binding activity may be suitably selected by those skilled in the art and are not particularly limited. Measurements can be carried out, for example, at 37° C. using HEPES buffer. Measurements can be carried out, for example, using a Biacore™ device (GE Healthcare). When the antigen is a soluble antigen, the antigen-binding activity of an antigen-binding molecule can be determined by assessing the binding activity to the soluble antigen by pouring the antigen as an analyte into a chip immobilized with the antigen-binding molecule. When the antigen is a membrane antigen, the binding activity to the membrane antigen can be assessed by pouring the antigen-binding molecule as an analyte into a chip immobilized with the antigen.

As long as the antigen-binding activity of an antigen-binding molecule of the present invention at a high proton concentration or low pH, i.e., in an acidic pH range is weaker than that at a low proton concentration or high pH, i.e., in a neutral pH range, the ratio of the antigen-binding activity between that at a high proton concentration or low pH, i.e., an acidic pH range, and at a low proton concentration or high pH, i.e., a neutral pH range is not particularly limited, and the value of KD (pH5.8)/KD (pH7.4), which is the ratio of the dissociation constant (KD) for an antigen at a high proton concentration or low pH, i.e., in an acidic pH range to the KD at a low proton concentration or high pH, i.e., in a neutral pH range, is preferably 2 or more; more preferably the value of KD (pH5.8)/KD (pH7.4) is 10 or more; and still more preferably the value of KD (pH5.8)/KD (pH7.4) is 40 or more. The upper limit of KD (pH5.8)/KD (pH7.4) value is not particularly limited, and may be any value such as 400, 1000, or 10000, as long as the molecule can be produced by the techniques of those skilled in the art.

When the antigen is a soluble antigen, the dissociation constant (KD) can be used as the value for antigen-binding activity. Meanwhile, when the antigen is a membrane antigen, the apparent dissociation constant (KD) can be used. The dissociation constant (KD) and apparent dissociation constant (KD) can be measured by methods known to those skilled in the art, and a Biacore™ device (GE Healthcare), Scatchard plot, flow cytometer, and such can be used.

Alternatively, for example, the dissociation rate constant (kd) can be suitably used as an index for indicating the ratio of the antigen-binding activity of an antigen-binding molecule of the present invention between that at a high proton concentration or low pH, i.e., an acidic pH range and a low proton concentration or high pH, i.e., a neutral pH range. When kd (dissociation rate constant) is used as an index for indicating the binding activity ratio instead of KD (dissociation constant), the value of kd (in an acidic pH range)/kd (in a neutral pH range), which is the ratio of kd (dissociation rate constant) for the antigen at a high proton concentration or low pH, i.e., in an acidic pH range to kd (dissociation rate constant) at a low proton concentration or high pH, i.e., in a neutral pH range, is preferably 2 or more, more preferably 5 or more, still more preferably 10 or more, and yet more preferably 30 or more. The upper limit of kd (in an acidic pH range)/kd (in a neutral pH range) value is not particularly limited, and may be any value such as 50, 100, or 200, as long as the molecule can be produced by the techniques of those skilled in the art.

When the antigen is a soluble antigen, the dissociation rate constant (kd) can be used as the value for antigen-binding activity and when the antigen is a membrane antigen, the apparent dissociation rate constant (kd) can be used. The dissociation rate constant (kd) and apparent dissociation rate constant (kd) can be determined by methods known to those skilled in the art, and a Biacore™ device (GE Healthcare), flow cytometer, and such may be used. In the present invention, when the antigen-binding activity of an antigen-binding molecule is measured at different proton concentrations, i.e., pHs, conditions other than the proton concentration, i.e., pH, are preferably the same.

For example, an antigen-binding domain or antigen-binding molecule whose antigen-binding activity at a high proton concentration or low pH, i.e., in an acidic pH range is lower than that at a low proton concentration or high pH, i.e., in a neutral pH range, which is one embodiment provided by the present invention, can be obtained via screening of antigen-binding domains or antigen-binding molecules, comprising the following steps (a) to (c):
(a) obtaining the antigen-binding activity of an antigen-binding domain or antigen-binding molecule in an acidic pH range;
(b) obtaining the antigen-binding activity of an antigen-binding domain or antigen-binding molecule in a neutral pH range; and
(c) selecting an antigen-binding domain or antigen-binding molecule whose antigen-binding activity in the acidic pH range is lower than that in the neutral pH range.

Alternatively, an antigen-binding domain or antigen-binding molecule whose antigen-binding activity at a high proton concentration or low pH, i.e., in an acidic pH range, is lower than that at a low proton concentration or high pH, i.e., in a neutral pH range, which is one embodiment provided by the present invention, can be obtained via screening of antigen-binding domains or antigen-binding molecules, or a library thereof, comprising the following steps (a) to (c):
(a) contacting an antigen-binding domain or antigen-binding molecule, or a library thereof, in a neutral pH range with an antigen;
(b) placing in an acidic pH range the antigen-binding domain or antigen-binding molecule bound to the antigen in step (a); and
(c) isolating the antigen-binding domain or antigen-binding molecule dissociated in step (b).

An antigen-binding domain or antigen-binding molecule whose antigen-binding activity at a high proton concentration or low pH, i.e., in an acidic pH range is lower than that at a low proton concentration or high pH, i.e., in a neutral pH range, which is another embodiment provided by the present invention, can be obtained via screening of antigen-binding domains or antigen-binding molecules, or a library thereof, comprising the following steps (a) to (d):
(a) contacting in an acidic pH range an antigen with a library of antigen-binding domains or antigen-binding molecules;
(b) selecting the antigen-binding domain or antigen-binding molecule which does not bind to the antigen in step (a);
(c) allowing the antigen-binding domain or antigen-binding molecule selected in step (b) to bind with the antigen in a neutral pH range; and
(d) isolating the antigen-binding domain or antigen-binding molecule bound to the antigen in step (c).

An antigen-binding domain or antigen-binding molecule whose antigen-binding activity at a high proton concentration or low pH, i.e., in an acidic pH range, is lower than that at a low proton concentration or high pH, i.e., in a neutral pH range, which is even another embodiment provided by the present invention, can be obtained by a screening method comprising the following steps (a) to (c):
(a) contacting in a neutral pH range a library of antigen-binding domains or antigen-binding molecules with a column immobilized with an antigen;
(b) eluting in an acidic pH range from the column the antigen-binding domain or antigen-binding molecule bound to the column in step (a); and
(c) isolating the antigen-binding domain or antigen-binding molecule eluted in step (b).

An antigen-binding domain or antigen-binding molecule whose antigen-binding activity at a high proton concentration or low pH, i.e., in an acidic pH, range is lower than that at a low proton concentration or high pH, i.e., in a neutral pH range, which is still another embodiment provided by the present invention, can be obtained by a screening method comprising the following steps (a) to (d):
(a) allowing, in an acidic pH range, a library of antigen-binding domains or antigen-binding molecules to pass a column immobilized with an antigen;
(b) collecting the antigen-binding domain or antigen-binding molecule eluted without binding to the column in step (a);
(c) allowing the antigen-binding domain or antigen-binding molecule collected in step (b) to bind with the antigen in a neutral pH range; and
(d) isolating the antigen-binding domain or antigen-binding molecule bound to the antigen in step (c).

An antigen-binding domain or antigen-binding molecule whose antigen-binding activity at a high proton concentration or low pH, i.e., in an acidic pH range, is lower than that at a low proton concentration or high pH, i.e., in a neutral pH range, which is yet another embodiment provided by the present invention, can be obtained by a screening method comprising the following steps (a) to (d):
(a) contacting an antigen with a library of antigen-binding domains or antigen-binding molecules in a neutral pH range;
(b) obtaining the antigen-binding domain or antigen-binding molecule bound to the antigen in step (a);
(c) placing in an acidic pH range the antigen-binding domain or antigen-binding molecule obtained in step (b); and
(d) isolating the antigen-binding domain or antigen-binding molecule whose antigen-binding activity in step (c) is weaker than the standard selected in step (b).

The above-described steps may be repeated twice or more times. Thus, the present invention provides antigen-binding domains and antigen-binding molecules whose antigen-binding activity in an acidic pH range is lower than that in a neutral pH range, which are obtained by a screening method that further comprises the steps of repeating twice or more times steps (a) to (c) or (a) to (d) in the above-described screening methods. The number of times that steps (a) to (c) or (a) to (d) is repeated is not particularly limited; however, the number is 10 or less in general.

In the screening methods of the present invention, the antigen-binding activity of an antigen-binding domain or antigen-binding molecule at a high proton concentration or low pH, i.e., in an acidic pH range, is not particularly limited, as long as it is the antigen-binding activity at a pH of between 4.0 and 6.5, and includes the antigen-binding activity at a pH of between 4.5 and 6.6 as the preferred pH. The antigen-binding activity also includes that at a pH of between 5.0 and 6.5, and that at a pH of between 5.5 and 6.5 as another preferred pH. The antigen-binding activity also includes that at the pH in the early endosome in vivo as the more preferred pH, and specifically, that at pH5.8. Meanwhile, the antigen-binding activity of an antigen-binding domain or antigen-binding molecule at a low proton concentration or high pH, i.e., in a neutral pH range, is not particularly limited, as long as it is the antigen-binding activity at a pH of between 6.7 and 10, and includes the antigen-binding activity at a pH of between 6.7 and 9.5 as the preferred pH. The antigen-binding activity also includes that at a pH of between 7.0 and 9.5 and that at a pH of between 7.0 and 8.0 as another preferred pH. The antigen-binding activity also includes that at the pH of plasma in vivo as the more preferred pH, and specifically, that at pH7.4.

The antigen-binding activity of an antigen-binding domain or antigen-binding molecule can be measured by methods known to those skilled in the art. Those skilled in the art can suitably determine conditions other than ionized calcium concentration. The antigen-binding activity of an antigen-binding domain or antigen-binding molecule can be assessed based on the dissociation constant (KD), apparent dissociation constant (KD), dissociation rate constant (kd), apparent dissociation rate constant (kd), and such. These can be determined by methods known to those skilled in the art, for example, using a Biacore™ device (GE Healthcare), Scatchard plot, or FACS.

Herein, the step of selecting an antigen-binding domain or antigen-binding molecule whose antigen-binding activity at a low proton concentration or high pH, i.e., in a neutral pH range, is higher than that at a high proton concentration or low pH, i.e., in an acidic pH range, is synonymous with the step of selecting an antigen-binding domain or antigen-binding molecule whose antigen-binding activity at a high proton concentration or low pH, i.e., in an acidic pH range, is lower than that at a low proton concentration or high pH, i.e., in a neutral pH range.

As long as the antigen-binding activity at a low proton concentration or high pH, i.e., in a neutral pH range, is higher than that at a high proton concentration or low pH, i.e., in an acidic pH range, the difference between the antigen-binding activity at a low proton concentration or high pH, i.e., a neutral pH range, and that at a high proton concentration or low pH, i.e., an acidic pH range, is not particularly limited; however, the antigen-binding activity at a low proton concentration or high pH, i.e., in a neutral pH range, is preferably twice or more, more preferably 10 times or more, and still more preferably 40 times or more than that at a high proton concentration or low pH, i.e., in an acidic pH range.

The antigen binding domain or antigen-binding molecule of the present invention that is screened by the screening methods described above may be any antigen-binding domain or antigen-binding molecule, and for example, an above-mentioned antigen-binding domain or antigen-binding molecule may be screened. For example, antigen-binding domains or antigen-binding molecules having a native sequence may be screened, and antigen-binding domains or antigen-binding molecules in which their amino acid sequences have been substituted may also be screened.

The antigen-binding domain or antigen-binding molecule of the present invention to be screened by the above-described screening methods may be prepared in any manner. For example, preexisting antigen-binding molecules, preexisting libraries (phage library, etc.), antibodies or libraries prepared from B cells of immunized animals or from hybridomas obtained by immunizing animals, antibodies or libraries (libraries with increased content of amino acids with a side chain pKa of 4.0-8.0 (for example, histidine and glutamic acid) or unnatural amino acids, libraries introduced with amino acids with a side chain pKa of 4.0-8.0 (for example, histidine and glutamic acid) or unnatural amino acid mutations at specific positions, etc.) obtained by introducing amino acids with a side chain pKa of 4.0-8.0 (for example, histidine and glutamic acid) or unnatural amino acid mutations into the above-described antibodies or libraries may be used.

Methods for obtaining an antigen-binding domain or antigen-binding molecule whose antigen-binding activity at a low proton concentration or high pH, i.e., in a neutral pH range, is higher than that at a high proton concentration or low pH, i.e., in an acidic pH range, from an antigen-binding domains or antibodies prepared from hybridomas obtained by immunizing animals or from B cells of immunized animals preferably include, for example, the antigen-binding molecule or antigen-binding molecule in which at least one of the amino acids of the antigen-binding domain or antigen-binding molecule is substituted with an amino acid with a side chain pKa of 4.0-8.0 (for example, histidine and glutamic acid) or an unnatural amino acid mutation, or the antigen-binding domain or antigen-binding molecule inserted with an amino acid with a side chain pKa of 4.0-8.0 (for example, histidine and glutamic acid) or unnatural amino acid, such as those described in International Publication No. WO 2009/125825.

The sites of introducing mutations of amino acids with a side chain pKa of 4.0-8.0 (for example, histidine and glutamic acid) or unnatural amino acids are not particularly limited, and may be any position as long as the antigen-binding activity in an acidic pH range becomes weaker than that in a neutral pH range (the value of KD (in an acidic pH range)/KD (in a neutral pH range) or kd (in an acidic pH range)/kd (in a neutral pH range) is increased) as compared to before substitution or insertion. For example, when the antigen-binding molecule is an antibody, antibody variable region and CDRs are suitable. Those skilled in the art can appropriately determine the number of amino acids to be substituted with or the number of amino acids with a side chain pKa of 4.0-8.0 (for example, histidine and glutamic acid) or unnatural amino acids to be inserted. It is possible to substitute with a single amino acid having a side chain pKa of 4.0-8.0 (for example, histidine and glutamic acid) or a single unnatural amino acid; it is possible to insert a single amino acid having a side chain pKa of 4.0-8.0 (for example, histidine and glutamic acid) or a single unnatural amino acid; it is possible to substitute with two or more amino acids having a side chain pKa of 4.0-8.0 (for example, histidine and glutamic acid) or two or more unnatural amino acids; and it is possible to insert two or more amino acids having a side chain pKa of 4.0-8.0 (for example, histidine and glutamic acid) or two or more unnatural amino acids. Alternatively, other amino acids can be deleted, added, inserted, and/or substituted concomitantly, aside from the substitution into amino acids having a side chain pKa of 4.0-8.0 (for example, histidine and glutamic acid) or unnatural amino acids, or the insertion of amino acids having a side chain pKa of 4.0-8.0 (for example, histidine and glutamic acid) or unnatural amino acids. Substitution into or insertion of amino acids with a side chain pKa of 4.0-8.0 (for example, histidine and glutamic acid) or unnatural amino acids can performed randomly by methods such as histidine scanning, in which the alanine of alanine scanning known to those skilled in the art is replaced with histidine. Antigen-binding molecules exhibiting a greater value of KD (in an acidic pH range)/KD (in a neutral pH range) or kd (in an acidic pH range)/kd (in a neutral pH range) as compared to before the mutation can be selected from antigen-binding domains or antibodies introduced with random insertions or substitution mutations of amino acids with a side chain pKa of 4.0-8.0 (for example, histidine and glutamic acid) or unnatural amino acids.

Preferred examples of antigen-binding molecules containing the mutation into amino acids with a side chain pKa of 4.0-8.0 (for example, histidine and glutamic acid) or unnatural amino acids as described above and whose antigen-binding activity in an acidic pH range is lower than that in a neutral pH range include, antigen-binding molecules whose antigen-binding activity in the neutral pH range after the mutation into amino acids with a side chain pKa of 4.0-8.0 (for example, histidine and glutamic acid) or unnatural amino acids is comparable to that before the mutation into amino acids with a side chain pKa of 4.0-8.0 (for example, histidine and glutamic acid) or unnatural amino acids. Herein, "an antigen-binding molecule after the mutation with amino acids having a side chain pKa of 4.0-8.0 (for example, histidine and glutamic acid) or unnatural amino acids has an antigen-binding activity comparable to that before the mutation with amino acids having a side chain pKa of 4.0-8.0 (for example, histidine and glutamic acid) or unnatural amino acids" means that, when taking the antigen-binding activity of an antigen-binding molecule before the mutation with amino acids having a side chain pKa of 4.0-8.0 (for example, histidine and glutamic acid) or unnatural amino acids as 100%, the antigen-binding activity of an antigen-binding molecule after the mutation with amino acids having a side chain pKa of 4.0-8.0 (for example, histidine and glutamic acid) or unnatural amino acids is at least 10% or more, preferably 50% or more, more preferably 80% or more, and still more preferably 90% or more. The antigen-binding activity after the mutation of amino acids with a side chain pKa of 4.0-8.0 (for example, histidine and glutamic acid) or unnatural amino acids at pH 7.4 may be higher than that before the mutation of amino acids with a side chain pKa of 4.0-8.0 (for example, histidine and glutamic acid) or unnatural amino acids at pH 7.4. If the antigen-binding activity of an antigen-binding molecule is decreased due to insertion of or substitution into amino acids with a side chain pKa of 4.0-8.0 (for example, histidine and glutamic acid) or unnatural amino acids, the antigen-binding activity can be made to be comparable to that before the insertion of or substitution into amino acids with a side chain pKa of 4.0-8.0 (for example, histidine and glutamic acid) or unnatural amino acids, by introducing a substitution, deletion, addition, and/or insertion of one or more amino acids of the antigen-binding molecule. The present invention also includes antigen-binding molecules whose binding activity has been adjusted to be comparable by substitution, deletion, addition, and/or insertion of one or more amino acids after substitution or insertion of amino acids with a side chain pKa of 4.0-8.0 (for example, histidine and glutamic acid) or unnatural amino acids.

Amino Acids that Alter the Antigen-Binding Activity of Antigen-Binding Domain Depending on the Proton Concentration Conditions Antigen-binding domains or antigen-binding molecules of the present invention to be screened by the above-described screening methods may be prepared in any manner. For example, when ion concentration condition is proton concentration condition or pH condition, preexisting antigen-binding molecules, preexisting libraries (phage library, etc.), antibodies or libraries prepared from B cells of immunized animals or from hybridomas obtained by immunizing animals, antibodies or libraries (libraries with increased content of amino acids with a side chain pKa of 4.0-8.0 (for example, histidine and glutamic acid) or unnatural amino acids, libraries introduced with mutations of amino acids with a side chain pKa of 4.0-8.0 (for example, histidine and glutamic acid) or unnatural amino acids at specific positions, etc.) obtained by introducing mutations of amino acids with a side chain pKa of 4.0-8.0 (for example, histidine and glutamic acid) or unnatural amino acids into the above-described antibodies or libraries may be used.

In one embodiment of the present invention, a library containing multiple antigen-binding molecules of the present invention whose sequences are different from one another can also be constructed by combining heavy chain variable regions, produced as a randomized variable region sequence library, with light chain variable regions introduced with "at least one amino acid residue that changes the antigen-binding activity of an antigen-binding molecule depending on the proton concentration condition".

Such amino acid residues include, but are not limited to, for example, amino acid residues contained in the light chain CDR1. The amino acid residues also include, but are not limited to, for example, amino acid residues contained in the light chain CDR2. The amino acid residues also include, but are not limited to, for example, amino acid residues contained in the light chain CDR3.

The above-described amino acid residues contained in the light chain CDR1 include, but are not limited to, for example, amino acid residues of positions 24, 27, 28, 31, 32, and/or 34 according to Kabat numbering in the CDR1 of light chain variable region. Meanwhile, the amino acid residues contained in the light chain CDR2 include, but are not limited to, for example, amino acid residues of positions 50, 51, 52, 53, 54, 55, and/or 56 according to Kabat numbering in the CDR2 of light chain variable region. Furthermore, the amino acid residues in the light chain CDR3 include, but are not limited to, for example, amino acid residues of positions 89, 90, 91, 92, 93, 94, and/or 95A according to Kabat numbering in the CDR3 of light chain variable region. Moreover, the amino acid residues can be contained alone or can be contained in combination of two or more amino acids as long as they allow the change in the antigen-binding activity of an antigen-binding molecule depending on the proton concentration.

Even when the heavy chain variable region produced as a randomized variable region sequence library is combined with the above-described light chain variable region introduced with "at least one amino acid residue that changes the antigen-binding activity of an antigen-binding molecule depending on the proton concentration condition", it is possible to design so that the flexible residues are contained in the sequence of the light chain variable region in the same manner as described above. The number and position of the flexible residues are not particularly limited to a specific embodiment, as long as the antigen-binding activity of an antigen-binding molecule of the present invention changes depending on the proton concentration condition. Specifically, the CDR and/or FR sequences of heavy chain and/or light chain can contain one or more flexible residues. For example, flexible residues to be introduced into the sequences of the light chain variable regions include, but are not limited to, for example, the amino acid residues listed in Tables 3 and 4. Meanwhile, amino acid sequences of light chain variable regions other than the flexible residues and amino acid residues that change the antigen-binding activity of an antigen-binding molecule depending on the proton concentration condition suitably include, but are not limited to, germ line sequences such as Vk1 (SEQ ID NO: 7), Vk2 (SEQ ID NO: 8), Vk3 (SEQ ID NO: 9), and Vk4 (SEQ ID NO: 10).

TABLE 3

| Position | Amino acid | | | | | | | |
|---|---|---|---|---|---|---|---|---|
| CDR1 | | | | | | | | |
| 28 | S: 100% | | | | | | | |
| 29 | I: 100% | | | | | | | |
| 30 | N: 25% | S: 25% | R: 25% | H: 25% | | | | |
| 31 | S: 100% | | | | | | | |
| 32 | H: 100% | | | | | | | |
| 33 | L: 100% | | | | | | | |
| 34 | A: 50% | N: 50% | | | | | | |
| CDR2 | | | | | | | | |
| 50 | H: 100% | | | | or | A: 25% | D: 25% | G: 25% | K: 25% |
| 51 | A: 100% | | | | | A: 100% | | | |
| 52 | S: 100% | | | | | S: 100% | | | |
| 53 | K: 33.3% | N: 33.3% | S: 33.3% | | | H: 100% | | | |
| 54 | L: 100% | | | | | L: 100% | | | |
| 55 | Q: 100% | | | | | Q: 100% | | | |
| 56 | S: 100% | | | | | S: 100% | | | |
| CDR3 | | | | | | | | |
| 90 | Q: 100% | | | | or | Q: 100% | | | |
| 91 | H: 100% | | | | | S: 33.3% | R: 33.3% | Y: 33.3% | |
| 92 | G: 25% | N: 25% | S: 25% | Y: 25% | | H: 100% | | | |
| 93 | H: 33.3% | N: 33.3% | S: 33.3% | | | H: 33.3% | N: 33.3% | S: 33.3% | |
| 94 | S: 50% | Y: 50% | | | | S: 50% | Y: 50% | | |
| 95 | P: 100% | | | | | P: 100% | | | |
| 96 | L: 50% | Y: 50% | | | | L: 50% | Y: 50% | | |

(Position indicates Kabat numbering)

TABLE 4

| CDR | Position | Amino acid | | | | |
|---|---|---|---|---|---|---|
| CDR1 | 28 | S: 100% | | | | |
| | 29 | I: 100% | | | | |
| | 30 | H: 30% | N: 10% | S: 50% | R: 10% | |
| | 31 | N: 35% | S: 65% | | | |
| | 32 | H: 40% | N: 20% | Y: 40% | | |
| | 33 | L: 100% | | | | |
| | 34 | A: 70% | N: 30% | | | |
| CDR2 | 50 | A: 25% | D: 15% | G: 25% | H: 30% | K: 5% |
| | 51 | A: 100% | | | | |
| | 52 | S: 100% | | | | |
| | 53 | H: 30% | K: 10% | N: 15% | S: 45% | |
| | 54 | L: 100% | | | | |
| | 55 | Q: 100% | | | | |
| | 56 | S: 100% | | | | |
| CDR3 | 90 | Q: 100% | | | | |
| | 91 | H: 30% | S: 15% | R: 10% | Y: 45% | |
| | 92 | G: 20% | H: 30% | N: 20% | S: 15% | Y: 15% |
| | 93 | H: 30% | N: 25% | S: 45% | | |
| | 94 | S: 50% | Y: 50% | | | |
| | 95 | P: 100% | | | | |
| | 96 | L: 50% | Y: 50% | | | |

(Position indicates Kabat numbering)

Any amino acid residue may be suitably used as the above-described amino acid residues that change the antigen-binding activity of an antigen-binding molecule depending on the proton concentration condition. Specifically, such amino acid residues include amino acids with a side chain pKa of 4.0-8.0. Such electron-releasing amino acids preferably include, for example, naturally occurring amino acids such as histidine and glutamic acid, as well as unnatural amino acids such as histidine analogs (US2009/0035836), m-NO2-Tyr (pKa 7.45), 3,5-Br2-Tyr (pKa 7.21), and 3,5-I2-Tyr (pKa 7.38) (Bioorg. Med. Chem. (2003) 11 (17), 3761-3768). Particularly preferred amino acid residues include, for example, amino acids with a side chain pKa of 6.0-7.0. Such electron-releasing amino acid residues preferably include, for example, histidine.

Known methods such as site-directed mutagenesis (Kunkel et al. (Proc. Natl. Acad. Sci. USA (1985) 82, 488-492)) and Overlap extension PCR can be appropriately employed to modify the amino acids of antigen-binding domains. Furthermore, various known methods can also be used as an amino acid modification method for substituting amino acids by those other than natural amino acids (Annu. Rev. Biophys. Biomol. Struct. (2006) 35, 225-249; Proc. Natl. Acad. Sci. U.S.A. (2003) 100 (11), 6353-6357). For example, a cell-free translation system (Clover Direct (Protein Express)) containing tRNAs in which amber suppressor tRNA, which is complementary to UAG codon (amber codon) that is a stop codon, is linked with an unnatural amino acid may be suitably used.

The preferred heavy chain variable region that is used in combination includes, for example, randomized variable region libraries. Known methods are appropriately combined as a method for producing a randomized variable region library. In a non-limiting embodiment of the present invention, an immune library constructed based on antibody genes derived from animals immunized with specific antigens, patients with infection or persons with an elevated antibody titer in blood as a result of vaccination, cancer patients, or lymphocytes of auto immune diseases may be suitably used as a randomized variable region library.

In another non-limiting embodiment of the present invention, in the same manner as described above, a synthetic library in which the CDR sequences of V genes from genomic DNA or functional reconstructed V genes are replaced with a set of synthetic oligonucleotides containing the sequences encoding codon sets of an appropriate length can also be suitably used as a randomized variable region library. In this case, the CDR3 sequence alone may be replaced because variety in the gene sequence of heavy chain CDR3 is observed. The basis for giving rise to amino acid variations in the variable region of an antigen-binding molecule is to generate variations of amino acid residues of surface-exposed positions of the antigen-binding molecule. The surface-exposed position refers to a position where an amino acid is exposed on the surface and/or contacted with an antigen based on the conformation, structural ensemble, and/or modeled structure of an antigen-binding molecule, and in general, such positions are preferably the CDRs. The surface-exposed positions are preferably determined using the coordinates derived from a three-dimensional model of the antigen-binding molecule using computer programs such as InsightII program (Accelrys). The surface-exposed positions can be determined using algorithms known in the art (for example, Lee and Richards (J. Mol. Biol. (1971) 55, 379-400); Connolly (J. Appl. Cryst. (1983) 16, 548-558)). The surface-exposed positions can be determined based on the information on the three dimensional structure of antibodies using software suitable for protein modeling. Software which is suitably used for this purpose includes the SYBYL biopolymer module software (Tripos Associates). When the algorithm requires the input size parameter from the user, the "size" of probe for use in computation is generally or preferably set at about 1.4 angstrom or less in radius. Furthermore, a method for determining surface-exposed region and area using PC software is described by Pacios (Comput. Chem. (1994) 18 (4), 377-386; and J. Mol. Model. (1995) 1, 46-53).

In still another non-limiting embodiment of the present invention, a naive library constructed from antibody genes derived from lymphocytes of healthy persons and consisting of naive sequences, which are unbiased repertoire of antibody sequences, can also be particularly suitably used as a randomized variable region library (Gejima et al. (Human Antibodies (2002) 11, 121-129); and Cardoso et al. (Scand. J. Immunol. (2000) 51, 337-344)).

Fc Region

An Fc region contains the amino acid sequence derived from the heavy chain constant region of an antibody. An Fc region is a portion of the heavy chain constant region of an antibody, starting from the N terminal end of the hinge region, which corresponds to the papain cleavage site at an amino acid around position 216 according to the EU numbering system, and contains the hinge, CH2, and CH3 domains. While the Fc region may be obtained from human IgG1, it is not limited to a particular subclass of IgG. As described later, a favorable example of the Fc region is an Fc region that has an FcRn-binding activity in an acidic pH range. Furthermore, a favorable example of the Fc region is an Fc region that has an Fcγ receptor-binding activity as described later. A non-limiting embodiment of such an Fc region is, for example, the Fc region of human IgG1 (SEQ ID NO: 13), IgG2 (SEQ ID NO: 14), IgG3 (SEQ ID NO: 15), or IgG4 (SEQ ID NO: 16).

FcRn

Unlike Fcγ receptor belonging to the immunoglobulin superfamily, human FcRn is structurally similar to polypeptides of major histocompatibility complex (MHC) class I, exhibiting 22% to 29% sequence identity to class I MHC molecules (Ghetie el al., Immunol. Today (1997) 18 (12): 592-598). FcRn is expressed as a heterodimer consisting of soluble β or light chain (β2 microglobulin) complexed with transmembrane a or heavy chain. Like MHC, FcRn α chain comprises three extracellular domains (α1, α2, and α3) and its short cytoplasmic domain anchors the protein onto the cell surface. α1 and α2 domains interact with the FcRn-binding domain of the antibody Fc region (Raghavan et al., Immunity (1994) 1: 303-315).

FcRn is expressed in maternal placenta and york sac of mammals, and is involved in mother-to-fetus IgG transfer. In addition, in neonatal small intestine of rodents, where FcRn is expressed, FcRn is involved in transfer of maternal IgG across brush border epithelium from ingested colostrum or milk. FcRn is expressed in a variety of other tissues and endothelial cell systems of various species. FcRn is also expressed in adult human endothelia, muscular blood vessels, and hepatic sinusoidal capillaries. FcRn is believed to play a role in maintaining the plasma IgG concentration by mediating recycling of IgG to serum upon binding to IgG. Typically, binding of FcRn to IgG molecules is strictly pH dependent. The optimal binding is observed in an acidic pH range below 7.0.

Human FcRn whose precursor is a polypeptide having the signal sequence of SEQ ID NO: 17 (the polypeptide with the signal sequence is shown in SEQ ID NO: 18) forms a complex with human β2-microglobulin in vivo. Soluble human FcRn complexed with β2-microglobulin is produced by using conventional recombinant expression techniques. FcRn regions of the present invention can be assessed for their binding activity to such a soluble human FcRn complexed with β2-microglobulin. Herein, unless otherwise specified, human FcRn refers to a form capable of binding to an FcRn region of the present invention. Examples include a complex between human FcRn and human β2-microglobulin. Anon-limiting embodiment is exemplified by a complex formed between a mouse FcRn (SEQ ID NO: 73) and a mouse β2-microglobulin (SEQ ID NO: 74).

Binding Activity of the Fc Region to FcRn, in Particular, Human FcRn

The binding activity of an Fc region of the present invention to FcRn, human FcRn in particular, can be measured by methods known to those skilled in the art, as described in the section "Binding Activity" above. Those skilled in the art can appropriately determine the conditions other than pH. The antigen-binding activity and human FcRn-binding activity of an antigen-binding molecule can be assessed based on the dissociation constant (KD), apparent dissociation constant (KD), dissociation rate (kd), apparent dissociation rate (kd), and such. These can be measured by methods known to those skilled in the art. For example, a Biacore™ device (GE Healthcare), Scatchard plot, or flow cytometer may be used.

When the human FcRn-binding activity of an Fc region of the present invention is measured, conditions other than the pH are not particularly limited, and can be appropriately selected by those skilled in the art. Measurements can be carried out, for example, at 37° C. using MES buffer, as described in International Publication No. WO 2009125825. Alternatively, the human FcRn-binding activity of an Fc region of the present invention can be measured by methods known to those skilled in the art, and may be measured by using, for example, a Biacore™ device (GE Healthcare) or such. The binding activity of an Fc region of the present invention to human FcRn can be assessed by pouring, as an analyte, human FcRn, an Fc region, or an antigen-binding molecule of the present invention containing the Fc region into a chip immobilized with an Fc region, an antigen-binding molecule of the present invention containing the Fc region, or human FcRn.

A neutral pH range as the condition where the Fc region contained in an antigen-binding molecule of the present invention has the FcRn-binding activity means pH6.7 to pH10.0 in general. Preferably, the neutral pH range is a range indicated with arbitrary pH values between pH7.0 and pH8.0, and is preferably selected from pH7.0, 7.1, 7.2, 7.3, 7.4, 7.5, 7.6, 7.7, 7.8, 7.9, and 8.0, and is particularly preferably pH7.4 that is close to the pH of plasma (blood) in vivo. When the binding affinity between the human FcRn-binding domain and human FcRn at pH7.4 is too low to assess, pH7.0 may be used instead of pH7.4. Herein, an acidic pH range as the condition where the Fc region contained in an antigen-binding molecule of the present invention has the FcRn-binding activity means pH4.0 to pH6.5 in general. Preferably, the acidic pH range means pH5.5 to pH6.5, particularly preferably pH5.8 to pH6.0 which is close to the pH in the early endosome in vivo. Regarding the temperature used as the measurement condition, the binding affinity between the human FcRn-binding domain and human FcRn may be assessed at any temperature between 10° C. and 50° C. Preferably, the binding affinity between the human FcRn-binding domain and human FcRn can be determined at 15° C. to 40° C. More preferably, the binding affinity between the human FcRn-binding domain and human FcRn can be determined in the same manner at an arbitrary temperature between 20° C. and 35° C., such as any one temperature of 20, 21, 22, 23, 24, 25, 26, 27, 28, 29, 30, 31, 32, 33, 34, and 35° C. In an embodiment of the present invention, the temperature includes, but is not limited to, for example, 25° C.

According to the Journal of Immunology (2009) 182, 7663-7671, the human FcRn-binding activity of native human IgG1 in an acidic pH range (pH 6.0) is 1.7 μM (KD), and the activity is almost undetectable in a neutral pH range. Thus, in a preferred embodiment, antigen-binding molecules comprising an Fc region of which human FcRn-binding activity in an acidic pH range is 20 μM (KD) or stronger may be screened. In a more preferred embodiment, the antigen-binding molecules comprising an Fc region of which human FcRn-binding activity in an acidic pH range is 2.0 μM (KD) or stronger may be screened. In a still more preferred embodiment, the antigen-binding molecules comprising an Fc region of which human FcRn-binding activity in an acidic pH range is 0.5 μM (KD) or stronger may be screened. The above-mentioned KD values are determined by the method described in the Journal of Immunology (2009) 182: 7663-7671 (by immobilizing the antigen-binding molecule onto a chip and loading human FcRn as an analyte).

In the present invention, preferred Fc regions have an FcRn-binding activity in an acidic pH range condition. When an Fc region originally has an FcRn-binding activity under an acidic pH range condition, the domain can be used as it is. When the domain has a weak or no FcRn-binding activity under an acidic pH range condition, an Fc region having a desired FcRn-binding activity can be obtained by modifying amino acids of an antigen-binding molecule. Fc regions having a desired or enhanced FcRn-binding activity under an acidic pH range condition can also be suitably obtained by modifying the amino acids of an Fc region. Amino acid modifications of an Fc region that result in such a desired binding activity can be found by comparing the FcRn-binding activity under an acidic pH range condition before and after amino acid modification. Those skilled in the art can appropriately modify the amino acids using known techniques similar to the aforementioned techniques used to modify the Fcγ-receptor-binding activity.

Fc regions comprised in the antigen-binding molecules of the present invention, which have an FcRn-binding activity under an acidic pH range condition, can be obtained by any method. Specifically, FcRn-binding domains having an FcRn-binding activity or an enhanced FcRn-binding activity under an acidic pH range condition can be obtained by modifying the amino acids of an IgG-type human immunoglobulin used as a starting Fc region. Preferred Fc regions of an IgG-type immunoglobulin for modification include, for example, those of human IgGs (IgG1, IgG2, IgG3, and IgG4, and variants thereof). As long as the Fc region has an FcRn-binding activity under an acidic pH range condition or can increase the human FcRn-binding activity under an acidic pH range condition, amino acids at any position may be modified into other amino acids. When the antigen-binding molecule contains the Fc region of human IgG1 as the Fc region, it is preferable that the resulting Fc region contains a modification that results in the effect of enhancing FcRn binding under an acidic pH range condition as compared to the binding activity of the starting human IgG1 Fc region. Amino acids that allow such modification include, for example, amino acids of positions 252, 254, 256, 309, 311, 315, 433, and/or 434 according to EU numbering, and their combination amino acids at positions 253, 310, 435, and/or 426 as described in WO 1997/034631. Favorable examples include amino acids of positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439, and/or 447 as indicated by EU numbering as described in WO 2000/042072. Similarly, favorable examples of amino acids that allow such modification include, amino acids of positions 251, 252, 254, 255, 256, 308, 309, 311, 312, 385, 386, 387, 389, 428, 433, 434, and/or 436 according to EU numbering as described in WO 2002/060919. Furthermore, amino acids that allow such modification include, for example, amino acids of positions 250, 314, and 428 according to EU numbering as described in WO2004/092219. In addition, favorable examples of amino acids that allow such modification include amino acids of positions 238, 244, 245, 249, 252, 256, 257, 258, 260, 262, 270, 272, 279, 283, 285, 286, 288, 293, 307, 311, 312, 316, 317, 318, 332, 339, 341, 343, 375, 376, 377, 378, 380, 382, 423, 427, 430, 431, 434, 436, 438, 440, and/or 442 as described in WO 2006/020114. Furthermore, favorable examples of amino acids that allow such modification include amino acids of positions 251, 252, 307, 308, 378, 428, 430, 434, and/or 436 according to EU numbering as described in WO 2010/045193. Modification of these amino acids enhances FcRn binding of the Fc region of an IgG-type immunoglobulin under an acidic pH range condition.

When the Fc region of human IgG1 is comprised as the Fc region, a non-limiting embodiment of the modification that results in the effect of enhancing FcRn binding under an acidic pH range condition as compared to the binding activity of the starting Fc region of human IgG1 includes at least one or more amino acid modifications selected from the group consisting of:

Arg or Leu for the amino acid of position 251;
Phe, Ser, Thr, or Tyr for the amino acid of position 252;
Ser or Thr for the amino acid of position 254;
Arg, Gly, Ile, or Leu for the amino acid of position 255;
Ala, Arg, Asn, Asp, Gln, Glu, or Thr for the amino acid of position 256;
Ile or Thr for the amino acid of position 308;
Pro for the amino acid of position 309;
Glu, Leu, or Ser for the amino acid of position 311;
Ala or Asp for the amino acid of position 312;
Ala or Leu for the amino acid of position 314;
Ala, Arg, Asp, Gly, His, Lys, Ser, or Thr for the amino acid of position 385;
Arg, Asp, Ile, Lys, Met, Pro, Ser, or Thr for the amino acid of position 386;
Ala, Arg, His, Pro, Ser, or Thr for the amino acid of position 387;
Asn, Pro, or Ser for the amino acid of position 389;
Leu, Met, Phe, Ser, or Thr for the amino acid of position 428;
Arg, Gln, His, Ile, Lys, Pro, or Ser for the amino acid of position 433;

His, Phe, or Tyr for the amino acid of position 434; and Arg, Asn, His, Lys, Met, or Thr for the amino acid of position 436, as indicated by EU numbering. Meanwhile, the number of amino acids to be modified is not particularly limited; and amino acid may be modified at only one site or amino acids may be modified at two or more sites.

When the Fc region of human IgG1 is comprised as the Fc region, a non-limiting embodiment of the modification that results in the effect of enhancing FcRn binding in an acidic pH range condition as compared to the binding activity of the starting Fc region of human IgG1 may be modifications including Ile for the amino acid of position 308, Pro for the amino acid of position 309, and/or Glu for the amino acid of position 311 according to EU numbering. Another non-limiting embodiment of this modification may include Thr for the amino acid of position 308, Pro for the amino acid of position 309, Leu for the amino acid of position 311, Ala for the amino acid of position 312, and/or Ala for the amino acid of position 314. Furthermore, another non-limiting embodiment of this modification may include Ile or Thr for the amino acid of position 308, Pro for the amino acid of position 309, Glu, Leu, or Ser for the amino acid of position 311, Ala for the amino acid of position 312, and/or Ala or Leu for the amino acid of position 314. Another non-limiting embodiment of this modification may include Thr for the amino acid of position 308, Pro for the amino acid of position 309, Ser for the amino acid of position 311, Asp for the amino acid of position 312, and/or Leu for the amino acid of position 314.

When the Fc region of human IgG1 is comprised as the Fc region, a non-limiting embodiment of the modification that results in the effect of enhancing FcRn binding under an acidic pH range condition as compared to the binding activity of the starting Fc region of human IgG1 may be modifications including Leu for the amino acid of position 251, Tyr for the amino acid of position 252, Ser or Thr for the amino acid of position 254, Arg for the amino acid of position 255, and/or Glu for the amino acid of position 256 according to EU numbering.

When the Fc region of human IgG1 is comprised as the Fc region, a non-limiting embodiment of the modification that results in the effect of enhancing FcRn binding under an acidic pH range condition as compared to the binding activity of the starting Fc region of human IgG1 may be modifications including Leu, Met, Phe, Ser, or Thr for the amino acid of position 428, Arg, Gln, His, Ile, Lys, Pro, or Ser for the amino acid of position 433, His, Phe, or Tyr for the amino acid of position 434, and/or Arg, Asn, His, Lys, Met, or Thr for the amino acid of position 436 according to EU numbering. Another non-limiting embodiment of this modification may include His or Met for the amino acid of position 428, and/or His or Met for the amino acid of position 434.

When the Fc region of human IgG1 is comprised as the Fc region, a non-limiting embodiment of the modification that results in the effect of enhancing FcRn binding under an acidic pH range condition as compared to the binding activity of the starting Fc region of human IgG1 may be modifications including Arg for the amino acid of position 385, Thr for the amino acid of position 386, Arg for the amino acid of position 387, and/or Pro for the amino acid of position 389 according to EU numbering. Another non-limiting embodiment of this modification may include Asp for the amino acid of position 385, Pro for the amino acid of position 386, and/or Ser for the amino acid of position 389.

Furthermore, when the Fc region of human IgG1 is comprised as the Fc region, a non-limiting embodiment of the modification that results in the effect of enhancing FcRn binding under an acidic pH range condition as compared to the binding activity of the starting Fc region of human IgG1 include at least one or more amino acid modifications selected from the group consisting of:
Gln or Glu for the amino acid of position 250; and
Leu or Phe for the amino acid of position 428 according to EU numbering. The number of amino acids to be modified is not particularly limited; and amino acid may be modified at only one site or amino acids may be modified at two sites.

When the Fc region of human IgG1 is comprised as the Fc region, a non-limiting embodiment of the modification that results in the effect of enhancing FcRn binding under an acidic pH range condition as compared to the binding activity of the starting Fc region of human IgG1 may be modifications including Gln for the amino acid of position 250, and/or Leu or Phe for the amino acid of position 428 according to EU numbering. Another non-limiting embodiment of this modification may include Glu for the amino acid of position 250, and/or Leu or Phe for the amino acid of position 428.

When the Fc region of human IgG1 is comprised as the Fc region, a non-limiting embodiment of the modification that results in the effect of enhancing FcRn binding under an acidic pH range condition as compared to the binding activity of the starting Fc region of human IgG1 include at least two or more amino acid modifications selected from the group consisting of:
Asp or Glu for the amino acid of position 251;
Tyr for the amino acid of position 252;
Gln for the amino acid of position 307;
Pro for the amino acid of position 308;
Val for the amino acid of position 378;
Ala for the amino acid of position 380;
Leu for the amino acid of position 428;
Ala or Lys for the amino acid of position 430;
Ala, His, Ser, or Tyr for the amino acid of position 434; and
Ile for the amino acid of position 436, as indicated by EU numbering. The number of amino acids to be modified is not particularly limited; and amino acid may be modified at only two sites or amino acids may be modified at three or more sites.

When the Fc region of human IgG1 is comprised as the Fc region, a non-limiting embodiment of the modification that results in the effect of enhancing FcRn binding under an acidic pH range condition as compared to the binding activity of the starting Fc region of human IgG1 may be modifications including Gln for the amino acid of position 307, and Ala or Ser for the amino acid of position 434 according to EU numbering. Another non-limiting embodiment of this modification may include Pro for the amino acid of position 308, and Ala for the amino acid of position 434. Furthermore, another non-limiting embodiment of this modification may include Tyr for the amino acid of position 252, and Ala for the amino acid of position 434. A different non-limiting embodiment of this modification may include Val for the amino acid of position 378, and Ala for the amino acid of position 434. Another different non-limiting embodiment of this modification may include Leu for the amino acid of position 428, and Ala for the amino acid of position 434. Another different non-limiting embodiment of this modification may include Ala for the amino acid of position 434, and Ile for the amino acid of position 436. Furthermore, another non-limiting embodiment of this modification may include Pro for the amino acid of position 308, and Tyr for the amino acid of position 434. In addition, another non-limiting embodiment of this modification may include Gln for the amino acid of position 307, and Ile for the amino acid of position 436.

When the Fc region of human IgG1 is comprised as the Fc region, a non-limiting embodiment of the modification that results in the effect of enhancing FcRn binding under an acidic pH range condition as compared to the binding activity of the starting Fc region of human IgG1 may be modifications including any one of Gln for the amino acid of position 307, Ala for the amino acid of position 380, and Ser for the amino acid of position 434 according to EU numbering. Another non-limiting embodiment of this modification may include Gln for the amino acid of position 307, Ala for the amino acid of position 380, and Ala for the amino acid of position 434. Furthermore, another non-limiting embodiment of this modification may include Tyr for the amino acid of position 252, Pro for the amino acid of position 308, and Tyr for the amino acid of position 434. A different non-limiting embodiment of this modification may include Asp for the amino acid of position 251, Gln for the amino acid of position 307, and His for the amino acid of position 434.

When the Fc region of human IgG1 is comprised as the Fc region, a non-limiting embodiment of the modification that results in the effect of enhancing FcRn binding under an acidic pH range condition as compared to the binding activity of the starting Fc region of human IgG1 include modification of at least two or more amino acids selected from the group consisting of:
Leu for the amino acid of position 238;
Leu for the amino acid of position 244;
Arg for the amino acid of position 245;
Pro for the amino acid of position 249;
Tyr for the amino acid of position 252;
Pro for the amino acid of position 256;
Ala, Ile, Met, Asn, Ser, or Val for the amino acid of position 257;
Asp for the amino acid of position 258;
Ser for the amino acid of position 260;
Leu for the amino acid of position 262;
Lys for the amino acid of position 270;
Leu or Arg for the amino acid of position 272;
Ala, Asp, Gly, His, Met, Asn, Gln, Arg, Ser, Thr, Trp, or Tyr for the amino acid of position 279;
Ala, Asp, Phe, Gly, His, Ile, Lys, Leu, Asn, Pro, Gln, Arg, Ser, Thr, Trp, or Tyr for the amino acid of position 283;
Asn for the amino acid of position 285;
Phe for the amino acid of position 286;
Asn or Pro for the amino acid of position 288;
Val for the amino acid of position 293;
Ala, Glu, or Met for the amino acid of position 307;
Ala, Ile, Lys, Leu, Met, Val, or Trp for the amino acid of position 311;
Pro for the amino acid of position 312;
Lys for the amino acid of position 316;
Pro for the amino acid of position 317;
Asn or Thr for the amino acid of position 318;
Phe, His, Lys, Leu, Met, Arg, Ser, or Trp for the amino acid of position 332;
Asn, Thr, or Trp for the amino acid of position 339;
Pro for the amino acid of position 341;
Glu, His, Lys, Gln, Arg, Thr, or Tyr for the amino acid of position 343;
Arg for the amino acid of position 375;
Gly, Ile, Met, Pro, Thr, or Val for the amino acid of position 376;
Lys for the amino acid of position 377;
Asp or Asn for the amino acid of position 378;
Asn, Ser, or Thr for the amino acid of position 380;
Phe, His, Ile, Lys, Leu, Met, Asn, Gln, Arg, Ser, Thr, Val, Trp, or Tyr for the amino acid of position 382;
Asn for the amino acid of position 423;
Asn for the amino acid of position 427;
Ala, Phe, Gly, His, Ile, Lys, Leu, Met, Asn, Gln, Arg, Ser, Thr, Val, or Tyr for the amino acid of position 430;
His or Asn for the amino acid of position 431;
Phe, Gly, His, Trp, or Tyr for the amino acid of position 434;
Ile, Leu, or Thr for the amino acid of position 436;
Lys, Leu, Thr, or Trp for the amino acid of position 438;
Lys for the amino acid of position 440; and
Lys for the amino acid of position 442 according to EU numbering. The number of amino acids to be modified is not particularly limited and amino acid at only two sites may be modified and amino acids at three or more sites may be modified.

When the Fc region of human IgG1 is comprised as the Fc region, a non-limiting embodiment of the modification that results in the effect of enhancing FcRn binding under an acidic pH range condition as compared to the binding activity of the starting Fc region of human IgG1 may be modifications including Ile for the amino acid of position 257, and Ile for the amino acid of position 311 according to EU numbering. Another non-limiting embodiment of this modification may include Ile for the amino acid of position 257, and His for the amino acid of position 434. Another non-limiting embodiment of this modification may include Val for the amino acid of position 376, and His for the amino acid of position 434.

Furthermore, in another non-limiting embodiment, one may screen for antigen-binding molecules comprising an Fc region with the characteristic of having a human FcRn-binding activity in the neutral pH range instead of the above-described characteristic of having a human FcRn-binding activity in the acidic pH range. In a preferred embodiment, one may screen for antigen-binding molecules comprising an Fc region whose human FcRn-binding activity in the neutral pH range is 40 μM (KD) or stronger. In a more preferred embodiment, one may screen for antigen-binding molecules comprising an Fc region whose human FcRn-binding activity in the neutral pH range is 15 μM (KD) or stronger.

Furthermore, in another non-limiting embodiment, one may screen for antigen-binding molecules comprising an Fc region with the characteristic of having a human FcRn-binding activity in the neutral pH range in addition to the above-described characteristic of having a human FcRn-binding activity in the acidic pH range. In a preferred embodiment, one may screen for antigen-binding molecules comprising an Fc region whose human FcRn-binding activity in the neutral pH range is 40 μM (KD) or stronger. In a more preferred embodiment, one may screen for antigen-binding molecules comprising an Fc region whose human FcRn-binding activity in the neutral pH range is 15 μM (KD) or stronger.

In the present invention, preferred Fc regions have a human FcRn-binding activity in the acidic pH range and/or neutral pH range. When an Fc region originally has a human FcRn-binding activity in the acidic pH range and/or neutral pH range, it can be used as it is. When an Fc region has a weak or no human FcRn-binding activity in the acidic pH range and/or neutral pH range, antigen-binding molecules comprising an Fc region having a desired human FcRn-binding activity can be obtained by modifying amino acids of the Fc region comprised in the antigen-binding molecules. Fc regions having a desired human FcRn-binding activity in the acidic pH range and/or neutral pH range can also be suitably obtained by modifying amino acids of a human Fc region. Alternatively, antigen-binding molecules comprising an Fc region having a desired human FcRn-binding activity can be obtained by modifying amino acids of an Fc region that originally has a human FcRn-binding activity in the acidic pH range and/or neutral pH range. Amino acid modifications of a human Fc region that result in such a desired binding activity can be found by comparing the human FcRn-binding activity in the acidic pH range and/or neutral pH range before and after amino acid modification. Those skilled in the art can appropriately modify amino acids using known methods.

Furthermore, an altered Fc region modified from a starting Fc region which has been already modified can also be used preferably as an altered Fc region of the present invention. The "starting Fc region" can refer to the polypeptide itself, a composition comprising the starting Fc region, or an amino acid sequence encoding the starting Fc region. Starting Fc regions can comprise a known IgG antibody Fc region produced via recombination described briefly in section "Antibodies". The origin of starting Fc regions is not limited, and they may be obtained from human or any nonhuman organisms. Such organisms preferably include mice, rats, guinea pigs, hamsters, gerbils, cats, rabbits, dogs, goats, sheep, bovines, horses, camels and organisms selected from nonhuman primates. In another embodiment, starting Fc regions can also be obtained from cynomolgus monkeys, marmosets, rhesus monkeys, chimpanzees, or humans. Starting Fc regions can be obtained preferably from human IgG1; however, they are not limited to any particular IgG subclass. This means that an Fc region represented by human IgG1 (SEQ ID NO: 13), IgG2 (SEQ ID NO: 14), IgG3 (SEQ ID NO: 15), or IgG4 (SEQ ID NO: 16) can be used appropriately as a starting Fc region, and herein also means that an Fc region of an arbitrary IgG class or subclass derived from any organisms described above can be preferably used as a starting Fc region. Examples of naturally-occurring IgG variants or modified forms are described in published documents (Curr. Opin. Biotechnol. (2009) 20 (6): 685-91; Curr. Opin. Immunol. (2008) 20 (4), 460-470; Protein Eng. Des. Sel. (2010) 23 (4): 195-202; International Publication Nos. WO 2009/086320, WO 2008/092117, WO 2007/041635, and WO 2006/105338); however, they are not limited to the examples.

Examples of alterations include those with one or more mutations, for example, mutations by substitution of different amino acid residues for amino acids of starting Fc regions, by insertion of one or more amino acid residues into starting Fc regions, or by deletion of one or more amino acids from starting Fc region. Preferably, the amino acid sequences of altered Fc regions comprise at least a part of the amino acid sequence of a non-native Fc region. Such variants necessarily have sequence identity or similarity less than 100% to their starting Fc region. In a preferred embodiment, the variants have amino acid sequence identity or similarity about 75% to less than 100%, more preferably about 80% to less than 100%, even more preferably about 85% to less than 100%, still more preferably about 90% to less than 100%, and yet more preferably about 95% to less than 100% to the amino acid sequence of their starting Fc region. In a non-limiting embodiment of the present invention, at least one amino acid is different between a modified Fc region of the present invention and its starting Fc region. Amino acid difference between a modified Fc region of the present invention and its starting Fc region can also be preferably specified based on amino acid differences at above-described particular amino acid positions according to EU numbering system.

Known methods such as site-directed mutagenesis (Kunkel et al. (Proc. Natl. Acad. Sci. USA (1985) 82, 488-492)) and Overlap extension PCR can be appropriately employed to modify the amino acids of Fc regions. Furthermore, various known methods can also be used as an amino acid modification method for substituting amino acids by those other than natural amino acids (Annu. Rev. Biophys. Biomol. Struct. (2006) 35, 225-249; Proc. Natl. Acad. Sci. U.S.A. (2003) 100 (11), 6353-6357). For example, a cell-free translation system (Clover Direct (Protein Express)) containing tRNAs in which amber suppressor tRNA, which is complementary to UAG codon (amber codon) that is a stop codon, is linked with an unnatural amino acid may be suitably used.

Fc regions comprised in the antigen-binding molecules of the present invention that have a human FcRn-binding activity in the acidic pH range can be obtained by any method. Specifically, one can screen for antigen-binding molecules comprising an Fc region of which human FcRn-binding activity in the acidic pH range is 20 µM (KD) or stronger; in a more favorable embodiment, an Fc region of which human FcRn-binding activity in the acidic pH range is 2.0 µM (KD) or stronger; and in an even more favorable embodiment, an Fc region of which human FcRn-binding activity in the acidic pH range is 0.5 µM (KD) or stronger as a result of modifying amino acids of an IgG-type human immunoglobulin used as a starting Fc region. Preferred Fc regions of IgG-type immunoglobulins for modification include, for example, those of human IgGs such as IgG1, IgG2, IgG3, and IgG4 shown in SEQ ID NOs: 13, 14, 15, and 15, respectively, and variants thereof.

When an antigen-binding molecule comprises the Fc region of human IgG1 as the Fc region, suitable examples of amino acids that may be modified to achieve the above-mentioned desired effects on FcRn binding under an acidic pH range condition by modifying amino acids of an IgG-type human immunoglobulin as a starting Fc region, include amino acids of positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439, and/or 447 according to EU numbering as described in WO 2000/042072. Similarly, favorable examples of amino acids that allow such modification include amino acids of positions 251, 252, 254, 255, 256, 308, 309, 311, 312, 385, 386, 387, 389, 428, 433, 434, and/or 436 according to EU numbering as described in WO 2002/060919. Furthermore, amino acids that allow such modification include, for example, amino acids of positions 250, 314, and 428 according to EU numbering as described in WO2004/092219. Furthermore, favorable examples of amino acids that allow such modification include amino acids of positions 251, 252, 307, 308, 378, 428, 430, 434, and/or 436 according to EU numbering as described in WO 2010/045193. Modification of these amino acids enhances FcRn binding of the Fc region of an IgG-type immunoglobulin under an acidic pH range condition.

Fc regions having human FcRn-binding activity in the neutral pH range can also be obtained by modifying amino acids of human immunoglobulin of IgG type used as the starting Fc region. The Fc regions of IgG type immunoglobulins adequate for modification include, for example, those of human IgGs such as IgG1, IgG2, IgG3, and IgG4 respectively represented by SEQ ID NOs: 13, 14, 15, and 16, and modified forms thereof. Amino acids of any positions may be modified into other amino acids, as long as the Fc regions have the human FcRn-binding activity in the neutral pH range or can increase the human FcRn-binding activity in the neutral range. When the antigen-binding molecule contains the Fc region of human IgG1 as the human Fc region, it is preferable that the resulting Fc region contains a modification that results in the effect of enhancing the human FcRn binding in the neutral pH range as compared to the binding activity of the starting Fc region of human IgG1. Amino acids that allow such modification include, for example, one ore more amino acids selected from the group of positions 221 to 225, 227, 228, 230, 232, 233 to 241, 243 to 252, 254 to 260, 262 to 272, 274, 276, 278 to 289, 291 to 312, 315 to 320, 324, 325, 327 to 339, 341, 343, 345, 360, 362, 370, 375 to 378, 380, 382, 385 to 387, 389, 396, 414, 416, 423, 424, 426 to 438, 440, and 442 according to EU numbering. Modification of these amino acids augments the human FcRn binding of the Fc region of IgG-type immunoglobulin in the neutral pH range.

From those described above, modifications that augment the human FcRn binding in the neutral pH range are appropriately selected for use in the present invention. Particularly preferred amino acids of the modified Fc regions include, for example, amino acids of positions 237, 248, 250, 252, 254, 255, 256, 257, 258, 265, 286, 289, 297, 298, 303, 305, 307, 308, 309, 311, 312, 314, 315, 317, 332, 334, 360, 376, 380, 382, 384, 385, 386, 387, 389, 424, 428, 433, 434, and 436 according to the EU numbering system. The human FcRn-binding activity in the neutral pH range of the Fc region contained in an antigen-binding molecule can be increased by substituting at least one amino acid selected from the above amino acids into a different amino acid.

Particularly preferred modifications include, for example:
Met for the amino acid of position 237;
Ile for the amino acid of position 248;
Ala, Phe, Ile, Met, Gln, Ser, Val, Trp, or Tyr for the amino acid of position 250;
Phe, Trp, or Tyr for the amino acid of position 252;
Thr for the amino acid of position 254;
Glu for the amino acid of position 255;
Asp, Asn, Glu, or Gln for the amino acid of position 256;
Ala, Gly, Ile, Leu, Met, Asn, Ser, Thr, or Val for the amino acid of position 257;
His for the amino acid of position 258:
Ala for the amino acid of position 265;
Ala or Glu for the amino acid of position 286;
His for the amino acid of position 289;
Ala for the amino acid of position 297;
Ala for the amino acid of position 303;
Ala for the amino acid of position 305;
Ala, Asp, Phe, Gly, His, Ile, Lys, Leu, Met, Asn, Pro, Gln, Arg, Ser, Val, Trp, or Tyr for the amino acid of position 307;
Ala, Phe, Ile, Leu, Met, Pro, Gln, or Thr for the amino acid of position 308;
Ala, Asp, Glu, Pro, or Arg for the amino acid of position 309;
Ala, His, or Ile for the amino acid of position 311;
Ala or His for the amino acid of position 312;
Lys or Arg for the amino acid of position 314;
Ala, Asp, or His for the amino acid of position 315;
Ala for the amino acid of position 317;
Val for the amino acid of position 332;
Leu for the amino acid of position 334;
His for the amino acid of position 360;
Ala for the amino acid of position 376;
Ala for the amino acid of position 380;
Ala for the amino acid of position 382;
Ala for the amino acid of position 384;

Asp or His for the amino acid of position 385;
Pro for the amino acid of position 386;
Glu for the amino acid of position 387;
Ala or Ser for the amino acid of position 389;
Ala for the amino acid of position 424;
Ala, Asp, Phe, Gly, His, Ile, Lys, Leu, Asn, Pro, Gln, Ser, Thr, Val, Trp, or Tyr for the amino acid of position 428;
Lys for the amino acid of position 433;
Ala, Phe, His, Ser, Trp, or Tyr for the amino acid of position 434; and
His, Ile, Leu, Phe, Thr, or Val for the amino acid of position 436 of the Fc region according to EU numbering. Meanwhile, the number of amino acids to be modified is not particularly limited and amino acid at only one site may be modified and amino acids at two or more sites may be modified. Combinations of these amino acid modifications include, for example, the amino acid modifications shown in Tables 5-1 to 5-33.

TABLE 5-1

| Variant | KD (M) | Site of amino acid modification |
|---|---|---|
| F1 | 8.10E−07 | N434W |
| F2 | 3.20E−06 | M252Y/S254T/T256E |
| F3 | 2.50E−06 | N434Y |
| F4 | 5.80E−06 | N434S |
| F5 | 6.80E−06 | N434A |
| F7 | 5.60E−06 | M252Y |
| F8 | 4.20E−06 | M252W |
| F9 | 1.40E−07 | M252Y/S254T/T256E/N434Y |
| F10 | 6.90E−08 | M252Y/S254T/T256E/K434W |
| F11 | 3.10E−07 | M252Y/N434Y |
| F12 | 1.70E−07 | M252Y/N434W |
| F13 | 3.20E−07 | M252W/N434Y |
| F14 | 1.80E−07 | M252W/N434W |
| F19 | 4.60E−07 | P257L/N434Y |
| F20 | 4.60E−07 | V308F/N434Y |
| F21 | 3.00E−08 | M252Y/V308P/N434Y |
| F22 | 2.00E−06 | M428L/N434S |
| F25 | 9.20E−09 | M252Y/S254T/T256E/V308P/N434W |
| F26 | 1.00E−06 | I332V |
| F27 | 7.40E−07 | G237M |
| F29 | 1.40E−06 | I332V/N434Y |
| F31 | 2.80E−06 | G237M/V308F |
| F32 | 8.00E−07 | S254T/N434W |
| F33 | 2.30E−06 | S254T/N434Y |
| F34 | 2.80E−07 | T256E/N434W |
| F35 | 8.40E−07 | T256E/N434Y |
| F36 | 3.60E−07 | S254T/T256E/N434W |
| F37 | 1.10E−06 | S254T/T256E/N434Y |
| F38 | 1.00E−07 | M252Y/S254T/N434W |
| F39 | 3.00E−07 | M252Y/S254T/N434Y |
| F40 | 8.20E−08 | M252Y/T256E/N434W |
| F41 | 1.50E−07 | M252Y/T256E/N434Y |

Table 5-2 is a continuation of Table 5-1.

TABLE 5-2

| F42 | 1.00E−06 | M252Y/S254T/T256E/N434A |
|---|---|---|
| F43 | 1.70E−06 | M252Y/N434A |
| F44 | 1.10E−06 | M252W/N434A |
| F47 | 2.40E−07 | M252Y/T256Q/N434W |
| F48 | 3.20E−07 | M252Y/T256Q/N434Y |
| F49 | 5.10E−07 | M252F/T256D/N434W |
| F50 | 1.20E−06 | M252F/T256D/N434Y |
| F51 | 8.10E−06 | N434F/Y436H |
| F52 | 3.10E−06 | H433K/N434F/Y436H |
| F53 | 1.00E−06 | I332V/N434W |
| F54 | 8.40E−08 | V308P/N434W |
| F56 | 9.40E−07 | I332V/M428L/N434Y |
| F57 | 1.10E−05 | G385D/Q386P/N389S |
| F58 | 7.70E−07 | G385D/Q386P/N389S/N434W |
| F59 | 2.40E−06 | G385D/Q386P/N389S/N434Y |
| F60 | 1.10E−05 | G385H |

TABLE 5-2-continued

| | | |
|---|---|---|
| F61 | 9.70E−07 | G385H/N434W |
| F62 | 1.90E−06 | G385H/N434Y |
| F63 | 2.50E−06 | N434F |
| F64 | 5.30E−06 | N434H |
| F65 | 2.90E−07 | M252Y/S254T/T256E/N434F |
| F66 | 4.30E−07 | M252Y/S254T/T256E/N434H |
| F67 | 6.30E−07 | M252Y/N434F |
| F68 | 9.30E−07 | M252Y/N434H |
| F69 | 5.10E−07 | M428L/N434W |
| F70 | 1.50E−06 | M428L/N434Y |
| F71 | 8.30E−08 | M252Y/S254T/T256E/M428L/N434W |
| F72 | 2.00E−07 | M252Y/S254T/T256E/M428L/N434Y |
| F73 | 1.70E−07 | M252Y/M428L/N434W |
| F74 | 4.60E−07 | M252Y/M428L/N434Y |
| F75 | 1.40E−06 | M252Y/M428L/N434A |
| F76 | 1.00E−06 | M252Y/S254T/T256E/M428L/N434A |
| F77 | 9.90E−07 | T256E/M428L/N434Y |
| F78 | 7.80E−07 | S254T/M428L/N434W |

Table 5-3 is a continuation of Table 5-2.

TABLE 5-3

| | | |
|---|---|---|
| F79 | 5.90E−06 | S254T/256E/N434A |
| F80 | 2.70E−06 | M252Y/T256Q/N434A |
| F81 | 1.60E−06 | M252Y/T256E/N434A |
| F82 | 1.10E−06 | T256Q/N434W |
| F83 | 2.60E−06 | T256Q/N434Y |
| F84 | 2.80E−07 | M252W/T256Q/N434W |
| F85 | 5.50E−07 | M252W/T256Q/N434Y |
| F86 | 1.50E−07 | S254T/T256Q/N434W |
| F87 | 4.30E−06 | S254T/T256Q/N434Y |
| F88 | 1.90E−07 | M252Y/S254T/T256Q/N434W |
| F89 | 3.60E−07 | M252Y/S254T/T256Q/N434Y |
| F90 | 1.90E−08 | M252Y/T256E/V308P/N434W |
| F91 | 4.80E−08 | M252Y/V308P/M428L/N434Y |
| F92 | 1.10E−08 | M252Y/S254T/T256E/V308P/M428L/N434W |
| F93 | 7.40E−07 | M252W/M428L/N434W |
| F94 | 3.70E−07 | P257L/M428L/N434Y |
| F95 | 2.60E−07 | M252Y/S254T/T256E/M428L/N434F |
| F99 | 6.20E−07 | M252Y/T256E/N434H |
| F101 | 1.10E−07 | M252W/T256Q/P257L/N434Y |
| F103 | 4.40E−08 | P238A/M252Y/V308P/N434Y |
| F104 | 3.70E−08 | M252Y/D265A/V308P/N434Y |
| F105 | 7.50E−08 | M252Y/T307A/V308P/N434Y |
| F106 | 3.70E−08 | M252Y/V303A/V308P/N434Y |
| F107 | 3.40E−08 | M252Y/V308P/D376A/N434Y |
| F108 | 4.10E−08 | M252Y/V305A/V308P/N434Y |
| F109 | 3.20E−08 | M252Y/V308P/Q311A/N434Y |
| F111 | 3.20E−08 | M252Y/V308P/K317A/N434Y |
| F112 | 6.40E−08 | M252Y/V308P/E380A/N434Y |
| F113 | 3.20E−08 | M252Y/V308P/E382A/N434Y |
| F114 | 3.80E−08 | M252Y/V308P/S424A/N434Y |
| F115 | 6.60E−06 | T307A/N434A |
| F116 | 8.70E−06 | E380A/N434A |
| F118 | 1.40E−05 | M428L |
| F119 | 5.40E−06 | T250Q/M428L |

Table 5-4 is a continuation of Table 5-3.

TABLE 5-4

| | | |
|---|---|---|
| F120 | 6.30E−08 | P257L/V308P/M428L/N434Y |
| F121 | 1.50E−08 | M252Y/T256E/V308P/M428L/N434W |
| F122 | 1.20E−07 | M252Y/T256E/M428L/N434W |
| F123 | 3.00E−08 | M252Y/T256E/V308P/N434Y |
| F124 | 2.90E−07 | M252Y/T256E/M428L/N434Y |
| F125 | 2.40E−08 | M252Y/S254T/T256E/V308P/M428L/N434Y |
| F128 | 1.70E−07 | P257L/M428L/N434W |
| F129 | 2.20E−07 | P257A/M428L/N434Y |
| P131 | 3.00E−06 | P257G/M428L/N434Y |
| F132 | 2.10E−07 | P257I/M428L/N434Y |
| F133 | 4.10E−08 | P257M/M428L/N434Y |
| F134 | 2.70E−07 | P257N/M428L/N434Y |
| F135 | 7.50E−07 | P257S/M428L/N434Y |
| F136 | 3.80E−07 | F257T/M428L/N434Y |
| F137 | 4.60E−07 | P257V/M428L/N434Y |

TABLE 5-4-continued

| | | |
|---|---|---|
| F139 | 1.50E−08 | M252W/V308P/N434W |
| F140 | 3.60E−08 | S239K/M252Y/V308P/N434Y |
| F141 | 3.50E−08 | M252Y/S298G/V308P/N434Y |
| F142 | 3.70E−08 | M252Y/D270F/V308P/N434Y |
| F143 | 2.00E−07 | M252Y/V308A/N434Y |
| F145 | 5.30E−08 | M252Y/V308F/N434Y |
| F147 | 2.40E−07 | M252Y/V308I/N434Y |
| F149 | 1.90E−07 | M252Y/V308L/N434Y |
| F150 | 2.00E−07 | M252Y/V308M/N434Y |
| F152 | 2.70E−07 | M252Y/V308Q/N434Y |
| F154 | 1.80E−07 | M252Y/V308T/N434Y |
| F157 | 1.50E−07 | P257A/V308P/M428L/N434Y |
| F158 | 5.90E−08 | P257T/V308P/M428L/N434Y |
| F159 | 4.40E−08 | P257V/V308P/M428L/N434Y |
| F160 | 8.50E−07 | M252W/M428I/N434Y |
| F162 | 1.60E−07 | M252W/M428Y/N434Y |
| F163 | 4.20E−07 | M252W/M428F/N434Y |
| F164 | 3.70E−07 | P238A/M252W/N434Y |
| F165 | 2.90E−07 | M252W/D265A/N434Y |

Table 5-5 is a continuation of Table 5-4.

TABLE 5-5

| | | |
|---|---|---|
| F166 | 1.50E−07 | M252W/T307Q/N434Y |
| F167 | 2.90E−07 | M252W/V303A/N434Y |
| F168 | 3.20E−07 | M252W/D376A/N434Y |
| F169 | 2.90E−07 | M252W/V305A/N434Y |
| F170 | 1.70E−07 | M252W/Q311A/N434Y |
| F171 | 1.90E−07 | M352W/D312A/N434Y |
| F172 | 2.20E−07 | M252W/K317A/N434Y |
| F173 | 7.70E−07 | M252W/E380A/N434Y |
| F174 | 3.40E−07 | M252W/E382A/N434Y |
| F175 | 2.70E−07 | M252W/S424A/N434Y |
| F176 | 2.90E−07 | S239K/M252W/N434Y |
| F177 | 2.80E−07 | M252W/S298G/N434Y |
| F178 | 2.70E−07 | M252W/D270F/N434Y |
| F179 | 3.10E−07 | M252W/N325G/N434Y |
| F182 | 6.60E−08 | P257A/M428L/N434W |
| F183 | 2.20E−07 | P257T/M428L/N434W |
| F184 | 2.70E−07 | P257V/M428L/N434W |
| F185 | 2.60E−07 | M252W/I332V/N434Y |
| F188 | 3.00E−06 | P257I/Q311I |
| F189 | 1.90E−07 | M252Y/T307A/N434Y |
| F190 | 1.10E−07 | M252Y/T307Q/N434Y |
| F191 | 1.60E−07 | P257L/T307A/M428L/N434Y |
| F192 | 1.10E−07 | P257A/T307A/M428L/N434Y |
| F193 | 8.50E−08 | P257T/T307A/M428L/N434Y |
| F194 | 1.20E−07 | P257V/T307A/M428L/N434Y |
| F195 | 5.60E−08 | P257L/T307Q/M428L/N434Y |
| F196 | 3.50E−08 | P257A/T307Q/M428L/N434Y |
| F197 | 3.30E−08 | P257T/T307Q/M428L/N434Y |
| F198 | 4.80E−08 | P257V/T307Q/M428L/N434Y |
| F201 | 2.10E−07 | M252Y/T307D/N434Y |
| F203 | 2.40E−07 | M252Y/T307F/N434Y |
| F204 | 2.10E−07 | M252Y/T307G/N434Y |
| F205 | 2.00E−07 | M252Y/T307H/N434Y |
| F206 | 2.30E−07 | M253Y/T307I/N434Y |

Table 5-6 is a continuation of Table 5-5.

TABLE 5-6

| | | |
|---|---|---|
| F207 | 9.40E−07 | M252Y/T307K/N434Y |
| F208 | 3.90E−07 | M252Y/T307L/N434Y |
| F209 | 1.30E−07 | M252Y/T307M/N434Y |
| F210 | 2.90E−07 | M252Y/T307N/N434Y |
| F211 | 2.40E−07 | M252Y/T307P/N434Y |
| F212 | 6.80E−07 | M252Y/T307R/N434Y |
| F213 | 2.30E−07 | M252Y/T307S/N434Y |
| F214 | 1.70E−07 | M252Y/T307V/N434Y |
| F215 | 9.60E−08 | M252Y/T307W/N434Y |
| F216 | 2.30E−07 | M252Y/T307Y/N434Y |
| F217 | 2.30E−07 | M252Y/K334L/N434Y |
| F218 | 2.60E−07 | M252Y/G385H/N434Y |
| F219 | 2.50E−07 | M252Y/T289H/N434Y |
| F220 | 2.50E−07 | M252Y/Q311H/N434Y |

TABLE 5-6-continued

| | | |
|---|---|---|
| F221 | 3.10E−07 | M252Y/D312H/N434Y |
| F222 | 3.40E−07 | M252Y/M315H/N434Y |
| F223 | 2.70E−07 | M252Y/K360H/N434Y |
| F225 | 1.50E−06 | M252Y/L314R/N434Y |
| F226 | 5.40E−07 | M252Y/L314K/N434Y |
| F227 | 1.20E−07 | M252Y/N286E/N434Y |
| F228 | 2.30E−07 | M252Y/L309E/N434Y |
| F229 | 5.10E−07 | M252Y/R255E/N434Y |
| F230 | 2.50E−07 | M252Y/P387E/N434Y |
| F236 | 8.90E−07 | K248I/M428L/N434Y |
| F237 | 2.30E−07 | M252Y/M428A/N434Y |
| F238 | 7.40E−07 | M252Y/M428D/N434Y |
| F240 | 7.20E−07 | M252Y/M428F/N434Y |
| F241 | 1.50E−06 | M252Y/M428G/N434Y |
| F242 | 8.50E−07 | M252Y/M428H/N434Y |
| F243 | 1.80E−07 | M252Y/M428I/N434Y |
| F244 | 1.30E−06 | M252Y/M428K/N434Y |
| F245 | 4.70E−07 | M252Y/M428N/N434Y |
| F246 | 1.10E−06 | M252Y/M428P/N434Y |
| F247 | 4.40E−07 | M252Y/M428Q/N434Y |

Table 5-7 is a continuation of Table 5-6.

TABLE 5-7

| | | |
|---|---|---|
| F249 | 6.40E−07 | M252Y/M428S/N434Y |
| F250 | 2.90E−07 | M252Y/M428T/N434Y |
| F251 | 1.90E−07 | M252Y/M428V/N434Y |
| F252 | 1.00E−06 | M252Y/M428W/N434Y |
| F253 | 7.10E−07 | M252Y/M428Y/N434Y |
| F254 | 7.50E−08 | M252W/T307Q/M428Y/N434Y |
| F255 | 1.10E−07 | M252W/Q311A/M428Y/N434Y |
| F256 | 5.40E−08 | M252W/T307Q/Q311A/M428Y/N434Y |
| F257 | 5.00E−07 | M252Y/T307A/M428Y/N434Y |
| F258 | 3.20E−07 | M252Y/T307Q/M428Y/N434Y |
| F259 | 2.80E−07 | M252Y/D270F/N434Y |
| F260 | 1.30E−07 | M252Y/T307A/Q311A/N434Y |
| F261 | 8.40E−08 | M252Y/T307Q/Q311A/N434Y |
| F262 | 1.90E−07 | M252Y/T307A/Q311H/N434Y |
| F263 | 1.10E−07 | M252Y/T307Q/Q311H/N434Y |
| F264 | 2.80E−07 | M252Y/E382A/N434Y |
| F265 | 6.80E−07 | M252Y/E382A/M428Y/N434Y |
| F266 | 4.70E−07 | M252Y/T307A/E382A/M428Y/N434Y |
| F267 | 3.20E−07 | M252Y/T307Q/E382A/M428Y/N434Y |
| F268 | 6.30E−07 | P238A/M252Y/M428F/N434Y |
| F269 | 5.20E−07 | M252Y/V305A/M428F/N434Y |
| F270 | 6.60E−07 | M252Y/N325G/M428/N434Y |
| F271 | 6.90E−07 | M252Y/D376A/M428F/N434Y |
| F272 | 6.80E−07 | M252Y/E380A/M428F/N434Y |
| F273 | 6.50E−07 | M252Y/E382A/M428F/N434Y |
| F274 | 7.60E−07 | M252Y/E380A/E382A/M428F/N434Y |
| F275 | 4.20E−08 | S239K/M252Y/V308P/E382A/N434Y |
| F276 | 4.10E−08 | M252Y/D270F/V308P/E382A/N434Y |
| F277 | 1.30E−07 | S239K/M252Y/V308P/M428Y/N434Y |
| F278 | 3.00E−08 | M252Y/T307Q/V308P/E382A/N434Y |
| F279 | 6.10E−08 | M252Y/V308P/Q311H/E382A/N434Y |
| F280 | 4.10E−08 | S239K/M252Y/D270F/V308P/N434Y |
| F281 | 9.20E−08 | M252Y/V308P/E382A/M428F/N434Y |
| F282 | 2.90E−08 | M252Y/V308P/E382A/M428L/N434Y |

Table 5-8 is a continuation of Table 5-7.

TABLE 5-8

| | | |
|---|---|---|
| F283 | 1.00E−07 | M252Y/V308P/E382A/M428Y/N434Y |
| F284 | 1.00E−07 | M252Y/V308P/M428Y/N434Y |
| F285 | 9.90E−08 | M252Y/V308P/M428F/N434Y |
| F286 | 1.20E−07 | S239K/M252Y/V308P/E382A/M428Y/N434Y |
| F287 | 1.00E−07 | M252Y/V308P/E380A/E382A/M428F/N434Y |
| F288 | 1.90E−07 | M252Y/T256E/E382A/N434Y |
| F289 | 4.80E−07 | M252Y/T256E/M428Y/N434Y |
| F290 | 4.60E−07 | M252Y/T256E/E382A/M428Y/N434Y |
| F292 | 2.30E−08 | S239K/M252Y/V308P/E382A/M428I/N434Y |
| F293 | 5.30E−08 | M252Y/V308P/E380A/E382A/M428I/N434Y |
| F294 | 1.10E−07 | S239K/M252Y/V308P/M428F/N434Y |
| F295 | 6.80E−07 | S239K/M252Y/E380A/E382A/M428F/N434Y |
| F296 | 4.90E−07 | M252Y/Q311A/M428Y/N434Y |

TABLE 5-8-continued

| | | |
|---|---|---|
| F297 | 5.10E−07 | M252Y/D312A/M428Y/N434Y |
| F298 | 4.80E−07 | M252Y/Q311A/D312A/M428Y/N434Y |
| F299 | 9.40E−08 | S239K/M252Y/V308P/Q311A/M428Y/N434Y |
| F300 | 8.30E−08 | S239K/M252Y/V308P/D312A/M428Y/N434Y |
| F301 | 7.20E−08 | S239K/M252Y/V308P/Q311A/D312A/M428Y/N434Y |
| F302 | 1.90E−07 | M252Y/T256E/T307P/N434Y |
| F303 | 6.70E−07 | M252Y/T307P/M428Y/N434Y |
| F304 | 1.60E−08 | M252W/V308P/M428Y/N434Y |
| F305 | 2.70E−08 | M252Y/T256E/V308P/E382A/N434Y |
| F306 | 3.60E−08 | M252W/V308P/E382A/N434Y |
| F307 | 3.60E−08 | S239K/M252W/V308P/E382A/N434Y |
| F308 | 1.90E−08 | S239K/M252W/V308P/E382A/M428Y/N434Y |
| F310 | 9.40E−08 | S239K/M252W/V308P/E382A/M428I/N434Y |
| F311 | 2.80E−08 | S239K/M252W/V308P/M428F/N434Y |
| F312 | 4.50E−07 | S239K/M252W/E380A/E382A/M428F/N434Y |
| F313 | 6.50E−07 | S239K/M252Y/T307P/M428Y/N434Y |
| F314 | 3.20E−07 | M252Y/T256E/Q311A/D312A/M428Y/N434Y |
| F315 | 6.80E−07 | S239K/M252Y/M428Y/N434Y |
| F316 | 7.00E−07 | S239K/M252Y/D270F/M428Y/N434Y |
| F317 | 1.10E−07 | S239K/M252Y/D270F/V308P/M428Y/N434Y |
| F318 | 1.80E−08 | S239K/M252Y/V308P/M428I/N434Y |

Table 5-9 is a continuation of Table 5-8.

TABLE 5-9

| | | |
|---|---|---|
| F320 | 2.00E−08 | S239K/M252Y/V308P/N325G/E382A/M428I/N434Y |
| F321 | 3.20E−08 | S239K/M252Y/D270F/V308P/N325G/N434Y |
| F322 | 9.20E−08 | S239K/M252Y/D270F/T307P/V308P/N434Y |
| F323 | 2.70E−08 | S239K/M252Y/T256E/D270F/V308P/N434Y |
| F324 | 2.80E−08 | S239K/M252Y/D270F/T307Q/V308P/N434Y |
| F325 | 2.10E−08 | S239K/M252Y/D270F/T307Q/V308P/Q311A/N434Y |
| F326 | 7.50E−08 | S239K/M252Y/D270F/T307Q/Q311A/N434Y |
| F327 | 6.50E−08 | S239K/M252Y/T256E/D270F/T307Q/Q311A/N434Y |
| F328 | 1.90E−08 | S239K/M252Y/D270F/V308P/M428I/N434Y |
| F329 | 1.20E−08 | S239K/M252Y/D270F/N286E/V308P/N434Y |
| F330 | 3.60E−08 | S239K/M252Y/D270F/V308P/L309E/N434Y |
| F331 | 3.00E−08 | S239K/M252Y/D270F/V308P/P387E/N434Y |
| F333 | 7.40E−08 | S239K/M252Y/D270F/T307Q/L309E/Q311A/N434Y |
| F334 | 1.90E−08 | S239K/M252Y/D270F/V308P/N325G/M428I/N434Y |
| F335 | 1.50E−08 | S239K/M252Y/T256E/D270F/V308P/M428I/N434Y |
| F336 | 1.40E−08 | S239K/M252Y/D270F/T307Q/V308P/Q311A/M428I/N434Y |
| F337 | 5.60E−08 | S239K/M252Y/D270F/T307Q/Q311A/M428I/N434Y |
| F338 | 7.70E−09 | S239K/M252Y/D270F/N286E/V308P/M428I/N434Y |
| F339 | 1.90E−08 | S239K/M252Y/D270F/V308P/L309E/M428I/N434Y |
| F343 | 3.20E−08 | S239K/M252Y/D270F/V308P/M428L/N434Y |
| F344 | 3.00E−08 | S239K/M252Y/V308P/M428L/N434Y |
| F349 | 1.50E−07 | S239K/M252Y/V308P/L309P/M428L/N434Y |
| F350 | 1.70E−07 | S239K/M252Y/V308P/L309R/M428L/N434Y |
| F352 | 6.00E−07 | S239K/M252Y/L309P/M428L/N434Y |
| F353 | 1.10E−06 | S239K/M252Y/L309R/M428L/N434Y |
| F354 | 2.80E−08 | S239K/M252Y/T307Q/V308P/M428L/N434Y |
| F356 | 3.40E−08 | S239K/M252Y/D270F/V308P/L309E/P387E/N434Y |
| F357 | 1.60E−08 | S239K/M252Y/T256E/D270F/V308P/N325G/M428I/N434Y |
| F358 | 1.00E−07 | S239K/M252Y/T307Q/N434Y |
| F359 | 4.20E−07 | P257V/T307Q/M428I/N434Y |
| F360 | 1.30E−06 | P257V/T307Q/M428V/N434Y |
| F362 | 5.40E−07 | P257V/T307Q/N325G/M428L/N434Y |
| F363 | 4.10E−08 | P257V/T307Q/Q311A/M428L/N434Y |
| F364 | 3.50E−08 | P257V/T307Q/Q311A/N325G/M428L/N434Y |

Table 5-10 is a continuation of Table 5-9.

TABLE 5-10

| | | |
|---|---|---|
| F365 | 5.10E−08 | P257V/V305A/T307Q/M428L/N434Y |
| F367 | 1.50E−08 | S239K/M252Y/E258H/D270F/T307Q/V308P/Q311A/N434Y |
| F368 | 2.00E−08 | S239K/M252Y/D270F/V308P/N325G/E382A/M428I/N434Y |
| F369 | 7.50E−08 | M252Y/P257V/T307Q/M428I/N434Y |
| F372 | 1.30E−08 | S239K/M252W/V308P/M428Y/N434Y |
| F373 | 1.10E−08 | S239K/M252W/V308P/Q311A/M428Y/N434Y |
| F374 | 1.20E−08 | S239K/M252W/T256E/V308P/M428Y/N434Y |
| F375 | 5.50E−09 | S239K/M252W/N286E/V308P/M428Y/N434Y |

TABLE 5-10-continued

| | | |
|---|---|---|
| F376 | 9.60E−09 | S239K/M252Y/T256E/D270F/N286E/V308P/N434Y |
| F377 | 1.30E−07 | S239K/M252W/T307P/M428Y/N434Y |
| F379 | 9.00E−09 | S239K/M252W/T256E/V308P/Q311A/M428Y/N434Y |
| F380 | 5.60E−09 | S239K/M252W/T256E/N286E/V308P/M428Y/N434Y |
| F381 | 1.10E−07 | P257V/T307A/Q311A/M428L/N434Y |
| F382 | 8.70E−08 | P257V/V305A/T307A/M428L/N434Y |
| F386 | 3.20E−08 | M252Y/V308P/L309E/N434Y |
| F387 | 1.50E−07 | M252Y/V308P/L309D/N434Y |
| F388 | 7.00E−08 | M252Y/V308P/L309A/N434Y |
| F389 | 1.70E−08 | M252W/V308P/L309E/M428Y/N434Y |
| F390 | 6.80E−08 | M252W/V308P/L309D/M428Y/N434Y |
| F391 | 3.60E−08 | M252W/V308P/L309A/M428Y/N434Y |
| F392 | 6.90E−09 | S239K/M252Y/N286E/V308P/M428I/N434Y |
| F393 | 1.20E−08 | S239K/M252Y/N286E/V308P/N434Y |
| F394 | 5.30E−08 | S239K/M252Y/T307Q/Q311A/M428I/N434Y |
| F395 | 2.40E−08 | S239K/M252Y/T256E/V308P/N434Y |
| F396 | 2.00E−08 | S239K/M252Y/D270F/N286E/T307Q/Q311A/M428I/N434Y |
| F397 | 4.50E−08 | S239K/M252Y/D270F/T307Q/Q311A/P387E/M428I/N434Y |
| F398 | 4.40E−09 | S239K/M252Y/D270F/N286E/T307Q/V308P/Q311A/M428I/N434Y |
| F399 | 6.50E−09 | S239K/M252Y/D270F/N286E/T307Q/V308P/M428I/N434Y |
| F400 | 6.10E−09 | S239K/M252Y/D270F/N286E/V308P/Q311A/M428I/N434Y |
| F401 | 6.90E−09 | S239K/M252Y/D270F/N286E/V308P/P387E/M428I/N434Y |
| F402 | 2.30E−08 | P257V/T307Q/M428L/N434W |
| F403 | 5.10E−08 | P257V/T307A/M428L/N434W |
| F404 | 9.40E−08 | P257A/T307Q/L309P/M428L/N434Y |
| F405 | 1.70E−07 | P257V/T307Q/L309P/M428L/N434Y |

Table 5-11 is a continuation of Table 5-10.

TABLE 5-11

| | | |
|---|---|---|
| F406 | 1.50E−07 | P257A/T307Q/L309R/M428L/N434Y |
| F407 | 1.60E−07 | P257V/T307Q/L309R/M428L/N434Y |
| F408 | 2.50E−07 | P257V/N286E/M428L/N434Y |
| F409 | 2.00E−07 | P257V/P387E/M428L/N434Y |
| F410 | 2.20E−07 | P257V/T307H/M428L/N434Y |
| F411 | 1.30E−07 | P257V/T307N/M428L/N434Y |
| F412 | 8.80E−08 | P257V/T307G/M428L/N434Y |
| F413 | 1.20E−07 | P257V/T307P/M428L/N434Y |
| F414 | 1.10E−07 | P257V/T307S/M428L/N434Y |
| F415 | 5.60E−08 | P257V/N286E/T307A/M428L/N434Y |
| F416 | 9.40E−08 | P257V/T307A/P387E/M428L/N434Y |
| F418 | 6.20E−08 | S239K/M252Y/T307P/N325G/M428Y/N434Y |
| F419 | 1.60E−07 | M252Y/T307A/Q311H/K360H/N434Y |
| F420 | 1.50E−07 | M252Y/T307A/Q311H/P387E/N434Y |
| F421 | 1.30E−07 | M252Y/T307A/Q311H/M428A/N434Y |
| F422 | 1.80E−07 | M252Y/T307A/Q311H/E382A/N434Y |
| F423 | 8.40E−08 | M252Y/T307W/Q311H/N434Y |
| F424 | 9.40E−08 | S239K/P257A/V308P/M428L/N434Y |
| F425 | 8.00E−08 | P257A/V308P/L309E/M428L/N434Y |
| F426 | 8.40E−08 | P257V/T307Q/N434Y |
| F427 | 1.10E−07 | M252Y/P257V/T307Q/M428V/N434Y |
| F428 | 8.00E−08 | M252Y/P257V/T307Q/M428L/N434Y |
| F429 | 3.70E−08 | M252Y/P257V/T307Q/N434Y |
| F430 | 8.10E−08 | M252Y/P257V/T307Q/M428Y/N434Y |
| F431 | 6.50E−08 | M252Y/P257V/T307Q/M428F/N434Y |
| F432 | 9.20E−07 | P257V/T307Q/Q311A/N325G/M428V/N434Y |
| F433 | 6.00E−08 | P257V/T307Q/Q311A/N325G/M434Y |
| F434 | 2.00E−08 | P257V/T307Q/Q311A/N325G/M428L/N434Y |
| F435 | 2.50E−08 | P257V/T307Q/Q311A/N325G/M428F/N434Y |
| F436 | 2.50E−07 | P257A/T307Q/M428V/N434Y |
| F437 | 5.70E−08 | P257A/T307Q/N434Y |
| F438 | 3.60E−08 | P257A/T307Q/M428Y/N434Y |
| F439 | 4.00E−08 | P257A/T307Q/M428F/N434Y |
| F440 | 1.50E−08 | P257V/N286E/T307Q/Q311A/N325G/M428L/N434Y |

Table 5-12 is a continuation of Table 5-11.

TABLE 5-12

| | | |
|---|---|---|
| F441 | 1.80E−07 | P257A/Q311A/M428L/N434Y |
| F442 | 2.00E−07 | P257A/Q311H/M428L/N434Y |
| F443 | 5.50E−08 | P257A/T307Q/Q311A/M428L/N434Y |
| F444 | 1.40E−07 | P257A/T307A/Q311A/M428L/N434Y |
| F445 | 6.20E−08 | P257A/T307Q/Q311H/M428L/N434Y |
| F446 | 1.10E−07 | P257A/T307A/Q311H/M428L/N434Y |
| F447 | 1.40E−08 | P257A/N286E/T307Q/M428/N434Y |
| F448 | 5.30E−08 | P257A/N286E/T307A/M428L/N434Y |
| F449 | 5.70E−07 | S239K/M252Y/D270F/T307P/N325G/M428Y/N434Y |
| F450 | 5.20E−07 | S239K/M252Y/T307P/L309E/N325G/M428Y/N434Y |
| F451 | 1.00E−07 | P257S/T307A/M428L/N434Y |
| F452 | 1.40E−07 | P257M/T307A/M428L/N434Y |
| F453 | 7.80E−08 | P257N/T307A/M428L/N434Y |
| F454 | 9.60E−08 | P257I/T307A/M428L/N434Y |
| F455 | 2.70E−08 | P257V/T307Q/M428Y/N434Y |
| F456 | 3.40E−08 | P257V/T307Q/M428F/N434Y |
| F457 | 4.00E−08 | S239K/P257V/V308P/M428L/N434Y |
| F458 | 1.50E−08 | P257V/T307Q/V308P/N325G/M428L/N434Y |
| F459 | 1.30E−08 | P257V/T307Q/V308P/Q311A/N325G/M428L/N434Y |
| F460 | 4.70E−08 | P257V/T307A/V308P/N325G/M428L/N434Y |
| F462 | 8.50E−08 | P257A/V308P/N325G/M428L/N434Y |
| F463 | 1.30E−07 | P257A/T307A/V308P/M428L/N434Y |
| F464 | 5.50E−08 | P257A/T307Q/V308P/M428L/N434Y |
| F465 | 2.10E−08 | P257V/N286E/T307Q/N325G/M428L/N434Y |
| F466 | 3.50E−07 | T256E/P257V/N434Y |
| F467 | 5.70E−07 | T256E/P257T/N434Y |
| F468 | 5.70E−08 | S239K/P257T/V308P/M428L/N434Y |
| F469 | 5.60E−08 | P257T/V308P/N325G/M428L/N434Y |
| F470 | 5.40E−08 | T256E/P257T/V308P/N325G/M428L/N434Y |
| F471 | 6.60E−08 | P257T/V308P/N325G/E382A/M428L/N434Y |
| F472 | 5.40E−08 | P257T/V308P/N325G/P387E/M428L/N434Y |
| F473 | 4.50E−07 | P257T/V308P/L309P/N325G/M428L/N434Y |
| F474 | 3.50E−07 | P257T/V308P/L309R/N325G/M428L/N434Y |
| F475 | 4.30E−08 | T256E/P257V/T307Q/M428L/N434Y |

Table 5-13 is a continuation of Table 5-12.

TABLE 5-13

| | | |
|---|---|---|
| F476 | 5.50E−08 | P257V/T307Q/E382A/M428L/N434Y |
| F477 | 4.30E−08 | P257V/T307Q/P387E/M428L/N434Y |
| F480 | 3.90E−08 | P257L/V308P/N434Y |
| F481 | 5.60E−08 | P257T/T307Q/N434Y |
| F482 | 7.00E−08 | P257V/T307Q/N325G/N434Y |
| F483 | 5.70E−08 | P257V/T307Q/Q311A/N434Y |
| F484 | 6.20E−08 | P257V/V305A/T307Q/N434Y |
| F485 | 9.70E−08 | P257V/N286E/T307A/N434Y |
| F486 | 3.40E−07 | P257V/T307Q/L309R/Q311H/M428L/N434Y |
| F488 | 3.50E−08 | P257V/V308P/N325G/M428L/N434Y |
| F490 | 7.50E−08 | S239K/P257V/V308P/Q311H/M428L/N434Y |
| F492 | 9.80E−08 | P257V/V305A/T307A/N325G/M428L/N434Y |
| F493 | 4.90E−07 | S239K/D270F/T307P/N325G/M428Y/N434Y |
| F497 | 3.10E−06 | P257T/T307A/M428V/N434Y |
| F498 | 1.30E−06 | P257A/M428V/N434Y |
| F499 | 5.20E−07 | P257A/T307A/M428V/N434Y |
| F500 | 4.30E−08 | P257S/T307Q/M428L/N434Y |
| F506 | 1.90E−07 | P257V/N297A/T307Q/M428L/N434Y |
| F507 | 5.10E−08 | P257V/N286A/T307Q/M428L/N434Y |
| F508 | 1.10E−07 | P257V/T307Q/N315A/M428L/N434Y |
| F509 | 5.80E−08 | P257V/T307Q/N384A/M428L/N434Y |
| F510 | 5.30E−08 | P257V/T307Q/N389A/M428L/N434Y |
| F511 | 4.20E−07 | P257V/N434Y |
| F512 | 5.80E−07 | P257T/N434Y |
| F517 | 3.10E−07 | P257V/N286E/N434Y |
| F518 | 4.20E−07 | P257T/N286E/N434Y |
| F519 | 2.60E−08 | P257V/N286E/T307Q/N434Y |
| F521 | 1.10E−08 | P257V/N286E/T307Q/M428Y/N434Y |
| F523 | 2.60E−08 | P257V/V305A/T307Q/M428Y/N434Y |
| F526 | 1.90E−08 | P257T/T307Q/M428Y/N434Y |
| F527 | 9.40E−09 | P257V/T307Q/V308P/N325G/M428Y/N434Y |
| F529 | 2.50E−08 | P257T/T307Q/M428Y/N434Y |
| F533 | 1.20E−08 | P257A/N286E/T307Q/M428F/N434Y |
| F534 | 1.20E−08 | P257A/N286E/T307Q/M428Y/N434Y |

Table 5-14 is a continuation of Table 5-13.

TABLE 5-14

| | | |
|---|---|---|
| F535 | 3.90E−08 | T250A/P257V/T307Q/M428L/N434Y |
| F538 | 9.90E−08 | T250F/P257V/T307Q/M428L/N434Y |
| F541 | 6.00E−08 | T250I/P257V/T307Q/M428L/N434Y |
| F544 | 3.10E−08 | T250M/P257V/T307Q/M428L/N434Y |
| F549 | 5.40E−08 | T250S/P257V/T307Q/M428L/N434Y |
| F550 | 5.90E−08 | T250V/P257V/T307Q/M428L/N434Y |
| F551 | 1.20E−07 | T250W/P257V/T307Q/M428L/N434Y |
| F552 | 1.10E−07 | T250Y/P257V/T307Q/M428L/N434Y |
| F553 | 1.70E−07 | M252Y/Q311A/N434Y |
| F554 | 2.80E−08 | S239K/M252Y/S254T/V308P/N434Y |
| F556 | 1.50E−06 | M252Y/T307Q/Q311A |
| F559 | 8.00E−08 | M252Y/S254T/N286E/N434Y |
| F560 | 2.80E−08 | M252Y/S254T/V308P/N434Y |
| F561 | 1.40E−07 | M252Y/S254T/T307A/N434Y |
| F562 | 8.30E−08 | M252Y/S254T/T307Q/N434Y |
| F563 | 1.30E−07 | M252Y/S254T/Q311A/N434Y |
| F564 | 1.90E−07 | M252Y/S254T/Q311H/N434Y |
| F565 | 9.20E−08 | M252Y/S254T/T307A/Q311A/N434Y |
| F566 | 6.10E−08 | M252Y/S254T/T307Q/Q311A/N434Y |
| F567 | 2.20E−07 | M252Y/S254T/M428I/N434Y |
| F568 | 1.10E−07 | M252Y/T256E/T307A/Q311H/N434Y |
| F569 | 2.00E−07 | M252Y/T256Q/T307A/Q311H/N434Y |
| F570 | 1.30E−07 | M252Y/S254T/T307A/Q311H/N434Y |
| F571 | 8.10E−08 | M252Y/N286E/T307A/Q311H/N434Y |
| F572 | 1.00E−07 | M252Y/T307A/Q311H/M428I/N434Y |
| F576 | 1.60E−06 | M252Y/T256E/T307Q/Q311H |
| F577 | 1.30E−06 | M252Y/N286E/T307A/Q311A |
| F578 | 5.70E−08 | M252Y/M286E/T307Q/Q311A |
| F580 | 8.60E−08 | M252Y/N286E/T307Q/Q311H |
| F581 | 7.20E−08 | M252Y/T256E/N286E/N434Y |
| F582 | 7.50E−08 | S239K/M252Y/V308P |
| F583 | 7.80E−08 | S239K/M252Y/V308P/E382A |
| F584 | 6.30E−08 | S239K/M252Y/T256E/V308P |
| F585 | 2.90E−08 | S239K/M252Y/N286E/V308P |

Table 5-15 is a continuation of Table 5-14.

TABLE 5-15

| | | |
|---|---|---|
| F586 | 1.40E−07 | S239K/M252Y/N286E/V308P/M428I |
| F587 | 1.90E−07 | M252Y/N286E/M428L/N434Y |
| F592 | 2.00E−07 | M252Y/S254T/E382A/N434Y |
| F593 | 3.10E−08 | S239K/M252Y/S254T/V308P/M428I/N434Y |
| F594 | 1.60E−08 | S239K/M252Y/T256E/V308P/M428I/N434Y |
| F595 | 1.80E−08 | S239K/M252Y/M428I/N434Y |
| F596 | 4.00E−07 | M252Y/D312A/E382A/M428Y/N434Y |
| F597 | 2.20E−07 | M252Y/E382A/P387E/N434Y |
| F598 | 1.40E−07 | M252Y/D312A/P387E/N434Y |
| F599 | 5.20E−08 | M252Y/P387E/M428Y/N434Y |
| F600 | 2.80E−07 | M252Y/T256Q/E382A/N434Y |
| F601 | 9.60E−09 | M252Y/N286E/V308P/N434Y |
| F608 | | G236A/S239D/I332E |
| F611 | 2.80E−08 | M252Y/V305T/T307P/V308I/L309A/N434Y |
| F612 | 3.60E−07 | M252Y/T307P/V308I/L309A/N434Y |
| F613 | | S239D/A330L/I332E |
| F616 | | S239D/K326D/L328Y |
| F617 | 7.40E−07 | S239K/N434W |
| F618 | 6.40E−07 | S239K/V308F/N434Y |
| F619 | 3.10E−07 | S239K/M252Y/N434Y |
| F620 | 2.10E−07 | S239K/M252Y/S254T/N434Y |
| F621 | 1.50E−07 | S239K/M252Y/T307A/Q311H/N434Y |
| F622 | 3.50E−07 | S239K/M252Y/T256Q/N434Y |
| F623 | 1.80E−07 | S239K/M252W/N434W |
| F624 | 1.40E−08 | S239K/P257A/N286E/T307Q/M428L/N434Y |
| F625 | 7.60E−08 | S239K/P257A/T307Q/M428L/N434Y |
| F626 | 1.30E−06 | V308P |
| F629 | 3.90E−08 | M252Y/V279L/V308P/N434Y |
| F630 | 3.70E−08 | S239K/M252Y/V279L/V308P/N434Y |
| F633 | 2.40E−08 | M252Y/V282D/V308P/N434Y |
| F634 | 3.20E−06 | S239K/M252Y/V282D/V308P/N434Y |
| F635 | 4.50E−08 | M252Y/V284K/V308P/N434Y |
| F636 | 4.80E−08 | S239K/M252Y/V284K/V308P/N434Y |
| F637 | 1.50E−07 | M252Y/K288S/V308P/N434Y |

Table 5-16 is a continuation of Table 5-15.

TABLE 5-16

| | | |
|---|---|---|
| F638 | 1.40E−07 | S239K/M252Y/K288S/V308P/N434Y |
| F639 | 2.70E−08 | M252Y/V308P/G385R/N434Y |
| F640 | 3.60E−08 | S239K/M252Y/V308P/G385R/N434Y |
| F641 | 3.00E−08 | M252Y/V308P/Q386K/N434Y |
| F642 | 3.00E−08 | S239K/M252Y/V308P/Q386K/N434Y |
| F643 | 3.20E−08 | L235G/G236R/S239K/M252Y/V308P/N434Y |
| F644 | 3.00E−08 | G236R/S239K/M252Y/V308P/N434Y |
| F645 | 3.30E−08 | S239K/M252Y/V308P/L328R/N434Y |
| F646 | 3.80E−08 | S239K/M252Y/N297A/V308P/N434Y |
| F647 | 2.90E−08 | P238D/M252Y/V308P/N434Y |
| F648 | | P238D |
| F649 | 1.20E−07 | S239K/M252Y/N286E/N434Y |
| F650 | 1.70E−07 | S239K/M252Y/T256E/N434Y |
| F651 | 1.80E−07 | S239K/M252Y/Q311A/N434Y |
| F652 | 2.40E−07 | P238D/M252Y/N434Y |
| F654 | 3.20E−08 | L235K/S239K/M252Y/V308P/N434Y |
| F655 | 3.40E−08 | L235R/S239K/M252Y/V308P/N434Y |
| F656 | 3.30E−08 | G237K/S239K/M252Y/V308P/N434Y |
| F657 | 3.20E−08 | G237R/S239K/M252Y/V308P/N434Y |
| F658 | 3.20E−08 | P238K/S239K/M252Y/V308P/N434Y |
| F659 | 3.00E−08 | P238R/S239K/M252Y/V308P/N434Y |
| F660 | 3.10E−08 | S239K/M252Y/V308P/P329K/N434Y |
| F661 | 3.40E−08 | S239K/M252Y/V308P/P329R/N434Y |
| P663 | 6.40E−09 | S239K/M252Y/N286E/T307Q/V308P/Q311A/N434Y |
| F664 | 3.90E−08 | M252Y/N286A/V308P/N434Y |
| F665 | 2.00E−08 | M252Y/N286D/V308P/N434Y |
| F666 | 2.10E−08 | M252Y/N286F/V308P/N434Y |
| F667 | 3.00E−08 | M252Y/N286G/V308P/N434Y |
| F668 | 4.00E−08 | M252Y/N286H/V308P/N434Y |
| F669 | 3.50E−08 | M252Y/N286I/V308P/N434Y |
| F670 | 2.10E−07 | M252Y/N286K/V308P/N434Y |
| F671 | 2.20E−08 | M252Y/N286L/V308P/N434Y |
| F672 | 2.40E−08 | M252Y/N286M/V308P/N434Y |
| F673 | 2.30E−08 | M252Y/N286P/V308P/N434Y |

Table 5-17 is a continuation of Table 5-16.

TABLE 5-17

| | | |
|---|---|---|
| F674 | 3.20E−08 | M252Y/N286Q/V308P/N434Y |
| F675 | 5.10E−08 | M252Y/N286R/V308P/N434Y |
| F676 | 3.20E−08 | M252Y/N286S/V308P/N434Y |
| F677 | 4.70E−08 | M252Y/N286T/V308P/N434Y |
| F678 | 3.30E−08 | M252Y/N286V/V308P/N434Y |
| F679 | 1.70E−08 | M252Y/N286W/V308P/N434Y |
| F680 | 1.50E−08 | M252Y/N286Y/V308P/N434Y |
| F681 | 4.90E−08 | M252Y/K288A/V308P/N434Y |
| F682 | 8.20E−08 | M252Y/K288D/V308P/N434Y |
| F683 | 5.00E−08 | M252Y/K288E/V308P/N434Y |
| F684 | 5.10E−08 | M252Y/K288F/V308P/N434Y |
| F685 | 5.30E−08 | M252Y/K288G/V308P/N434Y |
| F686 | 4.60E−08 | M252Y/K288H/V308P/N434Y |
| F687 | 4.90E−08 | M252Y/K288I/V308P/N434Y |
| F688 | 2.80E−08 | M252Y/K288L/V308P/N434Y |
| F689 | 4.10E−08 | M252Y/K288M/V308P/N434Y |
| F690 | 1.00E−07 | M252Y/K288N/V308P/N434Y |
| F691 | 3.20E−07 | M252Y/K288P/V308P/N434Y |
| F692 | 3.90E−08 | M252Y/K288Q/V308P/N434Y |
| F693 | 3.60E−08 | M252Y/K288R/V308P/N434Y |
| F694 | 4.70E−08 | M252Y/K288V/V308P/N434Y |
| F695 | 4.00E−08 | M252Y/K288W/V308P/N434Y |
| F696 | 4.40E−08 | M252Y/K288Y/V308P/N434Y |
| F697 | 3.10E−08 | S239K/M252Y/V308P/N325G/N434Y |
| F698 | 2.20E−08 | M252Y/N286E/T307Q/Q311A/N434Y |
| F699 | 2.30E−08 | S239K/M252Y/N286E/T307Q/Q311A/N434Y |
| F700 | 5.20E−08 | M252Y/V308P/L328E/N434Y |
| F705 | 7.10E−09 | M252Y/N286E/V308P/M428I/N434Y |
| F706 | 1.80E−08 | M252Y/N286E/T307Q/Q311A/M428I/N424Y |
| F707 | 5.90E−09 | M252Y/N286E/T307Q/V308P/Q311A/N434Y |
| F708 | 4.10E−09 | M252Y/N286E/T307Q/V308P/Q311A/M428I/N434Y |

TABLE 5-17-continued

| F709 | 2.00E−08 | S239K/M252Y/N286E/T307Q/Q311A/M428I/N434Y |
| F710 | 1.50E−08 | P238D/M252Y/N286E/T307Q/Q311A/M428I/N434Y |
| F711 | 6.50E−08 | S239K/M252Y/T307Q/Q311A/N434Y |

Table 5-18 is a continuation of Table 5-17.

TABLE 5-18

| F712 | 6.00E−08 | P238D/M252Y/T307Q/Q311A/N434Y |
| F713 | 2.00E−08 | P238D/M252Y/N286E/T307Q/Q311A/N434Y |
| F714 | 2.30E−07 | P238D/M252Y/N325S/N434Y |
| F715 | 2.30E−07 | P238D/M252Y/N325M/N434Y |
| F716 | 2.70E−07 | P238D/M252Y/N325L/N434Y |
| F717 | 2.60E−07 | P238D/M252Y/N325I/N434Y |
| F718 | 2.80E−07 | P238D/M252Y/Q295M/N434Y |
| F719 | 7.40E−08 | P238D/M252Y/N325G/N434Y |
| F720 | 2.40E−08 | M252Y/T307Q/V308P/Q311A/N434Y |
| F721 | 1.50E−08 | M252Y/T307Q/V308P/Q311A/M428I/N434Y |
| F722 | 2.70E−07 | P238D/M252Y/A327G/N434Y |
| F723 | 2.80E−07 | P238D/M252Y/L328D/N434Y |
| F724 | 2.50E−07 | P238D/M252Y/L328E/N434Y |
| F725 | 4.20E−08 | L235K/G237S/S239K/M252Y/V308P/N434Y |
| F726 | 3.70E−08 | L235K/P238K/S239K/M252Y/V308P/N434Y |
| F729 | 9.20E−07 | T307A/Q311A/N434Y |
| F730 | 6.00E−07 | T307Q/Q311A/N434Y |
| F731 | 8.50E−07 | T307A/Q311H/N434Y |
| F732 | 6.80E−07 | T307Q/Q311H/N434Y |
| F733 | 3.20E−07 | M252Y/L328E/N434Y |
| F734 | 3.10E−07 | G236D/M252Y/L328E/N434Y |
| F736 | 3.10E−07 | M252Y/S267M/L328E/N434Y |
| F737 | 3.10E−07 | M252Y/S267L/L328E/N434Y |
| F738 | 3.50E−07 | P238D/M252Y/T307P/N434Y |
| F739 | 2.20E−07 | M252Y/T307Q/Q311A/N434Y |
| F740 | 2.90E−07 | M252Y/T307P/Q311H/N434Y |
| F741 | 3.10E−07 | P238D/T250A/M252Y/N434Y |
| F744 | 9.90E−07 | P238D/T250F/M252Y/N434Y |
| F745 | 6.60E−07 | P238D/T250G/M252Y/N434Y |
| F746 | 6.00E−07 | P238D/T250H/M252Y/N434Y |
| F747 | 2.80E−07 | P238D/T250I/M252Y/N434Y |
| F749 | 5.10E−07 | P238D/T250L/M252Y/N434Y |
| F750 | 3.00E−07 | P238D/T250M/M252Y/N434Y |
| F751 | 5.30E−07 | P238D/T250N/M252Y/N434Y |

Table 5-19 is a continuation of Table 5-18.

TABLE 5-19

| F753 | 1.80E−07 | P238D/T250Q/M252Y/N434Y |
| F755 | 3.50E−07 | P238D/T250S/M252Y/N434Y |
| F756 | 3.70E−07 | P238D/T250V/M252Y/N434Y |
| F757 | 1.20E−06 | P238D/T250W/M252Y/N434Y |
| F758 | 1.40E−06 | P238D/T250Y/M252Y/N434Y |
| F759 |  | L235K/S239K |
| F760 |  | L235R/S239K |
| F761 | 1.10E−06 | P238D/N434Y |
| F762 | 3.60E−08 | L235K/S239K/M252Y/N286E/T307Q/Q311A/N434Y |
| F763 | 3.50E−08 | L235R/S239K/M252Y/N286E/T307Q/Q311A/N434Y |
| F764 | 6.30E−07 | P238D/T307Q/Q311A/N434Y |
| F765 | 8.50E−08 | P238D/M252Y/T307Q/L309E/Q311A/N434Y |
| F766 | 6.00E−07 | T307A/L309E/Q311A/N434Y |
| F767 | 4.30E−07 | T307Q/L309E/Q311A/N434Y |
| F768 | 6.40E−07 | T307A/L309E/Q311H/N434Y |
| F769 | 4.60E−07 | T307Q/L309E/Q311H/N434Y |
| F770 | 3.00E−07 | M252Y/T256A/N434Y |
| F771 | 4.00E−07 | M252Y/E272A/N434Y |
| F772 | 3.80E−07 | M252Y/K274A/N434Y |
| F773 | 3.90E−07 | M252Y/V282A/N434Y |
| F774 | 4.00E−07 | M252Y/N286A/N434Y |
| F775 | 6.20E−07 | M252Y/K338A/N434Y |
| F776 | 3.90E−07 | M252Y/K340A/N434Y |
| F777 | 3.90E−07 | M252Y/E345A/N434Y |
| F779 | 3.90E−07 | M252Y/N361A/N434Y |
| F780 | 3.90E−07 | M252Y/Q362A/N434Y |

TABLE 5-19-continued

| F781 | 3.70E−07 | M252Y/S375A/N434Y |
| F782 | 3.50E−07 | M252Y/Y391A/N434Y |
| F783 | 4.00E−07 | M252Y/D413A/N434Y |
| F784 | 5.00E−07 | M252Y/L309A/N434Y |
| F785 | 7.40E−07 | M252Y/L309H/N434Y |
| F786 | 2.80E−08 | M252Y/S254T/N286E/T307Q/Q311A/N434Y |
| F787 | 8.80E−08 | M252Y/S254T/T307Q/L309E/Q311A/N434Y |
| F788 | 4.10E−07 | M252Y/N315A/N434Y |

Table 5-20 is a continuation of Table 5-19.

TABLE 5-20

| F789 | 1.50E−07 | M252Y/N315D/N434Y |
| F790 | 2.70E−07 | M252Y/N315E/N434Y |
| F791 | 4.40E−07 | M252Y/N315F/N434Y |
| F792 | 4.40E−07 | M252Y/N315G/N434Y |
| F793 | 3.30E−07 | M252Y/N315I/N434Y |
| F794 | 4.10E−07 | M252Y/N315K/N434Y |
| F795 | 3.10E−07 | M252Y/N315L/N434Y |
| F796 | 3.40E−07 | M252Y/N315M/N434Y |
| F798 | 3.50E−07 | M252Y/N315Q/N434Y |
| F799 | 4.10E−07 | M252Y/N315R/N434Y |
| F800 | 3.80E−07 | M252Y/N315S/N434Y |
| F801 | 4.40E−07 | M252Y/N315T/N434Y |
| F802 | 2.30E−07 | M252Y/N315V/N434Y |
| F803 | 3.60E−07 | M252Y/N315W/N434Y |
| F804 | 4.00E−07 | M252Y/N315Y/N434Y |
| F805 | 3.00E−07 | M252Y/N325A/N434Y |
| F806 | 3.10E−07 | M252Y/N384A/N434Y |
| F807 | 3.20E−07 | M252Y/N389A/N434Y |
| F808 | 3.20E−07 | M252Y/N389A/N390A/N434Y |
| F809 | 2.20E−07 | M252Y/S254T/T256S/N434Y |
| F810 | 2.20E−07 | M252Y/A378V/N434Y |
| F811 | 4.90E−07 | M252Y/E380S/N434Y |
| F812 | 2.70E−07 | M252Y/E382V/N434Y |
| F813 | 2.80E−07 | M252Y/S424E/N434Y |
| F814 | 1.20E−07 | M252Y/N434Y/Y436I |
| F815 | 5.50E−07 | M252Y/N434Y/T437R |
| F816 | 3.60E−07 | P238D/T250V/M252Y/T307P/N434Y |
| F817 | 9.80E−08 | P238D/T250V/M252Y/T307Q/Q311A/N434Y |
| F819 | 1.40E−07 | P238D/M252Y/N286E/N434Y |
| F820 | 3.40E−07 | L235K/S239K/M252Y/N434Y |
| F821 | 3.10E−07 | L235R/S239K/M252Y/N434Y |
| F822 | 1.10E−06 | P238D/T250Y/M252Y/W313Y/N434Y |
| F823 | 1.10E−06 | P238D/T250Y/M252Y/W313F/N434Y |
| F828 | 2.50E−06 | P238D/T250V/M252Y/I253V/N434Y |

Table 5-21 is a continuation of Table 5-20.

TABLE 5-21

| F831 | 1.60E−06 | P238D/T250V/M252Y/R255A/N434Y |
| F832 | 2.60E−06 | P238D/T250V/M252Y/R255D/N434Y |
| F833 | 8.00E−07 | P238D/T250V/M252Y/R255E/N434Y |
| F834 | 8.10E−07 | P238D/T250V/M252Y/R255F/N434Y |
| F836 | 5.00E−07 | P238D/T250V/M252Y/R255H/N434Y |
| F837 | 5.60E−07 | P238D/T250V/M252Y/R255I/N434Y |
| F838 | 4.30E−07 | P238D/T250V/M252Y/R255K/N434Y |
| F839 | 3.40E−07 | P238D/T250V/M252Y/R255L/N434Y |
| F840 | 4.20E−07 | P238D/T250V/M252Y/R255M/N434Y |
| F841 | 1.10E−06 | P238D/T250V/M252Y/R255N/N434Y |
| F843 | 6.60E−07 | P238D/T250V/M252Y/R255Q/N434Y |
| F844 | 1.30E−06 | P238D/T250V/M252Y/R255S/N434Y |
| F847 | 3.40E−07 | P238D/T250V/M252Y/R255W/N434Y |
| F848 | 8.30E−07 | P238D/T250V/M252Y/R255Y/N434Y |
| F849 | 3.30E−07 | M252Y/D280A/N434Y |
| F850 | 2.90E−07 | M252Y/D280E/N434Y |
| F852 | 3.30E−07 | M252Y/D280G/N434Y |
| F853 | 3.20E−07 | M252Y/D280H/N434Y |
| F855 | 3.20E−07 | M252Y/D280K/N434Y |
| F858 | 3.20E−07 | M252Y/D280N/N434Y |
| F860 | 3.30E−07 | M252Y/D280Q/N434Y |
| F861 | 3.20E−07 | M252Y/D280R/N434Y |
| F862 | 3.00E−07 | M252Y/D280S/N434Y |
| F863 | 2.70E−07 | M252Y/D280T/N434Y |
| F867 | 2.80E−07 | M252Y/N384A/N389A/N434Y |

TABLE 5-21-continued

| | | |
|---|---|---|
| P868 | 2.00E−08 | G236A/S239D/M252Y/N286E/T307Q/Q311A/N434Y |
| F869 | | G236A/S239D |
| F870 | 7.30E−08 | L235K/S239K/M252Y/T307Q/Q311A/N434Y |
| F871 | 7.10E−08 | L235R/S239K/M252Y/T307Q/Q311A/N434Y |
| F872 | 1.30E−07 | L235K/S239K/M252Y/N286E/N434Y |
| F873 | 1.20E−07 | L235R/S239K/M252Y/N286E/N434Y |
| F875 | 4.80E−07 | M252Y/N434Y/Y436A |
| F877 | 8.30E−07 | M252Y/N434Y/Y436E |
| F878 | 1.90E−07 | M252Y/N434Y/Y436F |

Table 5-22 is a continuation of Table 5-21.

TABLE 5-22

| | | |
|---|---|---|
| F879 | 9.20E−07 | M252Y/N434Y/Y436G |
| F880 | 3.90E−07 | M252Y/N434Y/Y436H |
| F881 | 3.10E−07 | M252Y/N434Y/Y436K |
| F882 | 1.30E−07 | M252Y/N434Y/Y436L |
| F883 | 2.10E−07 | M252Y/N434Y/Y436M |
| F884 | 4.00E−07 | M252Y/N434Y/Y436N |
| F888 | 4.80E−07 | M252Y/N434Y/Y436S |
| F889 | 2.20E−07 | M252Y/N434Y/Y436T |
| F890 | 1.10E−07 | M252Y/N434Y/Y436V |
| F891 | 1.70E−07 | M252Y/N434Y/Y436W |
| F892 | 7.10E−08 | M252Y/S254T/N434Y/Y436I |
| F893 | 9.80E−08 | L235K/S239K/M252Y/N434Y/Y436I |
| F894 | 9.20E−08 | L235R/S239K/M252Y/N434Y/Y436I |
| F895 | 2.10E−08 | L235K/S239K/M252Y/N285E/T307Q/Q311A/N315E/N434Y |
| F896 | 2.00E−08 | L235R/S239K/M252Y/N286E/T307Q/Q311A/N315E/N434Y |
| F897 | 9.70E−08 | M252Y/N315D/N384A/N389A/N434Y |
| F898 | 1.70E−07 | M252Y/N315E/N384A/N389A/N434Y |
| F899 | 1.10E−07 | M252Y/N315D/G316A/N434Y |
| F900 | 1.70E−07 | M252Y/N315D/G316D/N434Y |
| F901 | 1.30E−07 | M252Y/N315D/G316E/N434Y |
| F902 | 2.20E−07 | M252Y/N315D/G316F/N434Y |
| F903 | 2.30E−07 | M252Y/N315D/G316H/N434Y |
| F904 | 1.00E−07 | M252Y/N315D/G316I/N434Y |
| F905 | 1.30E−07 | M252Y/N315D/G316K/N434Y |
| F906 | 1.50E−07 | M252Y/N315D/G316L/N434Y |
| F907 | 1.30E−07 | M252Y/N315D/G316M/N434Y |
| F908 | 1.50E−07 | M252Y/N315D/G316N/N434Y |
| F909 | 1.30E−07 | M252Y/N315D/G316P/N434Y |
| F910 | 1.40E−07 | M252Y/N315D/G316Q/N434Y |
| F911 | 1.30E−07 | M252Y/N315D/G316R/N434Y |
| F912 | 1.20E−07 | M252Y/N315D/G316S/N434Y |
| F913 | 1.10E−07 | M252Y/N315D/G316T/N434Y |
| F914 | 1.50E−07 | M252Y/N315D/G316V/N434Y |
| F915 | 2.30E−07 | M252Y/N315D/G316W/N434Y |

Table 5-23 is a continuation of Table 5-22.

TABLE 5-23

| | | |
|---|---|---|
| F917 | 2.50E−07 | M252Y/N286S/N434Y |
| F918 | 2.80E−07 | M252Y/D280E/N384A/N389A/N434Y |
| F919 | 3.30E−07 | M252Y/D280G/N384A/N389A/N434Y |
| F920 | 2.50E−07 | M252Y/N286S/N384A/N389A/N434Y |
| F921 | 1.20E−07 | M252Y/N286E/N384A/N389A/N434Y |
| F922 | 5.90E−08 | L235K/S239K/M252Y/N286E/N434Y/Y436I |
| F923 | 6.00E−08 | L235R/S239K/M252Y/N286E/N434Y/Y436I |
| F924 | 3.40E−08 | L235K/S239K/M252Y/T307Q/Q311A/N434Y/Y436I |
| F925 | 3.20E−08 | L235R/S239K/M252Y/T307Q/Q311A/N434Y/Y436I |
| F926 | 1.10E−07 | L235K/S239K/M252Y/S254T/N434Y/Y436I |
| F927 | 1.00E−07 | L235R/S239K/M252Y/S254T/N434Y/Y436I |
| F928 | 2.90E−08 | M252Y/T307Q/Q311A/N434Y/Y436I |
| F929 | 2.90E−08 | M252Y/S254T/T307Q/Q311A/N434Y/Y436I |
| F930 | 1.40E−07 | P238D/T250V/M252Y/N286E/N434Y |
| F931 | 1.20E−07 | P238D/T250V/M252Y/N434Y/Y436I |
| F932 | 3.20E−07 | T230V/M252Y/N434Y |
| F933 | 3.00E−07 | L234R/P238D/T250V/M252Y/N434Y |
| F934 | 3.10E−07 | G236K/P238D/T250V/M252Y/N434Y |
| F935 | 3.20E−07 | G237K/P238D/T250V/M252Y/N434Y |

TABLE 5-23-continued

| | | |
|---|---|---|
| F936 | 3.20E−07 | G237R/P238D/T250V/M252Y/N434Y |
| F937 | 3.10E−07 | P238D/S239K/T250V/M252Y/N434Y |
| F938 | 1.60E−07 | L235K/S239K/M252Y/N434Y/Y436V |
| F939 | 1.50E−07 | L235R/S239K/M252Y/N434Y/Y436V |
| F940 | 1.50E−07 | P238D/T250V/M252Y/N434Y/Y436V |
| F941 | 1.20E−08 | M252Y/N286E/T307Q/Q311A/N434Y/Y436V |
| F942 | 4.20E−08 | L235K/S239K/M252Y/T307Q/Q311A/N434Y/Y436V |
| F943 | 4.00E−08 | L235R/S239K/M252Y/T307Q/Q311A/N434Y/Y436V |
| F944 | 1.70E−07 | T250V/M252Y/N434Y/Y436V |
| F945 | 1.70E−08 | T250V/M252Y/V308P/N434Y/Y436V |
| F946 | 4.30E−08 | T250V/M252Y/T307Q/Q311A/N434Y/Y436V |
| F947 | 1.10E−08 | T250V/M252Y/T307Q/V308P/Q311A/N434Y/Y436V |
| F954 | 5.30E−07 | M252Y/N434Y/H435K/Y436V |
| F957 | 7.70E−07 | M252Y/N434Y/H435N/Y436V |
| F960 | 8.00E−07 | M252Y/N434Y/H435R/Y436V |

Table 5-24 is a continuation of Table 5-23.

TABLE 5-24

| | | |
|---|---|---|
| F966 | 3.10E−07 | M252Y/S254A/N434Y |
| F970 | 2.50E−06 | M252Y/S254G/N434Y |
| F971 | 2.60E−06 | M252Y/S254H/N434Y |
| F972 | 2.60E−07 | M252Y/S254I/N434Y |
| F978 | 1.30E−06 | M252Y/S254Q/N434Y |
| F980 | 1.80E−07 | M252Y/S254V/N434Y |
| F987 | 4.00E−08 | P238D/T250V/M252Y/T307Q/Q311A/N434Y/Y436V |
| F988 | 6.90E−08 | P238D/T250V/M252Y/N286E/N434Y/Y436V |
| F989 | 1.40E−08 | L235R/S239K/M252Y/V308P/N434Y/Y436V |
| F990 | 9.40E−09 | L235R/S239K/M252Y/T307Q/V308P/Q311A/N434Y/Y436V |
| F991 | 1.30E−08 | L235R/S239K/M252Y/N286E/T307Q/Q311A/N434Y/Y436V |
| F992 | 5.10E−08 | L235R/S239K/M252Y/T307Q/Q311A/M428I/N434Y/Y436V |
| F993 | 3.80E−08 | M252Y/T307Q/Q311A/N434Y/Y436V |
| F994 | 2.80E−07 | M252Y/N325G/N434Y |
| F995 | 2.90E−07 | L235R/P238D/S239K/M252Y/K434Y |
| F996 | 1.30E−07 | L235R/P238D/S239K/M252Y/N434Y/Y436V |
| F997 | 3.80E−07 | K248I/T250V/M252Y/N434Y/Y436V |
| F998 | 8.50E−07 | K248Y/T250V/M252Y/N434Y/Y436V |
| F999 | 2.10E−07 | T250V/M252Y/E258H/N434Y/Y436V |
| F1005 | | N325G |
| F1008 | 1.70E−07 | L235R/S239K/T250V/M252Y/N434Y/Y436V |
| F1009 | 1.20E−08 | L235R/S239K/T250V/M252Y/T307Q/V308P/Q311A/N434Y/Y436V |
| F1010 | 1.90E−07 | L235R/S239K/M252Y/T307A/Q311H/N434Y |
| F1011 | 4.50E−08 | T250V/M252Y/V308P/N434Y |
| F1012 | 4.70E−08 | L235R/S239K/T250V/M252Y/V308P/N434Y |
| F1013 | 3.00E−08 | T250V/M252Y/T307Q/V308P/Q311A/N434Y |
| F1014 | 3.20E−08 | L235R/S239K/T250V/M252Y/T307Q/V308P/Q311A/N434Y |
| F1015 | 2.20E−08 | L235R/S239K/M252Y/T307Q/V308P/Q311A/N434Y |
| F1016 | 3.80E−09 | T250V/M252Y/N286E/T307Q/V308P/Q311A/N434Y/Y436V |
| F1017 | 4.20E−09 | L235R/S239K/T250V/M252Y/N286E/T307Q/V308P/Q311A/N434Y/Y436V |
| F1018 | 3.20E−09 | L235R/S239K/M252Y/N286E/T307Q/V308P/Q311A/N434Y/Y436V |
| F1019 | 3.40E−07 | P238D/T250V/M252Y/N325G/N434Y |
| F1020 | 8.50E−08 | P238D/T250V/M252Y/T307Q/Q311A/N325G/N434Y |

Table 5-25 is a continuation of Table 5-24.

TABLE 5-25

| | | |
|---|---|---|
| F1021 | 3.30E−07 | P238D/T250V/M252Y/N325A/N434Y |
| F1022 | | K326D/L328Y |
| F1023 | 4.40E−08 | S239D/T250V/M252Y/T307Q/Q311A/N434Y/Y436V |

TABLE 5-25-continued

| | | |
|---|---|---|
| F1024 | 4.00E−08 | T250V/M252Y/T307Q/Q311A/K326D/L328Y/N434Y/Y436V |
| F1025 | 3.60E−08 | S239D/T250V/M252Y/T307Q/Q311A/K326D/L328Y/N434Y/Y436V |
| F1026 | 8.40E−08 | M252Y/T307A/Q311H/N434Y/Y436V |
| F1027 | 8.60E−08 | L235R/S239K/M252Y/T307A/Q311H/N434Y/Y436V |
| F1028 | 4.60E−08 | G236A/S239D/T250V/M252Y/T307Q/Q311A/N434Y/Y436V |
| F1029 | 5.10E−08 | T250V/M252Y/T307Q/Q311A/I332E/N434Y/Y436V |
| F1030 | | I332E |
| F1031 | 5.30E−08 | G236A/S239D/T250V/M252Y/T307Q/Q311A/I332E/N434Y/Y436V |
| F1032 | 4.30E−08 | P238D/T250V/M252Y/T307Q/Q311A/N325G/N434Y/Y436V |
| F1033 | 1.00E−06 | P238D/N434W |
| F1034 | 1.50E−08 | L235K/S239K/M252Y/V308P/N434Y/Y436V |
| F1035 | 1.00E−08 | L235K/S239K/M252Y/T307Q/V308P/Q311A/N434Y/Y436V |
| F1036 | 1.40E−08 | L235K/S239K/M252Y/N286E/T307Q/Q311A/N434Y/Y436V |
| F1037 | 6.10E−08 | L235K/S239K/M252Y/T307Q/Q311A/M428I/N434Y/Y436V |
| F1038 | 2.80E−07 | L235K/P238D/S239K/M252Y/N434Y |
| F1039 | 1.30E−07 | L235K/P238D/S239K/M252Y/N434Y/Y436V |
| F1040 | 2.00E−07 | L235K/S239K/T250V/M252Y/N434Y/Y436V |
| F1041 | 1.40E−08 | L235K/S239K/T250V/M252Y/T307Q/V308P/Q311A/N434Y/Y436V |
| F1042 | 2.00E−07 | L235K/S239K/M252Y/T307A/Q311H/N434Y |
| F1043 | 5.20E−08 | L235K/S239K/T250V/M252Y/V308P/N434Y |
| F1044 | 3.50E−08 | L235K/S239K/T250V/M252Y/T307Q/V308P/Q311A/N434Y |
| F1045 | 2.50E−08 | L235K/S239K/M252Y/T307Q/V308P/Q311A/N434Y |
| F1046 | 4.50E−09 | L235K/S239K/T250V/M252Y/K286E/T307Q/V308P/Q311A/N434Y/Y436V |
| F1047 | 3.40E−09 | L235K/S239K/M252Y/N286E/T307Q/V308P/Q311A/N434Y/Y436V |
| F1048 | 9.90E−08 | L235K/S239K/M252Y/T307A/Q311H/N434Y/Y436V |
| F1050 | 3.50E−09 | T250V/M252Y/N286E/T307Q/V308P/Q311A/M428I/N434Y/Y436V |
| F1051 | 3.90E−09 | L235R/S239K/T250V/M252Y/N286E/T307Q/V308P/Q311A/M428I/N434Y/Y436V |
| F1052 | 3.20E−09 | L235R/S239K/M252Y/N286E/T307Q/V308P/Q311A/M428I/N434Y/Y436V |

Table 5-26 is a continuation of Table 5-25.

TABLE 5-26

| | | |
|---|---|---|
| F1053 | 4.23E−08 | L235R/S239K/T250V/M252Y/T307Q/Q311A/N434Y/Y436V |
| F1058 | 1.31E−07 | M252Y/Q386E/N434Y/Y436V |
| F1059 | 1.39E−07 | M252Y/Q386R/N434Y/Y436V |
| F1060 | 1.43E−07 | M252Y/Q386S/N434Y/Y436V |
| F1061 | 1.19E−07 | M252Y/P387E/N434Y/Y436V |
| F1062 | 1.2E−07 | M252Y/P387R/N434Y/Y436V |
| F1063 | 1.43E−07 | M252Y/P387S/N434Y/Y436V |
| F1064 | 1.32E−07 | M252Y/V422E/N434Y/Y436V |
| F1065 | 1.38E−07 | M252Y/V422R/N434Y/Y436V |
| F1066 | 1.45E−07 | M252Y/V422S/N434Y/Y436V |
| F1067 | 1.26E−07 | M252Y/S424E/N434Y/Y436V |
| F1068 | 1.69E−07 | M252Y/S424R/N434Y/Y436V |
| F1069 | 1.39E−07 | M252Y/N434Y/Y436V/Q438E |
| F1070 | 1.73E−07 | M252Y/N434Y/Y436V/Q438R |
| F1071 | 1.24E−07 | M252Y/N434Y/Y436V/Q438S |
| F1072 | 1.35E−07 | M252Y/N434Y/Y436V/S440E |
| F1073 | 1.34E−07 | M252Y/N434Y/Y436V/S440R |
| F1074 | 1.32E−07 | S239D/M252Y/N434Y/Y436V |
| F1075 | 1.4E−07 | M252Y/K326D/L328Y/N434Y/Y436V |
| F1076 | 1.27E−07 | S239D/M252Y/K326D/L328Y/N434Y/Y436V |
| F1077 | 2.03E−06 | K248N/M252Y/N434Y |
| F1078 | 4.7E−07 | M252Y/E380N/E382S/N434Y |
| F1079 | 3.44E−07 | M252Y/E382N/N384S/N434Y |
| F1080 | 3.19E−07 | M252Y/S424N/N434Y |
| F1081 | 6.2E−07 | M252Y/N434Y/Y436N/Q438T |

TABLE 5-26-continued

| | | |
|---|---|---|
| F1082 | 2.76E−07 | M252Y/N434Y/Q438N |
| F1083 | 3.45E−07 | M252Y/N434Y/S440N |
| F1094 | 2.6E−07 | M252Y/N434Y/S442N |
| F1095 | 2.86E−07 | M252Y/S383N/G385S/N434Y |
| F1096 | 2.72E−07 | M252Y/Q386T/N434Y |
| F1097 | 2.82E−07 | M252Y/Q385N/P387S/N434Y |
| F1098 | 2.58E−07 | S239D/M252Y/N434Y |
| F1099 | 2.57E−07 | M252Y/K326D/L328Y/N434Y |
| F1100 | 2.41E−07 | S239D/M252Y/K326D/L328Y/N434Y |
| F1101 | 6.59E−08 | S239D/M252Y/T307Q/Q311A/N434Y |
| F1102 | 6.46E−08 | M252Y/T307Q/Q311A/K326D/L328Y/N434Y |
| F1103 | 6.11E−08 | S239D/M252Y/T307Q/Q311A/K326D/L328Y/N434Y |
| F1104 | 1.77E−07 | M252Y/V422E/S424R/N434Y/Y436V |
| F1105 | 1.54E−07 | M252Y/V422S/S424R/N434Y/Y436V |
| F1106 | 1.42E−07 | M252Y/N434Y/Y436V/Q438R/S440E |
| F1107 | 1.23E−07 | M252Y/422D/N434Y/Y436V |

Table 5-27 is a continuation of Table 5-26.

TABLE 5-27

| | | |
|---|---|---|
| F1108 | 1.26E−07 | M252Y/V422K/N434Y/Y436V |
| F1109 | 1.27E−07 | M252Y/V422T/N434Y/Y436V |
| F1110 | 1.33E−07 | M252Y/V422Q/N434Y/Y436V |
| F1111 | 1.65E−07 | M252Y/S424K/N434Y/Y436V |
| F1112 | 1.23E−07 | M252Y/N434Y/Y436V/Q438K |
| F1113 | 1.18E−07 | M252Y/N434Y/Y436V/S440D |
| F1114 | 1.31E−07 | M252Y/N434Y/Y436V/S440Q |
| F1115 | 1.35E−07 | M252Y/S424N/N434Y/Y436V |
| F1116 | 7.44E−08 | M252Y/T307Q/Q311A/S424N/N434Y |
| F1117 | 4.87E−08 | T250V/M252Y/T307Q/Q311A/S424N/N434Y/Y436V |
| F1118 | 1.32E−08 | T250V/M252Y/T307Q/V308P/Q311A/S424N/N434Y/Y436V |
| F1119 | 1.03E−08 | T250V/M252Y/T307Q/V308P/Q311A/V422E/N434Y/Y436V |
| F1120 | 1.04E−08 | T250V/M252Y/T307Q/V308P/Q311A/S424R/N434Y/Y436V |
| F1121 | 1.04E−08 | T250V/M252Y/T307Q/V308P/Q311A/V422E/S424R/N434Y/Y436V |
| F1122 | 1.37E−08 | T250V/M252Y/T307Q/V308P/Q311A/N434Y/Y436V/Q438R |
| F1123 | 9.55E−09 | T250V/M252Y/T307Q/V308P/Q311A/N434Y/Y436V/S440E |
| F1124 | 1.22E−08 | T250V/M252Y/T307Q/V308P/Q311A/N434Y/Y436V/Q438R/S440E |
| F1125 | 5.18E−08 | M252Y/T307Q/N434Y/Y436V |
| F1126 | 8.95E−08 | M252Y/T307A/N434Y/Y436V |
| F1127 | 7.94E−08 | M252Y/Q311A/N434Y/Y436V |
| F1128 | 1.17E−07 | M252Y/Q311H/N434Y/Y436V |
| F1129 | 4.48E−08 | M252Y/T307Q/Q311H/N434Y/Y436V |
| F1130 | 5.54E−08 | M252Y/T307A/Q311A/N434Y/Y436V |
| F1131 | 1.29E−07 | L235R/S239K/M252Y/V422E/N434Y/Y436V |
| F1132 | 1.4E−07 | L235R/S239K/M252Y/V422S/N434Y/Y436V |
| F1133 | 1.58E−07 | L235R/S239K/M252Y/S424R/N424Y/Y436V |
| F1134 | 1.66E−07 | L235R/S239K/M252Y/N434Y/Y436V/Q438R |
| F1135 | 1.26E−07 | L235R/S239K/M252Y/N434Y/Y436V/S440E |
| F1136 | 1.63E−07 | L235R/S239K/M252Y/V422E/S424R/N434Y/Y436V |
| F1137 | 1.58E−07 | L235R/S239K/M252Y/V422S/S424R/N434Y/Y436V |
| F1138 | 1.65E−07 | L235R/S239K/M252Y/N434Y/Y436V/Q438R/S440E |
| F1139 | 1.52E−07 | L235R/S239K/M252Y/S424N/N434Y/Y436V |
| F1140 | 1.62E−07 | M252Y/V422E/S424R/N434Y/Y436V/Q438R/S440E |
| F1141 | 1.77E−07 | M252Y/V422S/S424R/N434Y/Y436V/Q438R/S440E |
| F1142 | 1.87E−07 | L235R/S239K/M252Y/V422E/S424R/N434Y/Y436V/Q438R/S440E |
| F1143 | 1.98E−07 | L235R/S239K/M252Y/V422S/S424R/N434Y/Y436V/Q438R/S440E |
| F1144 | 1.44E−08 | L235R/S239K/T250V/M252Y/T307Q/V308P/Q311A/N434Y/Y436V/Q438R/S440E |
| F1145 | 5.23E−08 | T250V/M252Y/T307Q/Q311A/N434Y/Y436V/Q438R/S440E |

TABLE 5-27-continued

| | | |
|---|---|---|
| F1146 | 6.24E−08 | L235R/S239K/T250V/M252Y/T307Q/Q311A/N434Y/Y436V/Q438R/S440E |
| F1147 | 7.19E−08 | M252Y/T307Q/Q311A/N434Y/Q438R/S440E |

Table 5-28 is a continuation of Table 5-27.

TABLE 5-28

| | | |
|---|---|---|
| F1148 | 7.63E−08 | L235R/S239K/M252Y/T307Q/Q311A/N434Y/Q438R/S440E |
| F1151 | 2.51E−07 | L235R/S239K/M252Y/S424N/N434Y |
| F1152 | 7.38E−08 | L235R/S239K/M252Y/T307Q/Q311A/S424N/N434Y |
| F1153 | 4.85E−08 | L235R/S239K/T250V/M252Y/T307Q/Q311A/S424N/N434Y/Y436V |
| F1154 | 1.34E−08 | L235R/S239K/T250V/M252Y/T307Q/V308P/Q311A/S424N/N434Y/Y436V |
| F1157 | 2.09E−07 | M252Y/N434Y/Q438R/S440E |
| F1158 | 2.44E−07 | L235R/S239K/M252Y/N434Y/Q438R/S440E |
| F1159 | 4.79E−07 | S424N/N434W |
| F1160 | 2.88E−07 | V308F/S424N/N434Y |
| F1161 | 1.07E−06 | I332V/S424N/N434Y |
| F1162 | 3.43E−07 | P238D/T250Y/M252Y/N434Y/Y436V |
| F1163 | 1.54E−07 | P238D/T250Y/M252Y/T307Q/Q311A/N434Y |
| F1164 | 6.96E−08 | P238D/T250Y/M252Y/T307Q/Q311A/N434Y/Y436V |
| F1165 | 1.63E−08 | P238D/T250Y/M252Y/T307Q/V308P/Q311A/N434Y/Y436V |
| F1174 | 4.9E−07 | P257I/N434H |
| F1176 | 1.98E−06 | V308F |
| F1178 | 8.72E−07 | V259I/V308F/M428L |
| F1183 | 1.28E−06 | E380A/M428L/N434S |
| F1184 | 1E−06 | T307A/M428L/N434S |
| F1185 | 9.17E−07 | T307A/E380A/M428L/N434S |
| F1188 | 1.72E−06 | T307A/E380A/N434H |
| F1189 | 1.54E−07 | M252Y/H433D/N434Y/Y436V/Q438R/S440E |
| F1190 | 2.4E−07 | M252Y/H433E/N434Y/Y436V/Q438R/S440E |
| F1191 | 2.11E−07 | M252Y/N434Y/Y436V/T437A/Q438R/S440E |
| F1192 | 1.27E−07 | M252Y/N434Y/Y436V/T437G/Q438R/S440E |
| F1194 | 1.55E−07 | M252Y/N434Y/Y436V/Q438R/K439D/S440E |
| F1195 | 1.76E−07 | M252Y/N434Y/Y436V/Q438R/S440E/L441A |
| F1196 | 1.51E−07 | M252Y/N424Y/Y436V/Q438R/S440E/L441E |
| F1197 | 9.46E−08 | M252Y/S254T/N434Y/Y436V/Q438R/S440E |
| F1198 | 7.83E−08 | M252Y/T256E/N434Y/Y436V/Q438R/S440E |
| F1199 | 6.25E−08 | M252Y/S254T/T256E/N434Y/Y436V/Q438R/S440E |
| F1200 | 1.26E−07 | T250V/M252Y/S254T/N434Y/Y436V/Q438R/S440E |
| F1201 | 1.07E−07 | T250V/M252Y/T256E/N434Y/Y436V/Q438R/S440E |
| F1202 | 8.81E−08 | T250V/M252Y/S254T/T256E/N434Y/Y436V/Q438R/S440E |
| F1203 | 1.52E−07 | M252Y/T256Q/N434Y/Y436V/Q438R/S440E |
| F1204 | 1.18E−07 | M252Y/S254T/T256Q/N434Y/Y436V/Q438R/S440E |
| F1205 | 1.98E−07 | T250V/M252Y/T256Q/N434Y/Y436V/Q438R/S440E |
| F1206 | 1.69E−07 | T250V/M252V/S254T/T256Q/N434Y/Y436V/Q438R/S440E |
| F1207 | 1.11E−06 | I332E/M428L/N434S |
| F1208 | 5.71E−07 | L251A/M252Y/N434Y/Y436V |
| F1211 | 1.23E−06 | L251H/M252Y/N434Y/Y436V |

Table 5-29 is a continuation of Table 5-28.

TABLE 5-29

| | | |
|---|---|---|
| F1213 | 6.33E−07 | L251N/M252Y/N434Y/Y436V |
| F1216 | 1.16E−06 | L251S/M252Y/N434Y/Y436V |
| F1217 | 1.14E−06 | L251T/M252Y/N434Y/Y436V |
| F1218 | 2.51E−07 | L251V/M252Y/N434Y/Y436V |
| F1229 | 2.81E−06 | M252Y/I253V/N434Y/Y436V |
| F1230 | 1.12E−07 | M252Y/N434Y/Y436V/Q438R/S440D |
| F1231 | 9.73E−08 | M252Y/N434Y/Y436V/Q438K/S440E |
| F1232 | 9.79E−08 | M252Y/N434Y/Y436V/Q438K/S440D |
| F1243 | 1.25E−07 | L235R/S239K/M252Y/S254T/N434Y/Y436V/Q438R/S440E |
| F1244 | 1.02E−07 | L235R/S239K/M252Y/T256E/N434Y/Y436V/Q438R/S440E |
| F1245 | 8.2E−08 | L235R/S239K/M252Y/S254T/T256E/N434Y/Y436V/Q438R/S440E |
| F1246 | 1.73E−07 | L235R/S239K/T250V/M252Y/S254T/N434Y/Y436V/Q438R/S440E |
| F1247 | 1.45E−07 | L235R/S239K/T250V/M252Y/T256E/N434Y/Y436V/Q438R/S440E |
| F1248 | 1.2E−07 | L235R/S239K/T250V/M252Y/S254T/T256E/N434Y/Y436V/Q438R/S440E |
| F1249 | 2.06E−07 | L235R/S239K/M252Y/T256Q/N434Y/Y436V/Q438R/S440E |
| F1250 | 1.66E−07 | L235R/S239K/M252Y/S254T/T256Q/N434Y/Y436V/Q438R/S440E |
| F1251 | 2.77E−07 | L235R/S239K/T250V/M252Y/T256Q/N434Y/Y436V/Q438R/S440E |
| F1252 | 2.33E−07 | L235R/S239K/T250V/M252Y/S254T/T256Q/N434Y/Y436V/Q438R/S440E |
| F1253 | 1.12E−07 | L235R/S239K/M252Y/T307A/N434Y/Y436V/Q438R/S440E |
| F1254 | 6.42E−08 | L235R/S239K/M252Y/T307Q/N434Y/Y436V/Q438R/S440E |
| F1255 | 1.11E−07 | L235R/S239K/M252Y/Q311A/N434Y/Y436V/Q438R/S440E |
| F1256 | 1.56E−07 | L235R/S239K/M252Y/Q311H/N434Y/Y436V/Q438R/S440E |
| F1257 | 7.81E−08 | L235R/S239K/M252Y/T307A/Q311A/N434Y/Y436V/Q438R/S440E |
| F1258 | 1.05E−07 | L235R/S239K/M252Y/T307A/Q311H/N434Y/Y436V/Q438R/S440E |
| F1259 | 4.46E−08 | L235R/S239K/M252Y/T307Q/Q311A/N434Y/Y436V/Q438R/S440E |
| F1260 | 6.53E−08 | L235R/S239K/M252Y/T307Q/Q311H/N434Y/Y436V/Q438R/S440E |
| F1261 | 1.35E−07 | L235R/S239K/M252Y/N434Y/Y436V/Q438R/S440D |
| F1262 | 1.26E−07 | L235R/S239K/M252Y/N434Y/Y436V/Q438K/S440E |
| F1263 | 1.24E−07 | L235R/S239K/M252Y/N434Y/Y436V/Q438K/S440D |
| F1264 | 1.27E−07 | L235R/S239K/M252Y/T256A/N434Y/Y436V/Q438R/S440E |
| F1265 | 1.57E−07 | L235R/S239K/M252Y/T256G/N434Y/Y436V/Q438R/S440E |
| F1266 | 9.99E−08 | L235R/S239K/M252Y/T256N/N434Y/Y436V/Q438R/S440E |
| F1267 | 1.5E−07 | L235R/S239K/M252Y/S254A/N434Y/Y436V/Q438R/S440E |
| F1268 | 2E−07 | L235R/S239K/M252Y/H433D/N434Y/Y436V/Q438R/S440E |
| F1269 | 1.69E−07 | L235R/S239K/M252Y/H433D/N434Y/Y436V/Q438K/S440D |
| F1270 | 1.18E−07 | L235R/S239K/M252Y/S254A/N434Y/Y436V/Q438K/S440D |
| F1271 | 2.05E−07 | L235R/S239K/M252Y/S254A/H433D/N434Y/Y436V/Q438R/S440E |
| F1272 | 1.71E−07 | L235R/S239K/M252Y/S254A/H433D/N434Y/Y436V/Q438K/S440D |
| F1273 | 1.53E−07 | L235R/S239K/M252Y/T256Q/N434Y/Y436V/Q438K/S440D |
| F1274 | 2.48E−07 | L235R/S239K/M252Y/T256Q/H433D/N434Y/Y436V/Q438R/S440E |
| F1275 | 2.09E−07 | L235R/S239K/M252Y/T256Q/H433D/N434Y/Y436V/Q438K/S440D |

Table 5-30 is a continuation of Table 5-29.

TABLE 5-30

| | | |
|---|---|---|
| F1276 | 1.02E−07 | L235R/S239K/M252Y/T256A/N434Y/Y436V/Q438K/S44D |
| F1277 | 1.69E−07 | L235R/S239K/M252Y/T256A/H433D/N434Y/Y436V/Q438R/S440E |
| F1278 | 1.4E−07 | L235R/S239K/M252Y/T256A/H433D/N434Y/Y436V/Q438K/S440D |

TABLE 5-30-continued

| | | |
|---|---|---|
| F1279 | 1.23E−07 | L235R/S239K/M252Y/T256G/N434Y/Y436V/Q438K/S440D |
| F1280 | 2.09E−07 | L235R/S239K/M252Y/T256G/H433D/N434Y/Y436V/Q438R/S440E |
| F1281 | 1.74E−07 | L235R/S239K/M252Y/T256G/H433D/N434Y/Y436V/Q438K/S440D |
| F1282 | 7.69E−08 | L235R/S239K/M252Y/T256N/N434Y/Y436V/Q438K/S440D |
| F1283 | 1.34E−07 | L235R/S239K/M252Y/T256N/H433D/N434Y/Y436V/Q438K/S440E |
| F1284 | 1.12E−07 | L235R/S239K/M252Y/T256N/H433D/N434Y/Y436V/Q438K/S440D |
| F1285 | 9.36E−08 | L235R/S239K/M252Y/S254T/N434Y/Y436V/Q438K/S440D |
| F1286 | 1.57E−07 | L235R/S239K/M252Y/S254T/H433D/N434Y/Y436V/Q438K/S440E |
| F1287 | 1.5E−07 | L235R/S239K/M252Y/S254T/H433D/N434Y/Y436V/Q438K/S440D |
| F1288 | 7.95E−08 | L235R/S239K/M252Y/T256E/N434Y/Y436V/Q438K/S440D |
| F1289 | 1.33E−07 | L235R/S239K/M252Y/T256E/H433D/N434Y/Y436V/Q438K/S440E |
| F1290 | 1.11E−07 | L235R/S239K/M252Y/T256E/H433D/N434Y/Y436V/Q438K/S440D |
| F1291 | 1.51E−07 | L235R/S239K/M252Y/H433D/N434Y/Y436V |
| F1292 | 4.24E−07 | L235R/S239K/H433D/N434W/Y436V/Q438R/S440E |
| F1293 | 1.61E−07 | L235R/S239K/M252Y/T256E/N434Y/Q438R/S440E |
| F1294 | 2E−07 | L235R/S239K/M252Y/T256E/N434Y/Y436T/Q438R/S440E |
| F1295 | 9.84E−08 | L235R/S239K/M252Y/T256E/N434Y/Y436F/Q438R/S440E |
| F1296 | 2.27E−07 | L235R/S239K/M252Y/T256E/H433D/N434Y/Q438R/S440E |
| F1297 | 2.5E−07 | L235R/S239K/M252Y/T256E/H433D/N434Y/Y436T/Q438R/S440E |
| F1298 | 1.47E−07 | L235R/S239K/M252Y/T256E/H433D/N434Y/Y436F/Q438R/S440E |
| F1299 | 1.5E−07 | L235R/S239K/M252Y/T256E/N434Y/Q438K/S440D |
| F1300 | 1.63E−07 | L235R/S239K/M252Y/T256E/N434Y/Y436T/Q438K/S440D |
| F1301 | 8.3E−08 | L235R/S239K/M252Y/T256E/N434Y/Y436F/Q438K/S440D |
| F1302 | 2.15E−07 | L235R/S239K/M252Y/T256E/H433D/N434Y/Q438K/S440D |
| F1303 | 2.1E−07 | L235R/S239K/M252Y/T256E/H433D/N434Y/Y436T/Q438K/S440D |
| F1304 | 1.24E−07 | L235R/S239K/M252Y/T256E/H433D/N434Y/Y436F/Q438K/S440D |
| F1305 | 2.05E−07 | L235R/S239K/M252Y/H433D/N434Y/Y436V/Q438R/S440D |
| F1306 | 1.92E−07 | L235R/S239K/M252Y/H433D/N434Y/Y436V/Q438K/S440E |
| F1307 | 1.44E−07 | L235R/S239K/M252Y/V422A/S424A/N434Y/Y436V |
| F1308 | 2.06E−07 | L235R/S239K/M252Y/V422L/S424L/N434Y/Y436V |
| F1309 | 1.26E−07 | L235R/S239K/M252Y/N434Y/Y436V/Q438A/S440A |
| F1310 | 2.28E−07 | L235R/S239K/M252Y/N434Y/Y436V/Q438L/S440L |
| F1311 | 1.69E−07 | L235R/S239K/M252Y/V422A/S424A/H433D/N434Y/Y436V |
| F1312 | 1.79E−07 | L235R/S239K/M252Y/V422L/S424L/H433D/N434Y/Y436V |
| F1313 | 1.77E−07 | L235R/S239K/M252Y/H433D/N434Y/Y436V/Q438A/S440A |
| F1314 | 2.27E−07 | L235R/S239K/M252Y/H433D/N434Y/Y436V/Q438L/S440L |
| F1315 | 1.52E−07 | G237K/S239K/M252Y/N434Y/Y436V |
| F1316 | 1.49E−07 | G237R/S239K/M252Y/N434Y/Y436V |

Table 5-31 is a continuation of Table 5-30.

TABLE 5-31

| | | |
|---|---|---|
| F1317 | 1.38E−07 | S239K/M252Y/P329K/N434Y/Y436V |
| F1318 | 1.43E−07 | S239K/M252Y/P329R/N434Y/Y436V |
| F1319 | 2.67E−07 | M252Y/L328Y/N434Y |
| F1320 | 1.22E−07 | L235R/S239K/M252Y/S254T/N434Y/Y436V/Q438R/S440D |
| F1321 | 1.03E−07 | L235R/S239K/M252Y/S254T/N434Y/Y436V/Q438K/S440D |
| F1322 | 1.6E−07 | L235R/S239K/M252Y/S254T/H433D/N434Y/Y436V/Q438R/S440D |
| F1323 | 1.49E−07 | L235R/S239K/M252Y/S254T/H433D/N434Y/Y436V/Q438K/S440E |
| F1324 | 1.32E−07 | L234A/L235A/M252Y/N434Y/Y436V |
| F1325 | 2.13E−07 | L234A/L235A/M252Y/N297A/N434Y/Y436V |
| F1326 | 1.09E−08 | L234A/L235A/T250V/M252Y/T307Q/V308P/Q311A/N434Y/Y436V |
| F1327 | 1.41E−08 | L234A/L235A/T250V/M252Y/N297A/T307Q/V308P/Q311A/N434Y/Y436V |
| F1328 | 1.52E−07 | L235R/G236R/S239K/M252Y/N434Y/Y436V/Q438R/S440E |
| F1329 | 1.29E−07 | L235R/G236R/S239K/M252Y/S254T/N434Y/Y436V/Q438R/S440E |
| F1330 | 1.03E−07 | L235R/G236R/S239K/M252Y/T256E/N434Y/Y436V/Q438R/S440E |
| F1331 | 7.75E−08 | L235R/G236R/S239K/M252Y/S254T/T256E/N434Y/Y436V/Q438R/S440E |
| F1332 | | |
| F1333 | 1.23E−07 | L235R/G236R/S239K/M252Y/N434Y/Y436V |
| F1334 | 1.04E−07 | L235R/G236R/S239K/M252Y/N434Y/Y436V/Q438K/S440D |
| F1335 | 8.78E−08 | L235R/G236R/S239K/M252Y/S254T/N434Y/Y436V/Q438K/S440D |
| F1336 | 7.18E−08 | L235R/G236R/S239K/M252Y/T256E/N434Y/Y436V/Q438K/S440D |
| F1337 | 7.41E−08 | L235R/S239K/M252Y/T256E/N434Y/Y436V/Q438K/S440E |
| F1338 | 1.04E−07 | L235R/S239K/M252Y/T256E/H433D/N434Y/Y436V/Q438K/S440E |
| F1339 | 2.51E−07 | L235R/S239K/M252Y/S254T/T256E/H433D/N434Y/Y436T/Q438K/S440E |
| F1340 | 5.58E−08 | L235R/S239K/M252Y/S254T/T256E/N434Y/Y436V/Q438K/S440E |
| F1341 | 3.22E−07 | L235R/S239K/M252Y/S254T/N434Y/Y436T/Q438K/S440E |
| F1342 | 2.51E−07 | L235R/S239K/M252Y/T256E/N434Y/Y436T/Q438K/S440E |
| F1343 | 2.01E−07 | L235R/S239K/M252Y/S254T/T256E/N434Y/Y436T/Q438K/S440E |
| F1344 | 3.96E−07 | L235R/S239K/M252Y/N434Y/Y436T/Q438K/S440E |
| F1345 | 1.05E−07 | L235R/G236R/S239K/M252Y/N434Y/Y436V/Q438K/S440E |
| F1346 | 8.59E−08 | L235R/G236R/S239K/M252Y/S254T/N434Y/Y436V/Q438K/S440E |
| F1347 | 7.14E−08 | L235R/G236R/S239K/M252Y/T256E/N434Y/Y436V/Q438K/S440E |
| F1348 | 5.52E−08 | L235R/G236R/S239K/M252Y/S254T/T256E/N434Y/Y436V/Q438K/S440E |
| F1349 | 3.36E−07 | L235R/S239K/M252Y/N434Y/Y436T/Q438R/S440E |
| F1350 | 1.18E−07 | L235R/S239K/M252Y/N434Y/Y436F/Q438K/S440E |
| F1351 | 1.62E−07 | L235R/S239K/M252Y/N434Y/Y436F/Q438R/S440E |
| F1352 | 3.93E−07 | L235R/S239K/M252Y/H433D/N434Y/Y436T/Q438K/S440E |

TABLE 5-31-continued

| | | |
|---|---|---|
| F1353 | 4.33E−07 | L235R/S239K/M252Y/H433D/N434Y/Y436T/Q438R/S440E |
| F1354 | 2.29E−07 | L235R/S239K/M252Y/H433D/N434Y/Y436F/Q438K/S440E |
| F1355 | 2.47E−07 | L235R/S239K/M252Y/H433D/N434Y/Y436F/Q438R/S440E |
| F1356 | 1.58E−07 | G236R/M252Y/L328R/N434Y/Y436V |
| F1357 | 2.81E−07 | L235R/S239K/M252Y/S254T/N434Y/Y436T/Q438R/S440E |
| F1358 | 9.07E−08 | L235R/S239K/M252Y/S254T/N434Y/Y436F/Q438K/S440E |

Table 5-32 is a continuation of Table 5-31.

TABLE 5-32

| | | |
|---|---|---|
| F1359 | 1.28E−07 | L235R/S239K/M252Y/S254T/N434Y/Y436F/Q438R/S440E |
| F1360 | 3.12E−07 | L235R/S239K/M252Y/S254T/H433D/N434Y/Y436T/Q438K/S440E |
| F1361 | 3.52E−07 | L235R/S239K/M252Y/S254T/H433D/N434Y/Y436T/Q438R/S440E |
| F1362 | 1.41E−07 | L235R/S239K/M252Y/S254T/H433D/N434Y/Y436F/Q438K/S440E |
| F1363 | 1.9E−07 | L235R/S239K/M252Y/S254T/H433D/N434Y/Y436P/Q438R/S440E |
| F1364 | 7.49E−08 | L235R/S239K/M252Y/T256E/N434Y/Y436F/Q438K/S440E |
| F1365 | 3.14E−07 | L235R/S239K/M252Y/T256E/H433D/N434Y/Y436T/Q438K/S440E |
| F1366 | 1.17E−07 | L235R/S239K/M252Y/T256E/H433D/N434Y/Y436F/Q438K/S440E |
| F1367 | 1.79E−07 | L235R/S239K/M252Y/S254T/T256E/N434Y/Y436T/Q438R/S440E |
| F1368 | 5.49E−08 | L235R/S239K/M252Y/S254T/T256E/N434Y/Y436P/Q438K/S440E |
| F1369 | 7.6E−08 | L235R/S239K/M252Y/S254T/T256E/N434Y/Y436F/Q438R/S440E |
| F1370 | 9.14E−08 | L235R/S239K/M252Y/S254T/T256E/H433D/N434Y/Y436V/Q438K/S440E |
| F1371 | 1.09E−07 | L235R/S239K/M252Y/S254T/T256E/H433D/N434Y/Y436V/Q438R/S440E |
| F1372 | 2.28E−07 | L235R/S239K/M252Y/S254T/T256E/H433D/N434Y/Y436T/Q438R/S440E |
| F1373 | 8.67E−08 | L235R/S239K/M252Y/S254T/T256E/H433D/N434Y/Y436F/Q438K/S440E |
| F1374 | 1.2E−07 | L235R/S239K/M252Y/S254T/T256E/H433D/N434Y/Y436F/Q438R/S440E |
| F1375 | 1.03E−07 | L235R/S239K/M252Y/S254T/N434Y/Y436V |
| F1376 | 9.09E−08 | L235R/S239K/M252Y/S254T/T256E/N434Y/Y436V |
| F1377 | 8.27E−08 | L235R/S239K/M252Y/T256E/N434Y/Y436V |
| F1378 | 3.61E−07 | L235R/S239K/M252Y/N434Y/Y436T |
| F1379 | 2.85E−07 | L235R/S239K/M252Y/N434Y/Y436P |
| F1410 | 1.90E−06 | V308P/I332V |
| F1411 | 1.70E−07 | V308P/I332V/M428L/N434S |
| F1413 | 3.70E−08 | L235R/S239K/M252Y/S254T/T256E/T307Q/Q311A/H433D/N434Y/Y436V/Q438K/S440E |
| F1414 | 5.60E−08 | L235R/S239K/M252Y/S254T/T256E/T307Q/H433D/N434Y/Y436V/Q438K/S440E |
| F1415 | 5.90E−08 | L235R/S239K/M252Y/S254T/T256E/Q311A/H433D/N434Y/Y436V/Q438K/S440E |
| F1416 | 1.30E−08 | L235R/S239K/M252Y/S254T/T256E/V308P/H433D/N434Y/Y436V/Q438K/S440E |
| F1417 | 5.90E−08 | L235R/S239K/M252Y/S254T/T256E/H433D/N434W/Y436V/Q438K/S440E |
| F1418 | 7.50E−08 | L235R/S239K/M252Y/S254T/T256E/H433D/N434W/Y436V/Q438R/S440E |
| F1419 | 1.50E−07 | L235R/S239K/M252Y/H433D/N434W/Y436V/Q438R/S440E |
| F1420 | 1.30E−07 | L235R/S239K/M252Y/H433D/N434W/Y436V/Q438K/S440E |
| F1421 | 3.20E−08 | V308P/M428L/N434W |
| F1422 | 1.90E−08 | L235R/S239K/M252Y/T256E/V308P/H433D/N434Y/Y436V/Q438R/S440E |
| F1423 | 1.60E−08 | L235R/S239K/M252Y/T256E/V302D/V308P/H433D/N434Y/Y436V/Q438R/S440E |
| F1424 | 1.60E−08 | L235R/S239K/M252Y/T256E/V302E/V308P/H433D/N434Y/Y436V/Q438R/S440E |

Table 5-33 is a continuation of Table 5-32.

TABLE 5-33

| | | |
|---|---|---|
| F1425 | 1.90E−08 | L235R/S239K/M252Y/T256E/V303D/V308P/H433D/N434Y/Y436V/Q438R/S440E |
| F1426 | 1.80E−08 | L235R/S239K/M252Y/T256E/V303E/V308P/H433D/N434Y/Y436V/Q438R/S440E |
| F1428 | 1.50E−08 | L235R/S239K/M252Y/T256E/S304E/V308P/H433D/N434Y/Y436V/Q438R/S440E |
| F1430 | 3.10E−08 | L235R/S239K/M252Y/T256E/V305E/V308P/H433D/N434Y/Y436V/Q438R/S440E |
| F1433 | 4.50E−08 | L235R/S239K/M252Y/T256E/T307D/V308P/H433D/N434Y/Y436V/Q438R/S440E |
| F1434 | 3.60E−08 | L235R/S239K/M252Y/T256E/T307E/V308P/H433D/N434Y/Y436V/Q438R/S440E |

Fcγ Receptor

Fcγ receptor (also described as FcγR) refers to a receptor capable of binding to the Fc region of monoclonal IgG1, IgG2, IgG3, or IgG4 antibodies, and includes all members belonging to the family of proteins substantially encoded by an Fcγ receptor gene. In human, the family includes FcγRI (CD64) including isoforms FcγRIa, FcγRIb and FcγRIc; FcγRII (CD32) including isoforms FcγRIIa (including allotypes H131 and R131, i.e., FcγRIIa(H) and FcγRIIa(R)), FcγRIIb (including FcγRIIb-1 and FcγRIIb-2), and FcγRIIc; and FcγRIII (CD16) including isoforms FcγRIIIa (including allotypes V158 and F158, i.e., FcγRIIIa(V) and FcγRIIIa(F)) and FcγRIIIb (including allotypes FcγRIIIb-NA1 and FcγRIIIb-NA2); as well as all unidentified human FcγRs, FcγR isoforms, and allotypes thereof. However, Fcγ receptor is not limited to these examples. Without being limited thereto, FcγR includes those derived from humans, mice, rats, rabbits, and monkeys. FcγR may be derived from any organisms. Mouse FcγR includes, without being limited to, FcγRI (CD64), FcγRII (CD32), FcγRIII (CD16), and FcγRIII-2 (FcγRIV, CD16-2), as well as all unidentified mouse FcγRs, FcγR isoforms, and allotypes thereof. Such preferred Fcγ receptors include, for example, human FcγRI (CD64), FcγRIIa (CD32), FcγRIIb (CD32), FcγRIIIa (CD16), and/or FcγRIIIb (CD16). The polynucleotide sequence and amino acid sequence of FcγRI are shown in SEQ ID NOs: 19 (NM_000566.3) and 20 (NP_000557.1), respectively; the polynucleotide sequence and amino acid sequence of FcγRIIa (allotype H131) are shown in SEQ ID NOs: 21 (BC020823.1) and 22 (AAH20823.1) (allotype R131 is a sequence in which amino acid at position 166 of SEQ ID NO: 22 is substituted with Arg), respectively; the polynucleotide sequence and amino acid sequence of FcγIIB are shown in SEQ ID NOs: 23 (BC146678.1) and 24 (AA146679.1), respectively; the polynucleotide sequence and amino acid sequence of FcγRIIIa are shown in SEQ ID NOs: 25 (BC033678.1) and 26 (AAH33678.1), respectively; and the polynucleotide sequence and amino acid sequence of FcγRIIIb are shown in SEQ ID NOs: 27 (BC128562.1) and 28 (AAI28563.1), respectively (RefSeq accession number is shown in each parentheses). For example, as described as FcγRIIIaV when allotype V158 is used, unless otherwise specified, allotype F158 is used; however, the allotype of isoform FcγRIIIa described herein should not be interpreted as being particularly limited.

In FcγRI (CD64) including FcγRIa, FcγRIb, and FcγRIc, and FcγRIII (CD16) including isoforms FcγRIIIa (including allotypes V158 and F158) and FcγRIIIb (including allotypes FcγRIIIb-NA1 and FcγRIIIb-NA2), at chain that binds to the Fc portion of IgG is associated with common γ chain having ITAM responsible for transduction of intracellular activation signal. Meanwhile, the cytoplasmic domain of FcγRII (CD32) including isoforms FcγRIIa (including allotypes H131 and R131) and FcγRIIc contains ITAM. These receptors are expressed on many immune cells such as macrophages, mast cells, and antigen-presenting cells. The activation signal transduced upon binding of these receptors to the Fc portion of IgG results in enhancement of the phagocytic activity of macrophages, inflammatory cytokine production, mast cell degranulation, and the enhanced function of antigen-presenting cells. Fcγ receptors having the ability to transduce the activation signal as described above are also referred to as activating Fcγ receptors.

Meanwhile, the intracytoplasmic domain of FcγRIIb (including FcγRIIb-1 and FcγRIIb-2) contains ITIM responsible for transduction of inhibitory signals. The crosslinking between FcγRIIb and B cell receptor (BCR) on B cells suppresses the activation signal from BCR, which results in suppression of antibody production via BCR. The crosslinking of FcγRIII and FcγRIIb on macrophages suppresses the phagocytic activity and inflammatory cytokine production. Fcγ receptors having the ability to transduce the inhibitory signal as described above are also referred to as inhibitory Fcγ receptor.

FcγR-Binding Activity of Fc Region

As mentioned above, Fc regions having an Fcγ receptor-binding activity are examples of Fc regions comprised in the antigen-binding molecules of the present invention. A non-limiting embodiment of such an Fc region includes the Fc region of human IgG1 (SEQ ID NO: 13), IgG2 (SEQ ID NO: 14), IgG3 (SEQ ID NO: 15), or IgG4 (SEQ ID NO: 16). Whether an Fcγ receptor has binding activity to the Fc region of a monoclonal IgG1, IgG2, IgG3, or IgG4 antibody can be assessed by ALPHA screen (Amplified Luminescent Proximity Homogeneous Assay), surface plasmon resonance (SPR)-based Biacore™ method, and others (Proc. Natl. Acad. Sci. USA (2006) 103(11), 4005-4010), in addition to the above-described FACS and ELISA formats.

ALPHA screen is performed by the ALPHA technology based on the principle described below using two types of beads: donor and acceptor beads. A luminescent signal is detected only when molecules linked to the donor beads interact biologically with molecules linked to the acceptor beads and when the two beads are located in close proximity. Excited by laser beam, the photosensitizer in a donor bead converts oxygen around the bead into excited singlet oxygen. When the singlet oxygen diffuses around the donor beads and reaches the acceptor beads located in close proximity, a chemiluminescent reaction within the acceptor beads is induced. This reaction ultimately results in light emission. If molecules linked to the donor beads do not interact with molecules linked to the acceptor beads, the singlet oxygen produced by donor beads do not reach the acceptor beads and chemiluminescent reaction does not occur.

For example, a biotin-labeled antigen-binding molecule comprising Fc region is immobilized to the donor beads and glutathione S-transferase (GST)-tagged Fcγ receptor is immobilized to the acceptor beads. In the absence of an antigen-binding molecule comprising a competitive Fc region variant, Fcγ receptor interacts with a polypeptide complex comprising a wild-type Fc region, inducing a signal of 520 to 620 nm as a result. The antigen-binding molecule having a non-tagged Fc region variant competes with the antigen-binding molecule comprising a native Fc region for the interaction with Fcγ receptor. The relative binding affinity can be determined by quantifying the reduction of fluorescence as a result of competition. Methods for biotinylating the antigen-binding molecules such as antibodies using Sulfo-NHS-biotin or the like are known. Appropriate methods for adding the GST tag to an Fcγ receptor include methods that involve fusing polypeptides encoding Fcγ and GST in-frame, expressing the fused gene using cells introduced with a vector to which the gene is operablye linked, and then purifying using a glutathione column. The induced signal can be preferably analyzed, for example, by fitting to a one-site competition model based on nonlinear regression analysis using software such as GRAPHPAD PRISM (GraphPad; San Diego).

One of the substances for observing their interaction is immobilized as a ligand onto the gold thin layer of a sensor chip. When light is shed on the rear surface of the sensor chip so that total reflection occurs at the interface between the gold thin layer and glass, the intensity of reflected light is partially reduced at a certain site (SPR signal). The other substance for observing their interaction is injected as an analyte onto the surface of the sensor chip. The mass of immobilized ligand molecule increases when the analyte binds to the ligand. This alters the refraction index of solvent on the surface of the sensor chip. The change in refraction index causes a positional shift of SPR signal (conversely, the dissociation shifts the signal back to the original position). In the Biacore™ system, the amount of shift described above (i.e., the change of mass on the sensor chip surface) is plotted on the vertical axis, and thus the change of mass over time is shown as measured data (sensorgram). Kinetic parameters (association rate constant (ka) and dissociation rate constant (kd)) are determined from the curve of sensorgram, and affinity (KD) is determined from the ratio between these two constants. Inhibition assay is preferably used in the Biacore™ methods. Examples of such inhibition assay are described in Proc. Natl. Acad. Sci. USA (2006) 103(11), 4005-4010.

In addition to the Fc region of human IgG1 (SEQ ID NO: 13), IgG2 (SEQ ID NO: 14), IgG3 (SEQ ID NO: 15), or IgG4 (SEQ ID NO: 16), an Fc region with modified FcγR binding, which has a higher Fcγ receptor-binding activity than an Fc region of a native human IgG may be appropriately used as an Fc region included in the present invention. Herein, "Fc region of a native human IgG" refers to an Fc region in which the sugar chain bonded to position 297 (EU numbering) of the Fc region of human IgG1, IgG2, IgG3, or IgG4 shown in SEQ ID NOs: 13, 14, 15, or 16 is a fucose-containing sugar chain. Such Fc regions with modified FcγR binding may be produced by modifying amino acids of the Fc region of a native human IgG. Whether the FcγR-binding activity of an Fc region with modified FcγR binding is higher than that of an Fc region of a native human IgG can be determined appropriately using methods described in the abovementioned section on binding activity.

In the present invention, "modification of amino acids" or "amino acid modification" of an Fc region includes modification into an amino acid sequence which is different from that of the starting Fc region. The starting Fc region may be any Fc region, as long as a variant modified from the starting Fc region can bind to human Fcγ receptor in a neutral pH range. Furthermore, an Fc region modified from a starting Fc region which had been already modified can also be used preferably as an Fc region of the present invention. The "starting Fc region" can refer to the polypeptide itself, a composition comprising the starting Fc region, or an amino acid sequence encoding the starting Fc region. Starting Fc regions can comprise known Fc regions produced via recombination described briefly in the section "Antibodies". The origin of starting Fc regions is not limited, and they may be obtained from human or any nonhuman organisms. Such organisms preferably include mice, rats, guinea pigs, hamsters, gerbils, cats, rabbits, dogs, goats, sheep, bovines, horses, camels and organisms selected from nonhuman primates. In another embodiment, starting Fc regions can also be obtained from cynomolgus monkeys, marmosets, rhesus monkeys, chimpanzees, or humans. Starting Fc regions can be obtained preferably from human IgG1; however, they are not limited to any particular IgG class. This means that an Fc region of human IgG1, IgG2, IgG3, or IgG4 can be used appropriately as a starting Fc region, and herein also means that an Fc region of an arbitrary IgG class or subclass derived from any organisms described above can be preferably used as a starting Fc region. Examples of naturally-occurring IgG variants or modified forms are described in published documents (Curr. Opin. Biotechnol. (2009) 20 (6): 685-91; Curr. Opin. Immunol. (2008) 20 (4), 460-470; Protein Eng. Des. Sel. (2010) 23 (4): 195-202; International Publication Nos. WO 2009/086320, WO 2008/092117, WO 2007/041635, and WO 2006/105338); however, they are not limited to the examples.

Examples of alterations include those with one or more mutations, for example, mutations by substitution of different amino acid residues for amino acids of starting Fc regions, by insertion of one or more amino acid residues into starting Fc regions, or by deletion of one or more amino acids from starting Fc region. Preferably, the amino acid sequences of altered Fc regions comprise at least a part of the amino acid sequence of a non-native Fc region. Such variants necessarily have sequence identity or similarity less than 100% to their starting Fc region. In a preferred embodiment, the variants have amino acid sequence identity or similarity about 75% to less than 100%, more preferably about 80% to less than 100%, even more preferably about 85% to less than 100%, still more preferably about 90% to less than 100%, and yet more preferably about 95% to less than 100% to the amino acid sequence of their starting Fc region. In a non-limiting embodiment of the present invention, at least one amino acid is different between an FcγR-binding modified Fc region of the present invention and its starting Fc region. Amino acid difference between an FcγR-binding modified Fc region of the present invention and its starting Fc region can also be preferably specified based on the specific amino acid differences at the above-described specific amino acid positions according to EU numbering system.

Known methods such as site-directed mutagenesis (Kunkel et al. (Proc. Natl. Acad. Sci. USA (1985) 82, 488-492)) and Overlap extension PCR can be appropriately employed to modify the amino acids of Fc regions. Furthermore, various known methods can also be used as an amino acid modification method for substituting amino acids by those other than natural amino acids (Annu. Rev. Biophys. Biomol. Struct. (2006) 35, 225-249; Proc. Natl. Acad. Sci. U.S.A. (2003) 100 (11), 6353-6357). For example, a cell-free translation system (Clover Direct (Protein Express)) containing tRNAs in which amber suppressor tRNA, which is complementary to UAG codon (amber codon) that is a stop codon, is linked with an unnatural amino acid may be suitably used.

Included in the antigen-binding molecules of the present invention, an Fc region with modified FcγR binding, which has a higher Fcγ receptor-binding activity than that of an Fc region of a native human IgG, (an FcγR binding-modified Fc region) may be obtained by any method. Specifically, the Fc region with modified FcγR binding may be obtained by modifying amino acids of an IgG-type human immunoglobulin used as a starting Fc region. Preferred Fc regions of the IgG-type immunoglobulins for modification include, for example, those of human IgGs shown in SEQ ID NOs: 13, 14, 15, or 16 (IgG1, IgG2, IgG3, or IgG4, respectively, and variants thereof).

Amino acids of any positions may be modified into other amino acids, as long as the binding activity toward the Fcγ receptor is higher than that of the Fc region of a native human IgG. When the antigen-binding molecule contains a human IgG1 Fc region as the human Fc region, it preferably contains a modification that yields the effect of a higher Fcγ receptor-binding activity than that of the Fc region of a native human IgG, in which the sugar chain bound at position 297 (EU numbering) is a fucose-containing sugar chain. Such amino acid modifications have been reported, for example, in international publications such as WO2007/024249, WO2007/021841, WO2006/031370, WO2000/042072, WO2004/029207, WO2004/099249, WO2006/105338, WO2007/041635, WO2008/092117, WO2005/070963, WO2006/020114, WO2006/116260, and WO2006/023403.

Examples of such amino acids that may be modified include at least one or more amino acids selected from the group consisting of positions 221, 222, 223, 224, 225, 227, 228, 230, 231, 232, 233, 234, 235, 236, 237, 238, 239, 240, 241, 243, 244, 245, 246, 247, 249, 250, 251, 254, 255, 256, 258, 260, 262, 263, 264, 265, 266, 267, 268, 269, 270, 271, 272, 273, 274, 275, 276, 278, 279, 280, 281, 282, 283, 284, 285, 286, 288, 290, 291, 292, 293, 294, 295, 296, 297, 298, 299, 300, 301, 302, 303, 304, 305, 311, 313, 315, 317, 318, 320, 322, 323, 324, 325, 326, 327, 328, 329, 330, 331, 332, 333, 334, 335, 336, 337, 339, 376, 377, 378, 379, 380, 382, 385, 392, 396, 421, 427, 428, 429, 434, 436, and 440 (EU numbering). An Fc region (Fc region with modified FcγR binding) having a higher Fcγ receptor-binding activity than that of an Fc region of a native human IgG can be obtained by modifying these amino acids.

Examples of particularly preferable modifications for use in the present invention include at least one or more amino acid modifications selected from the group consisting of:

Lys or Tyr for the amino acid of position 221;
Phe, Trp, Glu, or Tyr for the amino acid of position 222;
Phe, Trp, Glu, or Lys for the amino acid of position 223;
Phe, Trp, Glu, or Tyr for the amino acid of position 224;
Glu, Lys, or Trp for the amino acid of position 225;
Glu, Gly, Lys, or Tyr for the amino acid of position 227;
Glu, Gly, Lys, or Tyr for the amino acid of position 228;
Ala, Glu, Gly, or Tyr for the amino acid of position 230;
Glu, Gly, Lys, Pro, or Tyr for the amino acid of position 231;
Glu, Gly, Lys, or Tyr for the amino acid of position 232;
Ala, Asp, Phe, Gly, His, Ile, Lys, Leu, Met, Asn, Gln, Arg, Ser, Thr, Val, Trp, or Tyr for the amino acid of position 233;
Ala, Asp, Glu, Phe, Gly, His, Ile, Lys, Met, Asn, Pro, Gln, Arg, Ser, Thr, Val, Trp, or Tyr for the amino acid of position 234;
Ala, Asp, Glu, Phe, Gly, His, Ile, Lys, Met, Asn, Pro, Gln, Arg, Ser, Thr, Val, Trp, or Tyr for the amino acid of position 235;
Ala, Asp, Glu, Phe, His, Ile, Lys, Leu, Met, Asn, Pro, Gln, Arg, Ser, Thr, Val, Trp, or Tyr for the amino acid of position 236;
Asp, Glu, Phe, His, Ile, Lys, Leu, Met, Asn, Pro, Gln, Arg, Ser, Thr, Val, Trp, or Tyr for the amino acid of position 237;
Asp, Glu, Phe, Gly, His, Ile, Lys, Leu, Met, Asn, Gln, Arg, Ser, Thr, Val, Trp, or Tyr for the amino acid of position 238;
Asp, Glu, Phe, Gly, His, Ile, Lys, Leu, Met, Asn, Pro, Gln, Arg, Thr, Val, Trp, or Tyr for the amino acid of position 239;
Ala, Ile, Met, or Thr for the amino acid of position 240;
Asp, Glu, Leu, Arg, Trp, or Tyr for the amino acid of position 241;
Leu, Glu, Leu, Gln, Arg, Trp, or Tyr for the amino acid of position 243;
His for the amino acid of position 244;
Ala for the amino acid of position 245;
Asp, Glu, His, or Tyr for the amino acid of position 246;
Ala, Phe, Gly, His, Ile, Leu, Met, Thr, Val, or Tyr for the amino acid of position 247;
Glu, His, Gln, or Tyr for the amino acid of position 249;
Glu or Gln for the amino acid of position 250;
Phe for the amino acid of position 251;
Phe, Met, or Tyr for the amino acid of position 254;
Glu, Leu, or Tyr for the amino acid of position 255;
Ala, Met, or Pro for the amino acid of position 256;
Asp, Glu, His, Ser, or Tyr for the amino acid of position 258;
Asp, Glu, His, or Tyr for the amino acid of position 260;
Ala, Glu, Phe, Ile, or Thr for the amino acid of position 262;
Ala, Ile, Met, or Thr for the amino acid of position 263;
Asp, Glu, Phe, Gly, His, Ile, Lys, Leu, Met, Asn, Pro, Gln, Arg, Ser, Thr, Trp, or Tyr for the amino acid of position 264;
Ala, Leu, Phe, Gly, His, Ile, Lys, Leu, Met, Asn, Pro, Gln, Arg, Ser, Thr, Val, Trp, or Tyr for the amino acid of position 265;
Ala, Ile, Met, or Thr for the amino acid of position 266;
Asp, Glu, Phe, His, Ile, Lys, Leu, Met, Asn, Pro, Gln, Arg, Thr, Val, Trp, or Tyr for the amino acid of position 267;
Asp, Glu, Phe, Gly, Ile, Lys, Leu, Met, Pro, Gln, Arg, Thr, Val, or Trp for the amino acid of position 268;
Phe, Gly, His, Ile, Lys, Leu, Met, Asn, Pro, Arg, Ser, Thr, Val, Trp, or Tyr for the amino acid of position 269;
Glu, Phe, Gly, His, Ile, Leu, Met, Pro, Gln, Arg, Ser, Thr, Trp, or Tyr for the amino acid of position 270;
Ala, Asp, Glu, Phe, Gly, His, Ile, Lys, Leu, Met, Asn, Gln, Arg, Ser, Thr, Val, Trp, or Tyr for the amino acid of position 271;
Asp, Phe, Gly, His, Ile, Lys, Leu, Met, Pro, Arg, Ser, Thr, Val, Trp, or Tyr for the amino acid of position 272;
Phe or Ile for the amino acid of position 273;
Asp, Glu, Phe, Gly, His, Ile, Leu, Met, Asn, Pro, Arg, Ser, Thr, Val, Trp, or Tyr for the amino acid of position 274;
Leu or Trp for the amino acid of position 275;
Asp, Glu, Phe, Gly, His, Ile, Leu, Met, Pro, Arg, Ser, Thr, Val, Trp, or Tyr for the amino acid of position 276;
Asp, Glu, Gly, His, Ile, Lys, Leu, Met, Asn, Pro, Gln, Arg, Ser, Thr, Val, or Trp for the amino acid of position 278;
Ala for the amino acid of position 279;
Ala, Gly, His, Lys, Leu, Pro, Gln, Trp, or Tyr for the amino acid of position 280;
Asp, Lys, Pro, or Tyr for the amino acid of position 281;
Glu, Gly, Lys, Pro, or Tyr for the amino acid of position 282;
Ala, Gly, His, Ile, Lys, Leu, Met, Pro, Arg, or Tyr for the amino acid of position 283;
Asp, Glu, Leu, Asn, Thr, or Tyr for the amino acid of position 284;
Asp, Glu, Lys, Gln, Trp, or Tyr for the amino acid of position 285;
Glu, Gly, Pro, or Tyr for the amino acid of position 286;
Asn, Asp, Glu, or Tyr for the amino acid of position 288;
Asp, Gly, His, Leu, Asn, Ser, Thr, Trp, or Tyr for the amino acid of position 290;
Asp, Glu, Gly, His, Ile, Gln, or Thr for the amino acid of position 291;
Ala, Asp, Glu, Pro, Thr, or Tyr for the amino acid of position 292;
Phe, Gly, His, Ile, Leu, Met, Asn, Pro, Arg, Ser, Thr, Val, Trp, or Tyr for the amino acid of position 293;
Phe, Gly, His, Ile, Lys, Leu, Met, Asn, Pro, Arg, Ser, Thr, Val, Trp, or Tyr for the amino acid of position 294;
Asp, Glu, Phe, Gly, His, Ile, Lys, Met, Asn, Pro, Arg, Ser, Thr, Val, Trp, or Tyr for the amino acid of position 295;
Ala, Asp, Glu, Gly, His, Ile, Lys, Leu, Met, Asn, Gln, Arg, Ser, Thr, or Val for the amino acid of position 296;
Asp, Glu, Phe, Gly, His, Ile, Lys, Leu, Met, Pro, Gln, Arg, Ser, Thr, Val, Trp, or Tyr for the amino acid of position 297;
Ala, Asp, Glu, Phe, His, Ile, Lys, Met, Asn, Gln, Arg, Thr, Val, Trp, or Tyr for the amino acid of position 298;
Ala, Asp, Glu, Phe, Gly, His, Ile, Lys, Leu, Met, Asn, Pro, Gln, Arg, Ser, Val, Trp, or Tyr for the amino acid of position 299;
Ala, Asp, Glu, Gly, His, Ile, Lys, Leu, Met, Asn, Pro, Gln, Arg, Ser, Thr, Val, or Trp for the amino acid of position 300;
Asp, Glu, His, or Tyr for the amino acid of position 301;
Ile for the amino acid of position 302;
Asp, Gly, or Tyr for the amino acid of position 303;
Asp, His, Leu, Asn, or Thr for the amino acid of position 304;
Glu, Ile, Thr, or Tyr for the amino acid of position 305;
Ala, Asp, Asn, Thr, Val, or Tyr for the amino acid of position 311;
Phe for the amino acid of position 313;
Leu for the amino acid of position 315;
Glu or Gln for the amino acid of position 317;
His, Leu, Asn, Pro, Gln, Arg, Thr, Val, or Tyr for the amino acid of position 318;
Asp, Phe, Gly, His, Ile, Leu, Asn, Pro, Ser, Thr, Val, Trp, or Tyr for the amino acid of position 320;
Ala, Asp, Phe, Gly, His, Ile, Pro, Ser, Thr, Val, Trp, or Tyr for the amino acid of position 322;
Ile for the amino acid of position 323;
Asp, Phe, Gly, His, Ile, Leu, Met, Pro, Arg, Thr, Val, Trp, or Tyr for the amino acid of position 324;
Ala, Asp, Glu, Phe, Gly, His, Ile, Lys, Leu, Met, Pro, Gln, Arg, Ser, Thr, Val, Trp, or Tyr for the amino acid of position 325;

Ala, Asp, Glu, Gly, Ile, Leu, Met, Asn, Pro, Gln, Ser, Thr, Val, Trp, or Tyr for the amino acid of position 326;
Ala, Asp, Glu, Phe, Gly, His, Ile, Lys, Leu, Met, Asn, Pro, Arg, Thr, Val, Trp, or Tyr for the amino acid of position 327;
Ala, Asp, Glu, Phe, Gly, His, Ile, Lys, Met, Asn, Pro, Gln, Arg, Ser, Thr, Val, Trp, or Tyr for the amino acid of position 328;
Asp, Glu, Phe, Gly, His, Ile, Lys, Leu, Met, Asn, Gln, Arg, Ser, Thr, Val, Trp, or Tyr for the amino acid of position 329;
Cys, Glu, Phe, Gly, His, Ile, Lys, Leu, Met, Asn, Pro, Arg, Ser, Thr, Val, Trp, or Tyr for the amino acid of position 330;
Asp, Phe, His, Ile, Leu, Met, Gln, Arg, Thr, Val, Trp, or Tyr for the amino acid of position 331;
Ala, Asp, Glu, Phe, Gly, His, Lys, Leu, Met, Asn, Pro, Gln, Arg, Ser, Thr, Val, Trp, or Tyr for the amino acid of position 332;
Ala, Asp, Glu, Phe, Gly, His, Ile, Leu, Met, Pro, Ser, Thr, Val, or Tyr for the amino acid of position 333;
Ala, Glu, Phe, Ile, Leu, Pro, or Thr for the amino acid of position 334;
Asp, Phe, Gly, His, Ile, Leu, Met, Asn, Pro, Arg, Ser, Val, Trp, or Tyr for the amino acid of position 335;
Glu, Lys, or Tyr for the amino acid of position 336;
Glu, His, or Asn for the amino acid of position 337;
Asp, Phe, Gly, Ile, Lys, Met, Asn, Gln, Arg, Ser, or Thr for the amino acid of position 339;
Ala or Val for the amino acid of position 376;
Gly or Lys for the amino acid of position 377;
Asp for the amino acid of position 378;
Asn for the amino acid of position 379;
Ala, Asn, or Ser for the amino acid of position 380;
Ala or Ile for the amino acid of position 382;
Glu for the amino acid of position 385;
Thr for the amino acid of position 392;
Leu for the amino acid of position 396;
Lys for the amino acid of position 421;
Asn for the amino acid of position 427;
Phe or Leu for the amino acid of position 428;
Met for the amino acid of position 429;
Trp for the amino acid of position 434;
Ile for the amino acid of position 436; and
Gly, His, Ile, Leu, or Tyr for the amino acid of position 440; as indicated by EU numbering. The number of amino acids to be modified is not particularly limited; and amino acid may be modified at only one site or amino acids may be modified at two or more sites. Examples of combinations for amino acid modifications at two or more sites include those described in Table 6 (Tables 6-1 to 6-3).

TABLE 6-1

| Combination of amino acids |
| --- |
| K370E/P396L/D270E |
| Q419H/P396L/D270E |
| V240A/P396L/D270E |
| R255L/P396L/D270E |
| R255L/P396L/D270E |
| R255L/P396L/D270E/R292G |
| R255L/P396L/D270E |
| R255L/P396L/D270E/Y300L |
| F243L/D270E/K392N/P396L |
| F243L/R255L/D270E/P396L |
| F243L/R292P/Y300L/V305I/P396L |
| F243L/R292P/Y300L/P396L |
| F243L/R292P/Y300L |
| F243L/R292P/P396L |
| F243L/R292P/V305I |
| F243L/R292P |
| S298A/E333A/K334A |

TABLE 6-1-continued

| Combination of amino acids |
| --- |
| E380A/T307A |
| K326M/E333S |
| K326A/E333A |
| S317A/K353A |
| A327D/I332E |
| A330L/I332E |
| A330Y/I332E |
| E258H/I332E |
| E272H/I332E |
| E272I/N276D |
| E272R/I332E |
| E283H/I332E |
| E293R/I332E |
| F241L/V262I |
| F241W/F243W |
| S239Q/I332Q |
| S267D/I332E |
| S267E/I332E |
| S267L/A327S |
| S267Q/A327S |
| S298A/I332E |
| S304T/I332E |
| S324G/I332D |
| S324G/I332E |
| S324I/I332D |
| S324I/I332E |
| T260H/I332E |
| T335D/I332E |
| V240I/V266I |
| V264I/I332E |
| D265F/N297E/I332E |
| D265Y/N297D/I332E |
| F243L/V262I/V264W |
| N297D/A330Y/I332E |
| N297D/T299E/I332E |
| N297D/T299F/I332E |
| N297D/T299H/I332E |
| N297D/T299I/I332E |
| N297D/T299L/I332E |
| N297D/T299V/I332E |
| P230A/E233D/I332E |
| P244H/P245A/P247V |
| S239D/A330L/I332E |
| S239D/A330Y/I332E |
| S239D/H268E/A330Y |
| S239D/I332E/A327A |
| S239D/I332E/A330I |

Table 6-2 is a continuation of Table 6-1.

TABLE 6-2

| F243L/V264I |
| --- |
| H268D/A330Y |
| H268E/A330Y |
| K246H/I332E |
| L234D/I332E |
| L234E/I332E |
| L234G/I332E |
| L234I/I332E |
| L234I/L235D |
| L234Y/I332E |
| L235D/I332E |
| L235E/I332E |
| L235I/I332E |
| L235S/I332E |
| L328A/I332D |
| L328D/I332D |
| L328D/I332E |
| L328E/I332D |
| L328E/I332E |
| L328F/I332D |
| L128F/I332E |
| L328H/I332E |
| L328I/I332D |
| L328I/I332E |

TABLE 6-2-continued

L328M/I332D
L328M/I332E
L328N/I332D
L328N/I332E
L328Q/I332D
L328Q/I332E
L328T/I332D
L328T/I332E
L328V/I332D
L328V/I332E
L328Y/I332D
S239D/N297D/I332E
S239D/S298A/I332E
S239D/V264I/I332E
S239E/N297D/I332E
S239E/V264I/I332E
S239N/A330L/I332E
S239N/A330Y/I332E
S239N/S298A/I332E
S239Q/V264I/I332E
V264E/N297D/I332E
V264I/A330L/I332E
V264I/A330Y/I332E
V264I/S298A/I332E
Y296D/N297D/I332E
Y296E/N297D/I332E
Y296H/N297D/I332E
Y296N/N297D/I332E
V296Q/N297D/I332E
Y296T/N297D/I332E
D265Y/N297D/T299L/I332E
F241E/F243Q/V262T/V264E
F241E/F243R/V262E/V264R
F241E/F243Y/V262T/V264R
F241L/F243L/V262I/V264I
F241R/F243Q/V262T/V264R
F241S/F243H/V262T/V264T
F241W/F243W/V262A/V264A
F241Y/F243Y/V262T/V264T
I332E/A330Y/H268E/A327A
N297D/I332E/S239D/A330L
N297D/S298A/A330Y/I332E
S239D/A330Y/I332E/K326E
S239D/A330Y/I332E/K326T
S239D/A330Y/I332E/L234I
S239D/A330Y/I332E/L235D

Table 6-3 is a continuation of Table 6-2.

TABLE 6-3

L328Y/I332E
N297D/I332E
N297E/I332E
N297S/I332E
P227G/I332E
P230A/E233D
Q295E/I332E
R255Y/I332E
S239D/I332D
S239D/I332E
S239D/I332N
S239D/I332Q
S239E/D265G
S239E/D265N
S239E/D265Q
S239E/I332D
S239E/I332E
S239E/I332N
S239E/I332Q
S239N/I332D
S239N/I332E
S239N/I332N
S239N/I332Q
S239Q/I332D
S239Q/I332E
S239Q/I332N
S267E/L328F

TABLE 6-3-continued

S239D/S267E
S239D/A330Y/I332E/V240I
S239D/A330Y/I332E/V264T
S239D/A330Y/I332E/V266I
S239D/D265F/N297D/I332E
S239D/D265H/N297D/I332E
S239D/D265I/N297D/I332E
S239D/D265L/N297D/I332E
S239D/D265T/N297D/I332E
S239D/D265V/N297D/I332E
S239D/D265Y/N297D/I332E
S239D/I332E/A330Y/A327A
S239D/I332E/H268E/A327A
S239D/I332E/H268E/A330Y
S239D/N297D/I332E/A330Y
S239D/N297D/I332E/K326E
S239D/N297D/1I332E/L235D
S239D/V264I/A330L/I332E
S239D/V264I/S298A/I332E
S239E/V654I/A330Y/I332E
F241E/F243Q/V262T/V264E/I332E
F241E/F243R/V262E/V264R/I332E
F241E/F243Y/V262T/V264R/I332E
F241R/F243Q/V262T/V264R/I332E
S239D/I332E/H268E/A330Y/A327A
S239E/V264I/S298A/A330Y/I332E
F241Y/F243Y/V262T/V264T/N297D/I332E
G236D/S267E

For the pH conditions to measure the binding activity of the Fc region and the Fcγ receptor contained in the antigen-binding molecule of the present invention, conditions in an acidic pH range or in a neutral pH range may be suitably used. The neutral pH range, as a condition to measure the binding activity of the Fc region and the Fcγ receptor contained in the antigen-binding molecule of the present invention, generally indicates pH 6.7 to pH10.0. Preferably, it is a range indicated with arbitrary pH values between pH 7.0 and pH8.0; and preferably, it is selected from pH 7.0, pH7.1, pH7.2, pH7.3, pH7.4, pH7.5, pH7.6, pH7.7, pH7.8, pH7.9, and pH 8.0; and particularly preferably, it is pH 7.4, which is close to the pH of plasma (blood) in vivo. Herein, the acidic pH range, as a condition for having a binding activity of the Fc region and the Fcγ receptor contained in the antigen-binding molecule of the present invention, generally indicates pH 4.0 to pH6.5. Preferably, it indicates pH 5.5 to pH6.5, and particularly preferably, it indicates pH5.8 to pH6.0, which is close to the pH in the early endosome in vivo. With regard to the temperature used as a measurement condition, the binding affinity between an Fc region and an Fcγ receptor can be evaluated at any temperature between 10° C. and 50° C. Preferably, a temperature between 15° C. and 40° C. is used to determine the binding affinity between an Fc region and an Fcγ receptor. More preferably, any temperature between 20° C. and 35° C., such as any single temperature from 20° C., 21° C., 22° C., 23° C., 24° C., 25° C., 26° C., 27° C., 28° C., 29° C., 30° C., 31° C., 32° C., 33° C., 34° C., and 35° C., can be similarly used to determine the binding affinity between an Fc region and an Fcγ receptor. A temperature of 25° C. is a non-limiting example in an embodiment of the present invention.

Herein, "Fc region with modified FcγR binding has a higher Fcγ receptor-binding activity than the native Fc region" means that the human Fcγ receptor-binding activity of the Fc region with modified FcγR binding toward any of the human Fcγ receptors of FcγRI, FcγRIIa, FcγRIIb, FcγRIIIa, and/or FcγRIIIb is higher than the binding activity of the native Fc region toward these human Fcγ receptors. For example, it means that based on an above-described analytical method, in comparison to the binding activity of an antigen-binding molecule containing a native human IgG Fc region as a control, the binding activity of the antigen-binding molecule comprising an Fc region with modified FcγR binding is 105% or more, preferably 110% or more, 115% or more, 120% or more, 125% or more, particularly preferably 130% or more, 135% or more, 140% or more, 145% or more, 150% or more, 155% or more, 160% or more, 165% or more, 170% or more, 175% or more, 180% or more, 185% or more, 190% or more, 195% or more, 2-fold or more, 2.5-fold or more, 3-fold or more, 3.5-fold or more, 4-fold or more, 4.5-fold or more, 5-fold or more, 7.5-fold or more, 10-fold or more, 20-fold or more, 30-fold or more, 40-fold or more, 50-fold or more, 60-fold or more, 70-fold or more, 80-fold or more, 90-fold or more, or 100-fold or more. The starting Fc region may be used as a native Fc region, and native Fc regions of antibodies of the same subclass may also be used.

In the present invention, an Fc region of a native human IgG in which the sugar chain bonded to the amino acid at position 297 (EU numbering) is a fucose-containing sugar chain, is suitably used as a native Fc region of human IgG to be used as a control. Whether or not the sugar chain bonded to the amino acid at position 297 (EU numbering) is a fucose-containing sugar chain can be determined using the technique described in Non-Patent Document 6. For example, it is possible to determine whether or not the sugar chain bonded to the native human IgG Fc region is a fucose-containing sugar chain by a method such as the one below. Sugar chain is dissociated from a native human IgG to be tested, by reacting the test native human IgG with N-Glycosidase F (Roche diagnostics) (Weitzhandler et al. (J. Pharma. Sciences (1994) 83, 12, 1670-1675)). Next, a dried concentrate of a reaction solution from which protein has been removed by reaction with ethanol (Schenk et al. (J. Clin. Investigation (2001) 108 (11) 1687-1695)) is fluorescently labeled with 2-aminopyridine or 2-aminobenzamide (Bigge et al. (Anal. Biochem. (1995) 230 (2) 229-238)). Reagents are removed by solid extraction using a cellulose cartridge, and the fluorescently labeled 2-AP or 2-AB-modified sugar chain is analyzed by normal-phase chromatography. It is possible to determine whether or not the sugar chain bonded to the native Fc region of a human IgG is a fucose-containing sugar chain by observing the detected chromatogram peaks.

As an antigen-binding molecule containing an Fc region of a native antibody of the same subclass, which is to be used as a control, an antigen-binding molecule having an Fc region of a monoclonal IgG antibody may be suitably used. The structures of the Fc regions are described in SEQ ID NO: 13 (A is added to the N terminus of RefSeq Accession No. AAC82527.1), SEQ ID NO: 14 (A is added to the N terminus of RefSeq Accession No. AAB59393.1), SEQ ID NO: 15 (RefSeq Accession No. CAA27268.1), and SEQ ID NO: 16 (A is added to the N terminus of RefSeq Accession No. AAB59394.1). Further, when an antigen-binding molecule containing an Fc region of a particular antibody isotype is used as the test substance, the effect of the antigen-binding molecule containing the test Fc region on Fcγ receptor-binding activity is tested by using as a control an antigen-binding molecule having an Fc region of a monoclonal IgG antibody of that particular isotype. In this way, antigen-binding molecules containing an Fc region of which Fcγ receptor-binding activity is demonstrated to be high are suitably selected.

Fc Regions Having a Selective Binding Activity to an Fcγ Receptor

Examples of Fc regions suitable for use in the present invention include Fc regions having a higher binding activity to a particular Fcγ receptor than to other Fcγ receptors (Fc regions having a selective binding activity to an Fcγ receptor). When an antibody is used as the antigen-binding molecule, a single antibody molecule can only bind to a single Fcγ receptor molecule. Therefore, a single antigen-binding molecule cannot bind to other activating FcγRs in an inhibitory Fcγ receptor-bound state, and cannot bind to other activating Fcγ receptors or inhibitory Fcγ receptors in an activating Fcγ receptor-bound state.

As described above, suitable examples of activating Fcγ receptors include FcγRI (CD64) which includes FcγRIa, FcγRIb, and FcγRIc; FcγRIII (CD16) which includes isoforms FcγRIIIa (including allotypes V158 or F158) and FcγRIIIb (including allotypes FcγRIIIb-NA1 and FcγRIIIb-NA2); and FcγRIIa (including allotypes H131 or R131). Meanwhile, suitable examples of inhibitory Fcγ receptors include FcγRIIb (including FcγRIIb-1 or FcγRIIb-2).

The Fc region comprised in an antigen-binding molecule of the present invention that contains a selective FcγR-binding domain, and an antigen-binding molecule comprising this Fc region may have a maintained or reduced binding activity to activating FcγR (FcγRIa, FcγRIb, FcγRIc, FcγRIIIa including allotype V158, FcγRIIIa including allotype F158, FcγRIIIb including allotype FcγRIIIb-NA1, FcγRIIIb including allotype FcγRIIIb-NA2, FcγRIIa including allotype H131, FcγRIIa including allotype R131 and/or FcγRIIc), when compared to the Fc region of human IgG1 (SEQ ID NO: 13), IgG2 (SEQ ID NO: 14), IgG3 (SEQ ID NO: 15), or IgG4 (SEQ ID NO: 16) (hereinafter referred to as wild-type Fc region) and an antigen-binding molecule comprising this wild-type Fc region.

In comparison to a wild-type Fc region and an antigen-binding molecule comprising a wild-type Fc region, an Fc region comprised in an antigen-binding molecule of the present invention that contains a selective FcγR-binding domain, and an antigen-binding molecule comprising this Fc region are reduced in their binding activity to the aforementioned activating FcγR at a level of, for example, 99% or less, 98% or less, 97% or less, 96% or less, 95% or less, 94% or less, 93% or less, 92% or less, 91% or less, 90% or less, 88% or less, 86% or less, 84% or less, 82% or less, 80% or less, 78% or less, 76% or less, 74% or less, 72% or less, 70% or less, 68% or less, 66% or less, 64% or less, 62% or less, 60% or less, 58% or less, 56% or less, 54% or less, 52% or less, 50% or less, 45% or less, 40% or less, 35% or less, 30% or less, 25% or less, 20% or less, 15% or less, 10% or less, 5% or less, 4% or less, 3% or less, 2% or less, 1% or less, 0.5% or less, 0.4% or less, 0.3% or less, 0.2% or less, 0.1% or less, 0.05% or less, 0.01% or less, or 0.005% or less.

The Fc region comprised in an antigen-binding molecule of the present invention that contains a selective FcγR-binding domain, and an antigen-binding molecule comprising this Fc region may have an enhanced binding activity to inhibitory FcγR (FcγRIIb-1 and/or FcγRIIb-2) when compared to the Fc region of human IgG1 (SEQ ID NO: 13), IgG2 (SEQ ID NO: 14), IgG3 (SEQ ID NO: 15), or IgG4 (SEQ ID NO: 16) (hereinafter referred to as wild-type Fc region), and an antigen-binding molecule comprising the wild-type Fc region.

In comparison to a wild-type Fc region and an antigen-binding molecule comprising a wild-type Fc region, the Fc region comprised in an antigen-binding molecule of the present invention that contains a selective FcγR-binding domain, and an antigen-binding molecule comprising this Fc region, are enhanced in their binding activity to the aforementioned inhibitory FcγR at a level of, for example, 101% or greater, 102% or greater, 103% or greater, 104% or greater, 105% or greater, 106% or greater, 107% or greater, 108% or greater, 109% or greater, 110% or greater, 112% or greater, 114% or greater, 116% or greater, 118% or greater, 120% or greater, 122% or greater, 124% or greater, 126% or greater, 128% or greater, 130% or greater, 132% or greater, 134% or greater, 136% or greater, 138% or greater, 140% or greater, 142% or greater, 144% or greater, 146% or greater, 148% or greater, 150% or greater, 155% or greater, 160% or greater, 165% or greater, 170% or greater, 175% or greater, 180% or greater, 185% or greater, 190% or greater, 195% or greater, 2-fold or greater, 3-fold or greater, 4-fold or greater, 5-fold or greater, 6-fold or greater, 7-fold or greater, 8-fold or greater, 9-fold or greater, 10-fold or greater, 20-fold or greater, 30-fold or greater, 40-fold or greater, 50-fold or greater, 60-fold or greater, 70-fold or greater, 80-fold or greater, 90-fold or greater, 100-fold or greater, 200-fold or greater, 300-fold or greater, 400-fold or greater, 500-fold or greater, 600-fold or greater, 700-fold or greater, 800-fold or greater, 900-fold or greater, 1000-fold or greater, 10000-fold or greater, or 100000-fold or greater.

The Fc region comprised in an antigen-binding molecule of the present invention that contains a selective FcγR-binding domain, and an antigen-binding molecule comprising this Fc region may have
a maintained or reduced binding activity to activating FcγR (FcγRIa, FcγRIb, FcγRIc, FcγRIIIa including allotype V158, FcγRIIIa including allotype F158, FcγRIIIb including allotype FcγRIIIb-NA1, FcγRIIIb including allotype FcγRIIIb-NA2, FcγRIIa including allotype H131, FcγRIIa including allotype R131, and/or FcγRIIc), when compared to the Fc region of human IgG1 (SEQ ID NO: 13), IgG2 (SEQ ID NO: 14), IgG3 (SEQ ID NO: 15), or IgG4 (SEQ ID NO: 16) (hereinafter referred to as wild-type Fc region), and an antigen-binding molecule comprising the wild-type Fc region; and
an enhanced binding activity to inhibitory FcγR (FcγRIIb-1 and/or FcγRIIb-2) when compared to the Fc region of human IgG1 (SEQ ID NO: 13), IgG2 (SEQ ID NO: 14), IgG3 (SEQ ID NO: 15), or IgG4 (SEQ ID NO: 16) (hereinafter referred to as wild-type Fc region), and an antigen-binding molecule comprising the wild-type Fc region.

In comparison to the Fc region of human IgG1 (SEQ ID NO: 13), IgG2 (SEQ ID NO: 14), IgG3 (SEQ ID NO: 15), or IgG4 (SEQ ID NO: 16) (hereinafter referred to as wild-type Fc region) and an antigen-binding molecule comprising the wild-type Fc region, the Fc region comprised in an antigen-binding molecule of the present invention that contains a selective FcγR-binding domain, and an antigen-binding molecule comprising this Fc region, have a higher level of enhancement in their binding activity to inhibitory FcγR (FcγRIIb-1 and/or FcγRIIb-2) than the level of enhancement in their binding activity to activating Fcγ receptor (FcγRIa, FcγRIb, FcγRIc, FcγRIIIa including allotype V158, FcγRIIIa including allotype F158, FcγRIIIb including allotype FcγRIIIb-NA1, FcγRIIIb including allotype FcγRIIIb-NA2, FcγRIIa including allotype H131, and FcγRIIa including allotype R131).

In the present invention, it is possible to add at least another modification to the Fc region whose amino acid at position 238 (EU numbering) is Asp or to the Fc region whose amino acid at position 328 (EU numbering) is Glu by the embodiments and such described in the aforementioned section on amino acid modifications. In addition to these modifications, additional modifications may also be included. Additional modifications can be selected, for example, from any of amino acid substitutions, deletions, and modifications, and combinations thereof. For example, modifications that enhance the FcγRIIb-binding activity while maintaining or decreasing the binding activity to FcγRIIa (H type) and FcγRIIa (R type) may be added. Addition of such modifications improves binding selectivity to FcγRIIb over FcγRIIa.

Furthermore, whether or not the binding activities of the polypeptides of the present invention towards various FcγRs were maintained, enhanced, or decreased can be determined from the increase or decrease in the amount of binding of the various FcγRs to the polypeptides of the present invention, which were determined according to the examples described above. Here, the amount of binding of the various FcγRs to the polypeptides refers to values obtained by determining the difference in the RU values of sensorgrams that changed before and after interaction of various FcγRs as the analyte with each polypeptide, and dividing them by differences in the RU values of sensorgrams that changed before and after capturing polypeptides to the sensor chips.

It is possible to determine whether the FcγRIIa (R type and H type)-binding activity of the polypeptides of the present invention is maintained or decreased, and whether the peptides are peptides with enhanced FcγRIIb-binding activity can be determined from the binding amount of the polypeptides to FcγRIIa and the binding amount of the polypeptides to FcγRIIb by following the above-mentioned examples.

An exemplary case is when the amount of a polypeptide of the present invention bound to FcγRIIb is increased compared to the FcγRIIb-binding amount of the parent polypeptide, and the amount of the polypeptide of the present invention bound to FcγRIIa (R type and H type) is equivalent to (maintained) or preferably decreased relative to the binding amount of the parent polypeptide to FcγRIIa (R type and H type). It is also possible to determine by appropriately combining the FcγRIa-binding amount and the FcγRIIIa-binding amount of the polypeptide determined by following the above-mentioned examples.

In a non-limiting embodiment of the present invention, an example of an Fc region having a higher inhibitory Fcγ receptor-binding activity than an activating Fcγ recptor-binding activity (having a selective binding activity toward an inhibitory Fcγ receptor) is the Fc region presented in US2009/0136485 or WO 2012/115241; and another suitable example is an Fc region in which the amino acid at position 238 or 328 as indicated by EU numbering in the aforementioned Fc region has been modified to an amino acid different from that of the native Fc region.

In a non-limiting embodiment of the present invention, a suitable example of an Fc region that has a higher binding activity toward an inhibitory Fcγ receptor than toward an activating Fcγ receptor (i.e., having a selective binding activity toward an inhibitory Fcγ receptor) is an Fc region with one or more of the following modifications in the amino acids (indicated by EU numbering) of the aforementioned Fc region: the amino acid at position 238 is modified to Asp and the amino acid at position 328 is modified to Glu. The Fc regions and modifications described in US2009/0136485 or WO 2012/115241 may be selected appropriately as the Fc region having a selective binding activity to an inhibitory Fcγ receptor.

In a non-limiting embodiment of the present invention, a suitable example is an Fc region in which one or more of the amino acids indicated by EU numbering at positions 238 and 328 according to EU numbering are respectively modified to Asp or Glu in the aforementioned Fc region.

Furthermore, in a non-limiting embodiment of the present invention, suitable examples of the Fc regions are those with substitution of Asp for Pro at position 238 (EU numbering), and one or more modifications selected from among Trp for the amino acid of position 237, Phe for the amino acid of position 237, Val for the amino acid of position 267, Gln for the amino acid of position 267, Asn for the amino acid of position 268, Gly for the amino acid of position 271, Leu for the amino acid of position 326, Gln for the amino acid of position 326, Glu for the amino acid of position 326, Met for the amino acid of position 326, Asp for the amino acid of position 239, Ala for the amino acid of position 267, Trp for the amino acid of position 234, Tyr for the amino acid of position 234, Ala for the amino acid of position 237, Asp for the amino acid of position 237, Glu for the amino acid of position 237, Leu for the amino acid of position 237, Met for the amino acid of position 237, Tyr for the amino acid of position 237, Lys for the amino acid of position 330, Arg for the amino acid of position 330, Asp for the amino acid of position 233, Asp for the amino acid of position 268, Glu for the amino acid of position 268, Asp for the amino acid of position 326, Ser for the amino acid of position 326, Thr for the amino acid of position 326, Ile for the amino acid of position 323, Leu for the amino acid of position 323, Met for the amino acid of position 323, Asp for the amino acid of position 296, Ala for the amino acid of position 326, Asn for the amino acid of position 326, and Met for the amino acid of position 330, according to EU numbering.

Antigen-Binding Molecule

In the present invention, an "antigen-binding molecule" is used in the broadest sense to refer to a molecule containing an antigen-binding domain and an Fc region. Specifically, the antigen-binding molecules include various types of molecules as long as they exhibit the antigen-binding activity. Molecules in which an antigen-binding domain is linked to an Fc region include, for example, antibodies. Antibodies may include single monoclonal antibodies (including agonistic antibodies and antagonistic antibodies), human antibodies, humanized antibodies, chimeric antibodies, and such. Alternatively, when used as antibody fragments, they preferably include antigen-binding domains and antigen-binding fragments (for example, Fab, F(ab')2, scFv, and Fv). Scaffold molecules where three dimensional structures, such as already-known stable α/β barrel protein structure, are used as a scaffold (base) and only some portions of the structures are made into libraries to construct antigen-binding domains are also included in antigen-binding molecules of the present invention.

An antigen-binding molecule of the present invention may contain at least some portions of an Fc region that mediates the binding to FcRn and Fcγ receptor. In a non-limiting embodiment, the antigen-binding molecule includes, for example, antibodies and Fc fusion proteins. A fusion protein refers to a chimeric polypeptide comprising a polypeptide having a first amino acid sequence that is linked to a polypeptide having a second amino acid sequence that would not naturally link in nature. For example, a fusion protein may comprise the amino acid sequence of at least a portion of an Fc region (for example, a portion of an Fc region responsible for the binding to FcRn or a portion of an Fc region responsible for the binding to Fcγ receptor) and a non-immunoglobulin polypeptide containing, for example, the amino acid sequence of the ligand-binding domain of a receptor or a receptor-binding domain of a ligand. The amino acid sequences may be present in separate proteins that are transported together to a fusion protein, or generally may be present in a single protein; however, they are included in a new rearrangement in a fusion polypeptide. Fusion proteins can be produced, for example, by chemical synthesis, or by genetic recombination techniques to express a polynucleotide encoding peptide regions in a desired arrangement.

Each of the domains of the antigen-binding domain, Fc region, and such of the present invention can be linked together via linkers or directly via polypeptide binding. The linkers comprise arbitrary peptide linkers that can be introduced by genetic engineering, synthetic linkers, and linkers disclosed in, for example, Protein Engineering (1996) 9(3), 299-305. However, peptide linkers are preferred in the present invention. The length of the peptide linkers is not particularly limited, and can be suitably selected by those skilled in the art according to the purpose. The length is preferably five amino acids or more (without particular limitation, the upper limit is generally 30 amino acids or less, preferably 20 amino acids or less), and particularly preferably 15 amino acids.

For example, such peptide linkers preferably include:

```
Ser

Gly•Ser

Gly•Gly•Ser

Ser•Gly•Gly
                                        (SEQ ID NO: 29)
Gly•Gly•Gly•Ser
                                        (SEQ ID NO: 30)
Ser•Gly•Gly•Gly
                                        (SEQ ID NO: 31)
Gly•Gly•Gly•Gly•Ser
                                        (SEQ ID NO: 32)
Ser•Gly•Gly•Gly•Gly
                                        (SEQ ID NO: 33)
Gly•Gly•Gly•Gly•Gly•Ser
                                        (SEQ ID NO: 34)
Ser•Gly•Gly•Gly•Gly•Gly
                                        (SEQ ID NO: 35)
Gly•Gly•Gly•Gly•Gly•Gly•Ser
                                        (SEQ ID NO: 36)
Ser•Gly•Gly•Gly•Gly•Gly•Gly (Gly•Gly•Gly•Gly•Ser (SEQ ID NO: 31))n (Ser•Gly•Gly•Gly•Gly (SEQ ID NO: 32))n
``` where n is an integer of 1 or larger. The length or sequences of peptide linkers can be selected accordingly by those skilled in the art depending on the purpose.

Synthetic linkers (chemical crosslinking agents) is routinely used to crosslink peptides, and for example:
N-hydroxy succinimide (NHS),
disuccinimidyl suberate (DSS),
bis(sulfosuccinimidyl) suberate ($BS^3$),
dithiobis(succinimidyl propionate) (DSP),
dithiobis(sulfosuccinimidyl propionate) (DTSSP),
ethylene glycol bis(succinimidyl succinate) (EGS),
ethylene glycol bis(sulfosuccinimidyl succinate) (sulfo-EGS), disuccinimidyl tartrate (DST), disulfosuccinimidyl tartrate (sulfo-DST),
bis[2-(succinimidoxycarbonyloxy)ethyl] sulfone (BSOCOES),
and bis[2-(sulfosuccinimidoxycarbonyloxy)ethyl] sulfone (sulfo-BSOCOES). These crosslinking agents are commercially available.

When multiple linkers for linking the respective domains are used, they may all be of the same type, or may be of different types.

In addition to the linkers exemplified above, linkers with peptide tags such as His tag, HA tag, myc tag, and FLAG tag may also be suitably used. Furthermore, hydrogen bonding, disulfide bonding, covalent bonding, ionic interaction, and properties of binding with each other as a result of combination thereof may be suitably used. For example, the affinity between CH1 and CL of antibody may be used, and Fc regions originating from the above-described bispecific antibodies may also be used for hetero Fc region association. Moreover, disulfide bonds formed between domains may also be suitably used.

In order to link the respective domains via peptide linkage, polynucleotides encoding the domains are linked in frame. Known methods for linking polynucleotides in frame include techniques such as ligation of restriction fragments, fusion PCR, and overlapping PCR. Such methods can be appropriately used alone or in combination to produce the antigen-binding molecules of the present invention. In the present invention, the terms "linked" and "fused", or "linkage" and "fusion" are used interchangeably. These terms mean that two or more elements or components such as polypeptides are linked together to form a single structure by any means including the above-described chemical linking means and recombination techniques. When two or more domains, elements, or components are polypeptides, linking in frame means linking two or more units of reading frames to form a longer continuous reading frame while maintaining the correct reading frames of the polypeptides. When two molecules of Fab are used as the antigen-binding domain, an antibody which is an antigen-binding molecule of the present invention in which the antigen-binding domain is linked in frame to an Fc region by a peptide bond and not via a linker can be used as a suitable antigen-binding molecule of the present application.

Complex Containing Two or More Antigen-Binding Molecules and Two or More Antigenic Binding Units As described in Example 1 (as shown in WO 2011/122011), Fv4-IgG1, of which sIL-6R-binding activity changes depending on the pH condition more greatly than that of H54/L28-IgG1, accelerates elimination of sIL-6R but does not accelerate the elimination more than when sIL-6R is used alone. To accelerate the elimination more than when sIL-6R is used alone, antigen-binding molecules comprising an Fc region with enhanced FcRn binding in the neutral pH range (for example, Fv4-IgG1-v2 and such of Example 1) must be used.

Meanwhile, surprisingly, GA2-IgG1, of which human IgA-binding activity varies depending on the Ca ion concentration, was revealed to accelerate the elimination of human IgA more than when human IgA is used alone, even though it contains an Fc region derived from native IgG1, which FcRn binding in the neutral pH range is not enhanced. Similarly, clone 278 of which human IgE-binding activity varies depending on the pH condition, was revealed to accelerate the elimination of human IgE more than when human IgE is used alone, even though it contains an Fc region derived from native IgG1, which does not have enhanced FcRn binding in the neutral pH range. Without being restricted to a particular theory, the following exemplary mechanism is thought to account for what happened with GA2-IgG1 and clone 278.

When the antigenic binding unit is one unit (i.e., a homomonomer), such as in sIL-6R, two molecules ((i.e., two antigenic binding units) of antigens bind to a single antibody molecule containing a divalent antigen-binding domain, and a complex of one anti-sIL-6R antibody molecule and two antigen molecules containing two antigenic binding units is formed. Therefore, this type of antigen-antibody complex has only one Fc region (native IgG1 Fc region) as shown in FIG. 1. Since this complex binds to two molecules of FcRn or one molecule of FcγR via a single Fc region, the affinity toward these receptors is the same as that of a general IgG antibody, and uptake into cells is thought to occur mostly non-specifically.

On the other hand, when the antigenic binding unit is two units as in human IgA, which is a dimer of a hetero-complex of heavy chains and light chains, there are two units of epitopes to which the antigen-binding domains will bind in the antigenic binding unit. However, when a bivalent anti-IgA antibody (i.e., the antigen-binding domains contained in one anti-IgA antibody molecule bind to a same epitope) binds to its antigen, IgA, it is thought that binding of each of the bivalent antigen-binding domains contained in the single anti-IgA antibody molecule to each of the two epitope units present on a single IgA molecule is difficult in view of the position of the epitopes. As a result, it is thought that separate anti-IgA antibody molecules bind to the two antigenic binding units present in the two molecules of IgA that bind to the bivalent antigen-binding domains present in a single anti-IgA antibody molecule, and consequently, antigen-antibody complexes (immune complexes) containing at least four molecules (that is, two IgA molecules which are antigen molecule, and two anti-IgA antibody molecules which are antigen-binding molecules) are formed.

Figure 7:
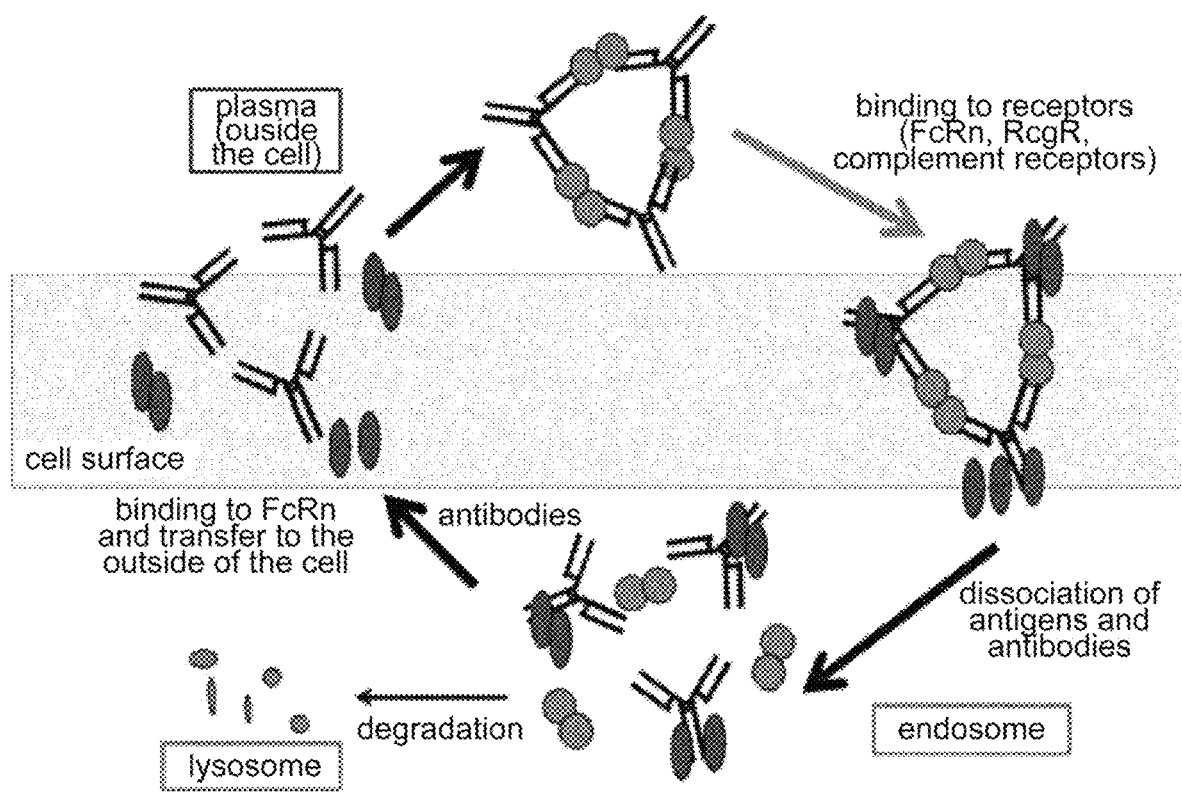
FIG. 7 is an illustrative diagram showing the efficiency of antigen elimination per antibody molecule for a pH/Ca-dependent antibody having the constant region of natural IgG which forms a large immune complex with a multimeric antigen.

When an antigen-binding molecule such as an antibody binding to an antigen molecule that contains two or more antigenic binding units, forms a large immune complex which is at least a tetramer, the immune complex can bind strongly with avidity through at least two or more multivalent Fc regions to FcγR, FcRn, complement receptors, and such. Therefore, as shown in FIG. 7, the complex is taken up into cells expressing these receptors with a higher efficiency than native IgG1. On the other hand, since the Fc region-mediated affinity toward these receptors of immune complexes formed of antigen molecules and antigen-binding molecules that for example bind to (monomeric) antigen molecules containing one antigenic binding unit is insufficient as mentioned above, the immune complexes are taken up mostly nonspecifically (less efficiently as compared to uptake mediated by avidity binding) into cells expressing these receptors, as shown in FIG. 1. Thus, the uptake is more inefficient than uptake mediated by avidity binding.

When the antigen-binding molecule such as an antibody that binds to an antigen molecule containing two or more antigenic binding units is an antibody that contains antigen-binding domains of which antigen-binding varies depending on an ion concentration condition such as pH- or Ca-dependent binding and which forms an antigen-antibody complex (immune complex) containing at least four molecules (two antigen molecules and two antibody molecules) in the plasma, once the immune complex is taken up into cells, the antigens dissociate from the antibodies in the endosomes where the ion concentration conditions are different from those in the plasma. Therefore, the immune complex formation is dissolved in the endosomes of cells that have taken up the immune complexes. Since the dissociated antigens cannot bind to FcRn in the endosomes, they are degraded after translocating to the lysosomes. On the other hand, the antigen-dissociated antibodies are thought to be recycled to the plasma after binding to FcRn in the endosomes (FIG. 7).

As described above, if an antibody that contains a native IgG1-type constant region against a multimeric antigen containing two or more antigenic binding units and shows pH- or Ca-dependent binding can form a large immune complex and bind to FcγR, FcRn, complement receptors, and such with avidity, it is thought that antigen elimination alone can be selectively and greatly accelerated. It is thought that when GA2-IgG1 which binds to human IgA is administered, such large immune complexes are formed. Indeed, as shown in Example 3, GA2-IgG1-FcγR(−) formed by introducing into GA2-IgG1 modifications that impair binding to mouse FcγR could not substantially accelerate elimination of human IgA like GA2-IgG1 when compared to human IgA alone, and showed an equivalent level of elimination as human IgA alone. Therefore, the reason that GA2-IgG1 could accelerate elimination of human IgA is because the immune complex containing GA2-IgG1 and human IgA, which is a multimeric antigen containing two or more antigenic binding units, binds with avidity to FcγR and is quickly taken up into cells expressing FcγR. The IgA that dissociates from the immune complex in the endosomes of cells that have taken up the immune complex is degraded in the lysosomes. At the same time, the IgA-dissociated antibody, which was bound to FcRn in the endosomes, is subsequently recycled to the plasma and can bind again to IgA in the plasma. Elimination of human IgA in the plasma is thought to be greatly accelerated in this manner. A method using an amino-acid-variant of the Fc region which binds to FcRn in the pH neutral range is described in WO2011/122011 as a method for accelerating elimination of antigens from the plasma. The present invention is useful as a method for accelerating the elimination from the plasma of multimeric antigens containing two or more antigenic binding units without using the above-mentioned variants, and as shown using GA2-N434W, can further accelerate the elimination of the multimeric antigens containing two or more antigenic binding units from the plasma through combination with the above-mentioned variants.

Method for Evaluating the Formation of Immune Complexes Comprising Two or More Antigen-Binding Molecules and Two or More Antigenic Binding Units In order to exhibit the effect of further accelerating the elimination of multimeric antigens comprising two or more antigenic binding units from the plasma as described above, it is considered preferable that a large immune complex of antigen-binding molecules and antigens are formed, and the Fc regions comprised in the antigen-binding molecules strongly bind to FcγR and/or FcRn with avidity. When the antigen contains two or more antigenic binding units, a large immune complex comprising two or more antigen-binding molecules and two or more antigenic binding units may be formed. Therefore, by screening for antigen-binding molecules of which binding activity to multimeric antigens containing two or more antigenic binding units changes according to an ion concentration and which bind with avidity to the above-mentioned receptors, antigen-binding molecules that further accelerate the elimination of multimeric antigens containing two or more antigenic binding units from plasma may be obtained.

Method for Evaluating Complex Formation

Figure 9:
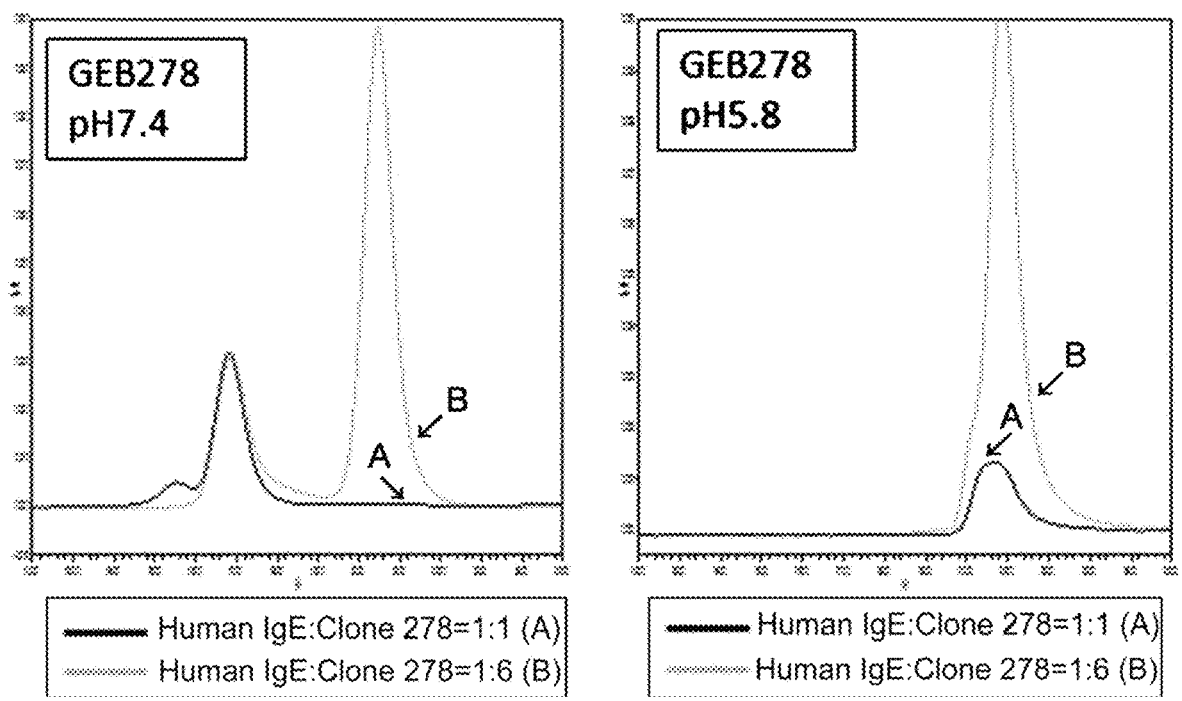
FIG. 9 shows the results of gel filtration chromatographic analyses which confirmed that human IgE and clone 278, which is a pH-dependent anti-IgE antibody, form large immune complexes in a pH-dependent manner.

Examples of methods for evaluating the formation of immune complexes comprising antigen-binding molecules and antigens include techniques in analytical chemistry, including methods that make use of the property that immune complexes become larger molecules than an antigen-binding molecule alone or an antigen molecule alone such as size exclusion (gel filtration) chromatography, ultracentrifugation analysis method, light-scattering method, electron microscopy, and mass spectrometry (Molecular Immunology (2002), 39, 77-84; Molecular Immunology (2009), 47, 357-364). For example, when size exclusion (gel filtration) chromatography is used as shown in FIG. 9, whether an immune complex is formed is evaluated by observing whether there are molecular species that are larger than those in analyses of the antigen molecule alone or the antigen-binding molecule alone.

Furthermore, when the antigen-binding molecule or antigen has an immunoglobulin constant region, examples include immunochemical methods including methods that use the property of the immune complex to bind more strongly to an Fc receptor or a complement component than the antigen-binding molecule alone or the antigen alone, such as ELISA, FACS, or SPR methods (for example, methods using a Biacore™ device) (The Journal of Biological Chemistry (2001) 276 (9), 6591-6604; Journal of Immunological Methods (1982) 50, 109-114; Journal of Immunology (2010) 184 (4), 1968-1976; mAbs (2009) 1 (5) 491-504). For example, when ELISA is performed by immobilizing an Fc receptor, formation of an immune complex is evaluated by observing whether the detected signal is increased as compared to when an antigen alone or an antigen-binding molecule alone is evaluated.

Method for Promoting the Elimination of Monomeric Antigens from Plasma Using a Cocktail of Antigen-Binding Molecules As described above, when the antigen is a multimeric antigen (a non-limiting example is an immunoglobulin such as IgA or IgE, or a member of the TNF superfamily such as TNF or CD154), a large immune complex comprising two or more antigen-binding molecules and two or more antigenic binding units may be formed. On the other hand, even when the antigen is monomeric, a mixture of two or more appropriate antigen-binding molecules that each binds to a separate epitope present on the monomeric antigen, where binding to the epitopes varies depending on an ion concentration condition (such as pH or Ca concentration) could also form a large immune complex containing two or more antigen-binding molecules and two or more antigenic binding units (monomeric antigens). Herein, the mixture of two or more appropriate antigen-binding molecules that each binds to a separate epitope present on a monomeric antigen, where binding to the epitopes varies depending on an ion concentration condition (such as pH or Ca concentration) is called an antigen-binding molecule cocktail. Among these antigen-binding molecules, at least one of (the antigen-binding domains comprised in) the antigen-binding molecules forming the immune complex needs to be an antigen-binding domain of which antigen-binding activity varies depending on an ion concentration condition.

Figure 8:
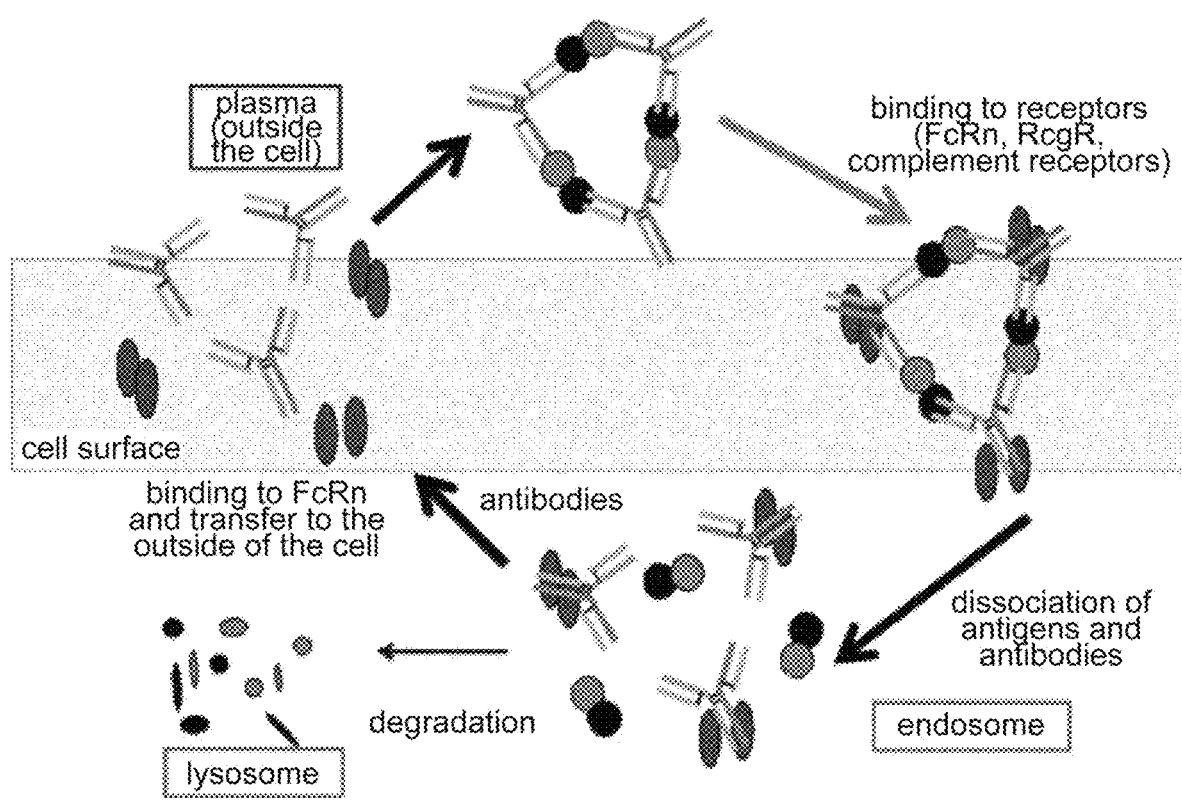
FIG. 8 is an illustrative diagram showing the efficiency of antigen elimination per antibody molecule for a pH/Ca-dependent multispecific antibody that recognizes two or more epitopes in a monomeric antigen and is suitable for formation of a large immune complex.

Method for Promoting Elimination of Monomeric Antigens from Plasma Using Multispecific or Multiparatopic Antigen-Binding Molecules Even in the case of a monomeric antigen, an antigen-binding molecule containing antigen-binding domains that each binds to a separate epitope present on the monomeric antigen, where binding of the antigen-binding domains to the respective epitopes varies depending on an ion concentration condition (such as pH or Ca concentration) could also form a large immune complex containing two or more antigen-binding molecules and two or more antigenic binding units (monomeric antigens). Examples of a non-limiting embodiment of such an antigen-binding molecule are multiparatopic antibodies or multispecific antibodies containing appropriate variable regions that bind to epitopes present on the monomeric antigen that differ from each other. As a non-limiting embodiment of such multispecific antibodies or multiparatopic antibodies, antibodies whose variable regions show pH- or Ca-dependent binding (bispecific antibodies or biparatopic antibodies containing a right-arm variable region that recognizes epitope A and a left-arm variable region that recognizes epitope B, as shown in FIG. 8) could also form a large immune complex containing two or more antibodies and two or more antigenic binding units (monomeric antigens).

Antigen-binding molecules that further accelerate the elimination of monomeric antigens from the plasma can be obtained by screening for combinations of antigen-binding domains that target different epitopes of a monomeric antigen, where the binding activity to each of the epitopes varies depending on an ion concentration condition, and which can bind with avidity to the abovementioned receptors. The ion concentration condition that changes the binding activity of a multispecific or multiparatopic antigen-binding domain toward each of the epitopes may be the same ion concentration condition or a different ion concentration condition. An antigen-binding molecule containing bispecific or biparatopic antigen-binding domains, where the epitope-binding activity of one of the bispecific or biparatopic antigen-binding domains varies depending on the pH condition or a metal ion concentration condition such as the Ca ion concentration, may be presented as an example of a non-limiting embodiment of the antigen-binding molecules of the present invention. Furthermore, an antigen-binding molecule containing bispecific or biparatopic antigen-binding domains, where the epitope-binding activity of one of the bispecific or biparatopic antigen-binding domains varies depending on the pH condition and the epitope-binding activity of the other antigen-binding domain varies depending on a metal ion concentration condition such as the Ca ion concentration, may also be presented as an example of a non-limiting embodiment of the antigen-binding molecules of the present invention. An antigen-binding molecule containing bispecific or biparatopic antigen-binding domains, where the epitope-binding activity of one of the bispecific or biparatopic antigen-binding domains varies depending on the pH condition and the epitope-binding activity of the other antigen-binding domain also varies depending on the pH condition, may also be presented as an example of a non-limiting embodiment of the antigen-binding molecules of the present invention. An antigen-binding molecule containing bispecific or biparatopic antigen-binding domains, where the epitope-binding activity of one of the bispecific or biparatopic antigen-binding domains varies depending on a metal ion concentration condition such as the Ca ion concentration and the epitope-binding activity of the other antigen-binding domain also varies depending on a metal ion concentration condition such as the Ca ion concentration, may also be presented as an example of a non-limiting embodiment of the antigen-binding molecules of the present invention.

Multispecific Antigen-Binding Molecules and Multiparatopic Antigen-Binding Molecules An antigen-binding molecule containing at least two antigen-binding domains, wherein at least one of the antigen-binding domains binds to a first epitope in an antigen molecule and at least another one of the antigen-binding domains binds to a second epitope in the antigen molecule, is called a multispecific antigen-binding molecule from the standpoint of its reaction specificity. When a single antigen-binding molecule binds to two different epitopes through two types of antigen-binding domains contained in the antigen-binding molecule, this antigen-binding molecule is called a bispecific antigen-binding molecule. When a single antigen-binding molecule binds to three different epitopes through three types of antigen-binding domains contained in the antigen-binding molecule, this antigen-binding molecule is called a trispecific antigen-binding molecule.

The paratope in an antigen-binding domain that binds to a first epitope in the antigen molecule has a different structure from that of the paratope in an antigen-binding domain that binds to a second epitope that is structurally different from the first epitope. Therefore, an antigen-binding molecule containing at least two antigen-binding domains, wherein at least one of the antigen-binding domains binds to a first epitope in an antigen molecule and at least another one of the antigen-binding domains binds to a second epitope in the antigen molecule, is called a multiparatopic antigen-binding molecule from the standpoint of its structure and specificity. When a single antigen-binding molecule binds to two different epitopes through two types of antigen-binding domains contained in the antigen-binding molecule, this antigen-binding molecule is called a biparatopic antigen-binding molecule. When a single antigen-binding molecule binds to three different epitopes through three types of antigen-binding domains contained in the antigen-binding molecule, this antigen-binding molecule is called a triparatopic antigen-binding molecule.

Multivalent multispecific or multiparatopic antigen-binding molecules comprising one or several antigen-binding domains and methods for preparing them have been described in Non-Patent Documents such as Conrath et al. (J. Biol. Chem. (2001) 276 (10) 7346-7350), Muyldermans (Rev. Mol. Biotech. (2001) 74, 277-302), and Kontermann R. E. (2011) Bispecific Antibodies (Springer-Verlag) and in Patent Documents such as WO 1996/034103 and WO 1999/023221. Antigen-binding molecules of the present invention can be produced using the multispecific or multiparatopic antigen-binding molecules and methods for preparing them described in these documents.

Bispecific Antibodies and Methods for Production Thereof

Bispecific antibodies and methods for production thereof are presented below as examples of an embodiment of the aforementioned multispecific or multiparatopic antigen-binding molecules and methods for production thereof. Bispecific antibodies are antibodies comprising two types of variable regions that bind specifically to different epitopes. IgG-type bispecific antibodies can be secreted from a hybrid hybridoma (quadroma) produced by fusing two types of hybridomas that produce IgG antibodies (Milstein et al., Nature (1983) 305, 537-540).

When a bispecific antibody is produced by using recombination techniques such as those described in the abovementioned section on antibodies, one may adopt a method that introduces genes encoding heavy chains containing the two types of variable regions of interest into cells to co-express them. However, even when only the heavy-chain combination is considered, such a co-expression method will produce a mixture of (i) a combination of a pair of heavy chains in which one of the heavy chains contains a variable region that binds to a first epitope and the other heavy chain contains a variable region that binds to a second epitope, (ii)

a combination of a pair of heavy chains which include only heavy chains containing a variable region that binds to the first epitope, and (iii) a combination of a pair of heavy chains which include only heavy chains containing a variable region that binds to the second epitope, which are present at a molecular ratio of 2:1:1. It is difficult to purify antigen-binding molecules containing the desired combination of heavy chains from the mixture of three types of heavy chain combinations.

When producing bispecific antibodies using such recombination techniques, bispecific antibodies containing a heteromeric combination of heavy chains can be preferentially secreted by adding appropriate amino acid substitutions in the CH3 domains constituting the heavy chains. Specifically, this method is conducted by substituting an amino acid having a larger side chain (knob (which means "bulge")) for an amino acid in the CH3 domain of one of the heavy chains, and substituting an amino acid having a smaller side chain (hole (which means "void")) for an amino acid in the CH3 domain of the other heavy chain so that the knob is placed in the hole. This promotes heteromeric heavy chain formation and simultaneously inhibits homomeric heavy chain formation (International Publication No. WO 1996027011; Ridgway et al., Protein Engineering (1996) 9, 617-621; Merchant et al., Nature Biotechnology (1998) 16, 677-681).

Furthermore, there are also known techniques for producing a bispecific antibody by applying methods for controlling polypeptide association, or association of polypeptide-formed heteromeric multimers to the association between heavy chains. Specifically, methods for controlling heavy chain formation may be employed to produce a bispecific antibody (International Publication No. WO 2006/106905), in which amino acid residues forming the interface between the heavy chains are altered to inhibit the association between the heavy chains having the same sequence and to allow the formation of heavy chains of different sequences. Such methods can be used for generating bispecific antibodies.

In a non-limiting embodiment of the present invention, two polypeptides forming an Fc region derived from a bispecific antibody described above can be suitably used as the Fc region contained in an antigen-binding molecule. More specifically, two polypeptides forming an Fc region may be suitably used, in which, of the amino acid sequence of one of the polypeptides, the amino acid at position 349 as indicated by EU numbering is Cys and the amino acid at position 366 is Trp, and of the amino acid sequence of the other of the polypeptides, the amino acid at position 356 as indicated by EU numbering is Cys, the amino acid at position 366 is Ser, the amino acid at position 368 is Ala, and the amino acid at position 407 is Val.

In another non-limiting embodiment of the present invention, two polypeptides forming an Fc region, in which, of the amino acid sequence of one of the polypeptides, the amino acid at position 409 according to EU numbering is Asp, and of the amino acid sequence of the other of the polypeptides, the amino acid at position 399 according to EU numbering is Lys, may be suitably used as the Fc region. In the above embodiment, the amino acid at position 409 may be Glu instead of Asp, and the amino acid at position 399 may be Arg instead of Lys. Moreover, in addition to the amino acid Lys at position 399, Asp may suitably be added as amino acid at position 360 or Asp may suitably be added as amino acid at position 392.

In still another non-limiting embodiment of the present invention, two polypeptides forming an Fc region, in which, of the amino acid sequence of one of the polypeptides, the amino acid at position 370 according to EU numbering is Glu, and of the amino acid sequence of the other of the polypeptides, the amino acid at position 357 according to EU numbering is Lys, may be suitably used as the Fc region.

In yet another non-limiting embodiment of the present invention, two polypeptides forming an Fc region, in which, of the amino acid sequence of one of the polypeptides, the amino acid at position 439 according to EU numbering is Glu, and of the amino acid sequence of the other of the polypeptides, the amino acid at position 356 according to EU numbering is Lys, may be suitably used as the Fc region.

In still yet another non-limiting embodiment of the present invention, any of the embodiments indicated below, in which the above have been combined, may be suitably used as the Fc region:

(i) two polypeptides forming an Fc region, in which, of the amino acid sequence of one of the polypeptides, the amino acid at position 409 according to EU numbering is Asp and the amino acid at position 370 is Glu, and of the amino acid sequence of the other of the polypeptides, the amino acid at position 399 according to EU numbering is Lys and the amino acid at position 357 is Lys (in this embodiment, the amino acid at position 370 according to EU numbering may be Asp instead of Glu, and the amino acid Asp at position 392 according to EU numbering may be used instead of the amino acid Glu at position 370 according to EU numbering);

(ii) two polypeptides forming an Fc region, in which, of the amino acid sequence of one of the polypeptides, the amino acid at position 409 according to EU numbering is Asp and the amino acid at position 439 is Glu, and of the amino acid sequence of the other of the polypeptides, the amino acid at position 399 according to EU numbering is Lys and the amino acid at position 356 is Lys (in this embodiment, the amino acid Asp at position 360 according to EU numbering, the amino acid Asp at position 392 according to EU numbering, or the amino acid Asp at position 439 according to EU numbering may be used instead of the amino acid Glu at position 439 according to EU numbering);

(iii) two polypeptides forming an Fc region, in which, of the amino acid sequence of one of the polypeptides, the amino acid at position 370 according to EU numbering is Glu and the amino acid at position 439 is Glu, and of the amino acid sequence of the other of the polypeptides, the amino acid at position 357 according to EU numbering is Lys and the amino acid at position 356 is Lys; and two polypeptides forming an Fc region, in which, of the amino acid sequence of one of the polypeptides, the amino acid at position 409 according to EU numbering is Asp, the amino acid at position 370 is Glu, and the amino acid at position 439 is Glu, and of the amino acid sequence of the other of the polypeptides, the amino acid at position 399 according to EU numbering is Lys, the amino acid at position 357 is Lys, and the amino acid at position 356 is Lys (in this embodiment, the amino acid at position 370 according to EU numbering may not be substituted to Glu, and futhermore, when the amino acid at position 370 is not substituted to Glu, the amino acid at position 439 may be Asp instead of Glu, or the amino acid Asp at position 392 may be used instead of the amino acid Glu at position 439).

Further, in another non-limiting embodiment of the present invention, two polypeptides forming an Fc region, in which, of the amino acid sequence of one of the polypeptides, the amino acid at position 356 according to EU numbering is Lys, and of the amino acid sequence of the other of the polypeptides, the amino acid at position 435 according to EU numbering is Arg and the amino acid at position 439 is Glu, may also be suitably used.

In still another non-limiting embodiment of the present invention, two polypeptides forming an Fc region, in which, of the amino acid sequence of one of the polypeptides, the amino acid at position 356 according to EU numbering is Lys and the amino acid at position 357 is Lys, and of the amino acid sequence of the other of the polypeptides, the amino acid at position 370 according to EU numbering is Glu, the amino acid at position 435 is Arg, and the amino acid at position 439 is Glu, may also be suitably used.

Furthermore, in addition to the above-mentioned technique of associating heterologous heavy chains, the CrossMab technology which is known as a technology for associating heterologous light chains, in which a light chain forming a variable region that binds to a first epitope and a light chain forming a variable region that binds to a second epitope are respectively associated with a heavy chain forming a variable region that binds to the first epitope and a heavy chain forming a variable region that binds to the second epitope (Scaefer et al. (Proc. Natl. Acad. Sci. U.S.A. (2011) 108, 11187-11192)), may also be used to produce the multispecific or multiparatopic antigen-binding molecules provided by the present invention.

Use of an Antigen-Binding Molecule to Eliminate Antigens Containing Two or More Antigenic Binding Units from the Plasma The present invention provides use of an antigen-binding molecule comprising (i) an Fc region and (ii) an antigen-binding domain of which antigen-binding activity varies depending on an ion concentration condition;
wherein the antigen-binding molecule can form an immune complex comprising (a) two or more of the antigen-binding molecules and (b) two or more antigen molecules provided that the antigens comprise two or more antigenic binding units, for eliminating the antigens from the plasma.

In the present invention, embodiments of the use of an antigen-binding molecule are not particularly limited as long as antigens can be eliminated from the plasma. Examples of a non-limiting embodiment of such use are pharmaceutical compositions containing an antigen-binding molecule provided by the present invention, and methods comprising administering to a subject an antigen-binding molecule provided by the present invention. An example of another non-limiting embodiment is use of the antigen-binding molecule in an ex vivo method for eliminating antigens from plasma, which includes contacting an immune complex formed through contact of an antigen-binding molecule of the present invention with plasma isolated from a subject, and containing two or more of the antigen-binding molecules and two or more antigens (provided that the antigens include two or more antigenic binding units) with FcRn- or Fcγ receptor-expressing cells.

Improvement of Pharmacokinetics

In the present invention, the "ability to eliminate antigens in plasma" refers to the ability to eliminate from the plasma antigens that are present in the plasma when the antigen-binding molecules are administered in vivo or when the antigen-binding molecules are secreted in vivo. Thus, in the present invention, the phrase "the ability of an antigen-binding molecule to eliminate an antigen in the plasma is increased" can be used when the rate of antigen elimination from the plasma is accelerated when the antigen-binding molecule is administered, as compared to administration of antigen-binding molecules that cannot form the immune complexes disclosed in the present invention, antigen-binding molecules containing antigen-binding domains of which antigen-binding activity is independent of the ion concentration, or antigen-binding molecules containing Fc regions with compromised binding activity toward FcγR or FcRn. Whether or not the ability of an antigen-binding molecule to eliminate an antigen in the plasma is increased can be assessed, for example, by administering a soluble antigen and the antigen-binding molecule in vivo and measuring the plasma concentration of the soluble antigen after administration. The ability of an antigen-binding molecule to eliminate an antigen in the plasma is judged to be increased if the concentration of a soluble antigen in the plasma is decreased after administration of the soluble antigen, and the antigen-binding molecule which is an antigen-binding molecule capable of forming an immune complex containing two or more antigen-binding molecules and antigens with two or more antigenic binding units, and of which antigen-binding activity changes depending on ion concentrations such as reduction of the antigen-binding activity in the acidic pH range compared to in the neutral pH range (or reduction of the antigen-binding activity at a low calcium ion concentration compared to at a high calcium ion concentration). The soluble antigen may be an antigen that is bound to an antigen-binding molecule or an antigen that is not bound to an antigen-binding molecule in the plasma, and its concentration can be determined as a "plasma concentration of the antigen bound to the antigen-binding molecule" or as a "plasma concentration of the antigen not bound to the antigen-binding molecule", respectively (the latter is synonymous with "free antigen concentration in plasma"). The "total antigen concentration in plasma" means the sum of concentrations of the antigen-binding molecule-bound antigen and the antigen not bound by an antigen-binding molecule, or the "free antigen concentration in plasma" which is the concentration of the antigen not bound by an antigen-binding molecule. Thus, the soluble antigen concentration can be determined as the "total antigen concentration in plasma". Various methods for measuring the "total antigen concentration in plasma" or the "free antigen concentration in plasma" are well known in the art as described hereinafter.

Herein, "enhancement of pharmacokinetics", "improvement of pharmacokinetics", and "superior pharmacokinetics" can be restated as "enhancement of plasma (blood) retention", "improvement of plasma (blood) retention", "superior plasma (blood) retention", and "prolonged plasma (blood) retention". These terms are synonymous.

Herein, "improvement of pharmacokinetics" means not only prolongation of the period until elimination from the plasma (for example, until the antigen-binding molecule is degraded intracellularly or the like and cannot return to the plasma) after administration of the antigen-binding molecule to humans, or non-human animals such as mice, rats, monkeys, rabbits, and dogs, but also prolongation of the plasma retention of the antigen-binding molecule in a form that allows antigen binding (for example, in an antigen-free form of the antigen-binding molecule) during the period of administration to elimination due to degradation. Human IgG having wild-type Fc region can bind to FcRn from non-human animals. For example, mouse can be preferably used to be administered in order to confirm the property of the antigen-binding molecule of the invention since human IgG having wild-type Fc region can bind to mouse FcRn stronger than to human FcRn (Int Immunol. (2001) 13(12): 1551-1559). As another example, mouse in which its native FcRn genes are disrupted and a transgene for human FcRn gene is harbored to be expressed (Methods Mol Biol. 2010; 602: 93-104) can also be preferably used to be administered in order to confirm the property of the antigen-binding molecule of the invention described hereinafter. Specifically, "improvement of pharmacokinetics" also includes prolongation of the period until elimination due to degradation of the antigen-binding molecule not bound to antigens (the antigen-free form of antigen-binding molecule). The antigen-binding molecule in plasma cannot bind to a new antigen if the antigen-binding molecule has already bound to an antigen. Thus, the longer the period that the antigen-binding molecule is not bound to an antigen, the longer the period that it can bind to a new antigen (the higher the chance of binding to another antigen). This enables reduction of the time period that an antigen is free of the antigen-binding molecule in vivo and prolongation of the period that an antigen is bound to the antigen-binding molecule. The plasma concentration of the antigen-free form of antigen-binding molecule can be increased and the period that the antigen is bound to the antigen-binding molecule can be prolonged by accelerating the antigen elimination from the plasma by administration of the antigen-binding molecule. Specifically, herein "improvement of the pharmacokinetics of antigen-binding molecule" includes the improvement of a pharmacokinetic parameter of the antigen-free form of the antigen-binding molecule (any of prolongation of the half-life in plasma, prolongation of mean retention time in plasma, and impairment of plasma clearance), prolongation of the period that the antigen is bound to the antigen-binding molecule after administration of the antigen-binding molecule, and acceleration of antigen-binding molecule-mediated antigen elimination from the plasma. The improvement of pharmacokinetics of antigen-binding molecule can be assessed by determining any one of the parameters, half-life in plasma, mean plasma retention time, and plasma clearance for the antigen-binding molecule or the antigen-free form thereof ("Pharmacokinetics: Enshuniyoru Rikai (Understanding through practice)" Nanzando). For example, the plasma concentration of the antigen-binding molecule or antigen-free form thereof is determined after administration of the antigen-binding molecule to mice, rats, monkeys, rabbits, dogs, or humans. Then, each parameter is determined. When the plasma half-life or mean plasma retention time is prolonged, the pharmacokinetics of the antigen-binding molecule can be judged to be improved. The parameters can be determined by methods known to those skilled in the art. The parameters can be appropriately assessed, for example, by noncompartmental analysis using the pharmacokinetics analysis software WinNonlin (Pharsight) according to the appended instruction manual. The plasma concentration of antigen-free antigen-binding molecule can be determined by methods known to those skilled in the art, for example, using the assay method described in Clin Pharmacol. 2008 April; 48(4): 406-417.

Herein, "improvement of pharmacokinetics" also includes prolongation of the period that an antigen is bound to an antigen-binding molecule after administration of the antigen-binding molecule. Whether the period that an antigen is bound to the antigen-binding molecule after administration of the antigen-binding molecule is prolonged can be assessed by determining the plasma concentration of free antigen. The prolongation can be judged based on the determined plasma concentration of free antigen or the time period required for an increase in the ratio of free antigen concentration to the total antigen concentration.

The plasma concentration of free antigen not bound to the antigen-binding molecule or the ratio of free antigen concentration to the total antigen concentration can be determined by methods known to those skilled in the art, for example, by the method used in Pharm Res. 2006 January; 23 (1): 95-103. Alternatively, when an antigen exhibits a particular function in vivo, whether the antigen is bound to an antigen-binding molecule that neutralizes the antigen function (antagonistic molecule) can be assessed by testing whether the antigen function is neutralized. Whether the antigen function is neutralized can be assessed by assaying an in vivo marker that reflects the antigen function. Whether the antigen is bound to an antigen-binding molecule that activates the antigen function (agonistic molecule) can be assessed by assaying an in vivo marker that reflects the antigen function.

Determination of the plasma concentration of free antigen and ratio of the amount of free antigen in plasma to the amount of total antigen in plasma, in vivo marker assay, and such measurements are not particularly limited; however, the assays are preferably carried out after a certain period of time has passed after administration of the antigen-binding molecule. In the present invention, the period after administration of the antigen-binding molecule is not particularly limited; those skilled in the art can determine the appropriate period depending on the properties and the like of the administered antigen-binding molecule. Such periods include, for example, one day after administration of the antigen-binding molecule, three days after administration of the antigen-binding molecule, seven days after administration of the antigen-binding molecule, 14 days after administration of the antigen-binding molecule, and 28 days after administration of the antigen-binding molecule. Herein, the concept "plasma antigen concentration" comprises both "total antigen concentration in plasma" which is the sum of antigen-binding molecule bound antigen and non-bound antigen concentration or "free antigen concentration in plasma" which is antigen-binding molecule non-bound antigen concentration.

The total antigen concentration in the plasma can be lowered by administration, as antigen-binding molecule, of the antigen-binding molecule of the present invention by 2-fold, 5-fold, 10-fold, 20-fold, 50-fold, 100-fold, 200-fold, 500-fold, 1,000-fold, or even higher as compared to administration of an antigen-binding molecule containing an antigen-binding domain whose antigen-binding activity is ion concentration-independent or an antigen-binding molecule containing an Fc region with an impaired FcγR-binding activity, or compared to when the antigen-binding domain molecule of the present invention is not administered.

Molar antigen/antigen-binding molecule ratio can be calculated as shown below:
value A: Molar antigen concentration at each time point
value B: Molar antigen-binding molecule concentration at each time point
value C: Molar antigen concentration per molar antigen-binding molecule concentration (molar antigen/antigen-binding molecule ratio) at each time point $C=A/B.$ Smaller value C indicates higher efficiency of antigen elimination per antigen-binding molecule whereas higher value C indicates lower efficiency of antigen elimination per antigen-binding molecule.

Molar antigen/antigen-binding molecule ratio can be calculated as described above.

Administering an antigen-binding molecule of the present invention can lower the molar antigen/antigen-binding molecule ratio by 2-fold, 5-fold, 10-fold, 20-fold, 50-fold, 100-fold, 200-fold, 500-fold, 1000-fold or more as compared to administration of antigen-binding molecules that cannot form the immune complexes disclosed in the present invention, antigen-binding molecules containing antigen-binding domains of which antigen-binding activity is independent of ion concentrations, or antigen-binding molecules containing Fc regions with compromised binding activity toward FcγR or FcRn.

In the present invention, as reference for comparison with the antigen-binding molecules of the present invention, antigen-binding molecules that cannot form the immune complexes disclosed in the present invention, antigen-binding molecules containing antigen-binding domains of which antigen-binding activity is independent of ion concentrations, or antigen-binding molecules containing Fc regions with compromised binding activity toward FcγR or FcRn.

When an FcRn-mediated pathway is used in the incorporation of antigen-binding molecules of the present invention from the plasma into cells, reduction in the total antigen concentration in plasma or the molar antigen/antibody ratio can also be assessed using human FcRn transgenic mouse line 32 or line 276 (Jackson Laboratories, Methods Mol Biol. 2010; 602: 93-104) by either antigen-antibody co-injection model or steady-state antigen infusion model when the antigen-binding molecule do not cross-react to the mouse counterpart antigen. When the antigen-binding molecule cross-react with the mouse counterpart, they can also be assessed by simply injecting the antigen-binding molecule to human FcRn transgenic mouse line 32 or line 276 (Jackson Laboratories). In the co-injection model, mixture of the antigen-binding molecule and antigen is administered to mice. In the steady-state antigen infusion model, infusion pump filled with an antigen solution is embedded into mice to achieve a constant plasma antigen concentration, and then the antigen-binding molecule is injected to the mice. Test antigen-binding molecules are administered at the same dosage. The total antigen concentration in plasma, free antigen concentration in plasma, and antigen-binding molecule concentration in plasma are measured at appropriate time points using method known to those skilled in the art.

When an FcγR-mediated pathway is used in the incorporation of antigen-binding molecules of the present invention from the plasma into cells, reduction in the total antigen concentration in plasma or the molar antigen/antibody ratio can be assessed by either the antigen-antibody co-injection model or the steady-state antigen infusion model using the conventionally used C57BL/6J mice (Charles River Japan) when the antigen-binding molecule does not cross-react with the mouse counterpart antigen. If the antigen-binding molecule cross-reacts with the mouse counterpart, assessment can be carried out simply by injecting the antigen-binding molecule into the conventionally used C57BL/6J mice (Charles River Japan).

In the co-injection model, a mixture of the antigen-binding molecule and antigen is administered to mice. In the steady-state antigen infusion model, an infusion pump filled with an antigen solution is embedded into mice to achieve a constant plasma antigen concentration, and then the antigen-binding molecule is injected into the mice. Test antigen-binding molecules are administered at the same dose. The total antigen concentration in plasma, free antigen concentration in plasma, and antigen-binding molecule concentration in plasma are measured at appropriate time points using methods known to those skilled in the art.

Total or free antigen concentration in plasma and molar antigen/antigen-binding molecule ratio can be measured at 2, 4, 7, 14, 28, 56, or 84 days after administration to evaluate the long-term effect of the present invention. In other words, a long term plasma antigen concentration is determined by measuring total or free antigen concentration in plasma and molar antigen/antigen-binding molecule ratio at 2, 4, 7, 14, 28, 56, or 84 days after administration of an antigen-binding molecule in order to evaluate the property of the antigen-binding molecule of the present invention. Whether the reduction of plasma antigen concentration or molar antigen/antigen-binding molecule ratio is achieved by antigen-binding molecule described in the present invention can be determined by the evaluation of the reduction at any one or more of the time points described above.

Total or free antigen concentration in plasma and molar antigen/antigen-binding molecule ratio can be measured at 15 min, 1, 2, 4, 8, 12, or 24 hours after administration to evaluate the short-term effect of the present invention. In other words, a short term plasma antigen concentration is determined by measuring total or free antigen concentration in plasma and molar antigen/antigen-binding molecule ratio at 15 min, 1, 2, 4, 8, 12, or 24 hours after administration of an antigen-binding molecule in order to evaluate the property of the antigen-binding molecule of the present invention.

The route of administration of an antigen-binding molecule of the present invention can be selected from intradermal, intravenous, intravitreal, subcutaneous, intraperitoneal, parenteral and intramuscular injection.

In the present invention, it is preferable that the pharmacokinetics of the antigen-binding molecule in human is improved. When the plasma retention in human is difficult to determine, it may be predicted based on the plasma retention in mice (for example, normal mice, human antigen-expressing transgenic mice, human FcRn-expressing transgenic mice) or monkeys (for example, cynomolgus monkeys).

Herein, "the improvement of the pharmacokinetics and prolonged plasma retention of an antigen-binding molecule" means improvement of any pharmacokinetic parameter (any of prolongation of the half-life in plasma, prolongation of mean retention time in plasma, reduction of plasma clearance, and bioavailability) after in vivo administration of the antigen-binding molecule, or an increase in the concentration of the antigen-binding molecule in the plasma in an appropriate time after administration. It may be determined by measuring any parameter such as half-life in plasma, mean retention time in plasma, plasma clearance, and bioavailability of the antigen-binding molecule (Pharmacokinetics: Enshu-niyoru Rikai (Understanding through practice), (Nanzando)). For example, when an antigen-binding molecule is administered to mice (normal mice and human FcRn transgenic mice), rats, monkeys, rabbits, dogs, humans, and so on, and the concentration of the antigen-binding molecule in the plasma is determined and each of the parameters is calculated, the pharmacokinetics of the antigen-binding molecule can be judged to be improved when the plasma half-life or mean retention time in the plasma is prolonged. These parameters can be determined by methods known to those skilled in the art. For example, the parameters can be appropriately assessed by non-compartmental analysis using pharmacokinetics analysis software WinNonlin (Pharsight) according to the attached instruction manual.

Without being restricted to a particular theory, the following mechanism is an example of a mechanism that allows elimination of antigenic binding units from the plasma by an antigen-binding molecule of the present invention which comprises (i) an Fc region and (ii) an antigen-binding domain of which antigen-binding activity varies depending on an ion concentration condition, wherein the antigen-binding molecule can form an immune complex containing two or more of the antigen-binding molecules and antigens comprising two or more antigenic binding units. When the antigenic binding unit is one unit (i.e., a monomer), such as in sIL-6R, two molecules ((i.e., two antigenic binding units) of antigens bind to a single antibody molecule containing a divalent antigen-binding domain, and a complex of one anti-sIL-6R antibody molecule and two antigen molecules containing two antigenic binding units is formed. Therefore, this type of antigen-antibody complex has only one Fc region (native IgG1 Fc region) as shown in FIG. 1. Since this complex binds to two molecules of FcRn or one molecule of FcγR via a single Fc region, the affinity toward these receptors is the same as that of a general IgG antibody, and uptake into cells is thought to occur mostly non-specifically.

On the other hand, when the antigenic binding unit is two units as in human IgA, which is a dimer of a hetero-complex of heavy chains and light chains, there are two units of epitopes to which the antigen-binding domains will bind in the antigenic binding unit. However, when a bivalent anti-IgA antibody (i.e., the antigen-binding domains contained in one anti-IgA antibody molecule bind to a same epitope) binds to its antigen, IgA, it is thought that binding of each of the bivalent antigen-binding domains contained in the single anti-IgA antibody molecule to each of the two epitope units present on a single IgA molecule is difficult in view of the position of the epitopes. As a result, it is thought that separate anti-IgA antibody molecules bind to the two antigenic binding units present in the two molecules of IgA that bind to the bivalent antigen-binding domains present in a single anti-IgA antibody molecule, and consequently, antigen-antibody complexes (immune complexes) containing at least four molecules (that is, two IgA molecules which are antigen molecule, and two anti-IgA antibody molecules which are antigen-binding molecules) are formed.

When an antigen-binding molecule such as an antibody binding to an antigen molecule that contains two or more antigenic binding units, forms a large immune complex which is at least a tetramer, the immune complex can bind strongly with avidity through at least two or more multivalent Fc regions to FcγR, FcRn, complement receptors, and such. Therefore, as shown in FIG. 7, the complex is taken up efficiently into cells expressing these receptors. On the other hand, since the Fc region-mediated affinity toward these receptors of immune complexes formed of antigen molecules and antigen-binding molecules that for example bind to (monomeric) antigen molecules containing one antigenic binding unit is insufficient as mentioned above, the immune complexes are taken up mostly nonspecifically (less efficiently as compared to uptake mediated by avidity binding) into cells expressing these receptors, as shown in FIG. 1. Thus, the uptake is more inefficient than uptake mediated by avidity binding.

When the antigen-binding molecule such as an antibody that binds to an antigen molecule containing two or more antigenic binding units is an antibody that contains antigen-binding domains of which antigen-binding varies depending on an ion concentration condition such as pH- or Ca-dependent binding and which forms an antigen-antibody complex (immune complex) containing at least four molecules (two antigen molecules and two antibody molecules) in the plasma, once the immune complex is taken up into cells, the antigens dissociate from the antibodies in the endosomes where the ion concentration conditions are different from those in the plasma. Therefore, the immune complex formation is dissolved in the endosomes of cells that have taken up the immune complexes. Since the dissociated antigens cannot bind to FcRn in the endosomes, they are degraded after translocating to the lysosomes. On the other hand, the antigen-dissociated antibodies are thought to be recycled to the plasma after binding to FcRn in the endosomes (FIG. 7).

As described above, if an antibody that contains a native IgG1-type constant region against a multimeric antigen containing two or more antigenic binding units and shows pH- or Ca-dependent binding can form a large immune complex and bind to FcγR, FcRn, complement receptors, and such with avidity, it is thought that antigen elimination alone can be selectively and greatly accelerated. It is thought that when GA2-IgG1 which binds to human IgA is administered, such large immune complexes are formed. Indeed, as shown in Example 3, GA2-IgG1-FcγR(−) formed by introducing into GA2-IgG1 modifications that impair binding to mouse FcγR could not substantially accelerate elimination of human IgA like GA2-IgG1 when compared to human IgA alone, and showed an equivalent level of elimination as human IgA alone. Therefore, the reason that GA2-IgG1 could accelerate elimination of human IgA is because the immune complex containing GA2-IgG1 and human IgA, which is a multimeric antigen containing two or more antigenic binding units, binds with avidity to FcγR and is quickly taken up into cells expressing FcγR. The IgA that dissociates from the immune complex in the endosomes of cells that have taken up the immune complex is degraded in the lysosomes. At the same time, the IgA-dissociated antibody, which was bound to FcRn in the endosomes, is subsequently recycled to the plasma and can bind again to IgA in the plasma. Elimination of human IgA in the plasma is thought to be greatly accelerated in this manner. A method using an amino-acid-variant of the Fc region which binds to FcRn in the pH neutral range is described in WO2011/122011 as a method for accelerating elimination of antigens from the plasma. The present invention is useful as a method for accelerating the elimination from the plasma of multimeric antigens containing two or more antigenic binding units without using the above-mentioned variants, and can further accelerate the elimination of the multimeric antigens containing two or more antigenic binding units from the plasma through combination with the above-mentioned variants.

Ex Vivo Method for Eliminating Antigens from the Plasma

An example of a non-limiting embodiment of the use of an antigen-binding molecule in the method provided by the present invention for eliminating antigens from the plasma includes use of the antigen-binding molecule in a so-called ex vivo method for eliminating antigens from the plasma, which includes forming an immune complex containing two or more of the antigen-binding molecules and two or more antigen molecules (provided that the antigens contain two or more antigenic binding units) by allowing the antigen-binding molecules of the present invention to contact plasma isolated from a subject, and allowing the immune complex to contact cells expressing FcRn and/or Fcγ receptors. The speed of antigen elimination from the plasma can also be promoted by substituting or combining a method for administering antigen-binding molecules in vivo with a so-called ex vivo method, in which the plasma containing antigen-binding molecules and antigens that bind to the antigen-binding molecules is temporarily taken out of the body and then contacted with cells expressing FcRn and/or Fcγ receptors for a certain period of time, and the plasma containing extracellularly recycled (or re-secreted or re-circulated) antigen-binding molecules that are not bound to antigen is returned to the body.

Furthermore, an example of a non-limiting embodiment of the use of an antigen-binding molecule in the method provided by the present invention for eliminating antigens from plasma includes use of the antigen-binding molecule in a so-called ex vivo method for eliminating antigens from the plasma, which includes contacting an immune complex containing two or more of the antigen-binding molecules and two or more antigen molecules (provided that the antigens comprise two or more antigenic binding units) present in the plasma isolated from a subject to whom the antigen-binding molecules of the present invention are administered with cells expressing FcRn and/or Fcγ receptors.

Whether or not an antigen is eliminated from the plasma can be confirmed, for example, by evaluating whether or not the speed of antigen elimination from the aforementioned plasma is promoted by using as a control, antigen-binding molecules that cannot form the immune complexes disclosed in the present invention, antigen-binding molecules containing antigen-binding domains with ion-concentration-independent antigen-binding activity, or antigen-binding molecules containing an Fc region with impaired binding activity toward FcγR or FcRn, instead of the antigen-binding molecules of the present invention.

Method of Screening for Antigen-Binding Molecules Containing an Fc Region and an Antigen-Binding Domain Whose Antigen-Binding Activity is Ion Concentration-Dependent The present invention provides a method of screening for an antigen-binding molecule having a function of eliminating antigens from the plasma, the method comprising:
(a) obtaining an antigen-binding domain of which antigen-binding activity varies depending on an ion concentration condition;
(b) obtaining a gene encoding the antigen-binding domain selected in (a) above;
(c) operably linking the gene obtained in (b) above with a gene encoding an Fc region;
(d) culturing a host cell comprising the genes operably linked in (c) above;
(e) isolating an antigen-binding molecule from a culture solution obtained in (d) above;
(f) contacting the antigen-binding molecule obtained in (e) above with an antigen; and
(g) evaluating the formation of an immune complex comprising the antigen-binding molecule and the antigen.

In a non-limiting embodiment of the present invention, after isolating a polynucleotide encoding an antigen-binding domain whose binding activity changes depending on the condition selected as described above, the polynucleotide is inserted into an appropriate expression vector. For example, when the antigen-binding domain is an antibody variable region, once a cDNA encoding the variable region is obtained, the cDNA is digested with restriction enzymes that recognize the restriction sites inserted at the two ends of the cDNA. Preferably, the restriction enzymes recognize and digest a nucleotide sequence that appears at a low frequency in the nucleotide sequence composing the gene of the antigen-binding molecule. Furthermore, restriction enzymes that provide cohesive ends are preferably inserted to insert a single copy of a digested fragment into the vector in the correct orientation. The cDNA encoding a variable region of an antigen-binding molecule digested as described above is inserted into an appropriate expression vector to obtain an expression vector for the antigen-binding molecule of the present invention. At this time, a gene encoding an antibody constant region (C region) may be fused in frame with the gene encoding the variable region.

To produce an antigen-binding molecule of interest, a polynucleotide encoding the antigen-binding molecule is inserted in a manner operably linked to a regulatory sequence into an expression vector. Regulatory sequences include, for example, enhancers and promoters. Furthermore, an appropriate signal sequence may be linked to the N terminus so that the expressed antigen-binding molecule is secreted to the outside of the cells. As signal sequence, for example, a peptide having the amino acid sequence MGWSCIILFLVATATGVHS (SEQ ID NO: 5) is used; however, it is also possible to link other appropriate signal sequences. The expressed polypeptide is cleaved at the carboxyl terminus of the above-described sequence, and the cleaved polypeptide is secreted as a mature polypeptide to the outside of cells. Then, appropriate host cells are transformed with this expression vector so that recombinant cells expressing the polynucleotide encoding the antigen-binding molecule of interest can be obtained. The antigen-binding molecules of the present invention can be produced from the recombinant cells by following the methods described above in the section on antibodies.

For a nucleic acid, "operably linked" means that the nucleic acid has a functional relationship with another nucleic acid sequence. For example, a DNA encoding a presequence or a secretory leader is operably linked to a DNA encoding a certain polypeptide if it is to be expressed as a precursor protein involved in the secretion of the polypeptide. A promoter or enhancer is operably linked to a coding sequence if it affects the transcription of the coding sequence. A ribosome binding site is operably linked to a coding sequence if it is in a position that facilitates translation. Generally, "operably linked" means that the linked DNA sequences are contiguous, and in the case of a secretory leader, it means that the linked DNA sequences are contiguous and in a reading frame. However, enhancers do not have to be contiguous. Linking is accomplished by ligation at suitable restriction sites. If such sites do not exist, synthetic oligonucleotide adaptors or linkers are used in accordance with conventional practice. Furthermore, linked nucleic acids may be produced by the above-mentioned overlap extension PCR technique.

In a non-limiting embodiment of the present invention, after isolating a polynucleotide encoding the above-described antigen-binding molecule whose binding activity varies depending on a selected condition, a variant of the polynucleotide is inserted into an appropriate expression vector. Such variants preferably include those prepared via humanization based on the polynucleotide sequence encoding an antigen-binding molecule of the present invention obtained by screening as a randomized variable region library a synthetic library or an immune library constructed originating from nonhuman animals. The same methods as described above for producing above-described humanized antibodies can be used as a method for producing humanized antigen-binding molecule variants.

In another embodiment, such variants preferably include those obtained by introducing an alteration that increases the antigen affinity (affinity maturation) of an antigen-binding molecule of the present invention into an isolated polynucleotide sequence for the molecule obtained by screening using a synthetic library or a naive library as a randomized variable region library. Such variants can be obtained by various known procedures for affinity maturation, including CDR mutagenesis (Yang et al. (J. Mol. Biol. (1995) 254, 392-403)), chain shuffling (Marks et al. (Bio/Technology (1992) 10, 779-783)), use of *E. coli* mutant strains (Low et al. (J. Mol. Biol. (1996) 250, 359-368)), DNA shuffling (Patten et al. (Curr. Opin. Biotechnol. (1997) 8, 724-733)), phage display (Thompson et al. (J. Mol. Biol. (1996) 256, 77-88)), and sexual PCR (Clameri et al. (Nature (1998) 391, 288-291)).

As described above, antigen-binding molecules that are produced by the production methods of the present invention include antigen-binding molecules having an Fc region. Various variants can be used as Fc regions. In an embodiment, variants of the present invention preferably include polynucleotides encoding antigen-binding molecules having a heavy chain in which a polynucleotide encoding an Fc region variant as described above is linked in frame to a polynucleotide encoding the above-described antigen-binding domain whose binding activity varies depending on a selected condition.

In a non-limiting embodiment of the present invention, Fc regions preferably include, for example, Fc constant regions of antibodies such as IgG1 of SEQ ID NO: 13 (Ala is added to the N terminus of AAC82527.1), IgG2 of SEQ ID NO: 14 (Ala is added to the N terminus of AAB59393.1), IgG3 of SEQ ID NO: 15 (CAA27268.1), and IgG4 of SEQ ID NO: 16 (Ala is added to the N terminus of AAB59394.1). The plasma retention of IgG molecules is relatively long (the elimination from plasma is slow) since FcRn, particularly human FcRn, functions as a salvage receptor for IgG molecules. IgG molecules incorporated into endosomes by pinocytosis bind under the endosomal acidic condition to FcRn, particularly human FcRn, expressed in endosomes. IgG molecules that cannot bind to FcRn, particularly human FcRn, are transferred to lysosomes, and degraded there. Meanwhile, IgG molecules bound to FcRn, particularly human FcRn, are transferred to cell surface, and then return to plasma as a result of dissociation from FcRn, particularly human FcRn, under the neutral condition in plasma.

Since antibodies comprising a typical Fc region do not have a binding activity to FcRn, particularly to human FcRn, under the plasma neutral pH range condition, typical antibodies and antibody-antigen complexes are incorporated into cells by non-specific endocytosis and transferred to cell surface by binding to FcRn, particularly human FcRn, in the endosomal acidic pH range condition. FcRn, particularly human FcRn, transports antibodies from the endosome to the cell surface. Thus, some of FcRn, particularly human FcRn, is thought to be also present on the cell surface. However, antibodies are recycled to plasma, since they dissociated from FcRn, particularly human FcRn, in the neutral pH range condition on cell surface.

Fc regions having human FcRn-binding activity in the neutral pH range, which can be included in the antigen-binding molecules of the present invention, can be obtained by any method. Specifically, Fc regions having human FcRn-binding activity in the neutral pH range can be obtained by altering amino acids of human IgG-type immunoglobulin as a starting Fc region. Preferred Fc regions of human IgG-type immunoglobulin for alteration include, for example, those of human IgGs (IgG1, IgG2, IgG3, and IgG4, and variants thereof). Amino acids at any positions may be altered to other amino acids as long as the resulting regions have the human FcRn-binding activity in the neutral pH range or increased human FcRn-binding activity in the neutral range. When an antigen-binding molecule comprises the Fc region of human IgG1 as human Fc region, it is preferable that the resulting region comprises an alteration that results in the effect to enhance the human FcRn binding in the neutral pH range as compared to the binding activity of the starting Fc region of human IgG1. Amino acids that allow such alterations include, for example, one or more amino acids selected from the group of positions 221 to 225, 227, 228, 230, 232, 233 to 241, 243 to 252, 254 to 260, 262 to 272, 274, 276, 278 to 289, 291 to 312, 315 to 320, 324, 325, 327 to 339, 341, 343, 345, 360, 362, 370, 375 to 378, 380, 382, 385 to 387, 389, 396, 414, 416, 423, 424, 426 to 438, 440, and 442 (indicated by EU numbering). More specifically, such amino acid alterations include those listed in Table 5. Alteration of these amino acids enhances the human FcRn binding of the Fc region of IgG-type immunoglobulin in the neutral pH range.

Among those described above, appropriate alterations that enhance the human FcRn binding in the neutral pH range are selected for use in the present invention. Particularly preferred amino acids for such Fc region variants include, for example, amino acids at positions 237, 248, 250, 252, 254, 255, 256, 257, 258, 265, 286, 289, 297, 298, 303, 305, 307, 308, 309, 311, 312, 314, 315, 317, 332, 334, 360, 376, 380, 382, 384, 385, 386, 387, 389, 424, 428, 433, 434, and 436 (indicated by EU numbering). The human FcRn-binding activity of the Fc region included in an antigen-binding molecule can be increased in the neutral pH range by substituting at least one amino acid with a different amino acid.

Particularly preferred alterations in the Fc region include, for example, at least one or more amino acid alterations selected from the group of:

Met for the amino acid at position 237;
Ile for the amino acid at position 248;
Ala, Phe, Ile, Met, Gln, Ser, Val, Trp, or Tyr for the amino acid at position 250;
Phe, Trp, or Tyr for the amino acid at position 252;
Thr for the amino acid at position 254;
Glu for the amino acid at position 255;
Asp, Asn, Glu, or Gln for the amino acid at position 256;
Ala, Gly, Ile, Leu, Met, Asn, Ser, Thr, or Val for the amino acid at position 257;
His for the amino acid at position 258;
Ala for the amino acid at position 265;
Ala or Glu for the amino acid at position 286;
His for the amino acid at position 289;
Ala for the amino acid at position 297;
Ala for the amino acid at position 303;
Ala for the amino acid at position 305;
Ala, Asp, Phe, Gly, His, Ile, Lys, Leu, Met, Asn, Pro, Gln, Arg, Ser, Val, Trp, or Tyr for the amino acid at position 307;
Ala, Phe, Ile, Leu, Met, Pro, Gln, or Thr for the amino acid at position 308;
Ala, Asp, Glu, Pro, or Arg for the amino acid at position 309;
Ala, His, or Ile for the amino acid at position 311;
Ala or His for the amino acid at position 312;
Lys or Arg for the amino acid at position 314;
Ala, Asp, or His for the amino acid at position 315;
Ala for the amino acid at position 317;
Val for the amino acid at position 332;
Leu for the amino acid at position 334;
His for the amino acid at position 360;
Ala for the amino acid at position 376;
Ala for the amino acid at position 380;
Ala for the amino acid at position 382;
Ala for the amino acid at position 384;
Asp or His for the amino acid at position 385;
Pro for the amino acid at position 386;
Glu for the amino acid at position 387;
Ala or Ser for the amino acid at position 389;
Ala for the amino acid at position 424;

Ala, Asp, Phe, Gly, His, Ile, Lys, Leu, Asn, Pro, Gln, Ser, Thr, Val, Trp, or Tyr for the amino acid at position 428;
Lys for the amino acid at position 433;
Ala, Phe, His, Ser, Trp, or Tyr for the amino acid at position 434; and
His, Ile, Leu, Phe, Thr, or Val for the amino acid at position 436 in the EU numbering system. Meanwhile, the number of altered amino acids is not particularly limited; such amino acid alterations include single amino acid alteration and alteration of amino acids at two or more sites. Combinations of amino acid alterations at two or more sites include, for example, those described in Tables 5-1 to 5-32.

In addition to the Fc region of human IgG1 (SEQ ID NO: 13), IgG2 (SEQ ID NO: 14), IgG3 (SEQ ID NO: 15), or IgG4 (SEQ ID NO: 16), as Fc regions included in the present invention, Fc regions with modified FcγR binding, which have a higher Fcγ receptor-binding activity than the Fc region of a native human IgG in which the sugar chain bound at position 297 (EU numbering) is a fucose-containing sugar chain, may be suitably used. Such Fc regions with modified FcγR binding may be produced by modifying amino acids in the Fc region of a native human IgG. Whether the FcγR-binding activity of an Fc region is higher than that of the Fc region of a native human IgG, in which the sugar chain bound at position 297 (EU numbering) is a fucose-containing sugar chain, can be appropriately determined using methods such as those described above.

In the present invention, "modification of amino acids" or "amino acid modification" of an Fc region includes modification into an amino acid sequence which is different from that of the starting Fc region. The starting Fc region may be any Fc region, as long as a variant modified from the starting Fc region can bind to human Fcγ receptor in a neutral pH range. Furthermore, an Fc region modified from a starting Fc region which had been already modified can also be used preferably as an Fc region of the present invention. The "starting Fc region" can refer to the polypeptide itself, a composition comprising the starting Fc region, or an amino acid sequence encoding the starting Fc region. Starting Fc regions can comprise a known Fc region produced via recombination described briefly in the section "Antibodies". The origin of starting Fc regions is not limited, and they may be obtained from human or any nonhuman organisms. Such organisms preferably include mice, rats, guinea pigs, hamsters, gerbils, cats, rabbits, dogs, goats, sheep, bovines, horses, camels and organisms selected from nonhuman primates. In another embodiment, starting Fc regions can also be obtained from cynomolgus monkeys, marmosets, rhesus monkeys, chimpanzees, or humans. Starting Fc regions can be obtained preferably from human IgG1; however, they are not limited to any particular IgG class. This means that an Fc region of human IgG1, IgG2, IgG3, or IgG4 can be used appropriately as a starting Fc region, and herein also means that an Fc region of an arbitrary IgG class or subclass derived from any organisms described above can be preferably used as a starting Fc region. Examples of naturally-occurring IgG variants or modified forms are described in published documents (Curr. Opin. Biotechnol. (2009) 20 (6): 685-91; Curr. Opin. Immunol. (2008) 20 (4), 460-470; Protein Eng. Des. Sel. (2010) 23 (4): 195-202; International Publication Nos. WO 2009/086320, WO 2008/092117, WO 2007/041635, and WO 2006/105338); however, they are not limited to the examples.

Examples of alterations include those with one or more mutations, for example, mutations by substitution of different amino acid residues for amino acids of starting Fc regions, by insertion of one or more amino acid residues into starting Fc regions, or by deletion of one or more amino acids from starting Fc region. Preferably, the amino acid sequences of altered Fc regions comprise at least a part of the amino acid sequence of a non-native Fc region. Such variants necessarily have sequence identity or similarity less than 100% to their starting Fc region. In a preferred embodiment, the variants have amino acid sequence identity or similarity about 75% to less than 100%, more preferably about 80% to less than 100%, even more preferably about 85% to less than 100%, still more preferably about 90% to less than 100%, and yet more preferably about 95% to less than 100% to the amino acid sequence of their starting Fc region. In a non-limiting embodiment of the present invention, at least one amino acid is different between an FcγR-binding modified Fc region of the present invention and its starting Fc region. The amino acid differences between an FcγR-binding modified Fc region of the present invention and its starting Fc region can also be suitably specified based on the amino acid differences at the above-described particular amino acid positions specified by the EU numbering system.

The Fc region with modified FcγR binding, which has a higher Fcγ receptor-binding activity than that of the Fc region of a native human IgG in which the sugar chain bound at position 297 (EU numbering) is a fucose-containing sugar chain, contained in the antigen-binding molecules of the present invention may be obtained by any method. Specifically, the Fc region with modified FcγR binding can be obtained by modifying amino acids in a human IgG-type immunoglobulin, and is used as the starting Fc region. Preferred Fc regions of IgG-type immunoglobulins for modification include, for example, Fc regions of human IgGs (IgG1, IgG2, IgG3, IgG4, and variants thereof).

Amino acids of any positions may be modified into other amino acids, as long as the binding activity toward the Fcγ receptor is higher than that of the Fc region of a native human IgG, in which the sugar chain bound at position 297 (EU numbering) is a fucose-containing sugar chain. When the antigen-binding molecule contains a human IgG1 Fc region as the human Fc region, it preferably contains a modification that yields the effect of a higher Fcγ receptor-binding activity than that of the Fc region of a native human IgG, in which the sugar chain bound at position 297 (EU numbering) is a fucose-containing sugar chain. Such amino acid modifications have been reported, for example, in international publications such as WO2007/024249, WO2007/021841, WO2006/031370, WO2000/042072, WO2004/029207, WO2004/099249, WO2006/105338, WO2007/041635, WO2008/092117, WO2005/070963, WO2006/020114, WO2006/116260, and WO2006/023403.

Examples of such amino acids that can be modified include at least one or more amino acids selected from the group of positions 221, 222, 223, 224, 225, 227, 228, 230, 231, 232, 233, 234, 235, 236, 237, 238, 239, 240, 241, 243, 244, 245, 246, 247, 249, 250, 251, 254, 255, 256, 258, 260, 262, 263, 264, 265, 266, 267, 268, 269, 270, 271, 272, 273, 274, 275, 276, 278, 279, 280, 281, 282, 283, 284, 285, 286, 288, 290, 291, 292, 293, 294, 295, 296, 297, 298, 299, 300, 301, 302, 303, 304, 305, 311, 313, 315, 317, 318, 320, 322, 323, 324, 325, 326, 327, 328, 329, 330, 331, 332, 333, 334, 335, 336, 337, 339, 376, 377, 378, 379, 380, 382, 385, 392, 396, 421, 427, 428, 429, 434, 436, and 440 (EU numbering). Modification of these amino acids can yield Fc regions (Fc regions with modified FcγR binding) having a higher Fcγ receptor-binding activity than the Fcγ receptor-binding activity of an Fc region of a native human IgG, in which the sugar chain bound at position 297 (EU numbering) is a fucose-containing sugar chain.

Examples of particularly preferred modifications for use in the present invention include at least one or more amino acid modifications in the Fc region selected from the group of:

Lys or Tyr for the amino acid of position 221;
Phe, Trp, Glu, or Tyr for the amino acid of position 222;
Phe, Trp, Glu, or Lys for the amino acid of position 223;
Phe, Trp, Glu, or Tyr for the amino acid of position 224;
Glu, Lys, or Trp for the amino acid of position 225;
Glu, Gly, Lys, or Tyr for the amino acid of position 227;
Glu, Gly, Lys, or Tyr for the amino acid of position 228;
Ala, Glu, Gly, or Tyr for the amino acid of position 230;
Glu, Gly, Lys, Pro, or Tyr for the amino acid of position 231;
Glu, Gly, Lys, or Tyr for the amino acid of position 232;
Ala, Asp, Phe, Gly, His, Ile, Lys, Leu, Met, Asn, Gln, Arg, Ser, Thr, Val, Trp, or Tyr for the amino acid of position 233;
Ala, Asp, Glu, Phe, Gly, His, Ile, Lys, Met, Asn, Pro, Gln, Arg, Ser, Thr, Val, Trp, or Tyr for the amino acid of position 234;
Ala, Asp, Glu, Phe, Gly, His, Ile, Lys, Met, Asn, Pro, Gln, Arg, Ser, Thr, Val, Trp, or Tyr for the amino acid of position 235;
Ala, Asp, Glu, Phe, His, Ile, Lys, Leu, Met, Asn, Pro, Gln, Arg, Ser, Thr, Val, Trp, or Tyr for the amino acid of position 236;
Asp, Glu, Phe, His, Ile, Lys, Leu, Met, Asn, Pro, Gln, Arg, Ser, Thr, Val, Trp, or Tyr for the amino acid of position 237;
Asp, Glu, Phe, Gly, His, Ile, Lys, Leu, Met, Asn, Gin, Arg, Ser, Thr, Val, Trp, or Tyr for the amino acid of position 238;
Asp, Glu, Phe, Gly, His, Ile, Lys, Leu, Met, Asn, Pro, Gln, Arg, Thr, Val, Trp, or Tyr for the amino acid of position 239;
Ala, Ile, Met, or Thr for the amino acid of position 240;
Asp, Glu, Leu, Arg, Trp, or Tyr for the amino acid of position 241;
Leu, Glu, Leu, Gln, Arg, Trp, or Tyr for the amino acid of position 243;
His for the amino acid of position 244;
Ala for the amino acid of position 245;
Asp, Glu, His, or Tyr for the amino acid of position 246;
Ala, Phe, Gly, His, Ile, Leu, Met, Thr, Val, or Tyr for the amino acid of position 247;
Glu, His, Gln, or Tyr for the amino acid of position 249;
Glu or Gln for the amino acid of position 250;
Phe for the amino acid of position 251;
Phe, Met, or Tyr for the amino acid of position 254;
Glu, Leu, or Tyr for the amino acid of position 255;
Ala, Met, or Pro for the amino acid of position 256;
Asp, Glu, His, Ser, or Tyr for the amino acid of position 258;
Asp, Glu, His, or Tyr for the amino acid of position 260;
Ala, Glu, Phe, Ile, or Thr for the amino acid of position 262;
Ala, Ile, Met, or Thr for the amino acid of position 263;
Asp, Glu, Phe, Gly, His, Ile, Lys, Leu, Met, Asn, Pro, Gln, Arg, Ser, Thr, Trp, or Tyr for the amino acid of position 264;
Ala, Leu, Phe, Gly, His, Ile, Lys, Leu, Met, Asn, Pro, Gln, Arg, Ser, Thr, Val, Trp, or Tyr for the amino acid of position 265;
Ala, Ile, Met, or Thr for the amino acid of position 266;
Asp, Glu, Phe, His, Ile, Lys, Leu, Met, Asn, Pro, Gln, Arg, Thr, Val, Trp, or Tyr for the amino acid of position 267;
Asp, Glu, Phe, Gly, Ile, Lys, Leu, Met, Pro, Gln, Arg, Thr, Val, or Trp for the amino acid of position 268;
Phe, Gly, His, Ile, Lys, Leu, Met, Asn, Pro, Arg, Ser, Thr, Val, Trp, or Tyr for the amino acid of position 269;
Glu, Phe, Gly, His, Ile, Leu, Met, Pro, Gln, Arg, Ser, Thr, Trp, or Tyr for the amino acid of position 270;
Ala, Asp, Glu, Phe, Gly, His, Ile, Lys, Leu, Met, Asn, Gln, Arg, Ser, Thr, Val, Trp, or Tyr for the amino acid of position 271;
Asp, Phe, Gly, His, Ile, Lys, Leu, Met, Pro, Arg, Ser, Thr, Val, Trp, or Tyr for the amino acid of position 272;
Phe or Ile for the amino acid of position 273;
Asp, Glu, Phe, Gly, His, Ile, Leu, Met, Asn, Pro, Arg, Ser, Thr, Val, Trp, or Tyr for the amino acid of position 274;
Leu or Trp for the amino acid of position 275;
Asp, Glu, Phe, Gly, His, Ile, Leu, Met, Pro, Arg, Ser, Thr, Val, Trp, or Tyr for the amino acid of position 276;
Asp, Glu, Gly, His, Ile, Lys, Leu, Met, Asn, Pro, Gln, Arg, Ser, Thr, Val, or Trp for the amino acid of position 278;
Ala for the amino acid of position 279;
Ala, Gly, His, Lys, Leu, Pro, Gln, Trp, or Tyr for the amino acid of position 280;
Asp, Lys, Pro, or Tyr for the amino acid of position 281;
Glu, Gly, Lys, Pro, or Tyr for the amino acid of position 282;
Ala, Gly, His, Ile, Lys, Leu, Met, Pro, Arg, or Tyr for the amino acid of position 283;
Asp, Glu, Leu, Asn, Thr, or Tyr for the amino acid of position 284;
Asp, Glu, Lys, Gln, Trp, or Tyr for the amino acid of position 285;
Glu, Gly, Pro, or Tyr for the amino acid of position 286;
Asn, Asp, Glu, or Tyr for the amino acid of position 288;
Asp, Gly, His, Leu, Asn, Ser, Thr, Trp, or Tyr for the amino acid of position 290;
Asp, Glu, Gly, His, Ile, Gln, or Thr for the amino acid of position 291;
Ala, Asp, Glu, Pro, Thr, or Tyr for the amino acid of position 292;
Phe, Gly, His, Ile, Leu, Met, Asn, Pro, Arg, Ser, Thr, Val, Trp, or Tyr for the amino acid of position 293;
Phe, Gly, His, Ile, Lys, Leu, Met, Asn, Pro, Arg, Ser, Thr, Val, Trp, or Tyr for the amino acid of position 294;
Asp, Glu, Phe, Gly, His, Ile, Lys, Met, Asn, Pro, Arg, Ser, Thr, Val, Trp, or Tyr for the amino acid of position 295;
Ala, Asp, Glu, Gly, His, Ile, Lys, Leu, Met, Asn, Gln, Arg, Ser, Thr, or Val for the amino acid of position 296;
Asp, Glu, Phe, Gly, His, Ile, Lys, Leu, Met, Pro, Gln, Arg, Ser, Thr, Val, Trp, or Tyr for the amino acid of position 297;
Ala, Asp, Glu, Phe, His, Ile, Lys, Met, Asn, Gln, Arg, Thr, Val, Trp, or Tyr for the amino acid of position 298;
Ala, Asp, Glu, Phe, Gly, His, Ile, Lys, Leu, Met, Asn, Pro, Gln, Arg, Ser, Val, Trp, or Tyr for the amino acid of position 299;
Ala, Asp, Glu, Gly, His, Ile, Lys, Leu, Met, Asn, Pro, Gin, Arg, Ser, Thr, Val, or Trp for the amino acid of position 300;
Asp, Glu, His, or Tyr for the amino acid of position 301;
Ile for the amino acid of position 302;
Asp, Gly, or Tyr for the amino acid of position 303;
Asp, His, Leu, Asn, or Thr for the amino acid of position 304;
Glu, Ile, Thr, or Tyr for the amino acid of position 305;
Ala, Asp, Asn, Thr, Val, or Tyr for the amino acid of position 311;
Phe for the amino acid of position 313;
Leu for the amino acid of position 315;
Glu or Gln for the amino acid of position 317;
His, Leu, Asn, Pro, Gln, Arg, Thr, Val, or Tyr for the amino acid of position 318;
Asp, Phe, Gly, His, Ile, Leu, Asn, Pro, Ser, Thr, Val, Trp, or Tyr for the amino acid of position 320;
Ala, Asp, Phe, Gly, His, Ile, Pro, Ser, Thr, Val, Trp, or Tyr for the amino acid of position 322;
Ile for the amino acid of position 323;

Asp, Phe, Gly, His, Ile, Leu, Met, Pro, Arg, Thr, Val, Trp, or Tyr for the amino acid of position 324;
Ala, Asp, Glu, Phe, Gly, His, Ile, Lys, Leu, Met, Pro, Gln, Arg, Ser, Thr, Val, Trp, or Tyr for the amino acid of position 325;
Ala, Asp, Glu, Gly, Ile, Leu, Met, Asn, Pro, Gln, Ser, Thr, Val, Trp, or Tyr for the amino acid of position 326;
Ala, Asp, Glu, Phe, Gly, His, Ile, Lys, Leu, Met, Asn, Pro, Arg, Thr, Val, Trp, or Tyr for the amino acid of position 327;
Ala, Asp, Glu, Phe, Gly, His, Ile, Lys, Met, Asn, Pro, Gln, Arg, Ser, Thr, Val, Trp, or Tyr for the amino acid of position 328;
Asp, Glu, Phe, Gly, His, Ile, Lys, Leu, Met, Asn, Gln, Arg, Ser, Thr, Val, Trp, or Tyr for the amino acid of position 329;
Cys, Glu, Phe, Gly, His, Ile, Lys, Leu, Met, Asn, Pro, Arg, Ser, Thr, Val, Trp, or Tyr for the amino acid of position 330;
Asp, Phe, His, Ile, Leu, Met, Gln, Arg, Thr, Val, Trp, or Tyr for the amino acid of position 331;
Ala, Asp, Glu, Phe, Gly, His, Lys, Leu, Met, Asn, Pro, Gln, Arg, Ser, Thr, Val, Trp, or Tyr for the amino acid of position 332;
Ala, Asp, Glu, Phe, Gly, His, Ile, Leu, Met, Pro, Ser, Thr, Val, or Tyr for the amino acid of position 333;
Ala, Glu, Phe, Ile, Leu, Pro, or Thr for the amino acid of position 334;
Asp, Phe, Gly, His, Ile, Leu, Met, Asn, Pro, Arg, Ser, Val, Trp, or Tyr for the amino acid of position 335;
Glu, Lys, or Tyr for the amino acid of position 336;
Glu, His, or Asn for the amino acid of position 337;
Asp, Phe, Gly, Ile, Lys, Met, Asn, Gln, Arg, Ser, or Thr for the amino acid of position 339;
Ala or Val for the amino acid of position 376;
Gly or Lys for the amino acid of position 377;
Asp for the amino acid of position 378;
Asn for the amino acid of position 379;
Ala, Asn, or Ser for the amino acid of position 380;
Ala or Ile for the amino acid of position 382;
Glu for the amino acid of position 385;
Thr for the amino acid of position 392;
Leu for the amino acid of position 396;
Lys for the amino acid of position 421;
Asn for the amino acid of position 427;
Phe or Leu for the amino acid of position 428;
Met for the amino acid of position 429;
Trp for the amino acid of position 434;
Ile for the amino acid of position 436; and
Gly, His, Ile, Leu, or Tyr for the amino acid of position 440; as indicated by EU numbering. Meanwhile, the number of amino acids to be modified is not particularly limited, and an amino acid at only one site may be modified or amino acids at two or more sites may be modified. Examples of combinations for the amino acid modifications at two or more sites include those described in Table 6 (Tables 6-1 to 6-3).

Among the Fc regions suitable for use in the present invention, a suitable example of an Fc region that has a higher binding activity toward an inhibitory Fcγ receptor than toward an activating Fcγ receptor (i.e., having a selective binding activity toward an inhibitory Fcγ receptor), which is used as a non-limiting embodiment of an Fc region with the property of having a higher binding activity toward a specific Fcγ receptor than toward other Fcγ receptors (i.e., an Fc region having a selective Fcγ receptor-binding activity), is an Fc region with one or more of the following modifications in the amino acids (indicated by EU numbering) of the aforementioned Fc region: the amino acid at position 238 is modified to Asp and the amino acid at position 328 is modified to Glu. The Fc regions and modifications described in US2009/0136485 may be selected appropriately as the Fc region having a selective binding activity to an inhibitory Fcγ receptor.

In a non-limiting embodiment of the present invention, a suitable example is an Fc region in which one or more of the amino acids indicated by EU numbering at positions 238 and 328 according to EU numbering are respectively modified to Asp or Glu in the aforementioned Fc region.

Furthermore, in a non-limiting embodiment of the present invention, suitable examples of the Fc regions are those with substitution of Asp for Pro at position 238 (EU numbering), and one or more modifications selected from among Trp for the amino acid of position 237, Phe for the amino acid of position 237, Val for the amino acid of position 267, Gln for the amino acid of position 267, Asn for the amino acid of position 268, Gly for the amino acid of position 271, Leu for the amino acid of position 326, Gln for the amino acid of position 326, Glu for the amino acid of position 326, Met for the amino acid of position 326, Asp for the amino acid of position 239, Ala for the amino acid of position 267, Trp for the amino acid of position 234, Tyr for the amino acid of position 234, Ala for the amino acid of position 237, Asp for the amino acid of position 237, Glu for the amino acid of position 237, Leu for the amino acid of position 237, Met for the amino acid of position 237, Tyr for the amino acid of position 237, Lys for the amino acid of position 330, Arg for the amino acid of position 330, Asp for the amino acid of position 233, Asp for the amino acid of position 268, Glu for the amino acid of position 268, Asp for the amino acid of position 326, Ser for the amino acid of position 326, Thr for the amino acid of position 326, Ile for the amino acid of position 323, Leu for the amino acid of position 323, Met for the amino acid of position 323, Asp for the amino acid of position 296, Ala for the amino acid of position 326, Asn for the amino acid of position 326, and Met for the amino acid of position 330, according to EU numbering.

Known methods such as site-directed mutagenesis (Kunkel et al. (Proc. Natl. Acad. Sci. USA (1985) 82, 488-492)) and Overlap extension PCR can be appropriately employed to modify the amino acids of Fc regions. Furthermore, various known methods can also be used as an amino acid modification method for substituting amino acids by those other than natural amino acids (Annu. Rev. Biophys. Biomol. Struct. (2006) 35, 225-249; Proc. Natl. Acad. Sci. U.S.A. (2003) 100 (11), 6353-6357). For example, a cell-free translation system (Clover Direct (Protein Express)) containing tRNAs in which amber suppressor tRNA, which is complementary to UAG codon (amber codon) that is a stop codon, is linked with an unnatural amino acid may be suitably used.

As described above, the antigen-binding molecules isolated from the culture solution of host cells containing operably linked genes encoding the antigen-binding molecules are contacted with antigens in the screening method of the present invention. In a non-limiting embodiment of the contacting step, the conditions described in, e.g., the aforementioned section on antigen binding antigens may be appropriately employed.

Next, whether immune complexes containing the test antigen-binding molecule and the test antigen are formed is evaluated. Examples of methods for evaluating the formation of immune complexes containing the antigen-binding molecules and antigens include methods that make use of the property that the immune complexes become larger molecules than the antigen-binding molecule alone or the antigen molecule alone, such as size exclusion (gel filtration) chromatography, ultracentrifugal analysis method, light-scattering method, electron microscopy, and mass spectrometry (Molecular Immunology (2002), 39, 77-84; Molecular Immunology (2009), 47, 357-364). For example, when size exclusion (gel filtration) chromatography is used as shown in FIG. 9, whether immune complexes are formed is evaluated based on whether larger molecular species are observed as compared to when the antigen molecule alone or the antigen-binding molecule alone is analyzed.

Furthermore, when the antigen-binding molecule or antigen has an immunoglobulin constant region, examples also include ELISA and FACS which use the property of the immune complex to bind more strongly to an Fc receptor or a complement component than the antigen-binding molecule alone or antigen alone (The Journal of Biological Chemistry (2001) 276 (9), 6591-6604; Journal of Immunological Methods (1982) 50, 109-114). For example, when ELISA is performed by immobilizing an Fc receptor, formation of an immune complex is evaluated by observing whether the detected signal is increased compared to when an antigen alone or an antigen-binding molecule alone is evaluated.

Methods for Producing an Antigen-Binding Molecule Containing an Fc Region and an Antigen-Binding Domain Showing Ion-Concentration-Dependent Antigen-Binding Activity The present invention provides a method for producing antigen-binding molecules having a function of eliminating antigens from plasma, the method comprising:
(a) contacting an antigen with an antigen-binding molecule comprising an Fc region and two or more antigen-binding domains, wherein at least one of the antigen-binding domains has an antigen-binding activity that varies depending on an ion concentration condition;
(b) evaluating formation of an immune complex comprising the antigen-binding molecule and the antigen;
(c) culturing a host cell comprising a vector that carries a gene encoding an antigen-binding domain which is confirmed to form an immune complex in (b) above; and
(d) isolating the antigen-binding molecule from a culture solution obtained in (c) above.

The present invention provides a method for producing an antigen-binding molecule having a function of eliminating antigens from the plasma, the method comprising:
(a) obtaining an antigen-binding domain of which antigen-binding activity varies depending on an ion concentration condition;
(b) obtaining a gene encoding the antigen-binding domain selected in (a) above;
(c) operably linking the gene obtained in (b) above with a gene encoding an Fc region;
(d) culturing a host cell comprising the genes operably linked in (c) above;
(e) isolating an antigen-binding molecule from a culture solution obtained in (d) above;
(f) contacting the antigen-binding molecule obtained in (e) above with an antigen;
(g) evaluating formation of an immune complex comprising the antigen-binding molecule and the antigen;
(h) culturing a host cell comprising a vector that carries a gene encoding an antigen-binding domain which is confirmed to form an immune complex in (g) above; and
(i) isolating the antigen-binding molecule from a culture solution obtained in (h) above.

The present invention further provides a method for producing an antigen-binding molecule having a function of eliminating antigens from the plasma, the method comprising:
(a) obtaining an antigen-binding domain of which antigen-binding activity varies depending on an ion concentration condition;
(b) obtaining a gene encoding the antigen-binding domain selected in (a) above;
(c) operably linking the gene obtained in (b) above with a gene encoding an Fc region;
(d) culturing a host cell comprising the genes operably linked in (c) above; and
(e) isolating an antigen-binding molecule from a culture solution obtained in (d) above; and wherein the method further comprises contacting the antigen-binding molecule obtained by the production method with an antigen, and evaluating the formation of an immune complex comprising the antigen-binding molecule and the antigen.

In a non-limiting embodiment of the present invention, after isolating a polynucleotide encoding an antigen-binding domain whose binding activity changes depending on the condition selected as described above, the polynucleotide is inserted into an appropriate expression vector. For example, when the antigen-binding domain is an antibody variable region, once a cDNA encoding the variable region is obtained, the cDNA is digested with restriction enzymes that recognize the restriction sites inserted at the two ends of the cDNA. Preferably, the restriction enzymes recognize and digest a nucleotide sequence that appears at a low frequency in the nucleotide sequence composing the gene of the antigen-binding molecule. Furthermore, restriction enzymes that provide cohesive ends are preferably inserted to insert a single copy of a digested fragment into the vector in the correct orientation. The cDNA encoding a variable region of an antigen-binding molecule digested as described above is inserted into an appropriate expression vector to obtain an expression vector for the antigen-binding molecule of the present invention. At this time, a gene encoding an antibody constant region (C region) may be fused in frame with the gene encoding the variable region.

To produce an antigen-binding molecule of interest, a polynucleotide encoding the antigen-binding molecule is inserted in a manner operably linked to a regulatory sequence into an expression vector. Regulatory sequences include, for example, enhancers and promoters. Furthermore, an appropriate signal sequence may be linked to the N terminus so that the expressed antigen-binding molecule is secreted to the outside of the cells. As signal sequence, for example, a peptide having the amino acid sequence MGWSCIILFLVATATGVHS (SEQ ID NO: 5) is used; however, it is also possible to link other appropriate signal sequences. The expressed polypeptide is cleaved at the carboxyl terminus of the above-described sequence, and the cleaved polypeptide is secreted as a mature polypeptide to the outside of cells. Then, appropriate host cells are transformed with this expression vector so that recombinant cells expressing the polynucleotide encoding the antigen-binding molecule of interest can be obtained. The antigen-binding molecules of the present invention can be produced from the recombinant cells by following the methods described above in the section on antibodies.

For a nucleic acid, "operably linked" means that the nucleic acid has a functional relationship with another nucleic acid sequence. For example, a DNA encoding a presequence or a secretory leader is operably linked to a DNA encoding a certain polypeptide if it is to be expressed as a precursor protein involved in the secretion of the polypeptide. A promoter or enhancer is operably linked to a coding sequence if it affects the transcription of the coding sequence. A ribosome binding site is operably linked to a coding sequence if it is in a position that facilitates translation. Generally, "operably linked" means that the linked DNA sequences are contiguous, and in the case of a secretory leader, it means that the linked DNA sequences are contiguous and in a reading frame. However, enhancers do not have to be contiguous. Linking is accomplished by ligation at suitable restriction sites. If such sites do not exist, synthetic oligonucleotide adaptors or linkers are used in accordance with conventional practice. Furthermore, linked nucleic acids may be produced by the above-mentioned overlap extension PCR technique.

In a non-limiting embodiment of the present invention, after isolating a polynucleotide encoding the above-described antigen-binding molecule whose binding activity varies depending on a selected condition, a variant of the polynucleotide is inserted into an appropriate expression vector. Such variants preferably include those prepared via humanization based on the polynucleotide sequence encoding an antigen-binding molecule of the present invention obtained by screening as a randomized variable region library a synthetic library or an immune library constructed originating from nonhuman animals. The same methods as described above for producing above-described humanized antibodies can be used as a method for producing humanized antigen-binding molecule variants.

In another embodiment, such variants preferably include those obtained by introducing an alteration that increases the antigen affinity (affinity maturation) of an antigen-binding molecule of the present invention into an isolated polynucleotide sequence for the molecule obtained by screening using a synthetic library or a naive library as a randomized variable region library. Such variants can be obtained by various known procedures for affinity maturation, including CDR mutagenesis (Yang et al. (J. Mol. Biol. (1995) 254, 392-403)), chain shuffling (Marks et al. (Bio/Technology (1992) 10, 779-783)), use of *E. coli* mutant strains (Low et al. (J. Mol. Biol. (1996) 250, 359-368)), DNA shuffling (Patten et al. (Curr. Opin. Biotechnol. (1997) 8, 724-733)), phage display (Thompson et al. (J. Mol. Biol. (1996) 256, 77-88)), and sexual PCR (Clameri et al. (Nature (1998) 391, 288-291)).

As described above, antigen-binding molecules that are produced by the production methods of the present invention include antigen-binding molecules having an Fc region. Various variants can be used as Fc regions. In an embodiment, variants of the present invention preferably include polynucleotides encoding antigen-binding molecules having a heavy chain in which a polynucleotide encoding an Fc region variant as described above is linked in frame to a polynucleotide encoding the above-described antigen-binding molecule whose binding activity varies depending on a selected condition.

In a non-limiting embodiment of the present invention, Fc regions preferably include, for example, Fc constant regions of antibodies such as IgG1 of SEQ ID NO: 13 (Ala is added to the N terminus of AAC82527.1), IgG2 of SEQ ID NO: 14 (Ala is added to the N terminus of AAB59393.1), IgG3 of SEQ ID NO: 15 (CAA27268.1), and IgG4 of SEQ ID NO: 16 (Ala is added to the N terminus of AAB59394.1). The plasma retention of IgG molecules is relatively long (the elimination from plasma is slow) since FcRn, particularly human FcRn, functions as a salvage receptor for IgG molecules. IgG molecules incorporated into endosomes by pinocytosis bind under the endosomal acidic condition to FcRn, particularly human FcRn, expressed in endosomes. IgG molecules that cannot bind to FcRn, particularly human FcRn, are transferred to lysosomes, and degraded there. Meanwhile, IgG molecules bound to FcRn, particularly human FcRn, are transferred to cell surface, and then return to plasma as a result of dissociation from FcRn, particularly human FcRn, under the neutral condition in plasma.

Since antibodies comprising a typical Fc region do not have a binding activity to FcRn, particularly to human FcRn, under the plasma neutral pH range condition, typical antibodies and antibody-antigen complexes are incorporated into cells by non-specific endocytosis and transferred to cell surface by binding to FcRn, particularly human FcRn, in the endosomal acidic pH range condition. FcRn, particularly human FcRn, transports antibodies from the endosome to the cell surface. Thus, some of FcRn, particularly human FcRn, is thought to be also present on the cell surface. However, antibodies are recycled to plasma, since they dissociated from FcRn, particularly human FcRn, in the neutral pH range condition on cell surface.

Fc regions having human FcRn-binding activity in the neutral pH range, which can be included in the antigen-binding molecules of the present invention, can be obtained by any method. Specifically, Fc regions having human FcRn-binding activity in the neutral pH range can be obtained by altering amino acids of human IgG-type immunoglobulin as a starting Fc region. Preferred Fc regions of human IgG-type immunoglobulin for alteration include, for example, those of human IgGs (IgG1, IgG2, IgG3, and IgG4, and variants thereof). Amino acids at any positions may be altered to other amino acids as long as the resulting regions have the human FcRn-binding activity in the neutral pH range or increased human FcRn-binding activity in the neutral range. When an antigen-binding molecule comprises the Fc region of human IgG1 as human Fc region, it is preferable that the resulting region comprises an alteration that results in the effect to enhance the human FcRn binding in the neutral pH range as compared to the binding activity of the starting Fc region of human IgG1. Amino acids that allow such alterations include, for example, at least one amino acid selected from the group of positions 221 to 225, 227, 228, 230, 232, 233 to 241, 243 to 252, 254 to 260, 262 to 272, 274, 276, 278 to 289, 291 to 312, 315 to 320, 324, 325, 327 to 339, 341, 343, 345, 360, 362, 370, 375 to 378, 380, 382, 385 to 387, 389, 396, 414, 416, 423, 424, 426 to 438, 440, and 442 (indicated by EU numbering). More specifically, such amino acid alterations include those listed in Table 5. Alteration of these amino acids enhances the human FcRn binding of the Fc region of IgG-type immunoglobulin in the neutral pH range.

Among those described above, appropriate alterations that enhance the human FcRn binding in the neutral pH range are selected for use in the present invention. Particularly preferred amino acids for such Fc region variants include, for example, amino acids at positions 237, 248, 250, 252, 254, 255, 256, 257, 258, 265, 286, 289, 297, 298, 303, 305, 307, 308, 309, 311, 312, 314, 315, 317, 332, 334, 360, 376, 380, 382, 384, 385, 386, 387, 389, 424, 428, 433, 434, and 436 (indicated by EU numbering). The human FcRn-binding activity of the Fc region included in an antigen-binding molecule can be increased in the neutral pH range by substituting at least one amino acid with a different amino acid.

Particularly preferred alterations in the Fc region include, for example, at least one or more amino acid alterations selected from the group of:
Met for the amino acid at position 237;
Ile for the amino acid at position 248;
Ala, Phe, Ile, Met, Gln, Ser, Val, Trp, or Tyr for the amino acid at position 250;

Phe, Trp, or Tyr for the amino acid at position 252;
Thr for the amino acid at position 254;
Glu for the amino acid at position 255;
Asp, Asn, Glu, or Gln for the amino acid at position 256;
Ala, Gly, Ile, Leu, Met, Asn, Ser, Thr, or Val for the amino acid at position 257;
His for the amino acid at position 258;
Ala for the amino acid at position 265;
Ala or Glu for the amino acid at position 286;
His for the amino acid at position 289;
Ala for the amino acid at position 297;
Ala for the amino acid at position 303;
Ala for the amino acid at position 305;
Ala, Asp, Phe, Gly, His, Ile, Lys, Leu, Met, Asn, Pro, Gln, Arg, Ser, Val, Trp, or Tyr for the amino acid at position 307;
Ala, Phe, Ile, Leu, Met, Pro, Gln, or Thr for the amino acid at position 308;
Ala, Asp, Glu, Pro, or Arg for the amino acid at position 309;
Ala, His, or Ile for the amino acid at position 311;
Ala or His for the amino acid at position 312;
Lys or Arg for the amino acid at position 314;
Ala, Asp, or His for the amino acid at position 315;
Ala for the amino acid at position 317;
Val for the amino acid at position 332;
Leu for the amino acid at position 334;
His for the amino acid at position 360;
Ala for the amino acid at position 376;
Ala for the amino acid at position 380;
Ala for the amino acid at position 382;
Ala for the amino acid at position 384;
Asp or His for the amino acid at position 385;
Pro for the amino acid at position 386;
Glu for the amino acid at position 387;
Ala or Ser for the amino acid at position 389;
Ala for the amino acid at position 424;
Ala, Asp, Phe, Gly, His, Ile, Lys, Leu, Asn, Pro, Gln, Ser, Thr, Val, Trp, or Tyr for the amino acid at position 428;
Lys for the amino acid at position 433;
Ala, Phe, His, Ser, Trp, or Tyr for the amino acid at position 434; and
His, Ile, Leu, Phe, Thr, or Val for the amino acid at position 436 in the EU numbering system. Meanwhile, the number of altered amino acids is not particularly limited; such amino acid alterations include single amino acid alteration and alteration of amino acids at two or more sites. Combinations of amino acid alterations at two or more sites include, for example, those described in Tables 5-1 to 5-33.

In addition to the Fc region of human IgG1 (SEQ ID NO: 13), IgG2 (SEQ ID NO: 14), IgG3 (SEQ ID NO: 15), or IgG4 (SEQ ID NO: 16), as Fc regions included in the present invention, Fc regions with modified FcγR binding, which have a higher Fcγ receptor-binding activity than the Fc region of a native human IgG in which the sugar chain bound at position 297 (EU numbering) is a fucose-containing sugar chain, may be suitably used. Such Fc regions with modified FcγR binding may be produced by modifying amino acids in the Fc region of a native human IgG. Whether the FcγR-binding activity of an Fc region is higher than that of the Fc region of a native human IgG, in which the sugar chain bound at position 297 (EU numbering) is a fucose-containing sugar chain, can be appropriately determined using methods such as those described above.

In the present invention, "modification of amino acids" or "amino acid modification" of an Fc region includes modification into an amino acid sequence which is different from that of the starting Fc region. The starting Fc region may be any Fc region, as long as a variant modified from the starting Fc region can bind to human Fcγ receptor in a neutral pH range. Furthermore, an Fc region modified from a starting Fc region which had been already modified can also be used preferably as an Fc region of the present invention. The "starting Fc region" can refer to the polypeptide itself, a composition comprising the starting Fc region, or an amino acid sequence encoding the starting Fc region. Starting Fc regions can comprise known Fc regions produced via recombination described briefly in the section "Antibodies". The origin of starting Fc regions is not limited, and they may be obtained from human or any nonhuman organisms. Such organisms preferably include mice, rats, guinea pigs, hamsters, gerbils, cats, rabbits, dogs, goats, sheep, bovines, horses, camels and organisms selected from nonhuman primates. In another embodiment, starting Fc regions can also be obtained from cynomolgus monkeys, marmosets, rhesus monkeys, chimpanzees, or humans. Starting Fc regions can be obtained preferably from human IgG1; however, they are not limited to any particular IgG class. This means that an Fc region of human IgG1, IgG2, IgG3, or IgG4 can be used appropriately as a starting Fc region, and herein also means that an Fc region of an arbitrary IgG class or subclass derived from any organisms described above can be preferably used as a starting Fc region. Examples of naturally-occurring IgG variants or modified forms are described in published documents (Curr. Opin. Biotechnol. (2009) 20 (6): 685-91; Curr. Opin. Immunol. (2008) 20 (4), 460-470; Protein Eng. Des. Sel. (2010) 23 (4): 195-202; International Publication Nos. WO 2009/086320, WO 2008/092117, WO 2007/041635, and WO 2006/105338); however, they are not limited to the examples.

Examples of alterations include those with one or more mutations, for example, mutations by substitution of different amino acid residues for amino acids of starting Fc regions, by insertion of one or more amino acid residues into starting Fc regions, or by deletion of one or more amino acids from starting Fc region. Preferably, the amino acid sequences of altered Fc regions comprise at least a part of the amino acid sequence of a non-native Fc region. Such variants necessarily have sequence identity or similarity less than 100% to their starting Fc region. In a preferred embodiment, the variants have amino acid sequence identity or similarity about 75% to less than 100%, more preferably about 80% to less than 100%, even more preferably about 85% to less than 100%, still more preferably about 90% to less than 100%, and yet more preferably about 95% to less than 100% to the amino acid sequence of their starting Fc region. In a non-limiting embodiment of the present invention, at least one amino acid is different between an FcγR-binding modified Fc region of the present invention and its starting Fc region. Amino acid difference between an FcγR-binding modified Fc region of the present invention and its starting Fc region can also be preferably specified based on the specific amino acid differences at the above-described specific amino acid positions according to EU numbering system.

The Fc region with modified FcγR binding, which has a higher Fcγ receptor-binding activity than that of the Fc region of a native human IgG in which the sugar chain bound at position 297 (EU numbering) is a fucose-containing sugar chain, contained in the antigen-binding molecules of the present invention may be obtained by any method. Specifically, the Fc region with modified FcγR binding can be obtained by modifying amino acids in a human IgG-type immunoglobulin, and is used as the starting Fc region. Preferred Fc regions of IgG-type immunoglobulins for modification include, for example, Fc regions of human IgGs (IgG1, IgG2, IgG3, IgG4, and variants thereof).

Amino acids of any positions may be modified into other amino acids, as long as the binding activity toward the Fcγ receptor is higher than that of the Fc region of a native human IgG, in which the sugar chain bound at position 297 (EU numbering) is a fucose-containing sugar chain. When the antigen-binding molecule contains a human IgG1 Fc region as the human Fc region, it preferably contains a modification that yields the effect of a higher Fcγ receptor-binding activity than that of the Fc region of a native human IgG, in which the sugar chain bound at position 297 (EU numbering) is a fucose-containing sugar chain. Such amino acid modifications have been reported, for example, in international publications such as WO2007/024249, WO2007/021841, WO2006/031370, WO2000/042072, WO2004/029207, WO2004/099249, WO2006/105338, WO2007/041635, WO2008/092117, WO2005/070963, WO2006/020114, WO2006/116260, and WO2006/023403.

Examples of such amino acids that can be modified include at least one or more amino acids selected from the group of positions 221, 222, 223, 224, 225, 227, 228, 230, 231, 232, 233, 234, 235, 236, 237, 238, 239, 240, 241, 243, 244, 245, 246, 247, 249, 250, 251, 254, 255, 256, 258, 260, 262, 263, 264, 265, 266, 267, 268, 269, 270, 271, 272, 273, 274, 275, 276, 278, 279, 280, 281, 282, 283, 284, 285, 286, 288, 290, 291, 292, 293, 294, 295, 296, 297, 298, 299, 300, 301, 302, 303, 304, 305, 311, 313, 315, 317, 318, 320, 322, 323, 324, 325, 326, 327, 328, 329, 330, 331, 332, 333, 334, 335, 336, 337, 339, 376, 377, 378, 379, 380, 382, 385, 392, 396, 421, 427, 428, 429, 434, 436, and 440 (EU numbering). By modifying these amino acids, one can obtain Fc regions (Fc regions with modified FcγR binding) with a higher binding activity toward the Fcγ receptor than the binding activity toward the Fcγ receptor of the Fc region of a native human IgG, in which the sugar chain bound at position 297 (EU numbering) is a fucose-containing sugar chain.

Examples of particularly preferred modifications for use in the present invention includeat least one or more amino acid modifications in the Fc region selected from the group of:

Lys or Tyr for the amino acid of position 221;
Phe, Trp, Glu, or Tyr for the amino acid of position 222;
Phe, Trp, Glu, or Lys for the amino acid of position 223;
Phe, Trp, Glu, or Tyr for the amino acid of position 224;
Glu, Lys, or Trp for the amino acid of position 225;
Glu, Gly, Lys, or Tyr for the amino acid of position 227;
Glu, Gly, Lys, or Tyr for the amino acid of position 228;
Ala, Glu, Gly, or Tyr for the amino acid of position 230;
Glu, Gly, Lys, Pro, or Tyr for the amino acid of position 231;
Glu, Gly, Lys, or Tyr for the amino acid of position 232;
Ala, Asp, Phe, Gly, His, Ile, Lys, Leu, Met, Asn, Gln, Arg, Ser, Thr, Val, Trp, or Tyr for the amino acid of position 233;
Ala, Asp, Glu, Phe, Gly, His, Ile, Lys, Met, Asn, Pro, Gln, Arg, Ser, Thr, Val, Trp, or Tyr for the amino acid of position 234;
Ala, Asp, Glu, Phe, Gly, His, Ile, Lys, Met, Asn, Pro, Gln, Arg, Ser, Thr, Val, Trp, or Tyr for the amino acid of position 235;
Ala, Asp, Glu, Phe, His, Ile, Lys, Leu, Met, Asn, Pro, Gln, Arg, Ser, Thr, Val, Trp, or Tyr for the amino acid of position 236;
Asp, Glu, Phe, His, Ile, Lys, Leu, Met, Asn, Pro, Gln, Arg, Ser, Thr, Val, Trp, or Tyr for the amino acid of position 237;
Asp, Glu, Phe, Gly, His, Ile, Lys, Leu, Met, Asn, Gln, Arg, Ser, Thr, Val, Trp, or Tyr for the amino acid of position 238;
Asp, Glu, Phe, Gly, His, Ile, Lys, Leu, Met, Asn, Pro, Gln, Arg, Thr, Val, Trp, or Tyr for the amino acid of position 239;
Ala, Ile, Met, or Thr for the amino acid of position 240;
Asp, Glu, Leu, Arg, Trp, or Tyr for the amino acid of position 241;
Leu, Glu, Leu, Gln, Arg, Trp, or Tyr for the amino acid of position 243;
His for the amino acid of position 244;
Ala for the amino acid of position 245;
Asp, Glu, His, or Tyr for the amino acid of position 246;
Ala, Phe, Gly, His, Ile, Leu, Met, Thr, Val, or Tyr for the amino acid of position 247;
Glu, His, Gln, or Tyr for the amino acid of position 249;
Glu or Gln for the amino acid of position 250;
Phe for the amino acid of position 251;
Phe, Met, or Tyr for the amino acid of position 254;
Glu, Leu, or Tyr for the amino acid of position 255;
Ala, Met, or Pro for the amino acid of position 256;
Asp, Glu, His, Ser, or Tyr for the amino acid of position 258;
Asp, Glu, His, or Tyr for the amino acid of position 260;
Ala, Glu, Phe, Ile, or Thr for the amino acid of position 262;
Ala, Ile, Met, or Thr for the amino acid of position 263;
Asp, Glu, Phe, Gly, His, Ile, Lys, Leu, Met, Asn, Pro, Gln, Arg, Ser, Thr, Trp, or Tyr for the amino acid of position 264;
Ala, Leu, Phe, Gly, His, Ile, Lys, Leu, Met, Asn, Pro, Gln, Arg, Ser, Thr, Val, Trp, or Tyr for the amino acid of position 265;
Ala, Ile, Met, or Thr for the amino acid of position 266;
Asp, Glu, Phe, His, Ile, Lys, Leu, Met, Asn, Pro, Gln, Arg, Thr, Val, Trp, or Tyr for the amino acid of position 267;
Asp, Glu, Phe, Gly, Ile, Lys, Leu, Met, Pro, Gln, Arg, Thr, Val, or Trp for the amino acid of position 268;
Phe, Gly, His, Ile, Lys, Leu, Met, Asn, Pro, Arg, Ser, Thr, Val, Trp, or Tyr for the amino acid of position 269;
Glu, Phe, Gly, His, Ile, Leu, Met, Pro, Gln, Arg, Ser, Thr, Trp, or Tyr for the amino acid of position 270;
Ala, Asp, Glu, Phe, Gly, His, Ile, Lys, Leu, Met, Asn, Gln, Arg, Ser, Thr, Val, Trp, or Tyr for the amino acid of position 271;
Asp, Phe, Gly, His, Ile, Lys, Leu, Met, Pro, Arg, Ser, Thr, Val, Trp, or Tyr for the amino acid of position 272;
Phe or Ile for the amino acid of position 273;
Asp, Glu, Phe, Gly, His, Ile, Leu, Met, Asn, Pro, Arg, Ser, Thr, Val, Trp, or Tyr for the amino acid of position 274;
Leu or Trp for the amino acid of position 275;
Asp, Glu, Phe, Gly, His, Ile, Leu, Met, Pro, Arg, Ser, Thr, Val, Trp, or Tyr for the amino acid of position 276;
Asp, Glu, Gly, His, Ile, Lys, Leu, Met, Asn, Pro, Gln, Arg, Ser, Thr, Val, or Trp for the amino acid of position 278;
Ala for the amino acid of position 279;
Ala, Gly, His, Lys, Leu, Pro, Gln, Trp, or Tyr for the amino acid of position 280;
Asp, Lys, Pro, or Tyr for the amino acid of position 281;
Glu, Gly, Lys, Pro, or Tyr for the amino acid of position 282;
Ala, Gly, His, Ile, Lys, Leu, Met, Pro, Arg, or Tyr for the amino acid of position 283;
Asp, Glu, Leu, Asn, Thr, or Tyr for the amino acid of position 284;
Asp, Glu, Lys, Gln, Trp, or Tyr for the amino acid of position 285;
Glu, Gly, Pro, or Tyr for the amino acid of position 286;
Asn, Asp, Glu, or Tyr for the amino acid of position 288;
Asp, Gly, His, Leu, Asn, Ser, Thr, Trp, or Tyr for the amino acid of position 290;
Asp, Glu, Gly, His, Ile, Gln, or Thr for the amino acid of position 291;

Ala, Asp, Glu, Pro, Thr, or Tyr for the amino acid of position 292;
Phe, Gly, His, Ile, Leu, Met, Asn, Pro, Arg, Ser, Thr, Val, Trp, or Tyr for the amino acid of position 293;
Phe, Gly, His, Ile, Lys, Leu, Met, Asn, Pro, Arg, Ser, Thr, Val, Trp, or Tyr for the amino acid of position 294;
Asp, Glu, Phe, Gly, His, Ile, Lys, Met, Asn, Pro, Arg, Ser, Thr, Val, Trp, or Tyr for the amino acid of position 295;
Ala, Asp, Glu, Gly, His, Ile, Lys, Leu, Met, Asn, Gln, Arg, Ser, Thr, or Val for the amino acid of position 296;
Asp, Glu, Phe, Gly, His, Ile, Lys, Leu, Met, Pro, Gln, Arg, Ser, Thr, Val, Trp, or Tyr for the amino acid of position 297;
Ala, Asp, Glu, Phe, His, Ile, Lys, Met, Asn, Gln, Arg, Thr, Val, Trp, or Tyr for the amino acid of position 298;
Ala, Asp, Glu, Phe, Gly, His, Ile, Lys, Leu, Met, Asn, Pro, Gln, Arg, Ser, Val, Trp, or Tyr for the amino acid of position 299;
Ala, Asp, Glu, Gly, His, Ile, Lys, Leu, Met, Asn, Pro, Gln, Arg, Ser, Thr, Val, or Trp for the amino acid of position 300;
Asp, Glu, His, or Tyr for the amino acid of position 301;
Ile for the amino acid of position 302;
Asp, Gly, or Tyr for the amino acid of position 303;
Asp, His, Leu, Asn, or Thr for the amino acid of position 304;
Glu, Ile, Thr, or Tyr for the amino acid of position 305;
Ala, Asp, Asn, Thr, Val, or Tyr for the amino acid of position 311;
Phe for the amino acid of position 313;
Leu for the amino acid of position 315;
Glu or Gln for the amino acid of position 317;
His, Leu, Asn, Pro, Gln, Arg, Thr, Val, or Tyr for the amino acid of position 318;
Asp, Phe, Gly, His, Ile, Leu, Asn, Pro, Ser, Thr, Val, Trp, or Tyr for the amino acid of position 320;
Ala, Asp, Phe, Gly, His, Ile, Pro, Ser, Thr, Val, Trp, or Tyr for the amino acid of position 322;
Ile for the amino acid of position 323;
Asp, Phe, Gly, His, Ile, Leu, Met, Pro, Arg, Thr, Val, Trp, or Tyr for the amino acid of position 324;
Ala, Asp, Glu, Phe, Gly, His, Ile, Lys, Leu, Met, Pro, Gln, Arg, Ser, Thr, Val, Trp, or Tyr for the amino acid of position 325;
Ala, Asp, Glu, Gly, Ile, Leu, Met, Asn, Pro, Gln, Ser, Thr, Val, Trp, or Tyr for the amino acid of position 326;
Ala, Asp, Glu, Phe, Gly, His, Ile, Lys, Leu, Met, Asn, Pro, Arg, Thr, Val, Trp, or Tyr for the amino acid of position 327;
Ala, Asp, Glu, Phe, Gly, His, Ile, Lys, Met, Asn, Pro, Gln, Arg, Ser, Thr, Val, Trp, or Tyr for the amino acid of position 328;
Asp, Glu, Phe, Gly, His, Ile, Lys, Leu, Met, Asn, Gln, Arg, Ser, Thr, Val, Trp, or Tyr for the amino acid of position 329;
Cys, Glu, Phe, Gly, His, Ile, Lys, Leu, Met, Asn, Pro, Arg, Ser, Thr, Val, Trp, or Tyr for the amino acid of position 330;
Asp, Phe, His, Ile, Leu, Met, Gln, Arg, Thr, Val, Trp, or Tyr for the amino acid of position 331;
Ala, Asp, Glu, Phe, Gly, His, Lys, Leu, Met, Asn, Pro, Gln, Arg, Ser, Thr, Val, Trp, or Tyr for the amino acid of position 332;
Ala, Asp, Glu, Phe, Gly, His, Ile, Leu, Met, Pro, Ser, Thr, Val, or Tyr for the amino acid of position 333;
Ala, Glu, Phe, Ile, Leu, Pro, or Thr for the amino acid of position 334;
Asp, Phe, Gly, His, Ile, Leu, Met, Asn, Pro, Arg, Ser, Val, Trp, or Tyr for the amino acid of position 335;
Glu, Lys, or Tyr for the amino acid of position 336;
Glu, His, or Asn for the amino acid of position 337;
Asp, Phe, Gly, Ile, Lys, Met, Asn, Gln, Arg, Ser, or Thr for the amino acid of position 339;
Ala or Val for the amino acid of position 376;
Gly or Lys for the amino acid of position 377;
Asp for the amino acid of position 378;
Asn for the amino acid of position 379;
Ala, Asn, or Ser for the amino acid of position 380;
Ala or Ile for the amino acid of position 382;
Glu for the amino acid of position 385;
Thr for the amino acid of position 392;
Leu for the amino acid of position 396;
Lys for the amino acid of position 421;
Asn for the amino acid of position 427;
Phe or Leu for the amino acid of position 428;
Met for the amino acid of position 429;
Trp for the amino acid of position 434;
Ile for the amino acid of position 436; and
Gly, His, Ile, Leu, or Tyr for the amino acid of position 440; as indicated by EU numbering. Furthermore, the number of amino acids to be modified is not particularly limited, and amino acid at only one site may be modified or amino acids at two or more sites may be modified. Examples of combinations for the amino acid modifications at two or more sites include those described in Table 6 (Tables 6-1 to 6-3).

Among the Fc regions suitable for use in the present invention, a suitable example of an Fc region that has a higher binding activity toward an inhibitory Fcγ receptor than toward an activating Fcγ receptor (i.e., having a selective binding activity toward an inhibitory Fcγ receptor), which is used as a non-limiting embodiment of an Fc region with the property of having a higher binding activity toward a specific Fcγ receptor than toward other Fcγ receptors (i.e., an Fc region having a selective Fcγ receptor-binding activity), is an Fc region with one or more of the following modifications in the amino acids (indicated by EU numbering) of the aforementioned Fc region: the amino acid at position 238 is modified to Asp and the amino acid at position 328 is modified to Glu. The Fc regions and modifications described in US2009/0136485 or WO 2012/115241 may be selected appropriately as the Fc region having a selective binding activity to an inhibitory Fcγ receptor.

In a non-limiting embodiment of the present invention, a suitable example is an Fc region in which one or more of the amino acids indicated by EU numbering at positions 238 and 328 according to EU numbering are respectively modified to Asp or Glu in the aforementioned Fc region.

Furthermore, in a non-limiting embodiment of the present invention, suitable examples of the Fc regions are those with substitution of Asp for Pro at position 238 (EU numbering), and one or more modifications selected from among Trp for the amino acid of position 237, Phe for the amino acid of position 237, Val for the amino acid of position 267, Gln for the amino acid of position 267, Asn for the amino acid of position 268, Gly for the amino acid of position 271, Leu for the amino acid of position 326, Gln for the amino acid of position 326, Glu for the amino acid of position 326, Met for the amino acid of position 326, Asp for the amino acid of position 239, Ala for the amino acid of position 267, Trp for the amino acid of position 234, Tyr for the amino acid of position 234, Ala for the amino acid of position 237, Asp for the amino acid of position 237, Glu for the amino acid of position 237, Leu for the amino acid of position 237, Met for the amino acid of position 237, Tyr for the amino acid of position 237, Lys for the amino acid of position 330, Arg for the amino acid of position 330, Asp for the amino acid of position 233, Asp for the amino acid of position 268, Glu for the amino acid of position 268, Asp for the amino acid of position 326, Ser for the amino acid of position 326, Thr for the amino acid of position 326, Ile for the amino acid of position 323, Leu for the amino acid of position 323, Met for the amino acid of position 296, Ala for the amino acid of position 326, Asn for the amino acid of position 326, and Met for the amino acid of position 330, according to EU numbering.

Appropriate known methods such as site-directed mutagenesis (Kunkel et al. (Proc. Natl. Acad. Sci. USA (1985) 82, 488-492)) and overlap extension PCR can be applied to alter the amino acids of Fc regions. Furthermore, various known methods can also be used as an amino acid alteration method for substituting amino acids with those other than natural amino acids (Annu. Rev. Biophys. Biomol. Struct. (2006) 35, 225-249; Proc. Natl. Acad. Sci. U.S.A. (2003) 100 (11), 6353-6357). For example, it is also preferable to use a cell-free translation system (Clover Direct (Protein Express)) comprising tRNAs in which an unnatural amino acid is linked to an amber suppressor tRNA, which is complementary to UAG stop codon (amber codon).

In an embodiment of variants of the present invention, polynucleotides encoding antigen-binding molecules which have a heavy chain where a polynucleotide encoding an Fc region modified to have an amino acid mutation as described above is linked in frame to a polynucleotide encoding the above-described antigen-binding domain whose binding activity varies depending on a selected condition.

The present invention provides methods for producing antigen-binding molecules, comprising collecting the antigen-binding molecules from culture media of cells introduced with vectors in which a polynucleotide encoding an Fc region is operably linked in frame to a polynucleotide encoding an antigen-binding domain whose binding activity varies depending on ion concentration condition. Furthermore, the present invention also provides methods for producing antigen-binding molecules, comprising collecting the antigen-binding molecules from culture media of cells introduced with vectors constructed by operably linking a polynucleotide encoding an antigen-binding domain whose binding activity varies depending on ion concentration condition to a polynucleotide encoding an Fc region which is in advance operably linked to a vector.

In the production methods of the present invention, one can add suitable modifications to the domain after obtaining an "antigen-binding domain confirmed to form an immune complex", as long as formation of the immune complex is enabled. Furthermore, a method for producing an antigen-binding molecule is also provided, which includes collecting the antigen-binding molecule from a culture solution of cells containing a vector that carries a polynucleotide encoding an antigen-binding molecule that has a heavy chain in which a polynucleotide encoding an antigen-binding domain capable of forming an immune complex and modified this way is linked in frame to a polynucleotide encoding an Fc region variant in which the above-mentioned amino acid mutations have been added.

Pharmaceutical Compositions

When a conventional neutralizing antibody against a soluble antigen is administered, the plasma retention of the antigen is expected to be prolonged by binding to the antibody. In general, antibodies have a long half-life (one week to three weeks) while the half-life of antigen is generally short (one day or less). Meanwhile, antibody-bound antigens have a significantly longer half-life in plasma as compared to when the antigens are present alone. For this reason, administration of existing neutralizing antibody results in an increased antigen concentration in plasma. Such cases have been reported with various neutralizing antibodies that target soluble antigens including, for example, IL-6 (J. Immunotoxicol. (2005) 3, 131-139), amyloid beta (mAbs (2010) 2 (5), 1-13), MCP-1 (ARTHRITIS & RHEUMATISM (2006) 54, 2387-2392), hepcidin (AAPS J. (2010) 4, 646-657), and sIL-6 receptor (Blood (2008) 112 (10), 3959-64). Administration of existing neutralizing antibodies has been reported to increase the total plasma antigen concentration to about 10 to 1,000 times (the level of increase varies depending on antigen) the base line. Herein, the total plasma antigen concentration refers to a concentration as a total amount of antigen in plasma, i.e., the sum of concentrations of antibody-bound and antibody-unbound antigens. An increase in the total plasma antigen concentration is undesirable for such antibody pharmaceuticals that target a soluble antigen. The reason is that the antibody concentration has to be higher than at least the total plasma antigen concentration to neutralize the soluble antigen. Specifically, "the total plasma antigen concentration is increased to 10 to 1,000 times" means that, in order to neutralize the antigen, the plasma antibody concentration (i.e., antibody dose) has to be 10 to 1,000 times higher as compared to when increase in the total plasma antigen concentration does not occur. Conversely, if the total plasma antigen concentration can be reduced by 10 to 1,000 times as compared to the existing neutralizing antibody, the antibody dose can also be reduced to similar extent. Thus, antibodies capable of decreasing the total plasma antigen concentration by eliminating the soluble antigen from plasma are highly useful as compared to existing neutralizing antibodies.

Without being restricted to a particular theory, the following mechanism is an example of a mechanism that can cause elimination of the antigenic binding units from the plasma by an antigen-binding molecule of the present invention, which contains (i) an Fc region and (ii) an antigen-binding domain of which antigen-binding activity varies depending on an ion concentration condition, and where the antigen-binding molecule can form an immune complex containing two or more of the antigen-binding molecules and antigens having two or more antigenic binding units. When the antigenic binding unit is one unit (i.e., a homomonomer), such as in sIL-6R, two molecules ((i.e., two antigenic binding units) of antigens bind to a single antibody molecule containing a divalent antibody-binding domain, and a complex of one anti-sIL-6R antibody molecule and two antigen molecules containing two antigenic binding units is formed. Therefore, this type of antigen-antibody complex has only one Fc region (native IgG1 Fc region) as shown in FIG. 1. Since this complex binds to two molecules of FcRn or one molecule of FcγR via a single Fc region, the affinity toward these receptors is the same as that of a general IgG antibody, and uptake into cells is thought to occur mostly non-specifically.

On the other hand, when the antigenic binding unit is two units as in human IgA, which is a dimer of a hetero-complex of heavy chains and light chains, there are two units of epitopes to which the antigen-binding domains will bind in the antigenic binding unit. However, when a bivalent anti-IgA antibody (i.e., the antigen-binding domains contained in one anti-IgA antibody molecule bind to a same epitope) binds to its antigen, IgA, it is thought that binding of each of the bivalent antigen-binding domains contained in the single anti-IgA antibody molecule to each of the two epitope units present on a single IgA molecule is difficult in view of the position of the epitopes. As a result, it is thought that separate anti-IgA antibody molecules bind to the two antigenic binding units present in the two molecules of IgA that bind to the bivalent antigen-binding domains present in a single anti-IgA antibody molecule, and consequently, antigen-antibody complexes (immune complexes) containing at least four molecules (that is, two IgA molecules which are antigen molecule, and two anti-IgA antibody molecules which are antigen-binding molecules) are formed.

When an antigen-binding molecule such as an antibody binding to an antigen molecule that contains two or more antigenic binding units, forms a large immune complex which is at least a tetramer, the immune complex can bind strongly with avidity through at least two or more multivalent Fc regions to FcγR, FcRn, complement receptors, and such. Therefore, as shown in FIG. 7, the complex is taken up efficiently into cells expressing these receptors. On the other hand, since the Fc region-mediated affinity toward these receptors of immune complexes formed of antigen molecules and antigen-binding molecules that for example bind to (monomeric) antigen molecules containing one antigenic binding unit is insufficient as mentioned above, the immune complexes are taken up mostly nonspecifically (less efficiently as compared to uptake mediated by avidity binding) into cells expressing these receptors, as shown in FIG. 1. Thus, the uptake is more inefficient than uptake mediated by avidity binding.

When the antigen-binding molecule such as an antibody that binds to an antigen molecule containing two or more antigenic binding units is an antibody that contains antigen-binding domains of which antigen-binding varies depending on an ion concentration condition such as pH- or Ca-dependent binding and which forms an antigen-antibody complex (immune complex) containing at least four molecules (two antigen molecules and two antibody molecules) in the plasma, once the immune complex is taken up into cells, the antigens dissociate from the antibodies in the endosomes where the ion concentration conditions are different from those in the plasma. Therefore, the immune complex formation is dissolved in the endosomes of cells that have taken up the immune complexes. Since the dissociated antigens cannot bind to FcRn in the endosomes, they are degraded after translocating to the lysosomes. On the other hand, the antigen-dissociated antibodies are thought to be recycled to the plasma after binding to FcRn in the endosomes (FIG. 7).

As described above, if an antibody that contains a native IgG1-type constant region against a multimeric antigen containing two or more antigenic binding units and shows pH- or Ca-dependent binding can form a large immune complex and bind to FcγR, FcRn, complement receptors, and such with avidity, it is thought that antigen elimination alone can be selectively and greatly accelerated. It is thought that when GA2-IgG1 which binds to human IgA is administered, such large immune complexes are formed. Indeed, as shown in Example 3, GA2-IgG1-FcγR(−) formed by introducing into GA2-IgG1 modifications that impair binding to mouse FcγR could not substantially accelerate elimination of human IgA like GA2-IgG1 when compared to human IgA alone, and showed an equivalent level of elimination as human IgA alone. Therefore, the reason that GA2-IgG1 could accelerate elimination of human IgA is because the immune complex containing GA2-IgG1 and human IgA, which is a multimeric antigen containing two or more antigenic binding units, binds with avidity to FcγR and is quickly taken up into cells expressing FcγR. The IgA that dissociates from the immune complex in the endosomes of cells that have taken up the immune complex is degraded in the lysosomes. At the same time, the IgA-dissociated antibody, which was bound to FcRn in the endosomes, is subsequently recycled to the plasma and can bind again to IgA in the plasma. Elimination of human IgA in the plasma is thought to be greatly accelerated in this manner. A method using an amino-acid-variant of the Fc region which binds to FcRn in the pH neutral range is described in WO2011/122011 as a method for accelerating elimination of antigens from the plasma. The present invention is useful as a method for accelerating the elimination from the plasma of multimeric antigens containing two or more antigenic binding units without using the above-mentioned variants, and as shown in GA2-N434W, can further accelerate the elimination of the multimeric antigens containing two or more antigenic binding units from the plasma through combination with the above-mentioned variants. Moreover, multimeric antigens containing two or more antigenic binding units may be eliminated, other than from the plasma, from the interstitial fluid, synovial fluid, peritoneal fluid, pleural fluid, and pericardial fluid, as long as the cells contacting interstitial fluid, synovial fluid, peritoneal fluid, pleural fluid, or pericardial fluid express FcγR or FcRn. A non-limiting embodiment of such cells includes immune cells and such present in the interstitial fluid, synovial fluid, peritoneal fluid, pleural fluid, and pericardial fluid.

Specifically, the present invention also relates to pharmaceutical compositions comprising antigen-binding molecules of the present invention, antigen-binding molecules produced by alteration methods of the present invention, or antigen-binding molecules produced by production methods of the present invention. Antigen-binding molecules of the present invention or antigen-binding molecules produced by production methods of the present invention are useful as pharmaceutical compositions since they, when administered, have the strong effect to reduce the plasma antigen concentration as compared to typical antigen-binding molecules, and exhibit the improved in vivo immune response, pharmacokinetics, and others in animals administered with the molecules. The pharmaceutical compositions of the present invention may comprise pharmaceutically acceptable carriers.

In the present invention, pharmaceutical compositions generally refer to agents for treating or preventing, or testing and diagnosing diseases.

The pharmaceutical compositions of the present invention can be formulated by methods known to those skilled in the art. For example, they can be used parenterally, in the form of injections of sterile solutions or suspensions including water or other pharmaceutically acceptable liquid. For example, such compositions can be formulated by mixing in the form of unit dose required in the generally approved medicine manufacturing practice, by appropriately combining with pharmacologically acceptable carriers or media, specifically with sterile water, physiological saline, vegetable oil, emulsifier, suspension, surfactant, stabilizer, flavoring agent, excipient, vehicle, preservative, binder, or such. In such formulations, the amount of active ingredient is adjusted to obtain an appropriate amount in a pre-determined range.

Sterile compositions for injection can be formulated using vehicles such as distilled water for injection, according to standard formulation practice. Aqueous solutions for injection include, for example, physiological saline and isotonic solutions containing dextrose or other adjuvants (for example, D-sorbitol, D-mannose, D-mannitol, and sodium chloride). It is also possible to use in combination appropriate solubilizers, for example, alcohols (ethanol and such), polyalcohols (propylene glycol, polyethylene glycol, and such), non-ionic surfactants (polysorbate 80(TM), HCO-50, and such).

Oils include sesame oil and soybean oils. Benzyl benzoate and/or benzyl alcohol can be used in combination as solubilizers. It is also possible to combine buffers (for example, phosphate buffer and sodium acetate buffer), soothing agents (for example, procaine hydrochloride), stabilizers (for example, benzyl alcohol and phenol), and/or antioxidants. Appropriate ampules are filled with the prepared injections.

The pharmaceutical compositions of the present invention are preferably administered parenterally. For example, the compositions in the dosage form for injections, transnasal administration, transpulmonary administration, or transdermal administration are administered. For example, they can be administered systemically or locally by intravenous injection, intramuscular injection, intraperitoneal injection, subcutaneous injection, or such.

Administration methods can be appropriately selected in consideration of the patient's age and symptoms. The dose of a pharmaceutical composition containing an antigen-binding molecule can be, for example, from 0.0001 to 1,000 mg/kg for each administration. Alternatively, the dose can be, for example, from 0.001 to 100,000 mg per patient. However, the present invention is not limited by the numeric values described above. The doses and administration methods vary depending on the patient's weight, age, symptoms, and such. Those skilled in the art can set appropriate doses and administration methods in consideration of the factors described above.

Furthermore, the present invention provides kits for use in the methods of the present invention, which comprise at least an antigen-binding molecule of the present invention. In addition to the above, pharmaceutically acceptable carriers, media, instruction manuals describing the using method, and such may be packaged into the kits.

Furthermore, the present invention relates to pharmaceutical agents for eliminating, from the plasma, complexes containing two or more antigenic binding units and two or more antigen-binding molecules present in the plasma, which contain as an active ingredient the antigen-binding molecules of the present invention or the antigen-binding molecules produced by the production methods of the present invention.

The present invention relates to methods for treating a disease, which includes administering to subjects (patients, human subjects, etc.) the antigen-binding molecules of the present invention or the antigen-binding molecules produced by the production methods of the present invention. A non-limiting example of the disease includes cancer and inflammatory diseases.

The present invention also relates to use of the antigen-binding molecules of the present invention or the antigen-binding molecules produced by the production methods of the present invention in the manufacture of a pharmaceutical agent for eliminating from the plasma complexes containing two or more antigenic binding units and two or more antigen-binding molecules present in the plasma.

The present invention further relates to use of the antigen-binding molecules of the present invention or the antigen-binding molecules produced by the production methods of the present invention for eliminating, from the plasma, complexes containing two or more antigenic binding units and two or more antigen-binding molecules present in the plasma.

In addition, the present invention relates to antigen-binding molecules of the present invention and antigen-binding molecules produced by the production methods of present invention for use in the methods of the present invention.

Amino acids contained in the amino acid sequences of the present invention may be post-translationally modified (for example, the modification of an N-terminal glutamine into a pyroglutamic acid by pyroglutamylation is well-known to those skilled in the art). Naturally, such post-translationally modified amino acids are included in the amino acid sequences in the present invention.

All prior art documents cited in this specification are incorporated herein by reference.

EXAMPLES

Herein below, the present invention will be specifically described with reference to examples, however, it is not to be construed as being limited thereto.

[Example 1] Preparation of Antibodies that Bind to Human IgA in a Calcium-Dependent Manner 1-1. Preparation of Human IgA (hIgA)

Human IgA (hereinafter also abbreviated as "hIgA") was prepared as an antigen by using the following recombinant techniques. hIgA was expressed by culturing host cells carrying recombinant vectors inserted with H (WT)-IgA1 (SEQ ID NO: 49) and L (WT) (SEQ ID NO: 50) and purified by a method known to those skilled in the art using ion-exchange chromatography and gel filtration chromatography.

1-2. Antibodies with Calcium-Dependent Binding

H54/L28-IgG1 described in International Publication No. WO 2009/125825 is a humanized anti-IL-6 receptor antibody. Fv4-IgG1 is a humanized anti-IL-6 receptor antibody that results from conferring H54/L28-IgG1 with the property of binding to soluble human IL-6 receptor in a pH-dependent manner (i.e., of binding under neutral condition and dissociating under acidic condition). The in vivo test described in International Publication No. WO 2009/125825 using mice demonstrated that elimination of soluble human IL-6 receptor is greatly accelerated in a group administered with a mixture of Fv4-IgG1 and soluble human IL-6 receptor as antigen as compared to a group administered with a mixture of H54/L28-IgG1 and soluble human IL-6 receptor as antigen.

Soluble human IL-6 receptor bound to a general antibody that binds to soluble human IL-6 receptor is recycled to the plasma along with the antibody via FcRn. Meanwhile, an antibody that binds to soluble human IL-6 receptor in a pH-dependent manner dissociates under the acidic conditions in the endosome from the soluble human IL-6 receptor that was bound to the antibody. The dissociated soluble human IL-6 receptor is degraded in the lysosome. Thus, this can greatly accelerate the elimination of soluble human IL-6 receptor from the plasma. Moreover, the antibody that binds to soluble human IL-6 receptor in a pH-dependent manner is recycled to the plasma via FcRn after it has dissociated from the soluble human IL-6 receptor, so that the recycled antibody can bind to a soluble human IL-6 receptor again. By repeating this cycle (Antibody that bound to antigens is taken up into cells >the antigens are dissociated from the antibody >the antigens are degraded and the antibody is recycled back to plasma), a single antibody molecule can repeatedly bind to soluble human IL-6 receptors multiple times (FIG. 1).

Meanwhile, as described in International Publication No. WO 2009/125825, H54/L28-IgG1 is a humanized anti-IL-6 receptor antibody and Fv4-IgG1 is a humanized anti-IL-6 receptor antibody that results from conferring H54/L28-IgG1 with the property of binding to soluble human IL-6 receptor in a pH-dependent manner (i.e., binding under neutral condition and dissociating under acidic condition). Fv4-IgG1-v2 is a humanized anti-IL-6 receptor antibody in which FcRn binding is increased over Fv4-IgG1 under neutral conditions. The in vivo test described in International Publication No. WO 2011/122011 using mice demonstrated that elimination of soluble human IL-6 receptor is greatly accelerated in a group administered with a mixture of Fv4-IgG1-v2 and soluble human IL-6 receptor as antigen as compared to a group administered with a mixture of Fv4-IgG1 and soluble human IL-6 receptor as antigen. Thus, it was reported that, by enhancing the binding toward FcRn under neutral condition (pH7.4) of an antibody that binds to antigens in a pH-dependent manner, the effect of the enhanced modified antibody to repeatedly bind to antigens and the effect of promoting elimination of antigens from the plasma can be further improved, and antigens can be eliminated from the plasma through administration of the antibody FIG. 2.

Figure 2:
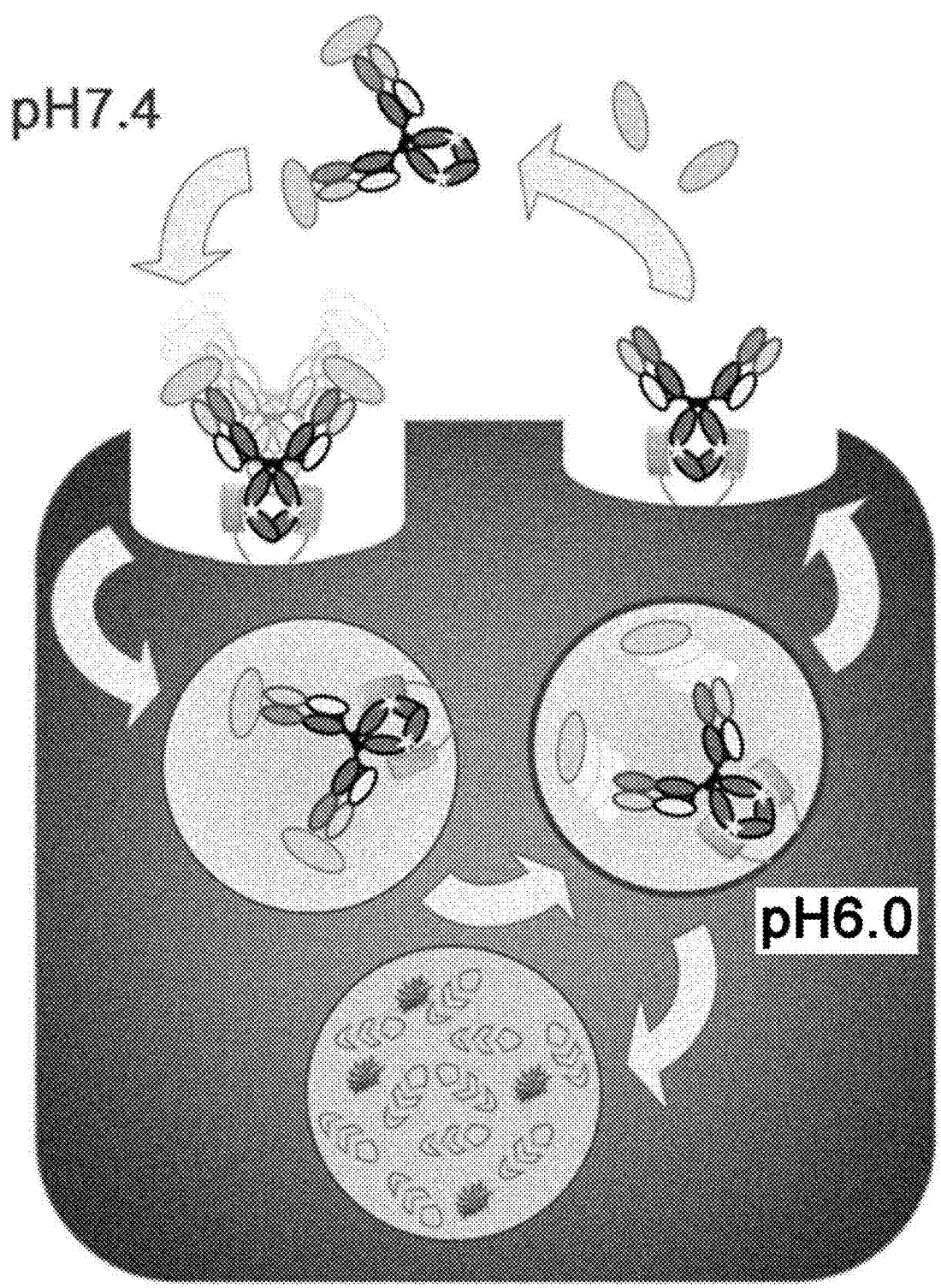
FIG. 2 is a diagram showing that enhancing FcRn binding under neutral conditions results in improving the effect of an antibody with pH-dependent binding to repeatedly bind to antigens. The following steps are illustrated: an antibody binds to soluble antigens; the antibody is internalized into a cell by pinocytosis via FcRn; the soluble antigens dissociate from the antibody in the endosome; the soluble antigens are transferred into the lysosome and degraded; after dissociation of the soluble antigens, the antibody is recycled to the plasma via FcRn; and the recycled antibody can bind to soluble antigens again.

In the actions of the antibodies that bind to antigens in a pH-dependent manner shown in FIGS. 1 and 2, the property of the antibodies to strongly bind to antigens in the plasma and to dissociate from the antigens in the endosomes based on the environmental difference between the plasma and endosomes, i.e., pH difference (pH 7.4 in the plasma; pH 6.0 in the endosomes), is used. The properties of environmental factors in the plasma and endosomes as well as the degree of their difference are important for using such differences to the antigen-binding ability of the antibody that binds in a pH-dependent manner in the plasma and endosomes. A pH difference corresponds to a difference in proton concentration. Specifically, the proton concentration in the plasma (pH 7.4) is about 40 nM, while the proton concentration in the endosome (pH 6.0) is about 1,000 nM; thus, the proton concentration which is regarded as an environmental factor in the plasma and endosome differs by about 25 times.

Moreover, the present inventors conceived that, in order to achieve the actions illustrated in FIGS. 1 and 2 by different embodiments or to achieve these embodiments in combination, it would be beneficial to use an antibody that binds to antigens depending on an environmental factor with a large difference in the plasma and endosome, other than the difference in proton concentration. Thus, the inventors searched for an environmental factor whose concentration is considerably different between the plasma and the endosome, and as a result, found calcium. The ionized calcium concentration is about 1.1 mM to 1.3 mM in the plasma and about 3 μM in the endosome; thus, the difference in the concentration of calcium ion, which is regarded as an environmental factor in the plasma and endosome, is about 400 times and was found to be greater than the difference in proton concentration (25 times). Thus, it was considered that, by using an antibody that binds to an antigen under a high calcium concentration condition (1.1 mM to 1.3 mM) and dissociates from the antigen under a low calcium concentration condition (3 μM), the antibody could dissociate from the antigen in the endosome at an equivalent or higher level as compared to an antibody that binds to the antigen in a pH-dependent manner.

1-3. Expression and Purification of Antibodies that Bind to hIgA

GA1-IgG1 (heavy chain SEQ ID NO: 37; light chain SEQ ID NO: 38) and GA2-IgG1 (heavy chain SEQ ID NO: 39; light chain SEQ ID NO: 40) are antibodies that bind to hIgA. The DNA sequences encoding GA1-IgG1 (heavy chain SEQ ID NO: 37; light chain SEQ ID NO: 38) and GA2-IgG1 (heavy chain SEQ ID NO: 39; light chain SEQ ID NO: 40) were inserted into animal cell expression plasmids by a method known to those skilled in the art. The antibodies were expressed by the method described below. Cells of human fetal kidney cell-derived line FreeStyle 293-F (Invitrogen) were suspended in FreeStyle 293 Expression Medium (Invitrogen). The cell suspension was seeded into a 6-well plate (3 mL/well) at a cell density of $1.33 \times 10^6$ cells/ml. Then, the constructed plasmids were introduced into the cells by a lipofection method. The cells were cultured for four days in a $CO_2$ incubator (37° C., 8% $CO_2$, 90 rpm). The antibodies were purified from the isolated culture supernatants by a method known to those skilled in the art using rProtein A Sepharose™ Fast Flow (Amersham Biosciences). The absorbance (wavelength: 280 nm) of the purified antibody solutions was measured using a spectrophotometer. The antibody concentrations were determined from the measured values using the absorption coefficient calculated by the PACE method (Protein Science (1995) 4, 2411-2423).

1-4. Assessment of Obtained Antibodies for Calcium-Dependent hIgA-Binding Activity The antibodies isolated as described in 1-3 were assessed for their hIgA-binding activity (dissociation constant KD (M)) using Biacore™ T200 (GE Healthcare). Running buffers used in the measurement were: 0.05% Tween® 20 polyethylene glycol sorbitan monolaurate/20 mmol/L ACES/150 mmol/L NaCl (pH 7.4 or 5.8) containing 3 μM or 1.2 mM $CaCl_2$); and 0.05% Tween® 20 polyethylene glycol sorbitan monolaurate/20 mmol/L ACES/150 mmol/L NaCl (pH 8.0) containing 0.1 μM or 10 mM $CaCl_2$).

Figure 3:
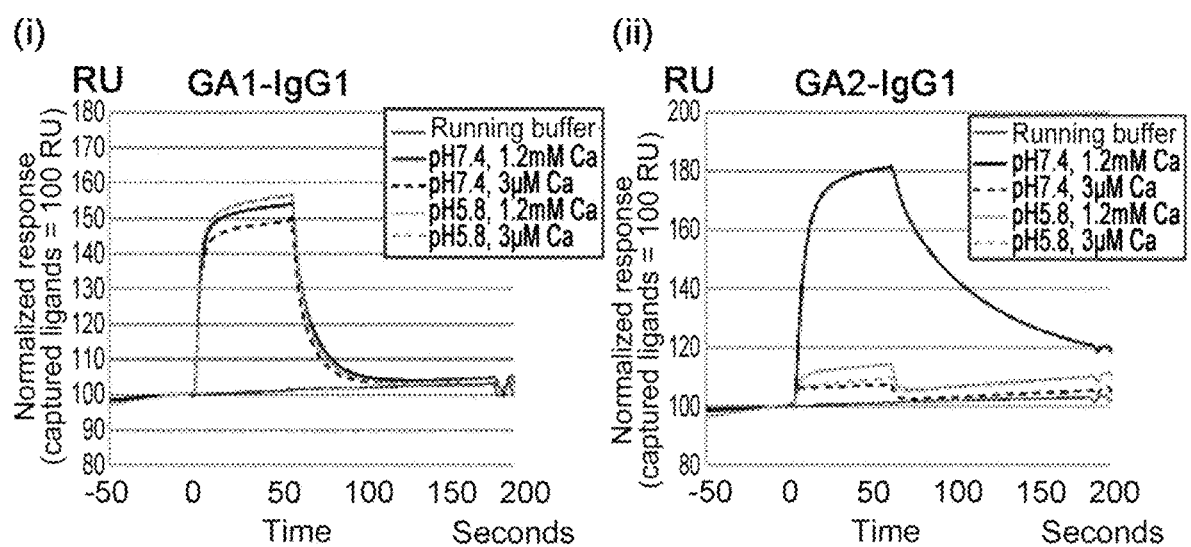
FIG. 3 is a set of two graphs, respectively designated (i) GA1-IgG1, and (ii) GA2-IgG1, illustrating Biacore™ sensorgrams showing the interaction of anti-human IgA antibodies with human IgA under the conditions of 1.2 mM $Ca^{2+}$ and 3 μM $Ca^{2+}$.

The antibody was allowed to bind to Sensor chip CM5 (GE Healthcare) immobilized with a suitable amount of recombinant Protein A/G (Thermo Scientific) by the amino coupling method. Then, an appropriate concentration of hIgA (described in 1-1) was injected as an analyte to allow interaction with the antibody on the sensor chip. The measurement was carried out at 37° C. After the measurement, 10 mmol/L glycine-HCl (pH 1.5) was injected to regenerate the sensor chip. The dissociation constant KD (M) was calculated from the measurement result by curve fitting analysis and equilibrium parameter analysis using Biacore™ T200 Evaluation Software (GE Healthcare). The result and obtained sensorgrams are shown in Table 7 and FIG. 3, respectively. It was revealed that GA2-IgG1 bound strongly to hIgA at a $Ca^{2+}$ concentration of 1.2 mM whereas the antibody bound weakly to hIgA at a $Ca^{2+}$ concentration of 3 μM. Furthermore, at a $Ca^{2+}$ concentration of 1.2 mM, GA2-IgG1 was shown to bind to human IgA strongly at pH 7.4 but weakly at pH 5.8. More specifically, GA2-IgG1 was revealed to bind to human IgA in a pH- and calcium-dependent manner.

TABLE 7

| Antibody name | Conditions | Fit | ka | kd | KD[M] |
|---|---|---|---|---|---|
| GA1-IgG1 | pH8.0, 10 mM Ca | 1:1binding model | 1.2E+06 | 1.2E−01 | 1.0E−07 |
| | pH8.0, 0.1 μM Ca | 1:1binding model | 1.1E+06 | 2.4E−01 | 2.2E−07 |

TABLE 7-continued

| Antibody name | Conditions | Fit | ka | kd | KD[M] |
|---|---|---|---|---|---|
| | pH7.4, 1.2 mM Ca | 1:1binding model | 5.7E+05 | 8.4E−02 | 1.5E−07 |
| | pH7.4, 3 μM Ca | 1:1binding model | 6.4E+05 | 1.2E−01 | 1.9E−07 |
| | pH5.8, 1.2 mM Ca | 1:1binding model | 6.8E+05 | 9.9E−02 | 1.4E−07 |
| | pH5,8, 3 μM Ca | 1:1binding model | 7.1E+05 | 1.1E−01 | 1.5E−07 |
| GA2-IgG1 | pH7.4, 1.2 mM Ca | 1:1binding model | 4.0E+05 | 1.6E−02 | 3.9E−08 |
| | pH7.4, 3 μM Ca | Steady State Affinity | — | — | 6.7E−06 |
| | pH5.8, 1.2 mM Ca | Steady State Affinity | — | — | 4.0E−06 |
| | pH5.8, 3 μM Ca | Steady State Affinity | — | — | 5.0E−06 |

[Example 2] Preparation of Modified Antibodies that Bind to hIgA in a Calcium-Dependent Manner Next, to further enhance antigen (hIgA) elimination from plasma, GA2-N434W (heavy chain SEQ ID NO: 41; light chain SEQ ID NO: 40) was constructed by introducing amino acid substitution N434W into GA2-IgG1, which binds to hIgA in a calcium-dependent manner, to potentiate the binding to mouse FcRn at pH 7.4. Furthermore, GA2-FcγR(−) (heavy chain SEQ ID NO: 42; light chain SEQ ID NO: 40) was constructed by introducing amino acid substitutions L235R and S239K into GA2-IgG1 to eliminate the FcγR-binding affinity. The modified antibodies were expressed by the method described above using animal expression plasmids inserted with DNA sequences encoding GA2-N434W (heavy chain SEQ ID NO: 41; light chain SEQ ID NO: 40) and GA2-FcγR(−) (heavy chain SEQ ID NO: 42; light chain SEQ ID NO: 40) by a method known to those skilled in the art. The antibody concentrations were determined after purification. GA2-FcγR(−) was assessed for its binding to various mouse FcγR (mFcγRI, mFcγRII, mFcγRIII, and mFcγRIV). The result showed that GA2-FcγR(−) did not bind to any of the receptors.

[Example 3] Assessment of the Effect of Ca-Dependent hIgA-Binding Antibodies on Plasma Retention of an Antigen Using Normal Mice 3-1. In Vivo Test Using Normal Mice In vivo kinetics of hIgA and anti-hIgA antibody was assessed after administration of hIgA (human IgA; prepared as described in Example 1) alone or in combination with an anti-hIgA antibody to normal mice (C57BL/6J mice; Charles River Japan). An hIgA solution (80 μg/mL) or a mixture of hIgA and anti-hIgA antibody was administered once at a dose of 10 mL/kg via the caudal vein. Anti-hIgA antibodies used were GA1-IgG1, GA2-IgG1, GA2-N434W, and GA2-FcγR(−) described above.

In every mixture, the hIgA concentration was 80 μg/mL. Meanwhile, the anti-hIgA antibody concentration varied depending on the antibody affinity for hIgA. GA1-IgG1 was prepared at 10 mg/mL; GA2-IgG1 at 2.69 mg/mL; GA2-N434W at 1 mg/mL; and GA2-FcγR(−) at 2.69 mg/mL. Under the conditions described above, the majority of hIgA is predicted to bind to the antibody since the anti-hIgA antibody is present sufficiently in excess over hIgA. Blood was collected from the mice five minutes, seven hours, one day, two days, three days, and seven days after administration. The collected blood was immediately centrifuged at 12,000 rpm and 4° C. for 15 minutes to obtain plasma. The separated plasma was stored in a freezer at −20° C. or below until measurement.

Figure 4:
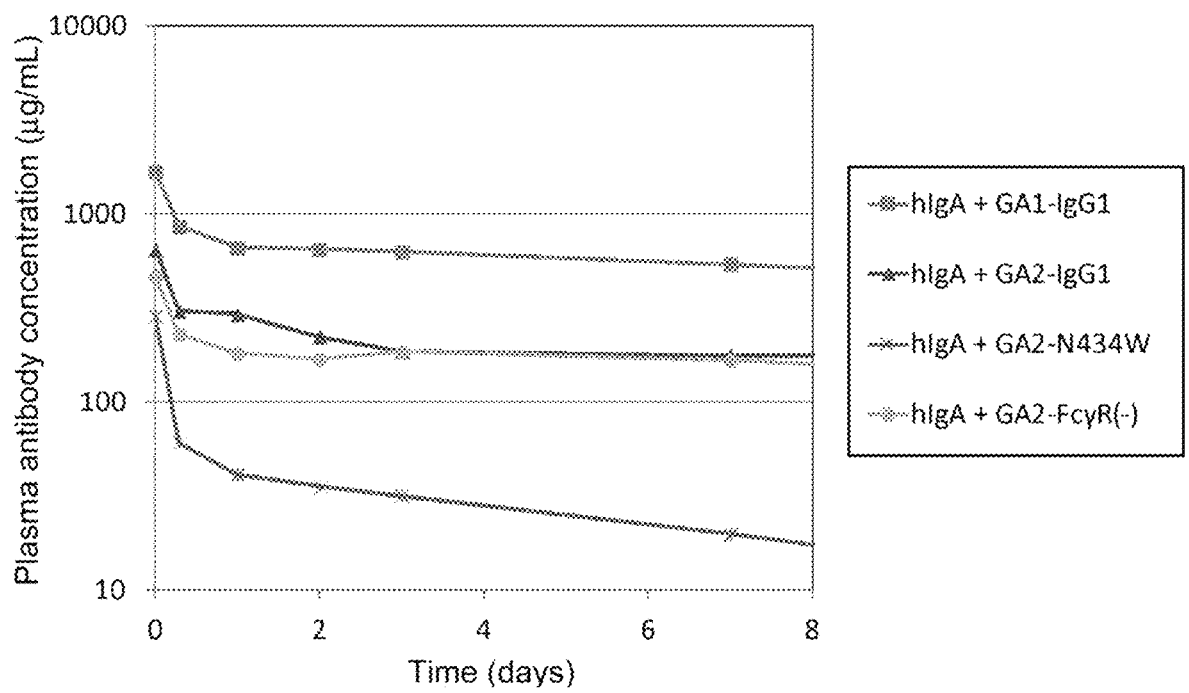
FIG. 4 is a graph showing the time-course changes in plasma antibody concentration in normal mice for the human IgA+GA1-IgG1 antibody-administered group, the human IgA+GA2-IgG1 antibody-administered group, the human IgA+GA2-FcγR(−) or GA2-N434W antibody-administered groups.

3-2. Determination of Plasma Anti-hIgA Antibody Concentration in Normal Mice by ELISA Anti-hIgA antibody concentrations in mouse plasma were determined by ELISA. First, Anti-Human IgG-immobilized plates were prepared by aliquoting Anti-Human IgG (γ-chain specific) F(ab')2 Fragment of Antibody (SIGMA) to each well of Nunc-Immuno Plate, MaxiSorp (Nalge nunc International) and allowing the plates to stand at 4° C. overnight. Anti-hIgA antibody standard curve samples prepared as standard solutions at plasma concentrations of 0.5, 0.25, 0.125, 0.0625, 0.03125, 0.01563, and 0.07813 μg/mL and assay samples prepared by diluting mouse plasma samples 100-fold or more were aliquoted into the Anti-Human IgG-immobilized plates, and then the plates were incubated at 25° C. for one hour. Next, Goat Anti-Human IgG (γ chain specific) Biotin (BIOT) Conjugate (Southern Biotechnology Associates Inc.) was aliquoted into each well of the plates, and then the plates were incubated at 25° C. for one hour. Then, Streptavidin-PolyHRP80 (Stereospecific Detection Technologies) was added to each well of the plates, after which the plates were incubated at 25° C. for one hour. The chromogenic reaction using as a substrate TMB One Component HRP Microwell Substrate (BioFX Laboratories) was terminated with 1N sulfuric acid (Showa Chemical), and then the reaction mixture in each well was measured using a microplate reader to measure the absorbance at 450 nm. The anti-hIgA antibody concentration in mouse plasma was calculated from the absorbance of the standard curve using analysis software SOFTmax PRO (Molecular Devices). The time course of plasma antibody concentrations of GA1-IgG1, GA2-IgG1, GA2-N434W, and GA2-FcγR(−) in normal mice, which were determined by the method described above, is shown in FIG. 4.

Figure 5:
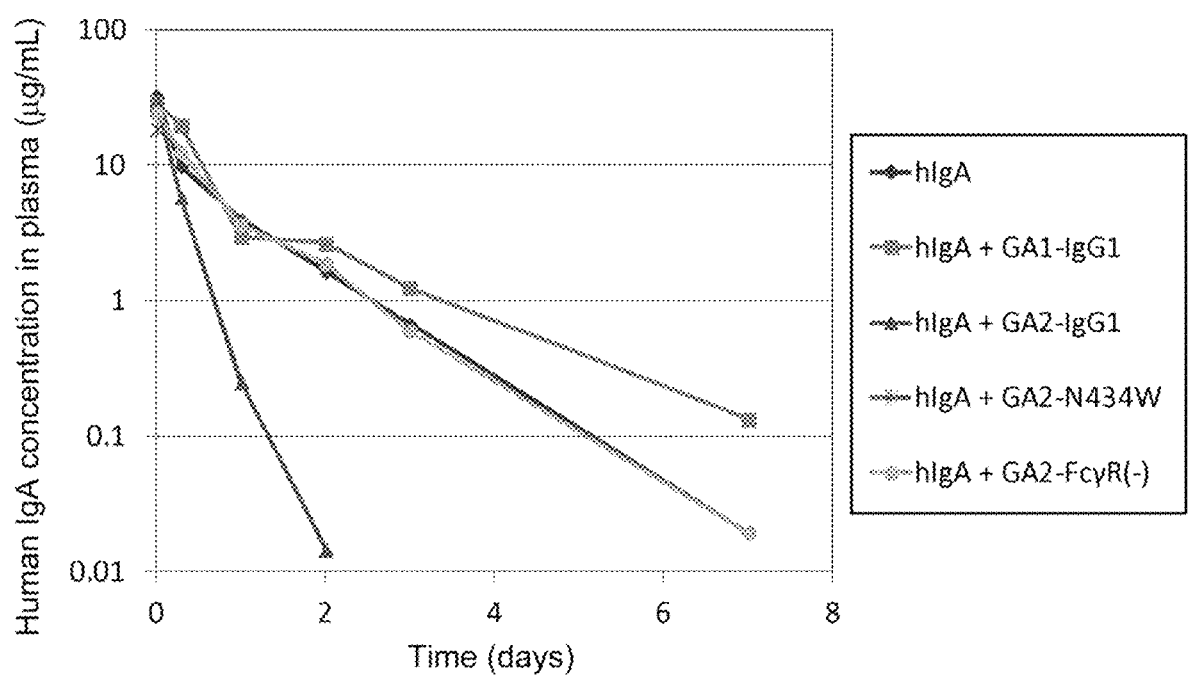
FIG. 5 is a graph showing the time-course changes in plasma concentration of human IgA in normal mice for the group administered with human IgA alone, the human IgA+GA1-IgG1 antibody-administered group, the human IgA+GA2-IgG1 antibody-administered group, the human IgA+GA2-FcγR(−) antibody-administered group, and the human IgA+GA2-N434W antibody-administered group.

3-3. Determination of hIgA Concentration in Plasma by ELISA hIgA concentrations in mouse plasma were measured by ELISA. First, Anti-Human IgA-immobilized plates were prepared by aliquoting Goat anti-Human IgA Antibody (BETHYL) into each well of Nunc-Immuno Plate, MaxiSorp (Nalge nunc International) and allowing the plates to stand at 4° C. overnight. hIgA standard curve samples prepared as standard solutions at plasma concentrations of 0.4, 0.2, 0.1, 0.05, 0.025, 0.0125, and 0.00625 μg/mL and assay samples prepared by diluting mouse plasma samples 100-fold or more, were aliquoted at 100 μL/well into the Anti-Human IgA-immobilized plates, after which 500 ng/mL hsIL-6R was added at 200 μL/well. The resulting plates were allowed to stand at room temperature for one hour. Next, after adding Biotinylated Anti-human IL-6R Antibody (R&D) into each well of the plates, the plates were incubated at room temperature for one hour. Then, after aliquoting Streptavidin-PolyHRP80 (Stereospecific Detection Technologies) into each well of the plates, the plates were incubated at room temperature for one hour. The chromogenic reaction using as a substrate TMB One Component HRP Microwell Substrate (BioFX Laboratories) was terminated with 1N sulfuric acid (Showa Chemical), and then the reaction mixture in each well was measured using a microplate reader to measure the absorbance at 450 nm. The concentration in mouse plasma was calculated from the absorbance of the standard curve using analysis software SOFTmax PRO (Molecular Devices). The time course of plasma hIgA concentrations in normal mice after intravenous administration, as determined by the method described above, is shown in FIG. 5.

Figure 6:
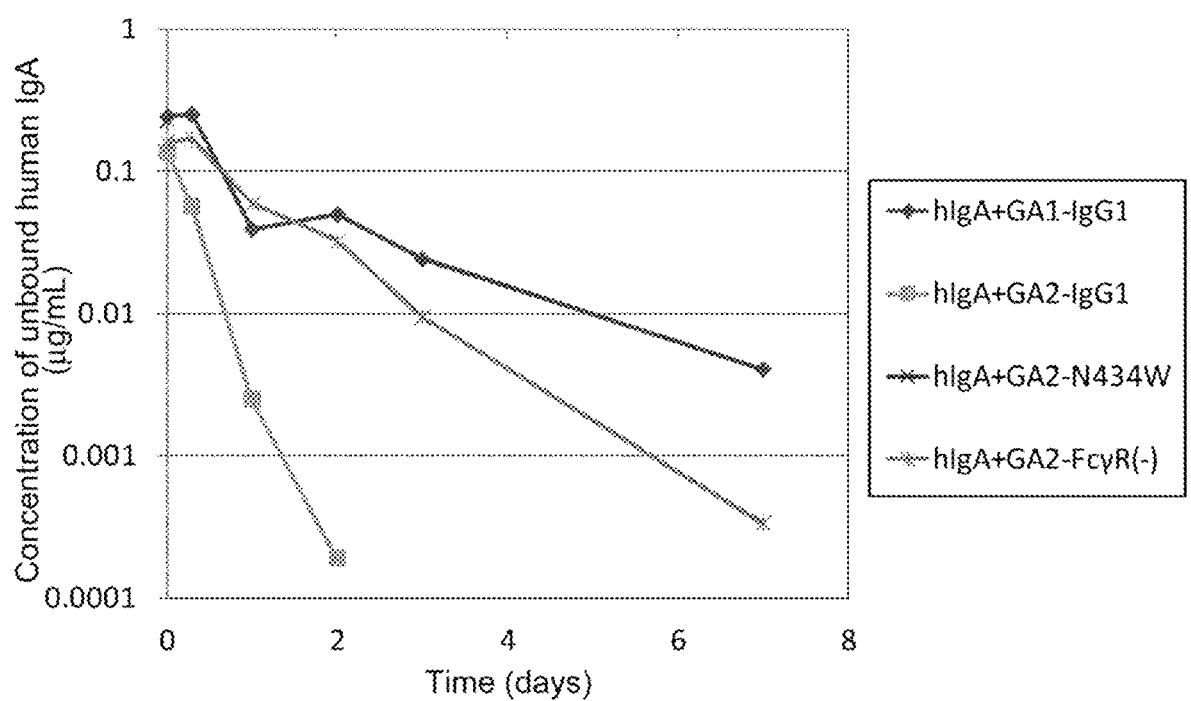
FIG. 6 is a graph showing the time-course changes in plasma concentration of unbound human IgA in normal mice for the human IgA+GA1-IgG1 antibody-administered group, the human IgA+GA2-IgG1 antibody-administered group, the human IgA+GA2-FcγR(−) antibody-administered group, and the human IgA+GA2-N434W antibody-administered group.

The result showed that the elimination of hIgA was retarded when hIgA was administered in combination with GA1-IgG1, an antibody that exhibits weak Ca-dependent binding (the degree of dependency is low), as compared to when hIgA was administered alone. In contrast, when hIgA was administered in combination with GA2-IgG1 whose Ca-dependent binding activity is 100 or more times greater, the elimination of hIgA was considerably accelerated, as compared to when hIgA was administered alone. The free hIgA concentration in plasma was determined from the plasma antibody concentration shown in FIG. 4, the plasma hIgA concentration shown in FIG. 5, and the KD value for each antibody shown in Table 7. The result is shown in FIG. 6. As shown in FIG. 6, the concentration of free antigen (hIgA) in the group administered with GA2-IgG1 which binds to hIgA in a calcium-dependent manner was lower than that in the group administered with GA1-IgG1. This demonstrates that the antibody-free antigen (hIgA) (antibody unbound form) can be reduced by accelerating antigen elimination by using antibodies that bind in a calcium-dependent manner. Furthermore, GA2-N434W with enhanced FcRn binding at pH 7.4 accelerated the antigen elimination more than GA2-IgG1 did, and seven hours after administration, the plasma hIgA concentration was below the detection limit.

[Example 4] Preparation of pH-Dependent Anti-IgE Antibody 4-1. Preparation of Anti-Human IgE Antibody To prepare pH-dependent anti-human IgE antibodies, human IgE (heavy chain SEQ ID NO: 43; light chain SEQ ID NO: 44) (the variable region is derived from an anti-human glypican3 antibody) as an antigen was expressed using FreeStyle293 (Life Technologies). Human IgE was prepared by purifying the expressed human IgE using a conventional chromatographic method known to those skilled in the art.

An antibody that binds to human IgE in a pH-dependent manner and forms a large immune complex consisting of two or more molecules of anti-IgE antibody and two or more molecules of IgE were selected from a number of obtained antibodies. The selected anti-human IgE antibody was expressed using human IgG1 heavy chain constant region and human light chain constant region, and then purified. The produced antibody was named clone 278 (heavy chain SEQ ID NO: 45; light chain SEQ ID NO: 46).

4-2. Assessment of Anti-Human IgE Antibodies for their Binding Activity and pH-Dependent Binding Activity Antibodies capable of dissociating from antigens within the endosome can be created not only by designing them so as to bind to antigens in a pH-dependent manner, but also by designing them so as to bind to antigens in a Ca-dependent manner. Thus, clone 278 and the control Xolair (omalizumab; Novartis) whose IgE-binding activity does not depend on pH/Ca were assessed for their pH dependency and pH/Ca dependency of the human IgE (hIgE)-binding activity.

More specifically, the hIgE-binding activities (dissociation constant $K_D$ (M)) of clone 278 and Xolair were assessed using Biacore™ T200 (GE Healthcare). Running buffers used in the assay were:

1.2 mmol/l $CaCl_2$/0.05% Tween® 20 polyethylene glycol sorbitan monolaurate, 20 mmol/l ACES, 150 mmol/l NaCl, pH 7.4;

1.2 mmol/l $CaCl_2$/0.05% Tween® 20 polyethylene glycol sorbitan monolaurate, 20 mmol/l ACES, 150 mmol/l NaCl, pH 5.8; and 3 μmol/l $CaCl_2$/0.05% Tween® 20 polyethylene glycol sorbitan monolaurate, 20 mmol/l ACES, 150 mmol/l NaCl, pH 5.8.

A chemically-synthetized peptide having a human glypican 3 protein-derived sequence (SEQ ID NO: 47) whose C-terminal Lys is biotinylated (hereinafter abbreviated as "biotinylated GPC3 peptide") was added in an appropriate amount and immobilized onto Sensor chip SA (GE Healthcare) based on the affinity between biotin and streptavidin. Human IgE was immobilized onto the chip by injecting it at an appropriate concentration so as to be trapped by the biotinylated GPC3 peptide. As an analyte, clone 278 was injected at an appropriate concentration and allowed to interact with the human IgE on the sensor chip. Then, 10 mmol/L glycine-HCl (pH 1.5) was injected to regenerate the sensor chip. The interaction was always measured at 37° C. The measurement result was analyzed by curve fitting using Biacore™ T200 Evaluation Software (GE Healthcare) to calculate the association rate constant ka (1/Ms) and dissociation rate constant kd (1/s). The dissociation constant KD (M) was calculated from the above-described constants. Furthermore, the KD ratios in each antibody under the conditions of [pH 5.8, 1.2 mM Ca] to [pH 7.4, 1.2 mM Ca] were calculated to assess the pH-dependent binding, while the KD ratios in each antibody under the conditions of [pH 5.8, 3 μM Ca] to [pH 7.4, 1.2 mM Ca] were calculated to assess the pH/Ca-dependent binding. The result is shown in Table 8.

TABLE 8

| Antibody name (abbreviation) | Buffer conditions | ka (1/Ms) | kd (1/s) | KD (M) | pH dependency KD (pH 5.8, 1.2 mM Ca)/ KD (pH 7.4, 1.2 mM Ca) | pH/Ca dependency KD (pH 5.8, 3 μM Ca)/ KD (pH 7.4, 1.2 mM Ca) |
|---|---|---|---|---|---|---|
| Clone 278 | pH 7.4, 1.2 mM Ca | 1.5E+06 | 3.6E−03 | 2.4E−09 | 842.5 | 1636.5 |
|  | pH 5.8, 1.2 mM Ca | 1.2E+05 | 2.3E−01 | 2.0E−06 |  |  |
|  | pH 5.8, 3 μM Ca | 6.2E+04 | 2.4E−01 | 3.9E−06 |  |  |
| Xolair | pH 7.4, 1.2 mM Ca | 2.5E+06 | 1.1E−02 | 4.4E−09 | 2.3 | 2.9 |
|  | pH 5.8, 1.2 mM Ca | 2.4E+06 | 2.4E−02 | 9.9E−09 |  |  |
|  | pH 5.8, 3 μM Ca | 1.4E+06 | 1.7E−02 | 1.3E−08 |  |  |

4-3. Evaluation of the Formation of Immune Complexes of Clone 278

Whether clone 278 forms large immune complexes of 2:2 or more with human IgE under neutral condition (pH7.4) and whether the immune complexes dissociate under acidic condition (pH5.8) were evaluated using gel filtration chromatography. Clone 278 which was dialyzed against 100 mM NaCl was diluted using a 20 mM Tris-HCl, 150 mM NaCl, 1.2 mM CaCl$_2$), pH 7.4 buffer for samples under neutral condition and using a 20 mM Bis-tris-HCl, 150 mM NaCl, 3 µM CaCl$_2$), pH 5.8 buffer for samples under acidic condition. Mixtures in which 100 µg/mL (0.60 µM) hIgE (Asp6) which is a human IgE (prepared in Example 5) and clone 278 were mixed at a molar ratio of 1:1 or 1:6 were left for two hours or longer at room temperature or in an autosampler at 25° C., and were then analyzed by gel filtration chromatography. A mobile phase of 20 mM Tris-HCl, 300 mM NaCl, 1.2 mM CaCl$_2$), pH 7.4 was used under neutral condition, and a mobile phase of 20 mM Bis-tris-HCl, 300 mM NaCl, 3 µM CaCl$_2$), pH 5.8 was used under acidic condition. Analyses were carried out using a G4000SW×1 (TOSOH) column and under conditions of a flow rate of 0.5 mL/min and 25° C. The results are shown in FIG. 9. As shown in FIG. 9, it was confirmed that clone 278 and human IgE formed large immune complexes consisting of tetramers (when assuming that one antibody molecule is a monomer) or larger multimers with an apparent molecular weight of about 670 kDa under neutral condition. Moreover, such immune complexes were not observed under acidic condition. Thus, these immune complexes were confirmed to dissociate in a pH-dependent manner, similarly as in the above-described evaluation on binding using a Biacore™ device.

From these results, it was considered that clone 278 was able to accelerate elimination of human IgE, similarly to the aforementioned anti-IgA antibody GA2-IgG1.

[Example 5] In Vivo Assessment of Clone 278 and Xolair 5-1. Preparation of Human IgE (hIgE(Asp6)) for In Vivo Assessment hIgE(Asp6) (the variable region is derived from an anti-human glypican3 antibody), which is a human IgE for in vivo assessment consisting of a heavy chain (SEQ ID NO: 48) and a light chain (SEQ ID NO: 44), was produced by the same method as described in Example 1. hIgE(Asp6) is a modified molecule resulting from asparagine-to-aspartic acid alteration at the six N-linked glycosylation sites in human IgE so that the heterogeneity in the N-linked sugar chain of human IgE is not affected by time-dependent changes in the plasma concentration of human IgE as an antigen.

5-2. Assessment of Clone 278 and Xolair for the Effect of Accelerating Human IgE Elimination Using Normal Mice In vivo kinetics of hIgE(Asp6) and anti-human IgE antibody was assessed after administration of hIgE(Asp6) alone or in combination with an anti-hIgE antibody (clone 278 and Xolair) to C57BL/6J mice (Charles river Japan). An hIgE (Asp6) solution (20 µg/mL) or a mixture of hIgE(Asp6) and anti-human IgE antibody (the concentrations are shown in Table 9) was administered once at a dose of 10 mL/kg via the caudal vein. Under the conditions described above, hIgE(Asp6) is predicted to bind almost completely to the antibody since each antibody is present sufficiently in excess over hIgE(Asp6). Blood was collected from the mice five minutes, two hours, seven hours, one day, two days, four or five days, seven days, 14 days, 21 days, and 28 days after administration. The collected blood was immediately centrifuged at 15,000 rpm and 4° C. for 5 minutes to obtain plasma. The separated plasma was stored in a freezer at −20° C. or below until measurement.

TABLE 9

| Anti-hIgE antibody | Concentration of hIgE(Asp6) in the administered solution (µg/mL) | Concentration of anti-hIgE antibody in the administered solution (µg/mL) |
|---|---|---|
| Clone 278 | 20 | 100 |
| Xolair | 20 | 308 |

Figure 11:
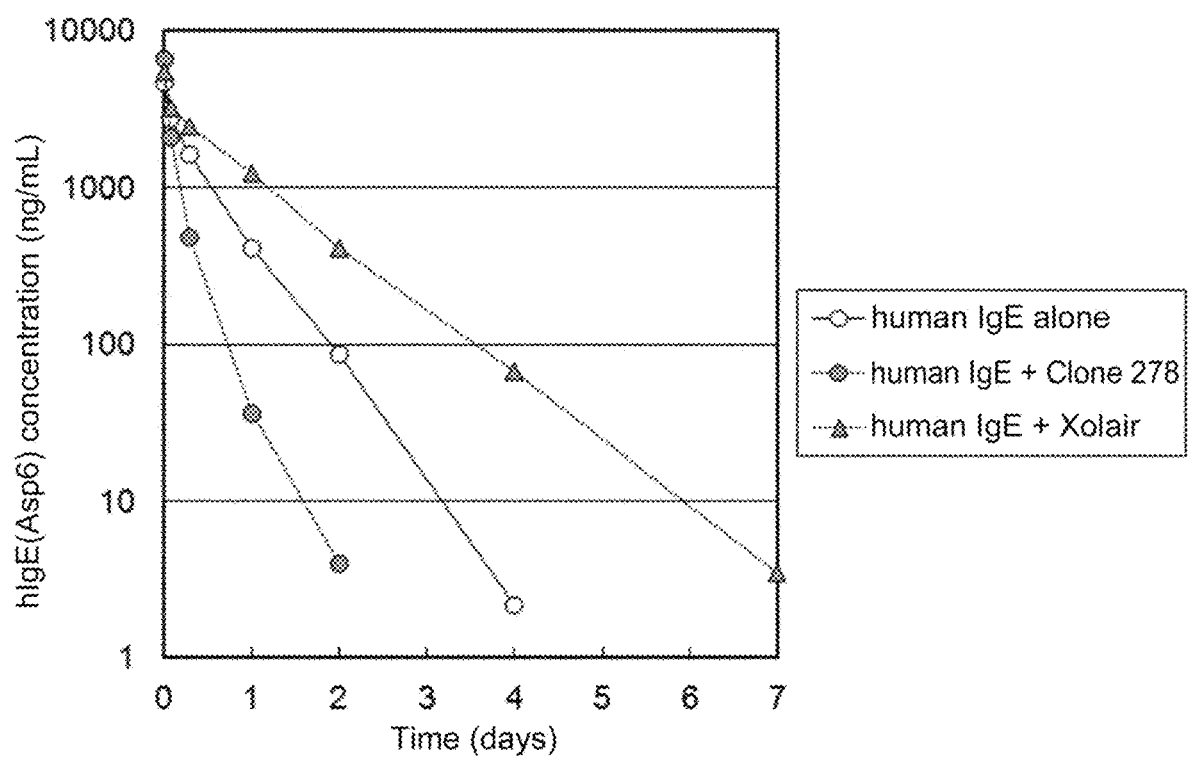
FIG. 11 is a graph showing the time-course changes in plasma concentration of human IgE in normal mice for the group administered with human IgE alone, the human IgE+ clone 278 antibody-administered group, and the human IgE+clone 278 antibody-administered group.

5-3. Determination of Plasma hIgE(Asp6) Concentration in Normal Mice hIgE(Asp6) concentrations in mouse plasma were determined by ELISA. Standard curve samples were prepared at plasma concentrations of 192, 96, 48, 24, 12, 6, and 3 ng/mL. Xolair (Novartis) was added at 10 µg/mL to the standard curve samples and mouse plasma assay samples to equalize the immune complex of hIgE(Asp6) and anti-hIgE antibody. After 30 minutes of incubation at room temperature, the standard curve samples and mouse plasma assay samples were aliquoted into immunoplates (MABTECH) immobilized with anti-human IgE antibody or immunoplates (Nunc F96 MicroWell Plate (Nalge nunc International)) immobilized with anti-human IgE antibody (clone 107; MABTECH). The plates were allowed to stand at room temperature for two hours or at 4° C. overnight. Then, human GPC3 core protein (SEQ ID NO: 51), anti-GPC3 antibody biotinylated with NHS-PEG4-Biotin (Thermo Fisher Scientific) (prepared in Chugai pharmaceutical Co., Ltd.), and Sterptavidin-PolyHRP80 (Stereospecific Detection Technologies) were reacted sequentially for one hour each. The chromogenic reaction using as a substrate TMB One Component HRP Microwell Substrate (BioFX Laboratories) was terminated with 1N sulfuric acid (Showa Chemical), and then the concentration in mouse plasma was determined by a method in which the color development is assessed by measuring the absorbance at 450 nm using a microplate reader or a method in which a luminescent reaction is carried out using SuperSignal® ELISA Pico Chemiluminescent Substrate (Thermo Fisher Scientific) as a substrate and the luminescence intensity is measured with a microplate reader. The concentration in mouse plasma was calculated from the absorbance or luminescence intensity of the standard curve using analysis software SOFTmax PRO (Molecular Devices). The time course of plasma hIgE(Asp6) concentration after intravenous administration, which was determined by the method described above, is shown in FIG. 11.

Figure 10:
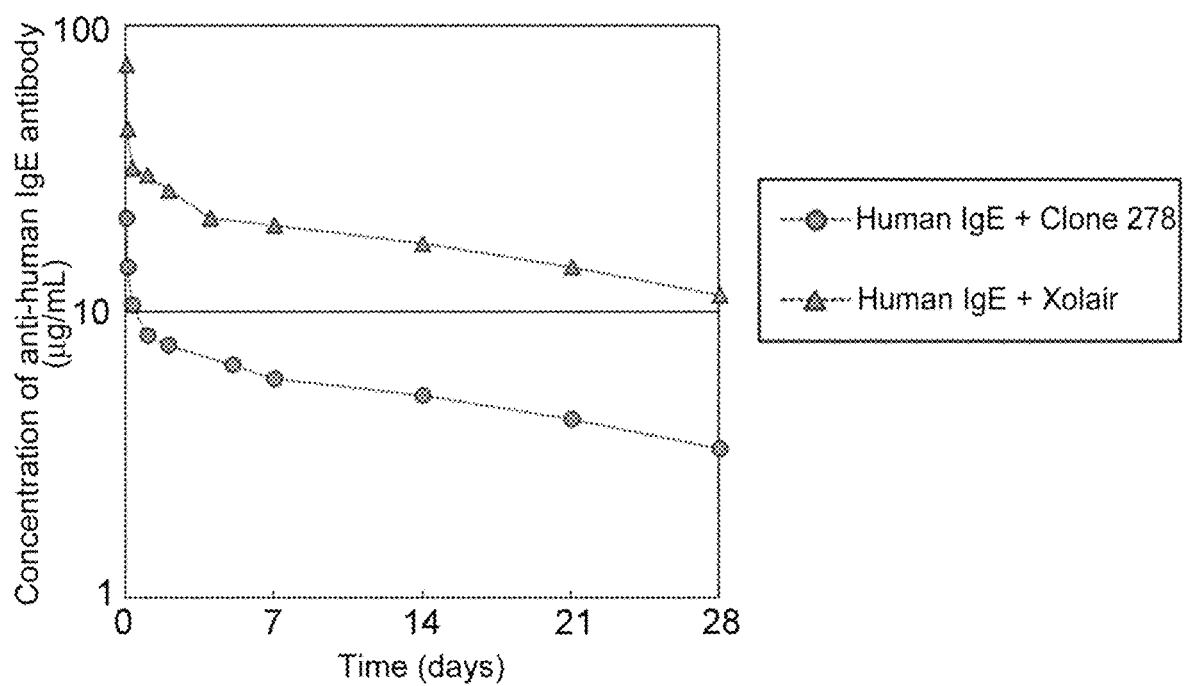
FIG. 10 is a graph showing the time-course changes in plasma antibody concentration in normal mice for the human IgE+clone 278-administered group and the human IgE+ Xolair antibody-administered group.

5-4. Determination of Plasma Anti-Human IgE Antibody Concentration in Normal Mice Anti-hIgE antibody concentrations in mouse plasma were determined by ELISA. Standard curve samples were prepared at plasma concentrations of 0.4, 0.2, 0.1, 0.05, 0.025, 0.0125, and 0.00625 µg/mL. hIgE(Asp6) was added at 1 µg/mL to the standard curve samples and mouse plasma assay samples to equalize the immune complex of hIgE (Asp6) and anti-hIgE antibody. After 30 minutes of incubation at room temperature, the standard curve samples and mouse plasma assay samples were aliquoted into immunoplates (Nunc-Immuno Plate, MaxiSorp (Nalge nunc International)) immobilized with Anti-Human Kappa Light Chain Antibody (Bethyl Laboratories). The plates were allowed to stand at room temperature for two hours or at 4° C. overnight. Then, Rabbit anti-Human IgG (Fc) Secondary antibody, Biotin conjugate (Pierce Biotechnology) and Streptavidin-Poly HRP80 (Stereospecific Detection Technologies) were reacted sequentially for one hour each. The chromogenic reaction using as a substrate TMB One Component HRP Microwell Substrate (BioFX Laboratories) was terminated with 1N sulfuric acid (Showa Chemical), and then the concentration in mouse plasma was determined by a method in which the color development is assessed by measuring the absorbance at 450 nm with a microplate reader. The concentration in mouse plasma was calculated from the absorbance of the standard curve using analysis software SOFTmax PRO (Molecular Devices). A time course of the plasma antibody concentration after intravenous administration, which was determined by the method described above, is shown in FIG. 10.

The result showed that the elimination of human IgE was retarded when human IgE was administered in combination with Xolair, a control anti-IgE antibody, as compared to when human IgE was administered alone. Meanwhile, the elimination of human IgE was markedly accelerated when administered in combination with clone 278, which has a strong pH-dependent human IgE-binding activity, as compared to when human IgE was administered alone. Specifically, it was demonstrated that not only in the case of IgA, but also in the case of IgE, antigen elimination was accelerated by administering an antibody that forms a large immune complex as compared to when the antigen is administered alone.

[Example 6] Preparation of Antibody Variants that Show Calcium-Dependent hIgA Binding Next, with the objective of further augmenting antigen (hIgA) elimination from plasma, Leu at position 328 (EU numbering) in GA2-IgG1, which shows calcium-dependent hIgA binding, was substituted with Tyr to enhance its binding to mouse FcγR, producing GA2-F1087 (heavy chain SEQ ID NO: 52). A DNA sequence encoding GA2-F1087 (heavy chain SEQ ID NO: 52, and light chain SEQ ID NO: 40) was inserted into an animal expression plasmid by a method known to those skilled in the art. These antibody variants were expressed using the plasmid according to the abovementioned method, and their concentrations were determined after purification. Antibodies containing this modification showed greatly enhanced binding to mouse FcγR as shown in Reference Example 5.

[Example 7] Assessment of the Effect on Plasma Retention of Antigen in Normal Mice Administered with Ca-Dependent hIgA-Binding Antibodies 7-1. In Vivo Test Using Normal Mice Normal mice (C57BL/6J mouse; Charles River Japan) were administered with hIgA (human IgA: produced in Example (1-1)) alone or co-administered with hIgA and an anti-hIgA antibody, and then assessed for the in vivo dynamics of hIgA and the anti-hIgA antibody. An hIgA solution (80 μg/mL), or a mixed solution of hIgA and an anti-hIgA antibody was administered once at a dose of 10 mL/kg into the tail vein. The anti-hIgA antibodies used were GA2-IgG1 and GA2-F1087 described above.

The hIgA concentration was 80 μg/mL in all cases, and the anti-hIgA antibody concentration was 2.69 mg/mL in the mixed solutions. The anti-hIgA antibody was sufficiently present in excess with respect to hIgA, and therefore almost all hIgA was considered to be bound by the antibody. From the GA-IgG1-administered group, blood was collected from the mice 5 minutes, 7 hours, 1 day, 2 days, 3 days, and 7 days after administration. From the GA-F1087-administered group, blood was collected from the mice 5 minutes, 30 minutes, 1 hour, 2 hours, 1 day, 3 days, and 7 days after administration. The collected blood samples were immediately centrifuged at 4° C. and 12,000 rpm for 15 minutes to obtain the plasma samples. The separated plasma samples were stored in a freezer at −20° C. or below until measurement.

Figure 12:
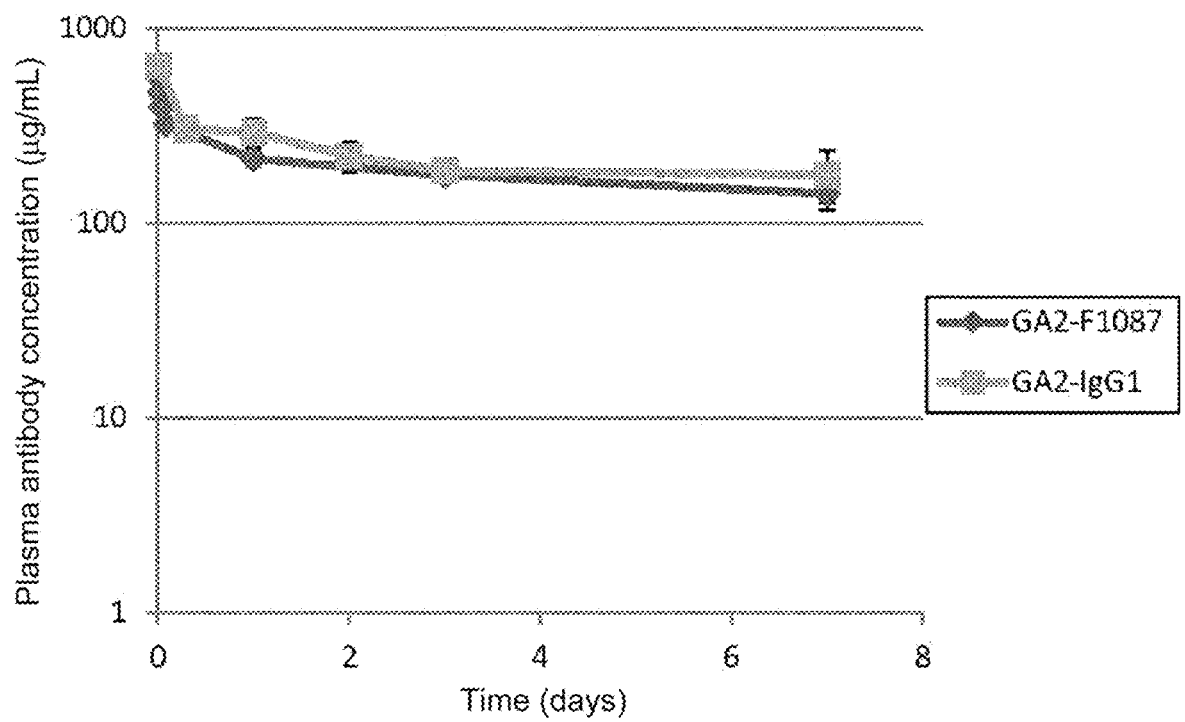
FIG. 12 is a graph showing the time-course changes in plasma concentrations of GA2-IgG1 and GA2-F1087 antibodies in normal mice.

7-2. Measurement of the Anti-hIgA Antibody Concentration in Normal Mouse Plasma by ELISA The anti-hIgA antibody concentration in mouse plasma was determined by ELISA. First, Anti-Human IgG (γ-chain specific) F(ab')2 Fragment of Antibody (SIGMA) was dispensed into each well of Nunc-Immuno Plates, MaxiSorp (Nalge nunc International), and allowed to stand overnight at 4° C. to prepare Anti-Human IgG-immobilized plates. Standard samples of anti-hIgA antibodies to be used as calibration curve samples were prepared at plasma concentrations of 0.5, 0.25, 0.125, 0.0625, 0.03125, 0.01563, and 0.007813 μg/mL; and mouse plasma assay samples diluted 100-fold or more were prepared and aliquoted into the above-mentioned Anti-Human IgG-immobilized plates, and then the plates were incubated at 25° C. for one hour. Then, Goat Anti-Human IgG (γ chain specific) Biotin (BIOT) Conjugate (Southern Biotechnology Associats Inc.) was dispensed into each well of the aforementioned plates, and then the plates were incubated to allow reaction to take place at 25° C. for one hour. Then, Streptavidin-PolyHRP80 (Stereospecific Detection Technologies) was dispensed into each well of the aforementioned plates, and then the plates were incubated to allow reaction to take place at 25° C. for one hour. A color development reaction was carried out using TMB One Component HRP Microwell Substrate (BioFX Laboratories) as a substrate. After stopping the reaction with 1N Sulfuric acid (Showa Chemical), absorbance of the reaction solution in each well at 450 nm was measured on a microplate reader. The mouse plasma concentration of the anti-hIgA antibody was calculated based on absorbance from the calibration curve using the analytical software SOFTmax PRO (Molecular Devices). Time-course changes in the plasma concentrations of the GA2-IgG1 and GA2-F1087 antibodies in normal mice determined by this method after intravenous administration are shown in FIG. 12. The results confirmed that the plasma antibody concentration of clone GA2-IgG1, which has a strong pH- and Ca-dependent hIgA-binding activity, does not decrease greatly even when FcγR binding is enhanced.

7-3. Determination of the Plasma hIgA Concentration by ELISA

Figure 13:
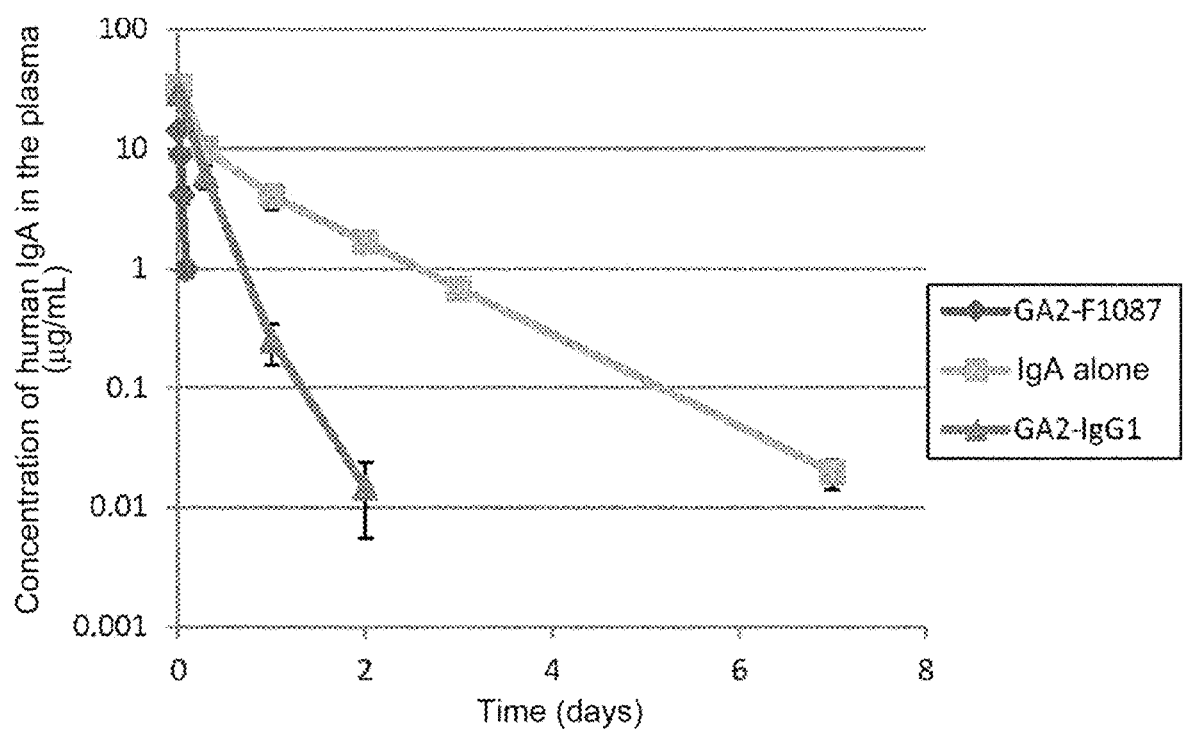
FIG. 13 is a graph showing the time-course changes in plasma concentration of hIgA in normal mice administered with GA2-IgG1 or GA2-F1087.

Concentration of hIgA in mouse plasma was determined by ELISA. First, Goat anti-Human IgA Antibody (BETHYL) was aliquoted into each well of a Nunc-Immuno Plate, MaxiSorp (Nalge nunc International). The plate was left to stand at 4° C. overnight to prepare an anti-human IgA-immobilized plate. Standard samples of hIgA to be used as calibration curve samples were prepared at plasma concentrations of 0.4, 0.2, 0.1, 0.05, 0.025, 0.0125, and 0.00625 μg/mL. Mouse plasma assay samples were prepared at 100-fold or greater dilution. 200 μl of 500 ng/ml hsIL-6R was added to 100 μL of each of the calibration curve samples and plasma samples. The resulting mixtures were allowed to stand at room temperature for one hour, and then the mixed solutions were aliquoted at 100 μl into the above-mentioned anti-human IgA-immobilized plate; and this was left to stand at room temperature for one hour. Next, a biotinylated Anti-human IL-6R antibody (R&D) was aliquoted into each well of the aforementioned plate, and then the plate was incubated at room temperature for one hour to allow reaction to take place. In addition, Streptavidin-PolyHRP80 (Stereospecific Detection Technologies) was aliquoted into each well of the aforementioned plate, and the plate was incubated at room temperature for one hour to allow reaction to take place. A color development reaction was carried out using the TMB One Component HRP Microwell Substrate (BioFX Laboratories) as a substrate. After the reaction was terminated with 1 N sulfuric acid (Showa Chemical), absorbance of the reaction solutions in each well at 450 nm was measured using a microplate reader. The concentrations in mouse plasma were calculated based on absorbance from the calibration curve using the analytical software SOFTmax PRO (Molecular Devices). Time-course changes in the plasma concentration of hIgA determined by this method in normal mice subjected to intravenous administration are shown in FIG. 13.

The results showed that when hIgA was co-administered to mice with GA2-IgG1, which exhibits a 100-fold or more Ca-dependent-binding activity, the elimination of hIgA was accelerated as compared to when hIgA was administered alone. Furthermore, when hIgA and GA2-F1087, which has enhanced binding to FcγR, were administered to mice, the plasma hIgA concentration decreased below the measurement range (0.006 μg/mL or more) one day after administration, and the elimination of plasma hIgA was significantly accelerated compared to when GA-IgG1 was administered to mice. The above indicates that in mice administered with an anti-hIgA antibody and hIgA forming an immune complex, the effect of an antibody with enhanced FcγR binding in removing antigen (hIgA) from plasma is enhanced compared to the effect of antigen (hIgA) removal by an antibody serving as the source for the antibody with enhanced FcγR binding.

[Example 8] Preparation of Antibody Variants that Show pH-Dependent Human IgE Binding Next, with the objective of further augmenting antigen (human IgE) elimination from plasma, Leu at position 328 (EU numbering) in 278-IgG1, which shows pH-dependent human IgE binding, was substituted with Tyr to enhance its binding to mouse FcγR, producing 278-F1087 (heavy chain SEQ ID NO: 53 and light chain SEQ ID NO: 46). A DNA sequence encoding 278-F1087 was inserted into an animal expression plasmid by a method known to those skilled in the art. Antibody variants were expressed according to the abovementioned method using animal cells introduced with the plasmid, and their concentrations were determined after purification.

[Example 9] In Vivo Assessment of 278-IgG1

9-1. Preparation of Human IgE(hIgE(Asp6)) for In Vivo Assessment

A method similar to the method described in Example 5-1 was used to prepare hIgE (Asp6) (in which the variable region is that of an anti-human Glypican 3 antibody), which is a human IgE for use in in vivo assessment. Human IgE (Asp6) is a molecule in which asparagine has been modified to aspartic acid at six N-glycosylation sites of human IgE, so that the heterogeneity of the N-glycosides of human IgE will not be affected by change in the plasma concentration of the antigen human IgE.

9-2. Verification of the Effect of Accelerating Removal of Human hIgE from Plasma of Normal Mouse Administered with Clone 278

It was demonstrated in Example 7 that the plasma antigen concentration was significantly reduced in mice administered with a molecule with enhanced binding to mouse FcγR through pH-dependent binding to the antigen human IgA. When mouse FcγR binding is enhanced, to further verify if the elimination effect on soluble antigen in plasma can be similarly observed in an organism administered with an antibody that shows enhanced binding to mouse FcγR and binds in a pH-dependent manner to antigens other than human IgA, tests using antibodies against the antigen human IgE were also carried out.

C57BL/6J mice (Charles River Japan) were administered with hIgE (Asp6) alone or co-administered with hIgE (Asp6) and an anti-hIgE antibody (278-IgG1 or 278-F1087), and then assessed for the in vivo dynamics of hIgE (Asp6) and the anti-human IgE antibody. An hIgE (Asp6) solution (20 μg/ml) or a mixed solution of hIgE (Asp6) and an anti-human IgE antibody (all antibody concentrations were adjusted to be the same concentrations as shown in Table 10) was administered once at 10 mL/kg into the tail vein. In this case, since each antibody was sufficiently present in excess with respect to hIgE (Asp6), nearly all hIgE (Asp6) was considered to be bound by the antibody. Blood was collected from the mice 5 minutes, 2 hours, 7 hours, 1 day, 2 days, 4 days, 5 days, 7 days, 14 days, and 21 days after administration in the clone 278 (278-IgG1)-administered group. Blood was collected from the mice 5 minutes, 30 minutes, 1 hour, 2 hours, 1 day, 3 days, 7 days, 14 days, and 21 days after administration in the 278-F1087-administered group. The collected blood samples were immediately centrifuged at 4° C. and 15,000 rpm for 5 minutes to obtain plasma samples. The separated plasma samples were stored in a freezer set to −20° C. or below until the assay was performed.

TABLE 10

| Anti-hIgE antibody | Concentration of hIgE(Asp6) in the administered solution (μg/mL) | Concentration of anti-hIgE antibody in the administered solution (μg/mL) |
| --- | --- | --- |
| 278-IgG1 | 20 | 100 |
| 278-F1087 | 20 | 100 |

Figure 14:
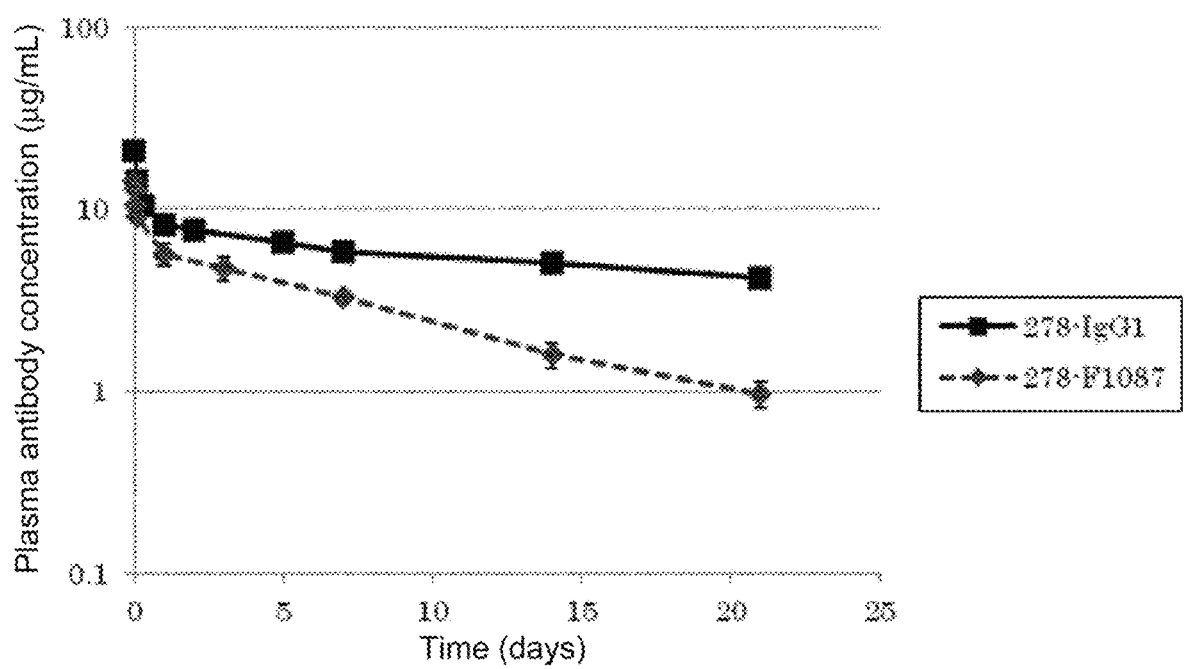
FIG. 14 is a graph showing the time-course changes in plasma concentrations of 278-IgG1 and 278-F1087 antibodies in C57BL/6J mice.

9-3. Determination of the Anti-Human IgE Antibody Concentration in Normal Mouse Plasma The anti-hIgE antibody concentration in mouse plasma was determined by ELISA. Calibration curve samples were prepared at plasma concentrations of 0.4, 0.2, 0.1, 0.05, 0.025, 0.0125, and 0.00625 μg/mL. To make the immune complex formed between hIgE(Asp6) and the anti-hIgE antibody homogeneous, hIgE(Asp6) was added at 1 μg/mL to the calibration curve samples and mouse plasma assay samples; and the 278-hIgG1-administered group and the corresponding calibration curve samples were left to stand at room temperature for 30 minutes. Furthermore, the 278-F1087-administered group and the corresponding calibration curve samples were stirred overnight at 37° C. The calibration curve samples and mouse plasma assay samples which were left to stand or stirred were aliquoted into the Anti-Human Kappa Light Chain Antibody (Bethyl Laboratories)-immobilized immuno plate (Nunc-Immuno Plate, MaxiSorp (Nalge nunc International)), and were left to stand/stirred at room temperature for two hours (samples of the 278-F1087-administered group and calibration curve samples of 278-F1087) or left to stand overnight at 4° C. (samples of the 278-hIgG1-administered group and the calibration curve samples of 278-hIgG1). Then, Rabbit anti-Human IgG (Fc) Secondary antibody, Biotin conjugate (Pierce Biotechnology), and Streptavidin-PolyHRP80 (Stereospecific Detection Technologies) were each reacted sequentially for one hour. A color development reaction was carried out using TMB One Component HRP Microwell Substrate (BioFX Laboratories) as a substrate. After the reaction was stopped with 1N Sulfuric acid (Showa Chemical), the mouse plasma concentration was determined by color development by measuring absorbance at 450 nm on a microplate reader. The concentrations in mouse plasma were calculated based on absorbance from the calibration curve using the analytical software SOFTmax PRO (Molecular Devices). Time-course changes in the plasma concentrations of antibodies after intravenous administration determined by this method are shown in FIG. 14. The results confirmed that in mice administered with a variant produced by enhancing FcγR binding of 278-IgG1, which has a strong pH-dependent binding activity to human IgE, antibody concentrations in the serum of these mice are not greatly decreased even when they are compared to those of 278-IgG1.

9-4. Determination of the hIgE(Asp6) Concentration in Normal Mouse Plasma

Figure 15:
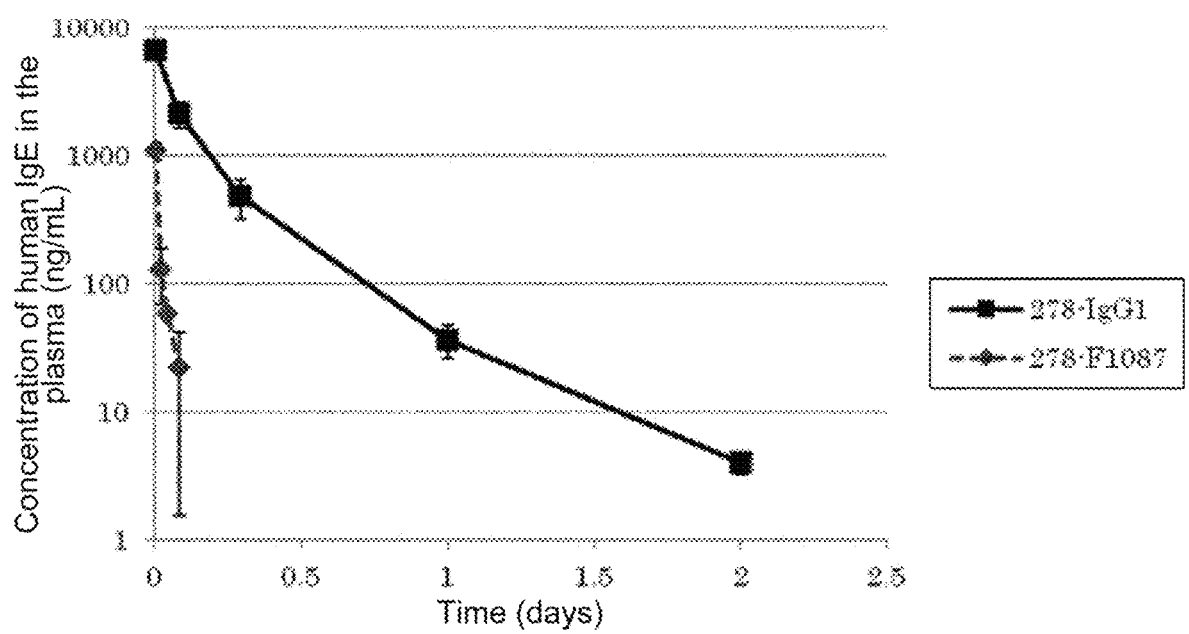
FIG. 15 is a graph showing the time-course changes in plasma concentration of hIgE(Asp6) in C57BL/6J mice administered with 278-IgG1 or 278-F1087.

The hIgE(Asp6) concentration in mouse plasma was determined by ELISA. Calibration curve samples were prepared at plasma concentrations of 192, 96, 48, 24, 12, 6, and 3 ng/mL. To make the immune complex formed between hIgE(Asp6) and the anti-hIgE antibody homogeneous, Xolair (Novartis) was added at 10 μg/mL to the calibration curve samples and the mouse plasma assay samples for the 278-hIgG1-administered group, and the samples were left to stand at room temperature for 30 minutes. In the 278-F1087-administered group, 278-F1022 (heavy chain SEQ ID NO: 54 and light chain SEQ ID NO: 46, prepared in a similar manner to Example 8) or 278-F760 (heavy chain SEQ ID NO: 55 and light chain SEQ ID NO: 46, prepared in a similar manner to Example 8) was added at 20 μg/mL, and then stirred at 37° C. for 60 hours. The mouse plasma assay samples were aliquoted into the anti-human IgE-immobilized immuno plate (MABTECH) or anti-human IgE (clone 107, MABTECH)-immobilized immuno plate (Nunc F96 MicroWell Plate (Nalge nunc International)); and the samples were left to stand or stirred at room temperature for two hours, or they were left to stand overnight at 4° C. Then, the human GPC3 core protein (SEQ ID NO: 51), an anti-GPC3 antibody (prepared in-house) biotinylated with NHS-PEG4-Biotin (Thermo Fisher Scientific), and Sterptavidin-PolyHRP80 (Stereospecific Detection Technologies) were each reacted sequentially for one hour. The concentration in mouse plasma was determined by the method of carrying out a color development reaction using TMB One Component HRP Microwell Substrate (BioFX Laboratories) as a substrate, stopping the reaction with 1N Sulfuric acid (Showa Chemical), and then measuring color development by the absorbance at 450 nm measured on a microplate reader; or the method of carrying out a color development reaction using the SuperSignal® ELISA Pico Chemiluminescent Substrate (Thermo Fisher Scientific) as a substrate, and then measuring luminescence intensity on a microplate reader. The concentrations in mouse plasma were calculated from the luminescence intensity, or based on absorbance from the calibration curve using the analytical software SOFTmax PRO (Molecular Devices). Time-course changes in plasma concentration of hIgE(Asp6) after intravenous administration determined by this method are shown in FIG. 15.

As a result, as opposed to elimination in the case of human IgE alone, elimination of human IgE was accelerated in mice co-administered with human IgE and 278-IgG1, which has a strong pH-dependent binding activity, as compared to human IgE alone. Furthermore, human IgE elimination was significantly accelerated in mice administered with human IgE and 278-F1087, which is produced by enhancing FcγR binding of 278-IgG1, compared to mice administered with human IgE alone and mice co-administered with human IgE and 278-IgG1. That is, antigen elimination was shown to be accelerated not only in mice administered with anti-IgA antibodies with enhanced FcγR binding discussed so far, but also in mice administered with anti-IgE antibodies with enhanced FcγR binding. The above-mentioned results showed that antigen elimination can be further accelerated by enhancing FcγR binding in each of the immune complex-forming hIgA-anti-hIgA antibody pair and hIgE-anti-hIgE antibody pair.

[Example 10] Preparation of Antibody Variants that Show Calcium-Dependent hIgA Binding Next, with the objective of augmenting antigen (hIgA) elimination from plasma, variants with enhanced binding to mouse FcRn were produced from GA2-IgG1, which shows calcium-dependent hIgA binding. First, with the objective of decreasing FcγR binding by the Fc region, GA2-F760 (heavy chain SEQ ID NO: 57) was produced by substituting Arg for Leu at position 235 and Lys for Ser at position 239 as indicated by EU numbering in GA2-IgG1. Furthermore, GA2-F1331, a variant showing stronger FcRn binding at pH 7.4 than GA2-F760, was produced by introducing the following substitutions into GA2-F760: Arg for Gly at position 236, Tyr for Met at position 252, Thr for Ser at position 254, Glu for Thr at position 256, Tyr for Asn at position 434, Val for Tyr at position 436, Arg for Gln at position 438, and Glu for Ser at position 440 as indicated by EU numbering. DNA sequences encoding GA2-F760 (heavy chain SEQ ID NO: 57, and light chain SEQ ID NO: 40) and GA2-F1331 (heavy chain SEQ ID NO: 56, and light chain SEQ ID NO: 40) were inserted into animal expression plasmids by a method known to those skilled in the art. These plasmids were used for expression by the method described above, and the concentrations of these antibody variants were determined after purification. Binding activities of GA2-F760 to mouse FcγRs (mFcγRI, mFcγRII, mFcγRIII, and mFcγRIV) were determined. As a result, GA2-F760 did not show significant binding to mouse FcγRs.

[Example 11] Assessment of the Effect on Plasma Retention of Antigen in Human FcRn Transgenic Mice Administered with Ca-Dependent hIgA-Binding Antibodies 11-1. In Vivo Testing Using Human FcRn Transgenic Mice Human FcRn transgenic mice (B6.mFcRn−/−.hFcRn Tg line 32+/+ mouse, Jackson Laboratories; Methods Mol Biol. (2010) 602, 93-104) were administered with hIgA (human IgA: produced in Example (1-1)) alone or co-administered with hIgA and an anti-hIgA antibody; and then the in vivo dynamics of hIgA and the anti-hIgA antibody were assessed. An hIgA solution (80 μg/mL) or a mixed solution of hIgA and the anti-hIgA antibody was administered once at a dose of 10 mL/kg into the tail vein. Any one of the above-mentioned GA2-IgG1, GA2-F760, and GA2-F1331 was used as an anti-hIgA antibody for administration.

Concentration of hIgA in the mixed solution was 80 μg/mL in all cases, and the anti-hIgA antibody concentration was 2.69 mg/mL. Since the anti-hIgA antibody was sufficiently present in excess with respect to hIgA, most of hIgA was considered to be bound by the antibody. Blood was collected from the mice 15 minutes, 1 hour, 2 hours, 7 hours, 1 day, 3 days, 7 days, and 14 days after antibody administration. The collected blood samples were immediately centrifuged at 4° C. and 12,000 rpm for 15 minutes to obtain the plasma samples. The separated plasma samples were stored in a freezer at −20° C. or below until measurement.

Figure 16:
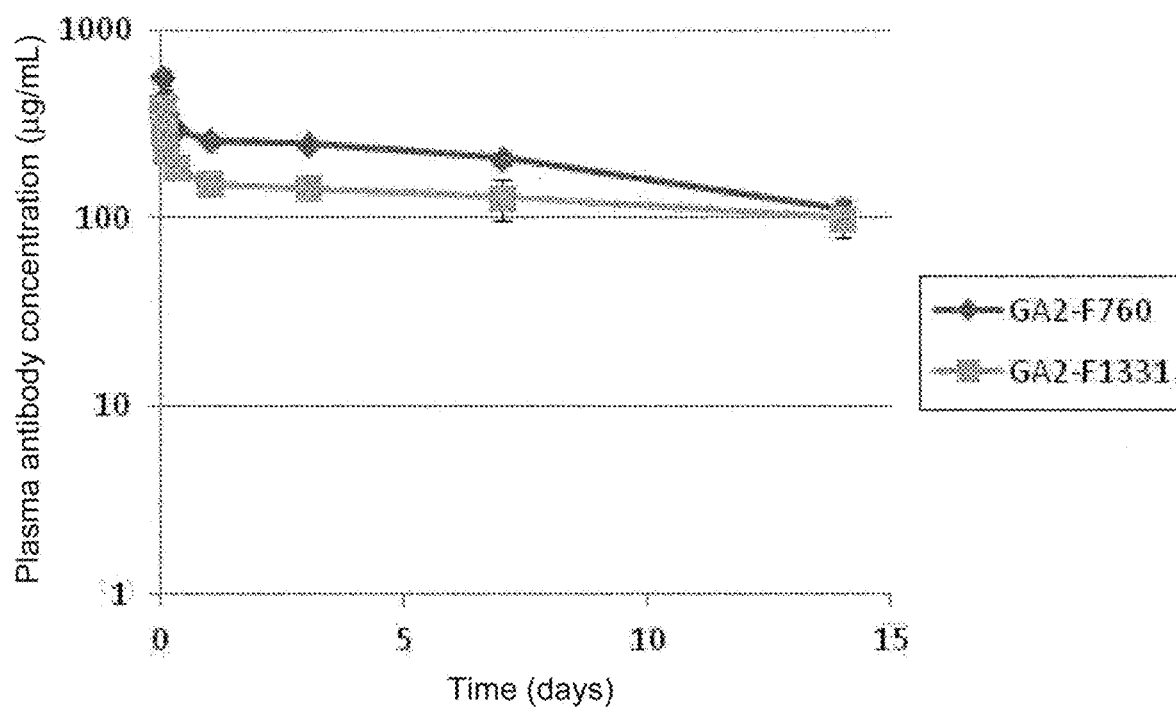
FIG. 16 is a graph showing the time-course changes in plasma concentration of GA2-F760 or GA2-F1331 in human FcRn transgenic mice administered with GA2-F760 or GA2-F1331.

11-2. ELISA Determination of the Anti-hIgA Antibody Concentration in Human FcRn Transgenic Mouse Plasma The anti-hIgA antibody concentration in mouse plasma was determined by ELISA. First, Anti-Human IgG (γ-chain specific) F(ab')2 Fragment of Antibody (SIGMA) was dispensed into each well of Nunc-Immuno Plates, MaxiSorp (Nalge nunc International), and this was left to stand overnight at 4° C. to prepare Anti-Human IgG-immobilized plates. Standard samples of the anti-hIgA antibodies to be used as calibration curve samples were prepared at plasma concentrations of 0.5, 0.25, 0.125, 0.0625, 0.03125, 0.01563, and 0.007813 µg/mL; and mouse plasma assay samples diluted 100-fold or more were prepared and aliquoted into the Anti-Human IgG-immobilized plates, and then the plates were incubated at 25° C. for one hour. Then, Goat Anti-Human IgG (γ chain specific) Biotin (BIOT) Conjugate (Southern Biotechnology Associates Inc.) was dispensed into each well of the aforementioned plates, and then the plates were incubated at 25° C. for one hour to allow reaction to take place. Then, Streptavidin-PolyHRP80 (Stereospecific Detection Technologies) was dispensed into each well of the aforementioned plates, and then the plates were incubated at 25° C. for one hour to allow reaction to take place. A color development reaction was carried out using TMB One Component HRP Microwell Substrate (BioFX Laboratories) as a substrate. After stopping the reaction with 1N Sulfuric acid (Showa Chemical), absorbance of the reaction solution in each well at 450 nm was measured on a microplate reader. The anti-hIgA antibody concentration in mouse plasma was calculated based on absorbance from the calibration curve using the analytical software SOFTmax PRO (Molecular Devices). Time-course changes in plasma concentrations of the GA2-F1331 and GA2-F760 antibodies in human FcRn transgenic mice after intravenous administration determined by this method are shown in FIG. 16.

11-3. Determination of the Plasma hIgA Concentration by ELISA

Figure 17:
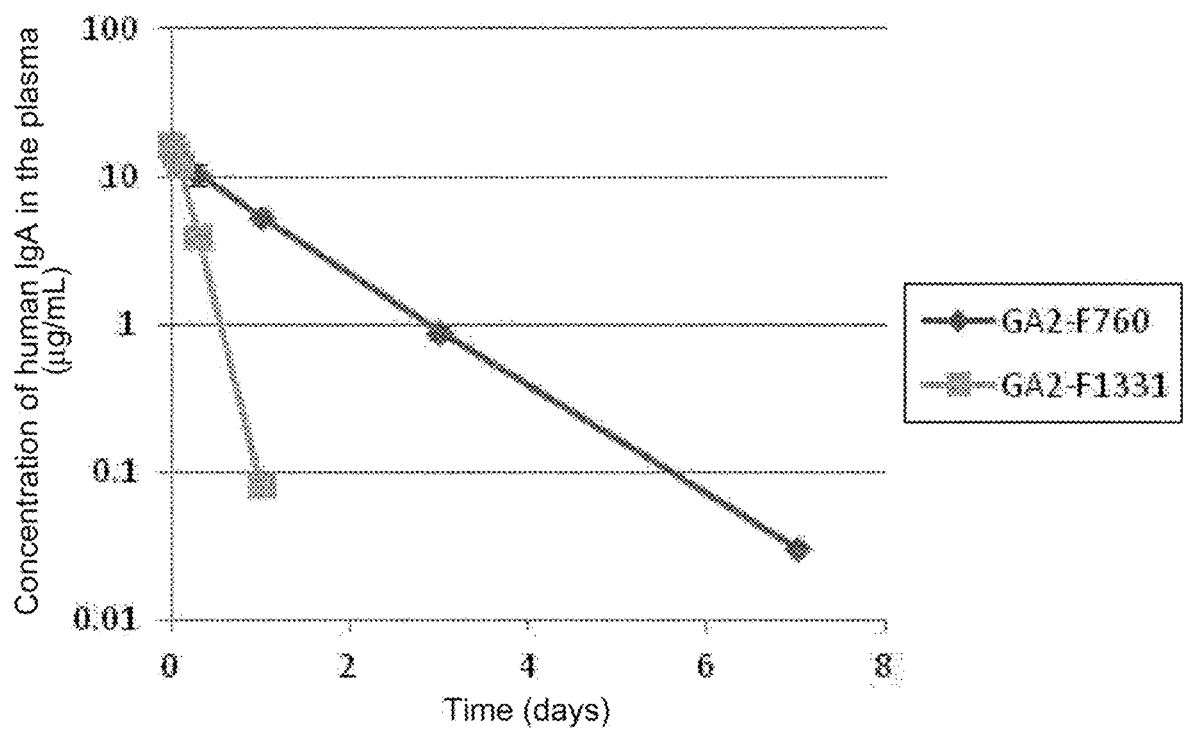
FIG. 17 is a graph showing the time-course changes in plasma concentration of human IgA in human FcRn transgenic mice administered with GA2-F760 or GA2-F1331.

Concentration of hIgA in mouse plasma was determined by ELISA. First, Goat anti-Human IgA antibody (BETHYL) was aliquoted into each well of a Nunc-Immuno Plate, MaxiSorp (Nalge nunc International). The plate was left to stand overnight at 4° C. to prepare an anti-human IgA-immobilized plate. Standard samples of hIgA to be used as calibration curve samples were prepared at plasma concentrations of 0.4, 0.2, 0.1, 0.05, 0.025, 0.0125, and 0.00625 µg/mL. Mouse plasma assay samples were prepared at a 100-fold or greater dilution. 200 µl of 500 ng/mL hsIL6R was added to 100 µL of each of the calibration curve samples and plasma samples. The resulting mixtures were left to stand at room temperature for one hour, and then the mixed solutions were aliquoted at 100 µl into the above-mentioned anti-human IgA-immobilized plate; and the plate was left to stand at room temperature for one hour. Next, Biotinylated Anti-human IL-6R Antibody (R&D) was aliquoted into each well of the aforementioned plate, and then the plate was incubated at RT for one hour to allow reaction to take place. In addition, Streptavidin-PolyHRP80 (Stereospecific Detection Technologies) was aliquoted into each well of the aforementioned plate, and then the plate was incubated at room temperature for one hour to allow reaction to take place. A color development reaction was carried out using TMB One Component HRP Microwell Substrate (BioFX Laboratories) as a substrate. After the reaction was terminated with 1 N sulfuric acid (Showa Chemical), absorbance of the reaction solution in each well at 450 nm was measured using a microplate reader. The concentrations in mouse plasma were calculated based on absorbance from the calibration curve using the analytical software SOFTmax PRO (Molecular Devices). Time-course changes in plasma concentration of hIgA in human FcRn transgenic mice determined by this method after intravenous administration are shown in FIG. 17.

The results showed that the elimination of hIgA from plasma was markedly accelerated in mice co-administered with hIgA and GA2-F1331, which has enhanced human FcRn binding, in comparison to the plasma hIgA elimination in mice co-administered with hIgA and GA2-F760, which has a low human FcRn-binding activity.

[Example 12] Preparation of Antibody Variants that Show pH-Dependent Human IgE Binding Next, with the objective of augmenting antigen (human IgE) elimination from plasma, variants with enhanced binding to mouse FcRn were produced from 278-IgG1, which shows pH-dependent human IgE binding. First, with the objective of decreasing mouse FcγR binding, 278-F760 (SEQ ID NO: 55) was produced by substituting Arg for Leu at position 235 and Lys for Ser at position 239 as indicated by EU numbering in 278-IgG1. Furthermore, 278-F1331, a variant showing stronger FcRn binding at pH 7.4 than 278-F760, was produced by introducing the following substitutions into 278-F760: Arg for Gly at position 236, Tyr for Met at position 252, Thr for Ser at position 254, Glu for Thr at position 256, Tyr for Asn at position 434, Val for Tyr at position 436, Arg for Gln at position 438, and Glu for Ser at position 440 as indicated by EU numbering. A DNA sequence encoding 278-F1331 (heavy chain SEQ ID NO: 58, and light chain SEQ ID NO: 46) or 278-F760 (heavy chain SEQ ID NO: 55, and light chain SEQ ID NO: 46) was inserted into an animal expression plasmid by a method known to those skilled in the art. These antibody variants were expressed by the above-mentioned method using animal cells introduced with the plasmid, and their concentrations were determined after purification.

[Example 13] Assessment of the Effect on Plasma Retention of Antigen in Human FcRn Transgenic Mice Administered with a pH-Dependent hIgE-Binding Antibody 13-1. In Vivo Test Using Human FcRn Transgenic Mice Human FcRn transgenic mice (B6.mFcRn−/−.hFcRn Tg line 32+/+ mouse, Jackson Laboratories; Methods Mol Biol. (2010) 602, 93-104) were co-administered with hIgE(Asp6) (human IgE(Asp6): produced in Example (5-1)), an anti-hIgE antibody (278-F760 or 278-F1331), and Sanglopor (human normal immunoglobulin, CSL Behring); and then the in vivo dynamics of hIgE(Asp6) and the anti-hIgE antibody were assessed. A mixed solution of hIgE(Asp6), an anti-hIgE antibody, and Sanglopor (concentrations are shown in Table 11) was administered once at a dose of 10 mL/kg into the tail vein. The above-mentioned 278-F760 or 278-F1331 was used as the anti-hIgE antibody for administration.

Since the anti-hIgE antibody was sufficiently present in excess with respect to hIgE(Asp6), most of the hIgE(Asp6)

was considered to be bound by the antibody. Blood was collected from the mice 5 minutes, 2 hours, 7 hours, 1 day, 2 days, 4 days, 5 days, 7 days, 14 days, 21 days, and 28 days after antibody administration. The collected blood samples were immediately centrifuged at 4° C. and 12,000 rpm for 15 minutes to obtain plasma samples. The separated plasma samples were stored in a freezer at −20° C. or below until measurement.

TABLE 11

| Anti-hIgE antibody | Concentration of hIgE(Asp6) in the administered solution (μg/mL) | Concentration of hIgE antibody in the administered solution (μg/mL) | Concentration of Sanglopor in the administered solution (μg/mL) |
|---|---|---|---|
| 278-F760 | 20 | 100 | 100 |
| 278-F1331 | 20 | 100 | 100 |

Figure 18:
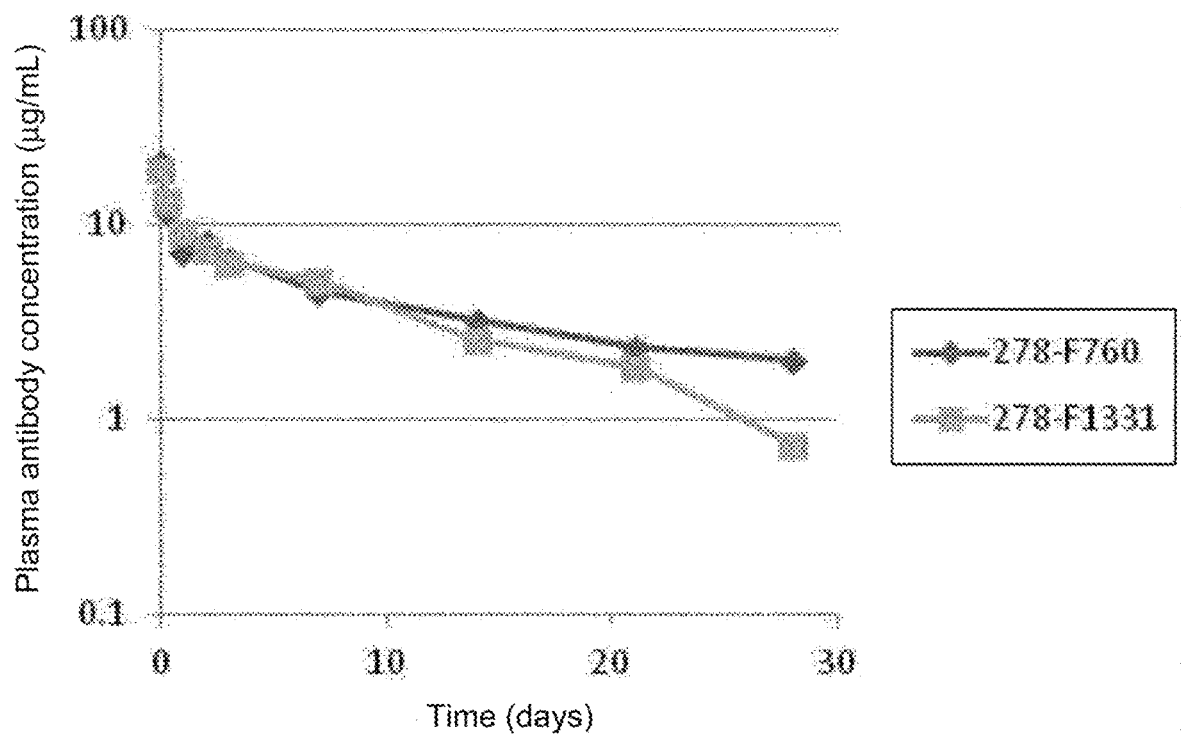
FIG. 18 is a graph showing the time-course changes in plasma concentration of 278-F760 or 278-F1331 in human FcRn transgenic mice administered with 278-F760 or 278-F1331.

13-2. Determination of the Anti-hIgE Antibody Concentration in Human FcRn Transgenic Mouse Plasma by ELISA The anti-hIgE antibody concentration in mouse plasma was determined by electrochemiluminescence (ECL) assay. Standard samples of the anti-hIgE antibodies to be used as calibration curve samples were prepared at plasma concentrations of 32, 16, 8, 4, 2, 1, 0.5, and 0.25 μg/mL. Each of the calibration curve samples and mouse plasma samples was aliquoted into each well of the hIgE(Asp6)-immobilized ECL plate, and then the plate was incubated at 4° C. for one hour/overnight to allow reaction to take place. Then, Goat Anti-Human IgG (γ chain specific) Biotin (BIOT) Conjugate (Southern Biotechnology Associates Inc.) was dispensed into each well of the aforementioned plate, and then the plate was incubated at 25° C. for one hour to allow reaction to take place. Furthermore, Streptavidin-PolyHRP80 (Stereospecific Detection Technologies) was dispensed into each well of the aforementioned plate, and then the plate was incubated at 25° C. for one hour to allow reaction to take place. Next, each reaction solution in the plate was made to react with a SULFO-tagged goat anti-rabbit antibody (Meso Scale Discovery) at room temperature for one hour. Finally, Read Buffer T (×4) (Meso Scale Discovery) was dispensed into each reaction solution, and this was immediately followed by luminescence measurement of the reaction solution using the Sector Imager 2400 Reader (Meso Scale Discovery). The anti-hIgE antibody concentration in mouse plasma was calculated based on response from the calibration curve using the analytical software SOFTmax PRO (Molecular Devices). Time-course changes in the plasma concentrations of the 278-F1331 and 278-F760 antibodies in human FcRn transgenic mice determined by this method after intravenous administration are shown in FIG. 18.

Figure 19:
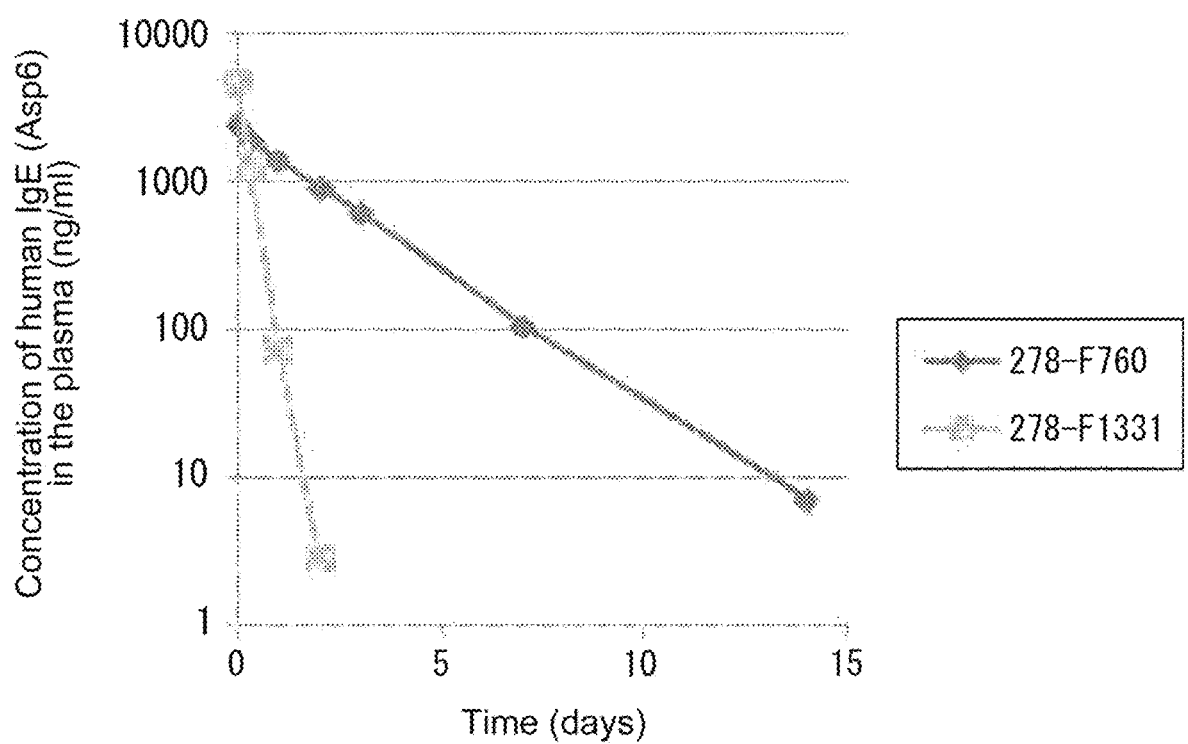
FIG. 19 is a graph showing the time-course changes in plasma concentration of human IgE in human FcRn transgenic mice administered with 278-F760 or 278-F1331.

13-3. Determination of the Plasma hIgE(Asp6) Concentration in Human FcRn Transgenic Mice Concentration of hIgE(Asp6) in mouse plasma was determined by ELISA. Calibration curve samples were prepared at plasma concentrations of 192, 96, 48, 24, 12, 6, and 3 ng/mL. To make the immune complex formed between hIgE(Asp6) and an anti-hIgE antibody homogeneous, calibration curve samples and mouse plasma assay samples were prepared by adding Xolair (Novartis) at 10 μg/mL for the 278-hIgG1-administered group, and the samples were left to stand at room temperature for 30 minutes. The mouse plasma assay samples were aliquoted into the anti-human IgE-immobilized immuno plate (MABTECH) or anti-human IgE (clone 107, MABTECH)-immobilized immuno plate (Nunc F96 MicroWell Plate (Nalge nunc International)), and the samples were left to stand at room temperature for two hours, or at 4° C. overnight. Then, the human GPC3 core protein (SEQ ID NO: 51), an anti-GPC3 antibody (prepared in-house) biotinylated with NHS-PEG4-Biotin (Thermo Fisher Scientific), and Sterptavidin-PolyHRP80 (Stereospecific Detection Technologies) were each reacted sequentially for one hour. The concentrations in mouse plasma were determined by the method of carrying out a color development reaction using TMB One Component HRP Microwell Substrate (BioFX Laboratories) as a substrate, stopping the reaction with 1N Sulfuric acid (Showa Chemical), and then measuring color development by the absorbance at 450 nm measured on a microplate reader; or the method of carrying out a luminescence reaction using SuperSignal® ELISA Pico Chemiluminescent Substrate (Thermo Fisher Scientific) as a substrate, and then measuring luminescence intensity on a microplate reader. The concentrations in mouse plasma were calculated from luminescence intensity, or based on absorbance from the calibration curve using the analytical software SOFTmax PRO (Molecular Devices). Time-course changes in the plasma concentration of hIgE(Asp6) determined by this method after intravenous administration are shown in FIG. 19.

The results showed that mouse plasma hIgE elimination was markedly accelerated in mice co-administered with hIgE and 278-F1331, which has enhanced human FcRn binding, in comparison to the plasma hIgE elimination in mice co-administered with hIgE and 278-F760, which has a low mouse FcγR-binding activity. That is, antigen elimination was shown to be accelerated not only in mice administered with anti-IgA antibodies having enhanced FcRn binding discussed so far, but also in mice administered with anti-IgE antibodies having enhanced FcRn binding. The above-mentioned results showed that antigen elimination can be further accelerated by enhancing FcRn binding in each of the immune complex-forming hIgA-anti-hIgA antibody pair and hIgE-anti-hIgE antibody pair.

[Example 14] Assessment of the Effect on Plasma Retention of Antigen in Normal Mice Co-Administered with Two Types of Anti-Human IL6 Receptor Antibodies 14-1. Preparation of Two Types of Anti-IL6R Antibodies Fv4-IgG1 (heavy chain SEQ ID NO: 59, and light chain SEQ ID NO: 60) is an anti-human IL6 receptor antibody having the property of binding to human IL6R in a pH-dependent manner (binds under a neutral condition and dissociates under an acidic condition) as described in WO 2011/122011. PHX-IgG1 (heavy chain SEQ ID NO: 61, and light chain SEQ ID NO: 62) is a human IL6R-binding antibody. A DNA sequence encoding Fv4-IgG1 (heavy chain SEQ ID NO: 59, and light chain SEQ ID NO: 60), PHX-IgG1 (heavy chain SEQ ID NO: 61, and light chain SEQ ID NO: 62), or PHX-F29 (heavy chain SEQ ID NO: 63, and light chain SEQ ID NO: 62) produced by making amino acid modifications to the heavy chain constant region of PHX-IgG1 was inserted into an animal expression plasmid by a method known to those skilled in the art. These antibody variants were expressed by the aforementioned method (described in Example 1) using the plasmids, and their concentrations were determined after purification.

14-2. Assessment of Human IL6 Receptor-Binding of PHX-IgG1

Interaction between IL-6R and PHX-IgG1 prepared in 14-1 was analyzed using Biacore™ T200 (GE Healthcare) to calculate the dissociation constant (KD). A 10 mM ACES, 150 mM NaCl, and 0.05% Tween® 20 polyethylene glycol sorbitan monolaurate, pH 7.4 buffer was used as the running buffer to analyze interactions at 37° C. Protein A/G (Thermo Scientific) was immobilized onto Series S Sensor chip CM4 (GE Healthcare) by an amine coupling method, and the chip was allowed to capture an antibody of interest. Then, the running buffer and IL-6R which was diluted using the running buffer to 800, 400, 200, 100, 50, 25, and 12.5 nM were made to flow over the antibody-captured chip at a flow rate of 2 µL/min to allow interaction to take place for 15 minutes. Antibodies captured onto the chips were washed by reaction with 10 mM glycine-HCl at pH 1.5; and the washed chips were regenerated, and used repeatedly for interaction analyses.

The dissociation constant KD (mol/L) of PHX-IgG1 for IL-6R was calculated by performing a steady-state affinity analysis on the sensorgrams obtained as the Biacore™ measurement results using the Biacore™ Evaluation Software. The dissociation constant (KD) of PHX-IgG1 for IL-6R at pH 7.4 calculated by this method was 1.4 E-7 (M).

Next, pH dependency of PHX-IgG1 in hIL-6R binding was evaluated using Biacore™ T100. A 10 mM ACES, 150 mM NaCl, 0.05% Tween° 20 polyethylene glycol sorbitan monolaurate, pH 7.4 buffer and a 10 mM ACES, 150 mM NaCl, 0.05% Tween° 20 polyethylene glycol sorbitan monolaurate, pH 6.0 buffer were used as running buffers to determine the binding of PHX-IgG1 to hIL-6R at 37° C. under conditions of pH 7.4 and pH6.0, respectively. Protein A/G (Thermo Scientific) was immobilized onto Series S Sensor chip CM4 (GE Healthcare) by an amine coupling method, and the chip was allowed to capture an antibody of interest. Then, the running buffer and IL-6R which was diluted using the running buffer to 1000, 250, and 62.5 nM were allowed to interact with the antibody-captured chip.

Figure 20:
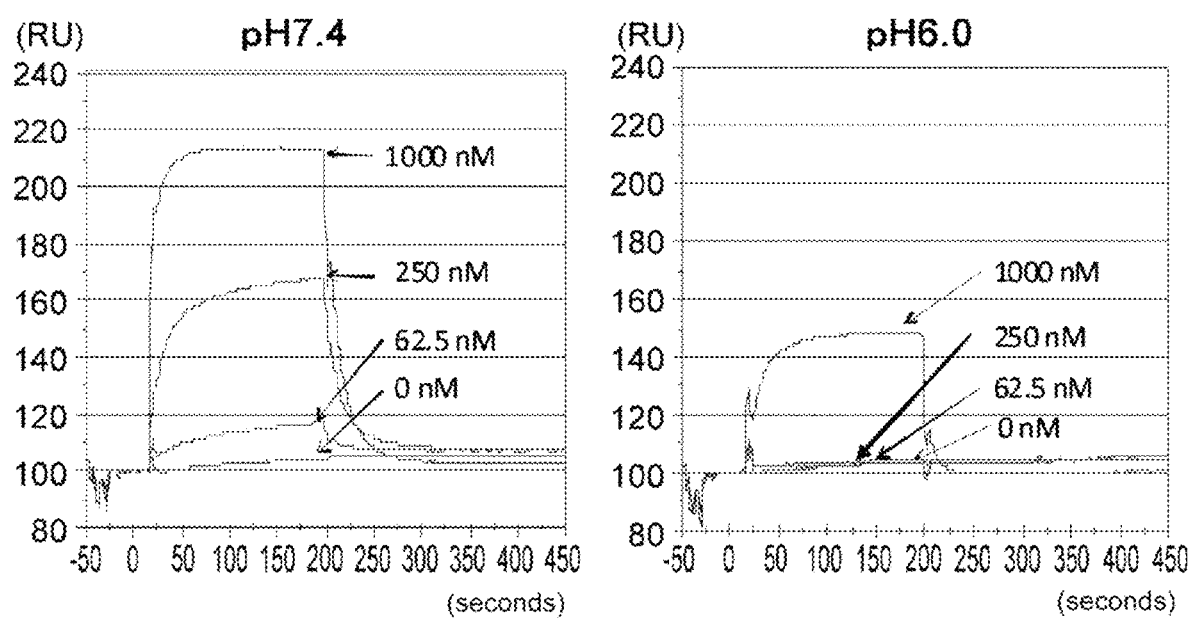
FIG. 20 presents sensorgrams showing the interaction of PHX-IgG1 with hsIL-6R at pH7.4 and pH6.0.

The sensorgrams obtained through measurements made by this method at pH 7.4 and pH 6.0 are shown in FIG. 20. FIG. 20 shows the hIL-6R-bound phase and the hIL-6R-dissociated phase of PHX-IgG1 when the amount of antibodies captured is normalized to 100 RU. Comparison of the results shown in FIG. 20 indicates that binding of PHX-IgG1 to hIl-6R is decreased at pH 6.0 when compared to the case at pH 7.4.

14-3. Assessment of the Property of Two Types of Antibodies to Simultaneously Bind the Same Antigen by an Electrochemiluminescence Method Whether or not two types of antibodies can bind to a single antigen simultaneously was evaluated by an electrochemiluminescence method. First, Fv4-IgG1 (1 µg/mL, 100 µL) biotinylated using EZ-Link Sulfo-NHS-Biotin (Thermo SCIENTIFIC) was added to a MULTI-ARRAY® 96-well Streptavidin Gold Plate, and this was incubated at room temperature for one hour to allow reaction to take place. After washing, 100 µL of the hsIL-6R solutions prepared at 0, 0.2, 1, 5, and 25 µg/mL was added, and they were allowed to react at room temperature for one hour. After another wash, PHX-F29 subjected to ruthenium labeling using SULFO-TAGNHS Ester (Meso Scale Discovery) (0, 0.2, 1, 5, 25, and 125 µg/mL; 100 µL) or Fv4-IgG1 subjected to ruthenium labeling by the same method (5 µg/mL; 100 µL) was added and allowed to react at room temperature for one hour. After washing, 150 µL of Read Buffer T (×4) (Meso Scale Discovery) was dispensed into each well, and this was immediately followed by chemiluminescence measurement using the SECTOR IMAGER 2400 Reader (Meso Scale Discovery).

Figure 21:
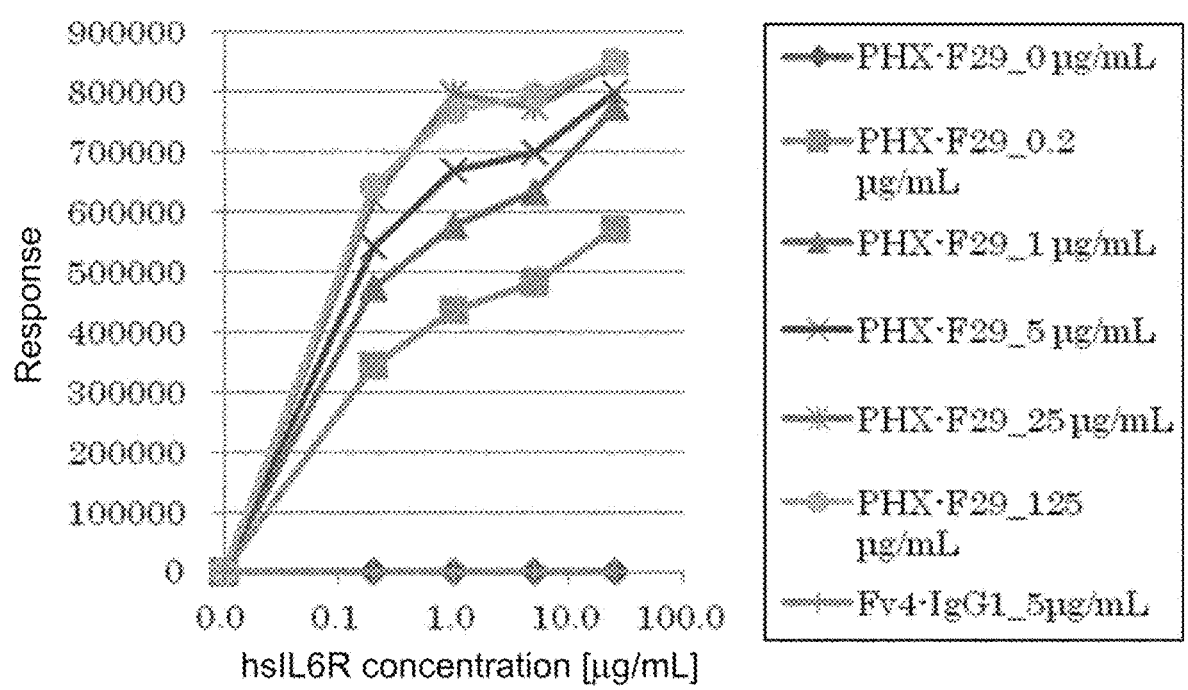
FIG. 21 shows the result of evaluating simultaneous binding of Fv4-IgG1 and PHX-F29 with IL6R by the electrochemiluminescence (ECL) method.

The results are shown in FIG. 21. When ruthenium-labeled Fv4-IgG1 was allowed to react, reaction was not observed regardless of antigen concentration. On the other hand, when ruthenium-labeled PHX-F29 was allowed to react, antigen (IL6R) concentration-dependent reaction was observed. These results show that PHX-F29 and Fv4-IgG1 bind simultaneously to IL6R. Therefore, this indicates that the epitope of IL6R recognized by PHX-F29 and the epitope recognized by Fv4-IgG1 are different; and by using antibodies carrying the PHX-F29 variable region and the Fv4-IgG1 variable region, respectively, two antigen-binding molecules can bind to a single IL6R molecule.

14-4. In Vivo Tests Using Normal Mice

Normal mice (C57BL/6J mouse; Charles River Japan) were administered with hsIL-6R (soluble human IL-6 receptor: prepared in Reference Example 1) alone or co-administered with hsIL-6R and anti-human IL-6 receptor antibodies, and then assessed for the in vivo dynamics of hsIL-6R and the anti-human IL-6 receptor antibodies. An hsIL-6R solution (5 µg/ml) or a mixed solution of hsIL-6R and an anti-human IL-6 receptor antibody was administered once at 10 mL/kg into the tail vein. The anti-human IL-6 receptor antibodies used were Fv4-IgG1 and PHX-IgG1.

Concentration of hsIL-6R in the mixed solution was 5 µg/mL in every case, and the anti-human IL-6 receptor antibody concentrations were different for each administration group as shown in Table 12. Since the anti-human IL-6 receptor antibody was sufficiently present in excess with respect to hsIL-6R, most of the hsIL-6R was considered to be bound by the antibody. Blood was collected from the mice 5 minutes, 7 hours, 1 day, 2 days, 3 days, 7 days, 14 days, and 21 days after administration. Blood was collected from the Fv4-IgG1 (1 mg/kg)-administered group (#1) 5 minutes, 7 hours, 1 day, 2 days, 3 days, 7 days, 15 days, and 22 days after antibody administration. The collected blood samples were immediately centrifuged at 4° C. and 12,000 rpm for 15 minutes to obtain the plasma samples. The separated plasma samples were stored in a freezer at −20° C. or below until measurement.

TABLE 12

| Administration group | Amount of administered Fv4-IgG1 (mg/kg) | Amount of administered PHX-IgG1 (mg/kg) |
|---|---|---|
| #1 | 1 | 0 |
| #2 | 1 | 1 |
| #3 | 1 | 5 |
| #4 | 1 | 25 |

Figure 22:
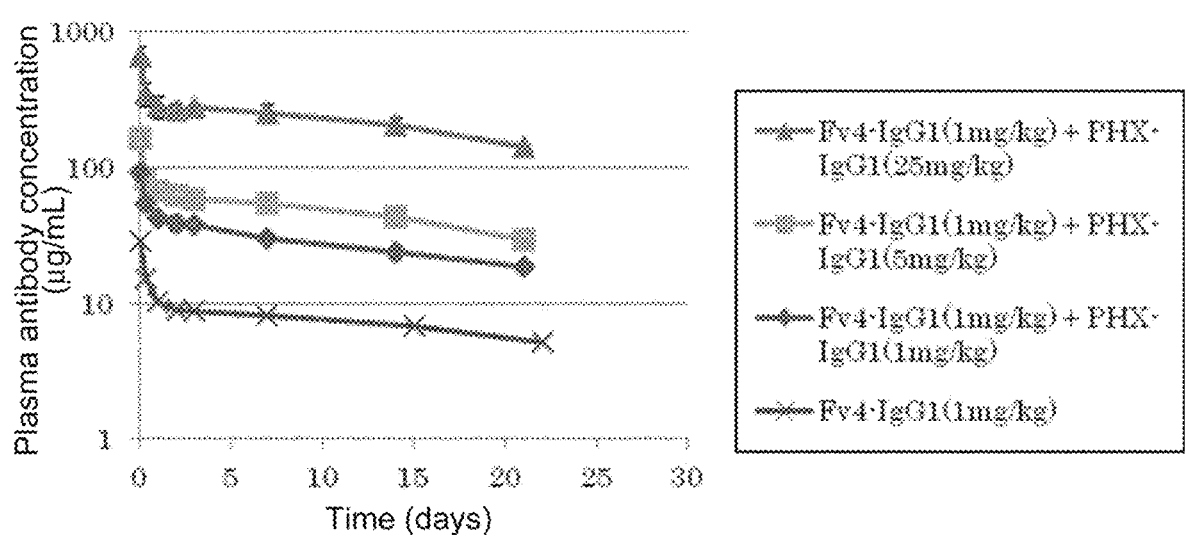
FIG. 22 is a graph showing the time-course changes in anti-IL6R antibody concentration in plasma of normal mice for the hsIL6R+Fv4-IgG1-administered group, and the hsIL6R+Fv4-IgG1+PHX-IgG1-administered groups.

14-5. Determination of the Anti-Human IL-6 Receptor Antibody Concentration in Normal Mouse Plasma by an Electrochemiluminescence Method The anti-human IL-6 receptor antibody concentration in mouse plasma was determined by an electrochemiluminescence method. First, an anti-human kappa capture antibody (Antibody Solutions) was dispensed onto Multi-ARRAY 96-Well plates (Meso Scale Discovery), and stirred at room temperature for one hour, and then a PBS-Tween solution containing 5% BSA (w/v) was used for blocking at room temperature for two hours to prepare anti-human IgG-immobilized plates. Calibration curve samples were prepared at plasma concentrations of 40.0, 13.3, 4.44, 1.48, 0.494, 0.165, and 0.0549 µg/mL; and mouse plasma assay samples prepared at 500-fold or more dilution were aliquoted into each well of the anti-human IgG-immobilized plates, and then the plates were stirred for one hour at room temperature. Then, an anti-human kappa capture antibody Biotin conjugate (Antibody Solutions) was dispensed into each well of the aforementioned plates, and then the plates were stirred at room temperature for one hour to allow reaction to take place. Furthermore, SULFO-TAG Labeled streptavidin (Meso Scale Discovery) was aliquoted into each well of the plates, and then the plates were stirred at room temperature for one hour to allow reaction to take place. After washing each well, Read Buffer T (×1) (Meso Scale Discovery) was dispensed into the wells, and chemiluminescence of the reaction solutions was measured immediately using the Sector Imager 2400 Reader (Meso Scale Discovery). The concentrations in mouse plasma were calculated based on the response from the calibration curve using the analytical software SOFTmax PRO (Molecular Devices). Time-course changes in the anti-human IL-6R antibody concentration are shown in FIG. 22.

14-6. Determination of the Plasma hsIL-6R Concentration by an Electrochemiluminescence Method The hsIL-6R concentration in mouse plasma was determined by an electrochemiluminescence method. Calibration curve samples of hsIL-6R were prepared at plasma concentrations of 12.5, 6.25, 3.13, 1.56, 0.781, 0.391, and 0.195 ng/mL. Mouse plasma assay samples were prepared at 50-fold or greater dilution. A mixed solution of the hsIL-6R sample or mouse plasma assay sample, a monoclonal anti-human IL-6R antibody (R&D) which has been ruthenium-labeled using SULFO-TAG NHS Ester (Meso Scale Discovery), a biotinylated anti-human IL-6 R antibody (R&D), and tocilizumab (heavy chain SEQ ID NO: 64, light chain SEQ ID NO: 65) were allowed to react overnight at 37° C. Then, a PBS-Tween solution containing 0.5% BSA (w/v) was used for blocking a Streptavidin Gold Multi-ARRAY Plate (Meso Scale Discovery) by incubation at 50C overnight, and the mixed solution was aliquoted into each well of that plate. After another two-hour incubation of this plate at room temperature to allow reaction to take place, each well of the plate was washed, and then Read Buffer T (×2) (Meso Scale Discovery) was dispensed into each well; and chemiluminescence of the reaction solutions was measured immediately using the SECTOR Imager 2400 Reader (Meso Scale Discovery). The hsIL-6R concentrations were calculated based on response from the calibration curve using the analytical software SOFTmax PRO (Molecular Devices).

Figure 23:
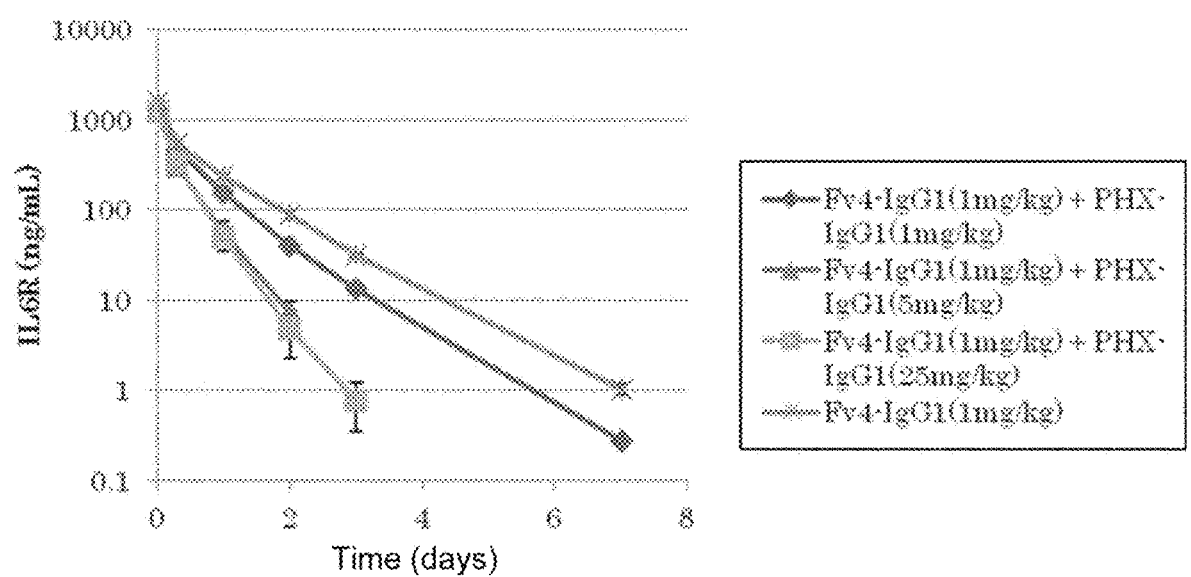
FIG. 23 is a graph showing the time-course changes in human IL6R concentration in plasma of normal mice for the hsIL6R+Fv4-IgG1-administered group, and the hsIL6R+Fv4-IgG1+PHX-IgG1-administered groups.

The calculated time-course changes in the concentration of human IL6R (which is also described as hsIL6R or hsIL-6R, and refers to the same protein) are shown in FIG. 23. Elimination of plasma IL6R was accelerated in mice administered with PHX-IgG1 together with Fv4-IgG1 compared to mice administered with Fv4-IgG1 alone.

Without being restricted to a particular theory, the following explanation may be given for the above-mentioned acceleration of plasma antigen elimination. Even when administered alone, Fv4-IgG1 was present in sufficient amount with respect to hsIL6R, and thus most of the hsIL6R was considered to be bound by Fv4-IgG1 in plasma. When PHX-IgG1, which has a different epitope from that of Fv4-IgG1 and can bind to hsIL6R with Fv4-IgG1, is administered, an immune complex comprising Fv4-IgG1 and PHX-IgG1 for a single hsIL6R molecule is formed. As a result, uptake into cells was promoted by enhanced binding to an Fcγ receptor and/or FcRn, and this may have resulted in acceleration of hsIL6R elimination from plasma. Specifically, formation of large immune complexes comprising two or more antibodies and two or more antigenic binding units (monomeric antigens) by multispecific antibodies comprising appropriate variable regions that bind to epitopes which are different from each other and are present on a monomeric antigen, or multiparatopic antibodies in a non-limiting embodiment, which are antibodies whose variable regions show pH- or Ca-dependent binding (bispecific antibodies or biparatopic antibodies comprising a right-arm variable region that recognizes epitope A and a left-arm variable region that recognizes epitope B, as shown in FIG. 8) enables acceleration of antigen elimination.

[Example 15] Assessment of Binding of an Immune Complex with FcγR Using a Biacore™ Device 15-1. Regarding Binding of an Immune Complex with FcγR As methods for evaluating formation of immune complexes comprising an antigen-binding molecule and an antigen, gel filtration (size exclusion) chromatography was used in Example 4, and an electrochemiluminescence (ECL) method was used in Example 14. When the antigen or antigen-binding molecule comprised in an immune complex contains an FcγR-binding domain such as an immunoglobulin constant region, the immune complex binds to FcγR with avidity. Therefore, formation of an immune complex comprising an FcγR-binding domain may be confirmed by a method that uses the property of stronger FcγR binding (in particular, the property of slower dissociation) than the antigen-binding molecule alone or the antigen alone (The Journal of Biological Chemistry (2001) 276(9), 6591-6604, mAbs (2009) 1 (5), 491-504).

15-2. Preparation of Antibodies and Antigens for Evaluation, and Histidine-Tagged Human FcγR IIIaV Xolair (Novartis), clone 278-IgG1 (prepared in Example 4), GA2-IgG1 (prepared in Example 1), Fv4-IgG1 (prepared in Example 14), and PHX-IgG1 (prepared in Example 14) to be used for assessment of immune complex formation were prepared by the aforementioned methods.

The hIgE (hIgE(Asp6); prepared in Example 5) and IL6R (Reference Example 1) to be used for assessment were prepared by the aforementioned methods, respectively. A recombinant of human IgA, hIgA-v2 (GC-hIgA), was prepared by the method below. A gene fragment encoding GC-hIgA-MYC (heavy chain SEQ ID NO: 66 and light chain SEQ ID NO: 67) was inserted into an animal cell expression vector. The constructed plasmid vector was introduced into FreeStyle 293 (Invitrogen) using 293Fectin (Invitrogen) along with an EBNA1-expressing gene. Then, the transfected cells were cultured at 37° C. under 8% $CO_2$ for six days, and the GC-hIgA protein was secreted into the culture supernatant. The cell culture containing GC-hIgA-MYC was filtered through a 0.22-μm bottle top filter to obtain the culture supernatant. Purified GC-hIgA-MYC was obtained using ion exchange chromatography and gel filtration chromatography according to methods known to those skilled in the art.

Histidine tagged human FcγR IIIaV was prepared by the method of Reference Example 2.

Binding of an antigen-antibody immune complex with FcγR was assessed using Biacore™ T200 (GE Healthcare).

Binding of an antigen-antibody immune complex with FcγR was assessed using Biacore T200 (GE Healthcare).

A suitable amount of the Penta-His Antibody (QIAGEN) was immobilized onto Sensor chip CM5 (GE Healthcare) by an amine coupling method; and a suitable concentration of his-tagged human FcγR IIIaV was injected. Human FcγR IIIaV was immobilized onto the chip by allowing the penta-His antibody immobilized on the chip to capture human FcγR IIIaV. A solution containing 200 nM antibody or a mixed solution containing 200 nM antibody and 200 nM antigen was injected as the analyte; and it was allowed to interact with human FcγR IIIaV immobilized on the sensor chip. Subsequently, a 10 mmol/L Glycine-HCl, pH2.5 solution was injected to regenerate the sensorchip. A 1.2 mmol/L CaCl$_2$)/0.05% Tween® 20 polyethylene glycol sorbitan monolaurate, 20 mmol/L ACES, 150 mmol/L NaCl, pH 7.4 buffer was used as the running buffer, and binding between the antigen-antibody immune complex and FcγR was measured at 25° C.

Figure 24:
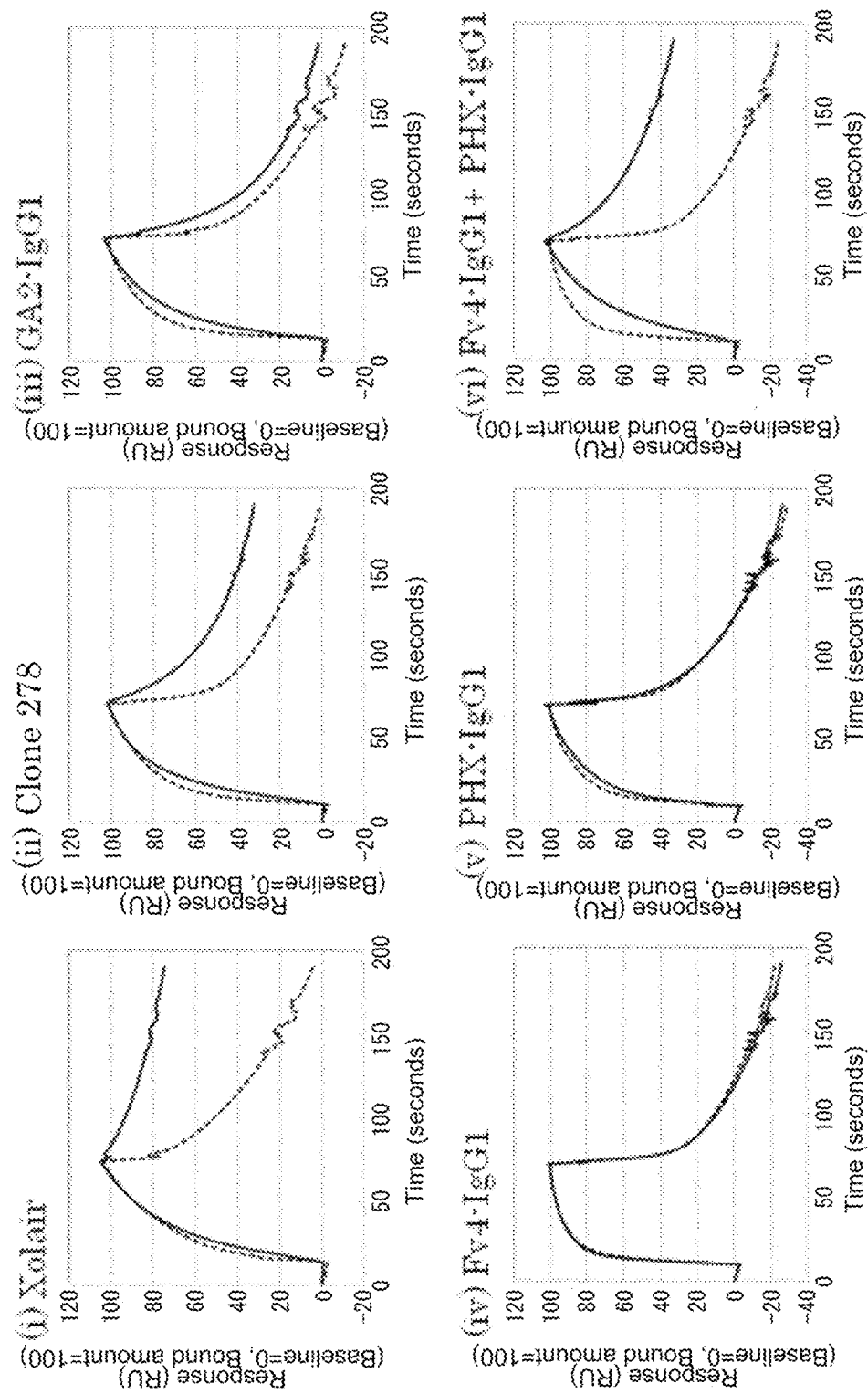
FIG. 24 is a set of six graphs, respectively designated (i) Xolair, (ii) Clone 278, (iii) GA2-IgG1, (iv) Fv4-IgG1, (v) PHX-IgG1, and (vi) Fv4-IgG1+PHX-IgG1, illustrating Biacore™ sensorgrams obtained when a solution of antibody alone or a mixed antibody-antigen solution was applied to FcγR. The dashed line in each graph shows the sensorgram obtained when the solution of antibody alone was applied, and the solid line in each graph shows the sensorgram obtained when the mixed antibody-antigen solution was applied.

The results of binding analyses of reacting an antibody-containing solution or a mixed antibody-antigen solution with human FcγR IIIaV are shown in FIG. 24. To focus on the dissociation, FIG. 24 shows sensorgrams in which the binding levels have been normalized to 100. Although Fv4-IgG1 binds to IL6R, it does not form an immune complex. Therefore, no differences were observed between dissociation in the reaction of an antibody-containing solution and FcγR, and dissociation when an antigen-antibody mixture was used. Meanwhile, when a mixed solution of hIgE and Xolair (J. Pharmacol. Exp. Ther. (1996) 279 (2) 1000-1008), which were reported to form an immune complex, was allowed to bind to FcγR, dissociation from FcγR was observed to be slower than when Xolair alone was allowed to bind to FcγR. Furthermore, regarding clone 278-IgG1, which has been confirmed to form an immune complex using size exclusion (gel filtration) chromatography in Example 4, when a mixed solution of clone 278-IgG1 and an antigen (hIgE) was allowed to bind to FcγR, dissociation from FcγR became slower than when clone 278-IgG1 alone was allowed to bind to FcγR. Furthermore, when a mixed solution of GA2-IgG1 and hIgA was allowed to bind to FcγR, dissociation from FcγR also became slower than when GA2-IgG1 alone was allowed to bind to FcγR. In addition, when a mixed solution of Fv4-IgG1, PHX-IgG1, and antigen (IL6R) was allowed to bind with FcγR, dissociation from FcγR also became slower than when Fv4-IgG1 or PHX-IgG1 was allowed to bind to FcγR.

Accordingly, when the antigen or antigen-binding molecule comprised in an immune complex contains an FcγR-binding domain such as an immunoglobulin constant region, the immune complex binds to FcγR with avidity. Therefore, a method for assessing delay in dissociation from FcγR when a mixed solution of an antigen-binding molecule containing an FcγR-binding domain or such and its antigen is allowed to bind to FcγR, or when a mixed solution of an antigen containing an FcγR-binding domain and an antigen-binding molecule that binds to this antigen is allowed to bind to FcγR, as compared to when a molecule containing an FcγR-binding domain such as an immunoglobulin constant region is allowed to bind by itself to FcγR, was found to be an effective method for assessing formation of immune complexes comprising an antigen-binding molecule and an antigen. The above-mentioned assessment of immune complexes using dissociation from FcγR as the criteria was shown to be effective in the case of immune complexes formed by an antibody against an antigen bound by a plurality of monomers, and also in the case of immune complexes formed by a monomeric antigen and a plurality of antibodies binding to different epitopes.

[Example 16] Assessment of Binding of an Immune Complex with FcRn Using a Biacore™ Device 16-1. Regarding Binding of an Immune Complex with FcRn In a method for evaluating formation of immune complexes comprising an antigen-binding molecule and an antigen, when the antigen or antigen-binding molecule comprised in an immune complex contains an FcRn-binding domain such as an immunoglobulin constant region, the immune complex binds to FcRn with avidity. Therefore, formation of an immune complex comprising an FcRn-binding domain can be confirmed by a method that uses the property of stronger FcRn binding (in particular, the property of slower dissociation) than the antigen-binding molecule alone or the antigen alone (Journal of Immunology (2010) 184 (4) 1968-1976). However, in the methods reported so far, binding between FcRn and the FcRn-binding domain has been assessed under the condition of pH 6.0. This condition is not only different from the condition in vivo, but is also inappropriate for assessing samples of which avidity changes with the change in pH. Such condition may have been used because binding at pH 7.4 could not be assessed due to the very low avidity between human FcRn and human IgG1. Thus, whether assessment of immune complexes under a pH7.4 condition, which is closer to the in vivo condition, is possible was examined.

16-2. Preparation of Antibodies and Antigens for Assessment and FcRn

Fv4-F22 used in the assessment is a heavy-chain constant region variant of Fv4-IgG1 (described in Example 14). Xolair-F22 is a heavy-chain constant region variant of Xolair (Novartis). A DNA sequence encoding Fv4-F22 (heavy chain SEQ ID NO: 68, and light chain SEQ ID NO: 60) and a DNA sequence encoding Xolair-F22 (heavy chain SEQ ID NO: 69, and light chain SEQ ID NO: 70) were inserted into an animal cell expression plasmid by a method known to those skilled in the art. Antibody variants were expressed according to the above-described method (described in Example 1) using animal cells introduced with the plasmid, and their concentrations were determined after purification. Clone 278-IgG1 (prepared in Example 4), Fv4-IgG1 (prepared in Example 14), and PHX-IgG1 (prepared in Example 14) were prepared by the aforementioned methods.

The hIgE (hIgE(Asp6), prepared in Example 5) and IL6R (prepared in Reference Example 1) used for the assessment were prepared by the respective aforementioned methods.

Human FcRn and mouse FcRn were prepared by methods described in Reference Examples 3 and 4, respectively.

16-3. Assessment of Binding of an Immune Complex with Human FcRn

Binding of an antigen-antibody immune complex with human FcRn was assessed using Biacore™ T100 (GE Healthcare).

A solution containing an antibody alone or a mixed antibody-antigen solution shown in Table 13 was injected as an analyte onto Sensor chip CM4 (GE Healthcare) onto which a suitable amount of human FcRn (hFcRn) had been immobilized by an amine coupling method, and interaction was allowed to take place with hFcRn on the sensor chip. Subsequently, a 20 mM Tris-HCl, 150 mM NaCl, pH 9.0 or pH 9.5 solution was injected to regenerate the sensor chip. A 50 mmol/L Na-Phosphate (phosphoric acid), 150 mmol/L NaCl, 0.05% Tween® 20 polyethylene glycol sorbitan monolaurate, pH 7.4 buffer was used as the running buffer, and binding between the antigen-antibody immune complex and FcRn was measured at 25° C.

TABLE 13

| Sample | Antibody | Antigen |
| --- | --- | --- |
| Fv4-F22 | Fv4-F22 (10 µg/mL) | — |
| Fv4-F22 + IL6R | Fv4-F22 (10 µg/mL) | hsIL6R (2.5 µg/mL) |

TABLE 13-continued

| Sample | Antibody | Antigen |
|---|---|---|
| Xolair-F22 | Xolair-F22 (10 µg/mL) | — |
| Xolair-F22 + IgE | Xolair-F22 (10 µg/mL) | hIgE(Asp6) (11.2 µg/mL) |

Figure 25:
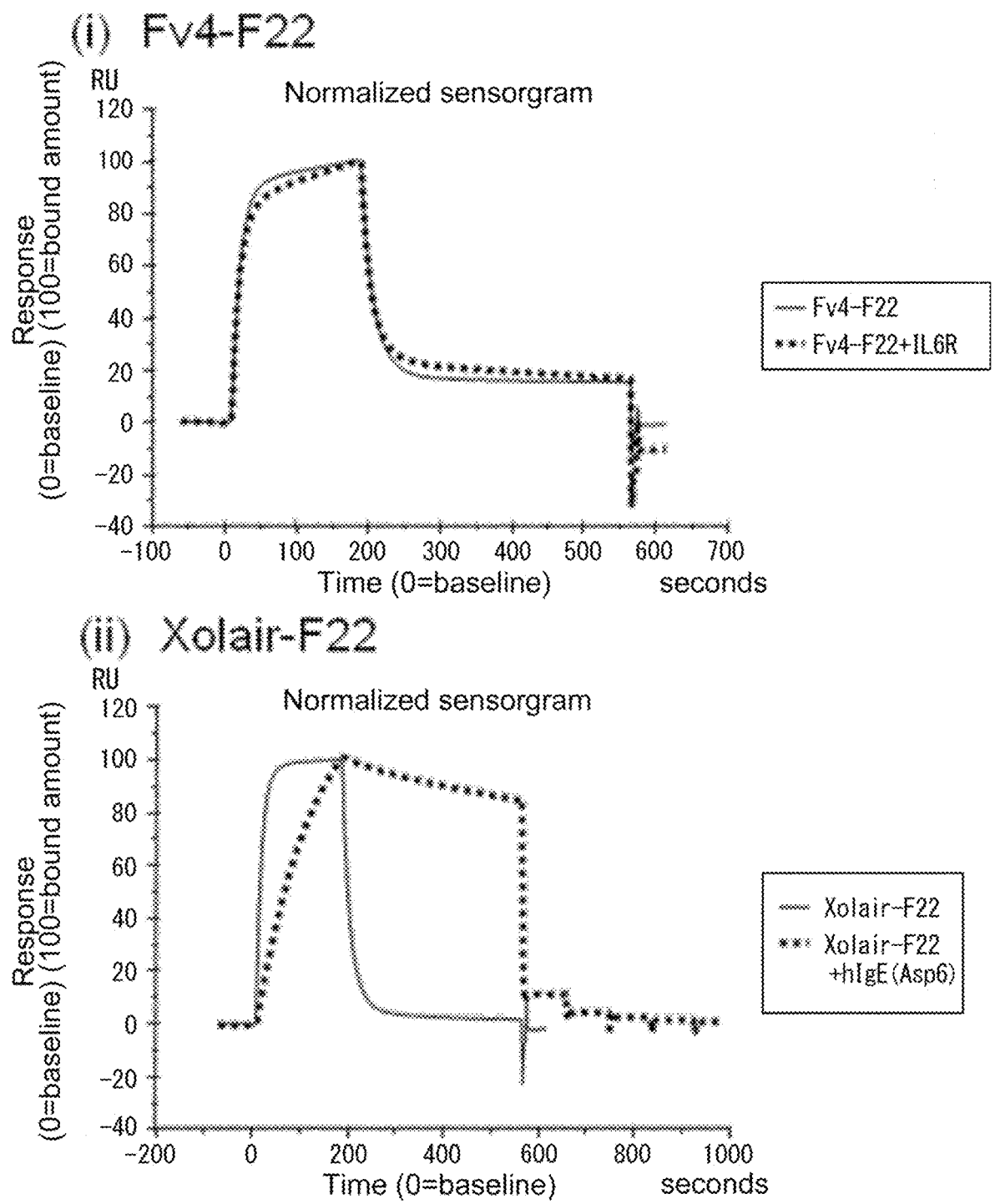
FIG. 25 is a set of two graphs, respectively designated (i) Fv4-F22 and (ii) Xolair-F22, illustrating Biacore™ sensorgrams obtained when a solution of antibody alone or a mixed antibody-antigen solution was applied to human FcRn. The solid line in each graph shows the sensorgram obtained when the solution of antibody alone was applied, and the dashed line in each graph shows the sensorgram obtained when the mixed antibody-antigen solution was applied.

The results of binding analyses, when an antibody-containing solution or a mixed antibody-antigen solution was allowed to react with hFcRn, are shown in FIG. 25. To focus on the dissociation, FIG. 25 shows sensorgrams in which the binding levels have been normalized to 100. While Fv4-F22 binds with IL6R, it does not form an immune complex containing a plurality of molecules that carry immunoglobulin constant regions; and thus no differences were observed between dissociation in the reaction of an antibody-containing solution and FcRn, and dissociation when a mixed antigen-antibody solution was used. Meanwhile, when a mixed solution of hIgE and Xolair-F22 carrying the variable region of Xolair which has been reported to form an immune complex with hIgE (J. Pharmacol. Exp. Ther. (1996) 279 (2) 1000-1008) was allowed to bind to FcRn, dissociation from FcRn was observed to be slower than the dissociation from FcRn when Xolair-F22 alone was bound to FcRn. The above showed that even under the condition of pH 7.4, hFcRn binding can be detected by using antibodies with enhanced binding to hFcRn. When the antigen-binding molecule or antigen comprised in an immune complex contains an FcRn-binding domain such as an immunoglobulin constant region, the immune complex binds more strongly to FcRn. Therefore, a method for assessing delay in dissociation from FcRn when a mixed solution of an antigen-binding molecule containing an FcRn-binding domain or such and its antigen is allowed to bind to FcRn, or when a mixed solution of an antigen containing an FcRn-binding domain and an antigen-binding molecule that binds to this antigen is allowed to bind to FcRn, as compared to when a molecule containing an FcRn-binding domain such as an immunoglobulin constant region or such is allowed to bind by itself to FcRn, was found to be an effective method for assessing formation of immune complexes comprising an antigen-binding molecule and an antigen.

16-4. Assessment of Binding of an Immune Complex with FcRn Using Biacore a Biacore™ Device In 16-3, FcRn binding of immune complexes containing variants of immunoglobulin constant regions with enhanced hFcRn binding was evaluated. Since native human IgG can bind more strongly to human FcRn than to mouse FcRn (Int. Immunol. (2001) 13 (12), 1551-1559), binding of an antibody containing a native human IgG constant region to mouse FcRn was assessed to examine if assessment of an immune complex formation is possible without modifying the immunoglobulin constant region.

Binding of an antigen-antibody immune complex with FcRn was assessed using Biacore™ T100 (GE Healthcare). A solution containing only antibodies or a mixed antibody-antigen solution as shown in Table 14 was injected as an analyte onto Sensor chip CM4 (GE Healthcare) that has been immobilized with a suitable amount of mouse FcRn (mFcRn) by an amine coupling method, and interaction was allowed to take place with mFcRn on the sensor chip. Subsequently, a 20 mM Tris-HCl, 150 mM NaCl, pH 9.0 or pH 9.5 solution was injected to regenerate the sensor chip. A 50 mmol/L Na-Phosphate (phosphoric acid), 150 mmol/L NaCl, 0.05% Tween® 20 polyethylene glycol sorbitan monolaurate, pH 7.4 buffer was used as the running buffer, and binding between the antigen-antibody immune complex and FcRn was measured at 25° C.

TABLE 14

| Sample name | Antibody | Antigen |
|---|---|---|
| Xolair | Xolair-IgG1 (50 µg/mL) | — |
| Xolair + hIgE(Asp6) | Xolair-IgG1 (50 µg/mL) | hIgE(Asp6) (56 µg/mL) |
| Clone 278 278 | Clone 278-IgG1 gG1 (50 µg/mL) | — |
| Clone 278 278 + hIgE(Asp6) | Clone 278-IgG1-F22 (50 µg/mL) | hIgE (Asp6) (56 µg/mL) |
| Fv4-IgG1 | Fv4-IgG1 (50 µg/mL) | — |
| Fv4-IgG1 + ILGR | Fv4-IgG1 (50 µg/mL) | hsIL6R (12.5 µg/mL) |
| PHX-IgG1 | PHX-IgG1 (50 µg/mL) | — |
| PHX-IgG1 + IL6R | PHX-IgG1 (50 µg/mL) | hsIL6R (12.5 µg/mL) |
| Pv4-IgG1 + PHX-IgG1 | PHX-IgG1 (25 µg/mL) + Fv4-IgG1 (25 µg/mL) | — |
| Fv4-IgG1 + PHX-IgG1 + IL6R | PHX-IgG1 (25 µg/mL) + Fv4-IgG1 (25 µg/mL) | hsIL6R (12.5 µg/mL) |

Figure 26:
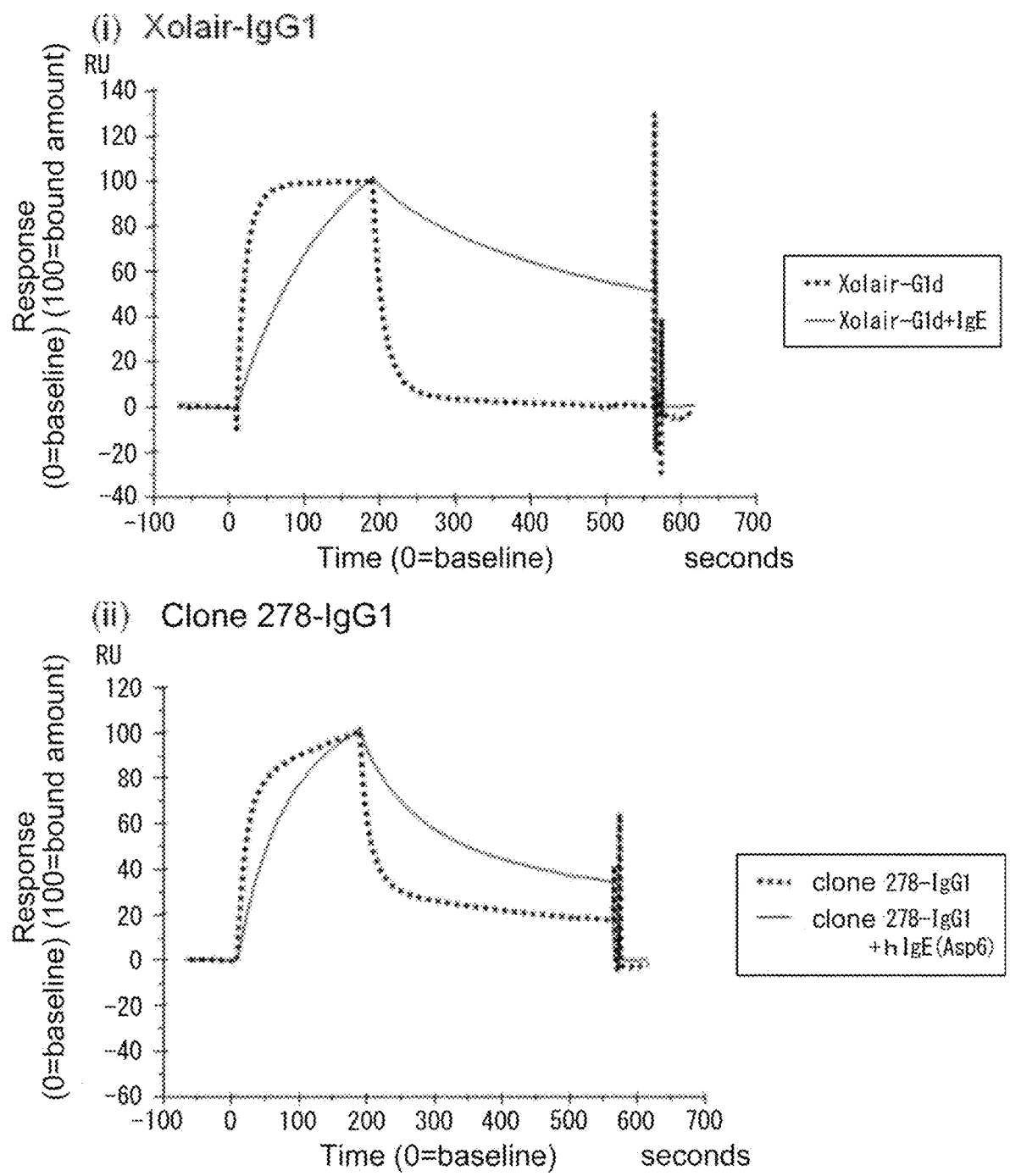
FIG. 26 is a set of two graphs, respectively designated (i) Xolair-IgG1 and (ii) clone 278-IgG1, illustrating Biacore™ sensorgrams obtained when a solution of antibody alone or a mixed antibody-antigen solution was applied to mouse FcRn. The dashed line in each graph shows the sensorgram obtained when the solution of antibody alone was applied, and the solid line in each graph shows the sensorgram obtained when the mixed antibody-antigen solution was applied.
Figure 27:
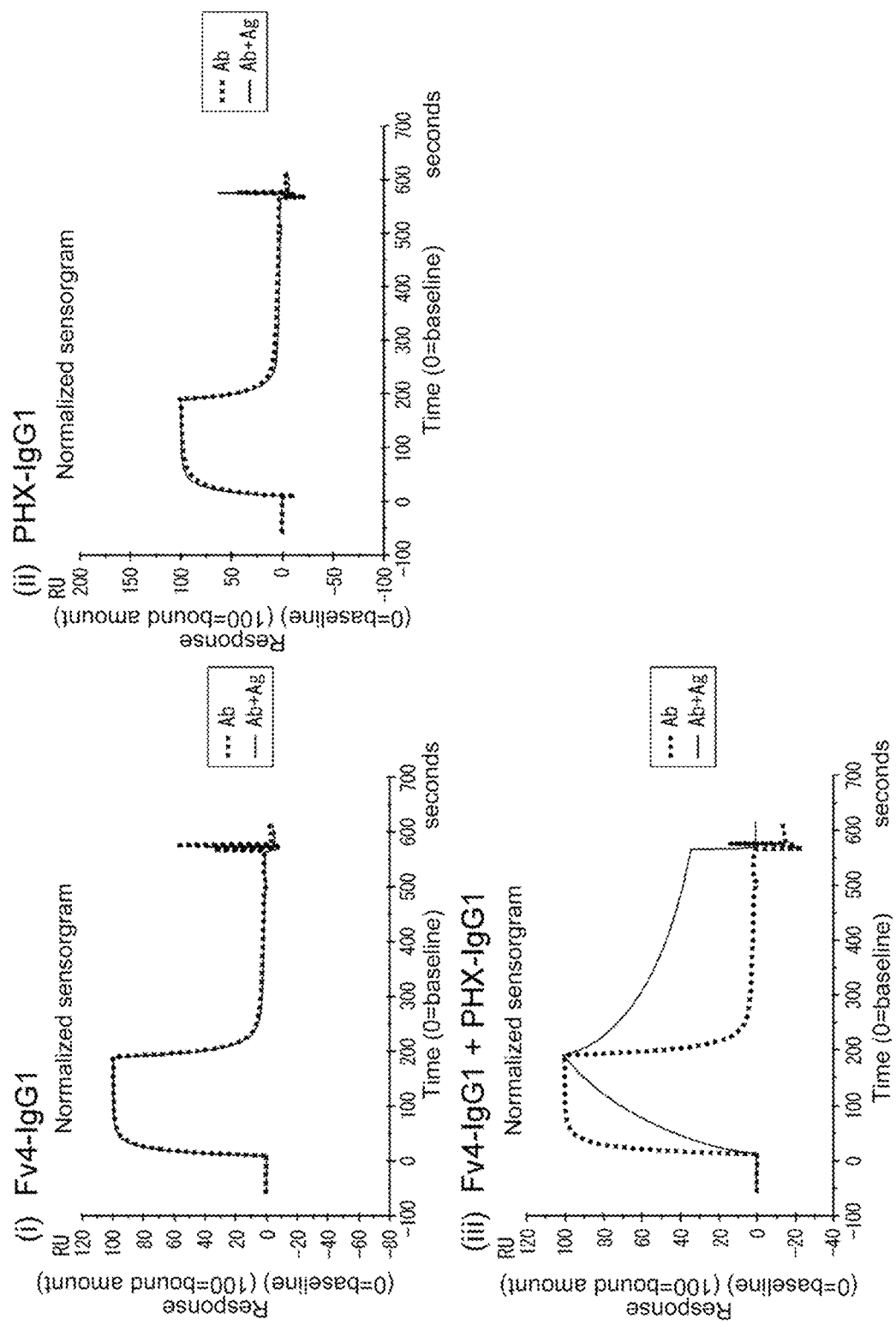
FIG. 27 is a set of three graphs, respectively designated (i) Fv4-IgG1, (ii) PHX-IgG1, and (iii) Fv4-IgG1+PHX-IgG1, illustrating Biacore™ sensorgrams obtained when a solution of antibody alone or a mixed antibody-antigen solution was applied to mouse FcRn. The dashed line in each graph shows the sensorgram obtained when the solution of antibody alone was applied, and the solid line in each graph shows the sensorgram obtained when the mixed antibody-antigen solution was applied.

The results of binding analyses, when a solution containing only antibodies or a mixed antibody-antigen solution was allowed to react with mFcRn, are shown in FIGS. 26 and 27. To focus on the dissociation, FIGS. 26 and 27 show sensorgrams in which the binding levels have been normalized to 100. When a mixed solution of an antigen (hIgE) and clone 278-IgG1, which has been confirmed to form an immune complex by size exclusion (gel filtration) chromatography in Example 4, was allowed to bind with mFcRn, dissociation from mFcRn also became slower than when clone 278-IgG1 alone was allowed to bind to mFcRn. Furthermore, when a mixed solution of hIgE and Xolair, which has been reported to form an immune complex (J. Pharmacol. Exp. Ther. (1996) 279 (2) 1000-1008), was allowed to bind with mFcRn, dissociation from mFcRn was observed to become slower than when Xolair alone was allowed to bind to mFcRn (FIG. 26). On the other hand, difference was not observed between dissociation from mFcRn when a solution containing Fv4-IgG1 was allowed to bind with mFcRn, and dissociation from mFcRn when a mixed solution of Fv4-IgG1 and IL6R was allowed to bind with mFcRn. Furthermore, difference was not observed between dissociation from mFcRn when a solution containing PHX-IgG1 was allowed to bind with mFcRn, and dissociation from mFcRn when a mixed solution of PHX-IgG1 and IL6R was allowed to bind with mFcRn (FIG. 27). This may be because the antigenic binding unit is one in IL6R when binding to a variable region contained in Fv4-IgG1; and when Fv4-IgG1 alone is used as the antigen-binding molecule for IL6R, an immune complex comprising two or more Fv4-IgG1 molecules for one molecule of IL6R is not formed. Since the antigenic binding unit is also one in IL6R when binding to a variable region in PHX-IgG1, there is only one epitope in IL6R; and therefore it is thought that when PHX-IgG1 alone is used as an antigen-binding molecule targeting IL6R, an immune complex comprising two or more PHX-IgG1 molecules for one molecule of IL6R is not formed. Herein, when a mixed solution of IL6R, and Fv4-IgG1 and PHX-IgG1, which are found in Example 14 to have epitopes that are different from each other, was allowed to bind to mFcRn, dissociation from mFcRn became slower than when a solution containing the Fv4-IgG1 antibody and the PHX-IgG1 antibody (only antibodies) was allowed to bind with mFcRn. Such phenomenon of slower dissociation is similar to the phenomenon observed with clone 278. This indicates that when a single type of antigen-binding molecule is used for the antigen-binding molecule that binds to a target antigen, even if the antigenic binding unit is one, the antigenic binding unit of the antigen can be changed to two or more by using a combination of antibody-binding molecules that have epitopes different from each other as antigen-binding molecules targeting the antigen; and as a result, an immune complex containing two or more antigen-binding molecules can be formed.

The above showed that by using mouse FcRn, even a native human IgG1 molecule without modifications that would affect interaction with FcRn can be assessed for FcRn binding under the condition of pH 7.4 which is the same as the in vivo condition. Furthermore, when an antigen-binding molecule or an antigen contains an FcRn-binding domain such as an immunoglobulin constant region, the immune complex binds strongly with FcRn; therefore, immune complex formation could be confirmed by evaluating delay in dissociation from FcRn of an immune complex comprising a plurality of molecules containing an FcRn-binding domain such as an immunoglobulin constant region as compared to dissociation from FcRn of a molecule containing an FcRn-binding domain of an immunoglobulin constant region. It was confirmed that the above-mentioned assessment of immune complex formation using FcRn can be used to verify the formation of both an immune complex formed from an antigen comprising a plurality of bound monomers and an antibody that binds to this antigen, and an immune complex formed from a monomeric antigen and a plurality of antibodies having different binding epitopes from each other that bind to this antigen.

[Reference Example 1] Preparation of Soluble Human IL-6 Receptor (hsIL-6R)

A recombinant form of human IL-6 receptor, which is an antigen, was prepared as follows. A CHO line that constantly expresses a soluble human IL-6 receptor (hereinafter referred to as hsIL-6R) composed of the amino acid sequence from the first to 357th amino acid from the N terminus as reported in J. Immunol. (1994) 152, 4958-4968 was constructed using a method known to those skilled in the art. hsIL-6R was expressed by culturing this CHO line. hsIL-6R was purified from the culture supernatant of the resulting CHO line by a two-step process involving the Blue Sepharose 6 FF column chromatography and gel filtration column chromatography. The fraction that eluted as the main peak in the final step was used as the final purified product.

[Reference Example 2] Preparation of Histidine-Tagged Human FcγRIIIaV

Histidine-tagged human FcγRIIIaV was prepared by the following method. First, a gene of the extracellular domain of FcγR was synthesized by a method well known to those skilled in the art. At that time, the sequence of each FcγR was produced based on the information registered at NCBI. Specifically, FcγRIIIa was produced based on the sequence of NCBI Accession No. NM_001127593.1, and a His tag was attached to the C terminus. Moreover, polymorphism is known for FcγRIIIa; however, production was carried out by referring to J. Clin. Invest., 1997, 100 (5): 1059-1070 for FcγRIIIa.

The obtained gene fragments were inserted into an animal cell expression vector, and expression vectors were produced. The produced expression vectors were introduced transiently into human embryonic kidney cancer cell line-derived FreeStyle293 cells (Invitrogen) to express the proteins of interest. Cells were cultured, and after collection of the obtained culture supernatant, this was passed through a 0.22 μm filter to obtain the culture supernatant. In principle, the obtained culture supematants were purified in the following four steps. The steps carried out were, cation exchange column chromatography (SP Sepharose FF) in step 1, affinity column chromatography (HisTrap HP) for His tag in step 2, gel filtration column chromatography (Superdex200) in step 3, and aseptic chromatography in step 4. The purified proteins were subjected to absorbance measurements at 280 nm using a spectrophotometer; and from the obtained values, the concentrations of the purified proteins were calculated using the absorption coefficient calculated using methods such as PACE (Protein Science 1995; 4: 2411-2423).

[Reference Example 3] Preparation of Soluble Human FcRn (hFcRn)

Human FcRn forms a complex with β2-microglobulin. Oligo-DNA primers were designed based on the reported human FcRn gene sequence (J Exp Med. 1994 Dec. 1; 180(6): 2377-81). A cDNA was amplified by PCR from a human cDNA (Human Placenta Marathon-Ready cDNA, Clontech) using the designed primers. The amplified cDNA encoding the extracellular domain containing the signal sequence (Met1-Leu290) was inserted into an animal cell expression vector. Similarly, primers were designed for β2-microglobulin based on the reported human β2-microglobulin sequence, and the cDNA was amplified by PCR. The cDNA fragment of Met1-Met119 containing a signal sequence was amplified and inserted into an animal cell expression vector.

Soluble human FcRn (called hFcRn) was prepared according to the procedure below. The vector for expressing human FcRn (SEQ ID NO: 71) and the vector for expressing β2-microglobulin (SEQ ID NO: 72) were transduced into HEK293H cells (Invitrogen) by the lipofection method using PEI (Polyscience). The transduced cells were cultured, and the culture solution was collected. Human FcRn was purified from the collected culture by each of the chromatographic methods, IgG Sepharose 6 Fast Flow (Amersham Biosciences) and HiTrap Q HP (GE Healthcare) (J Immunol. 2002 Nov. 1; 169(9): 5171-80).

[Reference Example 4] Preparation of Soluble Mouse FcRn (mFcRn)

Soluble mouse FcRn was prepared in a similar manner to soluble human FcRn. First, a gene encoding the extracellular domain of mouse FcRn and a gene encoding mouse β2-microglobulin were synthesized by methods known to those skilled in the art. For this operation, mouse FcRn and mouse β2-microglobulin sequences were produced based on the information registered at NCBI. Specifically, for mouse FcRn, a gene fragment encoding the amino acids of positions 1 to 290 containing the signal sequence was produced as the extracellular domain based on the sequence of NCBI accession #NP_034319.2 (SEQ ID NO: 73). Furthermore, for β2-microglobulin, a gene fragment was produced based on the sequence of NCBI accession #NP_033865 (SEQ ID NO: 74). An expression vector was produced by inserting the obtained gene fragments into an animal cell expression vector. The produced expression vector was introduced transiently into human embryonic kidney carcinoma cell-derived FreeStyle 293 cells (Invitrogen) to express the protein of interest. The transduced cells were cultured, and the culture solution was collected. Mouse FcRn was purified from the collected culture by each of the chromatographic methods, IgG Sepharose 6 Fast Flow (Amersham Biosciences) and Superdex 200 (GE Healthcare).

[Reference Example 5] Production of an Antigen-Binding Molecule with Higher FcγR-Binding Activity than that of the Native Human IgG Fc Region, and Enhanced Human FcRn-Binding Activity Under an Acidic pH Condition (5-1) Production of an Anti-Human IL-6 Receptor Antibody with Enhanced Binding to Mouse FcγR VH3-IgG1-F1087 (SEQ ID NO: 75), which is formed by substituting Asp for Lys at position 326 (EU numbering) in VH3-IgG1, and VH3-IgG1-F1182 (SEQ ID NO: 76), which is formed by substituting Asp for Ser at position 239, and Glu for Ile at position 332 (EU numbering) in VH3-IgG1, were produced as antigen-binding molecules with enhanced binding to mouse FcγR. Fv4-IgG1-F1087 containing VH3-IgG1-F1087 as the heavy chain and VL3-CK (SEQ ID NO: 77) as the light chain, and Fv4-IgG1-F1182 containing VH3-IgG1-F1182 as the heavy chain and VL3-CK as the light chain were produced using the method of Reference Example 2.

(5-2) Confirmation of Mouse FcγR-Binding Activity

VH3/L (WT)-IgG1-F1087 and VH3/L (WT)-IgG1-F1182, which contain VH3-IgG1-F1087 and VH3-IgG1-F1182 respectively as the heavy chain, and L (WT)-CK (SEQ ID NO: 78) as the light chain were produced. The mouse FcγR-binding activities of these antibodies and VH3/L (WT)-IgG1-F1022 were assessed, and the results are shown in Table 15. The number of folds enhanced in the mouse FcγR-binding activity of each of the variants compared to that of IgG1 before modification is shown in Table 16.

TABLE 15

| Name | KD (M) | | | |
|---|---|---|---|---|
| of variant | mFc γ RI | mFc γ RIIb | mFc γ RIII | mFc γ RIV |
| IgG1 | 5.3E−08 | 9.8E−07 | 2.4E−06 | 8.6E−08 |
| F1022 | 7.6E−09 | 1.0E−08 | 5.5E−09 | 1.4E−07 |
| F1087 | 2.9E−08 | 5.6E−08 | 5.2E−08 | 3.3E−07 |
| F1182 | 2.4E−09 | 1.1E−07 | 4.8E−07 | 5.3E−10 |

TABLE 16

| Name of | IgG1 binding ratio | | | |
|---|---|---|---|---|
| variant | mFc γ RI | mFc γ RIIb | mFc γ RIII | mFc γ RIV |
| IgG1 | 1.0 | 1.0 | 1.0 | 1.0 |
| F1022 | 7.0 | 93.6 | 440.5 | 0.6 |
| F1087 | 1.8 | 17.5 | 46.2 | 0.3 |
| F1182 | 22.1 | 9.1 | 5.0 | 162.3 |

INDUSTRIAL APPLICABILITY

The antigen-binding molecules of the present invention enable acceleration of elimination of antigens with two or more antigenic binding units from the plasma, by being equipped with the feature of forming large immune complexes comprising antigens with two or more antigenic binding units (epitopes) and two or more antigen-binding molecules (for example, antibodies). Antigen-binding molecules of the present invention also enable further acceleration of elimination of the antigens by being equipped with an ion-dependent antigen-binding activity in addition to the above-mentioned features. By being equipped with such technical features, antigen-binding molecules of the present invention become very useful as pharmaceuticals for treating diseases or symptoms (such as cancer and inflammatory disease).

The invention claimed is:

1. A method of reducing the amount of an antigen in the blood of a subject, the method comprising identifying a subject as being in need of a reduction in the amount of the antigen in the subject's blood; and administering an antibody to the subject in a manner that introduces the antibody into the subject's blood, wherein the antibody comprises (i) an Fc region, and (ii) two antigen-binding domains, including a first antigen-binding domain that binds to a first epitope on the antigen and a second antigen-binding domain that binds to a second epitope on the antigen, wherein (a) the first and second epitopes may be identical or different, (b) at least one of the antigen-binding domains is as described in one or both of (1) and (2) below:

(1) the antigen-binding domain:

comprises a light chain variable region comprising a histidine at one or more of Kabat numbering positions 24, 27, 28, 31, 32, 34, 50, 51, 52, 53, 54, 55, 56, 89, 90, 91, 92, 93, 94, and 95A; and has an antigen-binding activity that varies depending on pH and has a KD (pH 5.8)/KD (pH 7.4) value, defined as the ratio of (KD for the antigen at pH 5.8) to (KD for the antigen at pH 7.4), of 2 or higher, when the KD (pH 5.8) and KD (pH 7.4) values are determined using a surface plasmon resonance technique in which the antigen is immobilized, the antibody serves as analyte, and the following conditions are used: 37° C., 0.05% polyethylene glycol sorbitan monolaurate, 20 mmol/L N-(2-acetamido)-2-aminoethanesulfonic acid (ACES), 150 mmol/L NaCl, 1.2 mM $CaCl_2$), at either pH 5.8 or pH 7.4;

(2) the antigen-binding domain:

comprises a light chain variable region comprising a metal-chelating amino acid residue at one or more of Kabat numbering positions 30, 31, 32, 50, and 92; and has an antigen-binding activity that varies depending on calcium ion concentration and has a KD (3 μM Ca)/KD (1.2 mM Ca) value, defined as the ratio of (KD for the antigen at a calcium ion concentration of 3 μM) to (KD for the antigen at a calcium ion concentration of 1.2 mM), of 2 or higher, when the KD (3 μM Ca) and KD (1.2 mM Ca) values are determined using a surface plasmon resonance technique in which the antibody is immobilized, the antigen serves as analyte, and the following conditions are used: 37° C., 0.05% polyethylene glycol sorbitan monolaurate, 20 mmol/L ACES, 150 mmol/L NaCl, pH 7.4, and either 1.2 mM $CaCl_2$) or 3 μM $CaCl_2$), (c) the antibody forms an immune complex comprising two or more copies of the antibody and two or more copies of the antigen, and (d) the administration results in a reduction in the amount of the antigen in the subject's blood.

2. The method of claim 1, wherein the antigen-binding activity of at least one of the antigen-binding domains varies depending on calcium ion concentration and has a KD (3 μM Ca)/KD (1.2 mM Ca) value of 2 or higher.

3. The method of claim 1, wherein the antigen-binding activity of at least one of the antigen-binding domains varies with pH and has a KD (pH 5.8)/KD (pH 7.4) value of 2 or higher.

4. The method of claim 1, wherein the antigen is a multimer comprising two or more subunits that may be the same or different.

5. The method of claim 4, wherein each of at least two of the subunits comprises at least one of the epitopes.

6. The method of claim 4, wherein the antigen is any one of GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (myostatin), GDF-9, GDF-15 (MIC-1), TNF, TNF-alphabeta, TNF-beta2, TNFSF10 (TRAIL, Apo-2 ligand, TL2), TNFSF11 (TRANCE/RANK ligand, ODF, OPG ligand), TNFSF12 (TWEAK, Apo-3 ligand, DR3 ligand), TNFSF13 (APRIL, TALL2), TNFSF13B (BAFF, BLYS, TALL1, THANK, TNFSF20), TNFSF14 (LIGHT, HVEM ligand, LTg), TNFSF15 (TL1A/VEGI), TNFSF18 (GITR ligand, AITR ligand, TL6), TNFSF1A (TNF-a, Cachectin, DIF, TNFSF2), TNFSF1B (TNF-b, LTa, TNFSF1), TNFSF3 (LTb, TNFC, p33), TNFSF4 (OX40 ligand, gp34, TXGP1), TNFSF5 (CD40 ligand, CD154, gp39, HIGM1, IMD3, TRAP), TNFSF6 (Fas ligand, Apo-1 ligand, APT1 ligand), TNFSF7 (CD27 ligand, CD70), TNFSF8 (CD30 ligand, CD153), TNFSF9 (4-1BB ligand, CD137 ligand), VEGF, IgE, IgA, IgG, IgM, RANKL, TGF-alpha, TGF-beta, TGF-beta Pan Specific, and IL-8.

7. The method of claim 1, wherein the antigen is a monomer comprising the first and second epitopes.

8. The method of claim 1, wherein the antibody is a bispecific or biparatopic antibody.

9. The method of claim 1, wherein the Fc region of (i) comprises the sequence of any one of SEQ ID NOs: 13, 14, 15, and 16.

10. The method of claim 1, wherein the Fc region of (i) has, at a pH between 4 and 6.5, an FcRn-binding activity greater than that of a second Fc region at the same pH, wherein the amino acid sequence of the second Fc region is any one of SEQ ID NOs: 13, 14, 15, and 16.

11. The method of claim 10, wherein the Fc region of (i) comprises the amino acid sequence of any one of SEQ ID NOs: 13, 14, 15, and 16, except with an amino acid substitution at one or more positions selected from positions 238, 244, 245, 249, 250, 251, 252, 253, 254, 255, 256, 257, 258, 260, 262, 265, 270, 272, 279, 283, 285, 286, 288, 293, 303, 305, 307, 308, 309, 311, 312, 314, 316, 317, 318, 332, 339, 340, 341, 343, 356, 360, 362, 375, 376, 377, 378, 380, 382, 385, 386, 387, 388, 389, 400, 413, 415, 423, 424, 427, 428, 430, 431, 433, 434, 435, 436, 438, 439, 440, 442, and 447 (EU numbering).

12. The method of claim 11, wherein the Fc region of (i) comprises, at one or more of the following positions, the indicated amino acid (all positions by EU numbering):

Leu at position 238;
Leu at position 244;
Arg at position 245;
Pro at position 249;
Gln or Glu at position 250;
Arg, Asp, Glu, or Leu at position 251;
Phe, Ser, Thr, or Tyr at position 252;
Thr at position 254;
Gly, Ile, or Leu at position 255;
Ala, Arg, Asn, Asp, Gln, Glu, or Pro at position 256;
Ala, Ile, Met, Asn, Ser, or Val at position 257;
Asp at position 258;
Ser at position 260;
Leu at position 262;
Lys at position 270;
Leu or Arg at position 272;
Ala, Asp, Gly, His, Met, Asn, Gln, Arg, Ser, Thr, Trp, or Tyr at position 279;
Ala, Asp, Phe, Gly, His, Ile, Lys, Leu, Asn, Pro, Gln, Arg, Ser, Thr, Trp, or Tyr at position 283;
Asn at position 285;
Phe at position 286;
Asn or Pro at position 288;
Val at position 293;
Ala, Glu, Gln, or Met at position 307;
Ile, Pro, or Thr at position 308;
Ala, Glu, Ile, Lys, Leu, Met, Ser, Val, or Trp at position 311;
Pro at position 309;
Ala or Pro at position 312;
Ala at position 314;
Lys at position 316;
Pro at position 317;
Asn or Thr at position 318;
Phe, His, Lys, Leu, Met, Arg, Ser, or Trp at position 332;
Asn, Thr, or Trp at position 339;
Pro at position 341;
Glu, His, Lys, Gln, Arg, Thr, or Tyr at position 343;
Arg at position 375;
Gly, Ile, Met, Pro, Thr, or Val at position 376;
Lys at position 377;
Asp, Asn, or Val at position 378;
Ala, Asn, Ser, or Thr at position 380;
Phe, His, Ile, Lys, Leu, Met, Asn, Gln, Arg, Ser, Thr, Val, Trp, or Tyr at position 382;
Ala, Arg, Asp, His, Lys, Ser, or Thr at position 385;
Arg, Asp, Ile, Lys, Met, Pro, Ser, or Thr at position 386;
Ala, Arg, His, Ser, or Thr at position 387;
Pro or Ser at position 389;
Asn at position 423;
Asn at position 427;
Leu, Phe, Ser, or Thr at position 428;
Ala, Phe, Gly, His, Ile, Lys, Leu, Met, Asn, Gln, Arg, Ser, Thr, Val, or Tyr at position 430;
His or Asn at position 431;
Arg, Gln, Ile, Lys, Pro, or Ser at position 433;
Ala, Gly, His, Phe, Ser, Trp, or Tyr at position 434;
Arg, Asn, His, Ile, Leu, Lys, Met, or Thr at position 436;
Lys, Leu, Thr, or Trp at position 438;
Lys at position 440; and
Lys at position 442.

13. The method of claim 1, wherein the Fc region of (i) has, at pH 7.4, an FcRn-binding activity greater than that of a second Fc region at the same pH, wherein the amino acid sequence of the second Fc region is any one of SEQ ID NOs: 13, 14, 15, and 16.

14. The method of claim 13, wherein the Fc region of (i) comprises the amino acid sequence of any one of SEQ ID NOs: 13, 14, 15, and 16, except with an amino acid substitution at one or more positions selected from positions 237, 248, 250, 252, 255, 257, 258, 265, 286, 289, 297, 298, 303, 305, 307, 308, 309, 311, 312, 314, 315, 317, 332, 334, 360, 376, 382, 384, 387, 389, 424, 428, and 436 (EU numbering).

15. The method of claim 14, wherein the Fc region of (i) comprises, at one or more of the following positions, the indicated amino acid (all positions by EU numbering):
Met at position 237;
Ile at position 248;
Ala, Phe, Ile, Met, Ser, Val, Trp, or Tyr at position 250;
Trp at position 252;
Glu at position 255;
Gly, Leu, or Thr or Val at position 257;
His at position 258;
Ala at position 265;
Ala or Glu at position 286;
His at position 289;
Ala at position 297;
Ala at position 303;
Ala at position 305;
Asp, Phe, Gly, His, Ile, Lys, Leu, Asn, Pro, Arg, Ser, Val, Trp, or Tyr at position 307;
Ala, Phe, Leu, Met, or Gln at position 308;
Ala, Asp, Glu, or Arg at position 309;
His at position 311;
His at position 312;
Lys or Arg at position 314;
Ala, Asp, or His at position 315;
Ala at position 317;
Val at position 332;
Leu at position 334;
His at position 360;
Ala at position 376;
Ala at position 382;
Ala at position 384;
Glu at position 387;
Ala at position 389;
Ala at position 424;
Ala, Asp, Gly, His, Ile, Lys, Asn, Pro, Gln, Val, Trp, or Tyr at position 428; and
Phe or Val at position 436.

16. The method of claim 1, wherein the Fc region of (i) has a higher Fcγ receptor-binding activity at pH 7.4 than does the Fc region of a native human IgG at pH 7.4.

17. The method of claim 16, wherein the amino acid sequence of the Fc region of (i) differs from the amino acid sequence of the Fc region of the native human IgG at one or more positions, including at least one of the following positions (EU numbering): 221, 222, 223, 224, 225, 227, 228, 230, 231, 232, 233, 234, 235, 236, 237, 238, 239, 240, 241, 243, 244, 245, 246, 247, 249, 250, 251, 254, 255, 256, 258, 260, 262, 263, 264, 265, 266, 267, 268, 269, 270, 271, 272, 273, 274, 275, 276, 278, 279, 280, 281, 282, 283, 284, 285, 286, 288, 290, 291, 292, 293, 294, 295, 296, 297, 298, 299, 300, 301, 302, 303, 304, 305, 311, 313, 315, 317, 318, 320, 322, 323, 324, 325, 326, 327, 328, 329, 330, 331, 332, 333, 334, 335, 336, 337, 339, 376, 377, 378, 379, 380, 382, 385, 392, 396, 421, 427, 428, 429, 434, 436, and 440.

18. The method of claim 17, wherein the Fc region of (i) comprises, at one or more of the following positions, the indicated amino acid (all positions by EU numbering):
Lys or Tyr at position 221;
Phe, Trp, Glu, or Tyr at position 222;
Phe, Trp, Glu, or Lys at position 223;
Phe, Trp, Glu, or Tyr at position 224;
Glu, Lys, or Trp at position 225;
Glu, Gly, Lys, or Tyr at position 227;
Glu, Gly, Lys, or Tyr at position 228;
Ala, Glu, Gly, or Tyr at position 230;
Glu, Gly, Lys, Pro, or Tyr at position 231;
Glu, Gly, Lys, or Tyr at position 232;
Ala, Asp, Phe, Gly, His, Ile, Lys, Leu, Met, Asn, Gln, Arg, Ser, Thr, Val, Trp, or Tyr at position 233;
Ala, Asp, Glu, Phe, Gly, His, Ile, Lys, Met, Asn, Pro, Gln, Arg, Ser, Thr, Val, Trp, or Tyr at position 234;
Ala, Asp, Glu, Phe, Gly, His, Ile, Lys, Met, Asn, Pro, Gln, Arg, Ser, Thr, Val, Trp, or Tyr at position 235;
Ala, Asp, Glu, Phe, His, Ile, Lys, Leu, Met, Asn, Pro, Gln, Arg, Ser, Thr, Val, Trp, or Tyr at position 236;
Asp, Glu, Phe, His, Ile, Lys, Leu, Met, Asn, Pro, Gln, Arg, Ser, Thr, Val, Trp, or Tyr at position 237;
Asp, Glu, Phe, Gly, His, Ile, Lys, Leu, Met, Asn, Gln, Arg, Ser, Thr, Val, Trp, or Tyr at position 238;
Asp, Glu, Phe, Gly, His, Ile, Lys, Leu, Met, Asn, Pro, Gln, Arg, Thr, Val, Trp, or Tyr at position 239;
Ala, Ile, Met, or Thr at position 240;
Asp, Glu, Leu, Arg, Trp, or Tyr at position 241;
Leu, Glu, Leu, Gln, Arg, Trp, or Tyr at position 243;
His at position 244;
Ala at position 245;
Asp, Glu, His, or Tyr at position 246;
Ala, Phe, Gly, His, Ile, Leu, Met, Thr, Val, or Tyr at position 247;
Glu, His, Gln, or Tyr at position 249;
Glu or Gln at position 250;
Phe at position 251;
Phe, Met, or Tyr at position 254;
Glu, Leu, or Tyr at position 255;
Ala, Met, or Pro at position 256;
Asp, Glu, His, Ser, or Tyr at position 258;
Asp, Glu, His, or Tyr at position 260;
Ala, Glu, Phe, Ile, or Thr at position 262;
Ala, Ile, Met, or Thr at position 263;
Asp, Glu, Phe, Gly, His, Ile, Lys, Leu, Met, Asn, Pro, Gln, Arg, Ser, Thr, Trp, or Tyr at position 264;
Ala, Leu, Phe, Gly, His, Ile, Lys, Leu, Met, Asn, Pro, Gln, Arg, Ser, Thr, Val, Trp, or Tyr at position 265;
Ala, Ile, Met, or Thr at position 266;
Asp, Glu, Phe, His, Ile, Lys, Leu, Met, Asn, Pro, Gln, Arg, Thr, Val, Trp, or Tyr at position 267;
Asp, Glu, Phe, Gly, Ile, Lys, Leu, Met, Pro, Gln, Arg, Thr, Val, or Trp at position 268;
Phe, Gly, His, Ile, Lys, Leu, Met, Asn, Pro, Arg, Ser, Thr, Val, Trp, or Tyr at position 269;
Glu, Phe, Gly, His, Ile, Leu, Met, Pro, Gln, Arg, Ser, Thr, Trp, or Tyr at position 270;
Ala, Asp, Glu, Phe, Gly, His, Ile, Lys, Leu, Met, Asn, Gln, Arg, Ser, Thr, Val, Trp, or Tyr at position 271;
Asp, Phe, Gly, His, Ile, Lys, Leu, Met, Pro, Arg, Ser, Thr, Val, Trp, or Tyr at position 272;
Phe or Ile at position 273;
Asp, Glu, Phe, Gly, His, Ile, Leu, Met, Asn, Pro, Arg, Ser, Thr, Val, Trp, or Tyr at position 274;
Leu or Trp at position 275;
Asp, Glu, Phe, Gly, His, Ile, Leu, Met, Pro, Arg, Ser, Val, Trp, or Tyr at position 276;
Asp, Glu, Gly, His, Ile, Lys, Leu, Met, Asn, Pro, Gln, Arg, Ser, Thr, Val, or Trp at position 278;
Ala at position 279;
Ala, Gly, His, Lys, Leu, Pro, Gln, Trp, or Tyr at position 280;
Asp, Lys, Pro, or Tyr at position 281;
Glu, Gly, Lys, Pro, or Tyr at position 282;
Ala, Gly, His, Ile, Lys, Leu, Met, Pro, Arg, or Tyr at position 283;

Asp, Glu, Leu, Asn, Thr, or Tyr at position 284;
Asp, Glu, Lys, Gln, Trp, or Tyr at position 285;
Glu, Gly, Pro, or Tyr at position 286;
Asn, Asp, Glu, or Tyr at position 288;
Asp, Gly, His, Leu, Asn, Ser, Thr, Trp, or Tyr at position 290;
Asp, Glu, Gly, His, Ile, Gln, or Thr at position 291;
Ala, Asp, Glu, Pro, Thr, or Tyr at position 292;
Phe, Gly, His, Ile, Leu, Met, Asn, Pro, Arg, Ser, Thr, Val, Trp, or Tyr at position 293;
Phe, Gly, His, Ile, Lys, Leu, Met, Asn, Pro, Arg, Ser, Thr, Val, Trp, or Tyr at position 294;
Asp, Glu, Phe, Gly, His, Ile, Lys, Met, Asn, Pro, Arg, Ser, Thr, Val, Trp, or Tyr at position 295;
Ala, Asp, Glu, Gly, His, Ile, Lys, Leu, Met, Asn, Gln, Arg, Ser, Thr, or Val at position 296;
Asp, Glu, Phe, Gly, His, Ile, Lys, Leu, Met, Pro, Gln, Arg, Ser, Thr, Val, Trp, or Tyr at position 297;
Ala, Asp, Glu, Phe, His, Ile, Lys, Met, Asn, Gln, Arg, Thr, Val, Trp, or Tyr at position 298;
Ala, Asp, Glu, Phe, Gly, His, Ile, Lys, Leu, Met, Asn, Pro, Gln, Arg, Ser, Val, Trp, or Tyr at position 299;
Ala, Asp, Glu, Gly, His, Ile, Lys, Leu, Met, Asn, Pro, Gln, Arg, Ser, Thr, Val, or Trp at position 300;
Asp, Glu, His, or Tyr at position 301;
Ile at position 302;
Asp, Gly, or Tyr at position 303;
Asp, His, Leu, Asn, or Thr at position 304;
Glu, Ile, Thr, or Tyr at position 305;
Ala, Asp, Asn, Thr, Val, or Tyr at position 311;
Phe at position 313;
Leu at position 315;
Glu or Gln at position 317;
His, Leu, Asn, Pro, Gln, Arg, Thr, Val, or Tyr at position 318;
Asp, Phe, Gly, His, Ile, Leu, Asn, Pro, Ser, Thr, Val, Trp, or Tyr at position 320;
Ala, Asp, Phe, Gly, His, Ile, Pro, Ser, Thr, Val, Trp, or Tyr at position 322;
Ile at position 323;
Asp, Phe, Gly, His, Ile, Leu, Met, Pro, Arg, Thr, Val, Trp, or Tyr at position 324;
Ala, Asp, Glu, Phe, Gly, His, Ile, Lys, Leu, Met, Pro, Gln, Arg, Ser, Thr, Val, Trp, or Tyr at position 325;
Ala, Asp, Glu, Gly, His, Leu, Met, Asn, Pro, Gln, Ser, Thr, Val, Trp, or Tyr at position 326;
Ala, Asp, Glu, Phe, Gly, His, Ile, Lys, Leu, Met, Asn, Pro, Arg, Thr, Val, Trp, or Tyr at position 327;
Ala, Asp, Glu, Phe, Gly, His, Ile, Lys, Met, Asn, Pro, Gln, Arg, Ser, Thr, Val, Trp, or Tyr at position 328;
Asp, Glu, Phe, Gly, His, Ile, Lys, Leu, Met, Asn, Gln, Arg, Ser, Thr, Val, Trp, or Tyr at position 329;
Cys, Glu, Phe, Gly, His, Ile, Lys, Leu, Met, Asn, Pro, Arg, Ser, Thr, Val, Trp, or Tyr at position 330;
Asp, Phe, His, Ile, Leu, Met, Gln, Arg, Thr, Val, Trp, or Tyr at position 331;
Ala, Asp, Glu, Phe, Gly, His, Lys, Leu, Met, Asn, Pro, Gln, Arg, Ser, Thr, Val, Trp, or Tyr at position 332;
Ala, Asp, Glu, Phe, Gly, His, Ile, Leu, Met, Pro, Ser, Thr, Val, or Tyr at position 333;
Ala, Glu, Phe, Ile, Leu, Pro, or Thr at position 334;
Asp, Phe, Gly, His, Ile, Leu, Met, Asn, Pro, Arg, Ser, Val, Trp, or Tyr at position 335;
Glu, Lys, or Tyr at position 336;
Glu, His, or Asn at position 337;
Asp, Phe, Gly, Ile, Lys, Met, Asn, Gln, Arg, Ser, or Thr at position 339;

Ala or Val at position 376;
Gly or Lys at position 377;
Asp at position 378;
Asn at position 379;
Ala, Asn, or Ser at position 380;
Ala or Ile at position 382;
Glu at position 385;
Thr at position 392;
Leu at position 396;
Lys at position 421;
Asn at position 427;
Phe or Leu at position 428;
Met at position 429;
Trp at position 434;
Ile at position 436; and
Gly, His, Ile, Leu, or Tyr at position 440.

19. The method of claim 1, wherein, at pH 7.4, the Fc region has a higher binding activity toward an inhibitory Fcγ receptor than toward an activating Fcγ receptor.

20. The method of claim 19, wherein the inhibitory Fcγ receptor is human FcγRIIb, and the activating Fcγ receptor is human FcγRIa, human FcγRIIa (R), human FcγRIIa (H), human FcγRIIIa (V), or human FcγRIIIa (F).

21. The method of claim 19, wherein the amino acid at position 238 or 328 (EU numbering) in the Fc region of (i) is different from the amino acid in the corresponding position of a native human IgG Fc region.

22. The method of claim 21, wherein the amino acid at position 238 (EU numbering) of the Fc region of (i) is Asp, or the amino acid at position 328 (EU numbering) of the Fc region of (i) is Glu.

23. The method of claim 22, wherein the Fc region of (i) comprises, at one or more of the following positions, the indicated amino acid (all positions by EU numbering):
Asp at position 233;
Trp or Tyr at position 234;
Ala, Asp, Glu, Leu, Met, Phe, Trp, or Tyr at position 237;
Asp at position 239;
Ala, Gln, or Val at position 267;
Asn, Asp, or Glu at position 268;
Gly at position 271;
Ala, Asn, Asp, Gln, Glu, Leu, Met, Ser, or Thr at position 326;
Arg, Lys, or Met at position 330;
Ile, Leu, or Met at position 323; and
Asp at position 296.

24. A method of reducing the amount of an antigen in the blood of a subject, the method comprising
identifying a subject as being in need of a reduction in the amount of the antigen in the subject's blood; and
administering at least two different antibodies to the subject, the administering being in a manner that introduces the antibodies into the subject's blood, wherein the antibodies include (i) a first antibody that comprises a first Fc region and a first antigen-binding domain that binds to a first epitope on the antigen, and (ii) a second antibody that comprises a second Fc region and a second antigen binding domain that binds to a second epitope on the antigen,
wherein
(a) the first and second epitopes may be identical or different,
(b) at least one of the antigen-binding domains is as described in one or both of (1) and (2) below:
(1) the antigen-binding domain:
comprises a light chain variable region comprising a histidine at one or more of Kabat numbering positions 24, 27, 28, 31, 32, 34, 50, 51, 52, 53, 54, 55, 56, 89, 90, 91, 92, 93, 94, and 95A; and has an antigen-binding activity that varies depending on pH and has a KD (pH 5.8)/KD (pH 7.4) value, defined as the ratio of (KD for the antigen at pH 5.8) to (KD for the antigen at pH 7.4), of 2 or higher, when the KD (pH 5.8) and KD (pH 7.4) values are determined using a surface plasmon resonance technique in which the antigen is immobilized, the antibody serves as analyte, and the following conditions are used: 37° C., 0.05% polyethylene glycol sorbitan monolaurate, 20 mmol/L N-(2-acetamido)-2-aminoethanesulfonic acid (ACES), 150 mmol/L NaCl, 1.2 mM $CaCl_2$), at either pH 5.8 or pH 7.4;

(2) the antibody-binding domain:

comprises a light chain variable region comprising a metal-chelating amino acid residue at one or more of Kabat numbering positions 30, 31, 32, 50, and 92; and has an antigen-binding activity that varies depending on calcium ion concentration and has a KD (3 μM Ca)/KD (1.2 mM Ca) value, defined as the ratio of (KD for the antigen at a calcium ion concentration of 3 μM) to (KD for the antigen at a calcium ion concentration of 1.2 mM), of 2 or higher, when the KD (3 μM Ca) and KD (1.2 mM Ca) values are determined using a surface plasmon resonance technique in which the antibody is immobilized, the antigen serves as analyte, and the following conditions are used: 37° C., 0.05% polyethylene glycol sorbitan monolaurate, 20 mmol/L ACES, 150 mmol/L NaCl, pH 7.4, and either 1.2 mM $CaCl_2$) or 3 μM $CaCl_2$), and (c) when contacted with molecules of the antigen, the first and second antibodies form an immune complex comprising the first and second antibodies and two or more copies of the antigen.

25. The method of claim 24, wherein the at least two different antibodies are administered in admixture.

* * * * *

UNITED STATES PATENT AND TRADEMARK OFFICE
CERTIFICATE OF CORRECTION

PATENT NO. : 11,820,793 B2
APPLICATION NO. : 16/108897
DATED : November 21, 2023
INVENTOR(S) : Tomoyuki Igawa and Naoka Hironiwa Page 1 of 1

It is certified that error appears in the above-identified patent and that said Letters Patent is hereby corrected as shown below:

In the Claims

Column 321, Line 66: Claim 1, delete "higher," and insert -- higher --.

Column 322, Line 46: Claim 1, delete "CaCl2)," and insert -- CaCl2, --.

Column 322, Line 59: Claim 1, delete "higher," and insert -- higher --.

Column 322, Line 67: Claim 1, delete both instances of "CaCl2)" and insert in place of each -- CaCl2 --.

Column 329, Line 7: Claim 24, delete "higher," and insert -- higher --.

Column 329, Line 15: Claim 24, delete "CaCl2)," and insert -- CaCl2, --.

Column 330, Line 6: Claim 24, delete "higher," and insert -- higher --.

Column 330, Line 14: Claim 24, delete both instances of "CaCl2)" and insert in place of each -- CaCl2 --.

Signed and Sealed this
Ninth Day of April, 2024

Katherine Kelly Vidal
*Director of the United States Patent and Trademark Office*